US012559799B2

(12) United States Patent
Raymond et al.

(10) Patent No.: US 12,559,799 B2
(45) **Date of Patent: *Feb. 24, 2026**

(54) METHODS FOR THE DETECTION OF GENOMIC COPY CHANGES IN DNA SAMPLES

(71) Applicant: Resolution Bioscience, Inc., Kirkland, WA (US)

(72) Inventors: Christopher Raymond, Kirkland, WA (US); Lee Lim, Kirkland, WA (US); Jennifer Hernandez, Kirkland, WA (US)

(73) Assignee: Resolution Bioscience, Inc., Madison, WI (US)

(*) Notice: Subject to any disclaimer, the term of this patent is extended or adjusted under 35 U.S.C. 154(b) by 982 days.

This patent is subject to a terminal disclaimer.

(21) Appl. No.: 17/586,143

(22) Filed: Jan. 27, 2022

(65) Prior Publication Data

US 2022/0325353 A1 Oct. 13, 2022

Related U.S. Application Data

(63) Continuation of application No. 15/685,834, filed on Aug. 24, 2017, now Pat. No. 11,319,594.

(60) Provisional application No. 62/481,538, filed on Apr. 4, 2017, provisional application No. 62/379,593, filed on Aug. 25, 2016.

(51) Int. Cl.

| | |
|---|---|
| *C12Q 1/6886* | (2018.01) |
| *C12Q 1/68* | (2018.01) |
| *C12Q 1/6806* | (2018.01) |
| *C12Q 1/6809* | (2018.01) |
| *C12Q 1/686* | (2018.01) |
| *C12Q 1/6869* | (2018.01) |
| *G16B 20/00* | (2019.01) |
| *G16B 20/10* | (2019.01) |
| *G16B 20/20* | (2019.01) |
| *G16B 20/40* | (2019.01) |
| *G16B 25/10* | (2019.01) |
| *G16B 30/00* | (2019.01) |
| *G16B 30/10* | (2019.01) |
| *C12Q 1/6851* | (2018.01) |
| *C40B 40/08* | (2006.01) |

(52) U.S. Cl.
CPC ............. *C12Q 1/6886* (2013.01); *C12Q 1/68* (2013.01); *C12Q 1/6806* (2013.01); *C12Q 1/6809* (2013.01); *C12Q 1/686* (2013.01); *C12Q 1/6869* (2013.01); *G16B 20/00* (2019.02); *G16B 20/10* (2019.02); *G16B 20/20* (2019.02); *G16B 20/40* (2019.02); *G16B 25/10* (2019.02); *G16B 30/00* (2019.02); *G16B 30/10* (2019.02); *C12Q 1/6851* (2013.01); *C12Q 2525/191* (2013.01); *C12Q 2545/114* (2013.01); *C12Q 2563/159*

(2013.01); *C12Q 2563/179* (2013.01); *C12Q 2600/156* (2013.01); *C40B 40/08* (2013.01); *G01N 2570/00* (2013.01); *G01N 2800/7028* (2013.01)

(58) Field of Classification Search
CPC ...... C12Q 1/6886; C12Q 1/68; C12Q 1/6806; C12Q 2525/191; C40B 40/08
See application file for complete search history.

(56) References Cited

U.S. PATENT DOCUMENTS

| | | | |
|---|---|---|---|
| 5,185,243 | A | 2/1993 | Ullman et al. |
| 5,512,445 | A | 4/1996 | Yang et al. |
| 5,514,551 | A | 5/1996 | Yang et al. |
| 5,591,582 | A | 1/1997 | Bos et al. |
| 6,025,133 | A | 2/2000 | Stull et al. |
| 6,025,139 | A | 2/2000 | Yager et al. |
| 6,087,133 | A | 7/2000 | Dattagupta et al. |
| 6,214,587 | B1 | 4/2001 | Dattagupta et al. |
| 6,480,791 | B1 | 11/2002 | Strathmann |
| 6,812,341 | B1 | 11/2004 | Conrad |
| 7,081,527 | B2 | 7/2006 | Cunningham et al. |
| 7,393,665 | B2 | 7/2008 | Brenner |
| 7,537,897 | B2 | 5/2009 | Brenner et al. |
| 7,585,631 | B2 | 9/2009 | Cunningham et al. |
| 8,148,068 | B2 | 4/2012 | Brenner |
| 8,168,385 | B2 | 5/2012 | Brenner |
| 8,318,433 | B2 | 11/2012 | Brenner |
| 8,370,079 | B2 | 2/2013 | Sorenson et al. |

(Continued)

FOREIGN PATENT DOCUMENTS

| | | |
|---|---|---|
| CN | 101932729 A | 12/2010 |
| CN | 102264914 A | 11/2011 |

(Continued)

OTHER PUBLICATIONS

Lowe et al. (Nucleic Acids Research, vol. 18, No. 7, p. 1757-1761, 1990). (Year: 1990).*

(Continued)

*Primary Examiner* — Sahana S Kaup
(74) *Attorney, Agent, or Firm* — Casimir Jones, S.C.; Thomas A. Isenbarger

(57) ABSTRACT

The present invention includes compositions and methods useful for the detection of a mutational change, SNP, translocation, inversion, deletion, change in copy number, or other genetic variation within a sample of cellular genomic DNA or cell-free DNA (cfDNA). In some embodiments, the compositions and methods of the present invention provide an extremely high level of resolution that is particularly useful in detecting copy number variations in a small fraction of the total cfDNA from a biological sample (e.g., blood).

22 Claims, 116 Drawing Sheets

Specification includes a Sequence Listing.

(56) References Cited

U.S. PATENT DOCUMENTS

| | | | |
|---|---|---|---|
| 8,383,338 B2 | 2/2013 | Kitzman et al. | |
| 8,470,996 B2 | 6/2013 | Brenner | |
| 8,476,018 B2 | 7/2013 | Brenner | |
| 8,481,292 B2 | 7/2013 | Casbon et al. | |
| 8,722,368 B2 | 5/2014 | Casbon et al. | |
| 8,741,811 B2 | 6/2014 | Lo et al. | |
| 8,828,688 B2 | 9/2014 | Namsaraev | |
| 8,835,358 B2 | 9/2014 | Fodor et al. | |
| 8,865,410 B2 | 10/2014 | Shendure et al. | |
| 8,999,642 B2 | 4/2015 | Sabot et al. | |
| 9,018,365 B2 | 4/2015 | Brenner | |
| 9,085,798 B2 | 7/2015 | Chee | |
| 9,121,069 B2 | 9/2015 | Lo et al. | |
| 9,216,172 B2 | 12/2015 | Kohno et al. | |
| 9,290,808 B2 | 3/2016 | Fodor et al. | |
| 9,290,809 B2 | 3/2016 | Fodor et al. | |
| 9,297,011 B2 | 3/2016 | Downing et al. | |
| 9,315,857 B2 | 4/2016 | Fu et al. | |
| 9,340,830 B2 | 5/2016 | Lipson et al. | |
| 9,410,954 B2 | 8/2016 | Boshoff et al. | |
| 9,522,125 B1 | 12/2016 | Yao et al. | |
| 9,546,399 B2 | 1/2017 | Amorese et al. | |
| 9,598,731 B2 | 3/2017 | Talasaz | |
| 9,624,489 B2 | 4/2017 | Sabot et al. | |
| 9,702,002 B2 | 7/2017 | Boutell | |
| 9,708,659 B2 | 7/2017 | Fodor et al. | |
| 9,783,847 B2 | 10/2017 | Chee | |
| 9,783,853 B2 | 10/2017 | Chinnaiyan et al. | |
| 9,792,403 B2 | 10/2017 | Sun et al. | |
| 9,816,137 B2 | 11/2017 | Fodor et al. | |
| 9,834,822 B2 | 12/2017 | Talasaz | |
| 9,840,743 B2 | 12/2017 | Talasaz | |
| 9,850,523 B1 | 12/2017 | Chudova et al. | |
| 9,902,992 B2 | 2/2018 | Talasaz et al. | |
| 9,907,798 B2 | 3/2018 | Boshoff et al. | |
| 9,920,366 B2 | 3/2018 | Eltoukhy et al. | |
| 9,932,576 B2 | 4/2018 | Raymond et al. | |
| 9,965,585 B2 | 5/2018 | Lo et al. | |
| 10,000,800 B2 | 6/2018 | Chee | |
| 10,000,814 B2 | 6/2018 | Cronin et al. | |
| 10,011,870 B2 | 7/2018 | Zimmermann et al. | |
| 10,047,394 B2 | 8/2018 | Fodor et al. | |
| 10,059,991 B2 | 8/2018 | Fodor et al. | |
| 10,087,482 B2 | 10/2018 | Korfhage et al. | |
| 10,095,831 B2 | 10/2018 | Duenwald et al. | |
| 10,119,165 B2 | 11/2018 | Chee | |
| 10,202,646 B2 | 2/2019 | Fodor et al. | |
| 10,208,296 B2 | 2/2019 | Iavarone et al. | |
| 10,208,354 B2 | 2/2019 | Fernandez-Cuesta et al. | |
| 10,227,587 B2 | 3/2019 | Zhang et al. | |
| 10,240,209 B2 | 3/2019 | Lo et al. | |
| 10,266,883 B2 | 4/2019 | Chee | |
| 10,266,889 B2 | 4/2019 | Behlke et al. | |
| 10,287,630 B2 | 5/2019 | Xie et al. | |
| 10,297,342 B2 | 5/2019 | Lo et al. | |
| 10,329,627 B1 | 6/2019 | Beeler et al. | |
| 10,378,063 B2 | 8/2019 | Stransky et al. | |
| 10,378,064 B1 | 8/2019 | Schutz et al. | |
| 10,388,403 B2 | 8/2019 | Rava et al. | |
| 10,392,661 B2 | 8/2019 | Fodor et al. | |
| 10,407,509 B2 | 9/2019 | Stransky et al. | |
| 10,453,556 B2 | 10/2019 | Lo et al. | |
| 10,494,678 B2 | 12/2019 | Talasaz | |
| 10,501,793 B2 | 12/2019 | Chee | |
| 10,501,810 B2 | 12/2019 | Talasaz | |
| 10,538,759 B2 | 1/2020 | Stuelpnagel et al. | |
| 10,577,601 B2 | 3/2020 | Shendure et al. | |
| 10,597,653 B2 | 3/2020 | Sabot et al. | |
| 10,597,708 B2 | 3/2020 | Zimmermann et al. | |
| 10,597,709 B2 | 3/2020 | Zimmermann et al. | |
| 10,619,203 B2 | 4/2020 | Fodor et al. | |
| 10,619,214 B2 | 4/2020 | Lo et al. | |
| 10,689,699 B2 | 6/2020 | Salk et al. | |
| 10,704,085 B2 | 7/2020 | Talasaz et al. | |
| 10,704,086 B2 | 7/2020 | Talasaz et al. | |
| 10,705,087 B2 | 7/2020 | Takeuchi et al. | |
| 10,741,270 B2 | 8/2020 | Lo et al. | |
| 10,752,951 B2 | 8/2020 | Salk et al. | |
| 10,793,916 B2 | 10/2020 | Talasaz | |
| 10,801,063 B2 | 10/2020 | Eltoukhy et al. | |
| 10,813,936 B2 | 10/2020 | Arrigo et al. | |
| 10,815,533 B2 | 10/2020 | Lee et al. | |
| 10,847,249 B2 | 11/2020 | Sun et al. | |
| 10,876,152 B2 | 12/2020 | Talasaz et al. | |
| 10,883,139 B2 | 1/2021 | Eltoukhy et al. | |
| 10,889,858 B2 | 1/2021 | Talasaz et al. | |
| 10,894,974 B2 | 1/2021 | Talasaz et al. | |
| 10,907,149 B2 | 2/2021 | Raymond et al. | |
| 10,921,311 B2 | 2/2021 | Takeuchi et al. | |
| 10,947,600 B2 | 3/2021 | Talasaz | |
| 10,982,265 B2 | 4/2021 | Talasaz et al. | |
| 10,995,376 B1 | 5/2021 | Talasaz | |
| 11,091,796 B2 | 8/2021 | Talasaz et al. | |
| 11,142,759 B2 | 10/2021 | Sabot et al. | |
| 11,186,875 B2 | 11/2021 | Carpten et al. | |
| 11,186,878 B2 | 11/2021 | Beeler et al. | |
| 11,230,589 B2 | 1/2022 | Lipson et al. | |
| 11,319,594 B2 | 5/2022 | Raymond et al. | |
| 11,319,597 B2 | 5/2022 | Talasaz | |
| 11,339,391 B2 | 5/2022 | Raymond et al. | |
| 11,525,162 B2 | 12/2022 | Rabinowitz et al. | |
| 11,578,372 B2 | 2/2023 | Hawryluk et al. | |
| 11,633,402 B2 | 4/2023 | Kodama et al. | |
| 11,643,694 B2 | 5/2023 | Mortimer et al. | |
| 11,926,668 B2 | 3/2024 | Rietschel et al. | |
| 2003/0148310 A1 | 8/2003 | Sorge | |
| 2004/0058328 A1 | 3/2004 | Chan et al. | |
| 2005/0032057 A1 | 2/2005 | Shoemaker | |
| 2007/0037139 A1 | 2/2007 | Tomono et al. | |
| 2007/0117089 A1 | 5/2007 | Croker et al. | |
| 2007/0117224 A1 | 5/2007 | Croker et al. | |
| 2007/0128624 A1 | 6/2007 | Gormley et al. | |
| 2007/0172873 A1 | 7/2007 | Brenner et al. | |
| 2008/0038782 A1 | 2/2008 | Borns | |
| 2009/0117573 A1 | 5/2009 | Fu et al. | |
| 2009/0143243 A1 | 6/2009 | Gunning et al. | |
| 2009/0191563 A1 | 7/2009 | Steemers et al. | |
| 2009/0264305 A1 | 10/2009 | Brandon et al. | |
| 2010/0093550 A1 | 4/2010 | Stuelpnagel et al. | |
| 2010/0273219 A1 | 10/2010 | May et al. | |
| 2011/0014657 A1 | 1/2011 | Rigatti et al. | |
| 2011/0160078 A1 | 6/2011 | Fodor et al. | |
| 2011/0294689 A1 | 12/2011 | Namsaraev | |
| 2011/0313145 A1 | 12/2011 | Sharon et al. | |
| 2012/0157322 A1 | 6/2012 | Myllykangas et al. | |
| 2012/0283110 A1 | 11/2012 | Shendure et al. | |
| 2013/0288915 A1 | 10/2013 | Seligmann et al. | |
| 2014/0100792 A1 | 4/2014 | Deciu et al. | |
| 2014/0242581 A1 | 8/2014 | Johnson | |
| 2014/0274731 A1* | 9/2014 | Raymond | C12Q 1/6806 |
| | | | 506/17 |
| 2014/0274740 A1 | 9/2014 | Srinivasan et al. | |
| 2015/0046180 A1 | 2/2015 | Futscher De Deus et al. | |
| 2015/0072344 A1 | 3/2015 | Wiley | |
| 2015/0111757 A1 | 4/2015 | Boyden et al. | |
| 2015/0159222 A1 | 6/2015 | Gaulis et al. | |
| 2015/0275289 A1 | 10/2015 | Otwinowski et al. | |
| 2015/0376700 A1 | 12/2015 | Schnall-Levin et al. | |
| 2016/0053253 A1 | 2/2016 | Salathia et al. | |
| 2016/0053301 A1* | 2/2016 | Raymond | C12Q 1/6869 |
| | | | 702/20 |
| 2017/0088887 A1 | 3/2017 | Makarov et al. | |
| 2017/0096706 A1 | 4/2017 | Behlke et al. | |
| 2017/0242960 A1 | 8/2017 | Rabinowitz et al. | |
| 2017/0283869 A1 | 10/2017 | Fang et al. | |
| 2017/0355984 A1 | 12/2017 | Evans et al. | |
| 2017/0356053 A1 | 12/2017 | Otto et al. | |
| 2018/0142234 A1 | 5/2018 | Raymond et al. | |
| 2018/0163272 A1 | 6/2018 | Raymond et al. | |
| 2018/0179578 A1 | 6/2018 | Raymond et al. | |
| 2018/0245072 A1 | 8/2018 | Raymond et al. | |
| 2018/0300449 A1 | 10/2018 | Kermani et al. | |
| 2018/0300456 A1 | 10/2018 | Eltoukhy et al. | |
| 2018/0363066 A1 | 12/2018 | Chalmers et al. | |

(56) References Cited

U.S. PATENT DOCUMENTS

| | | |
|---|---|---|
| 2019/0032118 A1 | 1/2019 | Lipson et al. |
| 2019/0136301 A1 | 5/2019 | Lipson et al. |
| 2019/0233897 A1 | 8/2019 | Cronin et al. |
| 2020/0048703 A1 | 2/2020 | Chee |
| 2020/0299775 A1 | 9/2020 | Hawryluk et al. |
| 2021/0198658 A1 | 7/2021 | Raymond et al. |
| 2022/0073906 A1 | 3/2022 | Guo et al. |
| 2022/0267763 A1 | 8/2022 | Raymond et al. |

FOREIGN PATENT DOCUMENTS

| | | |
|---|---|---|
| CN | 102439177 A | 5/2012 |
| CN | 103103624 A | 5/2013 |
| CN | 103668471 A | 3/2014 |
| EP | 0709467 A2 | 5/1996 |
| EP | 0851033 A1 | 7/1998 |
| EP | 3192869 A1 | 7/2017 |
| EP | 3202915 A1 | 8/2017 |
| EP | 3329039 A1 | 6/2018 |
| EP | 3363904 A2 | 8/2018 |
| EP | 3421613 A1 | 1/2019 |
| EP | 3470533 A1 | 4/2019 |
| EP | 3502273 A1 | 6/2019 |
| EP | 3551769 A2 | 10/2019 |
| EP | 3567120 A1 | 11/2019 |
| EP | 3374525 B1 | 1/2021 |
| JP | 2013536679 A | 9/2013 |
| JP | 2014512817 A | 5/2014 |
| JP | 2017525371 A | 9/2017 |
| JP | 2019504618 A | 2/2019 |
| JP | 2019526257 A | 9/2019 |
| JP | 2020516281 A | 6/2020 |
| WO | WO-1999011819 A1 | 3/1999 |
| WO | WO-9923258 A1 | 5/1999 |
| WO | WO-0222890 A2 | 3/2002 |
| WO | WO-2004053127 A1 | 6/2004 |
| WO | WO-2008070375 A2 | 6/2008 |
| WO | WO-2009076238 A2 | 6/2009 |
| WO | WO-2009091798 A1 | 7/2009 |
| WO | WO-2009099602 A1 | 8/2009 |
| WO | WO-2010048605 A1 | 4/2010 |
| WO | WO-2010129937 A2 | 11/2010 |
| WO | WO-2011156529 A2 | 12/2011 |
| WO | WO-2012028746 A1 | 3/2012 |
| WO | WO-2012040387 A1 | 3/2012 |
| WO | WO-2012129363 A2 | 9/2012 |
| WO | WO-2012138365 A1 | 10/2012 |
| WO | WO-2012142213 A2 | 10/2012 |
| WO | WO-2012142334 A2 | 10/2012 |
| WO | WO-2012148477 A1 | 11/2012 |
| WO | WO-2014052487 A1 | 4/2014 |
| WO | WO-2014055790 A2 | 4/2014 |
| WO | WO-2014071295 A1 | 5/2014 |
| WO | WO-2014093330 A1 | 6/2014 |
| WO | WO-2014093825 A1 | 6/2014 |
| WO | WO-2014122288 A1 | 8/2014 |
| WO | WO 2015/100427 | 7/2015 |
| WO | WO-2015117040 A1 | 8/2015 |
| WO | WO-2015134552 A1 | 9/2015 |
| WO | WO-2016022833 A1 | 2/2016 |
| WO | WO-2016028316 A1 | 2/2016 |
| WO | WO-2016037389 A1 | 3/2016 |
| WO | WO-2016040901 A1 | 3/2016 |
| WO | WO-2016094853 A1 | 6/2016 |
| WO | WO-2016109452 A1 | 7/2016 |
| WO | WO-2017019322 A1 | 2/2017 |
| WO | WO-2017083562 A1 | 5/2017 |
| WO | WO-2018039463 A1 | 3/2018 |
| WO | WO-2018064629 A1 | 4/2018 |
| WO | WO-2018094183 A1 | 5/2018 |
| WO | WO-2018104908 A2 | 6/2018 |
| WO | WO-2020106906 A1 | 5/2020 |
| WO | WO-2021163546 A1 | 8/2021 |
| WO | WO-2022212574 A1 | 10/2022 |

OTHER PUBLICATIONS

[Author Unknown] "TruSeq™ RNA and DNA Library Preparation Kits v2". Data Sheet: Illumina® Sequencing, © 2011, 2014 Illumina, Inc., Pub. No. 770-2009-039 Current as of Nov. 17, 2014, 4 pages.

Hess, et al., "Library preparation for next generation sequencing: A review of automation strategies". Biotechnol Adv. (Jul.-Aug. 2020); 41: 107537, 14 pages. Epub Mar. 19, 2020.

Hong and Shin, "Bisulfite-Converted DNA Quantity Evaluation: A Multiplex Quantitative Real-Time PCR System for Evaluation of Bisulfite Conversion". Front Genet. (Feb. 25, 2021); 12: 618955. eCollection 2021.

Ma, et al., "Pan-cancer genome and transcriptome analyses of 1,699 paediatric leukaemias and solid tumours". Nature (2018); 55: 371-376. Epub Feb. 28, 2018.

Malone, et al., "Molecular profiling for precision cancer therapies". Genome Med. (Jan. 14, 2020); 12(1): 8, 19 pages.

Manier, et al., "Whole-exome sequencing of cell-free DNA and circulating tumor cells in multiple myeloma". Nat Commun. (Apr. 27, 2018); 9(1): 1691, 11 pages.

Wang, et al., "Enzymatic approaches for profiling cytosine methylation and hydroxymethylation". Mol Metab. (Mar. 2022); 57: 101314. Epub Aug. 8, 2021.

Wang, et al., "Low-pass genome sequencing versus chromosomal microarray analysis: implementation in prenatal diagnosis". Genet Med. (Mar. 2020); 22(3): 500-510. Epub Aug. 26, 2019.

Cheng Jie et al., "Construction of chlamys farreri Fosmid Library and analysis of Genomic Structure", Journal of Ocean University of China, Jan. 2008, vol. 38(01); 078-088 and English abstract, 11 pages.

Atamaniuk, et al., "Cell-free plasma DNA: a marker for apoptosis during hemodialysis." Clinical Chemistry (Mar. 2006), 52(3): 523-526.

[Author Unknown] "SureSelectXT Target Enrichment System for Illumina Paired-End Multiplexed Sequencing Library". Protocol, Version C3, Sep. 2019, Agilent Technologies, © Agilent Technologies, Inc. 2010-2019, 100 pages.

Begley, Sharon, "Psst, The Human Genome Was Never Completely Sequenced. Some Scientists Say It Should Be", STAT News, Jun. 20, 2017 (Year: 2017), downloaded Sep. 3, 2018 from https://www.statnews.com/2017 /06/20/human-genome-not-fully-sequenced/, 8 pages.

Beltran, et al., "Circulating tumor DNA profile recognizes transformation to castration-resistant neuroendocrine prostate cancer". J Clin Invest (Apr. 1, 2020), 130(4): 1653-1668.

Blake, R. D. et al., "Thermodynamic effects of formamide on DNa stability", Nucleic Acids Research, vol. 24, No. 11, Oxford University Press, 1996, 2095-2103.

Chan, et al., "Cancer genome scanning in plasma: detection of tumor-associated copy number aberrations, single-nucleotide variants, and tumoral heterogeneity by massively parallel sequencing." Clinical Chemistry (2013), 59(1): 211-224. Epub Oct. 11, 2012.

Cheng, et al., "Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology". J Mol Diagn. (May 2015), 17(3): 251-264. Epub Mar. 20, 2010.

Extended European Search Report in Application No. EP 13862440.8, dated Oct. 11, 2016, 19 pages.

Extended European Search Report in Application No. EP 16865029.9, dated Apr. 29, 2019, 11 pages.

Extended European Search Report in Application No. EP 17844424.6, dated Mar. 27, 2020, 8 pages.

Extended European Search Report in Application No. EP 19153893.3, dated Sep. 17, 2019, 9 pages.

Extended European Search Report in Application No. EP 21152311.3, dated Sep. 7, 2021, 14 pages.

Fakruddin, et al., "Nucleic acid amplification: Alternative methods of polymerase chain reaction". Journal of Pharmacy and Bioallied Sciences (Oct.-Dec. 2013), 5(4): 245-252.

(56)　　　　　References Cited

OTHER PUBLICATIONS

Forster, et al., "A human gut bacterial genome and culture collection for improved metagenomic analyses". Nat Biotechnol. (Feb. 2019), 37(2): 186-192. Epub Feb. 4, 2019.

Hoeijmakers et al., "Linear amplification for deep sequencing." Nature Protocols (2011), 6(7): 1026-1036.

Horn, Susanne, "Target Enrichment via DNA Hybridization Capture" in Ancient DNA: Methods and Protocols, Methods in Molecular Biology (2012), 840: 177-188. Epub Dec. 8, 2011.

Jacobs, et al., "The thermal stability of oligonucleotide duplexes is sequence independent in tetraalkylammonium salt solutions: application to identifying recombinant DNA clones". Nucleic Acids Res. (May 25, 1988), 16(10): 4637-4650.

KAPA Biosystems, "KAPA Library Quantification Kits Technical Data Sheet" (2011), 6 pages, www.kapabiosystems.com.

Leary, et al. "Detection of chromosomal alterations in the circulation of cancer patients with whole-genome sequencing." Science Translational Medicine (Nov. 28, 2012), 4(162): 162ra154.

Lin, et al., "Exon array profiling detects EML4-ALK fusion in breast, colorectal, and non-small cell lung cancers." Molecular Cancer Research (Sep. 2009), 7(9): 1466-1476. Epub Sep. 8, 2009.

Mamanova, et al., "Target-enrichment strategies for next-generation sequencing". Nature Methods. (Feb. 2010), 7(2): 111-118.

Mano, H., "Non-solid oncogenes in solid tumors: EML4-ALK fusion genes in lung cancer." Cancer Science (Dec. 2008), 99(12): 2349-2355. Epub Nov. 20, 2008.

McKernan, et al., "Sequence and structural variation in a human genome uncovered by short-read, massively parallel ligation sequencing using two-base encoding." Genome Research (Sep. 2009), 19(9): 1527-1541. Epub Jun. 22, 2009.

Melchior, W.B. and Hippel, P.H. "Alteration of the relative stability of dA• dT and dG. dC base pairs in DNA." Proceedings of the National Academy of Sciences USA (Feb. 1973), 70(2): 298-302.

Meyer et al., "From micrograms to picograms: quantitative PCR reduces the material demands of high-throughput sequencing" Nucleic Acids Research (2008), 36(1): e5, 6 pages. Epub Dec. 15, 2007.

Meyer, et al., "Targeted high-throughput sequencing of tagged nucleic acid samples." Nucleic Acids Research (2007), 35(15): e97, 5 pages. Epub Aug. 1, 2007.

Miura, et al., "Highly efficient single-stranded DNA ligation technique improves low-input whole-genome bisulfite sequencing by post-bisulfite adaptor tagging." Nucleic Acids Research (Sep. 5, 2019), 47(15): e85-e85, p. 1-10. Epub May 22, 2019.

Oxford Dictionary of Biochemistry and Molecular Biology, Definition of "base composition", general eds Attwood, et al. Revised Edition (2000), 3 pages.

Partial Supplementary European Search Report in European Application No. 13862440.8 dated Jul. 4, 2016, 11 pages.

PCT/US2013/074102, International Preliminary Report on Patentability dated Jun. 16, 2015.

PCT/US2013/074102, International Search Report and Written Opinion mailed Feb. 28, 2014.

PCT/US2014/052317, International Preliminary Report on Patentability dated Feb. 28, 2017, 8 pages.

PCT/US2014/052317, International Search Report and Written Opinion mailed Jan. 13, 2015, 13 pages.

PCT/US2016/061395, International Preliminary Report on Patentability dated May 15, 2018, 10 pages.

PCT/US2016/061395, International Search Report and Written Opinion mailed Feb. 7, 2017, 14 pages.

PCT/US2017/048434, International Preliminary Report on Patentability dated Feb. 26, 2019, 10 pages.

PCT/US2017/048434, International Search Report and Written Opinion mailed Dec. 26, 2017, 15 pages.

PCT/US2021/049448, International Search Report and Written Opinion dated Dec. 28, 2021, 12 pages.

Piovesan, et al., "On the length, weight and GC content of the human genome". BMC Res Notes (Feb. 27, 2019), 12: 106, 7 pages.

Ritti and Perbal, "Enzymes used in molecular biology: a useful guide." Journal of Cell Communication and Signaling (2008), 2(1-2): 25-45.

Samorodnitsky, et al., "Comparison of Custom Capture for Targeted Next-Generation DNA Sequencing." The Journal of Molecular Diagnostics (2015), 17(1): 64-75.

Shevelev and Hübscher, "The 3' 5' exonucleases", Nat Rev Mol Cell Biol. (May 2002), 3(5): 364-376.

Shiroguchi, et al., "Digital RNA sequencing minimizes sequence-dependent bias and amplification noise with optimized single-molecule barcodes." PNAS (Jan. 24, 2012), 109(4): 1347-1352, Supporting Information, 14 pages.

Stellwagen, Earle, et al., "Monovalent cation size and DNA conformational stability." Biochemistry (Mar. 16, 2011), 50(15): 3084-3094.

Taton, T. Andrew, et al., "Scanometric DNA array detection with nanoparticle probes." Science (Sep. 8, 2000), 289(5485): 1757-1760.

Vogelstein, Bert, et al. "Cancer genome landscapes." Science 339. 6127 (2013): 1546-1558.

Wikipedia, "List of sequenced bacterial genomes" Wikipedia.com, accessed Jan. 24, 2014, 57 pages. (Year: 2014).

Wisegeek, "How many species of bacteria are there?" WiseGeek. com, accessed Jan. 21, 2014, 2 pages. (Year: 2014).

Yegnasubramanian et al., "Preparation of Fragment Libraries for Next-Generation Sequencing on the Applied Biosystems SOLID Platform." Methods in Enzymology (2013), 529: 185-200.

Zhou, et al., "Systematic evaluation of library preparation methods and sequencing platforms for high-throughput whole genome bisulfite sequencing." Scientific Reports (2019), 9: 10383, 16 pages.

Cunningham, et al., "Abstract 881. Rapid Detection of Mycoplasma pneumoniae from Clinical Specimens by Transcription-Mediated Amplification". ICAAC 40th Anniversary, Toronto, Sep. 17-20, 2000, 2 pages.

Diaz Jr. and Bardelli, "Liquid biopsies: genotyping circulating tumor DNA". J Clin Oncol. Feb. 20, 2014; 32(6): 579-586. Epub Jan. 21, 2014.

European Patent Application No. 19153893.3: Agilent Resolution ctDx First Technical Information, submitted with Response to Summons to Attend Oral Proceedings as "Annex B", on Mar. 17, 2023; 50 pages.

European Patent Application No. 19153893.3: Auxiliary Request 1, submitted with Response to Summons to Attend Oral Proceedings, on Mar. 17, 2023; 2 pages.

European Patent Application No. 19153893.3: Auxiliary Request 10, submitted with Response to Summons to Attend Oral Proceedings, on Apr. 17, 2023; 2 pages.

European Patent Application No. 19153893.3: Auxiliary Request 2, submitted with Response to Summons to Attend Oral Proceedings, on Mar. 17, 2023; 2 pages.

European Patent Application No. 19153893.3: Auxiliary Request 3, submitted with Response to Summons to Attend Oral Proceedings, on Mar. 17, 2023; 2 pages.

European Patent Application No. 19153893.3: Auxiliary Request 4, submitted with Response to Summons to Attend Oral Proceedings, on Mar. 17, 2023; 2 pages.

European Patent Application No. 19153893.3: Auxiliary Request 5, submitted with Response to Summons to Attend Oral Proceedings, on Mar. 17, 2023; 2 pages.

European Patent Application No. 19153893.3: Auxiliary Request 6, submitted with Response to Summons to Attend Oral Proceedings, on Mar. 17, 2023; 2 pages.

European Patent Application No. 19153893.3: Auxiliary Request 7, submitted with Response to Summons to Attend Oral Proceedings, on Mar. 17, 2023; 2 pages.

European Patent Application No. 19153893.3: Auxiliary Request 8, submitted with Response to Summons to Attend Oral Proceedings, on Apr. 17, 2023; 2 pages.

European Patent Application No. 19153893.3: Auxiliary Request 9, submitted with Response to Summons to Attend Oral Proceedings, on Apr. 17, 2023; 2 pages.

(56)        References Cited

OTHER PUBLICATIONS

European Patent Application No. 19153893.3: Companion Diagnostics, submitted with Response to Summons to Attend Oral Proceedings as "Annex C", on Mar. 17, 2023; 2 pages.
European Patent Application No. 19153893.3: Declaration of Paul Stull with Exhibit B, signed Mar. 16, 2023, submitted with Response to Summons to Attend Oral Proceedings on Mar. 17, 2023; 8 total pages.
European Patent Application No. 19153893.3: Letter from Donna Roscoe, Ph.D. of Center for Devices and Radiological Health to Chris Pretzinger of Resolution Bioscience, Inc., signed Mar. 16, 2023, submitted with Response to Summons to Attend Oral Proceedings as "Annex A", on Mar. 17, 2023; 6 total pages.
European Patent Application No. 19153893.3: Main Request, submitted with Response to Summons to Attend Oral Proceedings, on Mar. 17, 2023; 2 pages.
European Patent Application No. 19153893.3: Response to Summons to Attend Oral Proceedings, dated Mar. 17, 2023; 31 pages.
Hocking, et al., "Liquid biopsies for liquid tumors: emerging potential of circulating free nucleic acid evaluation for the management of hematologic malignancies". Cancer Biol Med. Jun. 2016; 13(2): 215-225.
Jung, et al., "Cell-free DNA in the blood as a solid tumor biomarker—A critical appraisal of the literature". Clin Chim Acta. Nov. 11, 2010; 411(21-22): 1611-1624. Epub Aug. 2, 2010.
Kivioja, T., et al., "Counting absolute Nos. of molecules using unique molecular identifiers", Nature Methods (Nov. 20, 2011); 9(1): 72-74.
PCT/US2021/049448, International Preliminary Report on Patentability dated Mar. 23, 2023,7 pages.
Pollak, Julia, et al., "Analytical validation of the Agilent Resolution ctDx HRD plasma assay used to identify mCRPC patients with mutations, including homozygous deletions, in DNA repair genes as a companion diagnostic for niraparib". Poster Abstract# 52 RA# PR7000-3277, [publication date unknown], 1 page.
Stull and Blanchard, "Improvement in the Dispersion of Silica Nanoparticles". 241st ACS National Meeting, Mar. 28-31, 2011, Abstract, 1 page.
Stull and Blanchard, "Surface coatings on anisotropic nanoparticles". 246th ACS National Meeting, Sep. 11-12, 2013, Abstract, 1 page.
[Author Unknown] "NGS Library Preparation for Whole Genome Bisulfite Sequencing (WGBS) on Illumina® Sequencing Platforms", Qiagen, Cat # 180495 ["retrieved date unknown"] https://www.qiagen.com/us/resources/resourcedetail?id=20735cc3-6bec-4865-9d97-8cb574840500&lang=en, Oct. 2016; pp. 1-10.
[Author Unknown] "QIAseq™ Methyl Library Handbook for DNA library construction for whole genome bisulfite sequencing on Illumina® sequencing platforms", Qiagen, Cat # 180502 ["retrieved date unknown"] https://www.qiagen.com/us/products/discovery-and-translational-research/next-generation-sequencing/dna-methylation-analysis/qiaseq-methyl-library-kit/, Nov. 2017; pp. 1-40.
[Author Unknown] "QIAseq® Targeted Methyl Panel Handbook Targeted next-generation sequencing of methylated DNA", QIAgen, Cat # 335501 ["retrieved date unknown"] https://www.qiagen.com/us/products/discovery-and-translational-research/next-generation-sequencing/dna-methylation-analysis/qiaseq-targeted- methyl-panels/, Oct. 2019; pp. 1-60.
Porreca, G.J., et al., "Multiplex Amplification of Large Sets of Human Exons," Nature Methods, Oct. 14, 2007, vol. 4 (11), pp. 931-936.
Xia et al., AFSM sequencing approach: a simple and rapid method for genome-wide SNP and methylation site discovery and genetic mapping. Scientific Reports Dec. 3, 2014; 4:7300 pp. 1-8.
[Author Unknown] "An introduction to Next-Generation Sequencing Technology". Brochure, © 2017, Illumina, Inc., Pub. No. 770-2012-008-B, Retrieved online Aug. 7, 2022, https://www.illumina.com/content/dam/illumina-marketing/documents/products/illumina_sequencing_introduction.pdf, 16 pages.
Biswas, et al., "Sample quality control in agilent NGS solutions", Agilent (2018), 1-14, URL: https://www.agilent.com/cs/library/applications/application-ngs-electrophoresis-samplequalitycontrol-tapestation-5994-0127en-agilent.pdf.
International Search Report and Written Opinion for International Application No. PCT/US2022/022640, mailed Jul. 25, 2022, 15 pages.
Jang, et al., "Quality control probes for spot-uniformity and quantitative analysis of oligonucleotide array", Journal of Microbiology and Biotechnology (2009); 19(7): 658-665.

* cited by examiner

CNL assay:
required
reproducibility

← sample-to-sample →

Sample 1  Sample 2  Sample 3  Sample 4 gene-to-gene →

ATM
BRCA1
BRCA2
BRIP1
CHEK2
FANCA
HDAC2
PALB2
AR
TP53 lower unique read depth higher 249 tags → 1 anchor sequence

Shifting the UMI multiplier to increase the number of unique tags anchor     genomic DNA full length adaptor – 47 bp

FIG. 8A

| Sample | Input |
|---|---|
| Sample 1 | Female gDNA + 8% BRCA2 delete |
| Sample 2 | Female gDNA + 4% BRCA2 delete |
| Sample 3 | Female gDNA + 2% BRCA2 delete |
| Sample 4 | Pure Female gDNA |
| Sample 5 | Female gDNA + 8% ATM delete |
| Sample 6 | Female gDNA + 4% ATM delete |
| Sample 7 | Female gDNA + 2% ATM delete |
| Sample 8 | Pure Female gDNA |

AR

ATM

FIG. 9A

| Sample | Input |
|--------|-------|
| Sample 1 | Female gDNA + 8% BRCA2 delete |
| Sample 2 | Female gDNA + 4% BRCA2 delete |
| Sample 3 | Female gDNA + 2% BRCA2 delete |
| Sample 4 | Pure Female gDNA |
| Sample 5 | Female gDNA + 8% ATM delete |
| Sample 6 | Female gDNA + 4% ATM delete |
| Sample 7 | Female gDNA + 2% ATM delete |
| Sample 8 | Pure Female gDNA |

FIG. 10A

| Sample | Input |
|---|---|
| Sample 1 | F_cfDNA + 10% M_cfDNA |
| Sample 2 | F_cfDNA + 5% M_cfDNA |
| Sample 3 | Pure F_cfDNA |
| Sample 4 | Pure F_cfDNA |
| Sample 5 | F_cfDNA + 10% ATM |
| Sample 6 | F_cfDNA + 5% ATM |
| Sample 7 | F_cfDNA + 10% BRCA2 |
| Sample 8 | F_cfDNA + 5% BRCA2 |

Measured ΔATM SNP frequency: 5.5    2.5    Measured ΔBRCA2 SNP frequency:
7.2    2.6

FIG. 11A
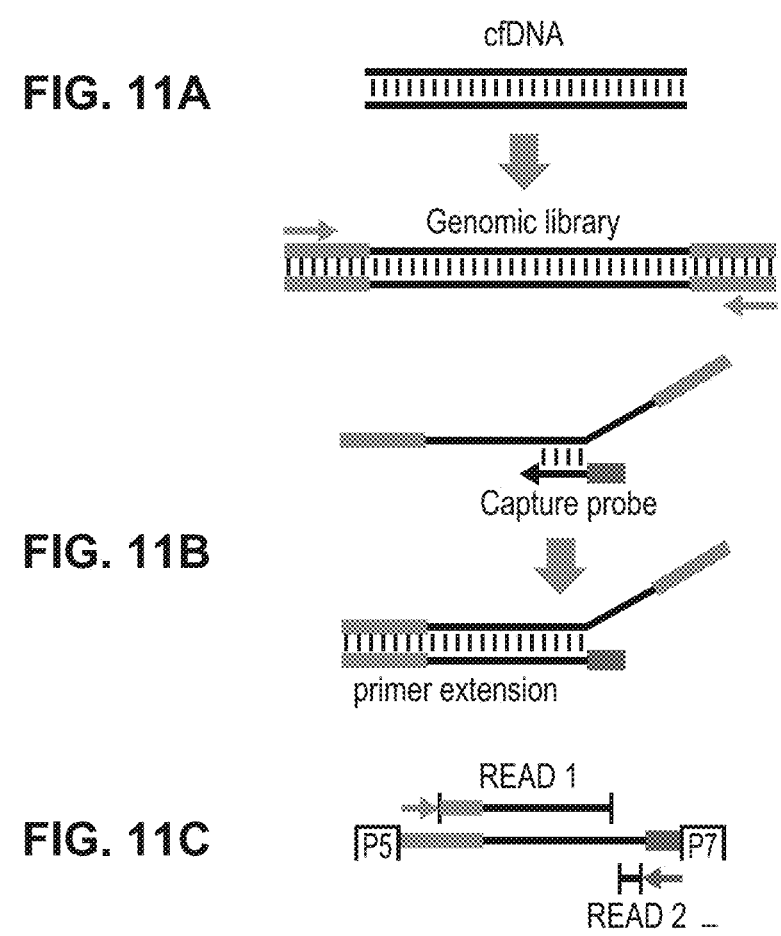
FIG. 11B
FIG. 11C
FIG. 11D
Distribution of targeted sequencing reads
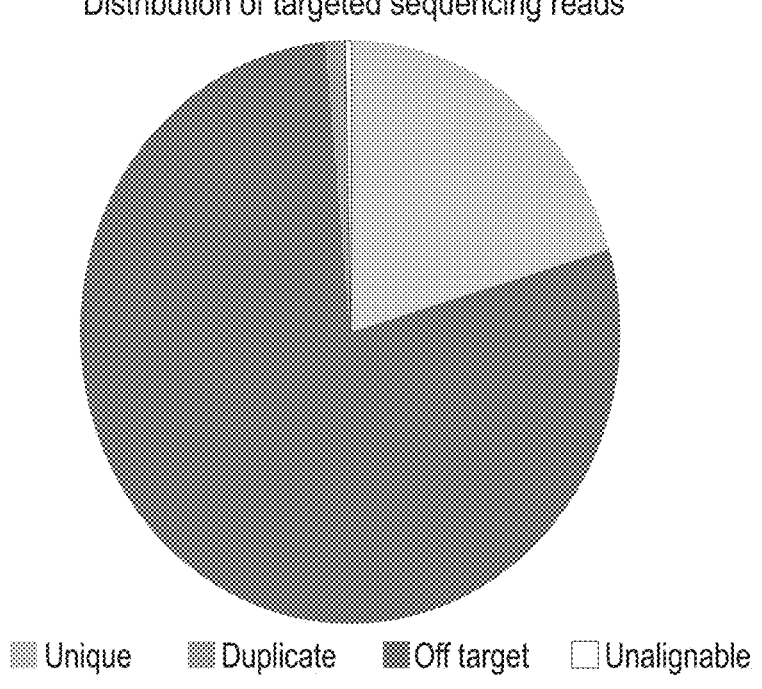

FIG. 12A

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CACGAGCTTANNNACGTATGCCA | 9 | TGCAGGACCAGAGAATTCGAATA CACCCTGTCGNNNACGTATGCCA | 249 | TGCAGGACCAGAGAATTCGAATA CAACGTCAACNNNACGTATGCCA | 489 |
| TGCAGGACCAGAGAATTCGAATA CATTGCTCACNNNACGTATGCCA | 10 | TGCAGGACCAGAGAATTCGAATA CATATCAATGNNNACGTATGCCA | 250 | TGCAGGACCAGAGAATTCGAATA CAGTGTCTAGNNNACGTATGCCA | 490 |
| TGCAGGACCAGAGAATTCGAATA CATAATACACNNNACGTATGCCA | 11 | TGCAGGACCAGAGAATTCGAATA CACTGCAGATNNNACGTATGCCA | 251 | TGCAGGACCAGAGAATTCGAATA CAGCGGCCAGTNNNACGTATGCCA | 491 |
| TGCAGGACCAGAGAATTCGAATA CATCAGCATGNNNACGTATGCCA | 12 | TGCAGGACCAGAGAATTCGAATA CAATCGGATCNNNACGTATGCCA | 252 | TGCAGGACCAGAGAATTCGAATA CAGCTCTGAANNNACGTATGCCA | 492 |
| TGCAGGACCAGAGAATTCGAATA CAACTGTAGCNNNACGTATGCCA | 13 | TGCAGGACCAGAGAATTCGAATA CACTGTTCCANNNACGTATGCCA | 253 | TGCAGGACCAGAGAATTCGAATA CAAGACTTGCNNNACGTATGCCA | 493 |
| TGCAGGACCAGAGAATTCGAATA CAATTATGCANNNACGTATGCCA | 14 | TGCAGGACCAGAGAATTCGAATA CATCACATTNNNACGTATGCCA | 254 | TGCAGGACCAGAGAATTCGAATA CAGATGGTCTNNNACGTATGCCA | 494 |
| TGCAGGACCAGAGAATTCGAATA CATGACCTTCNNNACGTATGCCA | 15 | TGCAGGACCAGAGAATTCGAATA CAGCGTGGCTNNNACGTATGCCA | 255 | TGCAGGACCAGAGAATTCGAATA CATTGTGAATNNNACGTATGCCA | 495 |
| TGCAGGACCAGAGAATTCGAATA CAAAAATCCTNNNACGTATGCCA | 16 | TGCAGGACCAGAGAATTCGAATA CACGGAGTAANNNACGTATGCCA | 256 | TGCAGGACCAGAGAATTCGAATA CACAGCGCGTNNNACGTATGCCA | 496 |
| TGCAGGACCAGAGAATTCGAATA CAGGTTCCGGNNNACGTATGCCA | 17 | TGCAGGACCAGAGAATTCGAATA CAGTGTCCGGNNNACGTATGCCA | 257 | TGCAGGACCAGAGAATTCGAATA CATGCCAAGTNNNACGTATGCCA | 497 |
| TGCAGGACCAGAGAATTCGAATA CAACGTGCATNNNACGTATGCCA | 18 | TGCAGGACCAGAGAATTCGAATA CATATTGTAGNNNACGTATGCCA | 258 | TGCAGGACCAGAGAATTCGAATA CACGTCGTTTNNNACGTATGCCA | 498 |
| TGCAGGACCAGAGAATTCGAATA CACGCCCATNNNACGTATGCCA | 19 | TGCAGGACCAGAGAATTCGAATA CATAGTATTGNNNACGTATGCCA | 259 | TGCAGGACCAGAGAATTCGAATA CACCAACGGCNNNACGTATGCCA | 499 |
| TGCAGGACCAGAGAATTCGAATA CAGTAAGCCTNNNACGTATGCCA | 20 | TGCAGGACCAGAGAATTCGAATA CAAGCGCTTANNNACGTATGCCA | 260 | TGCAGGACCAGAGAATTCGAATA CACAGTTATANNNACGTATGCCA | 500 |
| TGCAGGACCAGAGAATTCGAATA CAAGTAATAGNNNACGTATGCCA | 21 | TGCAGGACCAGAGAATTCGAATA CATGCAGGTTNNNACGTATGCCA | 261 | TGCAGGACCAGAGAATTCGAATA CACGAAGGCGNNNACGTATGCCA | 501 |
| TGCAGGACCAGAGAATTCGAATA CAAAGTCCCANNNACGTATGCCA | 22 | TGCAGGACCAGAGAATTCGAATA CACCTCCGGTNNNACGTATGCCA | 262 | TGCAGGACCAGAGAATTCGAATA CAATGGCTACNNNACGTATGCCA | 502 |
| TGCAGGACCAGAGAATTCGAATA CAAGTGCATCNNNACGTATGCCA | 23 | TGCAGGACCAGAGAATTCGAATA CAAGACGGATNNNACGTATGCCA | 263 | TGCAGGACCAGAGAATTCGAATA CATCGCATGANNNACGTATGCCA | 503 |
| TGCAGGACCAGAGAATTCGAATA CAGACATATTNNNACGTATGCCA | 24 | TGCAGGACCAGAGAATTCGAATA CATCTGTCTGNNNACGTATGCCA | 264 | TGCAGGACCAGAGAATTCGAATA CAATATCCTTNNNACGTATGCCA | 504 |
| TGCAGGACCAGAGAATTCGAATA CAGTCCACAANNNACGTATGCCA | 25 | TGCAGGACCAGAGAATTCGAATA CATTCACCGTNNNACGTATGCCA | 265 | TGCAGGACCAGAGAATTCGAATA CATGAAGCAGNNNACGTATGCCA | 505 |
| TGCAGGACCAGAGAATTCGAATA CATCTCAGAGNNNACGTATGCCA | 26 | TGCAGGACCAGAGAATTCGAATA CACGTAAAGGNNNACGTATGCCA | 266 | TGCAGGACCAGAGAATTCGAATA CAGACCACCGNNNACGTATGCCA | 506 |
| TGCAGGACCAGAGAATTCGAATA CAAAAACGTANNNACGTATGCCA | 27 | TGCAGGACCAGAGAATTCGAATA CAAGAAAGAANNNACGTATGCCA | 267 | TGCAGGACCAGAGAATTCGAATA CAAGATTAGANNNACGTATGCCA | 507 |
| TGCAGGACCAGAGAATTCGAATA CACTACCAAGNNNACGTATGCCA | 28 | TGCAGGACCAGAGAATTCGAATA CAAGTAGTTTNNNACGTATGCCA | 268 | TGCAGGACCAGAGAATTCGAATA CAAGATCTATNNNACGTATGCCA | 508 |
| TGCAGGACCAGAGAATTCGAATA CACCTGACTTNNNACGTATGCCA | 29 | TGCAGGACCAGAGAATTCGAATA CAGGTACCTANNNACGTATGCCA | 269 | TGCAGGACCAGAGAATTCGAATA CAACGTACACNNNACGTATGCCA | 509 |
| TGCAGGACCAGAGAATTCGAATA CACTCCTATGNNNACGTATGCCA | 30 | TGCAGGACCAGAGAATTCGAATA CAGAAGCACANNNACGTATGCCA | 270 | TGCAGGACCAGAGAATTCGAATA CACGGTTACANNNACGTATGCCA | 510 |
| TGCAGGACCAGAGAATTCGAATA CAATCATGATNNNACGTATGCCA | 31 | TGCAGGACCAGAGAATTCGAATA CACTAATAACNNNACGTATGCCA | 271 | TGCAGGACCAGAGAATTCGAATA CAAAAACCTATNNNACGTATGCCA | 511 |
| TGCAGGACCAGAGAATTCGAATA CATGACGGTTNNNACGTATGCCA | 32 | TGCAGGACCAGAGAATTCGAATA CAACGGACAANNNACGTATGCCA | 272 | TGCAGGACCAGAGAATTCGAATA CACTGATTTTNNNACGTATGCCA | 512 |
| TGCAGGACCAGAGAATTCGAATA CAGTCGGCGTNNNACGTATGCCA | 33 | TGCAGGACCAGAGAATTCGAATA CAATCCAGTGNNNACGTATGCCA | 273 | TGCAGGACCAGAGAATTCGAATA CATGAATATCNNNACGTATGCCA | 513 |
| TGCAGGACCAGAGAATTCGAATA CAGTTACCCTNNNACGTATGCCA | 34 | TGCAGGACCAGAGAATTCGAATA CAGGACAACANNNACGTATGCCA | 274 | TGCAGGACCAGAGAATTCGAATA CAACTGCGCGNNNACGTATGCCA | 514 |
| TGCAGGACCAGAGAATTCGAATA CACTTAACGGNNNACGTATGCCA | 35 | TGCAGGACCAGAGAATTCGAATA CAGAAAGTTANNNACGTATGCCA | 275 | TGCAGGACCAGAGAATTCGAATA CAGAACGACANNNACGTATGCCA | 515 |
| TGCAGGACCAGAGAATTCGAATA CACGGCTCCTGNNNACGTATGCCA | 36 | TGCAGGACCAGAGAATTCGAATA CAAACACAGGNNNACGTATGCCA | 276 | TGCAGGACCAGAGAATTCGAATA CATATATTGGNNNACGTATGCCA | 516 |
| TGCAGGACCAGAGAATTCGAATA CATCTCGGTTNNNACGTATGCCA | 37 | TGCAGGACCAGAGAATTCGAATA CACCAGAATCNNNACGTATGCCA | 277 | TGCAGGACCAGAGAATTCGAATA CATAGATGCCNNNACGTATGCCA | 517 |
| TGCAGGACCAGAGAATTCGAATA CAGCTCGAGCNNNACGTATGCCA | 38 | TGCAGGACCAGAGAATTCGAATA CATTCACCACNNNACGTATGCCA | 278 | TGCAGGACCAGAGAATTCGAATA CAGCAAGTAGNNNACGTATGCCA | 518 |
| TGCAGGACCAGAGAATTCGAATA CACGCTTCGCNNNACGTATGCCA | 39 | TGCAGGACCAGAGAATTCGAATA CATCGAGAGANNNACGTATGCCA | 279 | TGCAGGACCAGAGAATTCGAATA CAAACGACCTNNNACGTATGCCA | 519 |
| TGCAGGACCAGAGAATTCGAATA CAATCCAGACNNNACGTATGCCA | 40 | TGCAGGACCAGAGAATTCGAATA CACGATTGTCANNNACGTATGCCA | 280 | TGCAGGACCAGAGAATTCGAATA CAGTACAGTCNNNACGTATGCCA | 520 |
| TGCAGGACCAGAGAATTCGAATA CATAGCACTGNNNACGTATGCCA | 41 | TGCAGGACCAGAGAATTCGAATA CACGGCAGGANNNACGTATGCCA | 281 | TGCAGGACCAGAGAATTCGAATA CATATGCGGTNNNACGTATGCCA | 521 |

FIG. 12B

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CACTGGCTTTNNNACGTATGCCA | 42 | TGCAGGACCAGAGAATTCGAATA CAAGAACCAGNNNACGTATGCCA | 282 | TGCAGGACCAGAGAATTCGAATA CAATAATAGGNNNACGTATGCCA | 522 |
| TGCAGGACCAGAGAATTCGAATA CAGCAAATGGNNNACGTATGCCA | 43 | TGCAGGACCAGAGAATTCGAATA CAGATTTTGANNNACGTATGCCA | 283 | TGCAGGACCAGAGAATTCGAATA CAGTTACTAANNNACGTATGCCA | 523 |
| TGCAGGACCAGAGAATTCGAATA CAGGATGACANNNACGTATGCCA | 44 | TGCAGGACCAGAGAATTCGAATA CAAAACGTCNNNACGTATGCCA | 284 | TGCAGGACCAGAGAATTCGAATA CACCCTTGTANNNACGTATGCCA | 524 |
| TGCAGGACCAGAGAATTCGAATA CAGCCCCACTNNNACGTATGCCA | 45 | TGCAGGACCAGAGAATTCGAATA CAACCTCTACNNNACGTATGCCA | 285 | TGCAGGACCAGAGAATTCGAATA CAACATTTCTNNNACGTATGCCA | 525 |
| TGCAGGACCAGAGAATTCGAATA CACTAGCCGGNNNACGTATGCCA | 46 | TGCAGGACCAGAGAATTCGAATA CAGGCGTTANNNACGTATGCCA | 286 | TGCAGGACCAGAGAATTCGAATA CACCGACTTTNNNACGTATGCCA | 526 |
| TGCAGGACCAGAGAATTCGAATA CACCCTCCTCNNNACGTATGCCA | 47 | TGCAGGACCAGAGAATTCGAATA CACCCGAAGCNNNACGTATGCCA | 287 | TGCAGGACCAGAGAATTCGAATA CATATGAACTNNNACGTATGCCA | 527 |
| TGCAGGACCAGAGAATTCGAATA CATGTAGTGCNNNACGTATGCCA | 48 | TGCAGGACCAGAGAATTCGAATA CATACCTACNNNACGTATGCCA | 288 | TGCAGGACCAGAGAATTCGAATA CATTCTTTTCNNNACGTATGCCA | 528 |
| TGCAGGACCAGAGAATTCGAATA CAGAATGTGGNNNACGTATGCCA | 49 | TGCAGGACCAGAGAATTCGAATA CATTTACGCCNNNACGTATGCCA | 289 | TGCAGGACCAGAGAATTCGAATA CAATAGGTTTNNNACGTATGCCA | 529 |
| TGCAGGACCAGAGAATTCGAATA CAAATGATCTNNNACGTATGCCA | 50 | TGCAGGACCAGAGAATTCGAATA CAAGGTATGGNNNACGTATGCCA | 290 | TGCAGGACCAGAGAATTCGAATA CACGACGTTANNNACGTATGCCA | 530 |
| TGCAGGACCAGAGAATTCGAATA CACACTAACGNNNACGTATGCCA | 51 | TGCAGGACCAGAGAATTCGAATA CAACTACAATNNNACGTATGCCA | 291 | TGCAGGACCAGAGAATTCGAATA CAAGCATAGGNNNACGTATGCCA | 531 |
| TGCAGGACCAGAGAATTCGAATA CACGTCGGACNNNACGTATGCCA | 52 | TGCAGGACCAGAGAATTCGAATA CACTCCTCAANNNACGTATGCCA | 292 | TGCAGGACCAGAGAATTCGAATA CACTGCATCTNNNACGTATGCCA | 532 |
| TGCAGGACCAGAGAATTCGAATA CAGCAACTTGNNNACGTATGCCA | 53 | TGCAGGACCAGAGAATTCGAATA CAGATACAAANNNACGTATGCCA | 293 | TGCAGGACCAGAGAATTCGAATA CACGACGCCANNNACGTATGCCA | 533 |
| TGCAGGACCAGAGAATTCGAATA CACGGTGGAGNNNACGTATGCCA | 54 | TGCAGGACCAGAGAATTCGAATA CACCAACACANNNACGTATGCCA | 294 | TGCAGGACCAGAGAATTCGAATA CAAACGCCCGNNNACGTATGCCA | 534 |
| TGCAGGACCAGAGAATTCGAATA CAGTAACCGTNNNACGTATGCCA | 55 | TGCAGGACCAGAGAATTCGAATA CAACCCATTCNNNACGTATGCCA | 295 | TGCAGGACCAGAGAATTCGAATA CACTCTCGATNNNACGTATGCCA | 535 |
| TGCAGGACCAGAGAATTCGAATA CATAGTTTTCNNNACGTATGCCA | 56 | TGCAGGACCAGAGAATTCGAATA CATCTAAGCGNNNACGTATGCCA | 296 | TGCAGGACCAGAGAATTCGAATA CACCCTCACCNNNACGTATGCCA | 536 |
| TGCAGGACCAGAGAATTCGAATA CACTGTCGTTNNNACGTATGCCA | 57 | TGCAGGACCAGAGAATTCGAATA CACTTAAGGCNNNACGTATGCCA | 297 | TGCAGGACCAGAGAATTCGAATA CAGTTGTAATNNNACGTATGCCA | 537 |
| TGCAGGACCAGAGAATTCGAATA CATTCGAGGTNNNACGTATGCCA | 58 | TGCAGGACCAGAGAATTCGAATA CACGAATCCANNNACGTATGCCA | 298 | TGCAGGACCAGAGAATTCGAATA CAAAAAGACTNNNACGTATGCCA | 538 |
| TGCAGGACCAGAGAATTCGAATA CACCTCCACGNNNACGTATGCCA | 59 | TGCAGGACCAGAGAATTCGAATA CACAACTAATNNNACGTATGCCA | 299 | TGCAGGACCAGAGAATTCGAATA CATCCTAGCTNNNACGTATGCCA | 539 |
| TGCAGGACCAGAGAATTCGAATA CAGAGACTAGNNNACGTATGCCA | 60 | TGCAGGACCAGAGAATTCGAATA CATCACACCTNNNACGTATGCCA | 300 | TGCAGGACCAGAGAATTCGAATA CAACCAAAGGNNNACGTATGCCA | 540 |
| TGCAGGACCAGAGAATTCGAATA CATGAACTATNNNACGTATGCCA | 61 | TGCAGGACCAGAGAATTCGAATA CAGACCGTCGNNNACGTATGCCA | 301 | TGCAGGACCAGAGAATTCGAATA CAACGAGTTCNNNACGTATGCCA | 541 |
| TGCAGGACCAGAGAATTCGAATA CAGTTGATTANNNACGTATGCCA | 62 | TGCAGGACCAGAGAATTCGAATA CACTTTAAGANNNACGTATGCCA | 302 | TGCAGGACCAGAGAATTCGAATA CACTATGGTGNNNACGTATGCCA | 542 |
| TGCAGGACCAGAGAATTCGAATA CATCCACTCANNNACGTATGCCA | 63 | TGCAGGACCAGAGAATTCGAATA CATGTGATTANNNACGTATGCCA | 303 | TGCAGGACCAGAGAATTCGAATA CACCACCGTCNNNACGTATGCCA | 543 |
| TGCAGGACCAGAGAATTCGAATA CAGTGACTGTNNNACGTATGCCA | 64 | TGCAGGACCAGAGAATTCGAATA CAACCCAATGNNNACGTATGCCA | 304 | TGCAGGACCAGAGAATTCGAATA CAGAATCGCTNNNACGTATGCCA | 544 |
| TGCAGGACCAGAGAATTCGAATA CATTACGGCANNNACGTATGCCA | 65 | TGCAGGACCAGAGAATTCGAATA CAACGTGTACNNNACGTATGCCA | 305 | TGCAGGACCAGAGAATTCGAATA CAAGTGTTATNNNACGTATGCCA | 545 |
| TGCAGGACCAGAGAATTCGAATA CACACCTCCGNNNACGTATGCCA | 66 | TGCAGGACCAGAGAATTCGAATA CAATGAAATGNNNACGTATGCCA | 306 | TGCAGGACCAGAGAATTCGAATA CAACGCGTCGNNNACGTATGCCA | 546 |
| TGCAGGACCAGAGAATTCGAATA CAAAGAAGAANNNACGTATGCCA | 67 | TGCAGGACCAGAGAATTCGAATA CATCCTCGTANNNACGTATGCCA | 307 | TGCAGGACCAGAGAATTCGAATA CACTCGTGTTNNNACGTATGCCA | 547 |
| TGCAGGACCAGAGAATTCGAATA CAGAACCTGTNNNACGTATGCCA | 68 | TGCAGGACCAGAGAATTCGAATA CAGTAACAGGNNNACGTATGCCA | 308 | TGCAGGACCAGAGAATTCGAATA CATTGTAGATNNNACGTATGCCA | 548 |
| TGCAGGACCAGAGAATTCGAATA CAGAATAACANNNCTAGCGTTAC | 69 | TGCAGGACCAGAGAATTCGAATA CAACTCGGTANNNCTAGCGTTAC | 309 | TGCAGGACCAGAGAATTCGAATA CAGCCGCAGTNNNCTAGCGTTAC | 549 |
| TGCAGGACCAGAGAATTCGAATA CAGCCTCGTCNNNCTAGCGTTAC | 70 | TGCAGGACCAGAGAATTCGAATA CAACGCTTAGNNNCTAGCGTTAC | 310 | TGCAGGACCAGAGAATTCGAATA CAAGTGACGANNNCTAGCGTTAC | 550 |
| TGCAGGACCAGAGAATTCGAATA CACCCGCACTNNNCTAGCGTTAC | 71 | TGCAGGACCAGAGAATTCGAATA CATCAAGCTGNNNCTAGCGTTAC | 311 | TGCAGGACCAGAGAATTCGAATA CAATACCTCCNNNCTAGCGTTAC | 551 |
| TGCAGGACCAGAGAATTCGAATA CACCACGATANNNCTAGCGTTAC | 72 | TGCAGGACCAGAGAATTCGAATA CATAGCTAATNNNCTAGCGTTAC | 312 | TGCAGGACCAGAGAATTCGAATA CACTTTTTGANNNCTAGCGTTAC | 552 |
| TGCAGGACCAGAGAATTCGAATA CACGGTACATNNNCTAGCGTTAC | 73 | TGCAGGACCAGAGAATTCGAATA CACGGCATTANNNCTAGCGTTAC | 313 | TGCAGGACCAGAGAATTCGAATA CAATATCATGNNNCTAGCGTTAC | 553 |
| TGCAGGACCAGAGAATTCGAATA CACCATATCCNNNCTAGCGTTAC | 74 | TGCAGGACCAGAGAATTCGAATA CAAATGATGANNNCTAGCGTTAC | 314 | TGCAGGACCAGAGAATTCGAATA CATACATATGNNNCTAGCGTTAC | 554 |

FIG. 12C

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CACATACGGTNNNCTAGCGTTAC | 75 | TGCAGGACCAGAGAATTCGAATA CATCGCGATANNNCTAGCGTTAC | 315 | TGCAGGACCAGAGAATTCGAATA CAACTTTTGTNNNCTAGCGTTAC | 555 |
| TGCAGGACCAGAGAATTCGAATA CAAATAGCTTNNNCTAGCGTTAC | 76 | TGCAGGACCAGAGAATTCGAATA CACACAGGTTNNNCTAGCGTTAC | 316 | TGCAGGACCAGAGAATTCGAATA CATAATGTACNNNCTAGCGTTAC | 556 |
| TGCAGGACCAGAGAATTCGAATA CACCAGGTATNNNCTAGCGTTAC | 77 | TGCAGGACCAGAGAATTCGAATA CAACGGTGCCNNNCTAGCGTTAC | 317 | TGCAGGACCAGAGAATTCGAATA CAAACGACAGNNNCTAGCGTTAC | 557 |
| TGCAGGACCAGAGAATTCGAATA CACAACCTGANNNCTAGCGTTAC | 78 | TGCAGGACCAGAGAATTCGAATA CAGTTACAGCNNNCTAGCGTTAC | 318 | TGCAGGACCAGAGAATTCGAATA CAGCTCCTATNNNCTAGCGTTAC | 558 |
| TGCAGGACCAGAGAATTCGAATA CATGATGGTCNNNCTAGCGTTAC | 79 | TGCAGGACCAGAGAATTCGAATA CATGCGATGTNNNCTAGCGTTAC | 319 | TGCAGGACCAGAGAATTCGAATA CACCGAAACTNNNCTAGCGTTAC | 559 |
| TGCAGGACCAGAGAATTCGAATA CAGGAGCCGANNNCTAGCGTTAC | 80 | TGCAGGACCAGAGAATTCGAATA CAATGGTGCTNNNCTAGCGTTAC | 320 | TGCAGGACCAGAGAATTCGAATA CAGCTAGGAANNNCTAGCGTTAC | 560 |
| TGCAGGACCAGAGAATTCGAATA CAATGCGGCCNNNCTAGCGTTAC | 81 | TGCAGGACCAGAGAATTCGAATA CAACCCCAGGNNNCTAGCGTTAC | 321 | TGCAGGACCAGAGAATTCGAATA CAGCTTCCGCNNNCTAGCGTTAC | 561 |
| TGCAGGACCAGAGAATTCGAATA CATGCTGTAGNNNCTAGCGTTAC | 82 | TGCAGGACCAGAGAATTCGAATA CAGCAGACGGNNNCTAGCGTTAC | 322 | TGCAGGACCAGAGAATTCGAATA CAACAGCATCNNNCTAGCGTTAC | 562 |
| TGCAGGACCAGAGAATTCGAATA CAGCATTGACNNNCTAGCGTTAC | 83 | TGCAGGACCAGAGAATTCGAATA CACTGGCAGCNNNCTAGCGTTAC | 323 | TGCAGGACCAGAGAATTCGAATA CAACGAGAGTNNNCTAGCGTTAC | 563 |
| TGCAGGACCAGAGAATTCGAATA CATTTGTACTNNNCTAGCGTTAC | 84 | TGCAGGACCAGAGAATTCGAATA CAAGAGAGTCNNNCTAGCGTTAC | 324 | TGCAGGACCAGAGAATTCGAATA CAATCATATGNNNCTAGCGTTAC | 564 |
| TGCAGGACCAGAGAATTCGAATA CACATATGGCNNNCTAGCGTTAC | 85 | TGCAGGACCAGAGAATTCGAATA CACGTTTTATNNNCTAGCGTTAC | 325 | TGCAGGACCAGAGAATTCGAATA CATGAGATTNNNNCTAGCGTTAC | 565 |
| TGCAGGACCAGAGAATTCGAATA CAGCATGAAGNNNCTAGCGTTAC | 86 | TGCAGGACCAGAGAATTCGAATA CAAGAGGTCANNNCTAGCGTTAC | 326 | TGCAGGACCAGAGAATTCGAATA CAGCCGGCCGNNNCTAGCGTTAC | 566 |
| TGCAGGACCAGAGAATTCGAATA CACAGGAAACNNNCTAGCGTTAC | 87 | TGCAGGACCAGAGAATTCGAATA CATTCTCTCCNNNCTAGCGTTAC | 327 | TGCAGGACCAGAGAATTCGAATA CAAGGCGCAGNNNCTAGCGTTAC | 567 |
| TGCAGGACCAGAGAATTCGAATA CACCTAAGACNNNCTAGCGTTAC | 88 | TGCAGGACCAGAGAATTCGAATA CACGTGTCTTNNNCTAGCGTTAC | 328 | TGCAGGACCAGAGAATTCGAATA CAGTACACACNNNCTAGCGTTAC | 568 |
| TGCAGGACCAGAGAATTCGAATA CAACCTAGGTNNNCTAGCGTTAC | 89 | TGCAGGACCAGAGAATTCGAATA CACTCAGACATCNNNCTAGCGTTAC | 329 | TGCAGGACCAGAGAATTCGAATA CAAGATTTCANNNCTAGCGTTAC | 569 |
| TGCAGGACCAGAGAATTCGAATA CACCCATTGTCNNNCTAGCGTTAC | 90 | TGCAGGACCAGAGAATTCGAATA CATCTTATGTNNNCTAGCGTTAC | 330 | TGCAGGACCAGAGAATTCGAATA CATGCATCTCNNNCTAGCGTTAC | 570 |
| TGCAGGACCAGAGAATTCGAATA CATCGGTTTCNNNCTAGCGTTAC | 91 | TGCAGGACCAGAGAATTCGAATA CATCGGCACGNNNCTAGCGTTAC | 331 | TGCAGGACCAGAGAATTCGAATA CACTCAGAGTNNNCTAGCGTTAC | 571 |
| TGCAGGACCAGAGAATTCGAATA CACACCTGTTNNNCTAGCGTTAC | 92 | TGCAGGACCAGAGAATTCGAATA CACGTTTCTGNNNCTAGCGTTAC | 332 | TGCAGGACCAGAGAATTCGAATA CAACTCTGTCNNNCTAGCGTTAC | 572 |
| TGCAGGACCAGAGAATTCGAATA CAAGAGAGAGNNNCTAGCGTTAC | 93 | TGCAGGACCAGAGAATTCGAATA CAATGTGAGGNNNCTAGCGTTAC | 333 | TGCAGGACCAGAGAATTCGAATA CATTATCCGCNNNCTAGCGTTAC | 573 |
| TGCAGGACCAGAGAATTCGAATA CAATGGCCGCNNNCTAGCGTTAC | 94 | TGCAGGACCAGAGAATTCGAATA CAAGAAACATNNNCTAGCGTTAC | 334 | TGCAGGACCAGAGAATTCGAATA CAGCCCTTGCNNNCTAGCGTTAC | 574 |
| TGCAGGACCAGAGAATTCGAATA CATAGCGTGTNNNCTAGCGTTAC | 95 | TGCAGGACCAGAGAATTCGAATA CAGAGAGAAGNNNCTAGCGTTAC | 335 | TGCAGGACCAGAGAATTCGAATA CAAACTTCTTNNNCTAGCGTTAC | 575 |
| TGCAGGACCAGAGAATTCGAATA CAGAAGACACNNNCTAGCGTTAC | 96 | TGCAGGACCAGAGAATTCGAATA CACTTCAGGANNNCTAGCGTTAC | 336 | TGCAGGACCAGAGAATTCGAATA CATTGTAGGCNNNCTAGCGTTAC | 576 |
| TGCAGGACCAGAGAATTCGAATA CATCATTTGTNNNCTAGCGTTAC | 97 | TGCAGGACCAGAGAATTCGAATA CATCCCTCGGNNNCTAGCGTTAC | 337 | TGCAGGACCAGAGAATTCGAATA CATGACCCAANNNCTAGCGTTAC | 577 |
| TGCAGGACCAGAGAATTCGAATA CATCGAACACNNNCTAGCGTTAC | 98 | TGCAGGACCAGAGAATTCGAATA CACCTTCCTTNNNCTAGCGTTAC | 338 | TGCAGGACCAGAGAATTCGAATA CACCTCTGTANNNCTAGCGTTAC | 578 |
| TGCAGGACCAGAGAATTCGAATA CAAGCTTACGNNNCTAGCGTTAC | 99 | TGCAGGACCAGAGAATTCGAATA CATAGTTATGNNNCTAGCGTTAC | 339 | TGCAGGACCAGAGAATTCGAATA CAAGCCACTANNNCTAGCGTTAC | 579 |
| TGCAGGACCAGAGAATTCGAATA CACTCGGTTTNNNCTAGCGTTAC | 100 | TGCAGGACCAGAGAATTCGAATA CAGCATAGAGNNNCTAGCGTTAC | 340 | TGCAGGACCAGAGAATTCGAATA CATGTATGATNNNCTAGCGTTAC | 580 |
| TGCAGGACCAGAGAATTCGAATA CAAATCGTTANNNCTAGCGTTAC | 101 | TGCAGGACCAGAGAATTCGAATA CATAGCTCCTNNNCTAGCGTTAC | 341 | TGCAGGACCAGAGAATTCGAATA CACAGGTCGCNNNCTAGCGTTAC | 581 |
| TGCAGGACCAGAGAATTCGAATA CATAACAGTTNNNCTAGCGTTAC | 102 | TGCAGGACCAGAGAATTCGAATA CAACCACGTANNNCTAGCGTTAC | 342 | TGCAGGACCAGAGAATTCGAATA CATTTTTTTTNNNCTAGCGTTAC | 582 |
| TGCAGGACCAGAGAATTCGAATA CAATCCTGTCNNNCTAGCGTTAC | 103 | TGCAGGACCAGAGAATTCGAATA CACATCGTCTNNNCTAGCGTTAC | 343 | TGCAGGACCAGAGAATTCGAATA CATTTGCGGANNNCTAGCGTTAC | 583 |
| TGCAGGACCAGAGAATTCGAATA CAGTAATGTTNNNCTAGCGTTAC | 104 | TGCAGGACCAGAGAATTCGAATA CAAGAGATTANNNCTAGCGTTAC | 344 | TGCAGGACCAGAGAATTCGAATA CAAGCCTGTANNNCTAGCGTTAC | 584 |
| TGCAGGACCAGAGAATTCGAATA CATTGCGCGGNNNCTAGCGTTAC | 105 | TGCAGGACCAGAGAATTCGAATA CAATCAAAGANNNCTAGCGTTAC | 345 | TGCAGGACCAGAGAATTCGAATA CAGCCGGCACTNNNCTAGCGTTAC | 585 |
| TGCAGGACCAGAGAATTCGAATA CAGTCAGGAANNNCTAGCGTTAC | 106 | TGCAGGACCAGAGAATTCGAATA CAGGAGTACANNNCTAGCGTTAC | 346 | TGCAGGACCAGAGAATTCGAATA CATGTTGAGCNNNCTAGCGTTAC | 586 |
| TGCAGGACCAGAGAATTCGAATA CAGTTAAAAGNNNCTAGCGTTAC | 107 | TGCAGGACCAGAGAATTCGAATA CAATAGCAGGNNNCTAGCGTTAC | 347 | TGCAGGACCAGAGAATTCGAATA CAAAAAGTTGNNNCTAGCGTTAC | 587 |

FIG. 12D

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CATGTCATAANNNCTAGCGTTAC | 108 | TGCAGGACCAGAGAATTCGAATA CATCTAATTCNNNCTAGCGTTAC | 348 | TGCAGGACCAGAGAATTCGAATA CACGGTGCCANNNCTAGCGTTAC | 588 |
| TGCAGGACCAGAGAATTCGAATA CAACTTGAATNNNCTAGCGTTAC | 109 | TGCAGGACCAGAGAATTCGAATA CAGTTCCCGCNNNCTAGCGTTAC | 349 | TGCAGGACCAGAGAATTCGAATA CACAGCGGTCNNNCTAGCGTTAC | 589 |
| TGCAGGACCAGAGAATTCGAATA CATGTGGCATNNNCTAGCGTTAC | 110 | TGCAGGACCAGAGAATTCGAATA CATAGATTTGNNNCTAGCGTTAC | 350 | TGCAGGACCAGAGAATTCGAATA CAAGCTAACCNNNCTAGCGTTAC | 590 |
| TGCAGGACCAGAGAATTCGAATA CATCTACACCNNNCTAGCGTTAC | 111 | TGCAGGACCAGAGAATTCGAATA CACGGCAGAGNNNCTAGCGTTAC | 351 | TGCAGGACCAGAGAATTCGAATA CAACGGCGTCNNNCTAGCGTTAC | 591 |
| TGCAGGACCAGAGAATTCGAATA CATCATGCCTNNNCTAGCGTTAC | 112 | TGCAGGACCAGAGAATTCGAATA CACCTCGTGCNNNCTAGCGTTAC | 352 | TGCAGGACCAGAGAATTCGAATA CATAGTTCAANNNCTAGCGTTAC | 592 |
| TGCAGGACCAGAGAATTCGAATA CATCTAGCCTNNNCTAGCGTTAC | 113 | TGCAGGACCAGAGAATTCGAATA CACCCTTGATNNNCTAGCGTTAC | 353 | TGCAGGACCAGAGAATTCGAATA CAATGTAGCCNNNCTAGCGTTAC | 593 |
| TGCAGGACCAGAGAATTCGAATA CAATAAAGCANNNCTAGCGTTAC | 114 | TGCAGGACCAGAGAATTCGAATA CACGTCACGGNNNCTAGCGTTAC | 354 | TGCAGGACCAGAGAATTCGAATA CAAGAAGCACNNNCTAGCGTTAC | 594 |
| TGCAGGACCAGAGAATTCGAATA CATGCATAATNNNCTAGCGTTAC | 115 | TGCAGGACCAGAGAATTCGAATA CAGTTTGGCANNNCTAGCGTTAC | 355 | TGCAGGACCAGAGAATTCGAATA CAGAAGCGCGNNNCTAGCGTTAC | 595 |
| TGCAGGACCAGAGAATTCGAATA CACATGACGTNNNCTAGCGTTAC | 116 | TGCAGGACCAGAGAATTCGAATA CATGCTCTGTNNNCTAGCGTTAC | 356 | TGCAGGACCAGAGAATTCGAATA CACGGGTATACNNNCTAGCGTTAC | 596 |
| TGCAGGACCAGAGAATTCGAATA CACTTATCATNNNCTAGCGTTAC | 117 | TGCAGGACCAGAGAATTCGAATA CATCAGTATANNNCTAGCGTTAC | 357 | TGCAGGACCAGAGAATTCGAATA CATAACATACNNNCTAGCGTTAC | 597 |
| TGCAGGACCAGAGAATTCGAATA CACGGCCTGANNNCTAGCGTTAC | 118 | TGCAGGACCAGAGAATTCGAATA CACCCAAGTANNNCTAGCGTTAC | 358 | TGCAGGACCAGAGAATTCGAATA CACTGCTATCNNNCTAGCGTTAC | 598 |
| TGCAGGACCAGAGAATTCGAATA CACGTCAATGNNNCTAGCGTTAC | 119 | TGCAGGACCAGAGAATTCGAATA CAAAGCTAAANNNCTAGCGTTAC | 359 | TGCAGGACCAGAGAATTCGAATA CACGGCAACCNNNCTAGCGTTAC | 599 |
| TGCAGGACCAGAGAATTCGAATA CACTTATACTNNNCTAGCGTTAC | 120 | TGCAGGACCAGAGAATTCGAATA CAAGATCCACNNNCTAGCGTTAC | 360 | TGCAGGACCAGAGAATTCGAATA CACAAAAACANNNCTAGCGTTAC | 600 |
| TGCAGGACCAGAGAATTCGAATA CAGGAGGTATNNNCTAGCGTTAC | 121 | TGCAGGACCAGAGAATTCGAATA CAGCATCGGCNNNCTAGCGTTAC | 361 | TGCAGGACCAGAGAATTCGAATA CACGTTAGCANNNCTAGCGTTAC | 601 |
| TGCAGGACCAGAGAATTCGAATA CAATTGTTCTNNNCTAGCGTTAC | 122 | TGCAGGACCAGAGAATTCGAATA CACTCTGGAANNNCTAGCGTTAC | 362 | TGCAGGACCAGAGAATTCGAATA CACCCTAATCNNNCTAGCGTTAC | 602 |
| TGCAGGACCAGAGAATTCGAATA CAAACTCCAGNNNCTAGCGTTAC | 123 | TGCAGGACCAGAGAATTCGAATA CAAGTCTGACNNNCTAGCGTTAC | 363 | TGCAGGACCAGAGAATTCGAATA CATGTGGCCGNNNCTAGCGTTAC | 603 |
| TGCAGGACCAGAGAATTCGAATA CACGAGGTCCNNNCTAGCGTTAC | 124 | TGCAGGACCAGAGAATTCGAATA CAGAGGCCGANNNCTAGCGTTAC | 364 | TGCAGGACCAGAGAATTCGAATA CATCTAGAGCNNNCTAGCGTTAC | 604 |
| TGCAGGACCAGAGAATTCGAATA CACGCGACCANNNCTAGCGTTAC | 125 | TGCAGGACCAGAGAATTCGAATA CATGGTGGAANNNCTAGCGTTAC | 365 | TGCAGGACCAGAGAATTCGAATA CATACGCATGNNNCTAGCGTTAC | 605 |
| TGCAGGACCAGAGAATTCGAATA CATGCCGCCTNNNCTAGCGTTAC | 126 | TGCAGGACCAGAGAATTCGAATA CACGGGTGTTANNNCTAGCGTTAC | 366 | TGCAGGACCAGAGAATTCGAATA CATTGCCCCGNNNCTAGCGTTAC | 606 |
| TGCAGGACCAGAGAATTCGAATA CAGTTACGACNNNCTAGCGTTAC | 127 | TGCAGGACCAGAGAATTCGAATA CATCGCGCAGNNNCTAGCGTTAC | 367 | TGCAGGACCAGAGAATTCGAATA CATGGTTCCTNNNCTAGCGTTAC | 607 |
| TGCAGGACCAGAGAATTCGAATA CATTATCATCNNNCTAGCGTTAC | 128 | TGCAGGACCAGAGAATTCGAATA CAGCTGTGTANNNCTAGCGTTAC | 368 | TGCAGGACCAGAGAATTCGAATA CAAACGGTGANNNCTAGCGTTAC | 608 |
| TGCAGGACCAGAGAATTCGAATA CACCTTCTCTNNNGATCGACATG | 129 | TGCAGGACCAGAGAATTCGAATA CAACGTGCGCNNNGATCGACATG | 369 | TGCAGGACCAGAGAATTCGAATA CAGGCTATACNNNGATCGACATG | 609 |
| TGCAGGACCAGAGAATTCGAATA CAAACAGGTGNNNGATCGACATG | 130 | TGCAGGACCAGAGAATTCGAATA CAATCACCANNNNGATCGACATG | 370 | TGCAGGACCAGAGAATTCGAATA CAATTGGTTANNNGATCGACATG | 610 |
| TGCAGGACCAGAGAATTCGAATA CAACTTGTCCNNNGATCGACATG | 131 | TGCAGGACCAGAGAATTCGAATA CAGATACTTANNNGATCGACATG | 371 | TGCAGGACCAGAGAATTCGAATA CACAGGATGANNNGATCGACATG | 611 |
| TGCAGGACCAGAGAATTCGAATA CATTGGTAATNNNGATCGACATG | 132 | TGCAGGACCAGAGAATTCGAATA CAATTCGCCNNNNGATCGACATG | 372 | TGCAGGACCAGAGAATTCGAATA CACGTTATCCNNNGATCGACATG | 612 |
| TGCAGGACCAGAGAATTCGAATA CAGGACTCGCNNNGATCGACATG | 133 | TGCAGGACCAGAGAATTCGAATA CACTTAAAGTNNNGATCGACATG | 373 | TGCAGGACCAGAGAATTCGAATA CAGTTCAATANNNGATCGACATG | 613 |
| TGCAGGACCAGAGAATTCGAATA CATGCGTCAANNNGATCGACATG | 134 | TGCAGGACCAGAGAATTCGAATA CATATGCCCTNNNGATCGACATG | 374 | TGCAGGACCAGAGAATTCGAATA CACAAAATCTNNNGATCGACATG | 614 |
| TGCAGGACCAGAGAATTCGAATA CACAGAATAANNNGATCGACATG | 135 | TGCAGGACCAGAGAATTCGAATA CAACTTGACGNNNGATCGACATG | 375 | TGCAGGACCAGAGAATTCGAATA CACTGCAAACNNNGATCGACATG | 615 |
| TGCAGGACCAGAGAATTCGAATA CATCCCAGGCNNNGATCGACATG | 136 | TGCAGGACCAGAGAATTCGAATA CAAGGAACCANNNGATCGACATG | 376 | TGCAGGACCAGAGAATTCGAATA CAGGTGCCCANNNGATCGACATG | 616 |
| TGCAGGACCAGAGAATTCGAATA CAATTTCTTGNNNGATCGACATG | 137 | TGCAGGACCAGAGAATTCGAATA CATGAGCGAANNNGATCGACATG | 377 | TGCAGGACCAGAGAATTCGAATA CACGATAACCNNNGATCGACATG | 617 |
| TGCAGGACCAGAGAATTCGAATA CAACTTGTAANNNGATCGACATG | 138 | TGCAGGACCAGAGAATTCGAATA CATGCTGTGANNNGATCGACATG | 378 | TGCAGGACCAGAGAATTCGAATA CATTATGACANNNGATCGACATG | 618 |
| TGCAGGACCAGAGAATTCGAATA CACACGGTGCNNNGATCGACATG | 139 | TGCAGGACCAGAGAATTCGAATA CAGGTTCGTANNNGATCGACATG | 379 | TGCAGGACCAGAGAATTCGAATA CAACCTTCACNNNGATCGACATG | 619 |
| TGCAGGACCAGAGAATTCGAATA CAAACTCGGTNNNGATCGACATG | 140 | TGCAGGACCAGAGAATTCGAATA CAACAAACAANNNGATCGACATG | 380 | TGCAGGACCAGAGAATTCGAATA CATCTTCTCCNNNGATCGACATG | 620 |

FIG. 12E

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CAGCCTATTCNNNGATCGACATG | 141 | TGCAGGACCAGAGAATTCGAATA CAAGCTAGAGAGNNNGATCGACATG | 381 | TGCAGGACCAGAGAATTCGAATA CACCCCAGCTNNNGATCGACATG | 621 |
| TGCAGGACCAGAGAATTCGAATA CACCGCTAAANNNGATCGACATG | 142 | TGCAGGACCAGAGAATTCGAATA CATTAAATATNNNGATCGACATG | 382 | TGCAGGACCAGAGAATTCGAATA CACTAGTGTGNNNGATCGACATG | 622 |
| TGCAGGACCAGAGAATTCGAATA CAGTGAGATGNNNGATCGACATG | 143 | TGCAGGACCAGAGAATTCGAATA CAAGGAGTCANNNGATCGACATG | 383 | TGCAGGACCAGAGAATTCGAATA CAGTTCTAAANNNGATCGACATG | 623 |
| TGCAGGACCAGAGAATTCGAATA CATCTCTCAGNNNGATCGACATG | 144 | TGCAGGACCAGAGAATTCGAATA CACGCACAGCNNNGATCGACATG | 384 | TGCAGGACCAGAGAATTCGAATA CAGCGTTTTCNNNGATCGACATG | 624 |
| TGCAGGACCAGAGAATTCGAATA CATCTCTAGCNNNGATCGACATG | 145 | TGCAGGACCAGAGAATTCGAATA CAGCCGACAGNNNGATCGACATG | 385 | TGCAGGACCAGAGAATTCGAATA CAGTCTGCCCNNNGATCGACATG | 625 |
| TGCAGGACCAGAGAATTCGAATA CACAAGCGCCNNNGATCGACATG | 146 | TGCAGGACCAGAGAATTCGAATA CACGCTCGTCNNNGATCGACATG | 386 | TGCAGGACCAGAGAATTCGAATA CAACAGAAATNNNGATCGACATG | 626 |
| TGCAGGACCAGAGAATTCGAATA CAGGCAGTAANNNGATCGACATG | 147 | TGCAGGACCAGAGAATTCGAATA CATCTGATGGNNNGATCGACATG | 387 | TGCAGGACCAGAGAATTCGAATA CATTGCTATTNNNGATCGACATG | 627 |
| TGCAGGACCAGAGAATTCGAATA CATTGGCTGANNNGATCGACATG | 148 | TGCAGGACCAGAGAATTCGAATA CAGGCTAGAANNNGATCGACATG | 388 | TGCAGGACCAGAGAATTCGAATA CACCCTGTGCNNNGATCGACATG | 628 |
| TGCAGGACCAGAGAATTCGAATA CAACAGCGAANNNGATCGACATG | 149 | TGCAGGACCAGAGAATTCGAATA CAATGAGGCANNNGATCGACATG | 389 | TGCAGGACCAGAGAATTCGAATA CAGCAGTCCGNNNGATCGACATG | 629 |
| TGCAGGACCAGAGAATTCGAATA CAAAGTTTCANNNGATCGACATG | 150 | TGCAGGACCAGAGAATTCGAATA CACACCCGTCNNNGATCGACATG | 390 | TGCAGGACCAGAGAATTCGAATA CAGTAACCCANNNGATCGACATG | 630 |
| TGCAGGACCAGAGAATTCGAATA CACGCTCTATNNNGATCGACATG | 151 | TGCAGGACCAGAGAATTCGAATA CATCATCGGANNNGATCGACATG | 391 | TGCAGGACCAGAGAATTCGAATA CAACATTGTANNNGATCGACATG | 631 |
| TGCAGGACCAGAGAATTCGAATA CATAGGAGTGNNNGATCGACATG | 152 | TGCAGGACCAGAGAATTCGAATA CAGGCAAGCGNNNGATCGACATG | 392 | TGCAGGACCAGAGAATTCGAATA CAAAACCGTCNNNGATCGACATG | 632 |
| TGCAGGACCAGAGAATTCGAATA CATCAGCACANNNGATCGACATG | 153 | TGCAGGACCAGAGAATTCGAATA CACAGTCGATNNNGATCGACATG | 393 | TGCAGGACCAGAGAATTCGAATA CAATTCTGCCNNNGATCGACATG | 633 |
| TGCAGGACCAGAGAATTCGAATA CACGAACTACNNNGATCGACATG | 154 | TGCAGGACCAGAGAATTCGAATA CATGCTACTCNNNGATCGACATG | 394 | TGCAGGACCAGAGAATTCGAATA CATCTAGGCANNNGATCGACATG | 634 |
| TGCAGGACCAGAGAATTCGAATA CATACTAAACNNNGATCGACATG | 155 | TGCAGGACCAGAGAATTCGAATA CATCCTACACNNNGATCGACATG | 395 | TGCAGGACCAGAGAATTCGAATA CAGGTCTACANNNGATCGACATG | 635 |
| TGCAGGACCAGAGAATTCGAATA CAGGTACAAGNNNGATCGACATG | 156 | TGCAGGACCAGAGAATTCGAATA CAACCGCGACNNNGATCGACATG | 396 | TGCAGGACCAGAGAATTCGAATA CAGGTGAGCGNNNGATCGACATG | 636 |
| TGCAGGACCAGAGAATTCGAATA CAACAGGCTTNNNGATCGACATG | 157 | TGCAGGACCAGAGAATTCGAATA CAGGCAAAGTNNNGATCGACATG | 397 | TGCAGGACCAGAGAATTCGAATA CATGTCTTTANNNGATCGACATG | 637 |
| TGCAGGACCAGAGAATTCGAATA CAGAAACCCTNNNGATCGACATG | 158 | TGCAGGACCAGAGAATTCGAATA CAGGATCCCGNNNGATCGACATG | 398 | TGCAGGACCAGAGAATTCGAATA CATGGCTTGANNNGATCGACATG | 638 |
| TGCAGGACCAGAGAATTCGAATA CATCCGCATTNNNGATCGACATG | 159 | TGCAGGACCAGAGAATTCGAATA CACCTCTCTTNNNGATCGACATG | 399 | TGCAGGACCAGAGAATTCGAATA CAATTACGCGNNNGATCGACATG | 639 |
| TGCAGGACCAGAGAATTCGAATA CACAATCTGGNNNGATCGACATG | 160 | TGCAGGACCAGAGAATTCGAATA CATCGTCCACNNNGATCGACATG | 400 | TGCAGGACCAGAGAATTCGAATA CATGGCTCTTNNNGATCGACATG | 640 |
| TGCAGGACCAGAGAATTCGAATA CAACCTTACCNNNGATCGACATG | 161 | TGCAGGACCAGAGAATTCGAATA CACCTATGTCNNNGATCGACATG | 401 | TGCAGGACCAGAGAATTCGAATA CACACTCACTNNNGATCGACATG | 641 |
| TGCAGGACCAGAGAATTCGAATA CAGCGGTCTGNNNGATCGACATG | 162 | TGCAGGACCAGAGAATTCGAATA CAGGATGCTTNNNGATCGACATG | 402 | TGCAGGACCAGAGAATTCGAATA CACTGCAGGCNNNGATCGACATG | 642 |
| TGCAGGACCAGAGAATTCGAATA CAAATCACGCNNNGATCGACATG | 163 | TGCAGGACCAGAGAATTCGAATA CAATTGAGAANNNGATCGACATG | 403 | TGCAGGACCAGAGAATTCGAATA CACCCAATCTNNNGATCGACATG | 643 |
| TGCAGGACCAGAGAATTCGAATA CAAATAGTAGNNNGATCGACATG | 164 | TGCAGGACCAGAGAATTCGAATA CAGTGTTGTGNNNGATCGACATG | 404 | TGCAGGACCAGAGAATTCGAATA CAACGTAACCNNNGATCGACATG | 644 |
| TGCAGGACCAGAGAATTCGAATA CAGGCATCTANNNGATCGACATG | 165 | TGCAGGACCAGAGAATTCGAATA CAAAGCAATANNNGATCGACATG | 405 | TGCAGGACCAGAGAATTCGAATA CAACCGTCCCNNNGATCGACATG | 645 |
| TGCAGGACCAGAGAATTCGAATA CAACCGCCTGNNNGATCGACATG | 166 | TGCAGGACCAGAGAATTCGAATA CATTAGCGCANNNGATCGACATG | 406 | TGCAGGACCAGAGAATTCGAATA CATTCGCGAANNNGATCGACATG | 646 |
| TGCAGGACCAGAGAATTCGAATA CAGACCCGGTNNNGATCGACATG | 167 | TGCAGGACCAGAGAATTCGAATA CAAACGGATGNNNGATCGACATG | 407 | TGCAGGACCAGAGAATTCGAATA CACGCACAATNNNGATCGACATG | 647 |
| TGCAGGACCAGAGAATTCGAATA CACGGTAAAGNNNGATCGACATG | 168 | TGCAGGACCAGAGAATTCGAATA CAGCATGGAANNNGATCGACATG | 408 | TGCAGGACCAGAGAATTCGAATA CACAATCTCCNNNGATCGACATG | 648 |
| TGCAGGACCAGAGAATTCGAATA CAAGGATGCANNNGATCGACATG | 169 | TGCAGGACCAGAGAATTCGAATA CATCTCATATNNNGATCGACATG | 409 | TGCAGGACCAGAGAATTCGAATA CATCAGAGTCNNNGATCGACATG | 649 |
| TGCAGGACCAGAGAATTCGAATA CATTCTGGAGNNNGATCGACATG | 170 | TGCAGGACCAGAGAATTCGAATA CACTGCGCCTNNNGATCGACATG | 410 | TGCAGGACCAGAGAATTCGAATA CAAATCGTGCNNNGATCGACATG | 650 |
| TGCAGGACCAGAGAATTCGAATA CAGCTCAAACNNNGATCGACATG | 171 | TGCAGGACCAGAGAATTCGAATA CAGATTCGCANNNGATCGACATG | 411 | TGCAGGACCAGAGAATTCGAATA CACTAGCATGNNNGATCGACATG | 651 |
| TGCAGGACCAGAGAATTCGAATA CATAAGTTACNNNGATCGACATG | 172 | TGCAGGACCAGAGAATTCGAATA CAATCTATCTNNNGATCGACATG | 412 | TGCAGGACCAGAGAATTCGAATA CAGATTAACTNNNGATCGACATG | 652 |
| TGCAGGACCAGAGAATTCGAATA CACAACCCTTNNNGATCGACATG | 173 | TGCAGGACCAGAGAATTCGAATA CAGTCACCCCNNNGATCGACATG | 413 | TGCAGGACCAGAGAATTCGAATA CAGGCTACGCNNNGATCGACATG | 653 |

FIG. 12F

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CACCTTCCGGNNNGATCGACATG | 174 | TGCAGGACCAGAGAATTCGAATA CACGTTGTGANNNGATCGACATG | 414 | TGCAGGACCAGAGAATTCGAATA CAATACGAGGNNNGATCGACATG | 654 |
| TGCAGGACCAGAGAATTCGAATA CAGTGAGAGTNNNGATCGACATG | 175 | TGCAGGACCAGAGAATTCGAATA CAGCTCTGCCNNNGATCGACATG | 415 | TGCAGGACCAGAGAATTCGAATA CAAAATGTCTNNNGATCGACATG | 655 |
| TGCAGGACCAGAGAATTCGAATA CAGCGTCCAGNNNGATCGACATG | 176 | TGCAGGACCAGAGAATTCGAATA CACATCGATGNNNGATCGACATG | 416 | TGCAGGACCAGAGAATTCGAATA CAGCGCATCGNNNGATCGACATG | 656 |
| TGCAGGACCAGAGAATTCGAATA CATTTATTCGNNNGATCGACATG | 177 | TGCAGGACCAGAGAATTCGAATA CAAGTCGCCGNNNGATCGACATG | 417 | TGCAGGACCAGAGAATTCGAATA CACTCCCGTGNNNGATCGACATG | 657 |
| TGCAGGACCAGAGAATTCGAATA CAGTAATAAGNNNGATCGACATG | 178 | TGCAGGACCAGAGAATTCGAATA CAGATAGCGANNNGATCGACATG | 418 | TGCAGGACCAGAGAATTCGAATA CAGATAAGGCNNNGATCGACATG | 658 |
| TGCAGGACCAGAGAATTCGAATA CATACAAGCCNNNGATCGACATG | 179 | TGCAGGACCAGAGAATTCGAATA CATCTTTGGCNNNGATCGACATG | 419 | TGCAGGACCAGAGAATTCGAATA CAGCACATCANNNGATCGACATG | 659 |
| TGCAGGACCAGAGAATTCGAATA CAAAGCCGAANNNGATCGACATG | 180 | TGCAGGACCAGAGAATTCGAATA CATCTCATCGNNNGATCGACATG | 420 | TGCAGGACCAGAGAATTCGAATA CATCCTATGCNNNGATCGACATG | 660 |
| TGCAGGACCAGAGAATTCGAATA CAATACTTTCNNNGATCGACATG | 181 | TGCAGGACCAGAGAATTCGAATA CATGAGCGCCNNNGATCGACATG | 421 | TGCAGGACCAGAGAATTCGAATA CACGCATCCCNNNGATCGACATG | 661 |
| TGCAGGACCAGAGAATTCGAATA CACTGGATCANNNGATCGACATG | 182 | TGCAGGACCAGAGAATTCGAATA CAAGTCTCGANNNGATCGACATG | 422 | TGCAGGACCAGAGAATTCGAATA CAACCGGTCGNNNGATCGACATG | 662 |
| TGCAGGACCAGAGAATTCGAATA CAAACGCCTANNNGATCGACATG | 183 | TGCAGGACCAGAGAATTCGAATA CAAAGGTATANNNGATCGACATG | 423 | TGCAGGACCAGAGAATTCGAATA CACACGATGTNNNGATCGACATG | 663 |
| TGCAGGACCAGAGAATTCGAATA CAGTCGAGAANNNGATCGACATG | 184 | TGCAGGACCAGAGAATTCGAATA CAGGTGTCGCNNNGATCGACATG | 424 | TGCAGGACCAGAGAATTCGAATA CAAACTCGCANNNGATCGACATG | 664 |
| TGCAGGACCAGAGAATTCGAATA CATAATTCTCNNNGATCGACATG | 185 | TGCAGGACCAGAGAATTCGAATA CATCACATCCNNNGATCGACATG | 425 | TGCAGGACCAGAGAATTCGAATA CACCCCTTCCNNNGATCGACATG | 665 |
| TGCAGGACCAGAGAATTCGAATA CATAACCCTCNNNGATCGACATG | 186 | TGCAGGACCAGAGAATTCGAATA CAGCATACACNNNGATCGACATG | 426 | TGCAGGACCAGAGAATTCGAATA CATCTTCGTGNNNGATCGACATG | 666 |
| TGCAGGACCAGAGAATTCGAATA CAGCGCTTGGNNNGATCGACATG | 187 | TGCAGGACCAGAGAATTCGAATA CATCCAACAGNNNGATCGACATG | 427 | TGCAGGACCAGAGAATTCGAATA CATATTTAAANNNGATCGACATG | 667 |
| TGCAGGACCAGAGAATTCGAATA CACGGACACCNNNGATCGACATG | 188 | TGCAGGACCAGAGAATTCGAATA CATCTGCCTANNNGATCGACATG | 428 | TGCAGGACCAGAGAATTCGAATA CATTAATGCANNNGATCGACATG | 668 |
| TGCAGGACCAGAGAATTCGAATA CATGGAAGTGNNNTGCATCAGGT | 189 | TGCAGGACCAGAGAATTCGAATA CACACACCGGNNNTGCATCAGGT | 429 | TGCAGGACCAGAGAATTCGAATA CACTTTGGTCNNNTGCATCAGGT | 669 |
| TGCAGGACCAGAGAATTCGAATA CAAAGTCTATNNNTGCATCAGGT | 190 | TGCAGGACCAGAGAATTCGAATA CAGACCTCCCNNNTGCATCAGGT | 430 | TGCAGGACCAGAGAATTCGAATA CATACGAAGGNNNTGCATCAGGT | 670 |
| TGCAGGACCAGAGAATTCGAATA CAATGAATAGNNNTGCATCAGGT | 191 | TGCAGGACCAGAGAATTCGAATA CATGCAATCANNNTGCATCAGGT | 431 | TGCAGGACCAGAGAATTCGAATA CAAGTCACTGNNNTGCATCAGGT | 671 |
| TGCAGGACCAGAGAATTCGAATA CATTCTCCTCNNNTGCATCAGGT | 192 | TGCAGGACCAGAGAATTCGAATA CATCTCCGGCNNNTGCATCAGGT | 432 | TGCAGGACCAGAGAATTCGAATA CAGTTTATCTNNNTGCATCAGGT | 672 |
| TGCAGGACCAGAGAATTCGAATA CACCAGCCCTNNNTGCATCAGGT | 193 | TGCAGGACCAGAGAATTCGAATA CACCAGCGTGNNNTGCATCAGGT | 433 | TGCAGGACCAGAGAATTCGAATA CATTTCGAAANNNTGCATCAGGT | 673 |
| TGCAGGACCAGAGAATTCGAATA CAAACAAAACNNNTGCATCAGGT | 194 | TGCAGGACCAGAGAATTCGAATA CAAAATATAANNNTGCATCAGGT | 434 | TGCAGGACCAGAGAATTCGAATA CACAGATCACNNNTGCATCAGGT | 674 |
| TGCAGGACCAGAGAATTCGAATA CACGGCTCACCNNNTGCATCAGGT | 195 | TGCAGGACCAGAGAATTCGAATA CAGCAATTTANNNTGCATCAGGT | 435 | TGCAGGACCAGAGAATTCGAATA CATTGGAAGGNNNTGCATCAGGT | 675 |
| TGCAGGACCAGAGAATTCGAATA CATGGTGATCNNNTGCATCAGGT | 196 | TGCAGGACCAGAGAATTCGAATA CAACTCAGTGNNNTGCATCAGGT | 436 | TGCAGGACCAGAGAATTCGAATA CAGTGCCGCTNNNTGCATCAGGT | 676 |
| TGCAGGACCAGAGAATTCGAATA CAGTTGCTAGNNNTGCATCAGGT | 197 | TGCAGGACCAGAGAATTCGAATA CAAGAGGCATNNNTGCATCAGGT | 437 | TGCAGGACCAGAGAATTCGAATA CATGAAGGCANNNTGCATCAGGT | 677 |
| TGCAGGACCAGAGAATTCGAATA CATCACCCTANNNTGCATCAGGT | 198 | TGCAGGACCAGAGAATTCGAATA CATAGGCTTGNNNTGCATCAGGT | 438 | TGCAGGACCAGAGAATTCGAATA CAAAAAGTACNNNTGCATCAGGT | 678 |
| TGCAGGACCAGAGAATTCGAATA CAGACTCTGANNNTGCATCAGGT | 199 | TGCAGGACCAGAGAATTCGAATA CACACACAGTNNNTGCATCAGGT | 439 | TGCAGGACCAGAGAATTCGAATA CAGATGGAACNNNTGCATCAGGT | 679 |
| TGCAGGACCAGAGAATTCGAATA CACGTATGACNNNTGCATCAGGT | 200 | TGCAGGACCAGAGAATTCGAATA CATGATAGAANNNTGCATCAGGT | 440 | TGCAGGACCAGAGAATTCGAATA CAGCCCTCGAGNNNTGCATCAGGT | 680 |
| TGCAGGACCAGAGAATTCGAATA CATGCACCGGNNNTGCATCAGGT | 201 | TGCAGGACCAGAGAATTCGAATA CAGACACGANNNTGCATCAGGT | 441 | TGCAGGACCAGAGAATTCGAATA CAAAATAAATNNNTGCATCAGGT | 681 |
| TGCAGGACCAGAGAATTCGAATA CAACTGATGCNNNTGCATCAGGT | 202 | TGCAGGACCAGAGAATTCGAATA CACTGCCTCGNNNTGCATCAGGT | 442 | TGCAGGACCAGAGAATTCGAATA CATTCCCCCCNNNTGCATCAGGT | 682 |
| TGCAGGACCAGAGAATTCGAATA CATACGTTCCNNNTGCATCAGGT | 203 | TGCAGGACCAGAGAATTCGAATA CAGTTTCCCANNNTGCATCAGGT | 443 | TGCAGGACCAGAGAATTCGAATA CATTCTTCTTNNNTGCATCAGGT | 683 |
| TGCAGGACCAGAGAATTCGAATA CACGGCCGCGNNNTGCATCAGGT | 204 | TGCAGGACCAGAGAATTCGAATA CATTCAATAGNNNTGCATCAGGT | 444 | TGCAGGACCAGAGAATTCGAATA CATTGTGGCANNNTGCATCAGGT | 684 |
| TGCAGGACCAGAGAATTCGAATA CAATCTTTGTNNNTGCATCAGGT | 205 | TGCAGGACCAGAGAATTCGAATA CATAGCCATGNNNTGCATCAGGT | 445 | TGCAGGACCAGAGAATTCGAATA CATCCCATGTNNNTGCATCAGGT | 685 |
| TGCAGGACCAGAGAATTCGAATA CATTGTACTTNNNTGCATCAGGT | 206 | TGCAGGACCAGAGAATTCGAATA CAGTTGTTAANNNTGCATCAGGT | 446 | TGCAGGACCAGAGAATTCGAATA CAGTGTTGACNNNTGCATCAGGT | 686 |

FIG. 12G

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CATGTTAATGNNNTGCATCAGGT | 207 | TGCAGGACCAGAGAATTCGAATA CACTTGCACTNNNTGCATCAGGT | 447 | TGCAGGACCAGAGAATTCGAATA CATCGCCTATNNNTGCATCAGGT | 687 |
| TGCAGGACCAGAGAATTCGAATA CAAACATTGTNNNTGCATCAGGT | 208 | TGCAGGACCAGAGAATTCGAATA CATTAGAGCCNNNTGCATCAGGT | 448 | TGCAGGACCAGAGAATTCGAATA CACGCTGACGNNNTGCATCAGGT | 688 |
| TGCAGGACCAGAGAATTCGAATA CACGCCCGAANNNTGCATCAGGT | 209 | TGCAGGACCAGAGAATTCGAATA CAGCCCCTACNNNTGCATCAGGT | 449 | TGCAGGACCAGAGAATTCGAATA CATGGTGGTTNNNTGCATCAGGT | 689 |
| TGCAGGACCAGAGAATTCGAATA CACAGCGCACNNNTGCATCAGGT | 210 | TGCAGGACCAGAGAATTCGAATA CAAATGGACGNNNTGCATCAGGT | 450 | TGCAGGACCAGAGAATTCGAATA CACTATCTTANNNTGCATCAGGT | 690 |
| TGCAGGACCAGAGAATTCGAATA CACGAGTATCNNNTGCATCAGGT | 211 | TGCAGGACCAGAGAATTCGAATA CAAGACCTGTNNNTGCATCAGGT | 451 | TGCAGGACCAGAGAATTCGAATA CAATAACCTANNNTGCATCAGGT | 691 |
| TGCAGGACCAGAGAATTCGAATA CAATGGTGGANNNTGCATCAGGT | 212 | TGCAGGACCAGAGAATTCGAATA CACTTACATTNNNTGCATCAGGT | 452 | TGCAGGACCAGAGAATTCGAATA CAAGAGTGTGNNNTGCATCAGGT | 692 |
| TGCAGGACCAGAGAATTCGAATA CATCACACTCNNNTGCATCAGGT | 213 | TGCAGGACCAGAGAATTCGAATA CATAAGAAACNNNTGCATCAGGT | 453 | TGCAGGACCAGAGAATTCGAATA CAAATGGCGANNNTGCATCAGGT | 693 |
| TGCAGGACCAGAGAATTCGAATA CAGAAACGACNNNTGCATCAGGT | 214 | TGCAGGACCAGAGAATTCGAATA CAGATTCTTTNNNTGCATCAGGT | 454 | TGCAGGACCAGAGAATTCGAATA CAGTCTCTTGNNNTGCATCAGGT | 694 |
| TGCAGGACCAGAGAATTCGAATA CAGAGTTTTANNNTGCATCAGGT | 215 | TGCAGGACCAGAGAATTCGAATA CATCTAGGTGNNNTGCATCAGGT | 455 | TGCAGGACCAGAGAATTCGAATA CATGCCCCANNNTGCATCAGGT | 695 |
| TGCAGGACCAGAGAATTCGAATA CAGGCCTTTTNNNTGCATCAGGT | 216 | TGCAGGACCAGAGAATTCGAATA CAGTGTCTTCNNNTGCATCAGGT | 456 | TGCAGGACCAGAGAATTCGAATA CACGAGCTCGNNNTGCATCAGGT | 696 |
| TGCAGGACCAGAGAATTCGAATA CACAACTCTCNNNTGCATCAGGT | 217 | TGCAGGACCAGAGAATTCGAATA CATAAACTTGNNNTGCATCAGGT | 457 | TGCAGGACCAGAGAATTCGAATA CAACTGAACCNNNTGCATCAGGT | 697 |
| TGCAGGACCAGAGAATTCGAATA CATGTACTGGNNNTGCATCAGGT | 218 | TGCAGGACCAGAGAATTCGAATA CAGACATCCANNNTGCATCAGGT | 458 | TGCAGGACCAGAGAATTCGAATA CACTCGTATCNNNTGCATCAGGT | 698 |
| TGCAGGACCAGAGAATTCGAATA CATTTGGCTCNNNTGCATCAGGT | 219 | TGCAGGACCAGAGAATTCGAATA CATAAGTCCGNNNTGCATCAGGT | 459 | TGCAGGACCAGAGAATTCGAATA CACACTTCCANNNTGCATCAGGT | 699 |
| TGCAGGACCAGAGAATTCGAATA CAGAAGTATANNNTGCATCAGGT | 220 | TGCAGGACCAGAGAATTCGAATA CAAGGCGCGANNNTGCATCAGGT | 460 | TGCAGGACCAGAGAATTCGAATA CAGATCCTGANNNTGCATCAGGT | 700 |
| TGCAGGACCAGAGAATTCGAATA CAGAATCACCNNNTGCATCAGGT | 221 | TGCAGGACCAGAGAATTCGAATA CAGAGCTCTANNNTGCATCAGGT | 461 | TGCAGGACCAGAGAATTCGAATA CAAGAAGTATNNNTGCATCAGGT | 701 |
| TGCAGGACCAGAGAATTCGAATA CACTTACCGTNNNTGCATCAGGT | 222 | TGCAGGACCAGAGAATTCGAATA CATCATAATGNNNTGCATCAGGT | 462 | TGCAGGACCAGAGAATTCGAATA CAAACCCACANNNTGCATCAGGT | 702 |
| TGCAGGACCAGAGAATTCGAATA CATCTTTACANNNTGCATCAGGT | 223 | TGCAGGACCAGAGAATTCGAATA CAGGATGGTANNNTGCATCAGGT | 463 | TGCAGGACCAGAGAATTCGAATA CATGCCGAATNNNTGCATCAGGT | 703 |
| TGCAGGACCAGAGAATTCGAATA CACGAAGTGANNNTGCATCAGGT | 224 | TGCAGGACCAGAGAATTCGAATA CATAGCCTTCNNNTGCATCAGGT | 464 | TGCAGGACCAGAGAATTCGAATA CAATCAGAGGNNNTGCATCAGGT | 704 |
| TGCAGGACCAGAGAATTCGAATA CACTTGTGGANNNTGCATCAGGT | 225 | TGCAGGACCAGAGAATTCGAATA CAATCCCGCNNNTGCATCAGGT | 465 | TGCAGGACCAGAGAATTCGAATA CAGTCATATANNNTGCATCAGGT | 705 |
| TGCAGGACCAGAGAATTCGAATA CAGTTCTCTGNNNTGCATCAGGT | 226 | TGCAGGACCAGAGAATTCGAATA CAGATTGCTGNNNTGCATCAGGT | 466 | TGCAGGACCAGAGAATTCGAATA CAACCCACCCNNNTGCATCAGGT | 706 |
| TGCAGGACCAGAGAATTCGAATA CACCTTCAACNNNTGCATCAGGT | 227 | TGCAGGACCAGAGAATTCGAATA CAGTGATGAGNNNTGCATCAGGT | 467 | TGCAGGACCAGAGAATTCGAATA CACCCACAGGNNNTGCATCAGGT | 707 |
| TGCAGGACCAGAGAATTCGAATA CAAAATGCTTNNNTGCATCAGGT | 228 | TGCAGGACCAGAGAATTCGAATA CACGGAACGGNNNTGCATCAGGT | 468 | TGCAGGACCAGAGAATTCGAATA CATGCTGAACNNNTGCATCAGGT | 708 |
| TGCAGGACCAGAGAATTCGAATA CAATCGCGATNNNTGCATCAGGT | 229 | TGCAGGACCAGAGAATTCGAATA CAGCTCTTTGNNNTGCATCAGGT | 469 | TGCAGGACCAGAGAATTCGAATA CAGCAGCATTNNNTGCATCAGGT | 709 |
| TGCAGGACCAGAGAATTCGAATA CAGGCTCGTGNNNTGCATCAGGT | 230 | TGCAGGACCAGAGAATTCGAATA CAGTAATCGCNNNTGCATCAGGT | 470 | TGCAGGACCAGAGAATTCGAATA CAGGCGATGGNNNTGCATCAGGT | 710 |
| TGCAGGACCAGAGAATTCGAATA CAGACCCTAANNNTGCATCAGGT | 231 | TGCAGGACCAGAGAATTCGAATA CACTTGTTATNNNTGCATCAGGT | 471 | TGCAGGACCAGAGAATTCGAATA CATTCGATGGNNNTGCATCAGGT | 711 |
| TGCAGGACCAGAGAATTCGAATA CACAAATTTGNNNTGCATCAGGT | 232 | TGCAGGACCAGAGAATTCGAATA CACACACACANNNTGCATCAGGT | 472 | TGCAGGACCAGAGAATTCGAATA CATGGAGGCGNNNTGCATCAGGT | 712 |
| TGCAGGACCAGAGAATTCGAATA CATTTTTTCCNNNTGCATCAGGT | 233 | TGCAGGACCAGAGAATTCGAATA CATAAATAAANNNTGCATCAGGT | 473 | TGCAGGACCAGAGAATTCGAATA CAGTATTACANNNTGCATCAGGT | 713 |
| TGCAGGACCAGAGAATTCGAATA CATTTAACGANNNTGCATCAGGT | 234 | TGCAGGACCAGAGAATTCGAATA CAAACGCATCNNNTGCATCAGGT | 474 | TGCAGGACCAGAGAATTCGAATA CACGACAATCNNNTGCATCAGGT | 714 |
| TGCAGGACCAGAGAATTCGAATA CAGTGGTCTANNNTGCATCAGGT | 235 | TGCAGGACCAGAGAATTCGAATA CACATATGATNNNTGCATCAGGT | 475 | TGCAGGACCAGAGAATTCGAATA CAGTGGCCACNNNTGCATCAGGT | 715 |
| TGCAGGACCAGAGAATTCGAATA CATTCTAATCNNNTGCATCAGGT | 236 | TGCAGGACCAGAGAATTCGAATA CAGCGTCATANNNTGCATCAGGT | 476 | TGCAGGACCAGAGAATTCGAATA CATACGCGCGNNNTGCATCAGGT | 716 |
| TGCAGGACCAGAGAATTCGAATA CAATTGATTGNNNTGCATCAGGT | 237 | TGCAGGACCAGAGAATTCGAATA CATAAGCCTGNNNTGCATCAGGT | 477 | TGCAGGACCAGAGAATTCGAATA CACGAAGACANNNTGCATCAGGT | 717 |
| TGCAGGACCAGAGAATTCGAATA CATGCATAGCNNNTGCATCAGGT | 238 | TGCAGGACCAGAGAATTCGAATA CATAGCAGAGNNNTGCATCAGGT | 478 | TGCAGGACCAGAGAATTCGAATA CACCAATGACNNNTGCATCAGGT | 718 |
| TGCAGGACCAGAGAATTCGAATA CAGACAGATGNNNTGCATCAGGT | 239 | TGCAGGACCAGAGAATTCGAATA CACTTGGAACNNNTGCATCAGGT | 479 | TGCAGGACCAGAGAATTCGAATA CAAGCCTTCTNNNTGCATCAGGT | 719 |

FIG. 12H

| Pool-1 | SEQ ID NO: | Pool-2 | SEQ ID NO: | Pool-3 | SEQ ID NO: |
|---|---|---|---|---|---|
| TGCAGGACCAGAGAATTCGAATA CATGCTCTACNNNTGCATCAGGT | 240 | TGCAGGACCAGAGAATTCGAATA CAACCGAGAANNNTGCATCAGGT | 480 | TGCAGGACCAGAGAATTCGAATA CATATCACCCNNNTGCATCAGGT | 720 |
| TGCAGGACCAGAGAATTCGAATA CATGCGATACNNNTGCATCAGGT | 241 | TGCAGGACCAGAGAATTCGAATA CACTATCTATNNNTGCATCAGGT | 481 | TGCAGGACCAGAGAATTCGAATA CACCTTATGCNNNTGCATCAGGT | 721 |
| TGCAGGACCAGAGAATTCGAATA CAACACTGCANNNTGCATCAGGT | 242 | TGCAGGACCAGAGAATTCGAATA CACAATTTAGNNNTGCATCAGGT | 482 | TGCAGGACCAGAGAATTCGAATA CATTAATGACNNNTGCATCAGGT | 722 |
| TGCAGGACCAGAGAATTCGAATA CAGTCACTCTNNNTGCATCAGGT | 243 | TGCAGGACCAGAGAATTCGAATA CACTAAACGCNNNTGCATCAGGT | 483 | TGCAGGACCAGAGAATTCGAATA CACTACCTTGNNNTGCATCAGGT | 723 |
| TGCAGGACCAGAGAATTCGAATA CATTGTATTCNNNTGCATCAGGT | 244 | TGCAGGACCAGAGAATTCGAATA CATAGTAGAANNNTGCATCAGGT | 484 | TGCAGGACCAGAGAATTCGAATA CAAGGATCTCNNNTGCATCAGGT | 724 |
| TGCAGGACCAGAGAATTCGAATA CAAACCTAGCNNNTGCATCAGGT | 245 | TGCAGGACCAGAGAATTCGAATA CAGCAAAGTGNNNTGCATCAGGT | 485 | TGCAGGACCAGAGAATTCGAATA CAAAGATCAANNNTGCATCAGGT | 725 |
| TGCAGGACCAGAGAATTCGAATA CAGCCCGGATCNNNTGCATCAGGT | 246 | TGCAGGACCAGAGAATTCGAATA CACAAGTTATNNNTGCATCAGGT | 486 | TGCAGGACCAGAGAATTCGAATA CAGAATGAGCNNNTGCATCAGGT | 726 |
| TGCAGGACCAGAGAATTCGAATA CAAGGATCCTNNNTGCATCAGGT | 247 | TGCAGGACCAGAGAATTCGAATA CACAACTGACNNNTGCATCAGGT | 487 | TGCAGGACCAGAGAATTCGAATA CAACTAGATTNNNTGCATCAGGT | 727 |
| TGCAGGACCAGAGAATTCGAATA CATACTGGACNNNTGCATCAGGT | 248 | TGCAGGACCAGAGAATTCGAATA CATTCGTCGTNNNTGCATCAGGT | 488 | TGCAGGACCAGAGAATTCGAATA CATTTTCCGGNNNTGCATCAGGT | 728 |

FIG. 13A

| Pool-4 | SEQ ID NO: | Pool-5 | SEQ ID NO: | Pool-6 | SEQ ID NO: |
|---|---|---|---|---|---|
| TGCAGGACCAGAGAATTCGAATACATATGCGCANNNACGTATGCCA | 729 | TGCAGGACCAGAGAATTCGAATACAGCGGATTACNNNACGTATGCCA | 969 | TGCAGGACCAGAGAATTCGAATACACAATGACCNNNACGTATGCCA | 1209 |
| TGCAGGACCAGAGAATTCGAATACAGTTCACCTNNNACGTATGCCA | 730 | TGCAGGACCAGAGAATTCGAATACATGGTCCTCNNNACGTATGCCA | 970 | TGCAGGACCAGAGAATTCGAATACAGCTACGTANNNACGTATGCCA | 1210 |
| TGCAGGACCAGAGAATTCGAATACATCCTACACNNNACGTATGCCA | 731 | TGCAGGACCAGAGAATTCGAATACAGTTATAACNNNACGTATGCCA | 971 | TGCAGGACCAGAGAATTCGAATACAGCCAGCACNNNACGTATGCCA | 1211 |
| TGCAGGACCAGAGAATTCGAATACACTACTCTGNNNACGTATGCCA | 732 | TGCAGGACCAGAGAATTCGAATACGTATCTTCANNNACGTATGCCA | 972 | TGCAGGACCAGAGAATTCGAATACACGGATCCGGNNNACGTATGCCA | 1212 |
| TGCAGGACCAGAGAATTCGAATACACCTTCCCCNNNACGTATGCCA | 733 | TGCAGGACCAGAGAATTCGAATACAACGTTCGANNNACGTATGCCA | 973 | TGCAGGACCAGAGAATTCGAATACATTGGACACNNNACGTATGCCA | 1213 |
| TGCAGGACCAGAGAATTCGAATACAGAAGATCGNNNACGTATGCCA | 734 | TGCAGGACCAGAGAATTCGAATACAACTCGTGANNNACGTATGCCA | 974 | TGCAGGACCAGAGAATTCGAATACAACAATGCCNNNACGTATGCCA | 1214 |
| TGCAGGACCAGAGAATTCGAATACACTCCGCTGNNNACGTATGCCA | 735 | TGCAGGACCAGAGAATTCGAATACAGGACTACTNNNACGTATGCCA | 975 | TGCAGGACCAGAGAATTCGAATACACCCTTTATANNNACGTATGCCA | 1215 |
| TGCAGGACCAGAGAATTCGAATACATATGTCCCNNNACGTATGCCA | 736 | TGCAGGACCAGAGAATTCGAATACATCTGTACCNNNACGTATGCCA | 976 | TGCAGGACCAGAGAATTCGAATACAGTGGCTGCNNNACGTATGCCA | 1216 |
| TGCAGGACCAGAGAATTCGAATACATATTTGCTNNNACGTATGCCA | 737 | TGCAGGACCAGAGAATTCGAATACACCCTAACTNNNACGTATGCCA | 977 | TGCAGGACCAGAGAATTCGAATACAATCTCCGTNNNACGTATGCCA | 1217 |
| TGCAGGACCAGAGAATTCGAATACAGTCCAGGCNNNACGTATGCCA | 738 | TGCAGGACCAGAGAATTCGAATACATTGGAGAGNNNACGTATGCCA | 978 | TGCAGGACCAGAGAATTCGAATACAATGGCCATNNNACGTATGCCA | 1218 |
| TGCAGGACCAGAGAATTCGAATACAAAGATGGCNNNACGTATGCCA | 739 | TGCAGGACCAGAGAATTCGAATACAGAATCAAANNNACGTATGCCA | 979 | TGCAGGACCAGAGAATTCGAATACATTTGATAGNNNACGTATGCCA | 1219 |
| TGCAGGACCAGAGAATTCGAATACAGTCCCGAGNNNACGTATGCCA | 740 | TGCAGGACCAGAGAATTCGAATACAGTTTCGTCNNNACGTATGCCA | 980 | TGCAGGACCAGAGAATTCGAATACAGTCCCGGANNNACGTATGCCA | 1220 |
| TGCAGGACCAGAGAATTCGAATACAAGGTTTCGNNNACGTATGCCA | 741 | TGCAGGACCAGAGAATTCGAATACACTACACAGNNNACGTATGCCA | 981 | TGCAGGACCAGAGAATTCGAATACAGGCTTCAANNNACGTATGCCA | 1221 |
| TGCAGGACCAGAGAATTCGAATACATGCAAAGGNNNACGTATGCCA | 742 | TGCAGGACCAGAGAATTCGAATACAAGTCAGTCNNNACGTATGCCA | 982 | TGCAGGACCAGAGAATTCGAATACACCTTTTTTNNNACGTATGCCA | 1222 |
| TGCAGGACCAGAGAATTCGAATACAAGGTGTAGNNNACGTATGCCA | 743 | TGCAGGACCAGAGAATTCGAATACACAACGAGANNNACGTATGCCA | 983 | TGCAGGACCAGAGAATTCGAATACAACGCCCGANNNACGTATGCCA | 1223 |
| TGCAGGACCAGAGAATTCGAATACACACGAGTTNNNACGTATGCCA | 744 | TGCAGGACCAGAGAATTCGAATACATAGGCTCANNNACGTATGCCA | 984 | TGCAGGACCAGAGAATTCGAATACACCCCTAGCNNNACGTATGCCA | 1224 |
| TGCAGGACCAGAGAATTCGAATACACACACCGCCTNNNACGTATGCCA | 745 | TGCAGGACCAGAGAATTCGAATACAGGCCCATGNNNACGTATGCCA | 985 | TGCAGGACCAGAGAATTCGAATACACGGAGGCANNNACGTATGCCA | 1225 |
| TGCAGGACCAGAGAATTCGAATACAAAGCTACCNNNACGTATGCCA | 746 | TGCAGGACCAGAGAATTCGAATACAGGCAGTCNNNACGTATGCCA | 986 | TGCAGGACCAGAGAATTCGAATACACTATGAATNNNACGTATGCCA | 1226 |
| TGCAGGACCAGAGAATTCGAATACAGAACCGAANNNACGTATGCCA | 747 | TGCAGGACCAGAGAATTCGAATACATCGATTGGNNNACGTATGCCA | 987 | TGCAGGACCAGAGAATTCGAATACAGACCGCGTNNNACGTATGCCA | 1227 |
| TGCAGGACCAGAGAATTCGAATACAAGTACTGCNNNACGTATGCCA | 748 | TGCAGGACCAGAGAATTCGAATACATAGACAGGNNNACGTATGCCA | 988 | TGCAGGACCAGAGAATTCGAATACATACTAGTANNNACGTATGCCA | 1228 |
| TGCAGGACCAGAGAATTCGAATACAAACAATTCNNNACGTATGCCA | 749 | TGCAGGACCAGAGAATTCGAATACAACTAAGTTNNNACGTATGCCA | 989 | TGCAGGACCAGAGAATTCGAATACAACCAGTGTNNNACGTATGCCA | 1229 |
| TGCAGGACCAGAGAATTCGAATACAGTATTAACNNNACGTATGCCA | 750 | TGCAGGACCAGAGAATTCGAATACAATGTTCGGNNNACGTATGCCA | 990 | TGCAGGACCAGAGAATTCGAATACAGATGCCTANNNACGTATGCCA | 1230 |
| TGCAGGACCAGAGAATTCGAATACATGATTATGNNNACGTATGCCA | 751 | TGCAGGACCAGAGAATTCGAATACAAGCCCAATNNNACGTATGCCA | 991 | TGCAGGACCAGAGAATTCGAATACACCATATTTNNNACGTATGCCA | 1231 |
| TGCAGGACCAGAGAATTCGAATACAGCAAACCTNNNACGTATGCCA | 752 | TGCAGGACCAGAGAATTCGAATACAGTGAGTTCNNNACGTATGCCA | 992 | TGCAGGACCAGAGAATTCGAATACAAAACCACCNNNACGTATGCCA | 1232 |
| TGCAGGACCAGAGAATTCGAATACAGAATCTTANNNACGTATGCCA | 753 | TGCAGGACCAGAGAATTCGAATACAGTGCTAACNNNACGTATGCCA | 993 | TGCAGGACCAGAGAATTCGAATACAGCACGAAANNNACGTATGCCA | 1233 |
| TGCAGGACCAGAGAATTCGAATACAGAGGACGCNNNACGTATGCCA | 754 | TGCAGGACCAGAGAATTCGAATACAGCCACCGANNNACGTATGCCA | 994 | TGCAGGACCAGAGAATTCGAATACAACGACAGANNNACGTATGCCA | 1234 |
| TGCAGGACCAGAGAATTCGAATACAAGCCAAAGNNNACGTATGCCA | 755 | TGCAGGACCAGAGAATTCGAATACAAGTCCGATNNNACGTATGCCA | 995 | TGCAGGACCAGAGAATTCGAATACAATACCATANNNACGTATGCCA | 1235 |
| TGCAGGACCAGAGAATTCGAATACAGGACGCTCNNNACGTATGCCA | 756 | TGCAGGACCAGAGAATTCGAATACAGTTAAATCNNNACGTATGCCA | 996 | TGCAGGACCAGAGAATTCGAATACACCAGTTCTNNNACGTATGCCA | 1236 |
| TGCAGGACCAGAGAATTCGAATACAGCTGCCCTNNNACGTATGCCA | 757 | TGCAGGACCAGAGAATTCGAATACAACTGACTGNNNACGTATGCCA | 997 | TGCAGGACCAGAGAATTCGAATACATTGCTGGANNNACGTATGCCA | 1237 |
| TGCAGGACCAGAGAATTCGAATACACCCTTTTCNNNACGTATGCCA | 758 | TGCAGGACCAGAGAATTCGAATACACTTCATGCNNNACGTATGCCA | 998 | TGCAGGACCAGAGAATTCGAATACAGCCCATTNNNACGTATGCCA | 1238 |
| TGCAGGACCAGAGAATTCGAATACATCGCATANNNACGTATGCCA | 759 | TGCAGGACCAGAGAATTCGAATACAACAGCATNNNACGTATGCCA | 999 | TGCAGGACCAGAGAATTCGAATACAAACAGCTCNNNACGTATGCCA | 1239 |
| TGCAGGACCAGAGAATTCGAATACAATCGCATGNNNACGTATGCCA | 760 | TGCAGGACCAGAGAATTCGAATACAGGCGTCCANNNACGTATGCCA | 1000 | TGCAGGACCAGAGAATTCGAATACACTGTTCTGNNNACGTATGCCA | 1240 |

FIG. 13B

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CAAGATGGCANNNACGTATGCCA | 761 | TGCAGGACCAGAGAATTCGAATA CAAACAACCCNNNACGTATGCCA | 1001 | TGCAGGACCAGAGAATTCGAATA CATGCAATAANNNACGTATGCCA | 1241 |
| TGCAGGACCAGAGAATTCGAATA CATCATCGCTNNNACGTATGCCA | 762 | TGCAGGACCAGAGAATTCGAATA CAGGTCTTAGNNNACGTATGCCA | 1002 | TGCAGGACCAGAGAATTCGAATA CATTCCCTTCNNNACGTATGCCA | 1242 |
| TGCAGGACCAGAGAATTCGAATA CACGTGTTCTNNNACGTATGCCA | 763 | TGCAGGACCAGAGAATTCGAATA CAGCCCGGATNNNACGTATGCCA | 1003 | TGCAGGACCAGAGAATTCGAATA CACACGCAATNNNACGTATGCCA | 1243 |
| TGCAGGACCAGAGAATTCGAATA CAGGTTATTANNNACGTATGCCA | 764 | TGCAGGACCAGAGAATTCGAATA CAATCCCGAANNNACGTATGCCA | 1004 | TGCAGGACCAGAGAATTCGAATA CAGCTTATCCNNNACGTATGCCA | 1244 |
| TGCAGGACCAGAGAATTCGAATA CAAGAGTTAANNNACGTATGCCA | 765 | TGCAGGACCAGAGAATTCGAATA CATTTACTCANNNACGTATGCCA | 1005 | TGCAGGACCAGAGAATTCGAATA CAGGCATAGANNNACGTATGCCA | 1245 |
| TGCAGGACCAGAGAATTCGAATA CATGAAATTCNNNACGTATGCCA | 766 | TGCAGGACCAGAGAATTCGAATA CATCCACCGCNNNACGTATGCCA | 1006 | TGCAGGACCAGAGAATTCGAATA CAAGCGCCGTNNNACGTATGCCA | 1246 |
| TGCAGGACCAGAGAATTCGAATA CACTTACCTGNNNACGTATGCCA | 767 | TGCAGGACCAGAGAATTCGAATA CACCAGATTGNNNACGTATGCCA | 1007 | TGCAGGACCAGAGAATTCGAATA CACAAATTCANNNACGTATGCCA | 1247 |
| TGCAGGACCAGAGAATTCGAATA CAAACTCGTGNNNACGTATGCCA | 768 | TGCAGGACCAGAGAATTCGAATA CACATGGTCANNNACGTATGCCA | 1008 | TGCAGGACCAGAGAATTCGAATA CATAATGCATNNNACGTATGCCA | 1248 |
| TGCAGGACCAGAGAATTCGAATA CAGGACACGGNNNACGTATGCCA | 769 | TGCAGGACCAGAGAATTCGAATA CACCATTCGNNNACGTATGCCA | 1009 | TGCAGGACCAGAGAATTCGAATA CAACTCGTCTNNNACGTATGCCA | 1249 |
| TGCAGGACCAGAGAATTCGAATA CATCTCGCGCNNNACGTATGCCA | 770 | TGCAGGACCAGAGAATTCGAATA CATGTCGCGCNNNACGTATGCCA | 1010 | TGCAGGACCAGAGAATTCGAATA CAAATTTGTGNNNACGTATGCCA | 1250 |
| TGCAGGACCAGAGAATTCGAATA CACTTCCAGTNNNACGTATGCCA | 771 | TGCAGGACCAGAGAATTCGAATA CAAACAATAGNNNACGTATGCCA | 1011 | TGCAGGACCAGAGAATTCGAATA CATGGAGAGGTNNNACGTATGCCA | 1251 |
| TGCAGGACCAGAGAATTCGAATA CAATAGTTACNNNACGTATGCCA | 772 | TGCAGGACCAGAGAATTCGAATA CATTCGACGANNNACGTATGCCA | 1012 | TGCAGGACCAGAGAATTCGAATA CAGCCATACANNNACGTATGCCA | 1252 |
| TGCAGGACCAGAGAATTCGAATA CACGACTTGANNNACGTATGCCA | 773 | TGCAGGACCAGAGAATTCGAATA CACCTTGAGANNNACGTATGCCA | 1013 | TGCAGGACCAGAGAATTCGAATA CAGTCCTTCANNNACGTATGCCA | 1253 |
| TGCAGGACCAGAGAATTCGAATA CATGCTTTATNNNACGTATGCCA | 774 | TGCAGGACCAGAGAATTCGAATA CAACGCTCTTNNNACGTATGCCA | 1014 | TGCAGGACCAGAGAATTCGAATA CAGTGCGGAGNNNACGTATGCCA | 1254 |
| TGCAGGACCAGAGAATTCGAATA CAGCCACTTTNNNACGTATGCCA | 775 | TGCAGGACCAGAGAATTCGAATA CACACGAAGANNNACGTATGCCA | 1015 | TGCAGGACCAGAGAATTCGAATA CATTTAGACANNNACGTATGCCA | 1255 |
| TGCAGGACCAGAGAATTCGAATA CATATCGGACNNNACGTATGCCA | 776 | TGCAGGACCAGAGAATTCGAATA CAGGCCCACANNNACGTATGCCA | 1016 | TGCAGGACCAGAGAATTCGAATA CACACCCGCTNNNACGTATGCCA | 1256 |
| TGCAGGACCAGAGAATTCGAATA CAATTCCATTNNNACGTATGCCA | 777 | TGCAGGACCAGAGAATTCGAATA CATCTCTGAGNNNACGTATGCCA | 1017 | TGCAGGACCAGAGAATTCGAATA CAATTCTAGANNNACGTATGCCA | 1257 |
| TGCAGGACCAGAGAATTCGAATA CAAATGCTGCNNNACGTATGCCA | 778 | TGCAGGACCAGAGAATTCGAATA CAAAAGCCAGNNNACGTATGCCA | 1018 | TGCAGGACCAGAGAATTCGAATA CACGGACGAGNNNACGTATGCCA | 1258 |
| TGCAGGACCAGAGAATTCGAATA CAACGCGATTNNNACGTATGCCA | 779 | TGCAGGACCAGAGAATTCGAATA CACCAGTTGANNNACGTATGCCA | 1019 | TGCAGGACCAGAGAATTCGAATA CACGACCGCANNNACGTATGCCA | 1259 |
| TGCAGGACCAGAGAATTCGAATA CATAGCTAGCNNNACGTATGCCA | 780 | TGCAGGACCAGAGAATTCGAATA CACTTGTAGGNNNACGTATGCCA | 1020 | TGCAGGACCAGAGAATTCGAATA CACATATAGTNNNACGTATGCCA | 1260 |
| TGCAGGACCAGAGAATTCGAATA CAGCCAACGTTNNNACGTATGCCA | 781 | TGCAGGACCAGAGAATTCGAATA CAATATGCATNNNACGTATGCCA | 1021 | TGCAGGACCAGAGAATTCGAATA CATGTGATATNNNACGTATGCCA | 1261 |
| TGCAGGACCAGAGAATTCGAATA CACGTCCTATNNNACGTATGCCA | 782 | TGCAGGACCAGAGAATTCGAATA CACCAGGCGTNNNACGTATGCCA | 1022 | TGCAGGACCAGAGAATTCGAATA CAATCCTAAANNNACGTATGCCA | 1262 |
| TGCAGGACCAGAGAATTCGAATA CAGCCACACGNNNACGTATGCCA | 783 | TGCAGGACCAGAGAATTCGAATA CAATGTTTAGNNNACGTATGCCA | 1023 | TGCAGGACCAGAGAATTCGAATA CATGATGACGNNNACGTATGCCA | 1263 |
| TGCAGGACCAGAGAATTCGAATA CAGGCTTCCCNNNACGTATGCCA | 784 | TGCAGGACCAGAGAATTCGAATA CACTGTCCGCNNNACGTATGCCA | 1024 | TGCAGGACCAGAGAATTCGAATA CAGCTCGACGNNNACGTATGCCA | 1264 |
| TGCAGGACCAGAGAATTCGAATA CAGTTGACACNNNACGTATGCCA | 785 | TGCAGGACCAGAGAATTCGAATA CATTTTACCANNNACGTATGCCA | 1025 | TGCAGGACCAGAGAATTCGAATA CATTAGCTAANNNACGTATGCCA | 1265 |
| TGCAGGACCAGAGAATTCGAATA CAGCATCTTCNNNACGTATGCCA | 786 | TGCAGGACCAGAGAATTCGAATA CATGCCCTGCNNNACGTATGCCA | 1026 | TGCAGGACCAGAGAATTCGAATA CATGCTTTTANNNACGTATGCCA | 1266 |
| TGCAGGACCAGAGAATTCGAATA CAACAATTGTNNNACGTATGCCA | 787 | TGCAGGACCAGAGAATTCGAATA CACCTTTGACNNNACGTATGCCA | 1027 | TGCAGGACCAGAGAATTCGAATA CAATCACAGCNNNACGTATGCCA | 1267 |
| TGCAGGACCAGAGAATTCGAATA CAGATCCCCCNNNACGTATGCCA | 788 | TGCAGGACCAGAGAATTCGAATA CAATTATTTTNNNACGTATGCCA | 1028 | TGCAGGACCAGAGAATTCGAATA CAAATCTCGGNNNACGTATGCCA | 1268 |
| TGCAGGACCAGAGAATTCGAATA CAGCCCAGTGNNNCTAGCGTTAC | 789 | TGCAGGACCAGAGAATTCGAATA CAGTGTGGAANNNCTAGCGTTAC | 1029 | TGCAGGACCAGAGAATTCGAATA CAACACTGGTNNNCTAGCGTTAC | 1269 |
| TGCAGGACCAGAGAATTCGAATA CAGCCGGTGCTNNNCTAGCGTTAC | 790 | TGCAGGACCAGAGAATTCGAATA CAACTCGTAGNNNCTAGCGTTAC | 1030 | TGCAGGACCAGAGAATTCGAATA CATTTGTTTGNNNCTAGCGTTAC | 1270 |
| TGCAGGACCAGAGAATTCGAATA CATACGTGCANNNCTAGCGTTAC | 791 | TGCAGGACCAGAGAATTCGAATA CATCGCGTCCNNNCTAGCGTTAC | 1031 | TGCAGGACCAGAGAATTCGAATA CACGACGCNNNCTAGCGTTAC | 1271 |
| TGCAGGACCAGAGAATTCGAATA CACACCCACCNNNCTAGCGTTAC | 792 | TGCAGGACCAGAGAATTCGAATA CAGCCTAATGNNNCTAGCGTTAC | 1032 | TGCAGGACCAGAGAATTCGAATA CACGCGAGAGNNNCTAGCGTTAC | 1272 |

FIG. 13C

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CACACAGAAGNNNCTAGCGTTAC | 793 | TGCAGGACCAGAGAATTCGAATA CAGCGTGTTANNNCTAGCGTTAC | 1033 | TGCAGGACCAGAGAATTCGAATA CATAAGTAGANNNCTAGCGTTAC | 1273 |
| TGCAGGACCAGAGAATTCGAATA CACGCTAACANNNCTAGCGTTAC | 794 | TGCAGGACCAGAGAATTCGAATA CACGAGAAACNNNCTAGCGTTAC | 1034 | TGCAGGACCAGAGAATTCGAATA CAAAGACGTGNNNCTAGCGTTAC | 1274 |
| TGCAGGACCAGAGAATTCGAATA CAGACCTATGNNNCTAGCGTTAC | 795 | TGCAGGACCAGAGAATTCGAATA CAATGCTCAGNNNCTAGCGTTAC | 1035 | TGCAGGACCAGAGAATTCGAATA CACGGAACAANNNCTAGCGTTAC | 1275 |
| TGCAGGACCAGAGAATTCGAATA CAAAAAGGAANNNCTAGCGTTAC | 796 | TGCAGGACCAGAGAATTCGAATA CAGTCAGCTANNNCTAGCGTTAC | 1036 | TGCAGGACCAGAGAATTCGAATA CACTGTCGAANNNCTAGCGTTAC | 1276 |
| TGCAGGACCAGAGAATTCGAATA CAACAGAGGTNNNCTAGCGTTAC | 797 | TGCAGGACCAGAGAATTCGAATA CAGGTAGCGGNNNCTAGCGTTAC | 1037 | TGCAGGACCAGAGAATTCGAATA CAAGCCTACANNNCTAGCGTTAC | 1277 |
| TGCAGGACCAGAGAATTCGAATA CACGTAGCATNNNCTAGCGTTAC | 798 | TGCAGGACCAGAGAATTCGAATA CACCTGGTCCNNNCTAGCGTTAC | 1038 | TGCAGGACCAGAGAATTCGAATA CACCAATTCGNNNCTAGCGTTAC | 1278 |
| TGCAGGACCAGAGAATTCGAATA CATCCCCAGCNNNCTAGCGTTAC | 799 | TGCAGGACCAGAGAATTCGAATA CACAGCACCGNNNCTAGCGTTAC | 1039 | TGCAGGACCAGAGAATTCGAATA CAGAGTCTACNNNCTAGCGTTAC | 1279 |
| TGCAGGACCAGAGAATTCGAATA CAGTACCTGANNNCTAGCGTTAC | 800 | TGCAGGACCAGAGAATTCGAATA CACATTGTGGNNNCTAGCGTTAC | 1040 | TGCAGGACCAGAGAATTCGAATA CAAATGTTACNNNCTAGCGTTAC | 1280 |
| TGCAGGACCAGAGAATTCGAATA CAAGAGAGGANNNCTAGCGTTAC | 801 | TGCAGGACCAGAGAATTCGAATA CAAGGAACTGNNNCTAGCGTTAC | 1041 | TGCAGGACCAGAGAATTCGAATA CAAGTGGCAANNNCTAGCGTTAC | 1281 |
| TGCAGGACCAGAGAATTCGAATA CAGTAACTCGNNNCTAGCGTTAC | 802 | TGCAGGACCAGAGAATTCGAATA CAGTTATTAGNNNCTAGCGTTAC | 1042 | TGCAGGACCAGAGAATTCGAATA CAGGTTAACCNNNCTAGCGTTAC | 1282 |
| TGCAGGACCAGAGAATTCGAATA CAGGTACATCNNNCTAGCGTTAC | 803 | TGCAGGACCAGAGAATTCGAATA CAAATCTTCTNNNCTAGCGTTAC | 1043 | TGCAGGACCAGAGAATTCGAATA CATTGTGGTGNNNCTAGCGTTAC | 1283 |
| TGCAGGACCAGAGAATTCGAATA CAGTTAACCGNNNCTAGCGTTAC | 804 | TGCAGGACCAGAGAATTCGAATA CAGACAATCCNNNCTAGCGTTAC | 1044 | TGCAGGACCAGAGAATTCGAATA CAAAATGGCGNNNCTAGCGTTAC | 1284 |
| TGCAGGACCAGAGAATTCGAATA CAAACGAGTGNNNCTAGCGTTAC | 805 | TGCAGGACCAGAGAATTCGAATA CAATCTAGATNNNCTAGCGTTAC | 1045 | TGCAGGACCAGAGAATTCGAATA CACTGTAGGTNNNCTAGCGTTAC | 1285 |
| TGCAGGACCAGAGAATTCGAATA CATCTCACTGNNNCTAGCGTTAC | 806 | TGCAGGACCAGAGAATTCGAATA CAGCGACGTCNNNCTAGCGTTAC | 1046 | TGCAGGACCAGAGAATTCGAATA CACTAAGCGTNNNCTAGCGTTAC | 1286 |
| TGCAGGACCAGAGAATTCGAATA CATACGAGCTNNNCTAGCGTTAC | 807 | TGCAGGACCAGAGAATTCGAATA CACACCCCGTNNNCTAGCGTTAC | 1047 | TGCAGGACCAGAGAATTCGAATA CAGTTTATGANNNCTAGCGTTAC | 1287 |
| TGCAGGACCAGAGAATTCGAATA CACAGATACCNNNCTAGCGTTAC | 808 | TGCAGGACCAGAGAATTCGAATA CACGCCTCGTNNNCTAGCGTTAC | 1048 | TGCAGGACCAGAGAATTCGAATA CAACGACTGTNNNCTAGCGTTAC | 1288 |
| TGCAGGACCAGAGAATTCGAATA CATACATTCNNNCTAGCGTTAC | 809 | TGCAGGACCAGAGAATTCGAATA CACTGACACANNNCTAGCGTTAC | 1049 | TGCAGGACCAGAGAATTCGAATA CACCTAGTAGNNNCTAGCGTTAC | 1289 |
| TGCAGGACCAGAGAATTCGAATA CAGTGTAAGGNNNCTAGCGTTAC | 810 | TGCAGGACCAGAGAATTCGAATA CATGCTTTGCNNNCTAGCGTTAC | 1050 | TGCAGGACCAGAGAATTCGAATA CAGGTTCTGANNNCTAGCGTTAC | 1290 |
| TGCAGGACCAGAGAATTCGAATA CAGGTTGAAGNNNCTAGCGTTAC | 811 | TGCAGGACCAGAGAATTCGAATA CAACTGTCTCNNNCTAGCGTTAC | 1051 | TGCAGGACCAGAGAATTCGAATA CATACATCCCNNNCTAGCGTTAC | 1291 |
| TGCAGGACCAGAGAATTCGAATA CACGTCCCTGNNNCTAGCGTTAC | 812 | TGCAGGACCAGAGAATTCGAATA CATATTGTCTNNNCTAGCGTTAC | 1052 | TGCAGGACCAGAGAATTCGAATA CACTCGGAATNNNCTAGCGTTAC | 1292 |
| TGCAGGACCAGAGAATTCGAATA CAAATCCCTCNNNCTAGCGTTAC | 813 | TGCAGGACCAGAGAATTCGAATA CAATTTGACANNNCTAGCGTTAC | 1053 | TGCAGGACCAGAGAATTCGAATA CATCAGTTGGNNNCTAGCGTTAC | 1293 |
| TGCAGGACCAGAGAATTCGAATA CATGCCCCACNNNCTAGCGTTAC | 814 | TGCAGGACCAGAGAATTCGAATA CACGCACACGNNNCTAGCGTTAC | 1054 | TGCAGGACCAGAGAATTCGAATA CAAGTGCCTANNNCTAGCGTTAC | 1294 |
| TGCAGGACCAGAGAATTCGAATA CAGTATTATGNNNCTAGCGTTAC | 815 | TGCAGGACCAGAGAATTCGAATA CACCGCGAACNNNCTAGCGTTAC | 1055 | TGCAGGACCAGAGAATTCGAATA CAGTATGTATNNNCTAGCGTTAC | 1295 |
| TGCAGGACCAGAGAATTCGAATA CATTGATTGANNNCTAGCGTTAC | 816 | TGCAGGACCAGAGAATTCGAATA CATTAGGCGTNNNCTAGCGTTAC | 1056 | TGCAGGACCAGAGAATTCGAATA CAGCAGCACGNNNCTAGCGTTAC | 1296 |
| TGCAGGACCAGAGAATTCGAATA CATGCGACGCNNNCTAGCGTTAC | 817 | TGCAGGACCAGAGAATTCGAATA CATCGGAGCCNNNCTAGCGTTAC | 1057 | TGCAGGACCAGAGAATTCGAATA CAGCAGGTCCNNNCTAGCGTTAC | 1297 |
| TGCAGGACCAGAGAATTCGAATA CAGTGGTTCANNNCTAGCGTTAC | 818 | TGCAGGACCAGAGAATTCGAATA CAGTCTACAGNNNCTAGCGTTAC | 1058 | TGCAGGACCAGAGAATTCGAATA CATGTAGGCTNNNCTAGCGTTAC | 1298 |
| TGCAGGACCAGAGAATTCGAATA CAGCCGGCTANNNCTAGCGTTAC | 819 | TGCAGGACCAGAGAATTCGAATA CACCGCGTCTNNNCTAGCGTTAC | 1059 | TGCAGGACCAGAGAATTCGAATA CATAACGACCNNNCTAGCGTTAC | 1299 |
| TGCAGGACCAGAGAATTCGAATA CACCTTGCGCNNNCTAGCGTTAC | 820 | TGCAGGACCAGAGAATTCGAATA CATTAAACTGNNNCTAGCGTTAC | 1060 | TGCAGGACCAGAGAATTCGAATA CACGATCGGCNNNCTAGCGTTAC | 1300 |
| TGCAGGACCAGAGAATTCGAATA CAGGTAAGTGNNNCTAGCGTTAC | 821 | TGCAGGACCAGAGAATTCGAATA CAATAAGAACNNNCTAGCGTTAC | 1061 | TGCAGGACCAGAGAATTCGAATA CAGGCCAAGGNNNCTAGCGTTAC | 1301 |
| TGCAGGACCAGAGAATTCGAATA CAGTGTCCAANNNCTAGCGTTAC | 822 | TGCAGGACCAGAGAATTCGAATA CAATCATGCGNNNCTAGCGTTAC | 1062 | TGCAGGACCAGAGAATTCGAATA CAGACATAAANNNCTAGCGTTAC | 1302 |
| TGCAGGACCAGAGAATTCGAATA CATGCACTGANNNCTAGCGTTAC | 823 | TGCAGGACCAGAGAATTCGAATA CACCAACTGGNNNCTAGCGTTAC | 1063 | TGCAGGACCAGAGAATTCGAATA CACGCACATANNNCTAGCGTTAC | 1303 |
| TGCAGGACCAGAGAATTCGAATA CAGAAAACTTTNNNCTAGCGTTAC | 824 | TGCAGGACCAGAGAATTCGAATA CACTCGAGTANNNCTAGCGTTAC | 1064 | TGCAGGACCAGAGAATTCGAATA CAGCCTAGGCNNNCTAGCGTTAC | 1304 |

FIG. 13D

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CATGTGTAGCNNNCTAGCGTTAC | 825 | TGCAGGACCAGAGAATTCGAATA CACTTTGCCANNNCTAGCGTTAC | 1065 | TGCAGGACCAGAGAATTCGAATA CATCCGCAAANNNCTAGCGTTAC | 1305 |
| TGCAGGACCAGAGAATTCGAATA CATCTACCTGNNNCTAGCGTTAC | 826 | TGCAGGACCAGAGAATTCGAATA CAAATTCTGANNNCTAGCGTTAC | 1066 | TGCAGGACCAGAGAATTCGAATA CACTTATAGANNNCTAGCGTTAC | 1306 |
| TGCAGGACCAGAGAATTCGAATA CATCTCTTAANNNCTAGCGTTAC | 827 | TGCAGGACCAGAGAATTCGAATA CAGATCGCATNNNCTAGCGTTAC | 1067 | TGCAGGACCAGAGAATTCGAATA CACGGCGGAANNNCTAGCGTTAC | 1307 |
| TGCAGGACCAGAGAATTCGAATA CAATCGAATTNNNCTAGCGTTAC | 828 | TGCAGGACCAGAGAATTCGAATA CATGTGTTGGNNNCTAGCGTTAC | 1068 | TGCAGGACCAGAGAATTCGAATA CAGTAGCACTNNNCTAGCGTTAC | 1308 |
| TGCAGGACCAGAGAATTCGAATA CATTTTTGGTNNNCTAGCGTTAC | 829 | TGCAGGACCAGAGAATTCGAATA CAGTAACATTNNNCTAGCGTTAC | 1069 | TGCAGGACCAGAGAATTCGAATA CAGCTGTCAANNNCTAGCGTTAC | 1309 |
| TGCAGGACCAGAGAATTCGAATA CATCAGTCCTNNNCTAGCGTTAC | 830 | TGCAGGACCAGAGAATTCGAATA CAACGCATCANNNCTAGCGTTAC | 1070 | TGCAGGACCAGAGAATTCGAATA CAGTGCCAGCNNNCTAGCGTTAC | 1310 |
| TGCAGGACCAGAGAATTCGAATA CAGTGCACATNNNCTAGCGTTAC | 831 | TGCAGGACCAGAGAATTCGAATA CATAGGAAGCNNNCTAGCGTTAC | 1071 | TGCAGGACCAGAGAATTCGAATA CATTCATATCNNNCTAGCGTTAC | 1311 |
| TGCAGGACCAGAGAATTCGAATA CAGTAGAAGCNNNCTAGCGTTAC | 832 | TGCAGGACCAGAGAATTCGAATA CAGCAATGTCNNNCTAGCGTTAC | 1072 | TGCAGGACCAGAGAATTCGAATA CACCCATGCCNNNCTAGCGTTAC | 1312 |
| TGCAGGACCAGAGAATTCGAATA CACAGCATTGNNNCTAGCGTTAC | 833 | TGCAGGACCAGAGAATTCGAATA CAGCCGGCATNNNCTAGCGTTAC | 1073 | TGCAGGACCAGAGAATTCGAATA CATTAGTTGANNNCTAGCGTTAC | 1313 |
| TGCAGGACCAGAGAATTCGAATA CACGCCTAGGNNNCTAGCGTTAC | 834 | TGCAGGACCAGAGAATTCGAATA CACTGAGCGCNNNCTAGCGTTAC | 1074 | TGCAGGACCAGAGAATTCGAATA CAATCAGAAANNNCTAGCGTTAC | 1314 |
| TGCAGGACCAGAGAATTCGAATA CACAGTTTGGNNNCTAGCGTTAC | 835 | TGCAGGACCAGAGAATTCGAATA CACTGCTGCCNNNCTAGCGTTAC | 1075 | TGCAGGACCAGAGAATTCGAATA CATTAGAACTNNNCTAGCGTTAC | 1315 |
| TGCAGGACCAGAGAATTCGAATA CATCCCAAGANNNCTAGCGTTAC | 836 | TGCAGGACCAGAGAATTCGAATA CAGTGGCGGANNNCTAGCGTTAC | 1076 | TGCAGGACCAGAGAATTCGAATA CAGTGCTATGNNNCTAGCGTTAC | 1316 |
| TGCAGGACCAGAGAATTCGAATA CATTAGGACCNNNCTAGCGTTAC | 837 | TGCAGGACCAGAGAATTCGAATA CAAGGCTACTNNNCTAGCGTTAC | 1077 | TGCAGGACCAGAGAATTCGAATA CATTGGATCGNNNCTAGCGTTAC | 1317 |
| TGCAGGACCAGAGAATTCGAATA CAACAATTTGNNNCTAGCGTTAC | 838 | TGCAGGACCAGAGAATTCGAATA CAACTTTGTTNNNCTAGCGTTAC | 1078 | TGCAGGACCAGAGAATTCGAATA CACAAGAATANNNCTAGCGTTAC | 1318 |
| TGCAGGACCAGAGAATTCGAATA CATGCTCGAANNNCTAGCGTTAC | 839 | TGCAGGACCAGAGAATTCGAATA CAGCCATATGNNNCTAGCGTTAC | 1079 | TGCAGGACCAGAGAATTCGAATA CAAGCACCATNNNCTAGCGTTAC | 1319 |
| TGCAGGACCAGAGAATTCGAATA CAGGCGGTAGNNNCTAGCGTTAC | 840 | TGCAGGACCAGAGAATTCGAATA CAAGCCTGGCNNNCTAGCGTTAC | 1080 | TGCAGGACCAGAGAATTCGAATA CAACTAGACCNNNCTAGCGTTAC | 1320 |
| TGCAGGACCAGAGAATTCGAATA CAAAATTAACNNNCTAGCGTTAC | 841 | TGCAGGACCAGAGAATTCGAATA CAACGTGTGTNNNCTAGCGTTAC | 1081 | TGCAGGACCAGAGAATTCGAATA CAATCATTAGNNNCTAGCGTTAC | 1321 |
| TGCAGGACCAGAGAATTCGAATA CACGACACGGNNNCTAGCGTTAC | 842 | TGCAGGACCAGAGAATTCGAATA CATTTTCATGNNNCTAGCGTTAC | 1082 | TGCAGGACCAGAGAATTCGAATA CAAGAACCTCNNNCTAGCGTTAC | 1322 |
| TGCAGGACCAGAGAATTCGAATA CAGTGAGGATNNNCTAGCGTTAC | 843 | TGCAGGACCAGAGAATTCGAATA CAGCTGCCGACNNNCTAGCGTTAC | 1083 | TGCAGGACCAGAGAATTCGAATA CAGATTTTCTNNNCTAGCGTTAC | 1323 |
| TGCAGGACCAGAGAATTCGAATA CAAAATTAAANNNCTAGCGTTAC | 844 | TGCAGGACCAGAGAATTCGAATA CACAAAATAGNNNCTAGCGTTAC | 1084 | TGCAGGACCAGAGAATTCGAATA CAAGTACGGANNNCTAGCGTTAC | 1324 |
| TGCAGGACCAGAGAATTCGAATA CACATGCCAANNNCTAGCGTTAC | 845 | TGCAGGACCAGAGAATTCGAATA CACTAAACTANNNCTAGCGTTAC | 1085 | TGCAGGACCAGAGAATTCGAATA CACGCGTAAANNNCTAGCGTTAC | 1325 |
| TGCAGGACCAGAGAATTCGAATA CACCATCAGANNNCTAGCGTTAC | 846 | TGCAGGACCAGAGAATTCGAATA CAAAATGATGNNNCTAGCGTTAC | 1086 | TGCAGGACCAGAGAATTCGAATA CAAGTTGGTCNNNCTAGCGTTAC | 1326 |
| TGCAGGACCAGAGAATTCGAATA CAATATAAAANNNCTAGCGTTAC | 847 | TGCAGGACCAGAGAATTCGAATA CACTTGCTTGNNNCTAGCGTTAC | 1087 | TGCAGGACCAGAGAATTCGAATA CATGCGCACGNNNCTAGCGTTAC | 1327 |
| TGCAGGACCAGAGAATTCGAATA CAGCCTCCGTNNNCTAGCGTTAC | 848 | TGCAGGACCAGAGAATTCGAATA CAGATAGGCANNNCTAGCGTTAC | 1088 | TGCAGGACCAGAGAATTCGAATA CATTGGTACGNNNCTAGCGTTAC | 1328 |
| TGCAGGACCAGAGAATTCGAATA CATCCAATCCNNNGATCGACATG | 849 | TGCAGGACCAGAGAATTCGAATA CACAGATTATNNNGATCGACATG | 1089 | TGCAGGACCAGAGAATTCGAATA CAATGAGATANNNGATCGACATG | 1329 |
| TGCAGGACCAGAGAATTCGAATA CAAAATGCCCNNNGATCGACATG | 850 | TGCAGGACCAGAGAATTCGAATA CAGTTACGGTNNNGATCGACATG | 1090 | TGCAGGACCAGAGAATTCGAATA CAATCGGTACNNNGATCGACATG | 1330 |
| TGCAGGACCAGAGAATTCGAATA CAACTGTCGANNNGATCGACATG | 851 | TGCAGGACCAGAGAATTCGAATA CAACAGTTGCNNNGATCGACATG | 1091 | TGCAGGACCAGAGAATTCGAATA CATGTCGTTCNNNGATCGACATG | 1331 |
| TGCAGGACCAGAGAATTCGAATA CAGCTGTTGANNNGATCGACATG | 852 | TGCAGGACCAGAGAATTCGAATA CAAACTGCACNNNGATCGACATG | 1092 | TGCAGGACCAGAGAATTCGAATA CATGTGTATANNNGATCGACATG | 1332 |
| TGCAGGACCAGAGAATTCGAATA CAGGTAACCTNNNGATCGACATG | 853 | TGCAGGACCAGAGAATTCGAATA CAAGAATATGNNNGATCGACATG | 1093 | TGCAGGACCAGAGAATTCGAATA CAGTGGATCTNNNGATCGACATG | 1333 |
| TGCAGGACCAGAGAATTCGAATA CACTTTTCCCNNNGATCGACATG | 854 | TGCAGGACCAGAGAATTCGAATA CATCGTCCTANNNGATCGACATG | 1094 | TGCAGGACCAGAGAATTCGAATA CATCTTCAATNNNGATCGACATG | 1334 |
| TGCAGGACCAGAGAATTCGAATA CAGAGAGCCGNNNGATCGACATG | 855 | TGCAGGACCAGAGAATTCGAATA CACAGCAATCNNNGATCGACATG | 1095 | TGCAGGACCAGAGAATTCGAATA CACGCGTGTGNNNGATCGACATG | 1335 |
| TGCAGGACCAGAGAATTCGAATA CACAGACAGANNNGATCGACATG | 856 | TGCAGGACCAGAGAATTCGAATA CACTTGACAGNNNGATCGACATG | 1096 | TGCAGGACCAGAGAATTCGAATA CACTCCTCGGNNNGATCGACATG | 1336 |

FIG. 13E

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CATATATGACNNNGATCGACATG | 857 | TGCAGGACCAGAGAATTCGAATA CACTGGTAGTNNNGATCGACATG | 1097 | TGCAGGACCAGAGAATTCGAATA CAGACTAATTNNNGATCGACATG | 1337 |
| TGCAGGACCAGAGAATTCGAATA CAGTCCGACGNNNGATCGACATG | 858 | TGCAGGACCAGAGAATTCGAATA CACGGATCTANNNGATCGACATG | 1098 | TGCAGGACCAGAGAATTCGAATA CACAATAAGANNNGATCGACATG | 1338 |
| TGCAGGACCAGAGAATTCGAATA CAACTGCATGNNNGATCGACATG | 859 | TGCAGGACCAGAGAATTCGAATA CAAAAAAGAGNNNGATCGACATG | 1099 | TGCAGGACCAGAGAATTCGAATA CATTTACCGCNNNGATCGACATG | 1339 |
| TGCAGGACCAGAGAATTCGAATA CATACCTAAANNNGATCGACATG | 860 | TGCAGGACCAGAGAATTCGAATA CAGGAGACATNNNGATCGACATG | 1100 | TGCAGGACCAGAGAATTCGAATA CAGTGTATTANNNGATCGACATG | 1340 |
| TGCAGGACCAGAGAATTCGAATA CAACCAGATCNNNGATCGACATG | 861 | TGCAGGACCAGAGAATTCGAATA CATCCGGAGCNNNGATCGACATG | 1101 | TGCAGGACCAGAGAATTCGAATA CAAGATGTAANNNGATCGACATG | 1341 |
| TGCAGGACCAGAGAATTCGAATA CAGGCAAATGNNNGATCGACATG | 862 | TGCAGGACCAGAGAATTCGAATA CATGTTATTCNNNGATCGACATG | 1102 | TGCAGGACCAGAGAATTCGAATA CATTATTCGTNNNGATCGACATG | 1342 |
| TGCAGGACCAGAGAATTCGAATA CAGAACGTCTNNNGATCGACATG | 863 | TGCAGGACCAGAGAATTCGAATA CAGCGAGACGNNNGATCGACATG | 1103 | TGCAGGACCAGAGAATTCGAATA CAAGTCACACNNNGATCGACATG | 1343 |
| TGCAGGACCAGAGAATTCGAATA CACCACCAAANNNGATCGACATG | 864 | TGCAGGACCAGAGAATTCGAATA CATTATCGAANNNGATCGACATG | 1104 | TGCAGGACCAGAGAATTCGAATA CACTGACAACNNNGATCGACATG | 1344 |
| TGCAGGACCAGAGAATTCGAATA CATTTTCCAANNNGATCGACATG | 865 | TGCAGGACCAGAGAATTCGAATA CAGTGCCAATNNNGATCGACATG | 1105 | TGCAGGACCAGAGAATTCGAATA CAACGCCGGTNNNGATCGACATG | 1345 |
| TGCAGGACCAGAGAATTCGAATA CAGTTAGTTANNNGATCGACATG | 866 | TGCAGGACCAGAGAATTCGAATA CAGCTAAAAANNNGATCGACATG | 1106 | TGCAGGACCAGAGAATTCGAATA CAGGTGACCCNNNGATCGACATG | 1346 |
| TGCAGGACCAGAGAATTCGAATA CATCAGCTCTNNNGATCGACATG | 867 | TGCAGGACCAGAGAATTCGAATA CAATCCAATANNNGATCGACATG | 1107 | TGCAGGACCAGAGAATTCGAATA CACCTTAGCTNNNGATCGACATG | 1347 |
| TGCAGGACCAGAGAATTCGAATA CATGCGGAGGNNNGATCGACATG | 868 | TGCAGGACCAGAGAATTCGAATA CATTCAAGGCNNNGATCGACATG | 1108 | TGCAGGACCAGAGAATTCGAATA CACTCGCTATNNNGATCGACATG | 1348 |
| TGCAGGACCAGAGAATTCGAATA CATCTGCAAGNNNGATCGACATG | 869 | TGCAGGACCAGAGAATTCGAATA CATTATTAAANNNGATCGACATG | 1109 | TGCAGGACCAGAGAATTCGAATA CAAGCCTAGTNNNGATCGACATG | 1349 |
| TGCAGGACCAGAGAATTCGAATA CATCTAACCCNNNGATCGACATG | 870 | TGCAGGACCAGAGAATTCGAATA CAAACTCTAANNNGATCGACATG | 1110 | TGCAGGACCAGAGAATTCGAATA CAGAGAGTTGNNNGATCGACATG | 1350 |
| TGCAGGACCAGAGAATTCGAATA CACGTAGGAANNNGATCGACATG | 871 | TGCAGGACCAGAGAATTCGAATA CAGACTCCAANNNGATCGACATG | 1111 | TGCAGGACCAGAGAATTCGAATA CATAAGAGGCNNNGATCGACATG | 1351 |
| TGCAGGACCAGAGAATTCGAATA CACAAGACTCNNNGATCGACATG | 872 | TGCAGGACCAGAGAATTCGAATA CACAGCCTCCNNNGATCGACATG | 1112 | TGCAGGACCAGAGAATTCGAATA CAGTTAATACNNNGATCGACATG | 1352 |
| TGCAGGACCAGAGAATTCGAATA CATTCCGTGTNNNGATCGACATG | 873 | TGCAGGACCAGAGAATTCGAATA CAGAGTCACTNNNGATCGACATG | 1113 | TGCAGGACCAGAGAATTCGAATA CAGGTCCGCANNNGATCGACATG | 1353 |
| TGCAGGACCAGAGAATTCGAATA CAGTGAACGANNNGATCGACATG | 874 | TGCAGGACCAGAGAATTCGAATA CAAGAACTGGNNNGATCGACATG | 1114 | TGCAGGACCAGAGAATTCGAATA CATAAGCATTNNNGATCGACATG | 1354 |
| TGCAGGACCAGAGAATTCGAATA CAGCTAAACCNNNGATCGACATG | 875 | TGCAGGACCAGAGAATTCGAATA CAGCGTATTGNNNGATCGACATG | 1115 | TGCAGGACCAGAGAATTCGAATA CAGTACGCATNNNGATCGACATG | 1355 |
| TGCAGGACCAGAGAATTCGAATA CACAATTTTCNNNGATCGACATG | 876 | TGCAGGACCAGAGAATTCGAATA CACTTAAATGNNNGATCGACATG | 1116 | TGCAGGACCAGAGAATTCGAATA CAAACGAACGNNNGATCGACATG | 1356 |
| TGCAGGACCAGAGAATTCGAATA CATGAGGAACNNNGATCGACATG | 877 | TGCAGGACCAGAGAATTCGAATA CATTAGCCTCNNNGATCGACATG | 1117 | TGCAGGACCAGAGAATTCGAATA CAGTAGGTTCNNNGATCGACATG | 1357 |
| TGCAGGACCAGAGAATTCGAATA CAGTAATCTANNNGATCGACATG | 878 | TGCAGGACCAGAGAATTCGAATA CAACCAGAGANNNGATCGACATG | 1118 | TGCAGGACCAGAGAATTCGAATA CACTTTTTTCNNNGATCGACATG | 1358 |
| TGCAGGACCAGAGAATTCGAATA CATATCTCCGNNNGATCGACATG | 879 | TGCAGGACCAGAGAATTCGAATA CATCAGCCAANNNGATCGACATG | 1119 | TGCAGGACCAGAGAATTCGAATA CAATGACCCANNNGATCGACATG | 1359 |
| TGCAGGACCAGAGAATTCGAATA CAGCTACGGCNNNGATCGACATG | 880 | TGCAGGACCAGAGAATTCGAATA CACCGAATACNNNGATCGACATG | 1120 | TGCAGGACCAGAGAATTCGAATA CAATCAGTTANNNGATCGACATG | 1360 |
| TGCAGGACCAGAGAATTCGAATA CAATATCTGANNNGATCGACATG | 881 | TGCAGGACCAGAGAATTCGAATA CAGCCGGCAAGNNNGATCGACATG | 1121 | TGCAGGACCAGAGAATTCGAATA CATAGTAAAGNNNGATCGACATG | 1361 |
| TGCAGGACCAGAGAATTCGAATA CATACTTAGANNNGATCGACATG | 882 | TGCAGGACCAGAGAATTCGAATA CATAAATCGTNNNGATCGACATG | 1122 | TGCAGGACCAGAGAATTCGAATA CACCCGATGGNNNGATCGACATG | 1362 |
| TGCAGGACCAGAGAATTCGAATA CATCATTTTGNNNGATCGACATG | 883 | TGCAGGACCAGAGAATTCGAATA CAAAGCTTCGNNNGATCGACATG | 1123 | TGCAGGACCAGAGAATTCGAATA CACACAGCATNNNGATCGACATG | 1363 |
| TGCAGGACCAGAGAATTCGAATA CAGCGTGGAGNNNGATCGACATG | 884 | TGCAGGACCAGAGAATTCGAATA CAATGCATATNNNGATCGACATG | 1124 | TGCAGGACCAGAGAATTCGAATA CACAGGTACTNNNGATCGACATG | 1364 |
| TGCAGGACCAGAGAATTCGAATA CATAAGACGGNNNGATCGACATG | 885 | TGCAGGACCAGAGAATTCGAATA CATCTCTCCTNNNGATCGACATG | 1125 | TGCAGGACCAGAGAATTCGAATA CACATAACCGNNNGATCGACATG | 1365 |
| TGCAGGACCAGAGAATTCGAATA CAAGGCCTTANNNGATCGACATG | 886 | TGCAGGACCAGAGAATTCGAATA CATAGTGGTCNNNGATCGACATG | 1126 | TGCAGGACCAGAGAATTCGAATA CAGTACTGGTNNNGATCGACATG | 1366 |
| TGCAGGACCAGAGAATTCGAATA CACATCTCACNNNGATCGACATG | 887 | TGCAGGACCAGAGAATTCGAATA CAGAAACCTCNNNGATCGACATG | 1127 | TGCAGGACCAGAGAATTCGAATA CAGCAAGTCNNNGATCGACATG | 1367 |
| TGCAGGACCAGAGAATTCGAATA CATGCGATCANNNGATCGACATG | 888 | TGCAGGACCAGAGAATTCGAATA CATGACTATANNNGATCGACATG | 1128 | TGCAGGACCAGAGAATTCGAATA CACGTGCTCCNNNGATCGACATG | 1368 |

FIG. 13F

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CACGGAGGACNNNGATCGACATG | 889 | TGCAGGACCAGAGAATTCGAATA CACATGACTGNNNGATCGACATG | 1129 | TGCAGGACCAGAGAATTCGAATA CACACTACCTNNNGATCGACATG | 1369 |
| TGCAGGACCAGAGAATTCGAATA CAACTAATTGNNNGATCGACATG | 890 | TGCAGGACCAGAGAATTCGAATA CACCCAAAGTCNNNGATCGACATG | 1130 | TGCAGGACCAGAGAATTCGAATA CAGTGTATATNNNGATCGACATG | 1370 |
| TGCAGGACCAGAGAATTCGAATA CATGCCTAGANNNGATCGACATG | 891 | TGCAGGACCAGAGAATTCGAATA CACGCATTCNNNGATCGACATG | 1131 | TGCAGGACCAGAGAATTCGAATA CAATGCGTNNNGATCGACATG | 1371 |
| TGCAGGACCAGAGAATTCGAATA CACTATCCGTNNNGATCGACATG | 892 | TGCAGGACCAGAGAATTCGAATA CAACCCGGTGNNNGATCGACATG | 1132 | TGCAGGACCAGAGAATTCGAATA CAAGGCACTTNNNGATCGACATG | 1372 |
| TGCAGGACCAGAGAATTCGAATA CATGCCAGGCNNNGATCGACATG | 893 | TGCAGGACCAGAGAATTCGAATA CACTTGCGTTNNNGATCGACATG | 1133 | TGCAGGACCAGAGAATTCGAATA CAGGCAGGCANNNGATCGACATG | 1373 |
| TGCAGGACCAGAGAATTCGAATA CAGCGGAGCANNNGATCGACATG | 894 | TGCAGGACCAGAGAATTCGAATA CATTATGCAANNNGATCGACATG | 1134 | TGCAGGACCAGAGAATTCGAATA CACTATGTTTNNNGATCGACATG | 1374 |
| TGCAGGACCAGAGAATTCGAATA CAAGACCCATNNNGATCGACATG | 895 | TGCAGGACCAGAGAATTCGAATA CATATTTGAGNNNGATCGACATG | 1135 | TGCAGGACCAGAGAATTCGAATA CATAAATATTNNNGATCGACATG | 1375 |
| TGCAGGACCAGAGAATTCGAATA CATTGACCTCNNNGATCGACATG | 896 | TGCAGGACCAGAGAATTCGAATA CATGTTCGCTNNNGATCGACATG | 1136 | TGCAGGACCAGAGAATTCGAATA CAGACACCATNNNGATCGACATG | 1376 |
| TGCAGGACCAGAGAATTCGAATA CACTTGCTCANNNGATCGACATG | 897 | TGCAGGACCAGAGAATTCGAATA CATAGCATCGNNNGATCGACATG | 1137 | TGCAGGACCAGAGAATTCGAATA CATAGATACTNNNGATCGACATG | 1377 |
| TGCAGGACCAGAGAATTCGAATA CAATGCTGCANNNGATCGACATG | 898 | TGCAGGACCAGAGAATTCGAATA CATTCAGAGCNNNGATCGACATG | 1138 | TGCAGGACCAGAGAATTCGAATA CATACCCTGTNNNGATCGACATG | 1378 |
| TGCAGGACCAGAGAATTCGAATA CAAACGGACANNNGATCGACATG | 899 | TGCAGGACCAGAGAATTCGAATA CAAACGCGANNNGATCGACATG | 1139 | TGCAGGACCAGAGAATTCGAATA CAGTCGCCGANNNGATCGACATG | 1379 |
| TGCAGGACCAGAGAATTCGAATA CAGCGATCATNNNGATCGACATG | 900 | TGCAGGACCAGAGAATTCGAATA CATATGGCGTNNNGATCGACATG | 1140 | TGCAGGACCAGAGAATTCGAATA CACCTCTTAGNNNGATCGACATG | 1380 |
| TGCAGGACCAGAGAATTCGAATA CATGAGACAGNNNGATCGACATG | 901 | TGCAGGACCAGAGAATTCGAATA CAAGCCTATGNNNGATCGACATG | 1141 | TGCAGGACCAGAGAATTCGAATA CATAAGATTCNNNGATCGACATG | 1381 |
| TGCAGGACCAGAGAATTCGAATA CAGCCACTGGNNNGATCGACATG | 902 | TGCAGGACCAGAGAATTCGAATA CACACTCTACNNNGATCGACATG | 1142 | TGCAGGACCAGAGAATTCGAATA CACGCGTACGNNNGATCGACATG | 1382 |
| TGCAGGACCAGAGAATTCGAATA CAGGTTTGACNNNGATCGACATG | 903 | TGCAGGACCAGAGAATTCGAATA CAAAACTGAANNNGATCGACATG | 1143 | TGCAGGACCAGAGAATTCGAATA CACTGACCAANNNGATCGACATG | 1383 |
| TGCAGGACCAGAGAATTCGAATA CAAACTTGGCNNNGATCGACATG | 904 | TGCAGGACCAGAGAATTCGAATA CACTTCCGCGNNNGATCGACATG | 1144 | TGCAGGACCAGAGAATTCGAATA CAAAGACCGANNNGATCGACATG | 1384 |
| TGCAGGACCAGAGAATTCGAATA CAACCTAATANNNGATCGACATG | 905 | TGCAGGACCAGAGAATTCGAATA CAACGTCGGCNNNGATCGACATG | 1145 | TGCAGGACCAGAGAATTCGAATA CAAATGATTCNNNGATCGACATG | 1385 |
| TGCAGGACCAGAGAATTCGAATA CAGCCACAGAANNNGATCGACATG | 906 | TGCAGGACCAGAGAATTCGAATA CAGTACCAANNNGATCGACATG | 1146 | TGCAGGACCAGAGAATTCGAATA CACCCCCCAANNNGATCGACATG | 1386 |
| TGCAGGACCAGAGAATTCGAATA CATGTGTCAGNNNGATCGACATG | 907 | TGCAGGACCAGAGAATTCGAATA CAACCGCATANNNGATCGACATG | 1147 | TGCAGGACCAGAGAATTCGAATA CAGCCTGAATNNNGATCGACATG | 1387 |
| TGCAGGACCAGAGAATTCGAATA CAAGTAACAANNNGATCGACATG | 908 | TGCAGGACCAGAGAATTCGAATA CAAACCAGCTNNNGATCGACATG | 1148 | TGCAGGACCAGAGAATTCGAATA CATCGGTAGTNNNGATCGACATG | 1388 |
| TGCAGGACCAGAGAATTCGAATA CATCTGAGCANNNTGCATCAGGT | 909 | TGCAGGACCAGAGAATTCGAATA CAGAGCCAGCNNNTGCATCAGGT | 1149 | TGCAGGACCAGAGAATTCGAATA CATGGCTCGGNNNTGCATCAGGT | 1389 |
| TGCAGGACCAGAGAATTCGAATA CAAGTGGAACNNNTGCATCAGGT | 910 | TGCAGGACCAGAGAATTCGAATA CATTTTATTANNNTGCATCAGGT | 1150 | TGCAGGACCAGAGAATTCGAATA CACAATCCTCNNNTGCATCAGGT | 1390 |
| TGCAGGACCAGAGAATTCGAATA CAGAACTCGTNNNTGCATCAGGT | 911 | TGCAGGACCAGAGAATTCGAATA CAGCTAGGTTNNNTGCATCAGGT | 1151 | TGCAGGACCAGAGAATTCGAATA CATAGAGACGNNNTGCATCAGGT | 1391 |
| TGCAGGACCAGAGAATTCGAATA CAGCAGGCGANNNTGCATCAGGT | 912 | TGCAGGACCAGAGAATTCGAATA CATTTGACTTNNNTGCATCAGGT | 1152 | TGCAGGACCAGAGAATTCGAATA CAGCGGATGGNNNTGCATCAGGT | 1392 |
| TGCAGGACCAGAGAATTCGAATA CAGGCTCTCCNNNTGCATCAGGT | 913 | TGCAGGACCAGAGAATTCGAATA CACAAACATTNNNTGCATCAGGT | 1153 | TGCAGGACCAGAGAATTCGAATA CACTCACCATNNNTGCATCAGGT | 1393 |
| TGCAGGACCAGAGAATTCGAATA CAAATACATCNNNTGCATCAGGT | 914 | TGCAGGACCAGAGAATTCGAATA CATTGCAATANNNTGCATCAGGT | 1154 | TGCAGGACCAGAGAATTCGAATA CAATGGTAAANNNTGCATCAGGT | 1394 |
| TGCAGGACCAGAGAATTCGAATA CAAGGGTCAAGNNNTGCATCAGGT | 915 | TGCAGGACCAGAGAATTCGAATA CAACAAGGCANNNTGCATCAGGT | 1155 | TGCAGGACCAGAGAATTCGAATA CATATCAACANNNTGCATCAGGT | 1395 |
| TGCAGGACCAGAGAATTCGAATA CATGAGCCGCNNNTGCATCAGGT | 916 | TGCAGGACCAGAGAATTCGAATA CAGGTGCTGCNNNTGCATCAGGT | 1156 | TGCAGGACCAGAGAATTCGAATA CAAAAGTCAANNNTGCATCAGGT | 1396 |
| TGCAGGACCAGAGAATTCGAATA CATTAGTTTCNNNTGCATCAGGT | 917 | TGCAGGACCAGAGAATTCGAATA CAAGGTCGTTNNNTGCATCAGGT | 1157 | TGCAGGACCAGAGAATTCGAATA CACAAAGGCANNNTGCATCAGGT | 1397 |
| TGCAGGACCAGAGAATTCGAATA CAGTCGTAGTNNNTGCATCAGGT | 918 | TGCAGGACCAGAGAATTCGAATA CACAACGGAANNNTGCATCAGGT | 1158 | TGCAGGACCAGAGAATTCGAATA CACGATGACTNNNTGCATCAGGT | 1398 |
| TGCAGGACCAGAGAATTCGAATA CAAAAGGATTNNNTGCATCAGGT | 919 | TGCAGGACCAGAGAATTCGAATA CAGATCCAAGTNNNTGCATCAGGT | 1159 | TGCAGGACCAGAGAATTCGAATA CACGATTGTGNNNTGCATCAGGT | 1399 |
| TGCAGGACCAGAGAATTCGAATA CATTTTTAGCNNNTGCATCAGGT | 920 | TGCAGGACCAGAGAATTCGAATA CAGGAAGACTNNNTGCATCAGGT | 1160 | TGCAGGACCAGAGAATTCGAATA CATTATCTTGNNNTGCATCAGGT | 1400 |

FIG. 13G

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CAATAACTCANNNTGCATCAGGT | 921 | TGCAGGACCAGAGAATTCGAATA CAGGTAAATANNNTGCATCAGGT | 1161 | TGCAGGACCAGAGAATTCGAATA CAGTATTGATNNNTGCATCAGGT | 1401 |
| TGCAGGACCAGAGAATTCGAATA CATTTTAACCNNNTGCATCAGGT | 922 | TGCAGGACCAGAGAATTCGAATA CAGGTAGAACNNNTGCATCAGGT | 1162 | TGCAGGACCAGAGAATTCGAATA CAAGGAGGTTNNNTGCATCAGGT | 1402 |
| TGCAGGACCAGAGAATTCGAATA CAGTGCCGACNNNTGCATCAGGT | 923 | TGCAGGACCAGAGAATTCGAATA CAATATGAGANNNTGCATCAGGT | 1163 | TGCAGGACCAGAGAATTCGAATA CAACTGCCCCNNNTGCATCAGGT | 1403 |
| TGCAGGACCAGAGAATTCGAATA CAGAATAGATNNNTGCATCAGGT | 924 | TGCAGGACCAGAGAATTCGAATA CATGGAAATANNNTGCATCAGGT | 1164 | TGCAGGACCAGAGAATTCGAATA CAAAATCTCANNNTGCATCAGGT | 1404 |
| TGCAGGACCAGAGAATTCGAATA CAGCTGAGCNNNTGCATCAGGT | 925 | TGCAGGACCAGAGAATTCGAATA CATAACCAATNNNTGCATCAGGT | 1165 | TGCAGGACCAGAGAATTCGAATA CACCATGTGANNNTGCATCAGGT | 1405 |
| TGCAGGACCAGAGAATTCGAATA CAACAGGCAANNNTGCATCAGGT | 926 | TGCAGGACCAGAGAATTCGAATA CAGTCTGATGNNNTGCATCAGGT | 1166 | TGCAGGACCAGAGAATTCGAATA CACCCCTTTTNNNTGCATCAGGT | 1406 |
| TGCAGGACCAGAGAATTCGAATA CAGACCGCACNNNTGCATCAGGT | 927 | TGCAGGACCAGAGAATTCGAATA CATTTATGAGNNNTGCATCAGGT | 1167 | TGCAGGACCAGAGAATTCGAATA CAGCTAGCGCNNNTGCATCAGGT | 1407 |
| TGCAGGACCAGAGAATTCGAATA CACTTATTCANNNTGCATCAGGT | 928 | TGCAGGACCAGAGAATTCGAATA CAATGATTTGNNNTGCATCAGGT | 1168 | TGCAGGACCAGAGAATTCGAATA CAAACACCGCNNNTGCATCAGGT | 1408 |
| TGCAGGACCAGAGAATTCGAATA CAGTGTGCTANNNTGCATCAGGT | 929 | TGCAGGACCAGAGAATTCGAATA CACTCATCGTNNNTGCATCAGGT | 1169 | TGCAGGACCAGAGAATTCGAATA CACTGAGATCNNNTGCATCAGGT | 1409 |
| TGCAGGACCAGAGAATTCGAATA CAATTTASTGNNNTGCATCAGGT | 930 | TGCAGGACCAGAGAATTCGAATA CACTCCATACNNNTGCATCAGGT | 1170 | TGCAGGACCAGAGAATTCGAATA CAAATGCGTCNNNTGCATCAGGT | 1410 |
| TGCAGGACCAGAGAATTCGAATA CATCGGAGAANNNTGCATCAGGT | 931 | TGCAGGACCAGAGAATTCGAATA CAGCTAGCATNNNTGCATCAGGT | 1171 | TGCAGGACCAGAGAATTCGAATA CAATTGCCAGNNNTGCATCAGGT | 1411 |
| TGCAGGACCAGAGAATTCGAATA CACGCCGAACNNNTGCATCAGGT | 932 | TGCAGGACCAGAGAATTCGAATA CAAATCATCANNNTGCATCAGGT | 1172 | TGCAGGACCAGAGAATTCGAATA CATTAATTCCNNNTGCATCAGGT | 1412 |
| TGCAGGACCAGAGAATTCGAATA CAGCTTCGCCNNNTGCATCAGGT | 933 | TGCAGGACCAGAGAATTCGAATA CACGTCTCATNNNTGCATCAGGT | 1173 | TGCAGGACCAGAGAATTCGAATA CAAGCATATTNNNTGCATCAGGT | 1413 |
| TGCAGGACCAGAGAATTCGAATA CAACAATCATNNNTGCATCAGGT | 934 | TGCAGGACCAGAGAATTCGAATA CAACTCGTTCNNNTGCATCAGGT | 1174 | TGCAGGACCAGAGAATTCGAATA CACCCATTACNNNTGCATCAGGT | 1414 |
| TGCAGGACCAGAGAATTCGAATA CATGATCGCANNNTGCATCAGGT | 935 | TGCAGGACCAGAGAATTCGAATA CAAGTTCTGGNNNTGCATCAGGT | 1175 | TGCAGGACCAGAGAATTCGAATA CACTCGTTTGNNNTGCATCAGGT | 1415 |
| TGCAGGACCAGAGAATTCGAATA CACACAGTACNNNTGCATCAGGT | 936 | TGCAGGACCAGAGAATTCGAATA CAACTAGTATNNNTGCATCAGGT | 1176 | TGCAGGACCAGAGAATTCGAATA CAGGTATCGTNNNTGCATCAGGT | 1416 |
| TGCAGGACCAGAGAATTCGAATA CAGTCAAGTCNNNTGCATCAGGT | 937 | TGCAGGACCAGAGAATTCGAATA CAATTGCGCANNNTGCATCAGGT | 1177 | TGCAGGACCAGAGAATTCGAATA CAGTACCCTTNNNTGCATCAGGT | 1417 |
| TGCAGGACCAGAGAATTCGAATA CAGCTCCCACNNNTGCATCAGGT | 938 | TGCAGGACCAGAGAATTCGAATA CACGAGCGCTNNNTGCATCAGGT | 1178 | TGCAGGACCAGAGAATTCGAATA CACAACTTTTNNNTGCATCAGGT | 1418 |
| TGCAGGACCAGAGAATTCGAATA CATTACTTGTNNNTGCATCAGGT | 939 | TGCAGGACCAGAGAATTCGAATA CAACGACCATNNNTGCATCAGGT | 1179 | TGCAGGACCAGAGAATTCGAATA CAGAACTTGCNNNTGCATCAGGT | 1419 |
| TGCAGGACCAGAGAATTCGAATA CATAATGTGTNNNTGCATCAGGT | 940 | TGCAGGACCAGAGAATTCGAATA CATAAGTGAANNNTGCATCAGGT | 1180 | TGCAGGACCAGAGAATTCGAATA CATATTATGGNNNTGCATCAGGT | 1420 |
| TGCAGGACCAGAGAATTCGAATA CATACCATTTNNNTGCATCAGGT | 941 | TGCAGGACCAGAGAATTCGAATA CATCTCGCCGNNNTGCATCAGGT | 1181 | TGCAGGACCAGAGAATTCGAATA CAGCCCGCCGNNNTGCATCAGGT | 1421 |
| TGCAGGACCAGAGAATTCGAATA CAGTCCGTAANNNTGCATCAGGT | 942 | TGCAGGACCAGAGAATTCGAATA CAAATACTGTNNNTGCATCAGGT | 1182 | TGCAGGACCAGAGAATTCGAATA CAGCAAAGCNNNTGCATCAGGT | 1422 |
| TGCAGGACCAGAGAATTCGAATA CAAGCGGTAANNNTGCATCAGGT | 943 | TGCAGGACCAGAGAATTCGAATA CATATGTTCTNNNTGCATCAGGT | 1183 | TGCAGGACCAGAGAATTCGAATA CAGATACGCTNNNTGCATCAGGT | 1423 |
| TGCAGGACCAGAGAATTCGAATA CAGGAAACTGNNNTGCATCAGGT | 944 | TGCAGGACCAGAGAATTCGAATA CACCAGCGGTNNNTGCATCAGGT | 1184 | TGCAGGACCAGAGAATTCGAATA CACAGTATCGNNNTGCATCAGGT | 1424 |
| TGCAGGACCAGAGAATTCGAATA CAGGCCACGTNNNTGCATCAGGT | 945 | TGCAGGACCAGAGAATTCGAATA CACGGTTGATNNNTGCATCAGGT | 1185 | TGCAGGACCAGAGAATTCGAATA CACTCACTGTNNNTGCATCAGGT | 1425 |
| TGCAGGACCAGAGAATTCGAATA CATCATTGAANNNTGCATCAGGT | 946 | TGCAGGACCAGAGAATTCGAATA CACGCGTCAGNNNTGCATCAGGT | 1186 | TGCAGGACCAGAGAATTCGAATA CACCCGTCAGGNNNTGCATCAGGT | 1426 |
| TGCAGGACCAGAGAATTCGAATA CAGCGTCAATNNNTGCATCAGGT | 947 | TGCAGGACCAGAGAATTCGAATA CAGTCTAAATNNNTGCATCAGGT | 1187 | TGCAGGACCAGAGAATTCGAATA CAGCTTCTGTNNNTGCATCAGGT | 1427 |
| TGCAGGACCAGAGAATTCGAATA CACGGAAGCGNNNTGCATCAGGT | 948 | TGCAGGACCAGAGAATTCGAATA CAGTAATTACNNNTGCATCAGGT | 1188 | TGCAGGACCAGAGAATTCGAATA CATTATATTTNNNTGCATCAGGT | 1428 |
| TGCAGGACCAGAGAATTCGAATA CAGTTCGAACNNNTGCATCAGGT | 949 | TGCAGGACCAGAGAATTCGAATA CATTCCGGTTNNNTGCATCAGGT | 1189 | TGCAGGACCAGAGAATTCGAATA CAGGTTTACGNNNTGCATCAGGT | 1429 |
| TGCAGGACCAGAGAATTCGAATA CAGGCCCCTTNNNTGCATCAGGT | 950 | TGCAGGACCAGAGAATTCGAATA CAGAGCGTGGNNNTGCATCAGGT | 1190 | TGCAGGACCAGAGAATTCGAATA CAGGACGATANNNTGCATCAGGT | 1430 |
| TGCAGGACCAGAGAATTCGAATA CAATGGCTCANNNTGCATCAGGT | 951 | TGCAGGACCAGAGAATTCGAATA CAATTTACTCNNNTGCATCAGGT | 1191 | TGCAGGACCAGAGAATTCGAATA CAAGTCAGGANNNTGCATCAGGT | 1431 |
| TGCAGGACCAGAGAATTCGAATA CATTGACGGTNNNTGCATCAGGT | 952 | TGCAGGACCAGAGAATTCGAATA CACAACACTGNNNTGCATCAGGT | 1192 | TGCAGGACCAGAGAATTCGAATA CACTACGAACNNNTGCATCAGGT | 1432 |

FIG. 13H

| Pool-4 | SEQ ID NO: | Pool-5 | SEQ ID NO: | Pool-6 | SEQ ID NO: |
|---|---|---|---|---|---|
| TGCAGGACCAGAGAATTCGAATA CATGGACGTTNNNTGCATCAGGT | 953 | TGCAGGACCAGAGAATTCGAATA CACCGCGGCGNNNTGCATCAGGT | 1193 | TGCAGGACCAGAGAATTCGAATA CAAGCCATGTNNNTGCATCAGGT | 1433 |
| TGCAGGACCAGAGAATTCGAATA CATGACAGTCNNNTGCATCAGGT | 954 | TGCAGGACCAGAGAATTCGAATA CACTAAGCTGNNNTGCATCAGGT | 1194 | TGCAGGACCAGAGAATTCGAATA CATTCCACTGNNNTGCATCAGGT | 1434 |
| TGCAGGACCAGAGAATTCGAATA CACTACCTGTNNNTGCATCAGGT | 955 | TGCAGGACCAGAGAATTCGAATA CAATTCAAGTNNNTGCATCAGGT | 1195 | TGCAGGACCAGAGAATTCGAATA CAACCCTGTTNNNTGCATCAGGT | 1435 |
| TGCAGGACCAGAGAATTCGAATA CAAGGTCCCGNNNTGCATCAGGT | 956 | TGCAGGACCAGAGAATTCGAATA CAATTGGCGTNNNTGCATCAGGT | 1196 | TGCAGGACCAGAGAATTCGAATA CACCCTTTCTNNNTGCATCAGGT | 1436 |
| TGCAGGACCAGAGAATTCGAATA CATTCATCTANNNTGCATCAGGT | 957 | TGCAGGACCAGAGAATTCGAATA CATGATTTGANNNTGCATCAGGT | 1197 | TGCAGGACCAGAGAATTCGAATA CAATGTTGATNNNTGCATCAGGT | 1437 |
| TGCAGGACCAGAGAATTCGAATA CAGATAAAGTNNNTGCATCAGGT | 958 | TGCAGGACCAGAGAATTCGAATA CAACTGCCGGNNNTGCATCAGGT | 1198 | TGCAGGACCAGAGAATTCGAATA CACACTGGCGNNNTGCATCAGGT | 1438 |
| TGCAGGACCAGAGAATTCGAATA CACACGGAAANNNTGCATCAGGT | 959 | TGCAGGACCAGAGAATTCGAATA CATTAATCCTNNNTGCATCAGGT | 1199 | TGCAGGACCAGAGAATTCGAATA CATTCGGTAGNNNTGCATCAGGT | 1439 |
| TGCAGGACCAGAGAATTCGAATA CATGTGAGGANNNTGCATCAGGT | 960 | TGCAGGACCAGAGAATTCGAATA CACTACGCTTNNNTGCATCAGGT | 1200 | TGCAGGACCAGAGAATTCGAATA CAACCCTGCCNNNTGCATCAGGT | 1440 |
| TGCAGGACCAGAGAATTCGAATA CACGTGATCANNNTGCATCAGGT | 961 | TGCAGGACCAGAGAATTCGAATA CATAGCTATANNNTGCATCAGGT | 1201 | TGCAGGACCAGAGAATTCGAATA CAGTACCTAGNNNTGCATCAGGT | 1441 |
| TGCAGGACCAGAGAATTCGAATA CATGCGTTGANNNTGCATCAGGT | 962 | TGCAGGACCAGAGAATTCGAATA CATGCACTCTNNNTGCATCAGGT | 1202 | TGCAGGACCAGAGAATTCGAATA CACGATAATTNNNTGCATCAGGT | 1442 |
| TGCAGGACCAGAGAATTCGAATA CATCGCTCCGNNNTGCATCAGGT | 963 | TGCAGGACCAGAGAATTCGAATA CAGTGCTCCCNNNTGCATCAGGT | 1203 | TGCAGGACCAGAGAATTCGAATA CAGCCAACCGNNNTGCATCAGGT | 1443 |
| TGCAGGACCAGAGAATTCGAATA CACCAGTCAANNNTGCATCAGGT | 964 | TGCAGGACCAGAGAATTCGAATA CAGCCACCAGNNNTGCATCAGGT | 1204 | TGCAGGACCAGAGAATTCGAATA CATAACATCANNNTGCATCAGGT | 1444 |
| TGCAGGACCAGAGAATTCGAATA CACACATTCCNNNTGCATCAGGT | 965 | TGCAGGACCAGAGAATTCGAATA CATTATGTGANNNTGCATCAGGT | 1205 | TGCAGGACCAGAGAATTCGAATA CAGCCAAGAACNNNTGCATCAGGT | 1445 |
| TGCAGGACCAGAGAATTCGAATA CAGGTATATTNNNTGCATCAGGT | 966 | TGCAGGACCAGAGAATTCGAATA CAATACTCCCNNNTGCATCAGGT | 1206 | TGCAGGACCAGAGAATTCGAATA CAACGTGATCNNNTGCATCAGGT | 1446 |
| TGCAGGACCAGAGAATTCGAATA CATAAGATGANNNTGCATCAGGT | 967 | TGCAGGACCAGAGAATTCGAATA CAACTATGGCNNNTGCATCAGGT | 1207 | TGCAGGACCAGAGAATTCGAATA CACGTTCCTANNNTGCATCAGGT | 1447 |
| TGCAGGACCAGAGAATTCGAATA CATTAAAATTNNNTGCATCAGGT | 968 | TGCAGGACCAGAGAATTCGAATA CAACGGCCTGNNNTGCATCAGGT | 1208 | TGCAGGACCAGAGAATTCGAATA CAATGCCAGTNNNTGCATCAGGT | 1448 |

FIG. 14A

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CACAGGCTCGNNNACGTATGCCA | 1449 | TGCAGGACCAGAGAATTCGAATA CAACTACCAGNNNACGTATGCCA | 1689 | TGCAGGACCAGAGAATTCGAATA CAGAACGCCCNNNACGTATGCCA | 1929 |
| TGCAGGACCAGAGAATTCGAATA CATTGAAGCCNNNACGTATGCCA | 1450 | TGCAGGACCAGAGAATTCGAATA CATTATTGAGNNNACGTATGCCA | 1690 | TGCAGGACCAGAGAATTCGAATA CAACCAATGCNNNACGTATGCCA | 1930 |
| TGCAGGACCAGAGAATTCGAATA CACACAGAGANNNACGTATGCCA | 1451 | TGCAGGACCAGAGAATTCGAATA CAACTGTGTGNNNACGTATGCCA | 1691 | TGCAGGACCAGAGAATTCGAATA CAGACCGATTNNNACGTATGCCA | 1931 |
| TGCAGGACCAGAGAATTCGAATA CAGGACTCCGNNNACGTATGCCA | 1452 | TGCAGGACCAGAGAATTCGAATA CATTGATCGGNNNACGTATGCCA | 1692 | TGCAGGACCAGAGAATTCGAATA CAATGTTATGNNNACGTATGCCA | 1932 |
| TGCAGGACCAGAGAATTCGAATA CATTGGTTAANNNACGTATGCCA | 1453 | TGCAGGACCAGAGAATTCGAATA CATTCTCGGTNNNACGTATGCCA | 1693 | TGCAGGACCAGAGAATTCGAATA CAGGAAGAAGNNNACGTATGCCA | 1933 |
| TGCAGGACCAGAGAATTCGAATA CATACTAACANNNACGTATGCCA | 1454 | TGCAGGACCAGAGAATTCGAATA CACCCAGTTAGNNNACGTATGCCA | 1694 | TGCAGGACCAGAGAATTCGAATA CAGTTATACANNNACGTATGCCA | 1934 |
| TGCAGGACCAGAGAATTCGAATA CAGTCCAATGNNNACGTATGCCA | 1455 | TGCAGGACCAGAGAATTCGAATA CAAGAACAATNNNACGTATGCCA | 1695 | TGCAGGACCAGAGAATTCGAATA CACCTCCTAANNNACGTATGCCA | 1935 |
| TGCAGGACCAGAGAATTCGAATA CAAGGCACGGNNNACGTATGCCA | 1456 | TGCAGGACCAGAGAATTCGAATA CATCCGAAGTNNNACGTATGCCA | 1696 | TGCAGGACCAGAGAATTCGAATA CATAAACATCNNNACGTATGCCA | 1936 |
| TGCAGGACCAGAGAATTCGAATA CAATCATGTANNNACGTATGCCA | 1457 | TGCAGGACCAGAGAATTCGAATA CATCGGCTCCNNNACGTATGCCA | 1697 | TGCAGGACCAGAGAATTCGAATA CACGGCGGTTNNNACGTATGCCA | 1937 |
| TGCAGGACCAGAGAATTCGAATA CAAAAAGGTTNNNACGTATGCCA | 1458 | TGCAGGACCAGAGAATTCGAATA CACAGTCCCCNNNACGTATGCCA | 1698 | TGCAGGACCAGAGAATTCGAATA CATTAACAACNNNACGTATGCCA | 1938 |
| TGCAGGACCAGAGAATTCGAATA CAAGGCACCCNNNACGTATGCCA | 1459 | TGCAGGACCAGAGAATTCGAATA CAGTCAACTGNNNACGTATGCCA | 1699 | TGCAGGACCAGAGAATTCGAATA CATGGCCATANNNACGTATGCCA | 1939 |
| TGCAGGACCAGAGAATTCGAATA CATTGAAAGANNNACGTATGCCA | 1460 | TGCAGGACCAGAGAATTCGAATA CAGGCGGCTTNNNACGTATGCCA | 1700 | TGCAGGACCAGAGAATTCGAATA CAGAGTGATGNNNACGTATGCCA | 1940 |
| TGCAGGACCAGAGAATTCGAATA CACTCGACTTNNNACGTATGCCA | 1461 | TGCAGGACCAGAGAATTCGAATA CAATGCGCTANNNACGTATGCCA | 1701 | TGCAGGACCAGAGAATTCGAATA CACTAATGCGNNNACGTATGCCA | 1941 |
| TGCAGGACCAGAGAATTCGAATA CACCGAATTCNNNACGTATGCCA | 1462 | TGCAGGACCAGAGAATTCGAATA CAGCTCCGANNNACGTATGCCA | 1702 | TGCAGGACCAGAGAATTCGAATA CAAGGTTAAANNNACGTATGCCA | 1942 |
| TGCAGGACCAGAGAATTCGAATA CACCCCCGCGNNNACGTATGCCA | 1463 | TGCAGGACCAGAGAATTCGAATA CATGCTGGCGNNNACGTATGCCA | 1703 | TGCAGGACCAGAGAATTCGAATA CAACAGTACCNNNACGTATGCCA | 1943 |
| TGCAGGACCAGAGAATTCGAATA CAGATAAGCGNNNACGTATGCCA | 1464 | TGCAGGACCAGAGAATTCGAATA CACTAACGTGNNNACGTATGCCA | 1704 | TGCAGGACCAGAGAATTCGAATA CAATGTGATTNNNACGTATGCCA | 1944 |
| TGCAGGACCAGAGAATTCGAATA CAGAACGATGNNNACGTATGCCA | 1465 | TGCAGGACCAGAGAATTCGAATA CAGAATACAANNNACGTATGCCA | 1705 | TGCAGGACCAGAGAATTCGAATA CAGCTGCCGANNNACGTATGCCA | 1945 |
| TGCAGGACCAGAGAATTCGAATA CAAATATTATNNNACGTATGCCA | 1466 | TGCAGGACCAGAGAATTCGAATA CAATGACAANNNACGTATGCCA | 1706 | TGCAGGACCAGAGAATTCGAATA CACTTTTTAGNNNACGTATGCCA | 1946 |
| TGCAGGACCAGAGAATTCGAATA CATAAGCTATNNNACGTATGCCA | 1467 | TGCAGGACCAGAGAATTCGAATA CAACGGCTCGNNNACGTATGCCA | 1707 | TGCAGGACCAGAGAATTCGAATA CATCCCAAAGNNNACGTATGCCA | 1947 |
| TGCAGGACCAGAGAATTCGAATA CAACTCGGCGNNNACGTATGCCA | 1468 | TGCAGGACCAGAGAATTCGAATA CAACAGATAANNNACGTATGCCA | 1708 | TGCAGGACCAGAGAATTCGAATA CAGACACTACNNNACGTATGCCA | 1948 |
| TGCAGGACCAGAGAATTCGAATA CACGACTGCGNNNACGTATGCCA | 1469 | TGCAGGACCAGAGAATTCGAATA CATGTAGCCANNNACGTATGCCA | 1709 | TGCAGGACCAGAGAATTCGAATA CAATACCGACNNNACGTATGCCA | 1949 |
| TGCAGGACCAGAGAATTCGAATA CATCCGACTTNNNACGTATGCCA | 1470 | TGCAGGACCAGAGAATTCGAATA CACTTCTGCANNNACGTATGCCA | 1710 | TGCAGGACCAGAGAATTCGAATA CAGTTGAAAANNNACGTATGCCA | 1950 |
| TGCAGGACCAGAGAATTCGAATA CAGGAGGAGGNNNACGTATGCCA | 1471 | TGCAGGACCAGAGAATTCGAATA CATTACCTTANNNACGTATGCCA | 1711 | TGCAGGACCAGAGAATTCGAATA CAATTTCCTANNNACGTATGCCA | 1951 |
| TGCAGGACCAGAGAATTCGAATA CACAGGCAGGNNNACGTATGCCA | 1472 | TGCAGGACCAGAGAATTCGAATA CATCAATTCTNNNACGTATGCCA | 1712 | TGCAGGACCAGAGAATTCGAATA CAACGTTCAGNNNACGTATGCCA | 1952 |
| TGCAGGACCAGAGAATTCGAATA CAATCTCATTNNNACGTATGCCA | 1473 | TGCAGGACCAGAGAATTCGAATA CAAGGTTCGTNNNACGTATGCCA | 1713 | TGCAGGACCAGAGAATTCGAATA CAAATACGAANNNACGTATGCCA | 1953 |
| TGCAGGACCAGAGAATTCGAATA CAAGGCGATANNNACGTATGCCA | 1474 | TGCAGGACCAGAGAATTCGAATA CAATTTTAAANNNACGTATGCCA | 1714 | TGCAGGACCAGAGAATTCGAATA CACCAACTGANNNACGTATGCCA | 1954 |
| TGCAGGACCAGAGAATTCGAATA CACCTAGATGNNNACGTATGCCA | 1475 | TGCAGGACCAGAGAATTCGAATA CATTGCAGACNNNACGTATGCCA | 1715 | TGCAGGACCAGAGAATTCGAATA CAATCCGTCTNNNACGTATGCCA | 1955 |
| TGCAGGACCAGAGAATTCGAATA CACCTACCATNNNACGTATGCCA | 1476 | TGCAGGCCACTGAGAATTCGAATA CACCCCACTGNNNACGTATGCCA | 1716 | TGCAGGACCAGAGAATTCGAATA CACGTCCGCTNNNACGTATGCCA | 1956 |

FIG. 14B

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAAACGTCCANNNACGTATGCCA | 1477 | TGCAGGACCAGAGAATTCGAATA CACTTCCTGANNNACGTATGCCA | 1717 | TGCAGGACCAGAGAATTCGAATA CATATACACANNNACGTATGCCA | 1957 |
| TGCAGGACCAGAGAATTCGAATA CAGCACTTAGNNNACGTATGCCA | 1478 | TGCAGGACCAGAGAATTCGAATA CAAGAACTCCNNNACGTATGCCA | 1718 | TGCAGGACCAGAGAATTCGAATA CACTCTATATNNNACGTATGCCA | 1958 |
| TGCAGGACCAGAGAATTCGAATA CAGATCGGAANNNACGTATGCCA | 1479 | TGCAGGACCAGAGAATTCGAATA CACTGTAAGCNNNACGTATGCCA | 1719 | TGCAGGACCAGAGAATTCGAATA CACTCACAGANNNACGTATGCCA | 1959 |
| TGCAGGACCAGAGAATTCGAATA CACGCCATAANNNACGTATGCCA | 1480 | TGCAGGACCAGAGAATTCGAATA CAAGTCGATCNNNACGTATGCCA | 1720 | TGCAGGACCAGAGAATTCGAATA CAGCCGGTGTNNNACGTATGCCA | 1960 |
| TGCAGGACCAGAGAATTCGAATA CATTAAGTTGNNNACGTATGCCA | 1481 | TGCAGGACCAGAGAATTCGAATA CAGTAATAGANNNACGTATGCCA | 1721 | TGCAGGACCAGAGAATTCGAATA CATACGTCAGNNNACGTATGCCA | 1961 |
| TGCAGGACCAGAGAATTCGAATA CAGCCAGCTGNNNACGTATGCCA | 1482 | TGCAGGACCAGAGAATTCGAATA CACGGAGCTCNNNACGTATGCCA | 1722 | TGCAGGACCAGAGAATTCGAATA CATCTGCTCANNNACGTATGCCA | 1962 |
| TGCAGGACCAGAGAATTCGAATA CAAAACGCCTNNNACGTATGCCA | 1483 | TGCAGGACCAGAGAATTCGAATA CATTGTCTTANNNACGTATGCCA | 1723 | TGCAGGACCAGAGAATTCGAATA CAACGTATATNNNACGTATGCCA | 1963 |
| TGCAGGACCAGAGAATTCGAATA CAGTATTTCTNNNACGTATGCCA | 1484 | TGCAGGACCAGAGAATTCGAATA CATTTTCGTANNNACGTATGCCA | 1724 | TGCAGGACCAGAGAATTCGAATA CACGAGCCACNNNACGTATGCCA | 1964 |
| TGCAGGACCAGAGAATTCGAATA CAGGTCTCCCNNNACGTATGCCA | 1485 | TGCAGGACCAGAGAATTCGAATA CAAACGGAACNNNACGTATGCCA | 1725 | TGCAGGACCAGAGAATTCGAATA CATCGCTCTANNNACGTATGCCA | 1965 |
| TGCAGGACCAGAGAATTCGAATA CACAAGTCTGNNNACGTATGCCA | 1486 | TGCAGGACCAGAGAATTCGAATA CAACCACGGCNNNACGTATGCCA | 1726 | TGCAGGACCAGAGAATTCGAATA CACGGAAGATNNNACGTATGCCA | 1966 |
| TGCAGGACCAGAGAATTCGAATA CAGAGCACAANNNACGTATGCCA | 1487 | TGCAGGACCAGAGAATTCGAATA CAGAGTATTTNNNACGTATGCCA | 1727 | TGCAGGACCAGAGAATTCGAATA CATTAGCGGTNNNACGTATGCCA | 1967 |
| TGCAGGACCAGAGAATTCGAATA CATCAAACCGNNNACGTATGCCA | 1488 | TGCAGGACCAGAGAATTCGAATA CACCCGCCTANNNACGTATGCCA | 1728 | TGCAGGACCAGAGAATTCGAATA CATGAGCTCANNNACGTATGCCA | 1968 |
| TGCAGGACCAGAGAATTCGAATA CATTCCGCTANNNACGTATGCCA | 1489 | TGCAGGACCAGAGAATTCGAATA CAAGTATGCCNNNACGTATGCCA | 1729 | TGCAGGACCAGAGAATTCGAATA CATACACGTGNNNACGTATGCCA | 1969 |
| TGCAGGACCAGAGAATTCGAATA CAATTGCACGNNNACGTATGCCA | 1490 | TGCAGGACCAGAGAATTCGAATA CATAGCAGCTNNNACGTATGCCA | 1730 | TGCAGGACCAGAGAATTCGAATA CATAGTGTATNNNACGTATGCCA | 1970 |
| TGCAGGACCAGAGAATTCGAATA CAATACCTAANNNACGTATGCCA | 1491 | TGCAGGACCAGAGAATTCGAATA CACGCGTGACNNNACGTATGCCA | 1731 | TGCAGGACCAGAGAATTCGAATA CACATTAGGCNNNACGTATGCCA | 1971 |
| TGCAGGACCAGAGAATTCGAATA CAGGACCGGANNNACGTATGCCA | 1492 | TGCAGGACCAGAGAATTCGAATA CAAAATACGANNNACGTATGCCA | 1732 | TGCAGGACCAGAGAATTCGAATA CAACACCACANNNACGTATGCCA | 1972 |
| TGCAGGACCAGAGAATTCGAATA CATGTCCCGCNNNACGTATGCCA | 1493 | TGCAGGACCAGAGAATTCGAATA CACTAGATATNNNACGTATGCCA | 1733 | TGCAGGACCAGAGAATTCGAATA CAGTGCGTCGNNNACGTATGCCA | 1973 |
| TGCAGGACCAGAGAATTCGAATA CAGCCCCAGANNNACGTATGCCA | 1494 | TGCAGGACCAGAGAATTCGAATA CAATGTTGGCNNNACGTATGCCA | 1734 | TGCAGGACCAGAGAATTCGAATA CATATGTTTCNNNACGTATGCCA | 1974 |
| TGCAGGACCAGAGAATTCGAATA CACAAGCCCGNNNACGTATGCCA | 1495 | TGCAGGACCAGAGAATTCGAATA CACTACGCAANNNACGTATGCCA | 1735 | TGCAGGACCAGAGAATTCGAATA CAGTGGTCGCNNNACGTATGCCA | 1975 |
| TGCAGGACCAGAGAATTCGAATA CAGCCATTGANNNACGTATGCCA | 1496 | TGCAGGACCAGAGAATTCGAATA CATTTCTGTANNNACGTATGCCA | 1736 | TGCAGGACCAGAGAATTCGAATA CACTGGACCGNNNACGTATGCCA | 1976 |
| TGCAGGACCAGAGAATTCGAATA CATGAACACCNNNACGTATGCCA | 1497 | TGCAGGACCAGAGAATTCGAATA CACCTCCCTCNNNACGTATGCCA | 1737 | TGCAGGACCAGAGAATTCGAATA CAGGCCGTGTCNNNACGTATGCCA | 1977 |
| TGCAGGACCAGAGAATTCGAATA CAGAATCCGTNNNACGTATGCCA | 1498 | TGCAGGACCAGAGAATTCGAATA CAGACTTGACNNNACGTATGCCA | 1738 | TGCAGGACCAGAGAATTCGAATA CAAGTCTAATNNNACGTATGCCA | 1978 |
| TGCAGGACCAGAGAATTCGAATA CATTAATCGANNNACGTATGCCA | 1499 | TGCAGGACCAGAGAATTCGAATA CAGTCATCGANNNACGTATGCCA | 1739 | TGCAGGACCAGAGAATTCGAATA CACTCATGCTNNNACGTATGCCA | 1979 |
| TGCAGGACCAGAGAATTCGAATA CACGCCACTCNNNACGTATGCCA | 1500 | TGCAGGACCAGAGAATTCGAATA CAATCTAGTANNNACGTATGCCA | 1740 | TGCAGGACCAGAGAATTCGAATA CAAGTTCTCCNNNACGTATGCCA | 1980 |
| TGCAGGACCAGAGAATTCGAATA CACCCTTAGTNNNACGTATGCCA | 1501 | TGCAGGACCAGAGAATTCGAATA CACGAAGATGNNNACGTATGCCA | 1741 | TGCAGGACCAGAGAATTCGAATA CAGTGAAGGTNNNACGTATGCCA | 1981 |
| TGCAGGACCAGAGAATTCGAATA CATTCCTGGNNNACGTATGCCA | 1502 | TGCAGGACCAGAGAATTCGAATA CAATTTGCAANNNACGTATGCCA | 1742 | TGCAGGACCAGAGAATTCGAATA CAGTTTTAAGNNNACGTATGCCA | 1982 |
| TGCAGGACCAGAGAATTCGAATA CATTCAACGGNNNACGTATGCCA | 1503 | TGCAGGACCAGAGAATTCGAATA CAGACCGGCTNNNACGTATGCCA | 1743 | TGCAGGACCAGAGAATTCGAATA CAAAAGCAATNNNACGTATGCCA | 1983 |
| TGCAGGACCAGAGAATTCGAATA CATTGAGGAGNNNACGTATGCCA | 1504 | TGCAGGACCAGAGAATTCGAATA CACTTGTCACNNNACGTATGCCA | 1744 | TGCAGGACCAGAGAATTCGAATA CATGAAGCGANNNACGTATGCCA | 1984 |
| TGCAGGACCAGAGAATTCGAATA CATTCACGGCTNNNACGTATGCCA | 1505 | TGCAGGACCAGAGAATTCGAATA CACTCGTAAGNNNACGTATGCCA | 1745 | TGCAGGACCAGAGAATTCGAATA CAGTAGTGCTNNNACGTATGCCA | 1985 |

FIG. 14C

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CATCGCGGTGNNNACGTATGCCA | 1506 | TGCAGGACCAGAGAATTCGAATA CAGCCTTACTNNNACGTATGCCA | 1746 | TGCAGGACCAGAGAATTCGAATA CAACTATGTANNNACGTATGCCA | 1986 |
| TGCAGGACCAGAGAATTCGAATA CAAATTCCGGNNNACGTATGCCA | 1507 | TGCAGGACCAGAGAATTCGAATA CAGCATGTGTNNNACGTATGCCA | 1747 | TGCAGGACCAGAGAATTCGAATA CAGAAGTTCCNNNACGTATGCCA | 1987 |
| TGCAGGACCAGAGAATTCGAATA CACGTCATGANNNACGTATGCCA | 1508 | TGCAGGACCAGAGAATTCGAATA CACTACTGTCNNNACGTATGCCA | 1748 | TGCAGGACCAGAGAATTCGAATA CACGGTGCTGNNNACGTATGCCA | 1988 |
| TGCAGGACCAGAGAATTCGAATA CACGTTTATTNNNCTAGCGTTAC | 1509 | TGCAGGACCAGAGAATTCGAATA CAATCTAACANNNCTAGCGTTAC | 1749 | TGCAGGACCAGAGAATTCGAATA CATGCAAATTNNNCTAGCGTTAC | 1989 |
| TGCAGGACCAGAGAATTCGAATA CACTGCACGGNNNCTAGCGTTAC | 1510 | TGCAGGACCAGAGAATTCGAATA CAACGATTGGNNNCTAGCGTTAC | 1750 | TGCAGGACCAGAGAATTCGAATA CAACTTGTGGNNNCTAGCGTTAC | 1990 |
| TGCAGGACCAGAGAATTCGAATA CAACCTTGTCNNNCTAGCGTTAC | 1511 | TGCAGGACCAGAGAATTCGAATA CAAAACCTTANNNCTAGCGTTAC | 1751 | TGCAGGACCAGAGAATTCGAATA CATCGCTGCCNNNCTAGCGTTAC | 1991 |
| TGCCAGGACCAGAGAATTCGAATA CATCCACCCGNNNCTAGCGTTAC | 1512 | TGCAGGACCAGAGAATTCGAATA CACGTAAAAANNNCTAGCGTTAC | 1752 | TGCAGGACCAGAGAATTCGAATA CATCCTTCTNNNCTAGCGTTAC | 1992 |
| TGCAGGACCAGAGAATTCGAATA CAAAGGCCGGNNNCTAGCGTTAC | 1513 | TGCAGGACCAGAGAATTCGAATA CATCTGAGACNNNCTAGCGTTAC | 1753 | TGCAGGACCAGAGAATTCGAATA CACGGTACTANNNCTAGCGTTAC | 1993 |
| TGCAGGACCAGAGAATTCGAATA CAGGCAATAGNNNCTAGCGTTAC | 1514 | TGCAGGACCAGAGAATTCGAATA CATGGCGATTNNNCTAGCGTTAC | 1754 | TGCAGGACCAGAGAATTCGAATA CAAGATATCNNNCTAGCGTTAC | 1994 |
| TGCAGGACCAGAGAATTCGAATA CACGCTACGCNNNCTAGCGTTAC | 1515 | TGCAGGACCAGAGAATTCGAATA CACATCTTGCNNNCTAGCGTTAC | 1755 | TGCAGGACCAGAGAATTCGAATA CACTCAAGTGNNNCTAGCGTTAC | 1995 |
| TGCAGGACCAGAGAATTCGAATA CATGTTCTATNNNCTAGCGTTAC | 1516 | TGCAGGACCAGAGAATTCGAATA CATCTTTCGGNNNCTAGCGTTAC | 1756 | TGCAGGACCAGAGAATTCGAATA CAACCTCCTANNNCTAGCGTTAC | 1996 |
| TGCAGGACCAGAGAATTCGAATA CATTAATATANNNCTAGCGTTAC | 1517 | TGCAGGACCAGAGAATTCGAATA CAGCGAACANNNCTAGCGTTAC | 1757 | TGCAGGACCAGAGAATTCGAATA CAAGCAATTNNNCTAGCGTTAC | 1997 |
| TGCAGGACCAGAGAATTCGAATA CAATATGGTTNNNCTAGCGTTAC | 1518 | TGCAGGACCAGAGAATTCGAATA CAGAGTAGACNNNCTAGCGTTAC | 1758 | TGCAGGACCAGAGAATTCGAATA CAGCCCCGAANNNCTAGCGTTAC | 1998 |
| TGCAGGACCAGAGAATTCGAATA CAGCTGGTTANNNCTAGCGTTAC | 1519 | TGCAGGACCAGAGAATTCGAATA CACTCATGGANNNCTAGCGTTAC | 1759 | TGCAGGACCAGAGAATTCGAATA CACCAAATCGNNNCTAGCGTTAC | 1999 |
| TGCAGGACCAGAGAATTCGAATA CAAGACTGAGNNNCTAGCGTTAC | 1520 | TGCAGGACCAGAGAATTCGAATA CATTCCCGGCNNNCTAGCGTTAC | 1760 | TGCAGGACCAGAGAATTCGAATA CAGATCGGTTNNNCTAGCGTTAC | 2000 |
| TGCAGGACCAGAGAATTCGAATA CAGACTTGCANNNCTAGCGTTAC | 1521 | TGCAGGACCAGAGAATTCGAATA CATGGCCTAANNNCTAGCGTTAC | 1761 | TGCAGGACCAGAGAATTCGAATA CAACCCCTGCNNNCTAGCGTTAC | 2001 |
| TGCAGGACCAGAGAATTCGAATA CAGTCTATCCNNNCTAGCGTTAC | 1522 | TGCAGGACCAGAGAATTCGAATA CAAGCGCAAANNNCTAGCGTTAC | 1762 | TGCAGGACCAGAGAATTCGAATA CAACCCACTNNNCTAGCGTTAC | 2002 |
| TGCAGGACCAGAGAATTCGAATA CAAGCTATCGNNNCTAGCGTTAC | 1523 | TGCAGGACCAGAGAATTCGAATA CAATAGAAACNNNCTAGCGTTAC | 1763 | TGCAGGACCAGAGAATTCGAATA CAAGACCTTGNNNCTAGCGTTAC | 2003 |
| TGCAGGACCAGAGAATTCGAATA CAGGCGAACGNNNCTAGCGTTAC | 1524 | TGCAGGACCAGAGAATTCGAATA CATCGGCTGGNNNCTAGCGTTAC | 1764 | TGCAGGACCAGAGAATTCGAATA CACCTTGATCNNNCTAGCGTTAC | 2004 |
| TGCAGGACCAGAGAATTCGAATA CAACGAATGGNNNCTAGCGTTAC | 1525 | TGCAGGACCAGAGAATTCGAATA CAGTGCTCGGNNNCTAGCGTTAC | 1765 | TGCAGGACCAGAGAATTCGAATA CAAAGTATTCNNNCTAGCGTTAC | 2005 |
| TGCAGGACCAGAGAATTCGAATA CATCATGCTCNNNCTAGCGTTAC | 1526 | TGCAGGACCAGAGAATTCGAATA CAAATGCCACNNNCTAGCGTTAC | 1766 | TGCAGGACCAGAGAATTCGAATA CACATCCAAGNNNCTAGCGTTAC | 2006 |
| TGCAGGACCAGAGAATTCGAATA CATTGCTTATNNNCTAGCGTTAC | 1527 | TGCAGGACCAGAGAATTCGAATA CAATCACGTGNNNCTAGCGTTAC | 1767 | TGCAGGACCAGAGAATTCGAATA CACACAAGTCNNNCTAGCGTTAC | 2007 |
| TGCAGGACCAGAGAATTCGAATA CAAAGCCAGANNNCTAGCGTTAC | 1528 | TGCAGGACCAGAGAATTCGAATA CATCACGACANNNCTAGCGTTAC | 1768 | TGCAGGACCAGAGAATTCGAATA CATAAAATGGNNNCTAGCGTTAC | 2008 |
| TGCAGGACCAGAGAATTCGAATA CAGCAGCTCGNNNCTAGCGTTAC | 1529 | TGCAGGACCAGAGAATTCGAATA CATGTTACGGNNNCTAGCGTTAC | 1769 | TGCAGGACCAGAGAATTCGAATA CAATCTACAANNNCTAGCGTTAC | 2009 |
| TGCAGGACCAGAGAATTCGAATA CACCGAGTCGNNNCTAGCGTTAC | 1530 | TGCAGGACCAGAGAATTCGAATA CATTACCGCTNNNCTAGCGTTAC | 1770 | TGCAGGACCAGAGAATTCGAATA CAGCGAGAATNNNCTAGCGTTAC | 2010 |
| TGCAGGACCAGAGAATTCGAATA CAAACAGACGNNNCTAGCGTTAC | 1531 | TGCAGGACCAGAGAATTCGAATA CACCCTTTAGNNNCTAGCGTTAC | 1771 | TGCAGGACCAGAGAATTCGAATA CAGTAGCCATNNNCTAGCGTTAC | 2011 |
| TGCAGGACCAGAGAATTCGAATA CACCCAAACANNNCTAGCGTTAC | 1532 | TGCAGGACCAGAGAATTCGAATA CAGTCTTGAGNNNCTAGCGTTAC | 1772 | TGCAGGACCAGAGAATTCGAATA CAAAGGCAGTNNNCTAGCGTTAC | 2012 |
| TGCAGGACCAGAGAATTCGAATA CAAAGGCGATNNNCTAGCGTTAC | 1533 | TGCAGGACCAGAGAATTCGAATA CACTTTGACCNNNCTAGCGTTAC | 1773 | TGCAGGACCAGAGAATTCGAATA CAGTAGACTCNNNCTAGCGTTAC | 2013 |
| TGCAGGACCAGAGAATTCGAATA CACCTTAAAANNNCTAGCGTTAC | 1534 | TGCAGGACCAGAGAATTCGAATA CACTTCTCAGNNNCTAGCGTTAC | 1774 | TGCAGGACCAGAGAATTCGAATA CAGGTATGCTNNNCTAGCGTTAC | 2014 |

FIG. 14D

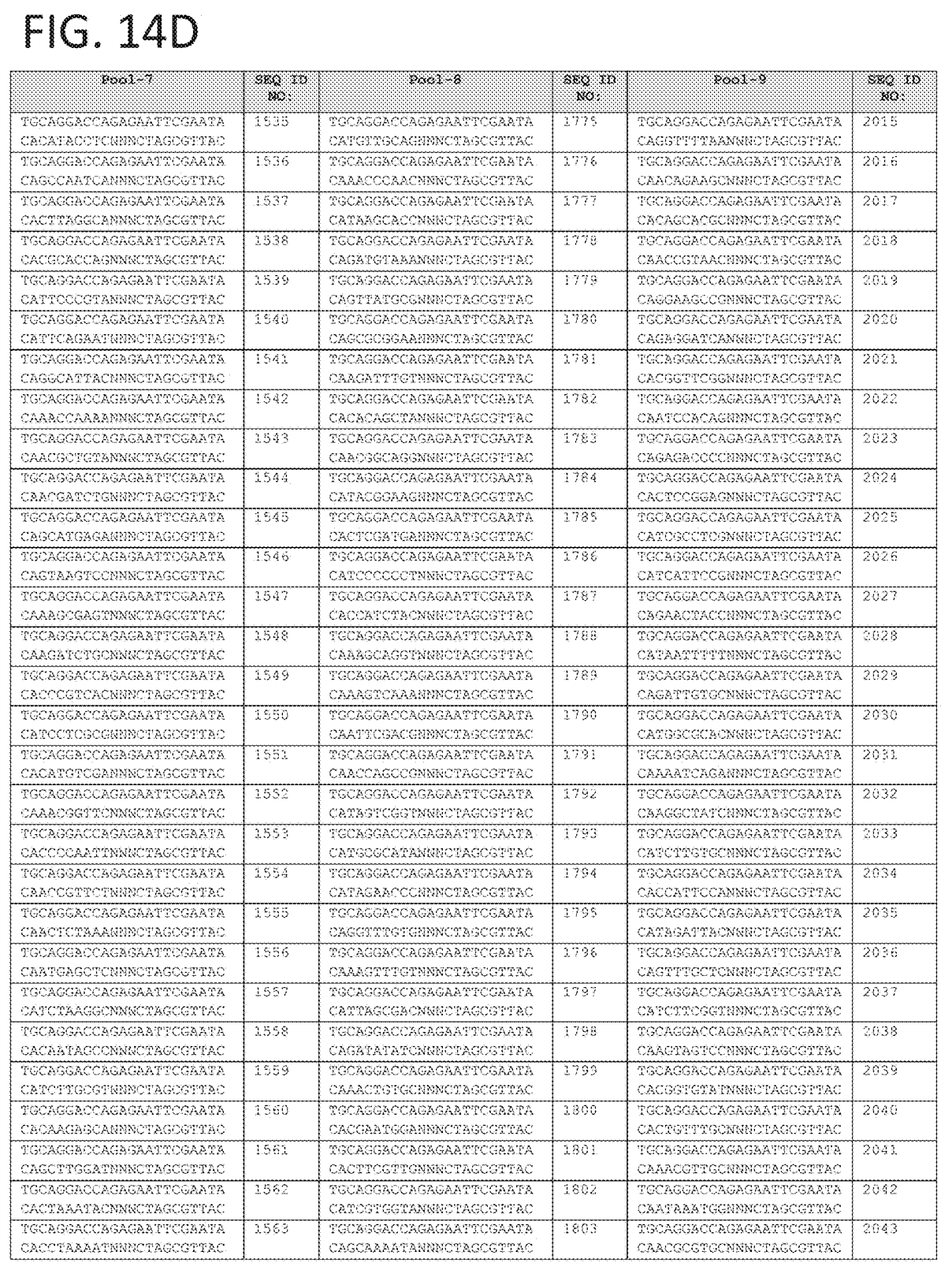

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CACATACCTCNNNCTAGCGTTAC | 1535 | TGCAGGACCAGAGAATTCGAATA CATGTTGCAGNNNCTAGCGTTAC | 1775 | TGCAGGACCAGAGAATTCGAATA CAGGTTTTAANNNCTAGCGTTAC | 2015 |
| TGCAGGACCAGAGAATTCGAATA CAGCCAATCANNNCTAGCGTTAC | 1536 | TGCAGGACCAGAGAATTCGAATA CAAACCCAACNNNCTAGCGTTAC | 1776 | TGCAGGACCAGAGAATTCGAATA CAACAGAAGCNNNCTAGCGTTAC | 2016 |
| TGCAGGACCAGAGAATTCGAATA CACTTAGGCANNNCTAGCGTTAC | 1537 | TGCAGGACCAGAGAATTCGAATA CATAAGCACCNNNCTAGCGTTAC | 1777 | TGCAGGACCAGAGAATTCGAATA CACAGCACGCNNNCTAGCGTTAC | 2017 |
| TGCAGGACCAGAGAATTCGAATA CACGCACCAGNNNCTAGCGTTAC | 1538 | TGCAGGACCAGAGAATTCGAATA CAGATGTAAANNNCTAGCGTTAC | 1778 | TGCAGGACCAGAGAATTCGAATA CAACCGTAACNNNCTAGCGTTAC | 2018 |
| TGCAGGACCAGAGAATTCGAATA CATTCCCGTANNNCTAGCGTTAC | 1539 | TGCAGGACCAGAGAATTCGAATA CAGTTATGCGNNNCTAGCGTTAC | 1779 | TGCAGGACCAGAGAATTCGAATA CAGGAAGCCGNNNCTAGCGTTAC | 2019 |
| TGCAGGACCAGAGAATTCGAATA CATTCAGAATNNNCTAGCGTTAC | 1540 | TGCAGGACCAGAGAATTCGAATA CAGCGCGGAANNNCTAGCGTTAC | 1780 | TGCAGGACCAGAGAATTCGAATA CAGAGGATCANNNCTAGCGTTAC | 2020 |
| TGCAGGACCAGAGAATTCGAATA CAGGCATTACNNNCTAGCGTTAC | 1541 | TGCAGGACCAGAGAATTCGAATA CAAGATTTGTNNNCTAGCGTTAC | 1781 | TGCAGGACCAGAGAATTCGAATA CACGGTTCGGNNNCTAGCGTTAC | 2021 |
| TGCAGGACCAGAGAATTCGAATA CAAACCAAANNNCTAGCGTTAC | 1542 | TGCAGGACCAGAGAATTCGAATA CACACAGCTANNNCTAGCGTTAC | 1782 | TGCAGGACCAGAGAATTCGAATA CAATCCACAGNNNCTAGCGTTAC | 2022 |
| TGCAGGACCAGAGAATTCGAATA CAACGCTGTANNNCTAGCGTTAC | 1543 | TGCAGGACCAGAGAATTCGAATA CAACGGCAGGNNNCTAGCGTTAC | 1783 | TGCAGGACCAGAGAATTCGAATA CAGAGACCCCNNNCTAGCGTTAC | 2023 |
| TGCAGGACCAGAGAATTCGAATA CAACGATCTGNNNCTAGCGTTAC | 1544 | TGCAGGACCAGAGAATTCGAATA CATACGGAAGNNNCTAGCGTTAC | 1784 | TGCAGGACCAGAGAATTCGAATA CACTCCGGAGNNNCTAGCGTTAC | 2024 |
| TGCAGGACCAGAGAATTCGAATA CAGCATGAGANNNCTAGCGTTAC | 1545 | TGCAGGACCAGAGAATTCGAATA CACTCGATGANNNCTAGCGTTAC | 1785 | TGCAGGACCAGAGAATTCGAATA CATGGCCTCGNNNCTAGCGTTAC | 2025 |
| TGCAGGACCAGAGAATTCGAATA CAGTAAGTCCNNNCTAGCGTTAC | 1546 | TGCAGGACCAGAGAATTCGAATA CATCCCCCCTNNNCTAGCGTTAC | 1786 | TGCAGGACCAGAGAATTCGAATA CATCATTCCGNNNCTAGCGTTAC | 2026 |
| TGCAGGACCAGAGAATTCGAATA CAAAGCGAGTNNNCTAGCGTTAC | 1547 | TGCAGGACCAGAGAATTCGAATA CACCATCTACNNNCTAGCGTTAC | 1787 | TGCAGGACCAGAGAATTCGAATA CAGAACTACCNNNCTAGCGTTAC | 2027 |
| TGCAGGACCAGAGAATTCGAATA CAAGATCTGNNNCTAGCGTTAC | 1548 | TGCAGGACCAGAGAATTCGAATA CAAAGCAGGTNNNCTAGCGTTAC | 1788 | TGCAGGACCAGAGAATTCGAATA CATAATTTTTNNNCTAGCGTTAC | 2028 |
| TGCAGGACCAGAGAATTCGAATA CACCCGTCACNNNCTAGCGTTAC | 1549 | TGCAGGACCAGAGAATTCGAATA CAAAGTCAAANNNCTAGCGTTAC | 1789 | TGCAGGACCAGAGAATTCGAATA CAGATTGTGCNNNCTAGCGTTAC | 2029 |
| TGCAGGACCAGAGAATTCGAATA CATCCTCGCGNNNCTAGCGTTAC | 1550 | TGCAGGACCAGAGAATTCGAATA CAATTCGACGNNNCTAGCGTTAC | 1790 | TGCAGGACCAGAGAATTCGAATA CATGGCGCACNNNCTAGCGTTAC | 2030 |
| TGCAGGACCAGAGAATTCGAATA CACATGTCGANNNCTAGCGTTAC | 1551 | TGCAGGACCAGAGAATTCGAATA CAACCAGCCGNNNCTAGCGTTAC | 1791 | TGCAGGACCAGAGAATTCGAATA CAAAATCAGANNNCTAGCGTTAC | 2031 |
| TGCAGGACCAGAGAATTCGAATA CAAACGGTTCNNNCTAGCGTTAC | 1552 | TGCAGGACCAGAGAATTCGAATA CATAGTCGGTNNNCTAGCGTTAC | 1792 | TGCAGGACCAGAGAATTCGAATA CAAGGCTATCNNNCTAGCGTTAC | 2032 |
| TGCAGGACCAGAGAATTCGAATA CACCCCAATTNNNCTAGCGTTAC | 1553 | TGCAGGACCAGAGAATTCGAATA CATGCGCATANNNCTAGCGTTAC | 1793 | TGCAGGACCAGAGAATTCGAATA CATCTTGTGCNNNCTAGCGTTAC | 2033 |
| TGCAGGACCAGAGAATTCGAATA CAACCGTTCTNNNCTAGCGTTAC | 1554 | TGCAGGACCAGAGAATTCGAATA CATAGAACCCNNNCTAGCGTTAC | 1794 | TGCAGGACCAGAGAATTCGAATA CACCATTCANNNCTAGCGTTAC | 2034 |
| TGCAGGACCAGAGAATTCGAATA CAACTCTAAANNNCTAGCGTTAC | 1555 | TGCAGGACCAGAGAATTCGAATA CAGGTTTGTGNNNCTAGCGTTAC | 1795 | TGCAGGACCAGAGAATTCGAATA CATAGATTACNNNCTAGCGTTAC | 2035 |
| TGCAGGACCAGAGAATTCGAATA CAATGAGCTCNNNCTAGCGTTAC | 1556 | TGCAGGACCAGAGAATTCGAATA CAAAGTTTGTNNNCTAGCGTTAC | 1796 | TGCAGGACCAGAGAATTCGAATA CAGTTTGCTCNNNCTAGCGTTAC | 2036 |
| TGCAGGACCAGAGAATTCGAATA CATCTAAGGCNNNCTAGCGTTAC | 1557 | TGCAGGACCAGAGAATTCGAATA CATTAGCGACNNNCTAGCGTTAC | 1797 | TGCAGGACCAGAGAATTCGAATA CATCTTCGGTNNNCTAGCGTTAC | 2037 |
| TGCAGGACCAGAGAATTCGAATA CACAATAGCCNNNCTAGCGTTAC | 1558 | TGCAGGACCAGAGAATTCGAATA CAGATATATCNNNCTAGCGTTAC | 1798 | TGCAGGACCAGAGAATTCGAATA CAAGTAGTCCNNNCTAGCGTTAC | 2038 |
| TGCAGGACCAGAGAATTCGAATA CATCTTGCGTNNNCTAGCGTTAC | 1559 | TGCAGGACCAGAGAATTCGAATA CAAACTGTGCNNNCTAGCGTTAC | 1799 | TGCAGGACCAGAGAATTCGAATA CACGGTGTATNNNCTAGCGTTAC | 2039 |
| TGCAGGACCAGAGAATTCGAATA CACAAGAGCANNNCTAGCGTTAC | 1560 | TGCAGGACCAGAGAATTCGAATA CACGAATGGANNNCTAGCGTTAC | 1800 | TGCAGGACCAGAGAATTCGAATA CACTGTTTGCNNNCTAGCGTTAC | 2040 |
| TGCAGGACCAGAGAATTCGAATA CAGCTTGGATNNNCTAGCGTTAC | 1561 | TGCAGGACCAGAGAATTCGAATA CACTTCGTTGNNNCTAGCGTTAC | 1801 | TGCAGGACCAGAGAATTCGAATA CAAACGGTGCNNNCTAGCGTTAC | 2041 |
| TGCAGGACCAGAGAATTCGAATA CACTAAATACNNNCTAGCGTTAC | 1562 | TGCAGGACCAGAGAATTCGAATA CATCGTGGTANNNCTAGCGTTAC | 1802 | TGCAGGACCAGAGAATTCGAATA CAATAAATGGNNNCTAGCGTTAC | 2042 |
| TGCAGGACCAGAGAATTCGAATA CACCTAAAATNNNCTAGCGTTAC | 1563 | TGCAGGACCAGAGAATTCGAATA CAGCAAAATANNNCTAGCGTTAC | 1803 | TGCAGGACCAGAGAATTCGAATA CAACGCGTGCNNNCTAGCGTTAC | 2043 |

FIG. 14E

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAGABCCTCANNNCTAGCGTTAC | 1564 | TGCAGGACCAGAGAATTCGAATA CAAGACTAAANNNCTAGCGTTAC | 1804 | TGCAGGACCAGAGAATTCGAATA CACGTTGGTANNNCTAGCGTTAC | 2044 |
| TGCAGGACCAGAGAATTCGAATA CAGAAGGCCTCNNNCTAGCGTTAC | 1565 | TGCAGGACCAGAGAATTCGAATA CATGCGAGTTNNNCTAGCGTTAC | 1805 | TGCAGGACCAGAGAATTCGAATA CAAGGCGTAANNNCTAGCGTTAC | 2045 |
| TGCAGGACCAGAGAATTCGAATA CAAGGTGATGNNNCTAGCGTTAC | 1566 | TGCAGGACCAGAGAATTCGAATA CAGTTCTGAGNNNCTAGCGTTAC | 1806 | TGCAGGACCAGAGAATTCGAATA CATGCCTATCNNNCTAGCGTTAC | 2046 |
| TGCAGGACCAGAGAATTCGAATA CAACGCGTTANNNCTAGCGTTAC | 1567 | TGCAGGACCAGAGAATTCGAATA CATCGGCGTGNNNCTAGCGTTAC | 1807 | TGCAGGACCAGAGAATTCGAATA CAAAAGCTCCNNNCTAGCGTTAC | 2047 |
| TGCAGGACCAGAGAATTCGAATA CAGGTGGCTCNNNCTAGCGTTAC | 1568 | TGCAGGACCAGAGAATTCGAATA CAGATCCGGCNNNCTAGCGTTAC | 1808 | TGCAGGACCAGAGAATTCGAATA CAAGGACGATNNNCTAGCGTTAC | 2048 |
| TGCAGGACCAGAGAATTCGAATA CAGAGATCAGNNNGATCGACATG | 1569 | TGCAGGACCAGAGAATTCGAATA CAGTGTATGCNNNGATCGACATG | 1809 | TGCAGGACCAGAGAATTCGAATA CACTTGAAGCNNNGATCGACATG | 2049 |
| TGCAGGACCAGAGAATTCGAATA CATACGTGTGNNNGATCGACATG | 1570 | TGCAGGACCAGAGAATTCGAATA CAAGTATTTGNNNGATCGACATG | 1810 | TGCAGGACCAGAGAATTCGAATA CATGCCCTCGNNNGATCGACATG | 2050 |
| TGCAGGACCAGAGAATTCGAATA CAAGTTATCANNNGATCGACATG | 1571 | TGCAGGACCAGAGAATTCGAATA CAAGTAAAACNNNGATCGACATG | 1811 | TGCAGGACCAGAGAATTCGAATA CAAGCGAAACNNNGATCGACATG | 2051 |
| TGCAGGACCAGAGAATTCGAATA CACAGTGATCNNNGATCGACATG | 1572 | TGCAGGACCAGAGAATTCGAATA CAAGCCACCGNNNGATCGACATG | 1812 | TGCAGGACCAGAGAATTCGAATA CATAGAGTGGNNNGATCGACATG | 2052 |
| TGCAGGACCAGAGAATTCGAATA CATACGCGGCNNNGATCGACATG | 1573 | TGCAGGACCAGAGAATTCGAATA CAAAGTGTCCNNNGATCGACATG | 1813 | TGCAGGACCAGAGAATTCGAATA CAAGCAGCAANNNGATCGACATG | 2053 |
| TGCAGGACCAGAGAATTCGAATA CAGTGTGTACNNNGATCGACATG | 1574 | TGCAGGACCAGAGAATTCGAATA CACTATTTGTNNNGATCGACATG | 1814 | TGCAGGACCAGAGAATTCGAATA CACCTATTATNNNGATCGACATG | 2054 |
| TGCAGGACCAGAGAATTCGAATA CAGTGTTTAANNNGATCGACATG | 1575 | TGCAGGACCAGAGAATTCGAATA CAGTGTATCGNNNGATCGACATG | 1815 | TGCAGGACCAGAGAATTCGAATA CAGCGACGAGNNNGATCGACATG | 2055 |
| TGCAGGACCAGAGAATTCGAATA CAGCTCTACTNNNGATCGACATG | 1576 | TGCAGGACCAGAGAATTCGAATA CAATAGTATCNNNGATCGACATG | 1816 | TGCAGGACCAGAGAATTCGAATA CAACGATTTANNNGATCGACATG | 2056 |
| TGCAGGACCAGAGAATTCGAATA CATTGTGCTCNNNGATCGACATG | 1577 | TGCAGGACCAGAGAATTCGAATA CACCCGCTGAGNNNGATCGACATG | 1817 | TGCAGGACCAGAGAATTCGAATA CAAATTGTTGNNNGATCGACATG | 2057 |
| TGCAGGACCAGAGAATTCGAATA CATATAAGCTNNNGATCGACATG | 1578 | TGCAGGACCAGAGAATTCGAATA CATTATTTTANNNGATCGACATG | 1818 | TGCAGGACCAGAGAATTCGAATA CACATTAAGTNNNGATCGACATG | 2058 |
| TGCAGGACCAGAGAATTCGAATA CAAGAACGACNNNGATCGACATG | 1579 | TGCAGGACCAGAGAATTCGAATA CAACAAGACGNNNGATCGACATG | 1819 | TGCAGGACCAGAGAATTCGAATA CAGACGGAGCNNNGATCGACATG | 2059 |
| TGCAGGACCAGAGAATTCGAATA CATACGATATNNNGATCGACATG | 1580 | TGCAGGACCAGAGAATTCGAATA CATAAGTATCNNNGATCGACATG | 1820 | TGCAGGACCAGAGAATTCGAATA CACCGATAGTNNNGATCGACATG | 2060 |
| TGCAGGACCAGAGAATTCGAATA CATAAACCTANNNGATCGACATG | 1581 | TGCAGGACCAGAGAATTCGAATA CAGGCACACCNNNGATCGACATG | 1821 | TGCAGGACCAGAGAATTCGAATA CAAGTATTGTNNNGATCGACATG | 2061 |
| TGCAGGACCAGAGAATTCGAATA CATAACGTTANNNGATCGACATG | 1582 | TGCAGGACCAGAGAATTCGAATA CAGTACCTCTNNNGATCGACATG | 1822 | TGCAGGACCAGAGAATTCGAATA CATTTCGGCTNNNGATCGACATG | 2062 |
| TGCAGGACCAGAGAATTCGAATA CAGCACGTGCNNNGATCGACATG | 1583 | TGCAGGACCAGAGAATTCGAATA CACTGTGATGNNNGATCGACATG | 1823 | TGCAGGACCAGAGAATTCGAATA CAGTAGACAGNNNGATCGACATG | 2063 |
| TGCAGGACCAGAGAATTCGAATA CACCCTCGACNNNGATCGACATG | 1584 | TGCAGGACCAGAGAATTCGAATA CAACAAGGACNNNGATCGACATG | 1824 | TGCAGGACCAGAGAATTCGAATA CAACGAAGTGNNNGATCGACATG | 2064 |
| TGCAGGACCAGAGAATTCGAATA CATTGCATCCNNNGATCGACATG | 1585 | TGCAGGACCAGAGAATTCGAATA CAAGAGGCTANNNGATCGACATG | 1825 | TGCAGGACCAGAGAATTCGAATA CACGTCTTTGNNNGATCGACATG | 2065 |
| TGCAGGACCAGAGAATTCGAATA CATCAACTGGNNNGATCGACATG | 1586 | TGCAGGACCAGAGAATTCGAATA CAATTGAGTTNNNGATCGACATG | 1826 | TGCAGGACCAGAGAATTCGAATA CAACACAGGANNNGATCGACATG | 2066 |
| TGCAGGACCAGAGAATTCGAATA CAATTGCCCTNNNGATCGACATG | 1587 | TGCAGGACCAGAGAATTCGAATA CACGTTCTCANNNGATCGACATG | 1827 | TGCAGGACCAGAGAATTCGAATA CAGGTCACTANNNGATCGACATG | 2067 |
| TGCAGGACCAGAGAATTCGAATA CATACATGTANNNGATCGACATG | 1588 | TGCAGGACCAGAGAATTCGAATA CAGGTAGCTTNNNGATCGACATG | 1828 | TGCAGGACCAGAGAATTCGAATA CAGAACGAACNNNGATCGACATG | 2068 |
| TGCAGGACCAGAGAATTCGAATA CAGACTTGGTNNNGATCGACATG | 1589 | TGCAGGACCAGAGAATTCGAATA CATCCTTGTGNNNGATCGACATG | 1829 | TGCAGGACCAGAGAATTCGAATA CACCTAACTCNNNGATCGACATG | 2069 |
| TGCAGGACCAGAGAATTCGAATA CAGTCCCATTNNNGATCGACATG | 1590 | TGCAGGACCAGAGAATTCGAATA CAGCCGACACNNNGATCGACATG | 1830 | TGCAGGACCAGAGAATTCGAATA CAAAGACTTTNNNGATCGACATG | 2070 |
| TGCAGGACCAGAGAATTCGAATA CAAGATGGTGNNNGATCGACATG | 1591 | TGCAGGACCAGAGAATTCGAATA CAACTAGAGGNNNGATCGACATG | 1831 | TGCAGGACCAGAGAATTCGAATA CAGGACATCTNNNGATCGACATG | 2071 |
| TGCAGGACCAGAGAATTCGAATA CAGACACAGANNNGATCGACATG | 1592 | TGCAGGACCAGAGAATTCGAATA CAACAGTCGTNNNGATCGACATG | 1832 | TGCAGGACCAGAGAATTCGAATA CAGGCGTAAANNNGATCGACATG | 2072 |

FIG. 14F

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CACGCGTTTTNNNGATCGACATG | 1593 | TGCAGGACCAGAGAATTCGAATA CACGAGGCGANNNGATCGACATG | 1833 | TGCAGGACCAGAGAATTCGAATA CAGTACCAGTNNNGATCGACATG | 2073 |
| TGCAGGACCAGAGAATTCGAATA CACCCAGAGCNNNGATCGACATG | 1594 | TGCAGGACCAGAGAATTCGAATA CAACCGAAAGNNNGATCGACATG | 1834 | TGCAGGACCAGAGAATTCGAATA CAGAATTTACNNNGATCGACATG | 2074 |
| TGCAGGACCAGAGAATTCGAATA CACGCAGCTGNNNGATCGACATG | 1595 | TGCAGGACCAGAGAATTCGAATA CAGTTTGAGCNNNGATCGACATG | 1835 | TGCAGGACCAGAGAATTCGAATA CAAACACCCANNNGATCGACATG | 2075 |
| TGCAGGACCAGAGAATTCGAATA CACTTTGGCTNNNGATCGACATG | 1596 | TGCAGGACCAGAGAATTCGAATA CAGTATGCGTNNNGATCGACATG | 1836 | TGCAGGACCAGAGAATTCGAATA CAAGTTATTGNNNGATCGACATG | 2076 |
| TGCAGGACCAGAGAATTCGAATA CAGTTGATCGNNNGATCGACATG | 1597 | TGCAGGACCAGAGAATTCGAATA CAATGTAACTNNNGATCGACATG | 1837 | TGCAGGACCAGAGAATTCGAATA CACTTCTTTTNNNGATCGACATG | 2077 |
| TGCAGGACCAGAGAATTCGAATA CAGTGAAGTGNNNGATCGACATG | 1598 | TGCAGGACCAGAGAATTCGAATA CAAGACGTAGNNNGATCGACATG | 1838 | TGCAGGACCAGAGAATTCGAATA CAGAGCTCCGNNNGATCGACATG | 2078 |
| TGCAGGACCAGAGAATTCGAATA CACACGTTGANNNGATCGACATG | 1599 | TGCAGGACCAGAGAATTCGAATA CATTGGCGCGNNNGATCGACATG | 1839 | TGCAGGACCAGAGAATTCGAATA CAGAACCCCGNNNGATCGACATG | 2079 |
| TGCAGGACCAGAGAATTCGAATA CACAATCCAGNNNGATCGACATG | 1600 | TGCAGGACCAGAGAATTCGAATA CAGGACTCATNNNGATCGACATG | 1840 | TGCAGGACCAGAGAATTCGAATA CAATTGTGATNNNGATCGACATG | 2080 |
| TGCAGGACCAGAGAATTCGAATA CAGCGCGAGANNNGATCGACATG | 1601 | TGCAGGACCAGAGAATTCGAATA CAGTCCGGTGNNNGATCGACATG | 1841 | TGCAGGACCAGAGAATTCGAATA CAAGTTCTTTNNNGATCGACATG | 2081 |
| TGCAGGACCAGAGAATTCGAATA CACTCTGATCNNNGATCGACATG | 1602 | TGCAGGACCAGAGAATTCGAATA CAGCAAGCCCNNNGATCGACATG | 1842 | TGCAGGACCAGAGAATTCGAATA CAGCACGGTCNNNGATCGACATG | 2082 |
| TGCAGGACCAGAGAATTCGAATA CATATGCCAGNNNGATCGACATG | 1603 | TGCAGGACCAGAGAATTCGAATA CAAGCATGGANNNGATCGACATG | 1843 | TGCAGGACCAGAGAATTCGAATA CAGTATCCCTNNNGATCGACATG | 2083 |
| TGCAGGACCAGAGAATTCGAATA CAGTTGGTCANNNGATCGACATG | 1604 | TGCAGGACCAGAGAATTCGAATA CAAGCAGCCCNNNGATCGACATG | 1844 | TGCAGGACCAGAGAATTCGAATA CAGCAAGTGANNNGATCGACATG | 2084 |
| TGCAGGACCAGAGAATTCGAATA CACCTCTCGGNNNGATCGACATG | 1605 | TGCAGGACCAGAGAATTCGAATA CAATCTCTATNNNGATCGACATG | 1845 | TGCAGGACCAGAGAATTCGAATA CATAAGATAGNNNGATCGACATG | 2085 |
| TGCAGGACCAGAGAATTCGAATA CATGGTACACNNNGATCGACATG | 1606 | TGCAGGACCAGAGAATTCGAATA CATAATGCCGNNNGATCGACATG | 1846 | TGCAGGACCAGAGAATTCGAATA CAGCAATCTGNNNGATCGACATG | 2086 |
| TGCAGGACCAGAGAATTCGAATA CACCTCGGCTNNNGATCGACATG | 1607 | TGCAGGACCAGAGAATTCGAATA CACAGGCGGANNNGATCGACATG | 1847 | TGCAGGACCAGAGAATTCGAATA CACTGCCAGGNNNGATCGACATG | 2087 |
| TGCAGGACCAGAGAATTCGAATA CAGCGACGGANNNGATCGACATG | 1608 | TGCAGGACCAGAGAATTCGAATA CAGCGAATGANNNGATCGACATG | 1848 | TGCAGGACCAGAGAATTCGAATA CAGGTTTATANNNGATCGACATG | 2088 |
| TGCAGGACCAGAGAATTCGAATA CACCCTGATTNNNGATCGACATG | 1609 | TGCAGGACCAGAGAATTCGAATA CAAGCGTACTNNNGATCGACATG | 1849 | TGCAGGACCAGAGAATTCGAATA CAAACTTGCGNNNGATCGACATG | 2089 |
| TGCAGGACCAGAGAATTCGAATA CAATTCTCTANNNGATCGACATG | 1610 | TGCAGGACCAGAGAATTCGAATA CACCCAGGCANNNGATCGACATG | 1850 | TGCAGGACCAGAGAATTCGAATA CACCAACGCGNNNGATCGACATG | 2090 |
| TGCAGGACCAGAGAATTCGAATA CACTGTCAAGNNNGATCGACATG | 1611 | TGCAGGACCAGAGAATTCGAATA CAGGCCTGTGNNNGATCGACATG | 1851 | TGCAGGACCAGAGAATTCGAATA CATGGAAGCANNNGATCGACATG | 2091 |
| TGCAGGACCAGAGAATTCGAATA CAATTACCGGNNNGATCGACATG | 1612 | TGCAGGACCAGAGAATTCGAATA CACCTAGGCGNNNGATCGACATG | 1852 | TGCAGGACCAGAGAATTCGAATA CAATTGAAGANNNGATCGACATG | 2092 |
| TGCAGGACCAGAGAATTCGAATA CATAATATCGNNNGATCGACATG | 1613 | TGCAGGACCAGAGAATTCGAATA CACCGTTTTGNNNGATCGACATG | 1853 | TGCAGGACCAGAGAATTCGAATA CATTTTCACANNNGATCGACATG | 2093 |
| TGCAGGACCAGAGAATTCGAATA CAATAGACTTNNNGATCGACATG | 1614 | TGCAGGACCAGAGAATTCGAATA CAGACGCACCNNNGATCGACATG | 1854 | TGCAGGACCAGAGAATTCGAATA CAACGAACTCNNNGATCGACATG | 2094 |
| TGCAGGACCAGAGAATTCGAATA CACCTGATAGNNNGATCGACATG | 1615 | TGCAGGACCAGAGAATTCGAATA CAACTTATGANNNGATCGACATG | 1855 | TGCAGGACCAGAGAATTCGAATA CAAGGCCGTCNNNGATCGACATG | 2095 |
| TGCAGGACCAGAGAATTCGAATA CAGCCGCACANNNGATCGACATG | 1616 | TGCAGGACCAGAGAATTCGAATA CAAGATCAAANNNGATCGACATG | 1856 | TGCAGGACCAGAGAATTCGAATA CATTGGAGCTNNNGATCGACATG | 2096 |
| TGCAGGACCAGAGAATTCGAATA CACGAATATTNNNGATCGACATG | 1617 | TGCAGGACCAGAGAATTCGAATA CATACTTCCGNNNGATCGACATG | 1857 | TGCAGGACCAGAGAATTCGAATA CAACAGACAGNNNGATCGACATG | 2097 |
| TGCAGGACCAGAGAATTCGAATA CAGTCAATCGNNNGATCGACATG | 1618 | TGCAGGACCAGAGAATTCGAATA CACGTTAGACNNNGATCGACATG | 1858 | TGCAGGACCAGAGAATTCGAATA CAATCGTCAGNNNGATCGACATG | 2098 |
| TGCAGGACCAGAGAATTCGAATA CATCAGCCCCNNNGATCGACATG | 1619 | TGCAGGACCAGAGAATTCGAATA CAGGAGTTAGNNNGATCGACATG | 1859 | TGCAGGACCAGAGAATTCGAATA CATTATGTCTNNNGATCGACATG | 2099 |
| TGCAGGACCAGAGAATTCGAATA CAGGAGTTCTNNNGATCGACATG | 1620 | TGCAGGACCAGAGAATTCGAATA CAGACCTCTTNNNGATCGACATG | 1860 | TGCAGGACCAGAGAATTCGAATA CAGTCACGATNNNGATCGACATG | 2100 |
| TGCAGGACCAGAGAATTCGAATA CAGTGAATCCNNNGATCGACATG | 1621 | TGCAGGACCAGAGAATTCGAATA CAGCCCGCAANNNGATCGACATG | 1861 | TGCAGGACCAGAGAATTCGAATA CACATTCTGCNNNGATCGACATG | 2101 |

FIG. 14G

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAACGATTATNNNGATCGACATG | 1622 | TGCAGGACCAGAGAATTCGAATA CAGAACCCATNNNGATCGACATG | 1862 | TGCAGGACCAGAGAATTCGAATA CAGAAAAACTNNNGATCGACATG | 2102 |
| TGCAGGACCAGAGAATTCGAATA CACAATCCGANNNGATCGACATG | 1623 | TGCAGGACCAGAGAATTCGAATA CACCACTGCCNNNGATCGACATG | 1863 | TGCAGGACCAGAGAATTCGAATA CATCCGTCGTTNNNGATCGACATG | 2103 |
| TGCAGGACCAGAGAATTCGAATA CAGGCAATGANNNGATCGACATG | 1624 | TGCAGGACCAGAGAATTCGAATA CACTAATTCNNNGATCGACATG | 1864 | TGCAGGACCAGAGAATTCGAATA CAATTGTGGCNNNGATCGACATG | 2104 |
| TGCAGGACCAGAGAATTCGAATA CACTGTCAGANNNGATCGACATG | 1625 | TGCAGGACCAGAGAATTCGAATA CACGGTCCAGNNNGATCGACATG | 1865 | TGCAGGACCAGAGAATTCGAATA CAACTGGACTNNNGATCGACATG | 2105 |
| TGCAGGACCAGAGAATTCGAATA CACAGACCTANNNGATCGACATG | 1626 | TGCAGGACCAGAGAATTCGAATA CATTTCGCACNNNGATCGACATG | 1866 | TGCAGGACCAGAGAATTCGAATA CACGTTGTTCNNNGATCGACATG | 2106 |
| TGCAGGACCAGAGAATTCGAATA CAGATCATCGNNNGATCGACATG | 1627 | TGCAGGACCAGAGAATTCGAATA CAGGATAAGCNNNGATCGACATG | 1867 | TGCAGGACCAGAGAATTCGAATA CACAAGACCTNNNGATCGACATG | 2107 |
| TGCAGGACCAGAGAATTCGAATA CAGAACGAGTNNNGATCGACATG | 1628 | TGCAGGACCAGAGAATTCGAATA CACTCGCAGGNNNGATCGACATG | 1868 | TGCAGGACCAGAGAATTCGAATA CATACCCCGNNNGATCGACATG | 2108 |
| TGCAGGACCAGAGAATTCGAATA CATCCGTGATNNNTGCATCAGGT | 1629 | TGCAGGACCAGAGAATTCGAATA CAACTGAAAANNNTGCATCAGGT | 1869 | TGCAGGACCAGAGAATTCGAATA CACCTACCGCNNNTGCATCAGGT | 2109 |
| TGCAGGACCAGAGAATTCGAATA CAATTGCAATNNNTGCATCAGGT | 1630 | TGCAGGACCAGAGAATTCGAATA CAAGTCTTTTNNNTGCATCAGGT | 1870 | TGCAGGACCAGAGAATTCGAATA CAAGACAGTGNNNTGCATCAGGT | 2110 |
| TGCAGGACCAGAGAATTCGAATA CATTAACGATNNNTGCATCAGGT | 1631 | TGCAGGACCAGAGAATTCGAATA CAGGTGTTACNNNTGCATCAGGT | 1871 | TGCAGGACCAGAGAATTCGAATA CAGTCCTATCNNNTGCATCAGGT | 2111 |
| TGCAGGACCAGAGAATTCGAATA CATGTACGTGNNNTGCATCAGGT | 1632 | TGCAGGACCAGAGAATTCGAATA CATATCCGCTNNNTGCATCAGGT | 1872 | TGCAGGACCAGAGAATTCGAATA CACGCGCTCTNNNTGCATCAGGT | 2112 |
| TGCAGGACCAGAGAATTCGAATA CAGCGTGTGCNNNTGCATCAGGT | 1633 | TGCAGGACCAGAGAATTCGAATA CAGCGTGAGGNNNTGCATCAGGT | 1873 | TGCAGGACCAGAGAATTCGAATA CATTGATTCTNNNTGCATCAGGT | 2113 |
| TGCAGGACCAGAGAATTCGAATA CACCATATAANNNTGCATCAGGT | 1634 | TGCAGGACCAGAGAATTCGAATA CAGCCGTTCCNNNTGCATCAGGT | 1874 | TGCAGGACCAGAGAATTCGAATA CAATAATGTCNNNTGCATCAGGT | 2114 |
| TGCAGGACCAGAGAATTCGAATA CAAAATTGAGNNNTGCATCAGGT | 1635 | TGCAGGACCAGAGAATTCGAATA CATTACCCCANNNTGCATCAGGT | 1875 | TGCAGGACCAGAGAATTCGAATA CAGAGTTAAANNNTGCATCAGGT | 2115 |
| TGCAGGACCAGAGAATTCGAATA CAGTATCACGNNNTGCATCAGGT | 1636 | TGCAGGACCAGAGAATTCGAATA CAGACCCCTCNNNTGCATCAGGT | 1876 | TGCAGGACCAGAGAATTCGAATA CACGACACATNNNTGCATCAGGT | 2116 |
| TGCAGGACCAGAGAATTCGAATA CACCTTAGGANNNTGCATCAGGT | 1637 | TGCAGGACCAGAGAATTCGAATA CATATGGAGGNNNTGCATCAGGT | 1877 | TGCAGGACCAGAGAATTCGAATA CATTGGCCGGNNNTGCATCAGGT | 2117 |
| TGCAGGACCAGAGAATTCGAATA CATAAAAAGCNNNTGCATCAGGT | 1638 | TGCAGGACCAGAGAATTCGAATA CAGACGGTCCNNNTGCATCAGGT | 1878 | TGCAGGACCAGAGAATTCGAATA CAGAACTTTANNNTGCATCAGGT | 2118 |
| TGCAGGACCAGAGAATTCGAATA CATGCATCCTNNNTGCATCAGGT | 1639 | TGCAGGACCAGAGAATTCGAATA CACTACGACANNNTGCATCAGGT | 1879 | TGCAGGACCAGAGAATTCGAATA CACCAAAACCNNNTGCATCAGGT | 2119 |
| TGCAGGACCAGAGAATTCGAATA CACAGCCTGGNNNTGCATCAGGT | 1640 | TGCAGGACCAGAGAATTCGAATA CATGACTACGNNNTGCATCAGGT | 1880 | TGCAGGACCAGAGAATTCGAATA CAATACCAGCNNNTGCATCAGGT | 2120 |
| TGCAGGACCAGAGAATTCGAATA CACACACTAGNNNTGCATCAGGT | 1641 | TGCAGGACCAGAGAATTCGAATA CAGGACGTTNNNTGCATCAGGT | 1881 | TGCAGGACCAGAGAATTCGAATA CAAGTAGAATNNNTGCATCAGGT | 2121 |
| TGCAGGACCAGAGAATTCGAATA CACGTATCCTNNNTGCATCAGGT | 1642 | TGCAGGACCAGAGAATTCGAATA CAAAGCCTCANNNTGCATCAGGT | 1882 | TGCAGGACCAGAGAATTCGAATA CAGTACTACGNNNTGCATCAGGT | 2122 |
| TGCAGGACCAGAGAATTCGAATA CATGGCTTAGNNNTGCATCAGGT | 1643 | TGCAGGACCAGAGAATTCGAATA CACTTTAAAGNNNTGCATCAGGT | 1883 | TGCAGGACCAGAGAATTCGAATA CATTCATGAANNNTGCATCAGGT | 2123 |
| TGCAGGACCAGAGAATTCGAATA CACTGTCATCNNNTGCATCAGGT | 1644 | TGCAGGACCAGAGAATTCGAATA CATTTGATTCNNNTGCATCAGGT | 1884 | TGCAGGACCAGAGAATTCGAATA CACCTAAGGTNNNTGCATCAGGT | 2124 |
| TGCAGGACCAGAGAATTCGAATA CATCCGAACNNNTGCATCAGGT | 1645 | TGCAGGACCAGAGAATTCGAATA CACTGTATTNNNTGCATCAGGT | 1885 | TGCAGGACCAGAGAATTCGAATA CAACAAAGGCNNNTGCATCAGGT | 2125 |
| TGCAGGACCAGAGAATTCGAATA CACGAGTACTNNNTGCATCAGGT | 1646 | TGCAGGACCAGAGAATTCGAATA CATTAATTGGNNNTGCATCAGGT | 1886 | TGCAGGACCAGAGAATTCGAATA CAGAGGCAGCNNNTGCATCAGGT | 2126 |
| TGCAGGACCAGAGAATTCGAATA CAGATCGAGANNNTGCATCAGGT | 1647 | TGCAGGACCAGAGAATTCGAATA CACAGAGTTCNNNTGCATCAGGT | 1887 | TGCAGGACCAGAGAATTCGAATA CACTACTCGTNNNTGCATCAGGT | 2127 |
| TGCAGGACCAGAGAATTCGAATA CAAGAATAACNNNTGCATCAGGT | 1648 | TGCAGGACCAGAGAATTCGAATA CAGCCATCTAGNNNTGCATCAGGT | 1888 | TGCAGGACCAGAGAATTCGAATA CAGGTAGTGANNNTGCATCAGGT | 2128 |
| TGCAGGACCAGAGAATTCGAATA CAGCGCACCANNNTGCATCAGGT | 1649 | TGCAGGACCAGAGAATTCGAATA CATTGTCTATNNNTGCATCAGGT | 1889 | TGCAGGACCAGAGAATTCGAATA CACCACCACCNNNTGCATCAGGT | 2129 |
| TGCAGGACCAGAGAATTCGAATA CACAGCAACTNNNTGCATCAGGT | 1650 | TGCAGGACCAGAGAATTCGAATA CACATCCTGTNNNTGCATCAGGT | 1890 | TGCAGGACCAGAGAATTCGAATA CATGTGTGACNNNTGCATCAGGT | 2130 |

FIG. 14H

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAGTGCCATANNNTGCATCAGGT | 1651 | TGCAGGACCAGAGAATTCGAATA CACATTCAAANNNTGCATCAGGT | 1891 | TGCAGGACCAGAGAATTCGAATA CACACCCTGCNNNTGCATCAGGT | 2131 |
| TGCAGGACCAGAGAATTCGAATA CAATCTATTCNNNTGCATCAGGT | 1652 | TGCAGGACCAGAGAATTCGAATA CAAAAGCCTCNNNTGCATCAGGT | 1892 | TGCAGGACCAGAGAATTCGAATA CATCGCCATTNNNTGCATCAGGT | 2132 |
| TGCAGGACCAGAGAATTCGAATA CAAGTATGTTNNNTGCATCAGGT | 1653 | TGCAGGACCAGAGAATTCGAATA CATGATCAATNNNTGCATCAGGT | 1893 | TGCAGGACCAGAGAATTCGAATA CAACTTCGCTNNNTGCATCAGGT | 2133 |
| TGCAGGACCAGAGAATTCGAATA CAGGTTCTTCNNNTGCATCAGGT | 1654 | TGCAGGACCAGAGAATTCGAATA CAATATGATCNNNTGCATCAGGT | 1894 | TGCAGGACCAGAGAATTCGAATA CATTGCTTTANNNTGCATCAGGT | 2134 |
| TGCAGGACCAGAGAATTCGAATA CATAGTGGCTNNNTGCATCAGGT | 1655 | TGCAGGACCAGAGAATTCGAATA CAGGACCGAGNNNTGCATCAGGT | 1895 | TGCAGGACCAGAGAATTCGAATA CAGCACGAGGNNNTGCATCAGGT | 2135 |
| TGCAGGACCAGAGAATTCGAATA CACCAACTTCNNNTGCATCAGGT | 1656 | TGCAGGACCAGAGAATTCGAATA CACCCCTAATNNNTGCATCAGGT | 1896 | TGCAGGACCAGAGAATTCGAATA CACGAATGTCNNNTGCATCAGGT | 2136 |
| TGCAGGACCAGAGAATTCGAATA CAAGTTCAATNNNTGCATCAGGT | 1657 | TGCAGGACCAGAGAATTCGAATA CACTCAAAGCNNNTGCATCAGGT | 1897 | TGCAGGACCAGAGAATTCGAATA CATGGCTAGTNNNTGCATCAGGT | 2137 |
| TGCAGGACCAGAGAATTCGAATA CATTGTTCGCNNNTGCATCAGGT | 1658 | TGCAGGACCAGAGAATTCGAATA CACTTCGTACNNNTGCATCAGGT | 1898 | TGCAGGACCAGAGAATTCGAATA CAGTGTTATANNNTGCATCAGGT | 2138 |
| TGCAGGACCAGAGAATTCGAATA CAGTCATGCANNNTGCATCAGGT | 1659 | TGCAGGACCAGAGAATTCGAATA CAATTGGCCANNNTGCATCAGGT | 1899 | TGCAGGACCAGAGAATTCGAATA CATTCCTTCCNNNTGCATCAGGT | 2139 |
| TGCAGGACCAGAGAATTCGAATA CACTGTAATANNNTGCATCAGGT | 1660 | TGCAGGACCAGAGAATTCGAATA CACGAAGGTANNNTGCATCAGGT | 1900 | TGCAGGACCAGAGAATTCGAATA CATCAACTAANNNTGCATCAGGT | 2140 |
| TGCAGGACCAGAGAATTCGAATA CATTCGGCCCNNNTGCATCAGGT | 1661 | TGCAGGACCAGAGAATTCGAATA CAGGCCTTGGNNNTGCATCAGGT | 1901 | TGCAGGACCAGAGAATTCGAATA CATTTACAAGNNNTGCATCAGGT | 2141 |
| TGCAGGACCAGAGAATTCGAATA CATCTCTCTCNNNTGCATCAGGT | 1662 | TGCAGGACCAGAGAATTCGAATA CAACAATATCNNNTGCATCAGGT | 1902 | TGCAGGACCAGAGAATTCGAATA CATCCTGCCGNNNTGCATCAGGT | 2142 |
| TGCAGGACCAGAGAATTCGAATA CACTTCGCGCNNNTGCATCAGGT | 1663 | TGCAGGACCAGAGAATTCGAATA CATCACAACGNNNTGCATCAGGT | 1903 | TGCAGGACCAGAGAATTCGAATA CATCGGCTAANNNTGCATCAGGT | 2143 |
| TGCAGGACCAGAGAATTCGAATA CAACAGATTCNNNTGCATCAGGT | 1664 | TGCAGGACCAGAGAATTCGAATA CAACTGTACGNNNTGCATCAGGT | 1904 | TGCAGGACCAGAGAATTCGAATA CAAGGAGCATNNNTGCATCAGGT | 2144 |
| TGCAGGACCAGAGAATTCGAATA CACAGACAAGNNNTGCATCAGGT | 1665 | TGCAGGACCAGAGAATTCGAATA CATCTCAATTNNNTGCATCAGGT | 1905 | TGCAGGACCAGAGAATTCGAATA CAGGAATACGNNNTGCATCAGGT | 2145 |
| TGCAGGACCAGAGAATTCGAATA CACAGCTACANNNTGCATCAGGT | 1666 | TGCAGGACCAGAGAATTCGAATA CAAGGCTCTANNNTGCATCAGGT | 1906 | TGCAGGACCAGAGAATTCGAATA CATGAGACGANNNTGCATCAGGT | 2146 |
| TGCAGGACCAGAGAATTCGAATA CAGACCGAGGNNNTGCATCAGGT | 1667 | TGCAGGACCAGAGAATTCGAATA CACCTTACCANNNTGCATCAGGT | 1907 | TGCAGGACCAGAGAATTCGAATA CACCACCAGGNNNTGCATCAGGT | 2147 |
| TGCAGGACCAGAGAATTCGAATA CACCTATAAANNNTGCATCAGGT | 1668 | TGCAGGACCAGAGAATTCGAATA CAGATTCCTCNNNTGCATCAGGT | 1908 | TGCAGGACCAGAGAATTCGAATA CAAGCTCATGNNNTGCATCAGGT | 2148 |
| TGCAGGACCAGAGAATTCGAATA CACCTAACCTNNNTGCATCAGGT | 1669 | TGCAGGACCAGAGAATTCGAATA CATGCCTGTTNNNTGCATCAGGT | 1909 | TGCAGGACCAGAGAATTCGAATA CATATACCGGNNNTGCATCAGGT | 2149 |
| TGCAGGACCAGAGAATTCGAATA CATTTAGCGGNNNTGCATCAGGT | 1670 | TGCAGGACCAGAGAATTCGAATA CATCACCAAGNNNTGCATCAGGT | 1910 | TGCAGGACCAGAGAATTCGAATA CAGATGCCATNNNTGCATCAGGT | 2150 |
| TGCAGGACCAGAGAATTCGAATA CATAAACCATNNNTGCATCAGGT | 1671 | TGCAGGACCAGAGAATTCGAATA CACTTCCGGCNNNTGCATCAGGT | 1911 | TGCAGGACCAGAGAATTCGAATA CATTGAGCTGNNNTGCATCAGGT | 2151 |
| TGCAGGACCAGAGAATTCGAATA CAGCTAACTGNNNTGCATCAGGT | 1672 | TGCAGGACCAGAGAATTCGAATA CAAAACGCAGNNNTGCATCAGGT | 1912 | TGCAGGACCAGAGAATTCGAATA CATAAATGGANNNTGCATCAGGT | 2152 |
| TGCAGGACCAGAGAATTCGAATA CAGTACAGAGNNNTGCATCAGGT | 1673 | TGCAGGACCAGAGAATTCGAATA CACGCATTCTNNNTGCATCAGGT | 1913 | TGCAGGACCAGAGAATTCGAATA CAACATGAAANNNTGCATCAGGT | 2153 |
| TGCAGGACCAGAGAATTCGAATA CACCCGACCANNNTGCATCAGGT | 1674 | TGCAGGACCAGAGAATTCGAATA CACGCCTATTNNNTGCATCAGGT | 1914 | TGCAGGACCAGAGAATTCGAATA CACTCGGAGCNNNTGCATCAGGT | 2154 |
| TGCAGGACCAGAGAATTCGAATA CACCTCTAGTNNNTGCATCAGGT | 1675 | TGCAGGACCAGAGAATTCGAATA CATCATCATTNNNTGCATCAGGT | 1915 | TGCAGGACCAGAGAATTCGAATA CAGTTTCCTGNNNTGCATCAGGT | 2155 |
| TGCAGGACCAGAGAATTCGAATA CAGCCCCTGTNNNTGCATCAGGT | 1676 | TGCAGGACCAGAGAATTCGAATA CAAATTCAGTNNNTGCATCAGGT | 1916 | TGCAGGACCAGAGAATTCGAATA CACAACATGCNNNTGCATCAGGT | 2156 |
| TGCAGGACCAGAGAATTCGAATA CACGGACTGCNNNTGCATCAGGT | 1677 | TGCAGGACCAGAGAATTCGAATA CAATTCTCGCNNNTGCATCAGGT | 1917 | TGCAGGACCAGAGAATTCGAATA CATGGTGCGCNNNTGCATCAGGT | 2157 |
| TGCAGGACCAGAGAATTCGAATA CACCCTCTGGNNNTGCATCAGGT | 1678 | TGCAGGACCAGAGAATTCGAATA CAATAGAGTANNNTGCATCAGGT | 1918 | TGCAGGACCAGAGAATTCGAATA CATACGGAGANNNTGCATCAGGT | 2158 |
| TGCAGGACCAGAGAATTCGAATA CAACCAAGTCNNNTGCATCAGGT | 1679 | TGCAGGACCAGAGAATTCGAATA CAGAGCGGACNNNTGCATCAGGT | 1919 | TGCAGGACCAGAGAATTCGAATA CAGGCGTGGANNNTGCATCAGGT | 2159 |

FIG. 14I

| Pool-7 | SEQ ID NO: | Pool-8 | SEQ ID NO: | Pool-9 | SEQ ID NO: |
|---|---|---|---|---|---|
| TGCAGGACCAGAGAATTCGAATA CAGCGTGGTCNNNTGCATCAGGT | 1680 | TGCAGGACCAGAGAATTCGAATA CAACTTTTACNNNTGCATCAGGT | 1920 | TGCAGGACCAGAGAATTCGAATA CATCTAACGGNNNTGCATCAGGT | 2160 |
| TGCAGGACCAGAGAATTCGAATA CACCGACGCANNNTGCATCAGGT | 1681 | TGCAGGACCAGAGAATTCGAATA CAAGTCAAAANNNTGCATCAGGT | 1921 | TGCAGGACCAGAGAATTCGAATA CATATAGCATNNNTGCATCAGGT | 2161 |
| TGCAGGACCAGAGAATTCGAATA CATTACCGGANNNTGCATCAGGT | 1682 | TGCAGGACCAGAGAATTCGAATA CATCTAGACGNNNTGCATCAGGT | 1922 | TGCAGGACCAGAGAATTCGAATA CACGCTCCGTNNNTGCATCAGGT | 2162 |
| TGCAGGACCAGAGAATTCGAATA CATCTTTGCGNNNTGCATCAGGT | 1683 | TGCAGGACCAGAGAATTCGAATA CACAAATGTTNNNTGCATCAGGT | 1923 | TGCAGGACCAGAGAATTCGAATA CAATACATGTNNNTGCATCAGGT | 2163 |
| TGCAGGACCAGAGAATTCGAATA CACACAATTANNNTGCATCAGGT | 1684 | TGCAGGACCAGAGAATTCGAATA CATGGCTTTCNNNTGCATCAGGT | 1924 | TGCAGGACCAGAGAATTCGAATA CAGGCTCGCANNNTGCATCAGGT | 2164 |
| TGCAGGACCAGAGAATTCGAATA CACCTACATCNNNTGCATCAGGT | 1685 | TGCAGGACCAGAGAATTCGAATA CAAGGCTGTTNNNTGCATCAGGT | 1925 | TGCAGGACCAGAGAATTCGAATA CAGTTTAGTANNNTGCATCAGGT | 2165 |
| TGCAGGACCAGAGAATTCGAATA CAATTACTGANNNTGCATCAGGT | 1686 | TGCAGGACCAGAGAATTCGAATA CAAACTATTGNNNTGCATCAGGT | 1926 | TGCAGGACCAGAGAATTCGAATA CACTGAAATTNNNTGCATCAGGT | 2166 |
| TGCAGGACCAGAGAATTCGAATA CATTTTTCGANNNTGCATCAGGT | 1687 | TGCAGGACCAGAGAATTCGAATA CAATGTATTGNNNTGCATCAGGT | 1927 | TGCAGGACCAGAGAATTCGAATA CAAACACCTGNNNTGCATCAGGT | 2167 |
| TGCAGGACCAGAGAATTCGAATA CAAGGTGCTTNNNTGCATCAGGT | 1688 | TGCAGGACCAGAGAATTCGAATA CACGTCGGCANNNTGCATCAGGT | 1928 | TGCAGGACCAGAGAATTCGAATA CAGGAAAACCNNNTGCATCAGGT | 2168 |

FIG. 15A

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAGCTTCTCANNNACGTATGCCA | 2169 | TGCAGGACCAGAGAATTCGAATACAATACGTATNNNACGTATGCCA | 2409 | TGCAGGACCAGAGAATTCGAATACATTGAGAAANNNACGTATGCCA | 2649 |
| TGCAGGACCAGAGAATTCGAATACAATGCTACGNNNACGTATGCCA | 2170 | TGCAGGACCAGAGAATTCGAATACAAACTAGCCNNNACGTATGCCA | 2410 | TGCAGGACCAGAGAATTCGAATACAAATATCCANNNACGTATGCCA | 2650 |
| TGCAGGACCAGAGAATTCGAATACATACTCTCGNNNACGTATGCCA | 2171 | TGCAGGACCAGAGAATTCGAATACACGGATTACNNNACGTATGCCA | 2411 | TGCAGGACCAGAGAATTCGAATACAATGGACCTNNNACGTATGCCA | 2651 |
| TGCAGGACCAGAGAATTCGAATACACGGTCGCANNNACGTATGCCA | 2172 | TGCAGGACCAGAGAATTCGAATACAGGACGCCTNNNACGTATGCCA | 2412 | TGCAGGACCAGAGAATTCGAATACAGGCATACTNNNACGTATGCCA | 2652 |
| TGCAGGACCAGAGAATTCGAATACAACGGTTACNNNACGTATGCCA | 2173 | TGCAGGACCAGAGAATTCGAATACACGTTAAATNNNACGTATGCCA | 2413 | TGCAGGACCAGAGAATTCGAATACACTAAAAAGNNNACGTATGCCA | 2653 |
| TGCAGGACCAGAGAATTCGAATACATAGCACACNNNACGTATGCCA | 2174 | TGCAGGACCAGAGAATTCGAATACAGGCTAGTTNNNACGTATGCCA | 2414 | TGCAGGACCAGAGAATTCGAATACAATACATACNNNACGTATGCCA | 2654 |
| TGCAGGACCAGAGAATTCGAATACACGTCTCTANNNACGTATGCCA | 2175 | TGCAGGACCAGAGAATTCGAATACATCAGAAGGNNNACGTATGCCA | 2415 | TGCAGGACCAGAGAATTCGAATACATATGGCCANNNACGTATGCCA | 2655 |
| TGCAGGACCAGAGAATTCGAATACAGCTCCGCTNNNACGTATGCCA | 2176 | TGCAGGACCAGAGAATTCGAATACAACCAACTGNNNACGTATGCCA | 2416 | TGCAGGACCAGAGAATTCGAATACAATGATGCCNNNACGTATGCCA | 2656 |
| TGCAGGACCAGAGAATTCGAATACAGTGGCACCNNNACGTATGCCA | 2177 | TGCAGGACCAGAGAATTCGAATACATCGACAACNNNACGTATGCCA | 2417 | TGCAGGACCAGAGAATTCGAATACAAGGTAGGTNNNACGTATGCCA | 2657 |
| TGCAGGACCAGAGAATTCGAATACAGCACTATGNNNACGTATGCCA | 2178 | TGCAGGACCAGAGAATTCGAATACAGTCGTACANNNACGTATGCCA | 2418 | TGCAGGACCAGAGAATTCGAATACATCCCTAGTNNNACGTATGCCA | 2658 |
| TGCAGGACCAGAGAATTCGAATACAAATAACGANNNACGTATGCCA | 2179 | TGCAGGACCAGAGAATTCGAATACAGCCAGAGGNNNACGTATGCCA | 2419 | TGCAGGACCAGAGAATTCGAATACAGTATTTGANNNACGTATGCCA | 2659 |
| TGCAGGACCAGAGAATTCGAATACAGGTATAGGNNNACGTATGCCA | 2180 | TGCAGGACCAGAGAATTCGAATACACATAGTATNNNACGTATGCCA | 2420 | TGCAGGACCAGAGAATTCGAATACAAGTGAATANNNACGTATGCCA | 2660 |
| TGCAGGACCAGAGAATTCGAATACAAGAACCCTNNNACGTATGCCA | 2181 | TGCAGGACCAGAGAATTCGAATACATAAATGTCNNNACGTATGCCA | 2421 | TGCAGGACCAGAGAATTCGAATACAAATCGCACNNNACGTATGCCA | 2661 |
| TGCAGGACCAGAGAATTCGAATACAGCCGCGTANNNACGTATGCCA | 2182 | TGCAGGACCAGAGAATTCGAATACAGCGTCGGTNNNACGTATGCCA | 2422 | TGCAGGACCAGAGAATTCGAATACAGTCCCCCANNNACGTATGCCA | 2662 |
| TGCAGGACCAGAGAATTCGAATACATTCCCTGANNNACGTATGCCA | 2183 | TGCAGGACCAGAGAATTCGAATACATTTGAACANNNACGTATGCCA | 2423 | TGCAGGACCAGAGAATTCGAATACAGCCCACTCNNNACGTATGCCA | 2663 |
| TGCAGGACCAGAGAATTCGAATACAATGGCATCNNNACGTATGCCA | 2184 | TGCAGGACCAGAGAATTCGAATACATAACTATGNNNACGTATGCCA | 2424 | TGCAGGACCAGAGAATTCGAATACAGAGATATANNNACGTATGCCA | 2664 |
| TGCAGGACCAGAGAATTCGAATACAAAGGATCGNNNACGTATGCCA | 2185 | TGCAGGACCAGAGAATTCGAATACATCAGATGCNNNACGTATGCCA | 2425 | TGCAGGACCAGAGAATTCGAATACAGCACTACANNNACGTATGCCA | 2665 |
| TGCAGGACCAGAGAATTCGAATACAGTGCATCANNNACGTATGCCA | 2186 | TGCAGGACCAGAGAATTCGAATACACTCAACAGNNNACGTATGCCA | 2426 | TGCAGGACCAGAGAATTCGAATACAACTTTGCCNNNACGTATGCCA | 2666 |
| TGCAGGACCAGAGAATTCGAATACAGTCGTCTTNNNACGTATGCCA | 2187 | TGCAGGACCAGAGAATTCGAATACAATAAAGTGNNNACGTATGCCA | 2427 | TGCAGGACCAGAGAATTCGAATACACTGAGGCCNNNACGTATGCCA | 2667 |
| TGCAGGACCAGAGAATTCGAATACACTTGAGGTNNNACGTATGCCA | 2188 | TGCAGGACCAGAGAATTCGAATACAAGAGCAGTNNNACGTATGCCA | 2428 | TGCAGGACCAGAGAATTCGAATACAAAGTAGGCNNNACGTATGCCA | 2668 |
| TGCAGGACCAGAGAATTCGAATACATACATCAANNNACGTATGCCA | 2189 | TGCAGGACCAGAGAATTCGAATACATATGTCTTNNNACGTATGCCA | 2429 | TGCAGGACCAGAGAATTCGAATACAGCTTCTACNNNACGTATGCCA | 2669 |
| TGCAGGACCAGAGAATTCGAATACACCGAACCGNNNACGTATGCCA | 2190 | TGCAGGACCAGAGAATTCGAATACAGCAGAGATNNNACGTATGCCA | 2430 | TGCAGGACCAGAGAATTCGAATACATGGAGGATNNNACGTATGCCA | 2670 |
| TGCAGGACCAGAGAATTCGAATACACCCACACCNNNACGTATGCCA | 2191 | TGCAGGACCAGAGAATTCGAATACATCTCACCANNNACGTATGCCA | 2431 | TGCAGGACCAGAGAATTCGAATACAGCTAACCANNNACGTATGCCA | 2671 |
| TGCAGGACCAGAGAATTCGAATACAACGTAAAANNNACGTATGCCA | 2192 | TGCAGGACCAGAGAATTCGAATACACCCCTTGGNNNACGTATGCCA | 2432 | TGCAGGACCAGAGAATTCGAATACAACCCTTACNNNACGTATGCCA | 2672 |
| TGCAGGACCAGAGAATTCGAATACAGTAGAGTGNNNACGTATGCCA | 2193 | TGCAGGACCAGAGAATTCGAATACACAGTGGCCNNNACGTATGCCA | 2433 | TGCAGGACCAGAGAATTCGAATACAGTCTTCTGNNNACGTATGCCA | 2673 |
| TGCAGGACCAGAGAATTCGAATACACCACATAGNNNACGTATGCCA | 2194 | TGCAGGACCAGAGAATTCGAATACACTGATGCANNNACGTATGCCA | 2434 | TGCAGGACCAGAGAATTCGAATACACGGAGCCTNNNACGTATGCCA | 2674 |
| TGCAGGACCAGAGAATTCGAATACATCTGTGCTNNNACGTATGCCA | 2195 | TGCAGGACCAGAGAATTCGAATACATGGTACGTNNNACGTATGCCA | 2435 | TGCAGGACCAGAGAATTCGAATACACCTGATGANNNACGTATGCCA | 2675 |
| TGCAGGACCAGAGAATTCGAATACATAGTACATNNNACGTATGCCA | 2196 | TGCAGGACCAGAGAATTCGAATACAGTACGGCCNNNACGTATGCCA | 2436 | TGCAGGACCAGAGAATTCGAATACATCGATACGNNNACGTATGCCA | 2676 |
| TGCAGGACCAGAGAATTCGAATACACCGGACACNNNACGTATGCCA | 2197 | TGCAGGACCAGAGAATTCGAATACACCATGCGGNNNACGTATGCCA | 2437 | TGCAGGACCAGAGAATTCGAATACAAAGAATGTNNNACGTATGCCA | 2677 |
| TGCAGGACCAGAGAATTCGAATACAGTAAGCTCNNNACGTATGCCA | 2198 | TGCAGGACCAGAGAATTCGAATACACAAGTAGGNNNACGTATGCCA | 2438 | TGCAGGACCAGAGAATTCGAATACATGCGCTCCNNNACGTATGCCA | 2678 |
| TGCAGGACCAGAGAATTCGAATACAACTTGGTGNNNACGTATGCCA | 2199 | TGCAGGACCAGAGAATTCGAATACACATCAAATNNNACGTATGCCA | 2439 | TGCAGGACCAGAGAATTCGAATACAAAGTCATTNNNACGTATGCCA | 2679 |
| TGCAGGACCAGAGAATTCGAATACACGACCTGGNNNACGTATGCCA | 2200 | TGCAGGACCAGAGAATTCGAATACAGACTCGGTNNNACGTATGCCA | 2440 | TGCAGGACCAGAGAATTCGAATACATGTAATGTNNNACGTATGCCA | 2680 |

FIG. 15B

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAT GAGGATGNNNACGTATGCCA | 2201 | TGCAGGACCAGAGAATTCGAATACAG CAAATTTNNNACGTATGCCA | 2441 | TGCAGGACCAGAGAATTCGAATACAA TCTACCCNNNACGTATGCCA | 2681 |
| TGCAGGACCAGAGAATTCGAATACAC TCGTGCCNNNACGTATGCCA | 2202 | TGCAGGACCAGAGAATTCGAATACAT TAGTGTANNNACGTATGCCA | 2442 | TGCAGGACCAGAGAATTCGAATACAT GCCACAANNNACGTATGCCA | 2682 |
| TGCAGGACCAGAGAATTCGAATACAT TGCTCGTNNNACGTATGCCA | 2203 | TGCAGGACCAGAGAATTCGAATACAG ATGAAATNNNACGTATGCCA | 2443 | TGCAGGACCAGAGAATTCGAATACAG AGTGTTCNNNACGTATGCCA | 2683 |
| TGCAGGACCAGAGAATTCGAATACAA CACTGACNNNACGTATGCCA | 2204 | TGCAGGACCAGAGAATTCGAATACAT TGCCGANNNNACGTATGCCA | 2444 | TGCAGGACCAGAGAATTCGAATACAA ACAGCCTNNNACGTATGCCA | 2684 |
| TGCAGGACCAGAGAATTCGAATACAG TTGGTACNNNACGTATGCCA | 2205 | TGCAGGACCAGAGAATTCGAATACAT CCTCCTTNNNACGTATGCCA | 2445 | TGCAGGACCAGAGAATTCGAATACAG GACGACGNNNACGTATGCCA | 2685 |
| TGCAGGACCAGAGAATTCGAATACAT TCAGTCCNNNACGTATGCCA | 2206 | TGCAGGACCAGAGAATTCGAATACAC CCCATTANNNACGTATGCCA | 2446 | TGCAGGACCAGAGAATTCGAATACAA TTCCCGANNNACGTATGCCA | 2686 |
| TGCAGGACCAGAGAATTCGAATACAG TAACAAANNNACGTATGCCA | 2207 | TGCAGGACCAGAGAATTCGAATACAG TTTGTTTNNNACGTATGCCA | 2447 | TGCAGGACCAGAGAATTCGAATACAG GTCTCAANNNACGTATGCCA | 2687 |
| TGCAGGACCAGAGAATTCGAATACAC AACTGGTNNNACGTATGCCA | 2208 | TGCAGGACCAGAGAATTCGAATACAT ATCCCGTNNNACGTATGCCA | 2448 | TGCAGGACCAGAGAATTCGAATACAC ACCATGANNNACGTATGCCA | 2688 |
| TGCAGGACCAGAGAATTCGAATACAT GGATACCNNNACGTATGCCA | 2209 | TGCAGGACCAGAGAATTCGAATACAT TCGGTGANNNACGTATGCCA | 2449 | TGCAGGACCAGAGAATTCGAATACAC AAACGGANNNACGTATGCCA | 2689 |
| TGCAGGACCAGAGAATTCGAATACAA TGCACCANNNACGTATGCCA | 2210 | TGCAGGACCAGAGAATTCGAATACAC GTAAGGANNNACGTATGCCA | 2450 | TGCAGGACCAGAGAATTCGAATACAA GAGCGTANNNACGTATGCCA | 2690 |
| TGCAGGACCAGAGAATTCGAATACAA CTCCTTGNNNACGTATGCCA | 2211 | TGCAGGACCAGAGAATTCGAATACAC TTTCTTTNNNACGTATGCCA | 2451 | TGCAGGACCAGAGAATTCGAATACAC CCCTGACNNNACGTATGCCA | 2691 |
| TGCAGGACCAGAGAATTCGAATACAA ATAGTTCNNNACGTATGCCA | 2212 | TGCAGGACCAGAGAATTCGAATACAG ACTTTTTNNNACGTATGCCA | 2452 | TGCAGGACCAGAGAATTCGAATACAC CAAGTTGNNNACGTATGCCA | 2692 |
| TGCAGGACCAGAGAATTCGAATACAT GAGAGCANNNACGTATGCCA | 2213 | TGCAGGACCAGAGAATTCGAATACAG GTTAAGGNNNACGTATGCCA | 2453 | TGCAGGACCAGAGAATTCGAATACAT GTGTAATNNNACGTATGCCA | 2693 |
| TGCAGGACCAGAGAATTCGAATACAT CACCCCGNNNACGTATGCCA | 2214 | TGCAGGACCAGAGAATTCGAATACAA TCACGGTNNNACGTATGCCA | 2454 | TGCAGGACCAGAGAATTCGAATACAA TTTGTGANNNACGTATGCCA | 2694 |
| TGCAGGACCAGAGAATTCGAATACAT AATGGAANNNACGTATGCCA | 2215 | TGCAGGACCAGAGAATTCGAATACAC ATTTAGANNNACGTATGCCA | 2455 | TGCAGGACCAGAGAATTCGAATACAG TAGCGTTNNNACGTATGCCA | 2695 |
| TGCAGGACCAGAGAATTCGAATACAT CCAAATANNNACGTATGCCA | 2216 | TGCAGGACCAGAGAATTCGAATACAC ACGCGCANNNACGTATGCCA | 2456 | TGCAGGACCAGAGAATTCGAATACAC ACGTGATNNNACGTATGCCA | 2696 |
| TGCAGGACCAGAGAATTCGAATACAG AGGCTCCNNNACGTATGCCA | 2217 | TGCAGGACCAGAGAATTCGAATACAC TGAATCGNNNACGTATGCCA | 2457 | TGCAGGACCAGAGAATTCGAATACAA ACAGCGANNNACGTATGCCA | 2697 |
| TGCAGGACCAGAGAATTCGAATACAT CCGCGTCNNNACGTATGCCA | 2218 | TGCAGGACCAGAGAATTCGAATACAT TGTGTAANNNACGTATGCCA | 2458 | TGCAGGACCAGAGAATTCGAATACAA AATGCGGNNNACGTATGCCA | 2698 |
| TGCAGGACCAGAGAATTCGAATACAG CATTGCANNNACGTATGCCA | 2219 | TGCAGGACCAGAGAATTCGAATACAC CGCGTGANNNACGTATGCCA | 2459 | TGCAGGACCAGAGAATTCGAATACAT ACCAAGCNNNACGTATGCCA | 2699 |
| TGCAGGACCAGAGAATTCGAATACAC CCCTTAANNNACGTATGCCA | 2220 | TGCAGGACCAGAGAATTCGAATACAA ACCAAGGNNNACGTATGCCA | 2460 | TGCAGGACCAGAGAATTCGAATACAC GACCCTCNNNACGTATGCCA | 2700 |
| TGCAGGACCAGAGAATTCGAATACAG ACCGCCANNNACGTATGCCA | 2221 | TGCAGGACCAGAGAATTCGAATACAT CGTTTGCNNNACGTATGCCA | 2461 | TGCAGGACCAGAGAATTCGAATACAA CACCCTTNNNACGTATGCCA | 2701 |
| TGCAGGACCAGAGAATTCGAATACAG ATCTGACNNNACGTATGCCA | 2222 | TGCAGGACCAGAGAATTCGAATACAC TATTCGCNNNACGTATGCCA | 2462 | TGCAGGACCAGAGAATTCGAATACAC TGTCGCCNNNACGTATGCCA | 2702 |
| TGCAGGACCAGAGAATTCGAATACAG CATGTTGNNNACGTATGCCA | 2223 | TGCAGGACCAGAGAATTCGAATACAA ACAGATANNNACGTATGCCA | 2463 | TGCAGGACCAGAGAATTCGAATACAA GCCGCCANNNACGTATGCCA | 2703 |
| TGCAGGACCAGAGAATTCGAATACAT AGCACGTNNNACGTATGCCA | 2224 | TGCAGGACCAGAGAATTCGAATACAC TATTATCNNNACGTATGCCA | 2464 | TGCAGGACCAGAGAATTCGAATACAT GTACAATNNNACGTATGCCA | 2704 |
| TGCAGGACCAGAGAATTCGAATACAG GTCCAATNNNACGTATGCCA | 2225 | TGCAGGACCAGAGAATTCGAATACAT CCCAATCNNNACGTATGCCA | 2465 | TGCAGGACCAGAGAATTCGAATACAG ATCTACGNNNACGTATGCCA | 2705 |
| TGCAGGACCAGAGAATTCGAATACAA CCCTCTANNNACGTATGCCA | 2226 | TGCAGGACCAGAGAATTCGAATACAC TAAAGTTNNNACGTATGCCA | 2466 | TGCAGGACCAGAGAATTCGAATACAC CAGTCTTNNNACGTATGCCA | 2706 |
| TGCAGGACCAGAGAATTCGAATACAT TACGACGNNNACGTATGCCA | 2227 | TGCAGGACCAGAGAATTCGAATACAA GCTAATTNNNACGTATGCCA | 2467 | TGCAGGACCAGAGAATTCGAATACAG CTGCAATNNNACGTATGCCA | 2707 |
| TGCAGGACCAGAGAATTCGAATACAC ATATCGGNNNACGTATGCCA | 2228 | TGCAGGACCAGAGAATTCGAATACAT TGTTATGNNNACGTATGCCA | 2468 | TGCAGGACCAGAGAATTCGAATACAG AAGAGTCNNNACGTATGCCA | 2708 |
| TGCAGGACCAGAGAATTCGAATACAG CGATATCNNNCTAGCGTTAC | 2229 | TGCAGGACCAGAGAATTCGAATACAT AGTACGCNNNCTAGCGTTAC | 2469 | TGCAGGACCAGAGAATTCGAATACAA CAACTCGNNNCTAGCGTTAC | 2709 |
| TGCAGGACCAGAGAATTCGAATACAT ACGAGGANNNCTAGCGTTAC | 2230 | TGCAGGACCAGAGAATTCGAATACAC AGGCTATNNNCTAGCGTTAC | 2470 | TGCAGGACCAGAGAATTCGAATACAT GCGCAATNNNCTAGCGTTAC | 2710 |
| TGCAGGACCAGAGAATTCGAATACAT CTTACATNNNCTAGCGTTAC | 2231 | TGCAGGACCAGAGAATTCGAATACAC ATTAGTANNNCTAGCGTTAC | 2471 | TGCAGGACCAGAGAATTCGAATACAT AAGAACANNNCTAGCGTTAC | 2711 |
| TGCAGGACCAGAGAATTCGAATACAG CGTCTCCNNNCTAGCGTTAC | 2232 | TGCAGGACCAGAGAATTCGAATACAC CTCTAACNNNCTAGCGTTAC | 2472 | TGCAGGACCAGAGAATTCGAATACAC GCTTGCCNNNCTAGCGTTAC | 2712 |

FIG. 15C

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAT AATCCGGNNNCTAGCGTTAC | 2233 | TGCAGGACCAGAGAATTCGAATACAT ACTGTCGNNNCTAGCGTTAC | 2473 | TGCAGGACCAGAGAATTCGAATACAT TACACGGNNNCTAGCGTTAC | 2713 |
| TGCAGGACCAGAGAATTCGAATACAC AGCATACNNNCTAGCGTTAC | 2234 | TGCAGGACCAGAGAATTCGAATACAC GCAGAGGNNNCTAGCGTTAC | 2474 | TGCAGGACCAGAGAATTCGAATACAC TCCACCGNNNCTAGCGTTAC | 2714 |
| TGCAGGACCAGAGAATTCGAATACAG TTCTCCANNNCTAGCGTTAC | 2235 | TGCAGGACCAGAGAATTCGAATACAG CGGTTCGNNNCTAGCGTTAC | 2475 | TGCAGGACCAGAGAATTCGAATACAC GACCCAGNNNCTAGCGTTAC | 2715 |
| TGCAGGACCAGAGAATTCGAATACAA GTTCCTCNNNCTAGCGTTAC | 2236 | TGCAGGACCAGAGAATTCGAATACAC CAGAGTTNNNCTAGCGTTAC | 2476 | TGCAGGACCAGAGAATTCGAATACAC GGTCAGCNNNCTAGCGTTAC | 2716 |
| TGCAGGACCAGAGAATTCGAATACAA AATCGAANNNCTAGCGTTAC | 2237 | TGCAGGACCAGAGAATTCGAATACAT GATGAAANNNCTAGCGTTAC | 2477 | TGCAGGACCAGAGAATTCGAATACAC ACTATCCNNNCTAGCGTTAC | 2717 |
| TGCAGGACCAGAGAATTCGAATACAA GATTATCNNNCTAGCGTTAC | 2238 | TGCAGGACCAGAGAATTCGAATACAG GTGAATGNNNCTAGCGTTAC | 2478 | TGCAGGACCAGAGAATTCGAATACAC TAGTCTCNNNCTAGCGTTAC | 2718 |
| TGCAGGACCAGAGAATTCGAATACAG TTTCACCNNNCTAGCGTTAC | 2239 | TGCAGGACCAGAGAATTCGAATACAG TATGTGCNNNCTAGCGTTAC | 2479 | TGCAGGACCAGAGAATTCGAATACAT ACCTTCGNNNCTAGCGTTAC | 2719 |
| TGCAGGACCAGAGAATTCGAATACAA TTACATGNNNCTAGCGTTAC | 2240 | TGCAGGACCAGAGAATTCGAATACAA ATACTACNNNCTAGCGTTAC | 2480 | TGCAGGACCAGAGAATTCGAATACAA ACCAGAGNNNCTAGCGTTAC | 2720 |
| TGCAGGACCAGAGAATTCGAATACAA CCATCCTNNNCTAGCGTTAC | 2241 | TGCAGGACCAGAGAATTCGAATACAT TCGGATGNNNCTAGCGTTAC | 2481 | TGCAGGACCAGAGAATTCGAATACAT GACTCGANNNCTAGCGTTAC | 2721 |
| TGCAGGACCAGAGAATTCGAATACAC AGACTACNNNCTAGCGTTAC | 2242 | TGCAGGACCAGAGAATTCGAATACAT ACATTAGNNNCTAGCGTTAC | 2482 | TGCAGGACCAGAGAATTCGAATACAA CCCAGATNNNCTAGCGTTAC | 2722 |
| TGCAGGACCAGAGAATTCGAATACAC ATTGGTGNNNCTAGCGTTAC | 2243 | TGCAGGACCAGAGAATTCGAATACAT GGCCCGANNNCTAGCGTTAC | 2483 | TGCAGGACCAGAGAATTCGAATACAT GCGCTTTNNNCTAGCGTTAC | 2723 |
| TGCAGGACCAGAGAATTCGAATACAG AGACCTTNNNCTAGCGTTAC | 2244 | TGCAGGACCAGAGAATTCGAATACAG TTGAGTCNNNCTAGCGTTAC | 2484 | TGCAGGACCAGAGAATTCGAATACAG GAGGACCNNNCTAGCGTTAC | 2724 |
| TGCAGGACCAGAGAATTCGAATACAT CAGGCCGNNNCTAGCGTTAC | 2245 | TGCAGGACCAGAGAATTCGAATACAG TTAGCACNNNCTAGCGTTAC | 2485 | TGCAGGACCAGAGAATTCGAATACAT CGTCCATNNNCTAGCGTTAC | 2725 |
| TGCAGGACCAGAGAATTCGAATACAC AACACACNNNCTAGCGTTAC | 2246 | TGCAGGACCAGAGAATTCGAATACAA GTTCCCTNNNCTAGCGTTAC | 2486 | TGCAGGACCAGAGAATTCGAATACAC GACCTCCNNNCTAGCGTTAC | 2726 |
| TGCAGGACCAGAGAATTCGAATACAC GACGTCGNNNCTAGCGTTAC | 2247 | TGCAGGACCAGAGAATTCGAATACAC ATGGAGANNNCTAGCGTTAC | 2487 | TGCAGGACCAGAGAATTCGAATACAA GATTCCGNNNCTAGCGTTAC | 2727 |
| TGCAGGACCAGAGAATTCGAATACAT AGACTATNNNCTAGCGTTAC | 2248 | TGCAGGACCAGAGAATTCGAATACAA ATCGTCGNNNCTAGCGTTAC | 2488 | TGCAGGACCAGAGAATTCGAATACAA CTCGAACNNNCTAGCGTTAC | 2728 |
| TGCAGGACCAGAGAATTCGAATACAC CGAGAAANNNCTAGCGTTAC | 2249 | TGCAGGACCAGAGAATTCGAATACAA CTCGCAANNNCTAGCGTTAC | 2489 | TGCAGGACCAGAGAATTCGAATACAA GACGATGNNNCTAGCGTTAC | 2729 |
| TGCAGGACCAGAGAATTCGAATACAT TCCATATNNNCTAGCGTTAC | 2250 | TGCAGGACCAGAGAATTCGAATACAT CAGCCTTNNNCTAGCGTTAC | 2490 | TGCAGGACCAGAGAATTCGAATACAG AACTTATNNNCTAGCGTTAC | 2730 |
| TGCAGGACCAGAGAATTCGAATACAG CCATGATNNNCTAGCGTTAC | 2251 | TGCAGGACCAGAGAATTCGAATACAT TGCCTCANNNCTAGCGTTAC | 2491 | TGCAGGACCAGAGAATTCGAATACAA CCAGCGCNNNCTAGCGTTAC | 2731 |
| TGCAGGACCAGAGAATTCGAATACAC GCGACGANNNCTAGCGTTAC | 2252 | TGCAGGACCAGAGAATTCGAATACAG GACCCACNNNCTAGCGTTAC | 2492 | TGCAGGACCAGAGAATTCGAATACAT ACCTCTGNNNCTAGCGTTAC | 2732 |
| TGCAGGACCAGAGAATTCGAATACAC CCAGTAANNNCTAGCGTTAC | 2253 | TGCAGGACCAGAGAATTCGAATACAT TCTCCAGNNNCTAGCGTTAC | 2493 | TGCAGGACCAGAGAATTCGAATACAC GGAGCGANNNCTAGCGTTAC | 2733 |
| TGCAGGACCAGAGAATTCGAATACAC TCAAACGNNNCTAGCGTTAC | 2254 | TGCAGGACCAGAGAATTCGAATACAG TCCTGCGNNNCTAGCGTTAC | 2494 | TGCAGGACCAGAGAATTCGAATACAA CCCGGAAANNNCTAGCGTTAC | 2734 |
| TGCAGGACCAGAGAATTCGAATACAC AGATCGNNNCTAGCGTTAC | 2255 | TGCAGGACCAGAGAATTCGAATACAA ATAGTCTNNNCTAGCGTTAC | 2495 | TGCAGGACCAGAGAATTCGAATACAG GATCGCCNNNCTAGCGTTAC | 2735 |
| TGCAGGACCAGAGAATTCGAATACAA GAAAATCNNNCTAGCGTTAC | 2256 | TGCAGGACCAGAGAATTCGAATACAG CTGGATTNNNCTAGCGTTAC | 2496 | TGCAGGACCAGAGAATTCGAATACAA TCAGCACNNNCTAGCGTTAC | 2736 |
| TGCAGGACCAGAGAATTCGAATACAA TCTTTCANNNCTAGCGTTAC | 2257 | TGCAGGACCAGAGAATTCGAATACAT TCGTCACNNNCTAGCGTTAC | 2497 | TGCAGGACCAGAGAATTCGAATACAA ACTCTCCNNNCTAGCGTTAC | 2737 |
| TGCAGGACCAGAGAATTCGAATACAC CCATCTANNNCTAGCGTTAC | 2258 | TGCAGGACCAGAGAATTCGAATACAA TTATGACNNNCTAGCGTTAC | 2498 | TGCAGGACCAGAGAATTCGAATACAT ATGAGTTNNNCTAGCGTTAC | 2738 |
| TGCAGGACCAGAGAATTCGAATACAC TAAGGTCNNNCTAGCGTTAC | 2259 | TGCAGGACCAGAGAATTCGAATACAT TTTAGAGNNNCTAGCGTTAC | 2499 | TGCAGGACCAGAGAATTCGAATACAA GGCGTCCNNNCTAGCGTTAC | 2739 |
| TGCAGGACCAGAGAATTCGAATACAC ACCGACGNNNCTAGCGTTAC | 2260 | TGCAGGACCAGAGAATTCGAATACAG ATATACTNNNCTAGCGTTAC | 2500 | TGCAGGACCAGAGAATTCGAATACAA GAATTAGNNNCTAGCGTTAC | 2740 |
| TGCAGGACCAGAGAATTCGAATACAG TTTAGATNNNCTAGCGTTAC | 2261 | TGCAGGACCAGAGAATTCGAATACAG CTACCCGNNNCTAGCGTTAC | 2501 | TGCAGGACCAGAGAATTCGAATACAG ATTTAGTNNNCTAGCGTTAC | 2741 |
| TGCAGGACCAGAGAATTCGAATACAT CCCCTCCNNNCTAGCGTTAC | 2262 | TGCAGGACCAGAGAATTCGAATACAA ACCTTTTNNNCTAGCGTTAC | 2502 | TGCAGGACCAGAGAATTCGAATACAT ATTTCTGNNNCTAGCGTTAC | 2742 |
| TGCAGGACCAGAGAATTCGAATACAT TAATCAGNNNCTAGCGTTAC | 2263 | TGCAGGACCAGAGAATTCGAATACAA TGTGTATNNNCTAGCGTTAC | 2503 | TGCAGGACCAGAGAATTCGAATACAG CTGTACANNNCTAGCGTTAC | 2743 |
| TGCAGGACCAGAGAATTCGAATACAC ATTCGAGNNNCTAGCGTTAC | 2264 | TGCAGGACCAGAGAATTCGAATACAT CCCACGCNNNCTAGCGTTAC | 2504 | TGCAGGACCAGAGAATTCGAATACAG CTTACGANNNCTAGCGTTAC | 2744 |

FIG. 15D

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAAACCGTGTNNNCTAGCGTTAC | 2265 | TGCAGGACCAGAGAATTCGAATACACGCCTCTGNNNCTAGCGTTAC | 2505 | TGCAGGACCAGAGAATTCGAATACACCCACGGANNNCTAGCGTTAC | 2745 |
| TGCAGGACCAGAGAATTCGAATACACCCAATTCNNNCTAGCGTTAC | 2266 | TGCAGGACCAGAGAATTCGAATACACTATAACANNNCTAGCGTTAC | 2506 | TGCAGGACCAGAGAATTCGAATACATGGATCTGNNNCTAGCGTTAC | 2746 |
| TGCAGGACCAGAGAATTCGAATACATTGGTGGTNNNCTAGCGTTAC | 2267 | TGCAGGACCAGAGAATTCGAATACAGACTGACTNNNCTAGCGTTAC | 2507 | TGCAGGACCAGAGAATTCGAATACATCCACGAANNNCTAGCGTTAC | 2747 |
| TGCAGGACCAGAGAATTCGAATACATGCTTAGGNNNCTAGCGTTAC | 2268 | TGCAGGACCAGAGAATTCGAATACACTCGGCCAGNNNCTAGCGTTAC | 2508 | TGCAGGACCAGAGAATTCGAATACATCAAGACCNNNCTAGCGTTAC | 2748 |
| TGCAGGACCAGAGAATTCGAATACAACACCCCCNNNCTAGCGTTAC | 2269 | TGCAGGACCAGAGAATTCGAATACAAAGCCAAGNNNCTAGCGTTAC | 2509 | TGCAGGACCAGAGAATTCGAATACAGGCAGCGGNNNCTAGCGTTAC | 2749 |
| TGCAGGACCAGAGAATTCGAATACACCATTGAGNNNCTAGCGTTAC | 2270 | TGCAGGACCAGAGAATTCGAATACACGCTTTTGNNNCTAGCGTTAC | 2510 | TGCAGGACCAGAGAATTCGAATACATTTTTACGNNNCTAGCGTTAC | 2750 |
| TGCAGGACCAGAGAATTCGAATACAACTTAAACNNNCTAGCGTTAC | 2271 | TGCAGGACCAGAGAATTCGAATACATTTCCCTCNNNCTAGCGTTAC | 2511 | TGCAGGACCAGAGAATTCGAATACAGCGTTTGANNNCTAGCGTTAC | 2751 |
| TGCAGGACCAGAGAATTCGAATACATATAGTACNNNCTAGCGTTAC | 2272 | TGCAGGACCAGAGAATTCGAATACACTTACTCGNNNCTAGCGTTAC | 2512 | TGCAGGACCAGAGAATTCGAATACAAGGTACTCNNNCTAGCGTTAC | 2752 |
| TGCAGGACCAGAGAATTCGAATACACAGTGTACNNNCTAGCGTTAC | 2273 | TGCAGGACCAGAGAATTCGAATACAATCGAGTCNNNCTAGCGTTAC | 2513 | TGCAGGACCAGAGAATTCGAATACATTCTGTTANNNCTAGCGTTAC | 2753 |
| TGCAGGACCAGAGAATTCGAATACAGCGTCTTTNNNCTAGCGTTAC | 2274 | TGCAGGACCAGAGAATTCGAATACATTGTACGGNNNCTAGCGTTAC | 2514 | TGCAGGACCAGAGAATTCGAATACACCGATGTANNNCTAGCGTTAC | 2754 |
| TGCAGGACCAGAGAATTCGAATACATGACTCAGNNNCTAGCGTTAC | 2275 | TGCAGGACCAGAGAATTCGAATACACACCATTCNNNCTAGCGTTAC | 2515 | TGCAGGACCAGAGAATTCGAATACAGTCGGTTANNNCTAGCGTTAC | 2755 |
| TGCAGGACCAGAGAATTCGAATACAACTTAGTANNNCTAGCGTTAC | 2276 | TGCAGGACCAGAGAATTCGAATACACCCTCTTTNNNCTAGCGTTAC | 2516 | TGCAGGACCAGAGAATTCGAATACACGAACCGGNNNCTAGCGTTAC | 2756 |
| TGCAGGACCAGAGAATTCGAATACAAAACATGANNNCTAGCGTTAC | 2277 | TGCAGGACCAGAGAATTCGAATACATGCATTAANNNCTAGCGTTAC | 2517 | TGCAGGACCAGAGAATTCGAATACATTCGACTCNNNCTAGCGTTAC | 2757 |
| TGCAGGACCAGAGAATTCGAATACAGTTAGGCTNNNCTAGCGTTAC | 2278 | TGCAGGACCAGAGAATTCGAATACACGTAGCGCNNNCTAGCGTTAC | 2518 | TGCAGGACCAGAGAATTCGAATACATTCAGCCTNNNCTAGCGTTAC | 2758 |
| TGCAGGACCAGAGAATTCGAATACATCCGCAGGNNNCTAGCGTTAC | 2279 | TGCAGGACCAGAGAATTCGAATACAGTCTCCTANNNCTAGCGTTAC | 2519 | TGCAGGACCAGAGAATTCGAATACACACTTGAGNNNCTAGCGTTAC | 2759 |
| TGCAGGACCAGAGAATTCGAATACAAGTACATTNNNCTAGCGTTAC | 2280 | TGCAGGACCAGAGAATTCGAATACATGCGCGANNNCTAGCGTTAC | 2520 | TGCAGGACCAGAGAATTCGAATACATCACGCGGNNNCTAGCGTTAC | 2760 |
| TGCAGGACCAGAGAATTCGAATACAGGTCGTATNNNCTAGCGTTAC | 2281 | TGCAGGACCAGAGAATTCGAATACACAATGATTNNNCTAGCGTTAC | 2521 | TGCAGGACCAGAGAATTCGAATACACACTGTAGNNNCTAGCGTTAC | 2761 |
| TGCAGGACCAGAGAATTCGAATACAAGACGACANNNCTAGCGTTAC | 2282 | TGCAGGACCAGAGAATTCGAATACAAGCGAGGCNNNCTAGCGTTAC | 2522 | TGCAGGACCAGAGAATTCGAATACAACCAAGCTNNNCTAGCGTTAC | 2762 |
| TGCAGGACCAGAGAATTCGAATACAAAGTTCTANNNCTAGCGTTAC | 2283 | TGCAGGACCAGAGAATTCGAATACATTGAATACNNNCTAGCGTTAC | 2523 | TGCAGGACCAGAGAATTCGAATACAACTGCAACNNNCTAGCGTTAC | 2763 |
| TGCAGGACCAGAGAATTCGAATACAACCGAACTNNNCTAGCGTTAC | 2284 | TGCAGGACCAGAGAATTCGAATACAACCGCCAGNNNCTAGCGTTAC | 2524 | TGCAGGACCAGAGAATTCGAATACATAACGGTCNNNCTAGCGTTAC | 2764 |
| TGCAGGACCAGAGAATTCGAATACAGGCAATTCNNNCTAGCGTTAC | 2285 | TGCAGGACCAGAGAATTCGAATACAGGCGACAGNNNCTAGCGTTAC | 2525 | TGCAGGACCAGAGAATTCGAATACAAGTTTGTANNNCTAGCGTTAC | 2765 |
| TGCAGGACCAGAGAATTCGAATACAGTCACACANNNCTAGCGTTAC | 2286 | TGCAGGACCAGAGAATTCGAATACAATATCCAANNNCTAGCGTTAC | 2526 | TGCAGGACCAGAGAATTCGAATACACACGTTTCNNNCTAGCGTTAC | 2766 |
| TGCAGGACCAGAGAATTCGAATACACGGAAATGNNNCTAGCGTTAC | 2287 | TGCAGGACCAGAGAATTCGAATACAATGTTGTANNNCTAGCGTTAC | 2527 | TGCAGGACCAGAGAATTCGAATACATTAAAACCNNNCTAGCGTTAC | 2767 |
| TGCAGGACCAGAGAATTCGAATACACTGTCTACNNNCTAGCGTTAC | 2288 | TGCAGGACCAGAGAATTCGAATACAGATTGTTANNNCTAGCGTTAC | 2528 | TGCAGGACCAGAGAATTCGAATACATTCGTAGGNNNCTAGCGTTAC | 2768 |
| TGCAGGACCAGAGAATTCGAATACAGAGCCAGGNNNGATCGACATG | 2289 | TGCAGGACCAGAGAATTCGAATACAGTCCACGGNNNGATCGACATG | 2529 | TGCAGGACCAGAGAATTCGAATACATGCGTAGTNNNGATCGACATG | 2769 |
| TGCAGGACCAGAGAATTCGAATACACACTCCTANNNGATCGACATG | 2290 | TGCAGGACCAGAGAATTCGAATACATGACTGACNNNGATCGACATG | 2530 | TGCAGGACCAGAGAATTCGAATACAGCTTTGCTNNNGATCGACATG | 2770 |
| TGCAGGACCAGAGAATTCGAATACACTTTCCCTNNNGATCGACATG | 2291 | TGCAGGACCAGAGAATTCGAATACATGATTTAGNNNGATCGACATG | 2531 | TGCAGGACCAGAGAATTCGAATACAGTAAATAGNNNGATCGACATG | 2771 |
| TGCAGGACCAGAGAATTCGAATACACTGAGCTANNNGATCGACATG | 2292 | TGCAGGACCAGAGAATTCGAATACACATACTANNNGATCGACATG | 2532 | TGCAGGACCAGAGAATTCGAATACACGCTGTCCNNNGATCGACATG | 2772 |
| TGCAGGACCAGAGAATTCGAATACAGTCTGACANNNGATCGACATG | 2293 | TGCAGGACCAGAGAATTCGAATACAGCATCCANNNGATCGACATG | 2533 | TGCAGGACCAGAGAATTCGAATACACTTAGAGCNNNGATCGACATG | 2773 |
| TGCAGGACCAGAGAATTCGAATACACTGACGCGNNNGATCGACATG | 2294 | TGCAGGACCAGAGAATTCGAATACAACGGCAAANNNGATCGACATG | 2534 | TGCAGGACCAGAGAATTCGAATACAGGACATAGNNNGATCGACATG | 2774 |
| TGCAGGACCAGAGAATTCGAATACAGTGATGGANNNGATCGACATG | 2295 | TGCAGGACCAGAGAATTCGAATACACTTTGCTGNNNGATCGACATG | 2535 | TGCAGGACCAGAGAATTCGAATACATCTACAGGNNNGATCGACATG | 2775 |
| TGCAGGACCAGAGAATTCGAATACAGAATTCTANNNGATCGACATG | 2296 | TGCAGGACCAGAGAATTCGAATACATTAACTAGNNNGATCGACATG | 2536 | TGCAGGACCAGAGAATTCGAATACACAAACTCGNNNGATCGACATG | 2776 |

FIG. 15E

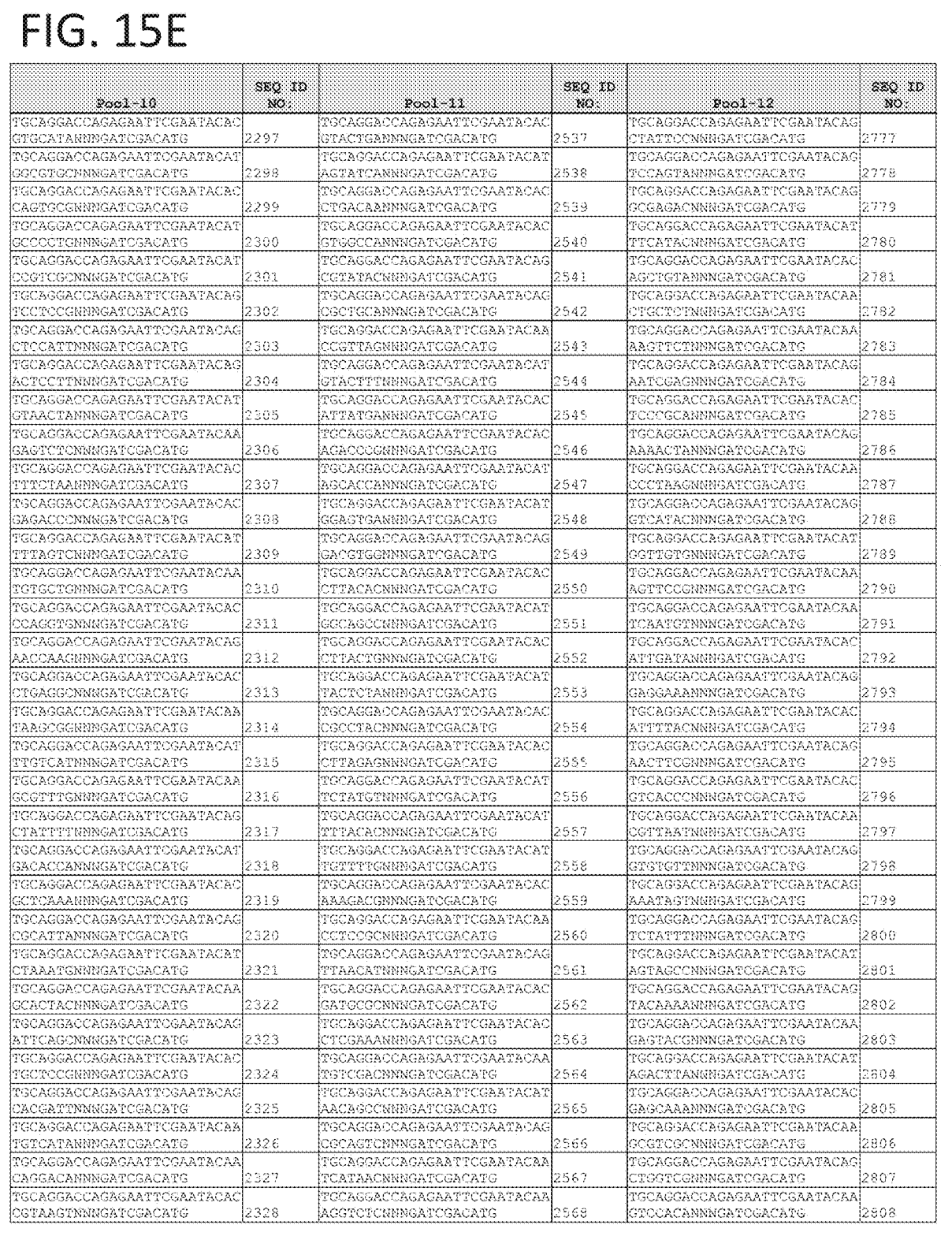

| Pool-10 | SEQ ID NO | Pool-11 | SEQ ID NO | Pool-12 | SEQ ID NO |
|---|---|---|---|---|---|
| TGCAGGACCAGAGAATTCGAATACAC GTGCATANNNGATCGACATG | 2297 | TGCAGGACCAGAGAATTCGAATACAC GTACTGANNNGATCGACATG | 2537 | TGCAGGACCAGAGAATTCGAATACAG CTATTCCNNNGATCGACATG | 2777 |
| TGCAGGACCAGAGAATTCGAATACAT GGCGTGCNNNGATCGACATG | 2298 | TGCAGGACCAGAGAATTCGAATACAT AGTATCANNNGATCGACATG | 2538 | TGCAGGACCAGAGAATTCGAATACAG TCCAGTANNNGATCGACATG | 2778 |
| TGCAGGACCAGAGAATTCGAATACAC CAGTGCGNNNGATCGACATG | 2299 | TGCAGGACCAGAGAATTCGAATACAC CTGACAANNNGATCGACATG | 2539 | TGCAGGACCAGAGAATTCGAATACAG GCGAGACNNNGATCGACATG | 2779 |
| TGCAGGACCAGAGAATTCGAATACAT GCCCCTGNNNGATCGACATG | 2300 | TGCAGGACCAGAGAATTCGAATACAC GTGGCCANNNGATCGACATG | 2540 | TGCAGGACCAGAGAATTCGAATACAT TTCATACNNNGATCGACATG | 2780 |
| TGCAGGACCAGAGAATTCGAATACAT CCGTCGCNNNGATCGACATG | 2301 | TGCAGGACCAGAGAATTCGAATACAG CGTATACNNNGATCGACATG | 2541 | TGCAGGACCAGAGAATTCGAATACAC AGCTGTANNNGATCGACATG | 2781 |
| TGCAGGACCAGAGAATTCGAATACAG TCCTCCGNNNGATCGACATG | 2302 | TGCAGGACCAGAGAATTCGAATACAG CGCTGCANNNGATCGACATG | 2542 | TGCAGGACCAGAGAATTCGAATACAA CTGCTCTNNNGATCGACATG | 2782 |
| TGCAGGACCAGAGAATTCGAATACAG CTCCATTNNNGATCGACATG | 2303 | TGCAGGACCAGAGAATTCGAATACAA CCGTTAGNNNGATCGACATG | 2543 | TGCAGGACCAGAGAATTCGAATACAA AAGTTCTNNNGATCGACATG | 2783 |
| TGCAGGACCAGAGAATTCGAATACAG ACTCCTTNNNGATCGACATG | 2304 | TGCAGGACCAGAGAATTCGAATACAT GTACTTTNNNGATCGACATG | 2544 | TGCAGGACCAGAGAATTCGAATACAG AATCGAGNNNGATCGACATG | 2784 |
| TGCAGGACCAGAGAATTCGAATACAT GTAACTANNNGATCGACATG | 2305 | TGCAGGACCAGAGAATTCGAATACAC ATTATGANNNGATCGACATG | 2545 | TGCAGGACCAGAGAATTCGAATACAC TCCCGCANNNGATCGACATG | 2785 |
| TGCAGGACCAGAGAATTCGAATACAA GAGTCTCNNNGATCGACATG | 2306 | TGCAGGACCAGAGAATTCGAATACAC AGACCCGNNNGATCGACATG | 2546 | TGCAGGACCAGAGAATTCGAATACAG AAAACTANNNGATCGACATG | 2786 |
| TGCAGGACCAGAGAATTCGAATACAC TTTCTAANNNGATCGACATG | 2307 | TGCAGGACCAGAGAATTCGAATACAT AGCACCANNNGATCGACATG | 2547 | TGCAGGACCAGAGAATTCGAATACAA CCCTAAGNNNGATCGACATG | 2787 |
| TGCAGGACCAGAGAATTCGAATACAC GAGACCCNNNGATCGACATG | 2308 | TGCAGGACCAGAGAATTCGAATACAT GGAGTGANNNGATCGACATG | 2548 | TGCAGGACCAGAGAATTCGAATACAG GTCATACNNNGATCGACATG | 2788 |
| TGCAGGACCAGAGAATTCGAATACAT TTTAGTCNNNGATCGACATG | 2309 | TGCAGGACCAGAGAATTCGAATACAG GACGTGGNNNGATCGACATG | 2549 | TGCAGGACCAGAGAATTCGAATACAT GGTTGTGNNNGATCGACATG | 2789 |
| TGCAGGACCAGAGAATTCGAATACAA TGTGCTGNNNGATCGACATG | 2310 | TGCAGGACCAGAGAATTCGAATACAC CTTACACNNNGATCGACATG | 2550 | TGCAGGACCAGAGAATTCGAATACAA AGTTCCGNNNGATCGACATG | 2790 |
| TGCAGGACCAGAGAATTCGAATACAC CCAGGTGNNNGATCGACATG | 2311 | TGCAGGACCAGAGAATTCGAATACAT GGCAGCCNNNGATCGACATG | 2551 | TGCAGGACCAGAGAATTCGAATACAA TCAATGTNNNGATCGACATG | 2791 |
| TGCAGGACCAGAGAATTCGAATACAG AACCAAGNNNGATCGACATG | 2312 | TGCAGGACCAGAGAATTCGAATACAC CTTACTGNNNGATCGACATG | 2552 | TGCAGGACCAGAGAATTCGAATACAC ATTGATANNNGATCGACATG | 2792 |
| TGCAGGACCAGAGAATTCGAATACAC CTGAGGCNNNGATCGACATG | 2313 | TGCAGGACCAGAGAATTCGAATACAT TACTCTANNNGATCGACATG | 2553 | TGCAGGACCAGAGAATTCGAATACAG GAGGAAANNNGATCGACATG | 2793 |
| TGCAGGACCAGAGAATTCGAATACAA TAAGCGGNNNGATCGACATG | 2314 | TGCAGGACCAGAGAATTCGAATACAC CGCCTACNNNGATCGACATG | 2554 | TGCAGGACCAGAGAATTCGAATACAC ATTTTACNNNGATCGACATG | 2794 |
| TGCAGGACCAGAGAATTCGAATACAT TTGTCATNNNGATCGACATG | 2315 | TGCAGGACCAGAGAATTCGAATACAC CTTAGAGNNNGATCGACATG | 2555 | TGCAGGACCAGAGAATTCGAATACAG AACTTCGNNNGATCGACATG | 2795 |
| TGCAGGACCAGAGAATTCGAATACAA GCGTTTGNNNGATCGACATG | 2316 | TGCAGGACCAGAGAATTCGAATACAT TCTATGTNNNGATCGACATG | 2556 | TGCAGGACCAGAGAATTCGAATACAC GTCACCCNNNGATCGACATG | 2796 |
| TGCAGGACCAGAGAATTCGAATACAG CTATTTTNNNGATCGACATG | 2317 | TGCAGGACCAGAGAATTCGAATACAT TTTACACNNNGATCGACATG | 2557 | TGCAGGACCAGAGAATTCGAATACAA CGTTAATNNNGATCGACATG | 2797 |
| TGCAGGACCAGAGAATTCGAATACAT GACACCANNNGATCGACATG | 2318 | TGCAGGACCAGAGAATTCGAATACAT TGTTTTGNNNGATCGACATG | 2558 | TGCAGGACCAGAGAATTCGAATACAT GTGTGTTNNNGATCGACATG | 2798 |
| TGCAGGACCAGAGAATTCGAATACAC GCTCAAANNNGATCGACATG | 2319 | TGCAGGACCAGAGAATTCGAATACAC AAAGACGNNNGATCGACATG | 2559 | TGCAGGACCAGAGAATTCGAATACAG AAATAGTNNNGATCGACATG | 2799 |
| TGCAGGACCAGAGAATTCGAATACAG CGCATTANNNGATCGACATG | 2320 | TGCAGGACCAGAGAATTCGAATACAA CCTCCGCNNNGATCGACATG | 2560 | TGCAGGACCAGAGAATTCGAATACAG TCTATTTNNNGATCGACATG | 2800 |
| TGCAGGACCAGAGAATTCGAATACAT CTAAATGNNNGATCGACATG | 2321 | TGCAGGACCAGAGAATTCGAATACAG TTAACATNNNGATCGACATG | 2561 | TGCAGGACCAGAGAATTCGAATACAT AGTAGCCNNNGATCGACATG | 2801 |
| TGCAGGACCAGAGAATTCGAATACAA GCACTACNNNGATCGACATG | 2322 | TGCAGGACCAGAGAATTCGAATACAC GATGCGCNNNGATCGACATG | 2562 | TGCAGGACCAGAGAATTCGAATACAG TACAAAANNNGATCGACATG | 2802 |
| TGCAGGACCAGAGAATTCGAATACAG ATTCAGNNNNGATCGACATG | 2323 | TGCAGGACCAGAGAATTCGAATACAC CTCGAAANNNGATCGACATG | 2563 | TGCAGGACCAGAGAATTCGAATACAA GAGTACGNNNGATCGACATG | 2803 |
| TGCAGGACCAGAGAATTCGAATACAC TGCTCCGNNNGATCGACATG | 2324 | TGCAGGACCAGAGAATTCGAATACAA TGTCGACNNNGATCGACATG | 2564 | TGCAGGACCAGAGAATTCGAATACAT AGACTTANNNGATCGACATG | 2804 |
| TGCAGGACCAGAGAATTCGAATACAG CACGATTNNNGATCGACATG | 2325 | TGCAGGACCAGAGAATTCGAATACAT AACAGCCNNNGATCGACATG | 2565 | TGCAGGACCAGAGAATTCGAATACAC GAGCAAANNNGATCGACATG | 2805 |
| TGCAGGACCAGAGAATTCGAATACAA TGTCATANNNGATCGACATG | 2326 | TGCAGGACCAGAGAATTCGAATACAG CGCAGTCNNNGATCGACATG | 2566 | TGCAGGACCAGAGAATTCGAATACAA GCGTCGCNNNGATCGACATG | 2806 |
| TGCAGGACCAGAGAATTCGAATACAA CAGGACANNNGATCGACATG | 2327 | TGCAGGACCAGAGAATTCGAATACAA TCATAACNNNGATCGACATG | 2567 | TGCAGGACCAGAGAATTCGAATACAG CTGGTCGNNNGATCGACATG | 2807 |
| TGCAGGACCAGAGAATTCGAATACAC CGTAAGTNNNGATCGACATG | 2328 | TGCAGGACCAGAGAATTCGAATACAA AGGTCTCNNNGATCGACATG | 2568 | TGCAGGACCAGAGAATTCGAATACAA GTCCACANNNGATCGACATG | 2808 |

FIG. 15F

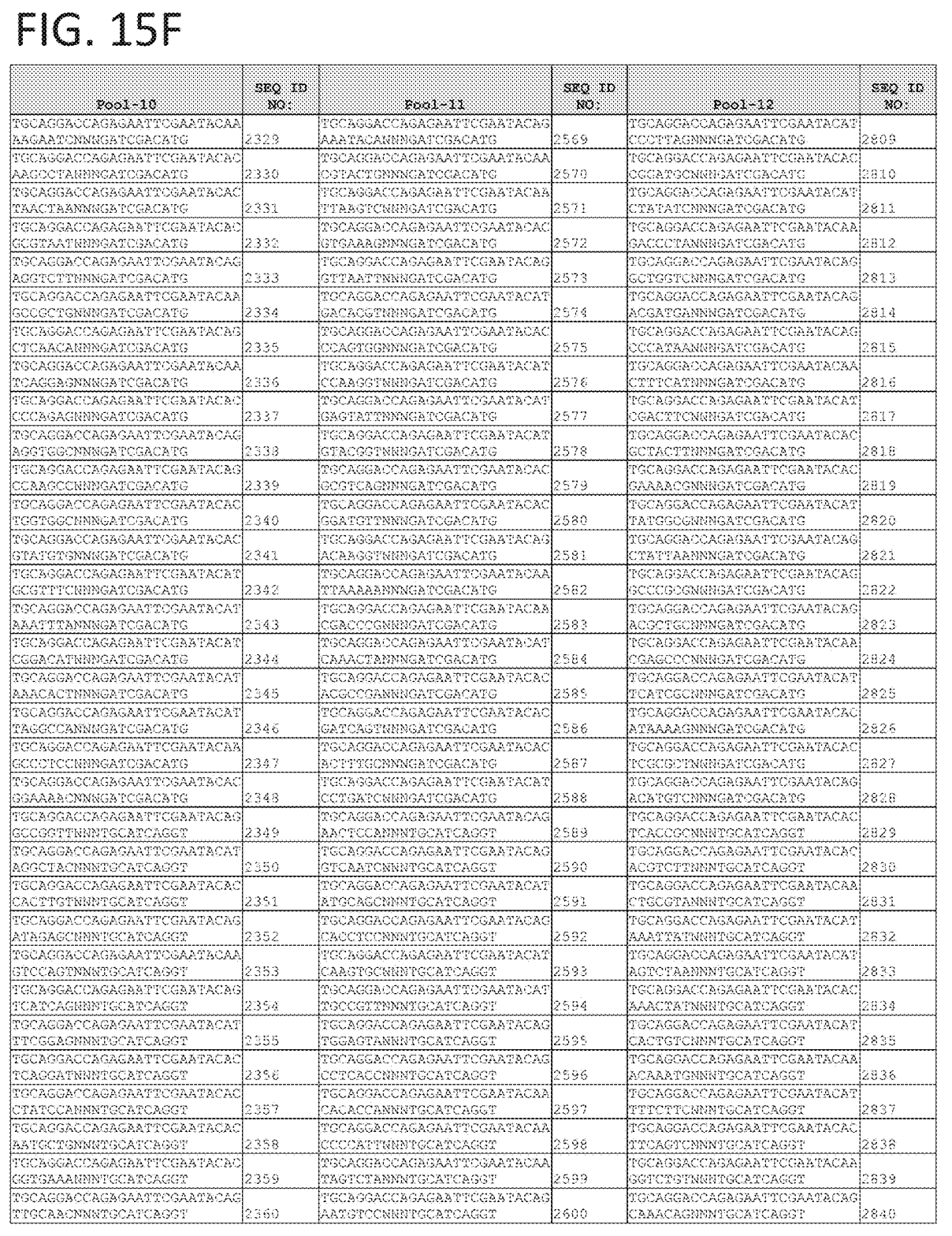

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAA AAGAATCNNNGATCGACATG | 2329 | TGCAGGACCAGAGAATTCGAATACAG AAATACANNNGATCGACATG | 2569 | TGCAGGACCAGAGAATTCGAATACAT CCCTTAGNNNGATCGACATG | 2809 |
| TGCAGGACCAGAGAATTCGAATACAC AAGCCTANNNGATCGACATG | 2330 | TGCAGGACCAGAGAATTCGAATACAA CGTACTGNNNGATCGACATG | 2570 | TGCAGGACCAGAGAATTCGAATACAC CGGATGCNNNGATCGACATG | 2810 |
| TGCAGGACCAGAGAATTCGAATACAC TAACTAANNNGATCGACATG | 2331 | TGCAGGACCAGAGAATTCGAATACAA TTAAGTCNNNGATCGACATG | 2571 | TGCAGGACCAGAGAATTCGAATACAT CTATATCNNNGATCGACATG | 2811 |
| TGCAGGACCAGAGAATTCGAATACAC GCGTAATNNNGATCGACATG | 2332 | TGCAGGACCAGAGAATTCGAATACAC GTGAAAGNNNGATCGACATG | 2572 | TGCAGGACCAGAGAATTCGAATACAA GACCCTANNNGATCGACATG | 2812 |
| TGCAGGACCAGAGAATTCGAATACAG AGGTCTTNNNGATCGACATG | 2333 | TGCAGGACCAGAGAATTCGAATACAG GTTAATTNNNGATCGACATG | 2573 | TGCAGGACCAGAGAATTCGAATACAG GCTGGTCNNNGATCGACATG | 2813 |
| TGCAGGACCAGAGAATTCGAATACAA GCCGCTGNNNGATCGACATG | 2334 | TGCAGGACCAGAGAATTCGAATACAT GACACGTNNNGATCGACATG | 2574 | TGCAGGACCAGAGAATTCGAATACAG ACGATGANNNGATCGACATG | 2814 |
| TGCAGGACCAGAGAATTCGAATACAG CTCAACANNNGATCGACATG | 2335 | TGCAGGACCAGAGAATTCGAATACAC CCAGTGGNNNGATCGACATG | 2575 | TGCAGGACCAGAGAATTCGAATACAG CCCATAANNNGATCGACATG | 2815 |
| TGCAGGACCAGAGAATTCGAATACAA TCAGGAGNNNGATCGACATG | 2336 | TGCAGGACCAGAGAATTCGAATACAT CCAAGGTNNNGATCGACATG | 2576 | TGCAGGACCAGAGAATTCGAATACAA CTTTCATNNNGATCGACATG | 2816 |
| TGCAGGACCAGAGAATTCGAATACAC CCCAGAGNNNGATCGACATG | 2337 | TGCAGGACCAGAGAATTCGAATACAT GAGTATTNNNGATCGACATG | 2577 | TGCAGGACCAGAGAATTCGAATACAT CGACTTCNNNGATCGACATG | 2817 |
| TGCAGGACCAGAGAATTCGAATACAG AGGTGGCNNNGATCGACATG | 2338 | TGCAGGACCAGAGAATTCGAATACAT GTACGGTNNNGATCGACATG | 2578 | TGCAGGACCAGAGAATTCGAATACAC GCTACTTNNNGATCGACATG | 2818 |
| TGCAGGACCAGAGAATTCGAATACAG CCAAGCCNNNGATCGACATG | 2339 | TGCAGGACCAGAGAATTCGAATACAC GCGTCAGNNNGATCGACATG | 2579 | TGCAGGACCAGAGAATTCGAATACAC GAAAACGNNNGATCGACATG | 2819 |
| TGCAGGACCAGAGAATTCGAATACAC TGGTGGCNNNGATCGACATG | 2340 | TGCAGGACCAGAGAATTCGAATACAC GGATGTTNNNGATCGACATG | 2580 | TGCAGGACCAGAGAATTCGAATACAT TATGGCGNNNGATCGACATG | 2820 |
| TGCAGGACCAGAGAATTCGAATACAC GTATGTGNNNGATCGACATG | 2341 | TGCAGGACCAGAGAATTCGAATACAG ACAAGGTNNNGATCGACATG | 2581 | TGCAGGACCAGAGAATTCGAATACAG CTATTAANNNGATCGACATG | 2821 |
| TGCAGGACCAGAGAATTCGAATACAT GCGTTCNNNGATCGACATG | 2342 | TGCAGGACCAGAGAATTCGAATACAA TTAAAAGNNNGATCGACATG | 2582 | TGCAGGACCAGAGAATTCGAATACAG GCCCGCGNNNGATCGACATG | 2822 |
| TGCAGGACCAGAGAATTCGAATACAT AAATTTANNNGATCGACATG | 2343 | TGCAGGACCAGAGAATTCGAATACAA CGACCCGNNNGATCGACATG | 2583 | TGCAGGACCAGAGAATTCGAATACAG ACGCTGCNNNGATCGACATG | 2823 |
| TGCAGGACCAGAGAATTCGAATACAT CGGACATNNNGATCGACATG | 2344 | TGCAGGACCAGAGAATTCGAATACAT CAAACTANNNGATCGACATG | 2584 | TGCAGGACCAGAGAATTCGAATACAA CGAGCCCNNNGATCGACATG | 2824 |
| TGCAGGACCAGAGAATTCGAATACAT AAACACTNNNGATCGACATG | 2345 | TGCAGGACCAGAGAATTCGAATACAC ACGCCGANNNGATCGACATG | 2585 | TGCAGGACCAGAGAATTCGAATACAT TCATCGCNNNGATCGACATG | 2825 |
| TGCAGGACCAGAGAATTCGAATACAT TAGGCCANNNGATCGACATG | 2346 | TGCAGGACCAGAGAATTCGAATACAC GATCAGTNNNGATCGACATG | 2586 | TGCAGGACCAGAGAATTCGAATACAC ATAAAAGNNNGATCGACATG | 2826 |
| TGCAGGACCAGAGAATTCGAATACAA GCCCTCCNNNGATCGACATG | 2347 | TGCAGGACCAGAGAATTCGAATACAC ACTTTGCNNNGATCGACATG | 2587 | TGCAGGACCAGAGAATTCGAATACAC TCGCGTNNNGATCGACATG | 2827 |
| TGCAGGACCAGAGAATTCGAATACAC GGAAAACNNNGATCGACATG | 2348 | TGCAGGACCAGAGAATTCGAATACAT CCTGATCNNNGATCGACATG | 2588 | TGCAGGACCAGAGAATTCGAATACAG ACATGTCNNNGATCGACATG | 2828 |
| TGCAGGACCAGAGAATTCGAATACAG GCCGGTTNNNTGCATCAGGT | 2349 | TGCAGGACCAGAGAATTCGAATACAG AACTCCANNNTGCATCAGGT | 2589 | TGCAGGACCAGAGAATTCGAATACAC TCACCGCNNNTGCATCAGGT | 2829 |
| TGCAGGACCAGAGAATTCGAATACAT AGGCTACNNNTGCATCAGGT | 2350 | TGCAGGACCAGAGAATTCGAATACAG GTCAATCNNNTGCATCAGGT | 2590 | TGCAGGACCAGAGAATTCGAATACAC ACGTCTTNNNTGCATCAGGT | 2830 |
| TGCAGGACCAGAGAATTCGAATACAC CACTTGTNNNTGCATCAGGT | 2351 | TGCAGGACCAGAGAATTCGAATACAT ATGCAGCNNNTGCATCAGGT | 2591 | TGCAGGACCAGAGAATTCGAATACAA CTGCGTANNNTGCATCAGGT | 2831 |
| TGCAGGACCAGAGAATTCGAATACAG ATAGAGCNNNTGCATCAGGT | 2352 | TGCAGGACCAGAGAATTCGAATACAG CACCTCCNNNTGCATCAGGT | 2592 | TGCAGGACCAGAGAATTCGAATACAT AAATTATNNNTGCATCAGGT | 2832 |
| TGCAGGACCAGAGAATTCGAATACAA GTCCAGTNNNTGCATCAGGT | 2353 | TGCAGGACCAGAGAATTCGAATACAT CAAGTGCNNNTGCATCAGGT | 2593 | TGCAGGACCAGAGAATTCGAATACAT AGTCTAANNNTGCATCAGGT | 2833 |
| TGCAGGACCAGAGAATTCGAATACAG TCATCAGNNNTGCATCAGGT | 2354 | TGCAGGACCAGAGAATTCGAATACAT TGCCGTTNNNTGCATCAGGT | 2594 | TGCAGGACCAGAGAATTCGAATACAC AAACTATNNNTGCATCAGGT | 2834 |
| TGCAGGACCAGAGAATTCGAATACAT TTCGGAGNNNTGCATCAGGT | 2355 | TGCAGGACCAGAGAATTCGAATACAG TGGAGTANNNTGCATCAGGT | 2595 | TGCAGGACCAGAGAATTCGAATACAT CACTGTCNNNTGCATCAGGT | 2835 |
| TGCAGGACCAGAGAATTCGAATACAC TCAGGATNNNTGCATCAGGT | 2356 | TGCAGGACCAGAGAATTCGAATACAG CCTCACCNNNTGCATCAGGT | 2596 | TGCAGGACCAGAGAATTCGAATACAA ACAACATGNNNTGCATCAGGT | 2836 |
| TGCAGGACCAGAGAATTCGAATACAC CTATCCANNNTGCATCAGGT | 2357 | TGCAGGACCAGAGAATTCGAATACAG CACACCANNNTGCATCAGGT | 2597 | TGCAGGACCAGAGAATTCGAATACAT TTTCTTCNNNTGCATCAGGT | 2837 |
| TGCAGGACCAGAGAATTCGAATACAC AATGCTGNNNTGCATCAGGT | 2358 | TGCAGGACCAGAGAATTCGAATACAA CCCCATTNNNTGCATCAGGT | 2598 | TGCAGGACCAGAGAATTCGAATACAC TTCAGTCNNNTGCATCAGGT | 2838 |
| TGCAGGACCAGAGAATTCGAATACAC GGTGAAANNNTGCATCAGGT | 2359 | TGCAGGACCAGAGAATTCGAATACAA TAGTCTANNNTGCATCAGGT | 2599 | TGCAGGACCAGAGAATTCGAATACAA GGTCTGTNNNTGCATCAGGT | 2839 |
| TGCAGGACCAGAGAATTCGAATACAG TTGCAACNNNTGCATCAGGT | 2360 | TGCAGGACCAGAGAATTCGAATACAG AATGTCCNNNTGCATCAGGT | 2600 | TGCAGGACCAGAGAATTCGAATACAG CAAACAGNNNTGCATCAGGT | 2840 |

FIG. 15G

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAG AGAGCTANNNTGCATCAGGT | 2361 | TGCAGGACCAGAGAATTCGAATACAC TAGATCGNNNTGCATCAGGT | 2601 | TGCAGGACCAGAGAATTCGAATACAC CGAGAGGNNNTGCATCAGGT | 2841 |
| TGCAGGACCAGAGAATTCGAATACAG CCTAACANNNTGCATCAGGT | 2362 | TGCAGGACCAGAGAATTCGAATACAG GCAACCCNNNTGCATCAGGT | 2602 | TGCAGGACCAGAGAATTCGAATACAA TATTGCANNNTGCATCAGGT | 2842 |
| TGCAGGACCAGAGAATTCGAATACAC TGAGACTNNNTGCATCAGGT | 2363 | TGCAGGACCAGAGAATTCGAATACAG GAGAGAANNNTGCATCAGGT | 2603 | TGCAGGACCAGAGAATTCGAATACAT CTCTGGTNNNTGCATCAGGT | 2843 |
| TGCAGGACCAGAGAATTCGAATACAA CGTTGCANNNTGCATCAGGT | 2364 | TGCAGGACCAGAGAATTCGAATACAG TTGTCCTNNNTGCATCAGGT | 2604 | TGCAGGACCAGAGAATTCGAATACAA TTGGAGGNNNTGCATCAGGT | 2844 |
| TGCAGGACCAGAGAATTCGAATACAG GAAGCTANNNTGCATCAGGT | 2365 | TGCAGGACCAGAGAATTCGAATACAT GGCATACNNNTGCATCAGGT | 2605 | TGCAGGACCAGAGAATTCGAATACAC ATCATTTNNNTGCATCAGGT | 2845 |
| TGCAGGACCAGAGAATTCGAATACAC CCTGTATNNNTGCATCAGGT | 2366 | TGCAGGACCAGAGAATTCGAATACAG ACGCAATNNNTGCATCAGGT | 2606 | TGCAGGACCAGAGAATTCGAATACAG AGGTGATNNNTGCATCAGGT | 2846 |
| TGCAGGACCAGAGAATTCGAATACAT AGCCTCTNNNTGCATCAGGT | 2367 | TGCAGGACCAGAGAATTCGAATACAT CTCACGTNNNTGCATCAGGT | 2607 | TGCAGGACCAGAGAATTCGAATACAC CCCGTCANNNTGCATCAGGT | 2847 |
| TGCAGGACCAGAGAATTCGAATACAA GGTACCTNNNTGCATCAGGT | 2368 | TGCAGGACCAGAGAATTCGAATACAC TGCGGCANNNTGCATCAGGT | 2608 | TGCAGGACCAGAGAATTCGAATACAG ACAGGTANNNTGCATCAGGT | 2848 |
| TGCAGGACCAGAGAATTCGAATACAT GTTATCTNNNTGCATCAGGT | 2369 | TGCAGGACCAGAGAATTCGAATACAC TTAATGANNNTGCATCAGGT | 2609 | TGCAGGACCAGAGAATTCGAATACAG CCTTAGANNNTGCATCAGGT | 2849 |
| TGCAGGACCAGAGAATTCGAATACAG ACTTACGNNNTGCATCAGGT | 2370 | TGCAGGACCAGAGAATTCGAATACAA ACTCACGNNNTGCATCAGGT | 2610 | TGCAGGACCAGAGAATTCGAATACAC CTTCTAGNNNTGCATCAGGT | 2850 |
| TGCAGGACCAGAGAATTCGAATACAA CTTCCACNNNTGCATCAGGT | 2371 | TGCAGGACCAGAGAATTCGAATACAA GCAGTGANNNTGCATCAGGT | 2611 | TGCAGGACCAGAGAATTCGAATACAA GGCTTGTNNNTGCATCAGGT | 2851 |
| TGCAGGACCAGAGAATTCGAATACAC CTTCTGANNNTGCATCAGGT | 2372 | TGCAGGACCAGAGAATTCGAATACAT AATACTGNNNTGCATCAGGT | 2612 | TGCAGGACCAGAGAATTCGAATACAT GGAGTCANNNTGCATCAGGT | 2852 |
| TGCAGGACCAGAGAATTCGAATACAC GACACTANNNTGCATCAGGT | 2373 | TGCAGGACCAGAGAATTCGAATACAA AAGTCCCNNNTGCATCAGGT | 2613 | TGCAGGACCAGAGAATTCGAATACAC CACCGAGNNNTGCATCAGGT | 2853 |
| TGCAGGACCAGAGAATTCGAATACAC TGTGAGTNNNTGCATCAGGT | 2374 | TGCAGGACCAGAGAATTCGAATACAG CTGGAANNNNTGCATCAGGT | 2614 | TGCAGGACCAGAGAATTCGAATACAG GAATGCANNNTGCATCAGGT | 2854 |
| TGCAGGACCAGAGAATTCGAATACAA GAGACACNNNTGCATCAGGT | 2375 | TGCAGGACCAGAGAATTCGAATACAA AGAGGAGNNNTGCATCAGGT | 2615 | TGCAGGACCAGAGAATTCGAATACAA CATTACANNNTGCATCAGGT | 2855 |
| TGCAGGACCAGAGAATTCGAATACAT AATTGTGNNNTGCATCAGGT | 2376 | TGCAGGACCAGAGAATTCGAATACAG TGGAAGTNNNTGCATCAGGT | 2616 | TGCAGGACCAGAGAATTCGAATACAA GTCTCTCNNNTGCATCAGGT | 2856 |
| TGCAGGACCAGAGAATTCGAATACAG TAATTTGNNNTGCATCAGGT | 2377 | TGCAGGACCAGAGAATTCGAATACAC GCGGACTNNNTGCATCAGGT | 2617 | TGCAGGACCAGAGAATTCGAATACAT AGTGCCANNNTGCATCAGGT | 2857 |
| TGCAGGACCAGAGAATTCGAATACAG ATACTATNNNTGCATCAGGT | 2378 | TGCAGGACCAGAGAATTCGAATACAT ACTTGTTNNNTGCATCAGGT | 2618 | TGCAGGACCAGAGAATTCGAATACAG CAATGCTNNNTGCATCAGGT | 2858 |
| TGCAGGACCAGAGAATTCGAATACAA GTGGATGNNNTGCATCAGGT | 2379 | TGCAGGACCAGAGAATTCGAATACAA ACTGACCNNNTGCATCAGGT | 2619 | TGCAGGACCAGAGAATTCGAATACAG TTGAATTNNNTGCATCAGGT | 2859 |
| TGCAGGACCAGAGAATTCGAATACAT TATAGACNNNTGCATCAGGT | 2380 | TGCAGGACCAGAGAATTCGAATACAT GCTGGTANNNTGCATCAGGT | 2620 | TGCAGGACCAGAGAATTCGAATACAC CACTTCANNNTGCATCAGGT | 2860 |
| TGCAGGACCAGAGAATTCGAATACAG AGTTTCGNNNTGCATCAGGT | 2381 | TGCAGGACCAGAGAATTCGAATACAA TATTTTTNNNTGCATCAGGT | 2621 | TGCAGGACCAGAGAATTCGAATACAT CCATTCGNNNTGCATCAGGT | 2861 |
| TGCAGGACCAGAGAATTCGAATACAC AGAGATGNNNTGCATCAGGT | 2382 | TGCAGGACCAGAGAATTCGAATACAT CCCCATANNNTGCATCAGGT | 2622 | TGCAGGACCAGAGAATTCGAATACAC ACTCTCANNNTGCATCAGGT | 2862 |
| TGCAGGACCAGAGAATTCGAATACAG ACTCAACNNNTGCATCAGGT | 2383 | TGCAGGACCAGAGAATTCGAATACAC AAGTTGCNNNTGCATCAGGT | 2623 | TGCAGGACCAGAGAATTCGAATACAG ACCTGATNNNTGCATCAGGT | 2863 |
| TGCAGGACCAGAGAATTCGAATACAT TCGCTGTNNNTGCATCAGGT | 2384 | TGCAGGACCAGAGAATTCGAATACAT GAACCGTNNNTGCATCAGGT | 2624 | TGCAGGACCAGAGAATTCGAATACAA GAGCTCTNNNTGCATCAGGT | 2864 |
| TGCAGGACCAGAGAATTCGAATACAC GTCCGAGNNNTGCATCAGGT | 2385 | TGCAGGACCAGAGAATTCGAATACAC GCATTGANNNTGCATCAGGT | 2625 | TGCAGGACCAGAGAATTCGAATACAC TGGATTGNNNTGCATCAGGT | 2865 |
| TGCAGGACCAGAGAATTCGAATACAG CATGCATNNNTGCATCAGGT | 2386 | TGCAGGACCAGAGAATTCGAATACAC GGCGTTGNNNTGCATCAGGT | 2626 | TGCAGGACCAGAGAATTCGAATACAT GCTATCANNNTGCATCAGGT | 2866 |
| TGCAGGACCAGAGAATTCGAATACAA AAGTGCCNNNTGCATCAGGT | 2387 | TGCAGGACCAGAGAATTCGAATACAC CCGCCCGNNNTGCATCAGGT | 2627 | TGCAGGACCAGAGAATTCGAATACAG ACGTTGTNNNTGCATCAGGT | 2867 |
| TGCAGGACCAGAGAATTCGAATACAG AAAGCACNNNTGCATCAGGT | 2388 | TGCAGGACCAGAGAATTCGAATACAC AAGCTACNNNTGCATCAGGT | 2628 | TGCAGGACCAGAGAATTCGAATACAA TTCATCTNNNTGCATCAGGT | 2868 |
| TGCAGGACCAGAGAATTCGAATACAG GCTGCTGNNNTGCATCAGGT | 2389 | TGCAGGACCAGAGAATTCGAATACAC GGTTCAANNNTGCATCAGGT | 2629 | TGCAGGACCAGAGAATTCGAATACAC GATTCAGNNNTGCATCAGGT | 2869 |
| TGCAGGACCAGAGAATTCGAATACAG CGGAAGCNNNTGCATCAGGT | 2390 | TGCAGGACCAGAGAATTCGAATACAC AACGTTGNNNTGCATCAGGT | 2630 | TGCAGGACCAGAGAATTCGAATACAT GGTGCATNNNTGCATCAGGT | 2870 |
| TGCAGGACCAGAGAATTCGAATACAA TCACATANNNTGCATCAGGT | 2391 | TGCAGGACCAGAGAATTCGAATACAG TACTAGCNNNTGCATCAGGT | 2631 | TGCAGGACCAGAGAATTCGAATACAT GTGTTTTNNNTGCATCAGGT | 2871 |
| TGCAGGACCAGAGAATTCGAATACAA CTCTCTGNNNTGCATCAGGT | 2392 | TGCAGGACCAGAGAATTCGAATACAT GAGTGTCNNNTGCATCAGGT | 2632 | TGCAGGACCAGAGAATTCGAATACAT GGCATCANNNTGCATCAGGT | 2872 |

FIG. 15H

| Pool-10 | SEQ ID NO: | Pool-11 | SEQ ID NO: | Pool-12 | SEQ ID NO: |
|---|---|---|---|---|---|
| TGCAGGACCAGAGAATTCGAATACAC GCCCCCGNNNTGCATCAGGT | 2393 | TGCAGGACCAGAGAATTCGAATACAC AAACAGGNNNTGCATCAGGT | 2633 | TGCAGGACCAGAGAATTCGAATACAT AAGCTGCNNNTGCATCAGGT | 2873 |
| TGCAGGACCAGAGAATTCGAATACAT TTAATCCNNNTGCATCAGGT | 2394 | TGCAGGACCAGAGAATTCGAATACAG CATGCTANNNTGCATCAGGT | 2634 | TGCAGGACCAGAGAATTCGAATACAA CGGACTTNNNTGCATCAGGT | 2874 |
| TGCAGGACCAGAGAATTCGAATACAC CGTCGGANNNTGCATCAGGT | 2395 | TGCAGGACCAGAGAATTCGAATACAG ATTCACGNNNTGCATCAGGT | 2635 | TGCAGGACCAGAGAATTCGAATACAT GAATTACNNNTGCATCAGGT | 2875 |
| TGCAGGACCAGAGAATTCGAATACAT GAGAAATNNNTGCATCAGGT | 2396 | TGCAGGACCAGAGAATTCGAATACAG TAGATCCNNNTGCATCAGGT | 2636 | TGCAGGACCAGAGAATTCGAATACAA ACAGAGCNNNTGCATCAGGT | 2876 |
| TGCAGGACCAGAGAATTCGAATACAC GTTATAANNNTGCATCAGGT | 2397 | TGCAGGACCAGAGAATTCGAATACAC GCCAACGNNNTGCATCAGGT | 2637 | TGCAGGACCAGAGAATTCGAATACAC ATGTTCCNNNTGCATCAGGT | 2877 |
| TGCAGGACCAGAGAATTCGAATACAT CTAAAACNNNTGCATCAGGT | 2398 | TGCAGGACCAGAGAATTCGAATACAG AGCATAGNNNTGCATCAGGT | 2638 | TGCAGGACCAGAGAATTCGAATACAT CGTCTACNNNTGCATCAGGT | 2878 |
| TGCAGGACCAGAGAATTCGAATACAA CACTCGANNNTGCATCAGGT | 2399 | TGCAGGACCAGAGAATTCGAATACAC GTGTCATNNNTGCATCAGGT | 2639 | TGCAGGACCAGAGAATTCGAATACAG TAGAGACNNNTGCATCAGGT | 2879 |
| TGCAGGACCAGAGAATTCGAATACAG CATCGTANNNTGCATCAGGT | 2400 | TGCAGGACCAGAGAATTCGAATACAT CTTCGACNNNTGCATCAGGT | 2640 | TGCAGGACCAGAGAATTCGAATACAT ATAGTGTNNNTGCATCAGGT | 2880 |
| TGCAGGACCAGAGAATTCGAATACAG TAAGACGNNNTGCATCAGGT | 2401 | TGCAGGACCAGAGAATTCGAATACAG ATCAGCTNNNTGCATCAGGT | 2641 | TGCAGGACCAGAGAATTCGAATACAG GAGAGTTNNNTGCATCAGGT | 2881 |
| TGCAGGACCAGAGAATTCGAATACAA AAGCCCTNNNTGCATCAGGT | 2402 | TGCAGGACCAGAGAATTCGAATACAT CGACCTTNNNTGCATCAGGT | 2642 | TGCAGGACCAGAGAATTCGAATACAT ACATTCTNNNTGCATCAGGT | 2882 |
| TGCAGGACCAGAGAATTCGAATACAC CATGGTANNNTGCATCAGGT | 2403 | TGCAGGACCAGAGAATTCGAATACAA GCCCACGNNNTGCATCAGGT | 2643 | TGCAGGACCAGAGAATTCGAATACAC ACAATGCNNNTGCATCAGGT | 2883 |
| TGCAGGACCAGAGAATTCGAATACAC GAAATAANNNTGCATCAGGT | 2404 | TGCAGGACCAGAGAATTCGAATACAG AGATCTCNNNTGCATCAGGT | 2644 | TGCAGGACCAGAGAATTCGAATACAG ATATTACNNNTGCATCAGGT | 2884 |
| TGCAGGACCAGAGAATTCGAATACAG ATCAAAANNNTGCATCAGGT | 2405 | TGCAGGACCAGAGAATTCGAATACAT CTTTAACNNNTGCATCAGGT | 2645 | TGCAGGACCAGAGAATTCGAATACAC GGCTTTTNNNTGCATCAGGT | 2885 |
| TGCAGGACCAGAGAATTCGAATACAA GTGCCGCNNNTGCATCAGGT | 2406 | TGCAGGACCAGAGAATTCGAATACAT CCCTAACNNNTGCATCAGGT | 2646 | TGCAGGACCAGAGAATTCGAATACAG CTGCTGGNNNTGCATCAGGT | 2886 |
| TGCAGGACCAGAGAATTCGAATACAC CCTGGCTNNNTGCATCAGGT | 2407 | TGCAGGACCAGAGAATTCGAATACAA CTCGACANNNTGCATCAGGT | 2647 | TGCAGGACCAGAGAATTCGAATACAA AGGCGCGNNNTGCATCAGGT | 2887 |
| TGCAGGACCAGAGAATTCGAATACAC AAGTTCGNNNTGCATCAGGT | 2408 | TGCAGGACCAGAGAATTCGAATACAT GAGAGACNNNTGCATCAGGT | 2648 | TGCAGGACCAGAGAATTCGAATACAA CGGTGAANNNTGCATCAGGT | 2888 |

FIG. 16A

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAC CACCGACNNNACGTATGCCA | 2889 | TGCAGGACCAGAGAATTCGAATACAC ATGCGTANNNACGTATGCCA | 3129 | TGCAGGACCAGAGAATTCGAATACAG TGTGATCNNNACGTATGCCA | 3369 |
| TGCAGGACCAGAGAATTCGAATACAA ATCCTCCNNNACGTATGCCA | 2890 | TGCAGGACCAGAGAATTCGAATACAT CGTGCCGNNNACGTATGCCA | 3130 | TGCAGGACCAGAGAATTCGAATACAA AAGCGCANNNACGTATGCCA | 3370 |
| TGCAGGACCAGAGAATTCGAATACAG TGGCCGTNNNACGTATGCCA | 2891 | TGCAGGACCAGAGAATTCGAATACAG TAGTGGANNNACGTATGCCA | 3131 | TGCAGGACCAGAGAATTCGAATACAT CGTGGATNNNACGTATGCCA | 3371 |
| TGCAGGACCAGAGAATTCGAATACAA GAGTAGCNNNACGTATGCCA | 2892 | TGCAGGACCAGAGAATTCGAATACAG TTGTTGGNNNACGTATGCCA | 3132 | TGCAGGACCAGAGAATTCGAATACAT CACCGAANNNACGTATGCCA | 3372 |
| TGCAGGACCAGAGAATTCGAATACAT CCTGCGCNNNACGTATGCCA | 2893 | TGCAGGACCAGAGAATTCGAATACAA GAGCTTCNNNACGTATGCCA | 3133 | TGCAGGACCAGAGAATTCGAATACAG CCGTTGGNNNACGTATGCCA | 3373 |
| TGCAGGACCAGAGAATTCGAATACAT TCTCGTGNNNACGTATGCCA | 2894 | TGCAGGACCAGAGAATTCGAATACAA TACTGTGNNNACGTATGCCA | 3134 | TGCAGGACCAGAGAATTCGAATACAA CACGGTTNNNACGTATGCCA | 3374 |
| TGCAGGACCAGAGAATTCGAATACAT GGTATGCNNNACGTATGCCA | 2895 | TGCAGGACCAGAGAATTCGAATACAA GCAACCTNNNACGTATGCCA | 3135 | TGCAGGACCAGAGAATTCGAATACAG CTCACGGNNNACGTATGCCA | 3375 |
| TGCAGGACCAGAGAATTCGAATACAA TCACTCCNNNACGTATGCCA | 2896 | TGCAGGACCAGAGAATTCGAATACAG CCCTGCTNNNACGTATGCCA | 3136 | TGCAGGACCAGAGAATTCGAATACAC AATCGCANNNACGTATGCCA | 3376 |
| TGCAGGACCAGAGAATTCGAATACAA ACAAGGCNNNACGTATGCCA | 2897 | TGCAGGACCAGAGAATTCGAATACAC TCTCGCGNNNACGTATGCCA | 3137 | TGCAGGACCAGAGAATTCGAATACAT AATATATNNNACGTATGCCA | 3377 |
| TGCAGGACCAGAGAATTCGAATACAC CGTCTTANNNACGTATGCCA | 2898 | TGCAGGACCAGAGAATTCGAATACAC TACTTGCNNNACGTATGCCA | 3138 | TGCAGGACCAGAGAATTCGAATACAC ATTACCCNNNACGTATGCCA | 3378 |
| TGCAGGACCAGAGAATTCGAATACAA AAAATTANNNACGTATGCCA | 2899 | TGCAGGACCAGAGAATTCGAATACAA TAATGAGNNNACGTATGCCA | 3139 | TGCAGGACCAGAGAATTCGAATACAG ACTACTGNNNACGTATGCCA | 3379 |
| TGCAGGACCAGAGAATTCGAATACAA CACAGAGNNNACGTATGCCA | 2900 | TGCAGGACCAGAGAATTCGAATACAC CGTAGTANNNACGTATGCCA | 3140 | TGCAGGACCAGAGAATTCGAATACAG TGCACGCNNNACGTATGCCA | 3380 |
| TGCAGGACCAGAGAATTCGAATACAA GTGCGCTNNNACGTATGCCA | 2901 | TGCAGGACCAGAGAATTCGAATACAA GCAACAGNNNACGTATGCCA | 3141 | TGCAGGACCAGAGAATTCGAATACAG GCTATTGNNNACGTATGCCA | 3381 |
| TGCAGGACCAGAGAATTCGAATACAC GTGACGCNNNACGTATGCCA | 2902 | TGCAGGACCAGAGAATTCGAATACAC TGTGTCTNNNACGTATGCCA | 3142 | TGCAGGACCAGAGAATTCGAATACAG GTGGTGGNNNACGTATGCCA | 3382 |
| TGCAGGACCAGAGAATTCGAATACAG ACCCCCTNNNACGTATGCCA | 2903 | TGCAGGACCAGAGAATTCGAATACAT CCAAACGNNNACGTATGCCA | 3143 | TGCAGGACCAGAGAATTCGAATACAT GCGTACANNNACGTATGCCA | 3383 |
| TGCAGGACCAGAGAATTCGAATACAA CATTTGANNNACGTATGCCA | 2904 | TGCAGGACCAGAGAATTCGAATACAT GTCAAGCNNNACGTATGCCA | 3144 | TGCAGGACCAGAGAATTCGAATACAA TTCTTCANNNACGTATGCCA | 3384 |
| TGCAGGACCAGAGAATTCGAATACAG GTGGCAGNNNACGTATGCCA | 2905 | TGCAGGACCAGAGAATTCGAATACAA GTGTCACNNNACGTATGCCA | 3145 | TGCAGGACCAGAGAATTCGAATACAT CTGGTCTNNNACGTATGCCA | 3385 |
| TGCAGGACCAGAGAATTCGAATACAG AGGCCAGNNNACGTATGCCA | 2906 | TGCAGGACCAGAGAATTCGAATACAC CTCAAGANNNACGTATGCCA | 3146 | TGCAGGACCAGAGAATTCGAATACAG CGAGCCTNNNACGTATGCCA | 3386 |
| TGCAGGACCAGAGAATTCGAATACAA CTCGAGTNNNACGTATGCCA | 2907 | TGCAGGACCAGAGAATTCGAATACAG TGAAAGCNNNACGTATGCCA | 3147 | TGCAGGACCAGAGAATTCGAATACAA GCCGTGCNNNACGTATGCCA | 3387 |
| TGCAGGACCAGAGAATTCGAATACAC CAAAAGGNNNACGTATGCCA | 2908 | TGCAGGACCAGAGAATTCGAATACAT TTGCGCCNNNACGTATGCCA | 3148 | TGCAGGACCAGAGAATTCGAATACAG ATAACCCNNNACGTATGCCA | 3388 |
| TGCAGGACCAGAGAATTCGAATACAA AGCCAACGNNNACGTATGCCA | 2909 | TGCAGGACCAGAGAATTCGAATACAG TATTGCGNNNACGTATGCCA | 3149 | TGCAGGACCAGAGAATTCGAATACAC GGAACCCNNNACGTATGCCA | 3389 |
| TGCAGGACCAGAGAATTCGAATACAA GCTTTGTNNNACGTATGCCA | 2910 | TGCAGGACCAGAGAATTCGAATACAA CAAATAGNNNACGTATGCCA | 3150 | TGCAGGACCAGAGAATTCGAATACAG TCCAGCGNNNACGTATGCCA | 3390 |
| TGCAGGACCAGAGAATTCGAATACAT GGATGCTNNNACGTATGCCA | 2911 | TGCAGGACCAGAGAATTCGAATACAC TACGCGGNNNACGTATGCCA | 3151 | TGCAGGACCAGAGAATTCGAATACAC GTGAGCCNNNACGTATGCCA | 3391 |
| TGCAGGACCAGAGAATTCGAATACAT CAATGGCNNNACGTATGCCA | 2912 | TGCAGGACCAGAGAATTCGAATACAT GTATACANNNACGTATGCCA | 3152 | TGCAGGACCAGAGAATTCGAATACAT CGGCCAGNNNACGTATGCCA | 3392 |
| TGCAGGACCAGAGAATTCGAATACAA ACTACTANNNACGTATGCCA | 2913 | TGCAGGACCAGAGAATTCGAATACAA GACCTACNNNACGTATGCCA | 3153 | TGCAGGACCAGAGAATTCGAATACAC CGGCAAGNNNACGTATGCCA | 3393 |
| TGCAGGACCAGAGAATTCGAATACAT TCCGATGNNNACGTATGCCA | 2914 | TGCAGGACCAGAGAATTCGAATACAT TCCCATGNNNACGTATGCCA | 3154 | TGCAGGACCAGAGAATTCGAATACAG GCTGTTANNNACGTATGCCA | 3394 |
| TGCAGGACCAGAGAATTCGAATACAG AGATACGNNNACGTATGCCA | 2915 | TGCAGGACCAGAGAATTCGAATACAT AGCCCTTNNNACGTATGCCA | 3155 | TGCAGGACCAGAGAATTCGAATACAT GAAAATGNNNACGTATGCCA | 3395 |
| TGCAGGACCAGAGAATTCGAATACAT CCTTTTTNNNACGTATGCCA | 2916 | TGCAGGACCAGAGAATTCGAATACAC GTTCACNNNACGTATGCCA | 3156 | TGCAGGACCAGAGAATTCGAATACAC TTCTATANNNACGTATGCCA | 3396 |
| TGCAGGACCAGAGAATTCGAATACAG TTAGCGTNNNACGTATGCCA | 2917 | TGCAGGACCAGAGAATTCGAATACAG ACGTTGNNNACGTATGCCA | 3157 | TGCAGGACCAGAGAATTCGAATACAT CCCCGCANNNACGTATGCCA | 3397 |
| TGCAGGACCAGAGAATTCGAATACAG CGGCGCCNNNACGTATGCCA | 2918 | TGCAGGACCAGAGAATTCGAATACAT GTTGATANNNACGTATGCCA | 3158 | TGCAGGACCAGAGAATTCGAATACAT GTCTACCNNNACGTATGCCA | 3398 |
| TGCAGGACCAGAGAATTCGAATACAA TGCTCTCNNNACGTATGCCA | 2919 | TGCAGGACCAGAGAATTCGAATACAA GTATTACNNNACGTATGCCA | 3159 | TGCAGGACCAGAGAATTCGAATACAT GTAGTTANNNACGTATGCCA | 3399 |
| TGCAGGACCAGAGAATTCGAATACAT TATCTACNNNACGTATGCCA | 2920 | TGCAGGACCAGAGAATTCGAATACAG AGAACACNNNACGTATGCCA | 3160 | TGCAGGACCAGAGAATTCGAATACAT GGTTTAANNNACGTATGCCA | 3400 |
| TGCAGGACCAGAGAATTCGAATACAT TCTATTGNNNACGTATGCCA | 2921 | TGCAGGACCAGAGAATTCGAATACAC CTAAATANNNACGTATGCCA | 3161 | TGCAGGACCAGAGAATTCGAATACAG AGACGGCNNNACGTATGCCA | 3401 |

FIG. 16B

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAC CAGTACANNNACGTATGCCA | 2922 | TGCAGGACCAGAGAATTCGAATACAA TTTCACTNNNACGTATGCCA | 3162 | TGCAGGACCAGAGAATTCGAATACAC GTCGAGCNNNACGTATGCCA | 3402 |
| TGCAGGACCAGAGAATTCGAATACAA CAGAATANNNACGTATGCCA | 2923 | TGCAGGACCAGAGAATTCGAATACAG TCAACGTNNNACGTATGCCA | 3163 | TGCAGGACCAGAGAATTCGAATACAC AACAGTCNNNACGTATGCCA | 3403 |
| TGCAGGACCAGAGAATTCGAATACAG TATATACNNNACGTATGCCA | 2924 | TGCAGGACCAGAGAATTCGAATACAG CGTGCTGNNNACGTATGCCA | 3164 | TGCAGGACCAGAGAATTCGAATACAT GTTGCGANNNACGTATGCCA | 3404 |
| TGCAGGACCAGAGAATTCGAATACAT ATTAACGNNNACGTATGCCA | 2925 | TGCAGGACCAGAGAATTCGAATACAA AACCCACNNNACGTATGCCA | 3165 | TGCAGGACCAGAGAATTCGAATACAC GTATTTTNNNACGTATGCCA | 3405 |
| TGCAGGACCAGAGAATTCGAATACAG GTTAGAGNNNACGTATGCCA | 2926 | TGCAGGACCAGAGAATTCGAATACAC CCCTGTGNNNACGTATGCCA | 3166 | TGCAGGACCAGAGAATTCGAATACAG TACGTCANNNACGTATGCCA | 3406 |
| TGCAGGACCAGAGAATTCGAATACAC TAGGATCNNNACGTATGCCA | 2927 | TGCAGGACCAGAGAATTCGAATACAC GTAGCCTNNNACGTATGCCA | 3167 | TGCAGGACCAGAGAATTCGAATACAC CTAGCCGNNNACGTATGCCA | 3407 |
| TGCAGGACCAGAGAATTCGAATACAG ACTAGGANNNACGTATGCCA | 2928 | TGCAGGACCAGAGAATTCGAATACAA TCCATGGNNNACGTATGCCA | 3168 | TGCAGGACCAGAGAATTCGAATACAA GAGCCGGNNNACGTATGCCA | 3408 |
| TGCAGGACCAGAGAATTCGAATACAA CTTATCTNNNACGTATGCCA | 2929 | TGCAGGACCAGAGAATTCGAATACAC GCATCTTNNNACGTATGCCA | 3169 | TGCAGGACCAGAGAATTCGAATACAG GCGCCCGNNNACGTATGCCA | 3409 |
| TGCAGGACCAGAGAATTCGAATACAG ACGTCCGNNNACGTATGCCA | 2930 | TGCAGGACCAGAGAATTCGAATACAA GAATCCCNNNACGTATGCCA | 3170 | TGCAGGACCAGAGAATTCGAATACAC AGCATGTNNNACGTATGCCA | 3410 |
| TGCAGGACCAGAGAATTCGAATACAA TGGAAATNNNACGTATGCCA | 2931 | TGCAGGACCAGAGAATTCGAATACAC CTTGTGTNNNACGTATGCCA | 3171 | TGCAGGACCAGAGAATTCGAATACAA GCTTAATNNNACGTATGCCA | 3411 |
| TGCAGGACCAGAGAATTCGAATACAT GTTCAGGNNNACGTATGCCA | 2932 | TGCAGGACCAGAGAATTCGAATACAG AAACCAGNNNACGTATGCCA | 3172 | TGCAGGACCAGAGAATTCGAATACAC TCACCCGNNNACGTATGCCA | 3412 |
| TGCAGGACCAGAGAATTCGAATACAT GCAATCGNNNACGTATGCCA | 2933 | TGCAGGACCAGAGAATTCGAATACAG GATACTCNNNACGTATGCCA | 3173 | TGCAGGACCAGAGAATTCGAATACAT CGGACGCNNNACGTATGCCA | 3413 |
| TGCAGGACCAGAGAATTCGAATACAT TATGGATNNNACGTATGCCA | 2934 | TGCAGGACCAGAGAATTCGAATACAG GGCCGAGNNNACGTATGCCA | 3174 | TGCAGGACCAGAGAATTCGAATACAA ACTGCCTNNNACGTATGCCA | 3414 |
| TGCAGGACCAGAGAATTCGAATACAA CATCGTGNNNACGTATGCCA | 2935 | TGCAGGACCAGAGAATTCGAATACAC ACTGTTCNNNACGTATGCCA | 3175 | TGCAGGACCAGAGAATTCGAATACAG CCTCCTGNNNACGTATGCCA | 3415 |
| TGCAGGACCAGAGAATTCGAATACAA AAGTAGTNNNACGTATGCCA | 2936 | TGCAGGACCAGAGAATTCGAATACAG TGGAGGCNNNACGTATGCCA | 3176 | TGCAGGACCAGAGAATTCGAATACAT AGTTAACNNNACGTATGCCA | 3416 |
| TGCAGGACCAGAGAATTCGAATACAT AATAACCNNNACGTATGCCA | 2937 | TGCAGGACCAGAGAATTCGAATACAA GTATCGCNNNACGTATGCCA | 3177 | TGCAGGACCAGAGAATTCGAATACAG GACTTCANNNACGTATGCCA | 3417 |
| TGCAGGACCAGAGAATTCGAATACAA TTCTCATNNNACGTATGCCA | 2938 | TGCAGGACCAGAGAATTCGAATACAT CGAGATCNNNACGTATGCCA | 3178 | TGCAGGACCAGAGAATTCGAATACAG CCGCATGNNNACGTATGCCA | 3418 |
| TGCAGGACCAGAGAATTCGAATACAA CATCCCTNNNACGTATGCCA | 2939 | TGCAGGACCAGAGAATTCGAATACAC GGTAGTTNNNACGTATGCCA | 3179 | TGCAGGACCAGAGAATTCGAATACAT GGAGTAGNNNACGTATGCCA | 3419 |
| TGCAGGACCAGAGAATTCGAATACAT GAAGTANNNNACGTATGCCA | 2940 | TGCAGGACCAGAGAATTCGAATACAC CGTATCTNNNACGTATGCCA | 3180 | TGCAGGACCAGAGAATTCGAATACAC TGTTATTNNNACGTATGCCA | 3420 |
| TGCAGGACCAGAGAATTCGAATACAG ACATTATNNNACGTATGCCA | 2941 | TGCAGGACCAGAGAATTCGAATACAA ACGCACTNNNACGTATGCCA | 3181 | TGCAGGACCAGAGAATTCGAATACAA AGAGCACNNNACGTATGCCA | 3421 |
| TGCAGGACCAGAGAATTCGAATACAG GATACGANNNACGTATGCCA | 2942 | TGCAGGACCAGAGAATTCGAATACAC CGATTGANNNACGTATGCCA | 3182 | TGCAGGACCAGAGAATTCGAATACAC GTCGAATNNNACGTATGCCA | 3422 |
| TGCAGGACCAGAGAATTCGAATACAG TACATATNNNACGTATGCCA | 2943 | TGCAGGACCAGAGAATTCGAATACAG CTCTAAGNNNACGTATGCCA | 3183 | TGCAGGACCAGAGAATTCGAATACAC TCGTGAANNNACGTATGCCA | 3423 |
| TGCAGGACCAGAGAATTCGAATACAT CATAGCGNNNACGTATGCCA | 2944 | TGCAGGACCAGAGAATTCGAATACAG GTGAGTANNNACGTATGCCA | 3184 | TGCAGGACCAGAGAATTCGAATACAG ATGGCAANNNACGTATGCCA | 3424 |
| TGCAGGACCAGAGAATTCGAATACAC TTGAACGNNNACGTATGCCA | 2945 | TGCAGGACCAGAGAATTCGAATACAG CCTATGANNNACGTATGCCA | 3185 | TGCAGGACCAGAGAATTCGAATACAT AGGTGGANNNACGTATGCCA | 3425 |
| TGCAGGACCAGAGAATTCGAATACAC TTCCCAANNNACGTATGCCA | 2946 | TGCAGGACCAGAGAATTCGAATACAA CGGAGCGNNNACGTATGCCA | 3186 | TGCAGGACCAGAGAATTCGAATACAG ATGACTCNNNACGTATGCCA | 3426 |
| TGCAGGACCAGAGAATTCGAATACAA GAGCCCGNNNACGTATGCCA | 2947 | TGCAGGACCAGAGAATTCGAATACAC TGTGACGNNNACGTATGCCA | 3187 | TGCAGGACCAGAGAATTCGAATACAG CTCTGTTNNNACGTATGCCA | 3427 |
| TGCAGGACCAGAGAATTCGAATACAA TAATCACNNNACGTATGCCA | 2948 | TGCAGGACCAGAGAATTCGAATACAC GTCCGTCNNNACGTATGCCA | 3188 | TGCAGGACCAGAGAATTCGAATACAA CGCAACTNNNACGTATGCCA | 3428 |
| TGCAGGACCAGAGAATTCGAATACAG ACGACAANNNCTAGCGTTAC | 2949 | TGCAGGACCAGAGAATTCGAATACAA TCGTGACNNNCTAGCGTTAC | 3189 | TGCAGGACCAGAGAATTCGAATACAC GAATGCTNNNCTAGCGTTAC | 3429 |
| TGCAGGACCAGAGAATTCGAATACAC GAATTATNNNCTAGCGTTAC | 2950 | TGCAGGACCAGAGAATTCGAATACAC CATGTCTNNNCTAGCGTTAC | 3190 | TGCAGGACCAGAGAATTCGAATACAA GCCAATCNNNCTAGCGTTAC | 3430 |
| TGCAGGACCAGAGAATTCGAATACAC GCGCTGANNNCTAGCGTTAC | 2951 | TGCAGGACCAGAGAATTCGAATACAC CTTTTGGNNNCTAGCGTTAC | 3191 | TGCAGGACCAGAGAATTCGAATACAG CAGTTTGNNNCTAGCGTTAC | 3431 |
| TGCAGGACCAGAGAATTCGAATACAT CAATTAGNNNCTAGCGTTAC | 2952 | TGCAGGACCAGAGAATTCGAATACAC GCGTCGANNNCTAGCGTTAC | 3192 | TGCAGGACCAGAGAATTCGAATACAC GCAATGTNNNCTAGCGTTAC | 3432 |
| TGCAGGACCAGAGAATTCGAATACAA TGAGCAGNNNCTAGCGTTAC | 2953 | TGCAGGACCAGAGAATTCGAATACAG CCCCCATNNNCTAGCGTTAC | 3193 | TGCAGGACCAGAGAATTCGAATACAT GCAGTGTNNNCTAGCGTTAC | 3433 |
| TGCAGGACCAGAGAATTCGAATACAT GACTTAANNNCTAGCGTTAC | 2954 | TGCAGGACCAGAGAATTCGAATACAG TCCTTCGNNNCTAGCGTTAC | 3194 | TGCAGGACCAGAGAATTCGAATACAA GTCCATGNNNCTAGCGTTAC | 3434 |

FIG. 16C

| Pool-13 | SEQ ID NO | Pool-14 | SEQ ID NO | Pool-15 | SEQ ID NO |
|---|---|---|---|---|---|
| TGCAGGACCAGAGAATTCGAATACATGAGAATANNNCTAGCGTTAC | 2955 | TGCAGGACCAGAGAATTCGAATACAATCCACGANNNCTAGCGTTAC | 3195 | TGCAGGACCAGAGAATTCGAATACACTATTCATNNNCTAGCGTTAC | 3435 |
| TGCAGGACCAGAGAATTCGAATACACTTTTTCTNNNCTAGCGTTAC | 2956 | TGCAGGACCAGAGAATTCGAATACATATGCATANNNCTAGCGTTAC | 3196 | TGCAGGACCAGAGAATTCGAATACAGTCGTTCTNNNCTAGCGTTAC | 3436 |
| TGCAGGACCAGAGAATTCGAATACAGTCGCAATNNNCTAGCGTTAC | 2957 | TGCAGGACCAGAGAATTCGAATACAGAGAAATTNNNCTAGCGTTAC | 3197 | TGCAGGACCAGAGAATTCGAATACACGTTGTAGNNNCTAGCGTTAC | 3437 |
| TGCAGGACCAGAGAATTCGAATACAATCCATCCNNNCTAGCGTTAC | 2958 | TGCAGGACCAGAGAATTCGAATACACCTCAATCNNNCTAGCGTTAC | 3198 | TGCAGGACCAGAGAATTCGAATACAGACAGCGGNNNCTAGCGTTAC | 3438 |
| TGCAGGACCAGAGAATTCGAATACAAGATATGANNNCTAGCGTTAC | 2959 | TGCAGGACCAGAGAATTCGAATACACAAAACAANNNCTAGCGTTAC | 3199 | TGCAGGACCAGAGAATTCGAATACATACACCCTNNNCTAGCGTTAC | 3439 |
| TGCAGGACCAGAGAATTCGAATACATAGCTACGNNNCTAGCGTTAC | 2960 | TGCAGGACCAGAGAATTCGAATACAGTGATGTCNNNCTAGCGTTAC | 3200 | TGCAGGACCAGAGAATTCGAATACACGTTAAGCNNNCTAGCGTTAC | 3440 |
| TGCAGGACCAGAGAATTCGAATACATTACAGGCNNNCTAGCGTTAC | 2961 | TGCAGGACCAGAGAATTCGAATACATGCCGTANNNNCTAGCGTTAC | 3201 | TGCAGGACCAGAGAATTCGAATACAATCGCCTTNNNCTAGCGTTAC | 3441 |
| TGCAGGACCAGAGAATTCGAATACAGACTACACNNNCTAGCGTTAC | 2962 | TGCAGGACCAGAGAATTCGAATACAGGCTCTAGNNNCTAGCGTTAC | 3202 | TGCAGGACCAGAGAATTCGAATACAGCTATGCANNNCTAGCGTTAC | 3442 |
| TGCAGGACCAGAGAATTCGAATACAATTTTAGGNNNCTAGCGTTAC | 2963 | TGCAGGACCAGAGAATTCGAATACAGGCGTGCTNNNCTAGCGTTAC | 3203 | TGCAGGACCAGAGAATTCGAATACAACGCACGCNNNCTAGCGTTAC | 3443 |
| TGCAGGACCAGAGAATTCGAATACATTTTCAGTNNNCTAGCGTTAC | 2964 | TGCAGGACCAGAGAATTCGAATACAGACGTCATNNNCTAGCGTTAC | 3204 | TGCAGGACCAGAGAATTCGAATACACGTCACAANNNCTAGCGTTAC | 3444 |
| TGCAGGACCAGAGAATTCGAATACAGCAGAACANNNCTAGCGTTAC | 2965 | TGCAGGACCAGAGAATTCGAATACATGTATTAGNNNCTAGCGTTAC | 3205 | TGCAGGACCAGAGAATTCGAATACACGCGATCGNNNCTAGCGTTAC | 3445 |
| TGCAGGACCAGAGAATTCGAATACACGAGTAGANNNCTAGCGTTAC | 2966 | TGCAGGACCAGAGAATTCGAATACAATGATTACNNNCTAGCGTTAC | 3206 | TGCAGGACCAGAGAATTCGAATACAGTTAGACCNNNCTAGCGTTAC | 3446 |
| TGCAGGACCAGAGAATTCGAATACAGTCGGAGGNNNCTAGCGTTAC | 2967 | TGCAGGACCAGAGAATTCGAATACAACTCCGAANNNCTAGCGTTAC | 3207 | TGCAGGACCAGAGAATTCGAATACATCGCGAGCNNNCTAGCGTTAC | 3447 |
| TGCAGGACCAGAGAATTCGAATACAATGTACTANNNCTAGCGTTAC | 2968 | TGCAGGACCAGAGAATTCGAATACATTCTTCCCNNNCTAGCGTTAC | 3208 | TGCAGGACCAGAGAATTCGAATACATGTAAACTNNNCTAGCGTTAC | 3448 |
| TGCAGGACCAGAGAATTCGAATACATACTCCGTNNNCTAGCGTTAC | 2969 | TGCAGGACCAGAGAATTCGAATACATCTCCTAGNNNCTAGCGTTAC | 3209 | TGCAGGACCAGAGAATTCGAATACATGCCATAGNNNCTAGCGTTAC | 3449 |
| TGCAGGACCAGAGAATTCGAATACACACATTGGNNNCTAGCGTTAC | 2970 | TGCAGGACCAGAGAATTCGAATACAGACTTATANNNCTAGCGTTAC | 3210 | TGCAGGACCAGAGAATTCGAATACATAATTACGNNNCTAGCGTTAC | 3450 |
| TGCAGGACCAGAGAATTCGAATACATTAGCAATNNNCTAGCGTTAC | 2971 | TGCAGGACCAGAGAATTCGAATACACGAGTGAANNNCTAGCGTTAC | 3211 | TGCAGGACCAGAGAATTCGAATACACCCGCGCCNNNCTAGCGTTAC | 3451 |
| TGCAGGACCAGAGAATTCGAATACATCCAACGANNNCTAGCGTTAC | 2972 | TGCAGGACCAGAGAATTCGAATACATATAAATTNNNCTAGCGTTAC | 3212 | TGCAGGACCAGAGAATTCGAATACACAATATCANNNCTAGCGTTAC | 3452 |
| TGCAGGACCAGAGAATTCGAATACATTGATCCCNNNCTAGCGTTAC | 2973 | TGCAGGACCAGAGAATTCGAATACAGCCGTGAGNNNCTAGCGTTAC | 3213 | TGCAGGACCAGAGAATTCGAATACAATTAAGGANNNCTAGCGTTAC | 3453 |
| TGCAGGACCAGAGAATTCGAATACATATTAATANNNCTAGCGTTAC | 2974 | TGCAGGACCAGAGAATTCGAATACAAGTCCCTTNNNCTAGCGTTAC | 3214 | TGCAGGACCAGAGAATTCGAATACAATATACACNNNCTAGCGTTAC | 3454 |
| TGCAGGACCAGAGAATTCGAATACATAAGTTTGNNNCTAGCGTTAC | 2975 | TGCAGGACCAGAGAATTCGAATACAAGACTTATNNNCTAGCGTTAC | 3215 | TGCAGGACCAGAGAATTCGAATACATATTGACANNNCTAGCGTTAC | 3455 |
| TGCAGGACCAGAGAATTCGAATACAGGCCGCGCNNNCTAGCGTTAC | 2976 | TGCAGGACCAGAGAATTCGAATACATGGCACTANNNCTAGCGTTAC | 3216 | TGCAGGACCAGAGAATTCGAATACAACGAAAATNNNCTAGCGTTAC | 3456 |
| TGCAGGACCAGAGAATTCGAATACATCACACGANNNCTAGCGTTAC | 2977 | TGCAGGACCAGAGAATTCGAATACAATTCCTATNNNCTAGCGTTAC | 3217 | TGCAGGACCAGAGAATTCGAATACAGTAGGACANNNCTAGCGTTAC | 3457 |
| TGCAGGACCAGAGAATTCGAATACAGAGTCGTTNNNCTAGCGTTAC | 2978 | TGCAGGACCAGAGAATTCGAATACACTGATATANNNCTAGCGTTAC | 3218 | TGCAGGACCAGAGAATTCGAATACACCCCCAGTNNNCTAGCGTTAC | 3458 |
| TGCAGGACCAGAGAATTCGAATACAAGAGCCTTNNNCTAGCGTTAC | 2979 | TGCAGGACCAGAGAATTCGAATACACAAGCACTNNNCTAGCGTTAC | 3219 | TGCAGGACCAGAGAATTCGAATACACCTACGTTNNNCTAGCGTTAC | 3459 |
| TGCAGGACCAGAGAATTCGAATACACCTTGCTANNNCTAGCGTTAC | 2980 | TGCAGGACCAGAGAATTCGAATACAGCGCATGCNNNCTAGCGTTAC | 3220 | TGCAGGACCAGAGAATTCGAATACATGGTGAGANNNCTAGCGTTAC | 3460 |
| TGCAGGACCAGAGAATTCGAATACAATCATAGTNNNCTAGCGTTAC | 2981 | TGCAGGACCAGAGAATTCGAATACATCCTCAATNNNCTAGCGTTAC | 3221 | TGCAGGACCAGAGAATTCGAATACACTAGCACANNNCTAGCGTTAC | 3461 |
| TGCAGGACCAGAGAATTCGAATACATAGCAATNNNNCTAGCGTTAC | 2982 | TGCAGGACCAGAGAATTCGAATACATCGCCACCNNNCTAGCGTTAC | 3222 | TGCAGGACCAGAGAATTCGAATACATCATGTAANNNCTAGCGTTAC | 3462 |
| TGCAGGACCAGAGAATTCGAATACACAATTGTANNNCTAGCGTTAC | 2983 | TGCAGGACCAGAGAATTCGAATACAGGACGGACNNNCTAGCGTTAC | 3223 | TGCAGGACCAGAGAATTCGAATACAGGACGAATNNNCTAGCGTTAC | 3463 |
| TGCAGGACCAGAGAATTCGAATACATTCGGCAANNNCTAGCGTTAC | 2984 | TGCAGGACCAGAGAATTCGAATACACGAACAGANNNCTAGCGTTAC | 3224 | TGCAGGACCAGAGAATTCGAATACAGGATGGCGNNNCTAGCGTTAC | 3464 |
| TGCAGGACCAGAGAATTCGAATACACCTAGTCTNNNCTAGCGTTAC | 2985 | TGCAGGACCAGAGAATTCGAATACATATCTCGCNNNCTAGCGTTAC | 3225 | TGCAGGACCAGAGAATTCGAATACATCCCAGTTNNNCTAGCGTTAC | 3465 |
| TGCAGGACCAGAGAATTCGAATACACTAGGCTANNNCTAGCGTTAC | 2986 | TGCAGGACCAGAGAATTCGAATACATGCATCAGNNNCTAGCGTTAC | 3226 | TGCAGGACCAGAGAATTCGAATACACGAGACAANNNCTAGCGTTAC | 3466 |
| TGCAGGACCAGAGAATTCGAATACAAATCAATCNNNCTAGCGTTAC | 2987 | TGCAGGACCAGAGAATTCGAATACACCTAAAGCNNNCTAGCGTTAC | 3227 | TGCAGGACCAGAGAATTCGAATACACAATACCGNNNCTAGCGTTAC | 3467 |

FIG. 16D

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAG CCCTCGTNNNCTAGCGTTAC | 2988 | TGCAGGACCAGAGAATTCGAATACAT TTGACAANNNCTAGCGTTAC | 3228 | TGCAGGACCAGAGAATTCGAATACAT TTATGTCNNNCTAGCGTTAC | 3468 |
| TGCAGGACCAGAGAATTCGAATACAA GGTTGAGNNNCTAGCGTTAC | 2989 | TGCAGGACCAGAGAATTCGAATACAC CCGCCATNNNCTAGCGTTAC | 3229 | TGCAGGACCAGAGAATTCGAATACAT GGTAACCNNNCTAGCGTTAC | 3469 |
| TGCAGGACCAGAGAATTCGAATACAC AGCCAGCNNNCTAGCGTTAC | 2990 | TGCAGGACCAGAGAATTCGAATACAT TGCATAANNNCTAGCGTTAC | 3230 | TGCAGGACCAGAGAATTCGAATACAA GCCCATANNNCTAGCGTTAC | 3470 |
| TGCAGGACCAGAGAATTCGAATACAA CTAATGTNNNCTAGCGTTAC | 2991 | TGCAGGACCAGAGAATTCGAATACAA CAGAGCANNNCTAGCGTTAC | 3231 | TGCAGGACCAGAGAATTCGAATACAA TCCTCCANNNCTAGCGTTAC | 3471 |
| TGCAGGACCAGAGAATTCGAATACAG GTAAGACNNNCTAGCGTTAC | 2992 | TGCAGGACCAGAGAATTCGAATACAG GTACGTTNNNCTAGCGTTAC | 3232 | TGCAGGACCAGAGAATTCGAATACAT TTTTGACNNNCTAGCGTTAC | 3472 |
| TGCAGGACCAGAGAATTCGAATACAC TCGCGAGNNNCTAGCGTTAC | 2993 | TGCAGGACCAGAGAATTCGAATACAG ATGCACTNNNCTAGCGTTAC | 3233 | TGCAGGACCAGAGAATTCGAATACAA TAGCCTGNNNCTAGCGTTAC | 3473 |
| TGCAGGACCAGAGAATTCGAATACAC TGCCGCTNNNCTAGCGTTAC | 2994 | TGCAGGACCAGAGAATTCGAATACAA TCTAAACNNNCTAGCGTTAC | 3234 | TGCAGGACCAGAGAATTCGAATACAG GAGTCTTNNNCTAGCGTTAC | 3474 |
| TGCAGGACCAGAGAATTCGAATACAA CTGCGGCNNNCTAGCGTTAC | 2995 | TGCAGGACCAGAGAATTCGAATACAA CGAGAACNNNCTAGCGTTAC | 3235 | TGCAGGACCAGAGAATTCGAATACAA CCCCACCNNNCTAGCGTTAC | 3475 |
| TGCAGGACCAGAGAATTCGAATACAC CTCTACANNNCTAGCGTTAC | 2996 | TGCAGGACCAGAGAATTCGAATACAC CGCAAGCNNNCTAGCGTTAC | 3236 | TGCAGGACCAGAGAATTCGAATACAC GCGGCATNNNCTAGCGTTAC | 3476 |
| TGCAGGACCAGAGAATTCGAATACAT GGCCACGNNNCTAGCGTTAC | 2997 | TGCAGGACCAGAGAATTCGAATACAA CGACAAGNNNCTAGCGTTAC | 3237 | TGCAGGACCAGAGAATTCGAATACAT CCAGACANNNCTAGCGTTAC | 3477 |
| TGCAGGACCAGAGAATTCGAATACAA CGCAATCNNNCTAGCGTTAC | 2998 | TGCAGGACCAGAGAATTCGAATACAC GCCGATGNNNCTAGCGTTAC | 3238 | TGCAGGACCAGAGAATTCGAATACAA AATGCAANNNCTAGCGTTAC | 3478 |
| TGCAGGACCAGAGAATTCGAATACAG GTTTGCANNNCTAGCGTTAC | 2999 | TGCAGGACCAGAGAATTCGAATACAA ATCCGCGNNNCTAGCGTTAC | 3239 | TGCAGGACCAGAGAATTCGAATACAA ATTCGCGNNNCTAGCGTTAC | 3479 |
| TGCAGGACCAGAGAATTCGAATACAA GTTAGGANNNCTAGCGTTAC | 3000 | TGCAGGACCAGAGAATTCGAATACAA TTAATGCNNNCTAGCGTTAC | 3240 | TGCAGGACCAGAGAATTCGAATACAG TGTCCTTNNNCTAGCGTTAC | 3480 |
| TGCAGGACCAGAGAATTCGAATACAT CCTCGGCNNNCTAGCGTTAC | 3001 | TGCAGGACCAGAGAATTCGAATACAG CGCTTCCNNNCTAGCGTTAC | 3241 | TGCAGGACCAGAGAATTCGAATACAC ATGTAATNNNCTAGCGTTAC | 3481 |
| TGCAGGACCAGAGAATTCGAATACAA AACACGGNNNCTAGCGTTAC | 3002 | TGCAGGACCAGAGAATTCGAATACAT ACAATTGNNNCTAGCGTTAC | 3242 | TGCAGGACCAGAGAATTCGAATACAA CGCATACNNNCTAGCGTTAC | 3482 |
| TGCAGGACCAGAGAATTCGAATACAG AAAATCANNNCTAGCGTTAC | 3003 | TGCAGGACCAGAGAATTCGAATACAG TGGAACANNNCTAGCGTTAC | 3243 | TGCAGGACCAGAGAATTCGAATACAA TGCCCCCNNNCTAGCGTTAC | 3483 |
| TGCAGGACCAGAGAATTCGAATACAC GTATCTCNNNCTAGCGTTAC | 3004 | TGCAGGACCAGAGAATTCGAATACAC TCTGTGTNNNCTAGCGTTAC | 3244 | TGCAGGACCAGAGAATTCGAATACAC TCCCCAGNNNCTAGCGTTAC | 3484 |
| TGCAGGACCAGAGAATTCGAATACAC GGCCACANNNCTAGCGTTAC | 3005 | TGCAGGACCAGAGAATTCGAATACAT GCAGTACNNNCTAGCGTTAC | 3245 | TGCAGGACCAGAGAATTCGAATACAT CTACTTANNNCTAGCGTTAC | 3485 |
| TGCAGGACCAGAGAATTCGAATACAT CATTCATNNNCTAGCGTTAC | 3006 | TGCAGGACCAGAGAATTCGAATACAG ACAACTCNNNCTAGCGTTAC | 3246 | TGCAGGACCAGAGAATTCGAATACAT ACCGGTANNNCTAGCGTTAC | 3486 |
| TGCAGGACCAGAGAATTCGAATACAA TAGATGANNNCTAGCGTTAC | 3007 | TGCAGGACCAGAGAATTCGAATACAC GAGAGGCNNNCTAGCGTTAC | 3247 | TGCAGGACCAGAGAATTCGAATACAA ACCTATANNNCTAGCGTTAC | 3487 |
| TGCAGGACCAGAGAATTCGAATACAG CACTGCGNNNCTAGCGTTAC | 3008 | TGCAGGACCAGAGAATTCGAATACAC TAAATGTNNNCTAGCGTTAC | 3248 | TGCAGGACCAGAGAATTCGAATACAG CGACTGCNNNCTAGCGTTAC | 3488 |
| TGCAGGACCAGAGAATTCGAATACAA CTCCCTANNNGATCGACATG | 3009 | TGCAGGACCAGAGAATTCGAATACAG GCTCACGNNNGATCGACATG | 3249 | TGCAGGACCAGAGAATTCGAATACAC GAGTCTANNNGATCGACATG | 3489 |
| TGCAGGACCAGAGAATTCGAATACAA CAAAACANNNGATCGACATG | 3010 | TGCAGGACCAGAGAATTCGAATACAA CGTTTCCNNNGATCGACATG | 3250 | TGCAGGACCAGAGAATTCGAATACAT ATGAAAGNNNGATCGACATG | 3490 |
| TGCAGGACCAGAGAATTCGAATACAT ATGTACANNNGATCGACATG | 3011 | TGCAGGACCAGAGAATTCGAATACAT GCCAGTANNNGATCGACATG | 3251 | TGCAGGACCAGAGAATTCGAATACAA CTGCCCGNNNGATCGACATG | 3491 |
| TGCAGGACCAGAGAATTCGAATACAT CGGTCTTNNNGATCGACATG | 3012 | TGCAGGACCAGAGAATTCGAATACAG TAAGTGGNNNGATCGACATG | 3252 | TGCAGGACCAGAGAATTCGAATACAC AACCATGNNNGATCGACATG | 3492 |
| TGCAGGACCAGAGAATTCGAATACAT CCATATTNNNGATCGACATG | 3013 | TGCAGGACCAGAGAATTCGAATACAC ACCTACTNNNGATCGACATG | 3253 | TGCAGGACCAGAGAATTCGAATACAA AGGTAGCNNNGATCGACATG | 3493 |
| TGCAGGACCAGAGAATTCGAATACAA TGACTCGNNNGATCGACATG | 3014 | TGCAGGACCAGAGAATTCGAATACAG ATTTGATNNNGATCGACATG | 3254 | TGCAGGACCAGAGAATTCGAATACAT TCTCAGCNNNGATCGACATG | 3494 |
| TGCAGGACCAGAGAATTCGAATACAT AATCTCTNNNGATCGACATG | 3015 | TGCAGGACCAGAGAATTCGAATACAA ACTACATNNNGATCGACATG | 3255 | TGCAGGACCAGAGAATTCGAATACAT TCAGGTGNNNGATCGACATG | 3495 |
| TGCAGGACCAGAGAATTCGAATACAG AATACTTNNNGATCGACATG | 3016 | TGCAGGACCAGAGAATTCGAATACAG CCTTGAANNNGATCGACATG | 3256 | TGCAGGACCAGAGAATTCGAATACAC CAATCCTNNNGATCGACATG | 3496 |
| TGCAGGACCAGAGAATTCGAATACAC CACTAGANNNGATCGACATG | 3017 | TGCAGGACCAGAGAATTCGAATACAT AATATTANNNGATCGACATG | 3257 | TGCAGGACCAGAGAATTCGAATACAG ACAGTTCNNNGATCGACATG | 3497 |
| TGCAGGACCAGAGAATTCGAATACAT TTGGACCNNNGATCGACATG | 3018 | TGCAGGACCAGAGAATTCGAATACAG GTTTAATNNNGATCGACATG | 3258 | TGCAGGACCAGAGAATTCGAATACAA TCTTTACNNNGATCGACATG | 3498 |
| TGCAGGACCAGAGAATTCGAATACAG AAGTCCTNNNGATCGACATG | 3019 | TGCAGGACCAGAGAATTCGAATACAC CCACCGTNNNGATCGACATG | 3259 | TGCAGGACCAGAGAATTCGAATACAG CAATATTNNNGATCGACATG | 3499 |
| TGCAGGACCAGAGAATTCGAATACAC CTATGCTNNNGATCGACATG | 3020 | TGCAGGACCAGAGAATTCGAATACAC TACTTCGNNNGATCGACATG | 3260 | TGCAGGACCAGAGAATTCGAATACAG TCTCCATNNNGATCGACATG | 3500 |

FIG. 16E

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAT CGATGTGNNNGATCGACATG | 3021 | TGCAGGACCAGAGAATTCGAATACAA TGCGTCANNNGATCGACATG | 3261 | TGCAGGACCAGAGAATTCGAATACAC AACAATTNNNGATCGACATG | 3501 |
| TGCAGGACCAGAGAATTCGAATACAT GTACACGNNNGATCGACATG | 3022 | TGCAGGACCAGAGAATTCGAATACAA ACATGTTNNNGATCGACATG | 3262 | TGCAGGACCAGAGAATTCGAATACAT CGTAGACNNNGATCGACATG | 3502 |
| TGCAGGACCAGAGAATTCGAATACAT CTTTAGTNNNGATCGACATG | 3023 | TGCAGGACCAGAGAATTCGAATACAC CTGTTTGNNNGATCGACATG | 3263 | TGCAGGACCAGAGAATTCGAATACAG TAGATAANNNGATCGACATG | 3503 |
| TGCAGGACCAGAGAATTCGAATACAC GTAGGCCNNNGATCGACATG | 3024 | TGCAGGACCAGAGAATTCGAATACAC ACAAGCTNNNGATCGACATG | 3264 | TGCAGGACCAGAGAATTCGAATACAA CATATACNNNGATCGACATG | 3504 |
| TGCAGGACCAGAGAATTCGAATACAA CCTTTATNNNGATCGACATG | 3025 | TGCAGGACCAGAGAATTCGAATACAG ATAAGATNNNGATCGACATG | 3265 | TGCAGGACCAGAGAATTCGAATACAC ACGACGCNNNGATCGACATG | 3505 |
| TGCAGGACCAGAGAATTCGAATACAC GTCTATCNNNGATCGACATG | 3026 | TGCAGGACCAGAGAATTCGAATACAA GACCTCANNNGATCGACATG | 3266 | TGCAGGACCAGAGAATTCGAATACAC ACAAAAANNNGATCGACATG | 3506 |
| TGCAGGACCAGAGAATTCGAATACAG TAGAAATNNNGATCGACATG | 3027 | TGCAGGACCAGAGAATTCGAATACAC TCCAAGANNNGATCGACATG | 3267 | TGCAGGACCAGAGAATTCGAATACAC GTACCGGNNNGATCGACATG | 3507 |
| TGCAGGACCAGAGAATTCGAATACAC GTACCAANNNGATCGACATG | 3028 | TGCAGGACCAGAGAATTCGAATACAG GTATTCGNNNGATCGACATG | 3268 | TGCAGGACCAGAGAATTCGAATACAC CACAATGNNNGATCGACATG | 3508 |
| TGCAGGACCAGAGAATTCGAATACAC ACCACCCNNNGATCGACATG | 3029 | TGCAGGACCAGAGAATTCGAATACAA CTCGGATNNNGATCGACATG | 3269 | TGCAGGACCAGAGAATTCGAATACAC GCTCTGCNNNGATCGACATG | 3509 |
| TGCAGGACCAGAGAATTCGAATACAT GCGGCGTNNNGATCGACATG | 3030 | TGCAGGACCAGAGAATTCGAATACAT ATATGCANNNGATCGACATG | 3270 | TGCAGGACCAGAGAATTCGAATACAG TCAAGCTNNNGATCGACATG | 3510 |
| TGCAGGACCAGAGAATTCGAATACAG CCCCCCGNNNGATCGACATG | 3031 | TGCAGGACCAGAGAATTCGAATACAA TCCACTCNNNGATCGACATG | 3271 | TGCAGGACCAGAGAATTCGAATACAA CTCTTCGNNNGATCGACATG | 3511 |
| TGCAGGACCAGAGAATTCGAATACAT AGTAAGANNNGATCGACATG | 3032 | TGCAGGACCAGAGAATTCGAATACAG AACTGGANNNGATCGACATG | 3272 | TGCAGGACCAGAGAATTCGAATACAA ACACGGANNNGATCGACATG | 3512 |
| TGCAGGACCAGAGAATTCGAATACAT CTGAATANNNGATCGACATG | 3033 | TGCAGGACCAGAGAATTCGAATACAG ATCAGAGNNNGATCGACATG | 3273 | TGCAGGACCAGAGAATTCGAATACAA CCGCGCANNNGATCGACATG | 3513 |
| TGCAGGACCAGAGAATTCGAATACAC TAATACANNNGATCGACATG | 3034 | TGCAGGACCAGAGAATTCGAATACAT TGAACTANNNGATCGACATG | 3274 | TGCAGGACCAGAGAATTCGAATACAC ACCTTGTNNNGATCGACATG | 3514 |
| TGCAGGACCAGAGAATTCGAATACAA TGTCACGNNNGATCGACATG | 3035 | TGCAGGACCAGAGAATTCGAATACAG CCAGCCANNNGATCGACATG | 3275 | TGCAGGACCAGAGAATTCGAATACAT TATGCGGNNNGATCGACATG | 3515 |
| TGCAGGACCAGAGAATTCGAATACAA ACAGAATNNNGATCGACATG | 3036 | TGCAGGACCAGAGAATTCGAATACAT TTACTGTNNNGATCGACATG | 3276 | TGCAGGACCAGAGAATTCGAATACAG ACTCTTCNNNGATCGACATG | 3516 |
| TGCAGGACCAGAGAATTCGAATACAG CCCAGGTNNNGATCGACATG | 3037 | TGCAGGACCAGAGAATTCGAATACAT GTCAGGTNNNGATCGACATG | 3277 | TGCAGGACCAGAGAATTCGAATACAG AGTCTTGNNNGATCGACATG | 3517 |
| TGCAGGACCAGAGAATTCGAATACAG CTCATGANNNGATCGACATG | 3038 | TGCAGGACCAGAGAATTCGAATACAC AGCGTTANNNGATCGACATG | 3278 | TGCAGGACCAGAGAATTCGAATACAT AGAATCTNNNGATCGACATG | 3518 |
| TGCAGGACCAGAGAATTCGAATACAC CCGTCGANNNGATCGACATG | 3039 | TGCAGGACCAGAGAATTCGAATACAT GTGATCGNNNGATCGACATG | 3279 | TGCAGGACCAGAGAATTCGAATACAC GACCACGNNNGATCGACATG | 3519 |
| TGCAGGACCAGAGAATTCGAATACAC AATTCCCNNNGATCGACATG | 3040 | TGCAGGACCAGAGAATTCGAATACAG CTCGTAANNNGATCGACATG | 3280 | TGCAGGACCAGAGAATTCGAATACAT GGATTCGNNNGATCGACATG | 3520 |
| TGCAGGACCAGAGAATTCGAATACAC CAGGCCANNNGATCGACATG | 3041 | TGCAGGACCAGAGAATTCGAATACAA TTCTACTNNNGATCGACATG | 3281 | TGCAGGACCAGAGAATTCGAATACAC GACTAGTNNNGATCGACATG | 3521 |
| TGCAGGACCAGAGAATTCGAATACAC CTGCGGANNNGATCGACATG | 3042 | TGCAGGACCAGAGAATTCGAATACAG ATCAGTCNNNGATCGACATG | 3282 | TGCAGGACCAGAGAATTCGAATACAC CCAAAACNNNGATCGACATG | 3522 |
| TGCAGGACCAGAGAATTCGAATACAG CTAAAGGNNNGATCGACATG | 3043 | TGCAGGACCAGAGAATTCGAATACAG GATTATTNNNGATCGACATG | 3283 | TGCAGGACCAGAGAATTCGAATACAT GACCCCCNNNGATCGACATG | 3523 |
| TGCAGGACCAGAGAATTCGAATACAT TTAAGGTNNNGATCGACATG | 3044 | TGCAGGACCAGAGAATTCGAATACAC CATTCGTNNNGATCGACATG | 3284 | TGCAGGACCAGAGAATTCGAATACAG CATTAGCNNNGATCGACATG | 3524 |
| TGCAGGACCAGAGAATTCGAATACAA AACGTAANNNGATCGACATG | 3045 | TGCAGGACCAGAGAATTCGAATACAG TACATGCNNNGATCGACATG | 3285 | TGCAGGACCAGAGAATTCGAATACAG CCAGATTNNNGATCGACATG | 3525 |
| TGCAGGACCAGAGAATTCGAATACAA ATTTGGTNNNGATCGACATG | 3046 | TGCAGGACCAGAGAATTCGAATACAC GTCGCAGNNNGATCGACATG | 3286 | TGCAGGACCAGAGAATTCGAATACAA CAACTATNNNGATCGACATG | 3526 |
| TGCAGGACCAGAGAATTCGAATACAA CGTTAGCNNNGATCGACATG | 3047 | TGCAGGACCAGAGAATTCGAATACAT ATTTGTCNNNGATCGACATG | 3287 | TGCAGGACCAGAGAATTCGAATACAG TAGGTCTNNNGATCGACATG | 3527 |
| TGCAGGACCAGAGAATTCGAATACAA AGTTTTGNNNGATCGACATG | 3048 | TGCAGGACCAGAGAATTCGAATACAA CAGTCCANNNGATCGACATG | 3288 | TGCAGGACCAGAGAATTCGAATACAA ATAAGGTNNNGATCGACATG | 3528 |
| TGCAGGACCAGAGAATTCGAATACAA GCGTTCANNNGATCGACATG | 3049 | TGCAGGACCAGAGAATTCGAATACAG CGATTGTNNNGATCGACATG | 3289 | TGCAGGACCAGAGAATTCGAATACAA AGAGAAANNNGATCGACATG | 3529 |
| TGCAGGACCAGAGAATTCGAATACAG GACTTGTNNNGATCGACATG | 3050 | TGCAGGACCAGAGAATTCGAATACAC CTGGAATNNNGATCGACATG | 3290 | TGCAGGACCAGAGAATTCGAATACAT TTTGTGTNNNGATCGACATG | 3530 |
| TGCAGGACCAGAGAATTCGAATACAC GTCAGATNNNGATCGACATG | 3051 | TGCAGGACCAGAGAATTCGAATACAA CGAGCAANNNGATCGACATG | 3291 | TGCAGGACCAGAGAATTCGAATACAA GGCGTTTNNNGATCGACATG | 3531 |
| TGCAGGACCAGAGAATTCGAATACAC CAGAAGANNNGATCGACATG | 3052 | TGCAGGACCAGAGAATTCGAATACAA CACCAACNNNGATCGACATG | 3292 | TGCAGGACCAGAGAATTCGAATACAA AAAGCTANNNGATCGACATG | 3532 |
| TGCAGGACCAGAGAATTCGAATACAG CGATCTANNNGATCGACATG | 3053 | TGCAGGACCAGAGAATTCGAATACAT TTAGTCTNNNGATCGACATG | 3293 | TGCAGGACCAGAGAATTCGAATACAA CCGGATTNNNGATCGACATG | 3533 |

FIG. 16F

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAATCACCGANNNGATCGACATG | 3054 | TGCAGGACCAGAGAATTCGAATACATGTAGCTGNNNGATCGACATG | 3294 | TGCAGGACCAGAGAATTCGAATACACTCAAATANNNGATCGACATG | 3534 |
| TGCAGGACCAGAGAATTCGAATACAACACTAATNNNGATCGACATG | 3055 | TGCAGGACCAGAGAATTCGAATACAGGCTTACANNNGATCGACATG | 3295 | TGCAGGACCAGAGAATTCGAATACACGAGAACANNNGATCGACATG | 3535 |
| TGCAGGACCAGAGAATTCGAATACAATATGAAGNNNGATCGACATG | 3056 | TGCAGGACCAGAGAATTCGAATACACGACCAGCNNNGATCGACATG | 3296 | TGCAGGACCAGAGAATTCGAATACACCCAGGACNNNGATCGACATG | 3536 |
| TGCAGGACCAGAGAATTCGAATACAAGTAAGCGNNNGATCGACATG | 3057 | TGCAGGACCAGAGAATTCGAATACAGCCAAAAGNNNGATCGACATG | 3297 | TGCAGGACCAGAGAATTCGAATACACCAGCTCCNNNGATCGACATG | 3537 |
| TGCAGGACCAGAGAATTCGAATACAGACGCTATNNNGATCGACATG | 3058 | TGCAGGACCAGAGAATTCGAATACACGAGGTAANNNGATCGACATG | 3298 | TGCAGGACCAGAGAATTCGAATACATATACATGNNNGATCGACATG | 3538 |
| TGCAGGACCAGAGAATTCGAATACATGACATCGNNNGATCGACATG | 3059 | TGCAGGACCAGAGAATTCGAATACACAGTCATGNNNGATCGACATG | 3299 | TGCAGGACCAGAGAATTCGAATACATATAGTTGNNNGATCGACATG | 3539 |
| TGCAGGACCAGAGAATTCGAATACAGCAGAAACNNNGATCGACATG | 3060 | TGCAGGACCAGAGAATTCGAATACATGACCACANNNGATCGACATG | 3300 | TGCAGGACCAGAGAATTCGAATACACATAGTTANNNGATCGACATG | 3540 |
| TGCAGGACCAGAGAATTCGAATACATTTTTGCANNNGATCGACATG | 3061 | TGCAGGACCAGAGAATTCGAATACAGAACACANNNGATCGACATG | 3301 | TGCAGGACCAGAGAATTCGAATACATCATTACNNNGATCGACATG | 3541 |
| TGCAGGACCAGAGAATTCGAATACACTACCCGCNNNGATCGACATG | 3062 | TGCAGGACCAGAGAATTCGAATACATAGTAATCNNNGATCGACATG | 3302 | TGCAGGACCAGAGAATTCGAATACATGCTACCTNNNGATCGACATG | 3542 |
| TGCAGGACCAGAGAATTCGAATACAATAATGCTNNNGATCGACATG | 3063 | TGCAGGACCAGAGAATTCGAATACACCGACGGTNNNGATCGACATG | 3303 | TGCAGGACCAGAGAATTCGAATACAGTAGCTTGNNNGATCGACATG | 3543 |
| TGCAGGACCAGAGAATTCGAATACAAAGCAGTGNNNGATCGACATG | 3064 | TGCAGGACCAGAGAATTCGAATACATTGCCTTGNNNGATCGACATG | 3304 | TGCAGGACCAGAGAATTCGAATACACCGGATATNNNGATCGACATG | 3544 |
| TGCAGGACCAGAGAATTCGAATACAACACGTCANNNGATCGACATG | 3065 | TGCAGGACCAGAGAATTCGAATACAGAGCGGCANNNGATCGACATG | 3305 | TGCAGGACCAGAGAATTCGAATACACAGCCGCANNNGATCGACATG | 3545 |
| TGCAGGACCAGAGAATTCGAATACAGTAATACTNNNGATCGACATG | 3066 | TGCAGGACCAGAGAATTCGAATACAGGCCTGCANNNGATCGACATG | 3306 | TGCAGGACCAGAGAATTCGAATACAGATCCTCTNNNGATCGACATG | 3546 |
| TGCAGGACCAGAGAATTCGAATACAAACAAACANNNGATCGACATG | 3067 | TGCAGGACCAGAGAATTCGAATACATCCGTCAAGNNNGATCGACATG | 3307 | TGCAGGACCAGAGAATTCGAATACAAGTACCCANNNGATCGACATG | 3547 |
| TGCAGGACCAGAGAATTCGAATACATACATGGCNNNGATCGACATG | 3068 | TGCAGGACCAGAGAATTCGAATACAGGACGGCANNNGATCGACATG | 3308 | TGCAGGACCAGAGAATTCGAATACAACGGAGTANNNGATCGACATG | 3548 |
| TGCAGGACCAGAGAATTCGAATACACGTGTCAANNNTGCATCAGGT | 3069 | TGCAGGACCAGAGAATTCGAATACAGCATGCCGNNNTGCATCAGGT | 3309 | TGCAGGACCAGAGAATTCGAATACAGTAAAAGTNNNTGCATCAGGT | 3549 |
| TGCAGGACCAGAGAATTCGAATACACTTTAACTNNNTGCATCAGGT | 3070 | TGCAGGACCAGAGAATTCGAATACACGTCTAAGNNNTGCATCAGGT | 3310 | TGCAGGACCAGAGAATTCGAATACATAGGTGTCNNNTGCATCAGGT | 3550 |
| TGCAGGACCAGAGAATTCGAATACAGTAAGGTGNNNTGCATCAGGT | 3071 | TGCAGGACCAGAGAATTCGAATACAGCGTGATTNNNTGCATCAGGT | 3311 | TGCAGGACCAGAGAATTCGAATACATAGACCGTNNNTGCATCAGGT | 3551 |
| TGCAGGACCAGAGAATTCGAATACAGAATAGCGNNNTGCATCAGGT | 3072 | TGCAGGACCAGAGAATTCGAATACATTAGTCCCNNNTGCATCAGGT | 3312 | TGCAGGACCAGAGAATTCGAATACAGCTCGTTTNNNTGCATCAGGT | 3552 |
| TGCAGGACCAGAGAATTCGAATACATAATTAATNNNTGCATCAGGT | 3073 | TGCAGGACCAGAGAATTCGAATACATGGCATTGNNNTGCATCAGGT | 3313 | TGCAGGACCAGAGAATTCGAATACAAAATCTTGNNNTGCATCAGGT | 3553 |
| TGCAGGACCAGAGAATTCGAATACACTCTTGTGNNNTGCATCAGGT | 3074 | TGCAGGACCAGAGAATTCGAATACAGACGGTGGNNNTGCATCAGGT | 3314 | TGCAGGACCAGAGAATTCGAATACAGACCAAGGNNNTGCATCAGGT | 3554 |
| TGCAGGACCAGAGAATTCGAATACATGCGCGTGNNNTGCATCAGGT | 3075 | TGCAGGACCAGAGAATTCGAATACAGCGCTTTTNNNTGCATCAGGT | 3315 | TGCAGGACCAGAGAATTCGAATACATCACCTACNNNTGCATCAGGT | 3555 |
| TGCAGGACCAGAGAATTCGAATACAGACGAAACNNNTGCATCAGGT | 3076 | TGCAGGACCAGAGAATTCGAATACACGTGGACCNNNTGCATCAGGT | 3316 | TGCAGGACCAGAGAATTCGAATACAGTTAATTGNNNTGCATCAGGT | 3556 |
| TGCAGGACCAGAGAATTCGAATACACGTTTAGGNNNTGCATCAGGT | 3077 | TGCAGGACCAGAGAATTCGAATACAATGTCTTTNNNTGCATCAGGT | 3317 | TGCAGGACCAGAGAATTCGAATACAGCAATTATNNNTGCATCAGGT | 3557 |
| TGCAGGACCAGAGAATTCGAATACAGTAGCCTANNNTGCATCAGGT | 3078 | TGCAGGACCAGAGAATTCGAATACATGAAAGCGNNNTGCATCAGGT | 3318 | TGCAGGACCAGAGAATTCGAATACAAACGAGACNNNTGCATCAGGT | 3558 |
| TGCAGGACCAGAGAATTCGAATACAATTCCCTGNNNTGCATCAGGT | 3079 | TGCAGGACCAGAGAATTCGAATACACCGTGCGANNNTGCATCAGGT | 3319 | TGCAGGACCAGAGAATTCGAATACAATCGGCATNNNTGCATCAGGT | 3559 |
| TGCAGGACCAGAGAATTCGAATACAAACGAAATNNNTGCATCAGGT | 3080 | TGCAGGACCAGAGAATTCGAATACATACAACATNNNTGCATCAGGT | 3320 | TGCAGGACCAGAGAATTCGAATACACCACACGGNNNTGCATCAGGT | 3560 |
| TGCAGGACCAGAGAATTCGAATACAAACCCCCCNNNTGCATCAGGT | 3081 | TGCAGGACCAGAGAATTCGAATACAATTACTCTNNNTGCATCAGGT | 3321 | TGCAGGACCAGAGAATTCGAATACAGGCCAGGANNNTGCATCAGGT | 3561 |
| TGCAGGACCAGAGAATTCGAATACAATATGATANNNTGCATCAGGT | 3082 | TGCAGGACCAGAGAATTCGAATACATTCCCTANNNTGCATCAGGT | 3322 | TGCAGGACCAGAGAATTCGAATACAGAGGAGTTNNNTGCATCAGGT | 3562 |
| TGCAGGACCAGAGAATTCGAATACATACATGATNNNTGCATCAGGT | 3083 | TGCAGGACCAGAGAATTCGAATACACACACGGCNNNTGCATCAGGT | 3323 | TGCAGGACCAGAGAATTCGAATACACCACCGCTNNNTGCATCAGGT | 3563 |
| TGCAGGACCAGAGAATTCGAATACATGTACATANNNTGCATCAGGT | 3084 | TGCAGGACCAGAGAATTCGAATACATAGAATTCNNNTGCATCAGGT | 3324 | TGCAGGACCAGAGAATTCGAATACAACGATGAGNNNTGCATCAGGT | 3564 |
| TGCAGGACCAGAGAATTCGAATACATACGAAAANNNTGCATCAGGT | 3085 | TGCAGGACCAGAGAATTCGAATACAGTTGAAGGNNNTGCATCAGGT | 3325 | TGCAGGACCAGAGAATTCGAATACATTAGCATANNNTGCATCAGGT | 3565 |
| TGCAGGACCAGAGAATTCGAATACACATAACATNNNTGCATCAGGT | 3086 | TGCAGGACCAGAGAATTCGAATACACTTAACTTNNNTGCATCAGGT | 3326 | TGCAGGACCAGAGAATTCGAATACAAGTCCCAANNNTGCATCAGGT | 3566 |

FIG. 16G

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAG GAGAATCNNNTGCATCAGGT | 3087 | TGCAGGACCAGAGAATTCGAATACAA CTTACCCNNNTGCATCAGGT | 3327 | TGCAGGACCAGAGAATTCGAATACAA GCCTCTTNNNTGCATCAGGT | 3567 |
| TGCAGGACCAGAGAATTCGAATACAT CTTGTCGNNNTGCATCAGGT | 3088 | TGCAGGACCAGAGAATTCGAATACAG AGTTCGTNNNTGCATCAGGT | 3328 | TGCAGGACCAGAGAATTCGAATACAT CACCATCNNNTGCATCAGGT | 3568 |
| TGCAGGACCAGAGAATTCGAATACAT AAGCGCTNNNTGCATCAGGT | 3089 | TGCAGGACCAGAGAATTCGAATACAT TTCCAATNNNTGCATCAGGT | 3329 | TGCAGGACCAGAGAATTCGAATACAC TCATCACNNNTGCATCAGGT | 3569 |
| TGCAGGACCAGAGAATTCGAATACAT TCTAGAANNNTGCATCAGGT | 3090 | TGCAGGACCAGAGAATTCGAATACAA TAAGTTCNNNTGCATCAGGT | 3330 | TGCAGGACCAGAGAATTCGAATACAA CGGCGAGNNNTGCATCAGGT | 3570 |
| TGCAGGACCAGAGAATTCGAATACAT TGCTTGCNNNTGCATCAGGT | 3091 | TGCAGGACCAGAGAATTCGAATACAA ATGTACTNNNTGCATCAGGT | 3331 | TGCAGGACCAGAGAATTCGAATACAC TCGGACGNNNTGCATCAGGT | 3571 |
| TGCAGGACCAGAGAATTCGAATACAC AGCGTATNNNTGCATCAGGT | 3092 | TGCAGGACCAGAGAATTCGAATACAG TCCAAGTNNNTGCATCAGGT | 3332 | TGCAGGACCAGAGAATTCGAATACAT ACGGCATNNNTGCATCAGGT | 3572 |
| TGCAGGACCAGAGAATTCGAATACAA AGGAGCTNNNTGCATCAGGT | 3093 | TGCAGGACCAGAGAATTCGAATACAT CGACCAANNNTGCATCAGGT | 3333 | TGCAGGACCAGAGAATTCGAATACAT TTAGTAGNNNTGCATCAGGT | 3573 |
| TGCAGGACCAGAGAATTCGAATACAC ATGCCTTNNNTGCATCAGGT | 3094 | TGCAGGACCAGAGAATTCGAATACAC TCGATAGNNNTGCATCAGGT | 3334 | TGCAGGACCAGAGAATTCGAATACAA GGAAGAGNNNTGCATCAGGT | 3574 |
| TGCAGGACCAGAGAATTCGAATACAC GCGGTGTNNNTGCATCAGGT | 3095 | TGCAGGACCAGAGAATTCGAATACAA CTTCCCANNNTGCATCAGGT | 3335 | TGCAGGACCAGAGAATTCGAATACAC CGCGCAANNNTGCATCAGGT | 3575 |
| TGCAGGACCAGAGAATTCGAATACAC TGAAAGGNNNTGCATCAGGT | 3096 | TGCAGGACCAGAGAATTCGAATACAT TAGATTGNNNTGCATCAGGT | 3336 | TGCAGGACCAGAGAATTCGAATACAG TCGTGGCNNNTGCATCAGGT | 3576 |
| TGCAGGACCAGAGAATTCGAATACAA GTTACGCNNNTGCATCAGGT | 3097 | TGCAGGACCAGAGAATTCGAATACAC ATTGCGANNNTGCATCAGGT | 3337 | TGCAGGACCAGAGAATTCGAATACAA TACACTANNNTGCATCAGGT | 3577 |
| TGCAGGACCAGAGAATTCGAATACAG CTAAGCTNNNTGCATCAGGT | 3098 | TGCAGGACCAGAGAATTCGAATACAC AGCACATNNNTGCATCAGGT | 3338 | TGCAGGACCAGAGAATTCGAATACAC CACGCCTNNNTGCATCAGGT | 3578 |
| TGCAGGACCAGAGAATTCGAATACAT CGCAGTANNNTGCATCAGGT | 3099 | TGCAGGACCAGAGAATTCGAATACAC CCGGCAANNNTGCATCAGGT | 3339 | TGCAGGACCAGAGAATTCGAATACAT GAAGTGGNNNTGCATCAGGT | 3579 |
| TGCAGGACCAGAGAATTCGAATACAC AGATCGTNNNTGCATCAGGT | 3100 | TGCAGGACCAGAGAATTCGAATACAA CAGATGGNNNTGCATCAGGT | 3340 | TGCAGGACCAGAGAATTCGAATACAG AGTTGTCNNNTGCATCAGGT | 3580 |
| TGCAGGACCAGAGAATTCGAATACAC GAAAAATNNNTGCATCAGGT | 3101 | TGCAGGACCAGAGAATTCGAATACAT GCGTATGNNNTGCATCAGGT | 3341 | TGCAGGACCAGAGAATTCGAATACAC CCGGCTTNNNTGCATCAGGT | 3581 |
| TGCAGGACCAGAGAATTCGAATACAG CCAGACCNNNTGCATCAGGT | 3102 | TGCAGGACCAGAGAATTCGAATACAA CAGGAGTNNNTGCATCAGGT | 3342 | TGCAGGACCAGAGAATTCGAATACAC AGATAGGNNNTGCATCAGGT | 3582 |
| TGCAGGACCAGAGAATTCGAATACAG CTGCACGNNNTGCATCAGGT | 3103 | TGCAGGACCAGAGAATTCGAATACAC ATCCATCNNNTGCATCAGGT | 3343 | TGCAGGACCAGAGAATTCGAATACAA AGTCCGTNNNTGCATCAGGT | 3583 |
| TGCAGGACCAGAGAATTCGAATACAC TGGAACTNNNTGCATCAGGT | 3104 | TGCAGGACCAGAGAATTCGAATACAC TACGCCCNNNTGCATCAGGT | 3344 | TGCAGGACCAGAGAATTCGAATACAA ATCAGAANNNTGCATCAGGT | 3584 |
| TGCAGGACCAGAGAATTCGAATACAA TAGCAAANNNTGCATCAGGT | 3105 | TGCAGGACCAGAGAATTCGAATACAG ACCTACANNNTGCATCAGGT | 3345 | TGCAGGACCAGAGAATTCGAATACAC ACTCAGANNNTGCATCAGGT | 3585 |
| TGCAGGACCAGAGAATTCGAATACAG AGCTATCNNNTGCATCAGGT | 3106 | TGCAGGACCAGAGAATTCGAATACAT CCCACCGNNNTGCATCAGGT | 3346 | TGCAGGACCAGAGAATTCGAATACAT TATTCCANNNTGCATCAGGT | 3586 |
| TGCAGGACCAGAGAATTCGAATACAA GGTATCCNNNTGCATCAGGT | 3107 | TGCAGGACCAGAGAATTCGAATACAC BTTCGCTNNNTGCATCAGGT | 3347 | TGCAGGACCAGAGAATTCGAATACAA AGTAACANNNTGCATCAGGT | 3587 |
| TGCAGGACCAGAGAATTCGAATACAT TGGAGTCNNNTGCATCAGGT | 3108 | TGCAGGACCAGAGAATTCGAATACAG ATCTGGTNNNTGCATCAGGT | 3348 | TGCAGGACCAGAGAATTCGAATACAT TGTGCCTNNNTGCATCAGGT | 3588 |
| TGCAGGACCAGAGAATTCGAATACAC GGCTTCCNNNTGCATCAGGT | 3109 | TGCAGGACCAGAGAATTCGAATACAT ATCGTTTNNNTGCATCAGGT | 3349 | TGCAGGACCAGAGAATTCGAATACAA AGAGTCGNNNTGCATCAGGT | 3589 |
| TGCAGGACCAGAGAATTCGAATACAT CAGGTTGNNNTGCATCAGGT | 3110 | TGCAGGACCAGAGAATTCGAATACAG GATTCTGNNNTGCATCAGGT | 3350 | TGCAGGACCAGAGAATTCGAATACAA GCTGTTGNNNTGCATCAGGT | 3590 |
| TGCAGGACCAGAGAATTCGAATACAC GGCGCGCNNNTGCATCAGGT | 3111 | TGCAGGACCAGAGAATTCGAATACAC CCGCATCCNNNTGCATCAGGT | 3351 | TGCAGGACCAGAGAATTCGAATACAA TATTGACNNNTGCATCAGGT | 3591 |
| TGCAGGACCAGAGAATTCGAATACAA TGTGTCGNNNTGCATCAGGT | 3112 | TGCAGGACCAGAGAATTCGAATACAG ACTAAAANNNTGCATCAGGT | 3352 | TGCAGGACCAGAGAATTCGAATACAA AATATTTNNNTGCATCAGGT | 3592 |
| TGCAGGACCAGAGAATTCGAATACAC TTTGGAGNNNTGCATCAGGT | 3113 | TGCAGGACCAGAGAATTCGAATACAC TGGATGTNNNTGCATCAGGT | 3353 | TGCAGGACCAGAGAATTCGAATACAC TCAAGACNNNTGCATCAGGT | 3593 |
| TGCAGGACCAGAGAATTCGAATACAC GCCCACTNNNTGCATCAGGT | 3114 | TGCAGGACCAGAGAATTCGAATACAC CGTTTACNNNTGCATCAGGT | 3354 | TGCAGGACCAGAGAATTCGAATACAA GACGAACNNNTGCATCAGGT | 3594 |
| TGCAGGACCAGAGAATTCGAATACAA ACACTGCNNNTGCATCAGGT | 3115 | TGCAGGACCAGAGAATTCGAATACAA ATTATCGNNNTGCATCAGGT | 3355 | TGCAGGACCAGAGAATTCGAATACAA GGCAGGCNNNTGCATCAGGT | 3595 |
| TGCAGGACCAGAGAATTCGAATACAG CGCCGTANNNTGCATCAGGT | 3116 | TGCAGGACCAGAGAATTCGAATACAC ACTCGAANNNTGCATCAGGT | 3356 | TGCAGGACCAGAGAATTCGAATACAA CTTATAGNNNTGCATCAGGT | 3596 |
| TGCAGGACCAGAGAATTCGAATACAG TAGCATCNNNTGCATCAGGT | 3117 | TGCAGGACCAGAGAATTCGAATACAG AACGTTCNNNTGCATCAGGT | 3357 | TGCAGGACCAGAGAATTCGAATACAC TACTAAANNNTGCATCAGGT | 3597 |
| TGCAGGACCAGAGAATTCGAATACAT GCAGCATNNNTGCATCAGGT | 3118 | TGCAGGACCAGAGAATTCGAATACAA CCCGCAGNNNTGCATCAGGT | 3358 | TGCAGGACCAGAGAATTCGAATACAT TTAGAGTNNNTGCATCAGGT | 3598 |
| TGCAGGACCAGAGAATTCGAATACAT GCAGACTNNNTGCATCAGGT | 3119 | TGCAGGACCAGAGAATTCGAATACAG TCTCTGTNNNTGCATCAGGT | 3359 | TGCAGGACCAGAGAATTCGAATACAC TGCTTCANNNTGCATCAGGT | 3599 |

FIG. 16H

| Pool-13 | SEQ ID NO: | Pool-14 | SEQ ID NO: | Pool-15 | SEQ ID NO: |
|---|---|---|---|---|---|
| TGCAGGACCAGAGAATTCGAATACAA AGATGCGNNNTGCATCAGGT | 3120 | TGCAGGACCAGAGAATTCGAATACAA TTGATCANNNTGCATCAGGT | 3360 | TGCAGGACCAGAGAATTCGAATACAA GGTTCTGNNNTGCATCAGGT | 3600 |
| TGCAGGACCAGAGAATTCGAATACAA ACATATCNNNTGCATCAGGT | 3121 | TGCAGGACCAGAGAATTCGAATACAA AGTTTACNNNTGCATCAGGT | 3361 | TGCAGGACCAGAGAATTCGAATACAA GTAGGTGNNNTGCATCAGGT | 3601 |
| TGCAGGACCAGAGAATTCGAATACAT GGAACGANNNTGCATCAGGT | 3122 | TGCAGGACCAGAGAATTCGAATACAT GTTGTAANNNTGCATCAGGT | 3362 | TGCAGGACCAGAGAATTCGAATACAC CCGATAANNNTGCATCAGGT | 3602 |
| TGCAGGACCAGAGAATTCGAATACAT GCTCTTGNNNTGCATCAGGT | 3123 | TGCAGGACCAGAGAATTCGAATACAC TCTCAACNNNTGCATCAGGT | 3363 | TGCAGGACCAGAGAATTCGAATACAC AGAGTGANNNTGCATCAGGT | 3603 |
| TGCAGGACCAGAGAATTCGAATACAA CTCCTGTNNNTGCATCAGGT | 3124 | TGCAGGACCAGAGAATTCGAATACAA ACGGCCCNNNTGCATCAGGT | 3364 | TGCAGGACCAGAGAATTCGAATACAG TTCGCTTNNNTGCATCAGGT | 3604 |
| TGCAGGACCAGAGAATTCGAATACAA AACGTGGNNNTGCATCAGGT | 3125 | TGCAGGACCAGAGAATTCGAATACAA ATGGTAANNNTGCATCAGGT | 3365 | TGCAGGACCAGAGAATTCGAATACAG TTATCAANNNTGCATCAGGT | 3605 |
| TGCAGGACCAGAGAATTCGAATACAT GTCCCTANNNTGCATCAGGT | 3126 | TGCAGGACCAGAGAATTCGAATACAT ACAACCGNNNTGCATCAGGT | 3366 | TGCAGGACCAGAGAATTCGAATACAA GATGCTCNNNTGCATCAGGT | 3606 |
| TGCAGGACCAGAGAATTCGAATACAA ATCGCTGNNNTGCATCAGGT | 3127 | TGCAGGACCAGAGAATTCGAATACAA TACGGTCNNNTGCATCAGGT | 3367 | TGCAGGACCAGAGAATTCGAATACAA ACGTAAANNNTGCATCAGGT | 3607 |
| TGCAGGACCAGAGAATTCGAATACAG AAGCATGNNNTGCATCAGGT | 3128 | TGCAGGACCAGAGAATTCGAATACAT GCGCTGGNNNTGCATCAGGT | 3368 | TGCAGGACCAGAGAATTCGAATACAG CATTTCCNNNTGCATCAGGT | 3608 |

FIG. 17A

| Pool-16 | SEQ ID NO: | Pool-17 | SEQ ID NO: | Pool-18 | SEQ ID NO: |
|---|---|---|---|---|---|
| TGCAGGACCAGAGAATTCGAATACATGATTCAANNNACGTATGCCA | 3609 | TGCAGGACCAGAGAATTCGAATACAATTTCCCGNNNACGTATGCCA | 3849 | TGCAGGACCAGAGAATTCGAATACAACGGAGACANNNACGTATGCCA | 4089 |
| TGCAGGACCAGAGAATTCGAATACAACAAGTAANNNACGTATGCCA | 3610 | TGCAGGACCAGAGAATTCGAATACAATCCCAGANNNACGTATGCCA | 3850 | TGCAGGACCAGAGAATTCGAATACACGCTAATGNNNACGTATGCCA | 4090 |
| TGCAGGACCAGAGAATTCGAATACATTGACCGTNNNACGTATGCCA | 3611 | TGCAGGACCAGAGAATTCGAATACACGGAGACGNNNACGTATGCCA | 3851 | TGCAGGACCAGAGAATTCGAATACATACGTGANNNACGTATGCCA | 4091 |
| TGCAGGACCAGAGAATTCGAATACAATCTCGTCNNNACGTATGCCA | 3612 | TGCAGGACCAGAGAATTCGAATACACGATACGTNNNACGTATGCCA | 3852 | TGCAGGACCAGAGAATTCGAATACAATTCGTGGNNNACGTATGCCA | 4092 |
| TGCAGGACCAGAGAATTCGAATACAGGCAACAANNNACGTATGCCA | 3613 | TGCAGGACCAGAGAATTCGAATACATCCTGCTANNNACGTATGCCA | 3853 | TGCAGGACCAGAGAATTCGAATACAGTAGAGGTNNNACGTATGCCA | 4093 |
| TGCAGGACCAGAGAATTCGAATACAAGGGCGCCTNNNACGTATGCCA | 3614 | TGCAGGACCAGAGAATTCGAATACAAATTACACNNNACGTATGCCA | 3854 | TGCAGGACCAGAGAATTCGAATACAGGCGGTTCNNNACGTATGCCA | 4094 |
| TGCAGGACCAGAGAATTCGAATACATGCTTACCNNNACGTATGCCA | 3615 | TGCAGGACCAGAGAATTCGAATACATTTCCGACNNNACGTATGCCA | 3855 | TGCAGGACCAGAGAATTCGAATACAATAGGCTCNNNACGTATGCCA | 4095 |
| TGCAGGACCAGAGAATTCGAATACACGCACGACNNNACGTATGCCA | 3616 | TGCAGGACCAGAGAATTCGAATACACTCCCCCTNNNACGTATGCCA | 3856 | TGCAGGACCAGAGAATTCGAATACATCCAATTTNNNACGTATGCCA | 4096 |
| TGCAGGACCAGAGAATTCGAATACAGAGGCTTTNNNACGTATGCCA | 3617 | TGCAGGACCAGAGAATTCGAATACAACAATTCANNNACGTATGCCA | 3857 | TGCAGGACCAGAGAATTCGAATACACTGCCGAGNNNACGTATGCCA | 4097 |
| TGCAGGACCAGAGAATTCGAATACACATTCATTNNNACGTATGCCA | 3618 | TGCAGGACCAGAGAATTCGAATACAAGCAGCGGNNNACGTATGCCA | 3858 | TGCAGGACCAGAGAATTCGAATACACTGTAGTGNNNACGTATGCCA | 4098 |
| TGCAGGACCAGAGAATTCGAATACACAATCATANNNACGTATGCCA | 3619 | TGCAGGACCAGAGAATTCGAATACAATCCGATGNNNACGTATGCCA | 3859 | TGCAGGACCAGAGAATTCGAATACAAACGGTCTNNNACGTATGCCA | 4099 |
| TGCAGGACCAGAGAATTCGAATACACTACGATGNNNACGTATGCCA | 3620 | TGCAGGACCAGAGAATTCGAATACATACGCACANNNACGTATGCCA | 3860 | TGCAGGACCAGAGAATTCGAATACACAGGCGTCNNNACGTATGCCA | 4100 |
| TGCAGGACCAGAGAATTCGAATACAGAGGTACANNNACGTATGCCA | 3621 | TGCAGGACCAGAGAATTCGAATACACCACCATTNNNACGTATGCCA | 3861 | TGCAGGACCAGAGAATTCGAATACACTTGCCTANNNACGTATGCCA | 4101 |
| TGCAGGACCAGAGAATTCGAATACACTCGTCTANNNACGTATGCCA | 3622 | TGCAGGACCAGAGAATTCGAATACAAAAGGTCGNNNACGTATGCCA | 3862 | TGCAGGACCAGAGAATTCGAATACACTTCCGTANNNACGTATGCCA | 4102 |
| TGCAGGACCAGAGAATTCGAATACAAGAAGGAGNNNACGTATGCCA | 3623 | TGCAGGACCAGAGAATTCGAATACAGCAGTGTTNNNACGTATGCCA | 3863 | TGCAGGACCAGAGAATTCGAATACACAGACGTTNNNACGTATGCCA | 4103 |
| TGCAGGACCAGAGAATTCGAATACAGTGACATCNNNACGTATGCCA | 3624 | TGCAGGACCAGAGAATTCGAATACATCGAACTGNNNACGTATGCCA | 3864 | TGCAGGACCAGAGAATTCGAATACAAGGAACGTNNNACGTATGCCA | 4104 |
| TGCAGGACCAGAGAATTCGAATACAGCGGTGGANNNACGTATGCCA | 3625 | TGCAGGACCAGAGAATTCGAATACATTCGCTACNNNACGTATGCCA | 3865 | TGCAGGACCAGAGAATTCGAATACATTGCGTAGNNNACGTATGCCA | 4105 |
| TGCAGGACCAGAGAATTCGAATACACACAAATTNNNACGTATGCCA | 3626 | TGCAGGACCAGAGAATTCGAATACATATTCATCNNNACGTATGCCA | 3866 | TGCAGGACCAGAGAATTCGAATACAGCCCGATGNNNACGTATGCCA | 4106 |
| TGCAGGACCAGAGAATTCGAATACACCGTGCAGNNNACGTATGCCA | 3627 | TGCAGGACCAGAGAATTCGAATACAAACTACTNNNACGTATGCCA | 3867 | TGCAGGACCAGAGAATTCGAATACAAACGTCTGNNNACGTATGCCA | 4107 |
| TGCAGGACCAGAGAATTCGAATACAAAATTACCNNNACGTATGCCA | 3628 | TGCAGGACCAGAGAATTCGAATACAGCCCGTAGNNNACGTATGCCA | 3868 | TGCAGGACCAGAGAATTCGAATACACTCTACACNNNACGTATGCCA | 4108 |
| TGCAGGACCAGAGAATTCGAATACAGCAGACAANNNACGTATGCCA | 3629 | TGCAGGACCAGAGAATTCGAATACAAGTCGTTGNNNACGTATGCCA | 3869 | TGCAGGACCAGAGAATTCGAATACAACGCGGGTCNNNACGTATGCCA | 4109 |
| TGCAGGACCAGAGAATTCGAATACATTCTAAGANNNACGTATGCCA | 3630 | TGCAGGACCAGAGAATTCGAATACATGACAGCTNNNACGTATGCCA | 3870 | TGCAGGACCAGAGAATTCGAATACACATCCAGANNNACGTATGCCA | 4110 |
| TGCAGGACCAGAGAATTCGAATACACATTGAGCNNNACGTATGCCA | 3631 | TGCAGGACCAGAGAATTCGAATACATCAGCGATNNNACGTATGCCA | 3871 | TGCAGGACCAGAGAATTCGAATACAAAGTCGAGNNNACGTATGCCA | 4111 |
| TGCAGGACCAGAGAATTCGAATACAATGAGAGCNNNACGTATGCCA | 3632 | TGCAGGACCAGAGAATTCGAATACAGACTAAATNNNACGTATGCCA | 3872 | TGCAGGACCAGAGAATTCGAATACAGGCAGCCTNNNACGTATGCCA | 4112 |
| TGCAGGACCAGAGAATTCGAATACATTTCCCGANNNACGTATGCCA | 3633 | TGCAGGACCAGAGAATTCGAATACAGCTGCCTCNNNACGTATGCCA | 3873 | TGCAGGACCAGAGAATTCGAATACATTATACAGNNNACGTATGCCA | 4113 |
| TGCAGGACCAGAGAATTCGAATACATTGCGAACNNNACGTATGCCA | 3634 | TGCAGGACCAGAGAATTCGAATACACTTGACGANNNACGTATGCCA | 3874 | TGCAGGACCAGAGAATTCGAATACACCCGTCGTNNNACGTATGCCA | 4114 |
| TGCAGGACCAGAGAATTCGAATACATGGAGATGNNNACGTATGCCA | 3635 | TGCAGGACCAGAGAATTCGAATACACTCCTTTCNNNACGTATGCCA | 3875 | TGCAGGACCAGAGAATTCGAATACATAATTTAANNNACGTATGCCA | 4115 |
| TGCAGGACCAGAGAATTCGAATACACCAACCCCNNNACGTATGCCA | 3636 | TGCAGGACCAGAGAATTCGAATACAACACAAGGNNNACGTATGCCA | 3876 | TGCAGGACCAGAGAATTCGAATACATTCATCATNNNACGTATGCCA | 4116 |
| TGCAGGACCAGAGAATTCGAATACAGACAATGGNNNACGTATGCCA | 3637 | TGCAGGACCAGAGAATTCGAATACATCTCCAGTNNNACGTATGCCA | 3877 | TGCAGGACCAGAGAATTCGAATACACATGTATANNNACGTATGCCA | 4117 |
| TGCAGGACCAGAGAATTCGAATACACAGAGCCCNNNACGTATGCCA | 3638 | TGCAGGACCAGAGAATTCGAATACATATTGGTANNNACGTATGCCA | 3878 | TGCAGGACCAGAGAATTCGAATACAGTAGTTATNNNACGTATGCCA | 4118 |
| TGCAGGACCAGAGAATTCGAATACAAGAATACNNNACGTATGCCA | 3639 | TGCAGGACCAGAGAATTCGAATACAGCTTCATCNNNACGTATGCCA | 3879 | TGCAGGACCAGAGAATTCGAATACATGTATCCGNNNACGTATGCCA | 4119 |
| TGCAGGACCAGAGAATTCGAATACAAGGTAAATNNNACGTATGCCA | 3640 | TGCAGGACCAGAGAATTCGAATACATTCGTTTANNNACGTATGCCA | 3880 | TGCAGGACCAGAGAATTCGAATACAAGAGGTTGNNNACGTATGCCA | 4120 |

FIG. 17B

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAGCCCCAAGNNNACGTATGCCA | 3641 | TGCAGGACCAGAGAATTCGAATACATACGTGACNNNACGTATGCCA | 3881 | TGCAGGACCAGAGAATTCGAATACAGCACAAGANNNACGTATGCCA | 4121 |
| TGCAGGACCAGAGAATTCGAATACACTGCTTGTNNNACGTATGCCA | 3642 | TGCAGGACCAGAGAATTCGAATACATGTTGGTGNNNACGTATGCCA | 3882 | TGCAGGACCAGAGAATTCGAATACAAACCCGGCNNNACGTATGCCA | 4122 |
| TGCAGGACCAGAGAATTCGAATACAACACGGCCNNNACGTATGCCA | 3643 | TGCAGGACCAGAGAATTCGAATACACATCACAGNNNACGTATGCCA | 3883 | TGCAGGACCAGAGAATTCGAATACATGTGGCTANNNACGTATGCCA | 4123 |
| TGCAGGACCAGAGAATTCGAATACAACGACCTANNNACGTATGCCA | 3644 | TGCAGGACCAGAGAATTCGAATACAAACGGCGGNNNACGTATGCCA | 3884 | TGCAGGACCAGAGAATTCGAATACAGTAGCTCANNNACGTATGCCA | 4124 |
| TGCAGGACCAGAGAATTCGAATACAATTAGAAGNNNACGTATGCCA | 3645 | TGCAGGACCAGAGAATTCGAATACAAATGTGAANNNACGTATGCCA | 3885 | TGCAGGACCAGAGAATTCGAATACAGGCTGGCTNNNACGTATGCCA | 4125 |
| TGCAGGACCAGAGAATTCGAATACAGCCGTACGNNNACGTATGCCA | 3646 | TGCAGGACCAGAGAATTCGAATACAGTAGCCGCNNNACGTATGCCA | 3886 | TGCAGGACCAGAGAATTCGAATACATACAGCTGNNNACGTATGCCA | 4126 |
| TGCAGGACCAGAGAATTCGAATACACAGAAAGCNNNACGTATGCCA | 3647 | TGCAGGACCAGAGAATTCGAATACATGTGAATTNNNACGTATGCCA | 3887 | TGCAGGACCAGAGAATTCGAATACACTTGTGTCNNNACGTATGCCA | 4127 |
| TGCAGGACCAGAGAATTCGAATACACCACCTTANNNACGTATGCCA | 3648 | TGCAGGACCAGAGAATTCGAATACACGGTAAGANNNACGTATGCCA | 3888 | TGCAGGACCAGAGAATTCGAATACAAGCATCGTNNNACGTATGCCA | 4128 |
| TGCAGGACCAGAGAATTCGAATACAAAGGATTANNNACGTATGCCA | 3649 | TGCAGGACCAGAGAATTCGAATACATCTGGTGANNNACGTATGCCA | 3889 | TGCAGGACCAGAGAATTCGAATACAAATAAAGCNNNACGTATGCCA | 4129 |
| TGCAGGACCAGAGAATTCGAATACAAGCAAATANNNACGTATGCCA | 3650 | TGCAGGACCAGAGAATTCGAATACAGTCCGTTTNNNACGTATGCCA | 3890 | TGCAGGACCAGAGAATTCGAATACACTATCGGANNNACGTATGCCA | 4130 |
| TGCAGGACCAGAGAATTCGAATACACACTTCGTNNNACGTATGCCA | 3651 | TGCAGGACCAGAGAATTCGAATACACCGTCGAGNNNACGTATGCCA | 3891 | TGCAGGACCAGAGAATTCGAATACACCGCCCGCNNNACGTATGCCA | 4131 |
| TGCAGGACCAGAGAATTCGAATACAATTCGTCCNNNACGTATGCCA | 3652 | TGCAGGACCAGAGAATTCGAATACATCGATCCTNNNACGTATGCCA | 3892 | TGCAGGACCAGAGAATTCGAATACATCGTTTCGNNNACGTATGCCA | 4132 |
| TGCAGGACCAGAGAATTCGAATACATTCTTGGCNNNACGTATGCCA | 3653 | TGCAGGACCAGAGAATTCGAATACATTTGCGTCNNNACGTATGCCA | 3893 | TGCAGGACCAGAGAATTCGAATACACCTAGCAANNNACGTATGCCA | 4133 |
| TGCAGGACCAGAGAATTCGAATACATTGGCTCTNNNACGTATGCCA | 3654 | TGCAGGACCAGAGAATTCGAATACACTCGGCTCNNNACGTATGCCA | 3894 | TGCAGGACCAGAGAATTCGAATACATGAACATCNNNACGTATGCCA | 4134 |
| TGCAGGACCAGAGAATTCGAATACAGGAGACTANNNACGTATGCCA | 3655 | TGCAGGACCAGAGAATTCGAATACATCCACGCCNNNACGTATGCCA | 3895 | TGCAGGACCAGAGAATTCGAATACATGTAACATNNNACGTATGCCA | 4135 |
| TGCAGGACCAGAGAATTCGAATACAAATACTTGNNNACGTATGCCA | 3656 | TGCAGGACCAGAGAATTCGAATACAACGTGCCGNNNACGTATGCCA | 3896 | TGCAGGACCAGAGAATTCGAATACAGTCGGAAANNNACGTATGCCA | 4136 |
| TGCAGGACCAGAGAATTCGAATACAGCTGTTAGNNNACGTATGCCA | 3657 | TGCAGGACCAGAGAATTCGAATACATGTGGTACNNNACGTATGCCA | 3897 | TGCAGGACCAGAGAATTCGAATACAGTTGGCCGNNNACGTATGCCA | 4137 |
| TGCAGGACCAGAGAATTCGAATACAACAACCTGNNNACGTATGCCA | 3658 | TGCAGGACCAGAGAATTCGAATACAAGCCGAAANNNACGTATGCCA | 3898 | TGCAGGACCAGAGAATTCGAATACAGCGATAGANNNACGTATGCCA | 4138 |
| TGCAGGACCAGAGAATTCGAATACATCGTGCCCNNNACGTATGCCA | 3659 | TGCAGGACCAGAGAATTCGAATACACTCCTAACNNNACGTATGCCA | 3899 | TGCAGGACCAGAGAATTCGAATACATTAACGTANNNACGTATGCCA | 4139 |
| TGCAGGACCAGAGAATTCGAATACAGACTCTCTNNNACGTATGCCA | 3660 | TGCAGGACCAGAGAATTCGAATACAGAAGGCGCNNNACGTATGCCA | 3900 | TGCAGGACCAGAGAATTCGAATACACCTTATATNNNACGTATGCCA | 4140 |
| TGCAGGACCAGAGAATTCGAATACATATAACACNNNACGTATGCCA | 3661 | TGCAGGACCAGAGAATTCGAATACACGTTCACTNNNACGTATGCCA | 3901 | TGCAGGACCAGAGAATTCGAATACAAAACAGATNNNACGTATGCCA | 4141 |
| TGCAGGACCAGAGAATTCGAATACATGAGCCTANNNACGTATGCCA | 3662 | TGCAGGACCAGAGAATTCGAATACAAGATGTGNNNACGTATGCCA | 3902 | TGCAGGACCAGAGAATTCGAATACATACCCATCNNNACGTATGCCA | 4142 |
| TGCAGGACCAGAGAATTCGAATACACAGACGAANNNACGTATGCCA | 3663 | TGCAGGACCAGAGAATTCGAATACAGCTCACTTNNNACGTATGCCA | 3903 | TGCAGGACCAGAGAATTCGAATACAAAAAGAGANNNACGTATGCCA | 4143 |
| TGCAGGACCAGAGAATTCGAATACACGGAATGANNNACGTATGCCA | 3664 | TGCAGGACCAGAGAATTCGAATACACGAAGCTTNNNACGTATGCCA | 3904 | TGCAGGACCAGAGAATTCGAATACACGTTCGAANNNACGTATGCCA | 4144 |
| TGCAGGACCAGAGAATTCGAATACAGGTGATGANNNACGTATGCCA | 3665 | TGCAGGACCAGAGAATTCGAATACATACTCGAGNNNACGTATGCCA | 3905 | TGCAGGACCAGAGAATTCGAATACAATGGATCCNNNACGTATGCCA | 4145 |
| TGCAGGACCAGAGAATTCGAATACACACCTCTANNNACGTATGCCA | 3666 | TGCAGGACCAGAGAATTCGAATACATTCTTGTANNNACGTATGCCA | 3906 | TGCAGGACCAGAGAATTCGAATACAGCTCGATANNNACGTATGCCA | 4146 |
| TGCAGGACCAGAGAATTCGAATACAACTGGTACNNNACGTATGCCA | 3667 | TGCAGGACCAGAGAATTCGAATACAGAAGAAGGNNNACGTATGCCA | 3907 | TGCAGGACCAGAGAATTCGAATACATGTAACCGNNNACGTATGCCA | 4147 |
| TGCAGGACCAGAGAATTCGAATACAGCAAATCCNNNACGTATGCCA | 3668 | TGCAGGACCAGAGAATTCGAATACAAGCCACGCNNNACGTATGCCA | 3908 | TGCAGGACCAGAGAATTCGAATACAATCTACTTNNNACGTATGCCA | 4148 |
| TGCAGGACCAGAGAATTCGAATACAAATATAAANNNCTAGCGTTAC | 3669 | TGCAGGACCAGAGAATTCGAATACACTATACCGGNNNCTAGCGTTAC | 3909 | TGCAGGACCAGAGAATTCGAATACAGATCGTACNNNCTAGCGTTAC | 4149 |
| TGCAGGACCAGAGAATTCGAATACATGGTTATANNNCTAGCGTTAC | 3670 | TGCAGGACCAGAGAATTCGAATACAAGATCTTANNNCTAGCGTTAC | 3910 | TGCAGGACCAGAGAATTCGAATACATGAACGTCNNNCTAGCGTTAC | 4150 |
| TGCAGGACCAGAGAATTCGAATACACCCGCTCNNNCTAGCGTTAC | 3671 | TGCAGGACCAGAGAATTCGAATACAACAACCCANNNCTAGCGTTAC | 3911 | TGCAGGACCAGAGAATTCGAATACATCCAACTCNNNCTAGCGTTAC | 4151 |
| TGCAGGACCAGAGAATTCGAATACATGCGAAAGNNNCTAGCGTTAC | 3672 | TGCAGGACCAGAGAATTCGAATACATGCTAACGNNNCTAGCGTTAC | 3912 | TGCAGGACCAGAGAATTCGAATACAGCGGAGGTNNNCTAGCGTTAC | 4152 |
| TGCAGGACCAGAGAATTCGAATACACGTCTGCCNNNCTAGCGTTAC | 3673 | TGCAGGACCAGAGAATTCGAATACATGTAGTCGNNNCTAGCGTTAC | 3913 | TGCAGGACCAGAGAATTCGAATACATGCCCATTNNNCTAGCGTTAC | 4153 |

FIG. 17C

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAAGTTGTATNNNCTAGCGTTAC | 3674 | TGCAGGACCAGAGAATTCGAATACAATCGGTCGTNNNCTAGCGTTAC | 3914 | TGCAGGACCAGAGAATTCGAATACAACGATCACNNNCTAGCGTTAC | 4154 |
| TGCAGGACCAGAGAATTCGAATACAGGCTACTANNNCTAGCGTTAC | 3675 | TGCAGGACCAGAGAATTCGAATACAAGTAGGACNNNCTAGCGTTAC | 3915 | TGCAGGACCAGAGAATTCGAATACATAAGGTAANNNCTAGCGTTAC | 4155 |
| TGCAGGACCAGAGAATTCGAATACAACATCATANNNCTAGCGTTAC | 3676 | TGCAGGACCAGAGAATTCGAATACAAAAAAAANNNCTAGCGTTAC | 3916 | TGCAGGACCAGAGAATTCGAATACAACCTACGANNNCTAGCGTTAC | 4156 |
| TGCAGGACCAGAGAATTCGAATACAATTCCAGGNNNCTAGCGTTAC | 3677 | TGCAGGACCAGAGAATTCGAATACAAGTTCATANNNCTAGCGTTAC | 3917 | TGCAGGACCAGAGAATTCGAATACACACACCAANNNCTAGCGTTAC | 4157 |
| TGCAGGACCAGAGAATTCGAATACATTTTGTTGNNNCTAGCGTTAC | 3678 | TGCAGGACCAGAGAATTCGAATACAGAAGGTCANNNCTAGCGTTAC | 3918 | TGCAGGACCAGAGAATTCGAATACATGGTCGGCNNNCTAGCGTTAC | 4158 |
| TGCAGGACCAGAGAATTCGAATACAAGTGGCANNNCTAGCGTTAC | 3679 | TGCAGGACCAGAGAATTCGAATACATGAATGCCNNNCTAGCGTTAC | 3919 | TGCAGGACCAGAGAATTCGAATACATTATCTGTNNNCTAGCGTTAC | 4159 |
| TGCAGGACCAGAGAATTCGAATACAGAGAGGTTNNNCTAGCGTTAC | 3680 | TGCAGGACCAGAGAATTCGAATACAACACCCGGNNNCTAGCGTTAC | 3920 | TGCAGGACCAGAGAATTCGAATACATCGGACCGNNNCTAGCGTTAC | 4160 |
| TGCAGGACCAGAGAATTCGAATACACTTCCCGGNNNCTAGCGTTAC | 3681 | TGCAGGACCAGAGAATTCGAATACACTAACGCANNNCTAGCGTTAC | 3921 | TGCAGGACCAGAGAATTCGAATACATACCGATGNNNCTAGCGTTAC | 4161 |
| TGCAGGACCAGAGAATTCGAATACAACCTCCATNNNCTAGCGTTAC | 3682 | TGCAGGACCAGAGAATTCGAATACAACCCCTATNNNCTAGCGTTAC | 3922 | TGCAGGACCAGAGAATTCGAATACAGAACGGATNNNCTAGCGTTAC | 4162 |
| TGCAGGACCAGAGAATTCGAATACACAAGAGGTNNNCTAGCGTTAC | 3683 | TGCAGGACCAGAGAATTCGAATACAAGATAGATNNNCTAGCGTTAC | 3923 | TGCAGGACCAGAGAATTCGAATACATTGTTCTANNNCTAGCGTTAC | 4163 |
| TGCAGGACCAGAGAATTCGAATACAGAAAGTCGNNNCTAGCGTTAC | 3684 | TGCAGGACCAGAGAATTCGAATACAGGAGTGATNNNCTAGCGTTAC | 3924 | TGCAGGACCAGAGAATTCGAATACAGGTCGTCGNNNCTAGCGTTAC | 4164 |
| TGCAGGACCAGAGAATTCGAATACACGCGAAAANNNCTAGCGTTAC | 3685 | TGCAGGACCAGAGAATTCGAATACAATAGAGGCNNNCTAGCGTTAC | 3925 | TGCAGGACCAGAGAATTCGAATACAATGCTTCCNNNCTAGCGTTAC | 4165 |
| TGCAGGACCAGAGAATTCGAATACACCTGGCAGNNNCTAGCGTTAC | 3686 | TGCAGGACCAGAGAATTCGAATACACCCCGCGCNNNCTAGCGTTAC | 3926 | TGCAGGACCAGAGAATTCGAATACATCAGGACTNNNCTAGCGTTAC | 4166 |
| TGCAGGACCAGAGAATTCGAATACAAGCAGATGNNNCTAGCGTTAC | 3687 | TGCAGGACCAGAGAATTCGAATACACCATACTCNNNCTAGCGTTAC | 3927 | TGCAGGACCAGAGAATTCGAATACAAAGACATANNNCTAGCGTTAC | 4167 |
| TGCAGGACCAGAGAATTCGAATACAAGAGGCCGNNNCTAGCGTTAC | 3688 | TGCAGGACCAGAGAATTCGAATACATGATTCCCNNNCTAGCGTTAC | 3928 | TGCAGGACCAGAGAATTCGAATACACCATCGTTNNNCTAGCGTTAC | 4168 |
| TGCAGGACCAGAGAATTCGAATACACGTGCGTGNNNCTAGCGTTAC | 3689 | TGCAGGACCAGAGAATTCGAATACAAGAACGGTNNNCTAGCGTTAC | 3929 | TGCAGGACCAGAGAATTCGAATACATAACACCGNNNCTAGCGTTAC | 4169 |
| TGCAGGACCAGAGAATTCGAATACATGGTAGGANNNCTAGCGTTAC | 3690 | TGCAGGACCAGAGAATTCGAATACAGCTTCAAGNNNCTAGCGTTAC | 3930 | TGCAGGACCAGAGAATTCGAATACACCTCCTCCNNNCTAGCGTTAC | 4170 |
| TGCAGGACCAGAGAATTCGAATACACGCGCCAANNNCTAGCGTTAC | 3691 | TGCAGGACCAGAGAATTCGAATACAAAATATCCNNNCTAGCGTTAC | 3931 | TGCAGGACCAGAGAATTCGAATACATCGGACTANNNCTAGCGTTAC | 4171 |
| TGCAGGACCAGAGAATTCGAATACATGAGCACTNNNCTAGCGTTAC | 3692 | TGCAGGACCAGAGAATTCGAATACACGTCCCANNNCTAGCGTTAC | 3932 | TGCAGGACCAGAGAATTCGAATACAGGCAAACANNNCTAGCGTTAC | 4172 |
| TGCAGGACCAGAGAATTCGAATACATCATCGTCNNNCTAGCGTTAC | 3693 | TGCAGGACCAGAGAATTCGAATACAACTAATCANNNCTAGCGTTAC | 3933 | TGCAGGACCAGAGAATTCGAATACAGGAAACACNNNCTAGCGTTAC | 4173 |
| TGCAGGACCAGAGAATTCGAATACAAGCCAAGANNNCTAGCGTTAC | 3694 | TGCAGGACCAGAGAATTCGAATACATGACGCGGNNNCTAGCGTTAC | 3934 | TGCAGGACCAGAGAATTCGAATACATACACTCCNNNCTAGCGTTAC | 4174 |
| TGCAGGACCAGAGAATTCGAATACACGAGGACGNNNCTAGCGTTAC | 3695 | TGCAGGACCAGAGAATTCGAATACAGCCGTGCCANNNCTAGCGTTAC | 3935 | TGCAGGACCAGAGAATTCGAATACACGGACCTGNNNCTAGCGTTAC | 4175 |
| TGCAGGACCAGAGAATTCGAATACATGTGACTGNNNCTAGCGTTAC | 3696 | TGCAGGACCAGAGAATTCGAATACAAAATTGGANNNCTAGCGTTAC | 3936 | TGCAGGACCAGAGAATTCGAATACAATCCTGAGNNNCTAGCGTTAC | 4176 |
| TGCAGGACCAGAGAATTCGAATACAACCTTGAGNNNCTAGCGTTAC | 3697 | TGCAGGACCAGAGAATTCGAATACATGTTCACCNNNCTAGCGTTAC | 3937 | TGCAGGACCAGAGAATTCGAATACACCCGTCTGNNNCTAGCGTTAC | 4177 |
| TGCAGGACCAGAGAATTCGAATACAGTTAAGTTNNNCTAGCGTTAC | 3698 | TGCAGGACCAGAGAATTCGAATACAATCCGCAANNNCTAGCGTTAC | 3938 | TGCAGGACCAGAGAATTCGAATACAGGCTCAATNNNCTAGCGTTAC | 4178 |
| TGCAGGACCAGAGAATTCGAATACAACCCAGGCNNNCTAGCGTTAC | 3699 | TGCAGGACCAGAGAATTCGAATACATCAGATTANNNCTAGCGTTAC | 3939 | TGCAGGACCAGAGAATTCGAATACAGTGCTTGANNNCTAGCGTTAC | 4179 |
| TGCAGGACCAGAGAATTCGAATACACCGATGATNNNCTAGCGTTAC | 3700 | TGCAGGACCAGAGAATTCGAATACACGCTAAGTNNNCTAGCGTTAC | 3940 | TGCAGGACCAGAGAATTCGAATACAATTAACTGNNNCTAGCGTTAC | 4180 |
| TGCAGGACCAGAGAATTCGAATACAGATCTCGANNNCTAGCGTTAC | 3701 | TGCAGGACCAGAGAATTCGAATACACACACCTTNNNCTAGCGTTAC | 3941 | TGCAGGACCAGAGAATTCGAATACATCCAGATGNNNCTAGCGTTAC | 4181 |
| TGCAGGACCAGAGAATTCGAATACAGGAGATGTNNNCTAGCGTTAC | 3702 | TGCAGGACCAGAGAATTCGAATACAAGCCTGTNNNCTAGCGTTAC | 3942 | TGCAGGACCAGAGAATTCGAATACACCGCGCGGNNNCTAGCGTTAC | 4182 |
| TGCAGGACCAGAGAATTCGAATACATAGGTAAANNNCTAGCGTTAC | 3703 | TGCAGGACCAGAGAATTCGAATACAGGTCCAGCNNNCTAGCGTTAC | 3943 | TGCAGGACCAGAGAATTCGAATACACCATAGACNNNCTAGCGTTAC | 4183 |
| TGCAGGACCAGAGAATTCGAATACATCTCAGCANNNCTAGCGTTAC | 3704 | TGCAGGACCAGAGAATTCGAATACATGTCGCTTNNNCTAGCGTTAC | 3944 | TGCAGGACCAGAGAATTCGAATACAGGTTGGTTNNNCTAGCGTTAC | 4184 |
| TGCAGGACCAGAGAATTCGAATACAAGATAGGCNNNCTAGCGTTAC | 3705 | TGCAGGACCAGAGAATTCGAATACAGAAATTTCNNNCTAGCGTTAC | 3945 | TGCAGGACCAGAGAATTCGAATACAGGCAGATANNNCTAGCGTTAC | 4185 |
| TGCAGGACCAGAGAATTCGAATACACGAATTGCNNNCTAGCGTTAC | 3706 | TGCAGGACCAGAGAATTCGAATACATACGGTGTNNNCTAGCGTTAC | 3946 | TGCAGGACCAGAGAATTCGAATACAATGCAACCNNNCTAGCGTTAC | 4186 |

FIG. 17D

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAT ACCAGGTNNNCTAGCGTTAC | 3707 | TGCAGGACCAGAGAATTCGAATACAC CGACCAGNNNCTAGCGTTAC | 3947 | TGCAGGACCAGAGAATTCGAATACAG CGCGCCGNNNCTAGCGTTAC | 4187 |
| TGCAGGACCAGAGAATTCGAATACAT ATACTCTNNNCTAGCGTTAC | 3708 | TGCAGGACCAGAGAATTCGAATACAT GATAAAGNNNCTAGCGTTAC | 3948 | TGCAGGACCAGAGAATTCGAATACAC AAAGTGGNNNCTAGCGTTAC | 4188 |
| TGCAGGACCAGAGAATTCGAATACAA GCTTCTCNNNCTAGCGTTAC | 3709 | TGCAGGACCAGAGAATTCGAATACAT ATGGCTGNNNCTAGCGTTAC | 3949 | TGCAGGACCAGAGAATTCGAATACAT AAAAGCANNNCTAGCGTTAC | 4189 |
| TGCAGGACCAGAGAATTCGAATACAA CCTGAGTNNNCTAGCGTTAC | 3710 | TGCAGGACCAGAGAATTCGAATACAC CCCTCCTNNNCTAGCGTTAC | 3950 | TGCAGGACCAGAGAATTCGAATACAA TCTGTGGNNNCTAGCGTTAC | 4190 |
| TGCAGGACCAGAGAATTCGAATACAC ATAGATTNNNCTAGCGTTAC | 3711 | TGCAGGACCAGAGAATTCGAATACAT CTTACCGNNNCTAGCGTTAC | 3951 | TGCAGGACCAGAGAATTCGAATACAC GTATATANNNCTAGCGTTAC | 4191 |
| TGCAGGACCAGAGAATTCGAATACAA GCGGAATNNNCTAGCGTTAC | 3712 | TGCAGGACCAGAGAATTCGAATACAG CAATCGTNNNCTAGCGTTAC | 3952 | TGCAGGACCAGAGAATTCGAATACAG GTATTGCNNNCTAGCGTTAC | 4192 |
| TGCAGGACCAGAGAATTCGAATACAG GCATGCCNNNCTAGCGTTAC | 3713 | TGCAGGACCAGAGAATTCGAATACAC TAGCGCGNNNCTAGCGTTAC | 3953 | TGCAGGACCAGAGAATTCGAATACAT ACAAACTNNNCTAGCGTTAC | 4193 |
| TGCAGGACCAGAGAATTCGAATACAA ATATCCGNNNCTAGCGTTAC | 3714 | TGCAGGACCAGAGAATTCGAATACAT ACTCTGCNNNCTAGCGTTAC | 3954 | TGCAGGACCAGAGAATTCGAATACAC TCTTAATNNNCTAGCGTTAC | 4194 |
| TGCAGGACCAGAGAATTCGAATACAG CTCAGCGNNNCTAGCGTTAC | 3715 | TGCAGGACCAGAGAATTCGAATACAA TGGCAGANNNCTAGCGTTAC | 3955 | TGCAGGACCAGAGAATTCGAATACAG GTCTGATNNNCTAGCGTTAC | 4195 |
| TGCAGGACCAGAGAATTCGAATACAC TTCAAGGNNNCTAGCGTTAC | 3716 | TGCAGGACCAGAGAATTCGAATACAC GAGGTTTNNNCTAGCGTTAC | 3956 | TGCAGGACCAGAGAATTCGAATACAT CAGGAAGNNNCTAGCGTTAC | 4196 |
| TGCAGGACCAGAGAATTCGAATACAT CAGTAATNNNCTAGCGTTAC | 3717 | TGCAGGACCAGAGAATTCGAATACAC CAGCTAANNNCTAGCGTTAC | 3957 | TGCAGGACCAGAGAATTCGAATACAC ACGCTTTNNNCTAGCGTTAC | 4197 |
| TGCAGGACCAGAGAATTCGAATACAC CGGCCAANNNCTAGCGTTAC | 3718 | TGCAGGACCAGAGAATTCGAATACAT GTGCCGGNNNCTAGCGTTAC | 3958 | TGCAGGACCAGAGAATTCGAATACAG GCGGCAANNNCTAGCGTTAC | 4198 |
| TGCAGGACCAGAGAATTCGAATACAA TGATCATNNNCTAGCGTTAC | 3719 | TGCAGGACCAGAGAATTCGAATACAT GCCGTTTNNNCTAGCGTTAC | 3959 | TGCAGGACCAGAGAATTCGAATACAG AAGTTGGNNNCTAGCGTTAC | 4199 |
| TGCAGGACCAGAGAATTCGAATACAG GCGCCGTNNNCTAGCGTTAC | 3720 | TGCAGGACCAGAGAATTCGAATACAC TCCGTGCNNNCTAGCGTTAC | 3960 | TGCAGGACCAGAGAATTCGAATACAG CAGGTGGNNNCTAGCGTTAC | 4200 |
| TGCAGGACCAGAGAATTCGAATACAA GTCCGCGNNNCTAGCGTTAC | 3721 | TGCAGGACCAGAGAATTCGAATACAA CACAATCNNNCTAGCGTTAC | 3961 | TGCAGGACCAGAGAATTCGAATACAT GTAATCANNNCTAGCGTTAC | 4201 |
| TGCAGGACCAGAGAATTCGAATACAC ACTGGTANNNCTAGCGTTAC | 3722 | TGCAGGACCAGAGAATTCGAATACAC ATCGTGANNNCTAGCGTTAC | 3962 | TGCAGGACCAGAGAATTCGAATACAG TCAACCANNNCTAGCGTTAC | 4202 |
| TGCAGGACCAGAGAATTCGAATACAC TAAGACCNNNCTAGCGTTAC | 3723 | TGCAGGACCAGAGAATTCGAATACAC AAGGTTCNNNCTAGCGTTAC | 3963 | TGCAGGACCAGAGAATTCGAATACAG AGCAACANNNCTAGCGTTAC | 4203 |
| TGCAGGACCAGAGAATTCGAATACAA CGCTACANNNCTAGCGTTAC | 3724 | TGCAGGACCAGAGAATTCGAATACAG AAAGGTCNNNCTAGCGTTAC | 3964 | TGCAGGACCAGAGAATTCGAATACAA CCGTCGGNNNCTAGCGTTAC | 4204 |
| TGCAGGACCAGAGAATTCGAATACAA CCAAAAANNNCTAGCGTTAC | 3725 | TGCAGGACCAGAGAATTCGAATACAA GAAGGTCNNNCTAGCGTTAC | 3965 | TGCAGGACCAGAGAATTCGAATACAT AGGCGCCNNNCTAGCGTTAC | 4205 |
| TGCAGGACCAGAGAATTCGAATACAC GAGTGCCNNNCTAGCGTTAC | 3726 | TGCAGGACCAGAGAATTCGAATACAC CATGCTTNNNCTAGCGTTAC | 3966 | TGCAGGACCAGAGAATTCGAATACAG AAGCAGTNNNCTAGCGTTAC | 4206 |
| TGCAGGACCAGAGAATTCGAATACAA ACCGGAANNNCTAGCGTTAC | 3727 | TGCAGGACCAGAGAATTCGAATACAT TCAACTNNNCTAGCGTTAC | 3967 | TGCAGGACCAGAGAATTCGAATACAT TGGTATANNNCTAGCGTTAC | 4207 |
| TGCAGGACCAGAGAATTCGAATACAA AAAGCATNNNCTAGCGTTAC | 3728 | TGCAGGACCAGAGAATTCGAATACAT CTGGCAANNNCTAGCGTTAC | 3968 | TGCAGGACCAGAGAATTCGAATACAG AAGTGTGNNNCTAGCGTTAC | 4208 |
| TGCAGGACCAGAGAATTCGAATACAC CCCCGGCNNNGATCGACATG | 3729 | TGCAGGACCAGAGAATTCGAATACAG TTTACAANNNGATCGACATG | 3969 | TGCAGGACCAGAGAATTCGAATACAC TGCTTTGNNNGATCGACATG | 4209 |
| TGCAGGACCAGAGAATTCGAATACAT TGGTTGGNNNGATCGACATG | 3730 | TGCAGGACCAGAGAATTCGAATACAA CCCACAANNNGATCGACATG | 3970 | TGCAGGACCAGAGAATTCGAATACAG TTCCGCCNNNGATCGACATG | 4210 |
| TGCAGGACCAGAGAATTCGAATACAT CCACGTTNNNGATCGACATG | 3731 | TGCAGGACCAGAGAATTCGAATACAG GCTCATANNNGATCGACATG | 3971 | TGCAGGACCAGAGAATTCGAATACAC GACTATGNNNGATCGACATG | 4211 |
| TGCAGGACCAGAGAATTCGAATACAA TGAAGTANNNGATCGACATG | 3732 | TGCAGGACCAGAGAATTCGAATACAA GCATTGCNNNGATCGACATG | 3972 | TGCAGGACCAGAGAATTCGAATACAC TGTAGCANNNGATCGACATG | 4212 |
| TGCAGGACCAGAGAATTCGAATACAA CAATAAGNNNGATCGACATG | 3733 | TGCAGGACCAGAGAATTCGAATACAA ACCCGATNNNGATCGACATG | 3973 | TGCAGGACCAGAGAATTCGAATACAG GCGGTCANNNGATCGACATG | 4213 |
| TGCAGGACCAGAGAATTCGAATACAC ATGTTTTNNNGATCGACATG | 3734 | TGCAGGACCAGAGAATTCGAATACAT GACCAACNNNGATCGACATG | 3974 | TGCAGGACCAGAGAATTCGAATACAT CCATGAGNNNGATCGACATG | 4214 |
| TGCAGGACCAGAGAATTCGAATACAT CCGGTCCNNNGATCGACATG | 3735 | TGCAGGACCAGAGAATTCGAATACAG CCGAGGANNNGATCGACATG | 3975 | TGCAGGACCAGAGAATTCGAATACAG GCTCCCTNNNGATCGACATG | 4215 |
| TGCAGGACCAGAGAATTCGAATACAG TTACGTGNNNGATCGACATG | 3736 | TGCAGGACCAGAGAATTCGAATACAA ATATGGANNNGATCGACATG | 3976 | TGCAGGACCAGAGAATTCGAATACAA GCCTAACNNNGATCGACATG | 4216 |
| TGCAGGACCAGAGAATTCGAATACAG GTCCTGGNNNGATCGACATG | 3737 | TGCAGGACCAGAGAATTCGAATACAT TTCGGTCNNNGATCGACATG | 3977 | TGCAGGACCAGAGAATTCGAATACAC GAGGAATNNNGATCGACATG | 4217 |
| TGCAGGACCAGAGAATTCGAATACAC TGTACAGNNNGATCGACATG | 3738 | TGCAGGACCAGAGAATTCGAATACAT TAGGTTANNNGATCGACATG | 3978 | TGCAGGACCAGAGAATTCGAATACAC CCGAGCANNNGATCGACATG | 4218 |
| TGCAGGACCAGAGAATTCGAATACAC ATAAGTTNNNGATCGACATG | 3739 | TGCAGGACCAGAGAATTCGAATACAA ACGCGTTNNNGATCGACATG | 3979 | TGCAGGACCAGAGAATTCGAATACAT ACAATACNNNGATCGACATG | 4219 |

FIG. 17E

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAA AATCCTANNNGATCGACATG | 3740 | TGCAGGACCAGAGAATTCGAATACAA GGTAAGCNNNGATCGACATG | 3980 | TGCAGGACCAGAGAATTCGAATACAT AACATGTNNNGATCGACATG | 4220 |
| TGCAGGACCAGAGAATTCGAATACAC ATCATGGNNNGATCGACATG | 3741 | TGCAGGACCAGAGAATTCGAATACAA ATTGACTNNNGATCGACATG | 3981 | TGCAGGACCAGAGAATTCGAATACAG TTGCGGCNNNGATCGACATG | 4221 |
| TGCAGGACCAGAGAATTCGAATACAT TCACTGCNNNGATCGACATG | 3742 | TGCAGGACCAGAGAATTCGAATACAC ACTGTAANNNGATCGACATG | 3982 | TGCAGGACCAGAGAATTCGAATACAA TCTGCAGNNNGATCGACATG | 4222 |
| TGCAGGACCAGAGAATTCGAATACAT TGCCGCCNNNGATCGACATG | 3743 | TGCAGGACCAGAGAATTCGAATACAT TCTCTGGNNNGATCGACATG | 3983 | TGCAGGACCAGAGAATTCGAATACAG GTTAGTCNNNGATCGACATG | 4223 |
| TGCAGGACCAGAGAATTCGAATACAT GTCCTGTNNNGATCGACATG | 3744 | TGCAGGACCAGAGAATTCGAATACAA GAAGAAANNNGATCGACATG | 3984 | TGCAGGACCAGAGAATTCGAATACAC TTAAGATNNNGATCGACATG | 4224 |
| TGCAGGACCAGAGAATTCGAATACAG GCGGTCTNNNGATCGACATG | 3745 | TGCAGGACCAGAGAATTCGAATACAA AATGAACNNNGATCGACATG | 3985 | TGCAGGACCAGAGAATTCGAATACAC TCCTACANNNGATCGACATG | 4225 |
| TGCAGGACCAGAGAATTCGAATACAA CCCACGGNNNGATCGACATG | 3746 | TGCAGGACCAGAGAATTCGAATACAA ACACACCNNNGATCGACATG | 3986 | TGCAGGACCAGAGAATTCGAATACAG CTCAGTANNNGATCGACATG | 4226 |
| TGCAGGACCAGAGAATTCGAATACAT CCTTTAANNNGATCGACATG | 3747 | TGCAGGACCAGAGAATTCGAATACAT BAATGCTNNNGATCGACATG | 3987 | TGCAGGACCAGAGAATTCGAATACAG GTACTACNNNGATCGACATG | 4227 |
| TGCAGGACCAGAGAATTCGAATACAT TACAAGTNNNGATCGACATG | 3748 | TGCAGGACCAGAGAATTCGAATACAA CCGGTANNNGATCGACATG | 3988 | TGCAGGACCAGAGAATTCGAATACAT AGTATGTNNNGATCGACATG | 4228 |
| TGCAGGACCAGAGAATTCGAATACAT CGAGGAANNNGATCGACATG | 3749 | TGCAGGACCAGAGAATTCGAATACAC CGGCGTANNNGATCGACATG | 3989 | TGCAGGACCAGAGAATTCGAATACAA AGCATCCNNNGATCGACATG | 4229 |
| TGCAGGACCAGAGAATTCGAATACAG ACACTCANNNGATCGACATG | 3750 | TGCAGGACCAGAGAATTCGAATACAC GTAGACTNNNGATCGACATG | 3990 | TGCAGGACCAGAGAATTCGAATACAA CTAAAAGNNNGATCGACATG | 4230 |
| TGCAGGACCAGAGAATTCGAATACAA CTCTAGGNNNGATCGACATG | 3751 | TGCAGGACCAGAGAATTCGAATACAG GAAGTCANNNGATCGACATG | 3991 | TGCAGGACCAGAGAATTCGAATACAA CTTTAAGNNNGATCGACATG | 4231 |
| TGCAGGACCAGAGAATTCGAATACAA TCTTACTNNNGATCGACATG | 3752 | TGCAGGACCAGAGAATTCGAATACAA GAATTGANNNGATCGACATG | 3992 | TGCAGGACCAGAGAATTCGAATACAA CGAATAANNNGATCGACATG | 4232 |
| TGCAGGACCAGAGAATTCGAATACAA AAGAGAANNNGATCGACATG | 3753 | TGCAGGACCAGAGAATTCGAATACAA CCCCTTANNNGATCGACATG | 3993 | TGCAGGACCAGAGAATTCGAATACAT AGCGTCANNNGATCGACATG | 4233 |
| TGCAGGACCAGAGAATTCGAATACAA CAGCAGANNNGATCGACATG | 3754 | TGCAGGACCAGAGAATTCGAATACAT ACAGACCNNNGATCGACATG | 3994 | TGCAGGACCAGAGAATTCGAATACAA TCATCCCNNNGATCGACATG | 4234 |
| TGCAGGACCAGAGAATTCGAATACAT GAGTACCNNNGATCGACATG | 3755 | TGCAGGACCAGAGAATTCGAATACAA TTAGACTNNNGATCGACATG | 3995 | TGCAGGACCAGAGAATTCGAATACAA AAACAACNNNGATCGACATG | 4235 |
| TGCAGGACCAGAGAATTCGAATACAG ACTGTCANNNGATCGACATG | 3756 | TGCAGGACCAGAGAATTCGAATACAC ACTAGACNNNGATCGACATG | 3996 | TGCAGGACCAGAGAATTCGAATACAC TATCAGGNNNGATCGACATG | 4236 |
| TGCAGGACCAGAGAATTCGAATACAT CGAGGCCNNNGATCGACATG | 3757 | TGCAGGACCAGAGAATTCGAATACAG CCCTAAANNNGATCGACATG | 3997 | TGCAGGACCAGAGAATTCGAATACAT ACTGTCCNNNGATCGACATG | 4237 |
| TGCAGGACCAGAGAATTCGAATACAG TCCATAGNNNGATCGACATG | 3758 | TGCAGGACCAGAGAATTCGAATACAA GAGTGGTNNNGATCGACATG | 3998 | TGCAGGACCAGAGAATTCGAATACAA GGACACANNNGATCGACATG | 4238 |
| TGCAGGACCAGAGAATTCGAATACAG ACTGTTGNNNGATCGACATG | 3759 | TGCAGGACCAGAGAATTCGAATACAA TCTGAATNNNGATCGACATG | 3999 | TGCAGGACCAGAGAATTCGAATACAG TGACGTTNNNGATCGACATG | 4239 |
| TGCAGGACCAGAGAATTCGAATACAA CACACTGNNNGATCGACATG | 3760 | TGCAGGACCAGAGAATTCGAATACAA GCATCACNNNGATCGACATG | 4000 | TGCAGGACCAGAGAATTCGAATACAC TTGTACCNNNGATCGACATG | 4240 |
| TGCAGGACCAGAGAATTCGAATACAA GGTGACANNNGATCGACATG | 3761 | TGCAGGACCAGAGAATTCGAATACAA ATTGGAANNNGATCGACATG | 4001 | TGCAGGACCAGAGAATTCGAATACAG GATGCGGNNNGATCGACATG | 4241 |
| TGCAGGACCAGAGAATTCGAATACAA AACAATGNNNGATCGACATG | 3762 | TGCAGGACCAGAGAATTCGAATACAC TAGCCCCNNNGATCGACATG | 4002 | TGCAGGACCAGAGAATTCGAATACAC TGATTGGNNNGATCGACATG | 4242 |
| TGCAGGACCAGAGAATTCGAATACAG ATTTGTANNNGATCGACATG | 3763 | TGCAGGACCAGAGAATTCGAATACAT CTTGCTGNNNGATCGACATG | 4003 | TGCAGGACCAGAGAATTCGAATACAG CAACTCANNNGATCGACATG | 4243 |
| TGCAGGACCAGAGAATTCGAATACAC CCCCGATNNNGATCGACATG | 3764 | TGCAGGACCAGAGAATTCGAATACAC CGTCCTGNNNGATCGACATG | 4004 | TGCAGGACCAGAGAATTCGAATACAT ACCTCACNNNGATCGACATG | 4244 |
| TGCAGGACCAGAGAATTCGAATACAA GGAGCGCNNNGATCGACATG | 3765 | TGCAGGACCAGAGAATTCGAATACAC CTAACGANNNGATCGACATG | 4005 | TGCAGGACCAGAGAATTCGAATACAT GCACCCCNNNGATCGACATG | 4245 |
| TGCAGGACCAGAGAATTCGAATACAC CCTGGAGNNNGATCGACATG | 3766 | TGCAGGACCAGAGAATTCGAATACAA AAATAGCNNNGATCGACATG | 4006 | TGCAGGACCAGAGAATTCGAATACAG TTCCTACNNNGATCGACATG | 4246 |
| TGCAGGACCAGAGAATTCGAATACAC GCACTCCNNNGATCGACATG | 3767 | TGCAGGACCAGAGAATTCGAATACAA AGCACTCNNNGATCGACATG | 4007 | TGCAGGACCAGAGAATTCGAATACAT ACTGTTTNNNGATCGACATG | 4247 |
| TGCAGGACCAGAGAATTCGAATACAG AAGTCAGNNNGATCGACATG | 3768 | TGCAGGACCAGAGAATTCGAATACAG TTCAACGNNNGATCGACATG | 4008 | TGCAGGACCAGAGAATTCGAATACAC TTCATATNNNGATCGACATG | 4248 |
| TGCAGGACCAGAGAATTCGAATACAG GCGTCGTNNNGATCGACATG | 3769 | TGCAGGACCAGAGAATTCGAATACAC GTCTGTTNNNGATCGACATG | 4009 | TGCAGGACCAGAGAATTCGAATACAT CTGCTGTNNNGATCGACATG | 4249 |
| TGCAGGACCAGAGAATTCGAATACAC ATTGTCCNNNGATCGACATG | 3770 | TGCAGGACCAGAGAATTCGAATACAG CACGGCTNNNGATCGACATG | 4010 | TGCAGGACCAGAGAATTCGAATACAT GGTATTANNNGATCGACATG | 4250 |
| TGCAGGACCAGAGAATTCGAATACAT AGTAACTNNNGATCGACATG | 3771 | TGCAGGACCAGAGAATTCGAATACAA CCCAAACNNNGATCGACATG | 4011 | TGCAGGACCAGAGAATTCGAATACAA GAATGTANNNGATCGACATG | 4251 |
| TGCAGGACCAGAGAATTCGAATACAT AGATGTTNNNGATCGACATG | 3772 | TGCAGGACCAGAGAATTCGAATACAC ATAAACTNNNGATCGACATG | 4012 | TGCAGGACCAGAGAATTCGAATACAG GCGAGCANNNGATCGACATG | 4252 |

FIG. 17F

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAAATGAGCGNNNGATCGACATG | 3773 | TGCAGGACCAGAGAATTCGAATACATCCGTAAGCNNNGATCGACATG | 4013 | TGCAGGACCAGAGAATTCGAATACAGCCACAATNNNGATCGACATG | 4253 |
| TGCAGGACCAGAGAATTCGAATACAACTTGCGANNNGATCGACATG | 3774 | TGCAGGACCAGAGAATTCGAATACAGAGCTTGTNNNGATCGACATG | 4014 | TGCAGGACCAGAGAATTCGAATACATATTCTCANNNGATCGACATG | 4254 |
| TGCAGGACCAGAGAATTCGAATACAGGCGTACCNNNGATCGACATG | 3775 | TGCAGGACCAGAGAATTCGAATACAGTTTTGTTNNNGATCGACATG | 4015 | TGCAGGACCAGAGAATTCGAATACAAAGACCTCNNNGATCGACATG | 4255 |
| TGCAGGACCAGAGAATTCGAATACAGGTCACATNNNGATCGACATG | 3776 | TGCAGGACCAGAGAATTCGAATACATGAGTAGGNNNGATCGACATG | 4016 | TGCAGGACCAGAGAATTCGAATACACACATAATNNNGATCGACATG | 4256 |
| TGCAGGACCAGAGAATTCGAATACACACTTAAANNNGATCGACATG | 3777 | TGCAGGACCAGAGAATTCGAATACATGAGTCTGNNNGATCGACATG | 4017 | TGCAGGACCAGAGAATTCGAATACAACCCTGAANNNGATCGACATG | 4257 |
| TGCAGGACCAGAGAATTCGAATACATTTACCTANNNGATCGACATG | 3778 | TGCAGGACCAGAGAATTCGAATACAAGAAGCTGNNNGATCGACATG | 4018 | TGCAGGACCAGAGAATTCGAATACAGTAGACCTNNNGATCGACATG | 4258 |
| TGCAGGACCAGAGAATTCGAATACAAGTTTGGCNNNGATCGACATG | 3779 | TGCAGGACCAGAGAATTCGAATACATAGAAGCGNNNGATCGACATG | 4019 | TGCAGGACCAGAGAATTCGAATACACCCTACCGNNNGATCGACATG | 4259 |
| TGCAGGACCAGAGAATTCGAATACAGAGACATGNNNGATCGACATG | 3780 | TGCAGGACCAGAGAATTCGAATACATCTTATGGNNNGATCGACATG | 4020 | TGCAGGACCAGAGAATTCGAATACATATCCCACNNNGATCGACATG | 4260 |
| TGCAGGACCAGAGAATTCGAATACAGAGGCATANNNGATCGACATG | 3781 | TGCAGGACCAGAGAATTCGAATACAGGCATATCNNNGATCGACATG | 4021 | TGCAGGACCAGAGAATTCGAATACAAGTCATTANNNGATCGACATG | 4261 |
| TGCAGGACCAGAGAATTCGAATACACCTGCTCGNNNGATCGACATG | 3782 | TGCAGGACCAGAGAATTCGAATACATCCGCTTANNNGATCGACATG | 4022 | TGCAGGACCAGAGAATTCGAATACAGGAACAACNNNGATCGACATG | 4262 |
| TGCAGGACCAGAGAATTCGAATACATTGCTAGGNNNGATCGACATG | 3783 | TGCAGGACCAGAGAATTCGAATACATTTATAGGNNNGATCGACATG | 4023 | TGCAGGACCAGAGAATTCGAATACAATCTCTGCNNNGATCGACATG | 4263 |
| TGCAGGACCAGAGAATTCGAATACATCCCGACNNNGATCGACATG | 3784 | TGCAGGACCAGAGAATTCGAATACAATGCTTAANNNGATCGACATG | 4024 | TGCAGGACCAGAGAATTCGAATACACTGTACCTNNNGATCGACATG | 4264 |
| TGCAGGACCAGAGAATTCGAATACACACGAATCNNNGATCGACATG | 3785 | TGCAGGACCAGAGAATTCGAATACATGACGTACNNNGATCGACATG | 4025 | TGCAGGACCAGAGAATTCGAATACAGATCCAGTNNNGATCGACATG | 4265 |
| TGCAGGACCAGAGAATTCGAATACAGCGTCGCANNNGATCGACATG | 3786 | TGCAGGACCAGAGAATTCGAATACAAGAGAAAANNNGATCGACATG | 4026 | TGCAGGACCAGAGAATTCGAATACATAAGTTCANNNGATCGACATG | 4266 |
| TGCAGGACCAGAGAATTCGAATACAAATCCAATNNNGATCGACATG | 3787 | TGCAGGACCAGAGAATTCGAATACATGTCTCGTNNNGATCGACATG | 4027 | TGCAGGACCAGAGAATTCGAATACACCGTTAGANNNGATCGACATG | 4267 |
| TGCAGGACCAGAGAATTCGAATACACGCGAACCNNNGATCGACATG | 3788 | TGCAGGACCAGAGAATTCGAATACACGTTATGGNNNGATCGACATG | 4028 | TGCAGGACCAGAGAATTCGAATACAAAGAGACCNNNGATCGACATG | 4268 |
| TGCAGGACCAGAGAATTCGAATACATATGATCANNNTGCATCAGGT | 3789 | TGCAGGACCAGAGAATTCGAATACATATTGAGTNNNTGCATCAGGT | 4029 | TGCAGGACCAGAGAATTCGAATACACGCCCTACNNNTGCATCAGGT | 4269 |
| TGCAGGACCAGAGAATTCGAATACATTGGCACANNNTGCATCAGGT | 3790 | TGCAGGACCAGAGAATTCGAATACAAATAGAGTNNNTGCATCAGGT | 4030 | TGCAGGACCAGAGAATTCGAATACAGACGGCCTNNNTGCATCAGGT | 4270 |
| TGCAGGACCAGAGAATTCGAATACACTACACCTNNNTGCATCAGGT | 3791 | TGCAGGACCAGAGAATTCGAATACACAGACATCNNNTGCATCAGGT | 4031 | TGCAGGACCAGAGAATTCGAATACACGCGGGAGNNNTGCATCAGGT | 4271 |
| TGCAGGACCAGAGAATTCGAATACATTAGAGTTNNNTGCATCAGGT | 3792 | TGCAGGACCAGAGAATTCGAATACAGAAGCCAANNNTGCATCAGGT | 4032 | TGCAGGACCAGAGAATTCGAATACAGCGATAAGNNNTGCATCAGGT | 4272 |
| TGCAGGACCAGAGAATTCGAATACAGGTGTTGTNNNTGCATCAGGT | 3793 | TGCAGGACCAGAGAATTCGAATACACAGTCCANNNTGCATCAGGT | 4033 | TGCAGGACCAGAGAATTCGAATACAACGCTAGTNNNTGCATCAGGT | 4273 |
| TGCAGGACCAGAGAATTCGAATACACCAGACGCNNNTGCATCAGGT | 3794 | TGCAGGACCAGAGAATTCGAATACATTCCGACTNNNTGCATCAGGT | 4034 | TGCAGGACCAGAGAATTCGAATACATTTGAATGNNNTGCATCAGGT | 4274 |
| TGCAGGACCAGAGAATTCGAATACATGTTGGCANNNTGCATCAGGT | 3795 | TGCAGGACCAGAGAATTCGAATACAACAGTATTNNNTGCATCAGGT | 4035 | TGCAGGACCAGAGAATTCGAATACATATTAAATNNNTGCATCAGGT | 4275 |
| TGCAGGACCAGAGAATTCGAATACATCTTCCTCNNNTGCATCAGGT | 3796 | TGCAGGACCAGAGAATTCGAATACAGAGAATATNNNTGCATCAGGT | 4036 | TGCAGGACCAGAGAATTCGAATACACGTGTTGANNNTGCATCAGGT | 4276 |
| TGCAGGACCAGAGAATTCGAATACACAAGATAANNNTGCATCAGGT | 3797 | TGCAGGACCAGAGAATTCGAATACAAGTAAGGCNNNTGCATCAGGT | 4037 | TGCAGGACCAGAGAATTCGAATACAAAGCTTATNNNTGCATCAGGT | 4277 |
| TGCAGGACCAGAGAATTCGAATACATACTAGCGNNNTGCATCAGGT | 3798 | TGCAGGACCAGAGAATTCGAATACAAGCGTATCNNNTGCATCAGGT | 4038 | TGCAGGACCAGAGAATTCGAATACACCCCGACTNNNTGCATCAGGT | 4278 |
| TGCAGGACCAGAGAATTCGAATACAGACACAAGNNNTGCATCAGGT | 3799 | TGCAGGACCAGAGAATTCGAATACATACGGTTGNNNTGCATCAGGT | 4039 | TGCAGGACCAGAGAATTCGAATACAGTCGTCAANNNTGCATCAGGT | 4279 |
| TGCAGGACCAGAGAATTCGAATACAGTTACCTCNNNTGCATCAGGT | 3800 | TGCAGGACCAGAGAATTCGAATACAAACGAAGGNNNTGCATCAGGT | 4040 | TGCAGGACCAGAGAATTCGAATACATACATCGGNNNTGCATCAGGT | 4280 |
| TGCAGGACCAGAGAATTCGAATACATCTACCACNNNTGCATCAGGT | 3801 | TGCAGGACCAGAGAATTCGAATACACATTCGGACNNNTGCATCAGGT | 4041 | TGCAGGACCAGAGAATTCGAATACAGACTTTCCNNNTGCATCAGGT | 4281 |
| TGCAGGACCAGAGAATTCGAATACATAGTCGTGNNNTGCATCAGGT | 3802 | TGCAGGACCAGAGAATTCGAATACATAAGGCTCNNNTGCATCAGGT | 4042 | TGCAGGACCAGAGAATTCGAATACATGCCCTATNNNTGCATCAGGT | 4282 |
| TGCAGGACCAGAGAATTCGAATACAAATGCAGGNNNTGCATCAGGT | 3803 | TGCAGGACCAGAGAATTCGAATACACGAAGCGGNNNTGCATCAGGT | 4043 | TGCAGGACCAGAGAATTCGAATACATGACGGAANNNTGCATCAGGT | 4283 |
| TGCAGGACCAGAGAATTCGAATACACATGGACTNNNTGCATCAGGT | 3804 | TGCAGGACCAGAGAATTCGAATACAGACGATTCNNNTGCATCAGGT | 4044 | TGCAGGACCAGAGAATTCGAATACAGCTGCCAGNNNTGCATCAGGT | 4284 |
| TGCAGGACCAGAGAATTCGAATACATTGCGAGTNNNTGCATCAGGT | 3805 | TGCAGGACCAGAGAATTCGAATACAGTCGATACNNNTGCATCAGGT | 4045 | TGCAGGACCAGAGAATTCGAATACATCATATAGNNNTGCATCAGGT | 4285 |

FIG. 17G

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAT TGCAAGCNNNTGCATCAGGT | 3806 | TGCAGGACCAGAGAATTCGAATACAC ATCAATANNNTGCATCAGGT | 4046 | TGCAGGACCAGAGAATTCGAATACAT GTGCGATNNNTGCATCAGGT | 4286 |
| TGCAGGACCAGAGAATTCGAATACAC CTCGGAGNNNTGCATCAGGT | 3807 | TGCAGGACCAGAGAATTCGAATACAC ACACATGNNNTGCATCAGGT | 4047 | TGCAGGACCAGAGAATTCGAATACAC ACGATCANNNTGCATCAGGT | 4287 |
| TGCAGGACCAGAGAATTCGAATACAT AACATTGNNNTGCATCAGGT | 3808 | TGCAGGACCAGAGAATTCGAATACAG CAGCGAGNNNTGCATCAGGT | 4048 | TGCAGGACCAGAGAATTCGAATACAG ACTGCCGNNNTGCATCAGGT | 4288 |
| TGCAGGACCAGAGAATTCGAATACAG AGGTTAGNNNTGCATCAGGT | 3809 | TGCAGGACCAGAGAATTCGAATACAT ACGGCTANNNTGCATCAGGT | 4049 | TGCAGGACCAGAGAATTCGAATACAG TGGTCATNNNTGCATCAGGT | 4289 |
| TGCAGGACCAGAGAATTCGAATACAA GAAACTANNNTGCATCAGGT | 3810 | TGCAGGACCAGAGAATTCGAATACAC AGCAGAANNNTGCATCAGGT | 4050 | TGCAGGACCAGAGAATTCGAATACAT GTGAGCTNNNTGCATCAGGT | 4290 |
| TGCAGGACCAGAGAATTCGAATACAT CCACCTANNNTGCATCAGGT | 3811 | TGCAGGACCAGAGAATTCGAATACAA AGATTAGNNNTGCATCAGGT | 4051 | TGCAGGACCAGAGAATTCGAATACAA ACCGTCANNNTGCATCAGGT | 4291 |
| TGCAGGACCAGAGAATTCGAATACAT CCTTCCTNNNTGCATCAGGT | 3812 | TGCAGGACCAGAGAATTCGAATACAG CAAAGACNNNTGCATCAGGT | 4052 | TGCAGGACCAGAGAATTCGAATACAA TTACAGTNNNTGCATCAGGT | 4292 |
| TGCAGGACCAGAGAATTCGAATACAA ACTCCGANNNTGCATCAGGT | 3813 | TGCAGGACCAGAGAATTCGAATACAA TAAACAGNNNTGCATCAGGT | 4053 | TGCAGGACCAGAGAATTCGAATACAG CAATAAANNNTGCATCAGGT | 4293 |
| TGCAGGACCAGAGAATTCGAATACAA ATTAGCTNNNTGCATCAGGT | 3814 | TGCAGGACCAGAGAATTCGAATACAT TCCAAAANNNTGCATCAGGT | 4054 | TGCAGGACCAGAGAATTCGAATACAA GCTTAGCNNNTGCATCAGGT | 4294 |
| TGCAGGACCAGAGAATTCGAATACAA TAGTAAGNNNTGCATCAGGT | 3815 | TGCAGGACCAGAGAATTCGAATACAT GGTATCGNNNTGCATCAGGT | 4055 | TGCAGGACCAGAGAATTCGAATACAT CATTGCCNNNTGCATCAGGT | 4295 |
| TGCAGGACCAGAGAATTCGAATACAG TTTTACTNNNTGCATCAGGT | 3816 | TGCAGGACCAGAGAATTCGAATACAA ACACTTANNNTGCATCAGGT | 4056 | TGCAGGACCAGAGAATTCGAATACAC ACTATAANNNTGCATCAGGT | 4296 |
| TGCAGGACCAGAGAATTCGAATACAC GCAATTGNNNTGCATCAGGT | 3817 | TGCAGGACCAGAGAATTCGAATACAA CCGTGGCNNNTGCATCAGGT | 4057 | TGCAGGACCAGAGAATTCGAATACAC TGCGTCCNNNTGCATCAGGT | 4297 |
| TGCAGGACCAGAGAATTCGAATACAC GAGGCGTNNNTGCATCAGGT | 3818 | TGCAGGACCAGAGAATTCGAATACAA GTCTAGCNNNTGCATCAGGT | 4058 | TGCAGGACCAGAGAATTCGAATACAC GATGACANNNTGCATCAGGT | 4298 |
| TGCAGGACCAGAGAATTCGAATACAG TAACTGCNNNTGCATCAGGT | 3819 | TGCAGGACCAGAGAATTCGAATACAA GACTCCANNNTGCATCAGGT | 4059 | TGCAGGACCAGAGAATTCGAATACAT AGAAGGCNNNTGCATCAGGT | 4299 |
| TGCAGGACCAGAGAATTCGAATACAT GTCAACGNNNTGCATCAGGT | 3820 | TGCAGGACCAGAGAATTCGAATACAC CAGGATTNNNTGCATCAGGT | 4060 | TGCAGGACCAGAGAATTCGAATACAA TACACCGNNNTGCATCAGGT | 4300 |
| TGCAGGACCAGAGAATTCGAATACAC GATTTTTNNNTGCATCAGGT | 3821 | TGCAGGACCAGAGAATTCGAATACAA GAATGATNNNTGCATCAGGT | 4061 | TGCAGGACCAGAGAATTCGAATACAT CCAGCAANNNTGCATCAGGT | 4301 |
| TGCAGGACCAGAGAATTCGAATACAC CGTATTCNNNTGCATCAGGT | 3822 | TGCAGGACCAGAGAATTCGAATACAA CGACATCNNNTGCATCAGGT | 4062 | TGCAGGACCAGAGAATTCGAATACAG TGTTCCTNNNTGCATCAGGT | 4302 |
| TGCAGGACCAGAGAATTCGAATACAG CCGCGATNNNTGCATCAGGT | 3823 | TGCAGGACCAGAGAATTCGAATACAG TAAAAACNNNTGCATCAGGT | 4063 | TGCAGGACCAGAGAATTCGAATACAG AAACGTGNNNTGCATCAGGT | 4303 |
| TGCAGGACCAGAGAATTCGAATACAG GCCCTAGNNNTGCATCAGGT | 3824 | TGCAGGACCAGAGAATTCGAATACAA TTAACACNNNTGCATCAGGT | 4064 | TGCAGGACCAGAGAATTCGAATACAC CCTCTAANNNTGCATCAGGT | 4304 |
| TGCAGGACCAGAGAATTCGAATACAA ACAGGCANNNTGCATCAGGT | 3825 | TGCAGGACCAGAGAATTCGAATACAA CAAATTCNNNTGCATCAGGT | 4065 | TGCAGGACCAGAGAATTCGAATACAA CCGAGCCNNNTGCATCAGGT | 4305 |
| TGCAGGACCAGAGAATTCGAATACAA CCTATGGNNNTGCATCAGGT | 3826 | TGCAGGACCAGAGAATTCGAATACAC GTCCATTNNNTGCATCAGGT | 4066 | TGCAGGACCAGAGAATTCGAATACAG CGCCCTTNNNTGCATCAGGT | 4306 |
| TGCAGGACCAGAGAATTCGAATACAT GTGTCGANNNTGCATCAGGT | 3827 | TGCAGGACCAGAGAATTCGAATACAA GAAATCANNNTGCATCAGGT | 4067 | TGCAGGACCAGAGAATTCGAATACAA AATAGACNNNTGCATCAGGT | 4307 |
| TGCAGGACCAGAGAATTCGAATACAG TGGATTCNNNTGCATCAGGT | 3828 | TGCAGGACCAGAGAATTCGAATACAA AATCACTNNNTGCATCAGGT | 4068 | TGCAGGACCAGAGAATTCGAATACAT GACACTGNNNTGCATCAGGT | 4308 |
| TGCAGGACCAGAGAATTCGAATACAT CGGACCGNNNTGCATCAGGT | 3829 | TGCAGGACCAGAGAATTCGAATACAC TCCACGCNNNTGCATCAGGT | 4069 | TGCAGGACCAGAGAATTCGAATACAA GCGCGAGNNNTGCATCAGGT | 4309 |
| TGCAGGACCAGAGAATTCGAATACAA AACATAGNNNTGCATCAGGT | 3830 | TGCAGGACCAGAGAATTCGAATACAG AATAATGNNNTGCATCAGGT | 4070 | TGCAGGACCAGAGAATTCGAATACAG CAGAAGTNNNTGCATCAGGT | 4310 |
| TGCAGGACCAGAGAATTCGAATACAA GAAGCGTNNNTGCATCAGGT | 3831 | TGCAGGACCAGAGAATTCGAATACAT GTGACCANNNTGCATCAGGT | 4071 | TGCAGGACCAGAGAATTCGAATACAG GCTGATTNNNTGCATCAGGT | 4311 |
| TGCAGGACCAGAGAATTCGAATACAC CCTCACGNNNTGCATCAGGT | 3832 | TGCAGGACCAGAGAATTCGAATACAT CGATTAANNNTGCATCAGGT | 4072 | TGCAGGACCAGAGAATTCGAATACAG TAGAATANNNTGCATCAGGT | 4312 |
| TGCAGGACCAGAGAATTCGAATACAA ACTGTCGNNNTGCATCAGGT | 3833 | TGCAGGACCAGAGAATTCGAATACAC GCCAAATNNNTGCATCAGGT | 4073 | TGCAGGACCAGAGAATTCGAATACAC CATCGAANNNTGCATCAGGT | 4313 |
| TGCAGGACCAGAGAATTCGAATACAT CTTGGAGNNNTGCATCAGGT | 3834 | TGCAGGACCAGAGAATTCGAATACAC TTGTAAANNNTGCATCAGGT | 4074 | TGCAGGACCAGAGAATTCGAATACAT TGCCTACNNNTGCATCAGGT | 4314 |
| TGCAGGACCAGAGAATTCGAATACAG TGAAATANNNTGCATCAGGT | 3835 | TGCAGGACCAGAGAATTCGAATACAA ATTAGAGNNNTGCATCAGGT | 4075 | TGCAGGACCAGAGAATTCGAATACAA CTCCCATNNNTGCATCAGGT | 4315 |
| TGCAGGACCAGAGAATTCGAATACAT GCTTCTGNNNTGCATCAGGT | 3836 | TGCAGGACCAGAGAATTCGAATACAT AGCTTGGNNNTGCATCAGGT | 4076 | TGCAGGACCAGAGAATTCGAATACAG TTTCCACNNNTGCATCAGGT | 4316 |
| TGCAGGACCAGAGAATTCGAATACAT GACTTCCNNNTGCATCAGGT | 3837 | TGCAGGACCAGAGAATTCGAATACAA TAGGAGCNNNTGCATCAGGT | 4077 | TGCAGGACCAGAGAATTCGAATACAG ATATTGTNNNTGCATCAGGT | 4317 |
| TGCAGGACCAGAGAATTCGAATACAC CCGGATGNNNTGCATCAGGT | 3838 | TGCAGGACCAGAGAATTCGAATACAT TATACTCNNNTGCATCAGGT | 4078 | TGCAGGACCAGAGAATTCGAATACAA CTGAGGANNNTGCATCAGGT | 4318 |

FIG. 17H

| Pool-16 | SEQ ID NO: | Pool-17 | SEQ ID NO: | Pool-18 | SEQ ID NO: |
|---|---|---|---|---|---|
| TGCAGGACCAGAGAATTCGAATACAG AGGACATNNNTGCATCAGGT | 3839 | TGCAGGACCAGAGAATTCGAATACAT TGTTGCCNNNTGCATCAGGT | 4079 | TGCAGGACCAGAGAATTCGAATACAG TAGTCTGNNNTGCATCAGGT | 4319 |
| TGCAGGACCAGAGAATTCGAATACAC AGGTATCNNNTGCATCAGGT | 3840 | TGCAGGACCAGAGAATTCGAATACAT TCCGAGANNNTGCATCAGGT | 4080 | TGCAGGACCAGAGAATTCGAATACAT GTAAATCNNNTGCATCAGGT | 4320 |
| TGCAGGACCAGAGAATTCGAATACAG TAGTATTNNNTGCATCAGGT | 3841 | TGCAGGACCAGAGAATTCGAATACAA TCCCATCNNNTGCATCAGGT | 4081 | TGCAGGACCAGAGAATTCGAATACAG CATATGCNNNTGCATCAGGT | 4321 |
| TGCAGGACCAGAGAATTCGAATACAA AGGAGGANNNTGCATCAGGT | 3842 | TGCAGGACCAGAGAATTCGAATACAT TTGCCACNNNTGCATCAGGT | 4082 | TGCAGGACCAGAGAATTCGAATACAA TTCGTAANNNTGCATCAGGT | 4322 |
| TGCAGGACCAGAGAATTCGAATACAA AGAGCCANNNTGCATCAGGT | 3843 | TGCAGGACCAGAGAATTCGAATACAG TGAGCGGNNNTGCATCAGGT | 4083 | TGCAGGACCAGAGAATTCGAATACAA ATCCACGNNNTGCATCAGGT | 4323 |
| TGCAGGACCAGAGAATTCGAATACAG TCTCTCANNNTGCATCAGGT | 3844 | TGCAGGACCAGAGAATTCGAATACAT CGCATCTNNNTGCATCAGGT | 4084 | TGCAGGACCAGAGAATTCGAATACAG CGCCGCGNNNTGCATCAGGT | 4324 |
| TGCAGGACCAGAGAATTCGAATACAA CGGTGTTNNNTGCATCAGGT | 3845 | TGCAGGACCAGAGAATTCGAATACAT CTGCAGANNNTGCATCAGGT | 4085 | TGCAGGACCAGAGAATTCGAATACAG GCTCGACNNNTGCATCAGGT | 4325 |
| TGCAGGACCAGAGAATTCGAATACAC GTACGATNNNTGCATCAGGT | 3846 | TGCAGGACCAGAGAATTCGAATACAG CCCAAGCNNNTGCATCAGGT | 4086 | TGCAGGACCAGAGAATTCGAATACAA CCCCGAGNNNTGCATCAGGT | 4326 |
| TGCAGGACCAGAGAATTCGAATACAG AGGTGTANNNTGCATCAGGT | 3847 | TGCAGGACCAGAGAATTCGAATACAT TTCTCGGNNNTGCATCAGGT | 4087 | TGCAGGACCAGAGAATTCGAATACAA GTCACCANNNTGCATCAGGT | 4327 |
| TGCAGGACCAGAGAATTCGAATACAC ACCACAANNNTGCATCAGGT | 3848 | TGCAGGACCAGAGAATTCGAATACAG GCCTACGNNNTGCATCAGGT | 4088 | TGCAGGACCAGAGAATTCGAATACAA AAATTCCNNNTGCATCAGGT | 4328 |

FIG. 18A

| Pool-19 | SEQ ID NO. | Pool-20 | SEQ ID NO. | Pool-21 | SEQ ID NO. |
|---|---|---|---|---|---|
| TGCAGGACCAGAGAATTCGAATA CAGCCCTCTGNNNACGTATGCCA | 4329 | TGCAGGACCAGAGAATTCGAATA CATGTTGTCCNNNACGTATGCCA | 4569 | TGCAGGACCAGAGAATTCGAATA CATGAAACAANNNACGTATGCCA | 4809 |
| TGCAGGACCAGAGAATTCGAATA CAGCAAAGGTNNNACGTATGCCA | 4330 | TGCAGGACCAGAGAATTCGAATA CATAACCAGCNNNACGTATGCCA | 4570 | TGCAGGACCAGAGAATTCGAATA CACCGTTGCCNNNACGTATGCCA | 4810 |
| TGCAGGACCAGAGAATTCGAATA CATTTCTATGNNNACGTATGCCA | 4331 | TGCAGGACCAGAGAATTCGAATA CATGCGCGACNNNACGTATGCCA | 4571 | TGCAGGACCAGAGAATTCGAATA CAGCATTGGTNNNACGTATGCCA | 4811 |
| TGCAGGACCAGAGAATTCGAATA CACGTGCAATNNNACGTATGCCA | 4332 | TGCAGGACCAGAGAATTCGAATA CAATCGTCTCNNNACGTATGCCA | 4572 | TGCAGGACCAGAGAATTCGAATA CATAGGCCATNNNACGTATGCCA | 4812 |
| TGCAGGACCAGAGAATTCGAATA CAGTTTAGGCNNNACGTATGCCA | 4333 | TGCAGGACCAGAGAATTCGAATA CATCCGCACCNNNACGTATGCCA | 4573 | TGCAGGACCAGAGAATTCGAATA CAACTCCTCANNNACGTATGCCA | 4813 |
| TGCAGGACCAGAGAATTCGAATA CAAAAATGACNNNACGTATGCCA | 4334 | TGCAGGACCAGAGAATTCGAATA CATTACTGAANNNACGTATGCCA | 4574 | TGCAGGACCAGAGAATTCGAATA CACTAGGCGCNNNACGTATGCCA | 4814 |
| TGCAGGACCAGAGAATTCGAATA CACTACTAGGNNNACGTATGCCA | 4335 | TGCAGGACCAGAGAATTCGAATA CAAGGTCCGCNNNACGTATGCCA | 4575 | TGCAGGACCAGAGAATTCGAATA CAAGTTTAGTNNNACGTATGCCA | 4815 |
| TGCAGGACCAGAGAATTCGAATA CACACCCAGGNNNACGTATGCCA | 4336 | TGCAGGACCAGAGAATTCGAATA CAGTGCCCTCNNNACGTATGCCA | 4576 | TGCAGGACCAGAGAATTCGAATA CATTGATACANNNACGTATGCCA | 4816 |
| TGCAGGACCAGAGAATTCGAATA CAGCCCGCCTNNNACGTATGCCA | 4337 | TGCAGGACCAGAGAATTCGAATA CAGCGTAGCCNNNACGTATGCCA | 4577 | TGCAGGACCAGAGAATTCGAATA CAACAATTACNNNACGTATGCCA | 4817 |
| TGCAGGACCAGAGAATTCGAATA CACAACGTCANNNACGTATGCCA | 4338 | TGCAGGACCAGAGAATTCGAATA CATAGCCAACNNNACGTATGCCA | 4578 | TGCAGGACCAGAGAATTCGAATA CAATACCGGTNNNACGTATGCCA | 4818 |
| TGCAGGACCAGAGAATTCGAATA CATCTCAAGGNNNACGTATGCCA | 4339 | TGCAGGACCAGAGAATTCGAATA CAATATACCANNNACGTATGCCA | 4579 | TGCAGGACCAGAGAATTCGAATA CATGAAGCCTNNNACGTATGCCA | 4819 |
| TGCAGGACCAGAGAATTCGAATA CATCATAAACNNNACGTATGCCA | 4340 | TGCAGGACCAGAGAATTCGAATA CATAAAATCCNNNACGTATGCCA | 4580 | TGCAGGACCAGAGAATTCGAATA CATTACCTGCNNNACGTATGCCA | 4820 |
| TGCAGGACCAGAGAATTCGAATA CATCCTCCCCNNNACGTATGCCA | 4341 | TGCAGGACCAGAGAATTCGAATA CAGATGGTGANNNACGTATGCCA | 4581 | TGCAGGACCAGAGAATTCGAATA CATATCAGATNNNACGTATGCCA | 4821 |
| TGCAGGACCAGAGAATTCGAATA CAAGTAACCCNNNACGTATGCCA | 4342 | TGCAGGACCAGAGAATTCGAATA CAGAACGTAGNNNACGTATGCCA | 4582 | TGCAGGACCAGAGAATTCGAATA CAGAAGAATTNNNACGTATGCCA | 4822 |
| TGCAGGACCAGAGAATTCGAATA CAGTGACAAGNNNACGTATGCCA | 4343 | TGCAGGACCAGAGAATTCGAATA CAATATTAATNNNACGTATGCCA | 4583 | TGCAGGACCAGAGAATTCGAATA CAGATCACGTNNNACGTATGCCA | 4823 |
| TGCAGGACCAGAGAATTCGAATA CAGCAATACCNNNACGTATGCCA | 4344 | TGCAGGACCAGAGAATTCGAATA CATACTGAATNNNACGTATGCCA | 4584 | TGCAGGACCAGAGAATTCGAATA CAAGGTAGACNNNACGTATGCCA | 4824 |
| TGCAGGACCAGAGAATTCGAATA CAAATACGTTNNNACGTATGCCA | 4345 | TGCAGGACCAGAGAATTCGAATA CAGTCCGAGCNNNACGTATGCCA | 4585 | TGCAGGACCAGAGAATTCGAATA CATTGACCGANNNACGTATGCCA | 4825 |
| TGCAGGACCAGAGAATTCGAATA CACCATGTAGNNNACGTATGCCA | 4346 | TGCAGGACCAGAGAATTCGAATA CACCTGGTAANNNACGTATGCCA | 4586 | TGCAGGACCAGAGAATTCGAATA CACCACTGTTNNNACGTATGCCA | 4826 |
| TGCAGGACCAGAGAATTCGAATA CACCCAACGGNNNACGTATGCCA | 4347 | TGCAGGACCAGAGAATTCGAATA CACCCTAGAANNNACGTATGCCA | 4587 | TGCAGGACCAGAGAATTCGAATA CAGTCAGAAGNNNACGTATGCCA | 4827 |
| TGCAGGACCAGAGAATTCGAATA CAGCCGGTTGCNNNACGTATGCCA | 4348 | TGCAGGACCAGAGAATTCGAATA CATTAAAGTCNNNACGTATGCCA | 4588 | TGCAGGACCAGAGAATTCGAATA CACCGACCTCNNNACGTATGCCA | 4828 |
| TGCAGGACCAGAGAATTCGAATA CAGTGATCTGNNNACGTATGCCA | 4349 | TGCAGGACCAGAGAATTCGAATA CAACCTGGCCNNNACGTATGCCA | 4589 | TGCAGGACCAGAGAATTCGAATA CAATTAGTGTNNNACGTATGCCA | 4829 |
| TGCAGGACCAGAGAATTCGAATA CATAAGCCGTNNNACGTATGCCA | 4350 | TGCAGGACCAGAGAATTCGAATA CAGCTATCCTNNNACGTATGCCA | 4590 | TGCAGGACCAGAGAATTCGAATA CAGCATACCANNNACGTATGCCA | 4830 |
| TGCAGGACCAGAGAATTCGAATA CATGTTTGTTNNNACGTATGCCA | 4351 | TGCAGGACCAGAGAATTCGAATA CAAGCGTTGTNNNACGTATGCCA | 4591 | TGCAGGACCAGAGAATTCGAATA CAAGTTTTTCNNNACGTATGCCA | 4831 |
| TGCAGGACCAGAGAATTCGAATA CAACGAGCGGNNNACGTATGCCA | 4352 | TGCAGGACCAGAGAATTCGAATA CACTTCGCTANNNACGTATGCCA | 4592 | TGCAGGACCAGAGAATTCGAATA CATTCGCGTTNNNACGTATGCCA | 4832 |
| TGCAGGACCAGAGAATTCGAATA CATAGATCGCNNNACGTATGCCA | 4353 | TGCAGGACCAGAGAATTCGAATA CACATTTTTGNNNACGTATGCCA | 4593 | TGCAGGACCAGAGAATTCGAATA CATGGAGCCCNNNACGTATGCCA | 4833 |
| TGCAGGACCAGAGAATTCGAATA CATGATACGCNNNACGTATGCCA | 4354 | TGCAGGACCAGAGAATTCGAATA CAAACTTCGGNNNACGTATGCCA | 4594 | TGCAGGACCAGAGAATTCGAATA CACGTGGCACNNNACGTATGCCA | 4834 |
| TGCAGGACCAGAGAATTCGAATA CATAGTTACANNNACGTATGCCA | 4355 | TGCAGGACCAGAGAATTCGAATA CATACCGTGANNNACGTATGCCA | 4595 | TGCAGGACCAGAGAATTCGAATA CATCTTACTANNNACGTATGCCA | 4835 |
| TGCAGGACCAGAGAATTCGAATA CACTTGGTCANNNACGTATGCCA | 4356 | TGCAGGACCAGAGAATTCGAATA CAAGCTTTTTNNNACGTATGCCA | 4596 | TGCAGGACCAGAGAATTCGAATA CAATCCGGTANNNACGTATGCCA | 4836 |
| TGCAGGACCAGAGAATTCGAATA CATTAATCTCNNNACGTATGCCA | 4357 | TGCAGGACCAGAGAATTCGAATA CATGTTCTCGNNNACGTATGCCA | 4597 | TGCAGGACCAGAGAATTCGAATA CAGACACCTANNNACGTATGCCA | 4837 |
| TGCAGGACCAGAGAATTCGAATA CATTAGACACNNNACGTATGCCA | 4358 | TGCAGGACCAGAGAATTCGAATA CAAATCGCTGNNNACGTATGCCA | 4598 | TGCAGGACCAGAGAATTCGAATA CATCCGTCTANNNACGTATGCCA | 4838 |
| TGCAGGACCAGAGAATTCGAATA CAACACCAGTNNNACGTATGCCA | 4359 | TGCAGGACCAGAGAATTCGAATA CATGAACCACNNNACGTATGCCA | 4599 | TGCAGGACCAGAGAATTCGAATA CAAGATTACTNNNACGTATGCCA | 4839 |
| TGCAGGACCAGAGAATTCGAATA CAACCAGGACNNNACGTATGCCA | 4360 | TGCAGGACCAGAGAATTCGAATA CAATTTCATCNNNACGTATGCCA | 4600 | TGCAGGACCAGAGAATTCGAATA CAAGATTGAANNNACGTATGCCA | 4840 |
| TGCAGGACCAGAGAATTCGAATA CAATGCATGCNNNACGTATGCCA | 4361 | TGCAGGACCAGAGAATTCGAATA CACAGTCACANNNACGTATGCCA | 4601 | TGCAGGACCAGAGAATTCGAATA CATTTAAAGCNNNACGTATGCCA | 4841 |

FIG. 18B

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CATACACATNNNACGTATGCCA | 4362 | TGCAGGACCAGAGAATTCGAATA CACCCATAGANNNACGTATGCCA | 4602 | TGCAGGACCAGAGAATTCGAATA CAGAAATTGCCNNNACGTATGCCA | 4842 |
| TGCAGGACCAGAGAATTCGAATA CATCGTTCAANNNACGTATGCCA | 4363 | TGCAGGACCAGAGAATTCGAATA CACAGAATGGNNNACGTATGCCA | 4603 | TGCAGGACCAGAGAATTCGAATA CATTACGTCCNNNACGTATGCCA | 4843 |
| TGCAGGACCAGAGAATTCGAATA CACTATCAAANNNACGTATGCCA | 4364 | TGCAGGACCAGAGAATTCGAATA CAGTATGAAANNNACGTATGCCA | 4604 | TGCAGGACCAGAGAATTCGAATA CAATGAGGACNNNACGTATGCCA | 4844 |
| TGCAGGACCAGAGAATTCGAATA CATTACCAAANNNACGTATGCCA | 4365 | TGCAGGACCAGAGAATTCGAATA CAGTTTAAGTNNNACGTATGCCA | 4605 | TGCAGGACCAGAGAATTCGAATA CAATTGTTAGNNNACGTATGCCA | 4845 |
| TGCAGGACCAGAGAATTCGAATA CACCGGCGATNNNACGTATGCCA | 4366 | TGCAGGACCAGAGAATTCGAATA CAGCGTTATGNNNACGTATGCCA | 4606 | TGCAGGACCAGAGAATTCGAATA CAGCTTGTAGNNNACGTATGCCA | 4846 |
| TGCAGGACCAGAGAATTCGAATA CAGTTGTATANNNACGTATGCCA | 4367 | TGCAGGACCAGAGAATTCGAATA CATCCGTTACNNNACGTATGCCA | 4607 | TGCAGGACCAGAGAATTCGAATA CATTGCTTCGNNNACGTATGCCA | 4847 |
| TGCAGGACCAGAGAATTCGAATA CAATACGGCTNNNACGTATGCCA | 4368 | TGCAGGACCAGAGAATTCGAATA CACGAAACCTNNNACGTATGCCA | 4608 | TGCAGGACCAGAGAATTCGAATA CAAAAGGCTGNNNACGTATGCCA | 4848 |
| TGCAGGACCAGAGAATTCGAATA CATGGCAACTNNNACGTATGCCA | 4369 | TGCAGGACCAGAGAATTCGAATA CACGGCCATGNNNACGTATGCCA | 4609 | TGCAGGACCAGAGAATTCGAATA CACTTACCAGNNNACGTATGCCA | 4849 |
| TGCAGGACCAGAGAATTCGAATA CAGATTTCAANNNACGTATGCCA | 4370 | TGCAGGACCAGAGAATTCGAATA CACGAAAAGCNNNACGTATGCCA | 4610 | TGCAGGACCAGAGAATTCGAATA CAATCTATAGNNNACGTATGCCA | 4850 |
| TGCAGGACCAGAGAATTCGAATA CAGTATCTTTNNNACGTATGCCA | 4371 | TGCAGGACCAGAGAATTCGAATA CAAGGTTGTCNNNACGTATGCCA | 4611 | TGCAGGACCAGAGAATTCGAATA CAGGTACACTNNNACGTATGCCA | 4851 |
| TGCAGGACCAGAGAATTCGAATA CAGCAACAGANNNACGTATGCCA | 4372 | TGCAGGACCAGAGAATTCGAATA CAACGAAGGTNNNACGTATGCCA | 4612 | TGCAGGACCAGAGAATTCGAATA CACCCCCTCANNNACGTATGCCA | 4852 |
| TGCAGGACCAGAGAATTCGAATA CAGCGTTCAANNNACGTATGCCA | 4373 | TGCAGGACCAGAGAATTCGAATA CATCCCCCGANNNACGTATGCCA | 4613 | TGCAGGACCAGAGAATTCGAATA CACAGACGGNNNACGTATGCCA | 4853 |
| TGCAGGACCAGAGAATTCGAATA CAGTATTCCGNNNACGTATGCCA | 4374 | TGCAGGACCAGAGAATTCGAATA CAAGCGATCTNNNACGTATGCCA | 4614 | TGCAGGACCAGAGAATTCGAATA CAATCATGGCNNNACGTATGCCA | 4854 |
| TGCAGGACCAGAGAATTCGAATA CATCCTATATNNNACGTATGCCA | 4375 | TGCAGGACCAGAGAATTCGAATA CACTATAATGNNNACGTATGCCA | 4615 | TGCAGGACCAGAGAATTCGAATA CATATAGGTNNNACGTATGCCA | 4855 |
| TGCAGGACCAGAGAATTCGAATA CAAGTCGTACNNNACGTATGCCA | 4376 | TGCAGGACCAGAGAATTCGAATA CATTCGTCTGNNNACGTATGCCA | 4616 | TGCAGGACCAGAGAATTCGAATA CAGATTTAACNNNACGTATGCCA | 4856 |
| TGCAGGACCAGAGAATTCGAATA CACCTAGACANNNACGTATGCCA | 4377 | TGCAGGACCAGAGAATTCGAATA CAGCGCCTTCNNNACGTATGCCA | 4617 | TGCAGGACCAGAGAATTCGAATA CAATGGAACGNNNACGTATGCCA | 4857 |
| TGCAGGACCAGAGAATTCGAATA CAATTGGTCGNNNACGTATGCCA | 4378 | TGCAGGACCAGAGAATTCGAATA CACGCAATCANNNACGTATGCCA | 4618 | TGCAGGACCAGAGAATTCGAATA CAGCTTTCACNNNACGTATGCCA | 4858 |
| TGCAGGACCAGAGAATTCGAATA CAGGTCACGCNNNACGTATGCCA | 4379 | TGCAGGACCAGAGAATTCGAATA CAGTCGGTCGNNNACGTATGCCA | 4619 | TGCAGGACCAGAGAATTCGAATA CAGTTCCGTGNNNACGTATGCCA | 4859 |
| TGCAGGACCAGAGAATTCGAATA CACACCAAACNNNACGTATGCCA | 4380 | TGCAGGACCAGAGAATTCGAATA CATAGCAGGANNNACGTATGCCA | 4620 | TGCAGGACCAGAGAATTCGAATA CATACTCCCANNNACGTATGCCA | 4860 |
| TGCAGGACCAGAGAATTCGAATA CAGAATTCATNNNACGTATGCCA | 4381 | TGCAGGACCAGAGAATTCGAATA CAGATGGAGTNNNACGTATGCCA | 4621 | TGCAGGACCAGAGAATTCGAATA CAGCCCGTCTNNNACGTATGCCA | 4861 |
| TGCAGGACCAGAGAATTCGAATA CATTCCGCACTNNNACGTATGCCA | 4382 | TGCAGGACCAGAGAATTCGAATA CAAAGCACCTNNNACGTATGCCA | 4622 | TGCAGGACCAGAGAATTCGAATA CAGTCACTGANNNACGTATGCCA | 4862 |
| TGCAGGACCAGAGAATTCGAATA CACCGGTTAAGNNNACGTATGCCA | 4383 | TGCAGGACCAGAGAATTCGAATA CAAGCGGCCTNNNACGTATGCCA | 4623 | TGCAGGACCAGAGAATTCGAATA CAAGCCGAGGNNNACGTATGCCA | 4863 |
| TGCAGGACCAGAGAATTCGAATA CACGCCTGCTNNNACGTATGCCA | 4384 | TGCAGGACCAGAGAATTCGAATA CACGTTTGCTNNNACGTATGCCA | 4624 | TGCAGGACCAGAGAATTCGAATA CAGCTATATANNNACGTATGCCA | 4864 |
| TGCAGGACCAGAGAATTCGAATA CAAAAAACAGTNNNACGTATGCCA | 4385 | TGCAGGACCAGAGAATTCGAATA CACCTGCATTNNNACGTATGCCA | 4625 | TGCAGGACCAGAGAATTCGAATA CATCTCTCGANNNACGTATGCCA | 4865 |
| TGCAGGACCAGAGAATTCGAATA CAGAGATTTNNNACGTATGCCA | 4386 | TGCAGGACCAGAGAATTCGAATA CAATTGAATCNNNACGTATGCCA | 4626 | TGCAGGACCAGAGAATTCGAATA CAACAATAGANNNACGTATGCCA | 4866 |
| TGCAGGACCAGAGAATTCGAATA CAACCAGTTGNNNACGTATGCCA | 4387 | TGCAGGACCAGAGAATTCGAATA CATCCGTGCCNNNACGTATGCCA | 4627 | TGCAGGACCAGAGAATTCGAATA CAGAGAGCATNNNACGTATGCCA | 4867 |
| TGCAGGACCAGAGAATTCGAATA CAAGTTCGCANNNACGTATGCCA | 4388 | TGCAGGACCAGAGAATTCGAATA CATCTCAGGANNNACGTATGCCA | 4628 | TGCAGGACCAGAGAATTCGAATA CACGATATGCNNNACGTATGCCA | 4868 |
| TGCAGGACCAGAGAATTCGAATA CAGATGACCTNNNCTAGCGTTAC | 4389 | TGCAGGACCAGAGAATTCGAATA CAAAGCCGTTNNNCTAGCGTTAC | 4629 | TGCAGGACCAGAGAATTCGAATA CACTTCCTCTNNNCTAGCGTTAC | 4869 |
| TGCAGGACCAGAGAATTCGAATA CACACGTATGNNNCTAGCGTTAC | 4390 | TGCAGGACCAGAGAATTCGAATA CACACCCTCGNNNCTAGCGTTAC | 4630 | TGCAGGACCAGAGAATTCGAATA CAAACAGTTTNNNCTAGCGTTAC | 4870 |
| TGCAGGACCAGAGAATTCGAATA CATGTCGGCGNNNCTAGCGTTAC | 4391 | TGCAGGACCAGAGAATTCGAATA CAGCTAGTTGNNNCTAGCGTTAC | 4631 | TGCAGGACCAGAGAATTCGAATA CATGTGGACTNNNCTAGCGTTAC | 4871 |
| TGCAGGACCAGAGAATTCGAATA CAGACCAAAGNNNCTAGCGTTAC | 4392 | TGCAGGACCAGAGAATTCGAATA CACCGTTACTNNNCTAGCGTTAC | 4632 | TGCAGGACCAGAGAATTCGAATA CACCTCGCACNNNCTAGCGTTAC | 4872 |
| TGCAGGACCAGAGAATTCGAATA CACTGCTACTNNNCTAGCGTTAC | 4393 | TGCAGGACCAGAGAATTCGAATA CATAAGCGTCNNNCTAGCGTTAC | 4633 | TGCAGGACCAGAGAATTCGAATA CACGGTTTCTNNNCTAGCGTTAC | 4873 |
| TGCAGGACCAGAGAATTCGAATA CACTCCAACTNNNCTAGCGTTAC | 4394 | TGCAGGACCAGAGAATTCGAATA CAGGTAAACGNNNCTAGCGTTAC | 4634 | TGCAGGACCAGAGAATTCGAATA CAACGTCGATNNNCTAGCGTTAC | 4874 |

FIG. 18C

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CACAATCCCTNNNCTAGCGTTAC | 4395 | TGCAGGACCAGAGAATTCGAATA CAGAACCAGANNNCTAGCGTTAC | 4635 | TGCAGGACCAGAGAATTCGAATA CATTGGCTTCNNNCTAGCGTTAC | 4875 |
| TGCAGGACCAGAGAATTCGAATA CATCGTGCAANNNCTAGCGTTAC | 4396 | TGCAGGACCAGAGAATTCGAATA CAGGACTGTTNNNCTAGCGTTAC | 4636 | TGCAGGACCAGAGAATTCGAATA CAATGGACGANNNCTAGCGTTAC | 4876 |
| TGCAGGACCAGAGAATTCGAATA CAAAGCCATCNNNCTAGCGTTAC | 4397 | TGCAGGACCAGAGAATTCGAATA CAATCGTGTGNNNCTAGCGTTAC | 4637 | TGCAGGACCAGAGAATTCGAATA CATGCAAGAGNNNCTAGCGTTAC | 4877 |
| TGCAGGACCAGAGAATTCGAATA CAATGAACTTNNNCTAGCGTTAC | 4398 | TGCAGGACCAGAGAATTCGAATA CAGTCACGGCNNNCTAGCGTTAC | 4638 | TGCAGGACCAGAGAATTCGAATA CAGAAATATGNNNCTAGCGTTAC | 4878 |
| TGCAGGACCAGAGAATTCGAATA CATGGCCGGTNNNCTAGCGTTAC | 4399 | TGCAGGACCAGAGAATTCGAATA CATCTCGTACNNNCTAGCGTTAC | 4639 | TGCAGGACCAGAGAATTCGAATA CAACACATATNNNCTAGCGTTAC | 4879 |
| TGCAGGACCAGAGAATTCGAATA CATGCCACGGNNNCTAGCGTTAC | 4400 | TGCAGGACCAGAGAATTCGAATA CAAGTCGCGCNNNCTAGCGTTAC | 4640 | TGCAGGACCAGAGAATTCGAATA CAGTACGACTNNNCTAGCGTTAC | 4880 |
| TGCAGGACCAGAGAATTCGAATA CAGTCTTCGTNNNCTAGCGTTAC | 4401 | TGCAGGACCAGAGAATTCGAATA CACATAGTCGNNNCTAGCGTTAC | 4641 | TGCAGGACCAGAGAATTCGAATA CACGCCGCGGNNNCTAGCGTTAC | 4881 |
| TGCAGGACCAGAGAATTCGAATA CAAACGTAGGNNNCTAGCGTTAC | 4402 | TGCAGGACCAGAGAATTCGAATA CACATGTACGNNNCTAGCGTTAC | 4642 | TGCAGGACCAGAGAATTCGAATA CATAGTGCACNNNCTAGCGTTAC | 4882 |
| TGCAGGACCAGAGAATTCGAATA CAATGCAGCANNNCTAGCGTTAC | 4403 | TGCAGGACCAGAGAATTCGAATA CAGCCGTATCANNNCTAGCGTTAC | 4643 | TGCAGGACCAGAGAATTCGAATA CATCAATGCGNNNCTAGCGTTAC | 4883 |
| TGCAGGACCAGAGAATTCGAATA CATGACGGCCNNNCTAGCGTTAC | 4404 | TGCAGGACCAGAGAATTCGAATA CACAATTCTTNNNCTAGCGTTAC | 4644 | TGCAGGACCAGAGAATTCGAATA CAATGTAAGANNNCTAGCGTTAC | 4884 |
| TGCAGGACCAGAGAATTCGAATA CACTTAGGACNNNCTAGCGTTAC | 4405 | TGCAGGACCAGAGAATTCGAATA CAACTCTATTNNNCTAGCGTTAC | 4645 | TGCAGGACCAGAGAATTCGAATA CATATGTTAGNNNCTAGCGTTAC | 4885 |
| TGCAGGACCAGAGAATTCGAATA CAGACAGAGTNNNCTAGCGTTAC | 4406 | TGCAGGACCAGAGAATTCGAATA CATCATCCANNNCTAGCGTTAC | 4646 | TGCAGGACCAGAGAATTCGAATA CATCAAATCANNNCTAGCGTTAC | 4886 |
| TGCAGGACCAGAGAATTCGAATA CAAAGTCGTCNNNCTAGCGTTAC | 4407 | TGCAGGACCAGAGAATTCGAATA CAGGCTTGGCNNNCTAGCGTTAC | 4647 | TGCAGGACCAGAGAATTCGAATA CACACTTAGGNNNCTAGCGTTAC | 4887 |
| TGCAGGACCAGAGAATTCGAATA CATACAAAAGNNNCTAGCGTTAC | 4408 | TGCAGGACCAGAGAATTCGAATA CAGTTCCTTGNNNCTAGCGTTAC | 4648 | TGCAGGACCAGAGAATTCGAATA CATAGGATAANNNCTAGCGTTAC | 4888 |
| TGCAGGACCAGAGAATTCGAATA CATCTCCTGANNNCTAGCGTTAC | 4409 | TGCAGGACCAGAGAATTCGAATA CAATGAGAATNNNCTAGCGTTAC | 4649 | TGCAGGACCAGAGAATTCGAATA CAATCCCGTTNNNCTAGCGTTAC | 4889 |
| TGCAGGACCAGAGAATTCGAATA CAAGCTGGTTNNNCTAGCGTTAC | 4410 | TGCAGGACCAGAGAATTCGAATA CACTGTATCCNNNCTAGCGTTAC | 4650 | TGCAGGACCAGAGAATTCGAATA CAACAATCCGNNNCTAGCGTTAC | 4890 |
| TGCAGGACCAGAGAATTCGAATA CAAATCAAGANNNCTAGCGTTAC | 4411 | TGCAGGACCAGAGAATTCGAATA CATACGCCCCNNNCTAGCGTTAC | 4651 | TGCAGGACCAGAGAATTCGAATA CACTATTAAGNNNCTAGCGTTAC | 4891 |
| TGCAGGACCAGAGAATTCGAATA CAACCACAACNNNCTAGCGTTAC | 4412 | TGCAGGACCAGAGAATTCGAATA CATGGCCGACNNNCTAGCGTTAC | 4652 | TGCAGGACCAGAGAATTCGAATA CAGCGTATGTNNNCTAGCGTTAC | 4892 |
| TGCAGGACCAGAGAATTCGAATA CAGCTATAATNNNCTAGCGTTAC | 4413 | TGCAGGACCAGAGAATTCGAATA CACCGCTGCTNNNCTAGCGTTAC | 4653 | TGCAGGACCAGAGAATTCGAATA CAATTGGTATNNNCTAGCGTTAC | 4893 |
| TGCAGGACCAGAGAATTCGAATA CAGGACCGCTNNNCTAGCGTTAC | 4414 | TGCAGGACCAGAGAATTCGAATA CAGGTAGCCCNNNCTAGCGTTAC | 4654 | TGCAGGACCAGAGAATTCGAATA CATTTCTGCGNNNCTAGCGTTAC | 4894 |
| TGCAGGACCAGAGAATTCGAATA CAGTCCTATNNNCTAGCGTTAC | 4415 | TGCAGGACCAGAGAATTCGAATA CATGACGTTGNNNCTAGCGTTAC | 4655 | TGCAGGACCAGAGAATTCGAATA CAGAATCCCANNNCTAGCGTTAC | 4895 |
| TGCAGGACCAGAGAATTCGAATA CATTGCTGAGNNNCTAGCGTTAC | 4416 | TGCAGGACCAGAGAATTCGAATA CACCCACTATNNNCTAGCGTTAC | 4656 | TGCAGGACCAGAGAATTCGAATA CACTTTCACGNNNCTAGCGTTAC | 4896 |
| TGCAGGACCAGAGAATTCGAATA CATTGGCCTTNNNCTAGCGTTAC | 4417 | TGCAGGACCAGAGAATTCGAATA CAAAGTGTAANNNCTAGCGTTAC | 4657 | TGCAGGACCAGAGAATTCGAATA CACGGATCATNNNCTAGCGTTAC | 4897 |
| TGCAGGACCAGAGAATTCGAATA CAATCATTTCNNNCTAGCGTTAC | 4418 | TGCAGGACCAGAGAATTCGAATA CAGGAGTATGNNNCTAGCGTTAC | 4658 | TGCAGGACCAGAGAATTCGAATA CAACAGTGCTNNNCTAGCGTTAC | 4898 |
| TGCAGGACCAGAGAATTCGAATA CAGATGTATTNNNCTAGCGTTAC | 4419 | TGCAGGACCAGAGAATTCGAATA CAAGTGATAANNNCTAGCGTTAC | 4659 | TGCAGGACCAGAGAATTCGAATA CACTTAGTCCNNNCTAGCGTTAC | 4899 |
| TGCAGGACCAGAGAATTCGAATA CAGATCATATNNNCTAGCGTTAC | 4420 | TGCAGGACCAGAGAATTCGAATA CATAATTCGANNNCTAGCGTTAC | 4660 | TGCAGGACCAGAGAATTCGAATA CAAGTGCCCGNNNCTAGCGTTAC | 4900 |
| TGCAGGACCAGAGAATTCGAATA CACCCCGCTANNNCTAGCGTTAC | 4421 | TGCAGGACCAGAGAATTCGAATA CAAGCTTTGGNNNCTAGCGTTAC | 4661 | TGCAGGACCAGAGAATTCGAATA CATGAAATCTNNNCTAGCGTTAC | 4901 |
| TGCAGGACCAGAGAATTCGAATA CAAAAATCGANNNCTAGCGTTAC | 4422 | TGCAGGACCAGAGAATTCGAATA CAACATGTCGNNNCTAGCGTTAC | 4662 | TGCAGGACCAGAGAATTCGAATA CATCAGTTAANNNCTAGCGTTAC | 4902 |
| TGCAGGACCAGAGAATTCGAATA CAATGTACATNNNCTAGCGTTAC | 4423 | TGCAGGACCAGAGAATTCGAATA CATCAGCGCGNNNCTAGCGTTAC | 4663 | TGCAGGACCAGAGAATTCGAATA CAAACCCTGANNNCTAGCGTTAC | 4903 |
| TGCAGGACCAGAGAATTCGAATA CAGCCATCTTNNNCTAGCGTTAC | 4424 | TGCAGGACCAGAGAATTCGAATA CAGCCGGTANNNCTAGCGTTAC | 4664 | TGCAGGACCAGAGAATTCGAATA CATCATGATANNNCTAGCGTTAC | 4904 |
| TGCAGGACCAGAGAATTCGAATA CAAATGCTCGNNNCTAGCGTTAC | 4425 | TGCAGGACCAGAGAATTCGAATA CACCATTCACNNNCTAGCGTTAC | 4665 | TGCAGGACCAGAGAATTCGAATA CAAAGCCTTGNNNCTAGCGTTAC | 4905 |
| TGCAGGACCAGAGAATTCGAATA CACACGTCGGNNNCTAGCGTTAC | 4426 | TGCAGGACCAGAGAATTCGAATA CATTCCCCTNNNCTAGCGTTAC | 4666 | TGCAGGACCAGAGAATTCGAATA CAAGCATACNNNCTAGCGTTAC | 4906 |
| TGCAGGACCAGAGAATTCGAATA CACTATGCGANNNCTAGCGTTAC | 4427 | TGCAGGACCAGAGAATTCGAATA CAACCCTCCGNNNCTAGCGTTAC | 4667 | TGCAGGACCAGAGAATTCGAATA CAGGCATTTGNNNCTAGCGTTAC | 4907 |

FIG. 18D

| Pool-19 | SEQ ID NO. | Pool-20 | SEQ ID NO. | Pool-21 | SEQ ID NO. |
|---|---|---|---|---|---|
| TGCAGGACCAGAGAATTCGAATA CAGTCTGGTANNNCTAGCGTTAC | 4428 | TGCAGGACCAGAGAATTCGAATA CACACCTTACNNNCTAGCGTTAC | 4663 | TGCAGGACCAGAGAATTCGAATA CAGCGAGTCCNNNCTAGCGTTAC | 4908 |
| TGCAGGACCAGAGAATTCGAATA CAGTCAGTGTNNNCTAGCGTTAC | 4429 | TGCAGGACCAGAGAATTCGAATA CAGGAGTTGANNNCTAGCGTTAC | 4669 | TGCAGGACCAGAGAATTCGAATA CATTTTGAGANNNCTAGCGTTAC | 4909 |
| TGCAGGACCAGAGAATTCGAATA CACTCCAGTTNNNCTAGCGTTAC | 4430 | TGCAGGACCAGAGAATTCGAATA CAGACAAGACNNNCTAGCGTTAC | 4670 | TGCAGGACCAGAGAATTCGAATA CAATCCTTATNNNCTAGCGTTAC | 4910 |
| TGCAGGACCAGAGAATTCGAATA CAGATGAAGCNNNCTAGCGTTAC | 4431 | TGCAGGACCAGAGAATTCGAATA CAGTCTACGANNNCTAGCGTTAC | 4671 | TGCAGGACCAGAGAATTCGAATA CATCGAAAAANNNCTAGCGTTAC | 4911 |
| TGCAGGACCAGAGAATTCGAATA CAAAACCATTNNNCTAGCGTTAC | 4432 | TGCAGGACCAGAGAATTCGAATA CATCGCTCATNNNCTAGCGTTAC | 4672 | TGCAGGACCAGAGAATTCGAATA CAGCTCCGTCNNNCTAGCGTTAC | 4912 |
| TGCAGGACCAGAGAATTCGAATA CACCTGCGCTNNNCTAGCGTTAC | 4433 | TGCAGGACCAGAGAATTCGAATA CACCAAGCCGNNNCTAGCGTTAC | 4673 | TGCAGGACCAGAGAATTCGAATA CACCAGTTCNNNCTAGCGTTAC | 4913 |
| TGCAGGACCAGAGAATTCGAATA CACACCCGAGNNNCTAGCGTTAC | 4434 | TGCAGGACCAGAGAATTCGAATA CACCCTCGGTNNNCTAGCGTTAC | 4674 | TGCAGGACCAGAGAATTCGAATA CACTTCGGCTNNNCTAGCGTTAC | 4914 |
| TGCAGGACCAGAGAATTCGAATA CATACTACAANNNCTAGCGTTAC | 4435 | TGCAGGACCAGAGAATTCGAATA CAAACTAGTTNNNCTAGCGTTAC | 4675 | TGCAGGACCAGAGAATTCGAATA CACCGCCATCNNNCTAGCGTTAC | 4915 |
| TGCAGGACCAGAGAATTCGAATA CATAACCGACNNNCTAGCGTTAC | 4436 | TGCAGGACCAGAGAATTCGAATA CAGAGTGAGTNNNCTAGCGTTAC | 4676 | TGCAGGACCAGAGAATTCGAATA CAGATCGATCNNNCTAGCGTTAC | 4916 |
| TGCAGGACCAGAGAATTCGAATA CATCTATAGANNNCTAGCGTTAC | 4437 | TGCAGGACCAGAGAATTCGAATA CACACTACTANNNCTAGCGTTAC | 4677 | TGCAGGACCAGAGAATTCGAATA CAACGCCGTCNNNCTAGCGTTAC | 4917 |
| TGCAGGACCAGAGAATTCGAATA CAGGTGAGGCNNNCTAGCGTTAC | 4438 | TGCAGGACCAGAGAATTCGAATA CACCTTTGGTNNNCTAGCGTTAC | 4678 | TGCAGGACCAGAGAATTCGAATA CATCTCGAGANNNCTAGCGTTAC | 4918 |
| TGCAGGACCAGAGAATTCGAATA CACATACTCCNNNCTAGCGTTAC | 4439 | TGCAGGACCAGAGAATTCGAATA CATTCACACCNNNCTAGCGTTAC | 4679 | TGCAGGACCAGAGAATTCGAATA CAATTGGCACNNNCTAGCGTTAC | 4919 |
| TGCAGGACCAGAGAATTCGAATA CATAAGAGTANNNCTAGCGTTAC | 4440 | TGCAGGACCAGAGAATTCGAATA CAGTTATCCNNNCTAGCGTTAC | 4680 | TGCAGGACCAGAGAATTCGAATA CACGCCGAGTNNNCTAGCGTTAC | 4920 |
| TGCAGGACCAGAGAATTCGAATA CAGTGTGAGANNNCTAGCGTTAC | 4441 | TGCAGGACCAGAGAATTCGAATA CAAAACTTGTNNNCTAGCGTTAC | 4681 | TGCAGGACCAGAGAATTCGAATA CACTTCAGCTNNNCTAGCGTTAC | 4921 |
| TGCAGGACCAGAGAATTCGAATA CATTCCCGATNNNCTAGCGTTAC | 4442 | TGCAGGACCAGAGAATTCGAATA CACAACCCAANNNCTAGCGTTAC | 4682 | TGCAGGACCAGAGAATTCGAATA CAAAATAAGCNNNCTAGCGTTAC | 4922 |
| TGCAGGACCAGAGAATTCGAATA CAAGTACGAGNNNCTAGCGTTAC | 4443 | TGCAGGACCAGAGAATTCGAATA CAGTTCACGANNNCTAGCGTTAC | 4683 | TGCAGGACCAGAGAATTCGAATA CAGCCTAAGTNNNCTAGCGTTAC | 4923 |
| TGCAGGACCAGAGAATTCGAATA CAGGTGAACANNNCTAGCGTTAC | 4444 | TGCAGGACCAGAGAATTCGAATA CACGTCTACTNNNCTAGCGTTAC | 4684 | TGCAGGACCAGAGAATTCGAATA CAGATGTTCGNNNCTAGCGTTAC | 4924 |
| TGCAGGACCAGAGAATTCGAATA CACACTAGCANNNCTAGCGTTAC | 4445 | TGCAGGACCAGAGAATTCGAATA CATCAACAGCNNNCTAGCGTTAC | 4685 | TGCAGGACCAGAGAATTCGAATA CAAACGAGGTNNNCTAGCGTTAC | 4925 |
| TGCAGGACCAGAGAATTCGAATA CAAGCAGAACNNNCTAGCGTTAC | 4446 | TGCAGGACCAGAGAATTCGAATA CATTGAGTCGNNNCTAGCGTTAC | 4686 | TGCAGGACCAGAGAATTCGAATA CAATAGACAANNNCTAGCGTTAC | 4926 |
| TGCAGGACCAGAGAATTCGAATA CATTTTAAANNNNCTAGCGTTAC | 4447 | TGCAGGACCAGAGAATTCGAATA CAGCATCTGANNNCTAGCGTTAC | 4687 | TGCAGGACCAGAGAATTCGAATA CATATTTGGANNNCTAGCGTTAC | 4927 |
| TGCAGGACCAGAGAATTCGAATA CACTTCGAGANNNCTAGCGTTAC | 4448 | TGCAGGACCAGAGAATTCGAATA CATGGAGTTNNNCTAGCGTTAC | 4688 | TGCAGGACCAGAGAATTCGAATA CATCCGTGTTNNNCTAGCGTTAC | 4928 |
| TGCAGGACCAGAGAATTCGAATA CATGCAATGCNNNGATCGACATG | 4449 | TGCAGGACCAGAGAATTCGAATA CAGATCTCTCNNNGATCGACATG | 4689 | TGCAGGACCAGAGAATTCGAATA CATCCTCGATNNNGATCGACATG | 4929 |
| TGCAGGACCAGAGAATTCGAATA CAGACGCCACNNNGATCGACATG | 4450 | TGCAGGACCAGAGAATTCGAATA CAGAGCGCANNNGATCGACATG | 4690 | TGCAGGACCAGAGAATTCGAATA CATTTGGAGCNNNGATCGACATG | 4930 |
| TGCAGGACCAGAGAATTCGAATA CAGTTTTTCANNNGATCGACATG | 4451 | TGCAGGACCAGAGAATTCGAATA CACTCTCTAGNNNGATCGACATG | 4691 | TGCAGGACCAGAGAATTCGAATA CACTTCCACANNNGATCGACATG | 4931 |
| TGCAGGACCAGAGAATTCGAATA CAGTTTTATCNNNGATCGACATG | 4452 | TGCAGGACCAGAGAATTCGAATA CACGTGGCGTNNNGATCGACATG | 4692 | TGCAGGACCAGAGAATTCGAATA CAAATTTGCANNNGATCGACATG | 4932 |
| TGCAGGACCAGAGAATTCGAATA CAACACCGGCNNNGATCGACATG | 4453 | TGCAGGACCAGAGAATTCGAATA CAAGCTAGTCNNNGATCGACATG | 4693 | TGCAGGACCAGAGAATTCGAATA CAAATCTGATNNNGATCGACATG | 4933 |
| TGCAGGACCAGAGAATTCGAATA CACGCTTTACNNNGATCGACATG | 4454 | TGCAGGACCAGAGAATTCGAATA CAGCTATGTGNNNGATCGACATG | 4694 | TGCAGGACCAGAGAATTCGAATA CATCCACTTGNNNGATCGACATG | 4934 |
| TGCAGGACCAGAGAATTCGAATA CAGTAAATGANNNGATCGACATG | 4455 | TGCAGGACCAGAGAATTCGAATA CATCTGCTTGNNNGATCGACATG | 4695 | TGCAGGACCAGAGAATTCGAATA CATGGTTAGCNNNGATCGACATG | 4935 |
| TGCAGGACCAGAGAATTCGAATA CATTTGAAGTNNNGATCGACATG | 4456 | TGCAGGACCAGAGAATTCGAATA CAGTACGCTANNNGATCGACATG | 4696 | TGCAGGACCAGAGAATTCGAATA CACTGTAACGNNNGATCGACATG | 4936 |
| TGCAGGACCAGAGAATTCGAATA CACACCACTTNNNGATCGACATG | 4457 | TGCAGGACCAGAGAATTCGAATA CAGACCCGTGNNNGATCGACATG | 4697 | TGCAGGACCAGAGAATTCGAATA CATATTAGTGNNNGATCGACATG | 4937 |
| TGCAGGACCAGAGAATTCGAATA CATGTAAGAANNNGATCGACATG | 4458 | TGCAGGACCAGAGAATTCGAATA CAGTCATGACNNNGATCGACATG | 4698 | TGCAGGACCAGAGAATTCGAATA CATGCACATGNNNGATCGACATG | 4938 |
| TGCAGGACCAGAGAATTCGAATA CACGCTGAATNNNGATCGACATG | 4459 | TGCAGGACCAGAGAATTCGAATA CACGCTAGATNNNGATCGACATG | 4699 | TGCAGGACCAGAGAATTCGAATA CAACCTTCGTNNNGATCGACATG | 4939 |
| TGCAGGACCAGAGAATTCGAATA CACTTATTGTNNNGATCGACATG | 4460 | TGCAGGACCAGAGAATTCGAATA CAGTAATGAANNNGATCGACATG | 4700 | TGCAGGACCAGAGAATTCGAATA CAGCGTGCACNNNGATCGACATG | 4940 |

FIG. 18E

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CACGTGAGAANNNGATCGACATG | 4461 | TGCAGGACCAGAGAATTCGAATA CATCGTATTTNNNGATCGACATG | 4701 | TGCAGGACCAGAGAATTCGAATA CACGGCCTTTANNNGATCGACATG | 4941 |
| TGCAGGACCAGAGAATTCGAATA CAACCGGCTGNNNGATCGACATG | 4462 | TGCAGGACCAGAGAATTCGAATA CACACGTACANNNGATCGACATG | 4702 | TGCAGGACCAGAGAATTCGAATA CATTGTAAACNNNGATCGACATG | 4942 |
| TGCAGGACCAGAGAATTCGAATA CACAAAATTCNNNGATCGACATG | 4463 | TGCAGGACCAGAGAATTCGAATA CATGACTAATNNNGATCGACATG | 4703 | TGCAGGACCAGAGAATTCGAATA CAAACGCAAGNNNGATCGACATG | 4943 |
| TGCAGGACCAGAGAATTCGAATA CAACTAAAGANNNGATCGACATG | 4464 | TGCAGGACCAGAGAATTCGAATA CACTACCGCCNNNGATCGACATG | 4704 | TGCAGGACCAGAGAATTCGAATA CAGTAATCATNNNGATCGACATG | 4944 |
| TGCAGGACCAGAGAATTCGAATA CATAGTCTCCNNNGATCGACATG | 4465 | TGCAGGACCAGAGAATTCGAATA CAGGCACTTANNNGATCGACATG | 4705 | TGCAGGACCAGAGAATTCGAATA CAGTCTGCTTNNNGATCGACATG | 4945 |
| TGCAGGACCAGAGAATTCGAATA CACTAACATANNNGATCGACATG | 4466 | TGCAGGACCAGAGAATTCGAATA CATCCTTAGCNNNGATCGACATG | 4706 | TGCAGGACCAGAGAATTCGAATA CAGATGGTTCNNNGATCGACATG | 4946 |
| TGCAGGACCAGAGAATTCGAATA CATGCACGCGNNNGATCGACATG | 4467 | TGCAGGACCAGAGAATTCGAATA CAGCTATAGCNNNGATCGACATG | 4707 | TGCAGGACCAGAGAATTCGAATA CACTTGGCAANNNGATCGACATG | 4947 |
| TGCAGGACCAGAGAATTCGAATA CAACTGGAAGNNNGATCGACATG | 4468 | TGCAGGACCAGAGAATTCGAATA CAAATGAACANNNGATCGACATG | 4708 | TGCAGGACCAGAGAATTCGAATA CATACCGAACNNNGATCGACATG | 4948 |
| TGCAGGACCAGAGAATTCGAATA CAGCAATCCANNNGATCGACATG | 4469 | TGCAGGACCAGAGAATTCGAATA CAGTAGTAAANNNGATCGACATG | 4709 | TGCAGGACCAGAGAATTCGAATA CAGTGAGTGANNNGATCGACATG | 4949 |
| TGCAGGACCAGAGAATTCGAATA CAAATCCTAANNNGATCGACATG | 4470 | TGCAGGACCAGAGAATTCGAATA CATAGTTCGNNNGATCGACATG | 4710 | TGCAGGACCAGAGAATTCGAATA CACAGGTGAANNNGATCGACATG | 4950 |
| TGCAGGACCAGAGAATTCGAATA CAAAGCGGTANNNGATCGACATG | 4471 | TGCAGGACCAGAGAATTCGAATA CAGTTGTGACNNNGATCGACATG | 4711 | TGCAGGACCAGAGAATTCGAATA CAAGGTCAGANNNGATCGACATG | 4951 |
| TGCAGGACCAGAGAATTCGAATA CAGTCAGAGANNNGATCGACATG | 4472 | TGCAGGACCAGAGAATTCGAATA CACGCGTAGCNNNGATCGACATG | 4712 | TGCAGGACCAGAGAATTCGAATA CAGAGCGTTTNNNGATCGACATG | 4952 |
| TGCAGGACCAGAGAATTCGAATA CATCGGATGTNNNGATCGACATG | 4473 | TGCAGGACCAGAGAATTCGAATA CACTATGTGGNNNGATCGACATG | 4713 | TGCAGGACCAGAGAATTCGAATA CAGAAATGGCNNNGATCGACATG | 4953 |
| TGCAGGACCAGAGAATTCGAATA CATCACGCTTNNNGATCGACATG | 4474 | TGCAGGACCAGAGAATTCGAATA CATTCGGCGTANNNGATCGACATG | 4714 | TGCAGGACCAGAGAATTCGAATA CAGAGTGTCTNNNGATCGACATG | 4954 |
| TGCAGGACCAGAGAATTCGAATA CATTAGGTGCNNNGATCGACATG | 4475 | TGCAGGACCAGAGAATTCGAATA CAATTATCCTNNNGATCGACATG | 4715 | TGCAGGACCAGAGAATTCGAATA CAAAACATCTNNNGATCGACATG | 4955 |
| TGCAGGACCAGAGAATTCGAATA CATCCGACGGNNNGATCGACATG | 4476 | TGCAGGACCAGAGAATTCGAATA CACTTTGAAANNNGATCGACATG | 4716 | TGCAGGACCAGAGAATTCGAATA CATAAAGCTTNNNGATCGACATG | 4956 |
| TGCAGGACCAGAGAATTCGAATA CAAAAGCAGCNNNGATCGACATG | 4477 | TGCAGGACCAGAGAATTCGAATA CACTAGTACGNNNGATCGACATG | 4717 | TGCAGGACCAGAGAATTCGAATA CATTAGTGCGNNNGATCGACATG | 4957 |
| TGCAGGACCAGAGAATTCGAATA CAGTGCCGGTNNNGATCGACATG | 4478 | TGCAGGACCAGAGAATTCGAATA CATCCCACATNNNGATCGACATG | 4718 | TGCAGGACCAGAGAATTCGAATA CAGTTCGCCCNNNGATCGACATG | 4958 |
| TGCAGGACCAGAGAATTCGAATA CAACGATATTNNNGATCGACATG | 4479 | TGCAGGACCAGAGAATTCGAATA CAGTATCGACNNNGATCGACATG | 4719 | TGCAGGACCAGAGAATTCGAATA CAGTGACCTANNNGATCGACATG | 4959 |
| TGCAGGACCAGAGAATTCGAATA CAACAACAGGNNNGATCGACATG | 4480 | TGCAGGACCAGAGAATTCGAATA CAGGCCTCAGNNNGATCGACATG | 4720 | TGCAGGACCAGAGAATTCGAATA CAGGACAATGNNNGATCGACATG | 4960 |
| TGCAGGACCAGAGAATTCGAATA CACTCCGAAANNNGATCGACATG | 4481 | TGCAGGACCAGAGAATTCGAATA CACGGCTTANNNGATCGACATG | 4721 | TGCAGGACCAGAGAATTCGAATA CATATAGGAANNNGATCGACATG | 4961 |
| TGCAGGACCAGAGAATTCGAATA CATCAAGCCANNNGATCGACATG | 4482 | TGCAGGACCAGAGAATTCGAATA CACATAGCACNNNGATCGACATG | 4722 | TGCAGGACCAGAGAATTCGAATA CACTAGCGGCNNNGATCGACATG | 4962 |
| TGCAGGACCAGAGAATTCGAATA CACATTAACANNNGATCGACATG | 4483 | TGCAGGACCAGAGAATTCGAATA CACCCACTTTGNNNGATCGACATG | 4723 | TGCAGGACCAGAGAATTCGAATA CAGCGTTTAGNNNGATCGACATG | 4963 |
| TGCAGGACCAGAGAATTCGAATA CAAACACGAGNNNGATCGACATG | 4484 | TGCAGGACCAGAGAATTCGAATA CATGTGATGCNNNGATCGACATG | 4724 | TGCAGGACCAGAGAATTCGAATA CAGTATGTCGNNNGATCGACATG | 4964 |
| TGCAGGACCAGAGAATTCGAATA CATCCATCACNNNGATCGACATG | 4485 | TGCAGGACCAGAGAATTCGAATA CAATCGCTAGNNNGATCGACATG | 4725 | TGCAGGACCAGAGAATTCGAATA CACATGTGACNNNGATCGACATG | 4965 |
| TGCAGGACCAGAGAATTCGAATA CAGTCGCACGNNNGATCGACATG | 4486 | TGCAGGACCAGAGAATTCGAATA CAGAATTAGANNNGATCGACATG | 4726 | TGCAGGACCAGAGAATTCGAATA CAATCAAAGNNNGATCGACATG | 4966 |
| TGCAGGACCAGAGAATTCGAATA CATGGCACGCNNNGATCGACATG | 4487 | TGCAGGACCAGAGAATTCGAATA CAGCGGTCGTNNNGATCGACATG | 4727 | TGCAGGACCAGAGAATTCGAATA CAATAAACTCNNNGATCGACATG | 4967 |
| TGCAGGACCAGAGAATTCGAATA CATTTCAGAANNNGATCGACATG | 4488 | TGCAGGACCAGAGAATTCGAATA CAAATTGCATNNNGATCGACATG | 4728 | TGCAGGACCAGAGAATTCGAATA CACCGGATCGNNNGATCGACATG | 4968 |
| TGCAGGACCAGAGAATTCGAATA CATACGTCTCNNNGATCGACATG | 4489 | TGCAGGACCAGAGAATTCGAATA CATGGAACCTNNNGATCGACATG | 4729 | TGCAGGACCAGAGAATTCGAATA CACCCGCTAGNNNGATCGACATG | 4969 |
| TGCAGGACCAGAGAATTCGAATA CACCGATCTTNNNGATCGACATG | 4490 | TGCAGGACCAGAGAATTCGAATA CAAGCGCATTNNNGATCGACATG | 4730 | TGCAGGACCAGAGAATTCGAATA CACTGTGGTANNNGATCGACATG | 4970 |
| TGCAGGACCAGAGAATTCGAATA CAATTAAGCTNNNGATCGACATG | 4491 | TGCAGGACCAGAGAATTCGAATA CATTCCCTCTNNNGATCGACATG | 4731 | TGCAGGACCAGAGAATTCGAATA CAGAACGTGANNNGATCGACATG | 4971 |
| TGCAGGACCAGAGAATTCGAATA CAAACTTCCCNNNGATCGACATG | 4492 | TGCAGGACCAGAGAATTCGAATA CAATTGTCGNNNGATCGACATG | 4732 | TGCAGGACCAGAGAATTCGAATA CACCGGCTCANNNGATCGACATG | 4972 |
| TGCAGGACCAGAGAATTCGAATA CAGTCGCTTTNNNGATCGACATG | 4493 | TGCAGGACCAGAGAATTCGAATA CATAATGCGCNNNGATCGACATG | 4733 | TGCAGGACCAGAGAATTCGAATA CAGGCATCATNNNGATCGACATG | 4973 |

FIG. 18F

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CAGCCAGTATNNNGATCGACATG | 4494 | TGCAGGACCAGAGAATTCGAATA CAACGCCATTGNNNGATCGACATG | 4734 | TGCAGGACCAGAGAATTCGAATA CACCGCAGGTNNNGATCGACATG | 4974 |
| TGCAGGACCAGAGAATTCGAATA CAGAGAAAAANNNGATCGACATG | 4495 | TGCAGGACCAGAGAATTCGAATA CATGTCCGTANNNGATCGACATG | 4735 | TGCAGGACCAGAGAATTCGAATA CATCCTACTGNNNGATCGACATG | 4975 |
| TGCAGGACCAGAGAATTCGAATA CAATAGCCCANNNGATCGACATG | 4496 | TGCAGGACCAGAGAATTCGAATA CATTTTCAACNNNGATCGACATG | 4736 | TGCAGGACCAGAGAATTCGAATA CATCCCGACCNNNGATCGACATG | 4976 |
| TGCAGGACCAGAGAATTCGAATA CACACGTCCCNNNGATCGACATG | 4497 | TGCAGGACCAGAGAATTCGAATA CATAAGTACTNNNGATCGACATG | 4737 | TGCAGGACCAGAGAATTCGAATA CATGTAGGTCNNNGATCGACATG | 4977 |
| TGCAGGACCAGAGAATTCGAATA CAAAGTTATCNNNGATCGACATG | 4498 | TGCAGGACCAGAGAATTCGAATA CAAATTAGTCNNNGATCGACATG | 4738 | TGCAGGACCAGAGAATTCGAATA CACGGCGCTANNNGATCGACATG | 4978 |
| TGCAGGACCAGAGAATTCGAATA CACTTTTCGGNNNGATCGACATG | 4499 | TGCAGGACCAGAGAATTCGAATA CAGGAAATATNNNGATCGACATG | 4739 | TGCAGGACCAGAGAATTCGAATA CACCTATTTANNNGATCGACATG | 4979 |
| TGCAGGACCAGAGAATTCGAATA CACAATCGTGNNNGATCGACATG | 4500 | TGCAGGACCAGAGAATTCGAATA CATTTTTTAANNNGATCGACATG | 4740 | TGCAGGACCAGAGAATTCGAATA CAGAACAAGCNNNGATCGACATG | 4980 |
| TGCAGGACCAGAGAATTCGAATA CAGGACGTAANNNGATCGACATG | 4501 | TGCAGGACCAGAGAATTCGAATA CACACGTAACNNNGATCGACATG | 4741 | TGCAGGACCAGAGAATTCGAATA CATCCCATTGNNNGATCGACATG | 4981 |
| TGCAGGACCAGAGAATTCGAATA CACCCGAACGNNNGATCGACATG | 4502 | TGCAGGACCAGAGAATTCGAATA CAGTTTCCGTNNNGATCGACATG | 4742 | TGCAGGACCAGAGAATTCGAATA CATACTGTGGNNNGATCGACATG | 4982 |
| TGCAGGACCAGAGAATTCGAATA CATCCGTATCNNNGATCGACATG | 4503 | TGCAGGACCAGAGAATTCGAATA CAAGTACTANNNGATCGACATG | 4743 | TGCAGGACCAGAGAATTCGAATA CAGCCGCTTANNNGATCGACATG | 4983 |
| TGCAGGACCAGAGAATTCGAATA CATTTCGTTANNNGATCGACATG | 4504 | TGCAGGACCAGAGAATTCGAATA CATCTAGTGGNNNGATCGACATG | 4744 | TGCAGGACCAGAGAATTCGAATA CAGCCTCCCANNNGATCGACATG | 4984 |
| TGCAGGACCAGAGAATTCGAATA CATGCTACAGNNNGATCGACATG | 4505 | TGCAGGACCAGAGAATTCGAATA CAGAGTACAGNNNGATCGACATG | 4745 | TGCAGGACCAGAGAATTCGAATA CACACGATACNNNGATCGACATG | 4985 |
| TGCAGGACCAGAGAATTCGAATA CAGTTACTTTNNNGATCGACATG | 4506 | TGCAGGACCAGAGAATTCGAATA CAACTCCAGANNNGATCGACATG | 4746 | TGCAGGACCAGAGAATTCGAATA CAGTGTCAACNNNGATCGACATG | 4986 |
| TGCAGGACCAGAGAATTCGAATA CAAATGCCTGNNNGATCGACATG | 4507 | TGCAGGACCAGAGAATTCGAATA CAAAACACAANNNGATCGACATG | 4747 | TGCAGGACCAGAGAATTCGAATA CATACGCCGGNNNGATCGACATG | 4987 |
| TGCAGGACCAGAGAATTCGAATA CACCAGGCACNNNGATCGACATG | 4508 | TGCAGGACCAGAGAATTCGAATA CAGCCGCAACNNNGATCGACATG | 4748 | TGCAGGACCAGAGAATTCGAATA CAAATCCGACNNNGATCGACATG | 4988 |
| TGCAGGACCAGAGAATTCGAATA CATGGCGACCNNNTGCATCAGGT | 4509 | TGCAGGACCAGAGAATTCGAATA CAGATCTTAANNNTGCATCAGGT | 4749 | TGCAGGACCAGAGAATTCGAATA CAGCCGCCGGNNNTGCATCAGGT | 4989 |
| TGCAGGACCAGAGAATTCGAATA CAAAGAGGCTNNNTGCATCAGGT | 4510 | TGCAGGACCAGAGAATTCGAATA CACTAGAGTCNNNTGCATCAGGT | 4750 | TGCAGGACCAGAGAATTCGAATA CACCTGCCGTNNNTGCATCAGGT | 4990 |
| TGCAGGACCAGAGAATTCGAATA CATTACCCACNNNTGCATCAGGT | 4511 | TGCAGGACCAGAGAATTCGAATA CAGCATTCTCNNNTGCATCAGGT | 4751 | TGCAGGACCAGAGAATTCGAATA CACGTTACCTNNNTGCATCAGGT | 4991 |
| TGCAGGACCAGAGAATTCGAATA CATGCGGATTNNNTGCATCAGGT | 4512 | TGCAGGACCAGAGAATTCGAATA CAGCAGCCACNNNTGCATCAGGT | 4752 | TGCAGGACCAGAGAATTCGAATA CACGATTAGCNNNTGCATCAGGT | 4992 |
| TGCAGGACCAGAGAATTCGAATA CACAGGTTGTNNNTGCATCAGGT | 4513 | TGCAGGACCAGAGAATTCGAATA CAAGCTGCGCNNNTGCATCAGGT | 4753 | TGCAGGACCAGAGAATTCGAATA CAAACCTAATNNNTGCATCAGGT | 4993 |
| TGCAGGACCAGAGAATTCGAATA CAAAACATAGANNNTGCATCAGGT | 4514 | TGCAGGACCAGAGAATTCGAATA CACCCGCTACNNNTGCATCAGGT | 4754 | TGCAGGACCAGAGAATTCGAATA CAATCGGCTACNNNTGCATCAGGT | 4994 |
| TGCAGGACCAGAGAATTCGAATA CAGAAATGATNNNTGCATCAGGT | 4515 | TGCAGGACCAGAGAATTCGAATA CACAAGGCAANNNTGCATCAGGT | 4755 | TGCAGGACCAGAGAATTCGAATA CAGGAACCCCNNNTGCATCAGGT | 4995 |
| TGCAGGACCAGAGAATTCGAATA CATGTGCTGANNNTGCATCAGGT | 4516 | TGCAGGACCAGAGAATTCGAATA CAGATGTTATNNNTGCATCAGGT | 4756 | TGCAGGACCAGAGAATTCGAATA CATCCACACGNNNTGCATCAGGT | 4996 |
| TGCAGGACCAGAGAATTCGAATA CAAGGCAGATNNNTGCATCAGGT | 4517 | TGCAGGACCAGAGAATTCGAATA CACGGTATTGNNNTGCATCAGGT | 4757 | TGCAGGACCAGAGAATTCGAATA CACTATTGAANNNTGCATCAGGT | 4997 |
| TGCAGGACCAGAGAATTCGAATA CATAGGTTATNNNTGCATCAGGT | 4518 | TGCAGGACCAGAGAATTCGAATA CAGTATTTAGNNNTGCATCAGGT | 4758 | TGCAGGACCAGAGAATTCGAATA CACGCGATATNNNTGCATCAGGT | 4998 |
| TGCAGGACCAGAGAATTCGAATA CATTTTTGTGNNNTGCATCAGGT | 4519 | TGCAGGACCAGAGAATTCGAATA CAGGATCAGANNNTGCATCAGGT | 4759 | TGCAGGACCAGAGAATTCGAATA CACTTATGTTNNNTGCATCAGGT | 4999 |
| TGCAGGACCAGAGAATTCGAATA CAAAACAAGTNNNTGCATCAGGT | 4520 | TGCAGGACCAGAGAATTCGAATA CAATCGAAAANNNTGCATCAGGT | 4760 | TGCAGGACCAGAGAATTCGAATA CAATTTGGTANNNTGCATCAGGT | 5000 |
| TGCAGGACCAGAGAATTCGAATA CACGTGGTTANNNTGCATCAGGT | 4521 | TGCAGGACCAGAGAATTCGAATA CAGCCATTCNNNTGCATCAGGT | 4761 | TGCAGGACCAGAGAATTCGAATA CAAGGCAACANNNTGCATCAGGT | 5001 |
| TGCAGGACCAGAGAATTCGAATA CACTTTCGACNNNTGCATCAGGT | 4522 | TGCAGGACCAGAGAATTCGAATA CATCAGACCANNNTGCATCAGGT | 4762 | TGCAGGACCAGAGAATTCGAATA CAGACCTTTCNNNTGCATCAGGT | 5002 |
| TGCAGGACCAGAGAATTCGAATA CATAGACGTCNNNTGCATCAGGT | 4523 | TGCAGGACCAGAGAATTCGAATA CATTTGTTCANNNTGCATCAGGT | 4763 | TGCAGGACCAGAGAATTCGAATA CAGGAACCAANNNTGCATCAGGT | 5003 |
| TGCAGGACCAGAGAATTCGAATA CATCTAGTCNNNTGCATCAGGT | 4524 | TGCAGGACCAGAGAATTCGAATA CAACCCTATCNNNTGCATCAGGT | 4764 | TGCAGGACCAGAGAATTCGAATA CACGTGTAACNNNTGCATCAGGT | 5004 |
| TGCAGGACCAGAGAATTCGAATA CAAACAGATNNNTGCATCAGGT | 4525 | TGCAGGACCAGAGAATTCGAATA CAAAAAGCCGNNNTGCATCAGGT | 4765 | TGCAGGACCAGAGAATTCGAATA CACAGATCCANNNTGCATCAGGT | 5005 |
| TGCAGGACCAGAGAATTCGAATA CATAATGAAGNNNTGCATCAGGT | 4526 | TGCAGGACCAGAGAATTCGAATA CAGAGTGCGCNNNTGCATCAGGT | 4766 | TGCAGGACCAGAGAATTCGAATA CACCAGCACGNNNTGCATCAGGT | 5006 |

FIG. 18G

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CATATTCGCCNNNTGCATCAGGT | 4527 | TGCAGGACCAGAGAATTCGAATA CAATCATACANNNTGCATCAGGT | 4767 | TGCAGGACCAGAGAATTCGAATA CACGAGTCCGNNNTGCATCAGGT | 5007 |
| TGCAGGACCAGAGAATTCGAATA CATTGCACGANNNTGCATCAGGT | 4528 | TGCAGGACCAGAGAATTCGAATA CACAGATGAGNNNTGCATCAGGT | 4768 | TGCAGGACCAGAGAATTCGAATA CAGTCGAATCNNNTGCATCAGGT | 5008 |
| TGCAGGACCAGAGAATTCGAATA CAACTACTAANNNTGCATCAGGT | 4529 | TGCAGGACCAGAGAATTCGAATA CACAGCTTAGNNNTGCATCAGGT | 4769 | TGCAGGACCAGAGAATTCGAATA CATCCATAAANNNTGCATCAGGT | 5009 |
| TGCAGGACCAGAGAATTCGAATA CAACTCATAANNNTGCATCAGGT | 4530 | TGCAGGACCAGAGAATTCGAATA CAACTTCTTANNNTGCATCAGGT | 4770 | TGCAGGACCAGAGAATTCGAATA CAGTCCCACCNNNTGCATCAGGT | 5010 |
| TGCAGGACCAGAGAATTCGAATA CAAGGACTGANNNTGCATCAGGT | 4531 | TGCAGGACCAGAGAATTCGAATA CACAACAGAGNNNTGCATCAGGT | 4771 | TGCAGGACCAGAGAATTCGAATA CATGGTTGACNNNTGCATCAGGT | 5011 |
| TGCAGGACCAGAGAATTCGAATA CACACATCCTNNNTGCATCAGGT | 4532 | TGCAGGACCAGAGAATTCGAATA CACGTAGATCNNNTGCATCAGGT | 4772 | TGCAGGACCAGAGAATTCGAATA CAAGACAACGNNNTGCATCAGGT | 5012 |
| TGCAGGACCAGAGAATTCGAATA CAATAGCGAGNNNTGCATCAGGT | 4533 | TGCAGGACCAGAGAATTCGAATA CACCTCCCGANNNTGCATCAGGT | 4773 | TGCAGGACCAGAGAATTCGAATA CAATATTCAGNNNTGCATCAGGT | 5013 |
| TGCAGGACCAGAGAATTCGAATA CAAGGAGTCNNNTGCATCAGGT | 4534 | TGCAGGACCAGAGAATTCGAATA CAGACTTTGGNNNTGCATCAGGT | 4774 | TGCAGGACCAGAGAATTCGAATA CAGAGCAACTNNNTGCATCAGGT | 5014 |
| TGCAGGACCAGAGAATTCGAATA CAGAAGCCTNNNTGCATCAGGT | 4535 | TGCAGGACCAGAGAATTCGAATA CAGAGAACATCNNNTGCATCAGGT | 4775 | TGCAGGACCAGAGAATTCGAATA CAGAGAGAACNNNTGCATCAGGT | 5015 |
| TGCAGGACCAGAGAATTCGAATA CACCCGCTTCNNNTGCATCAGGT | 4536 | TGCAGGACCAGAGAATTCGAATA CACAGCATCANNNTGCATCAGGT | 4776 | TGCAGGACCAGAGAATTCGAATA CAGCAACAAGNNNTGCATCAGGT | 5016 |
| TGCAGGACCAGAGAATTCGAATA CAAGAAACCGNNNTGCATCAGGT | 4537 | TGCAGGACCAGAGAATTCGAATA CACTTCTGACNNNTGCATCAGGT | 4777 | TGCAGGACCAGAGAATTCGAATA CACTAAACCGNNNTGCATCAGGT | 5017 |
| TGCAGGACCAGAGAATTCGAATA CAGACATCTGNNNTGCATCAGGT | 4538 | TGCAGGACCAGAGAATTCGAATA CATCCCGTTANNNTGCATCAGGT | 4778 | TGCAGGACCAGAGAATTCGAATA CAGGAGGTCGNNNTGCATCAGGT | 5018 |
| TGCAGGACCAGAGAATTCGAATA CAACGCCCTCNNNTGCATCAGGT | 4539 | TGCAGGACCAGAGAATTCGAATA CATTTCCATANNNTGCATCAGGT | 4779 | TGCAGGACCAGAGAATTCGAATA CACGCGCGTANNNTGCATCAGGT | 5019 |
| TGCAGGACCAGAGAATTCGAATA CAGTCACCGGNNNTGCATCAGGT | 4540 | TGCAGGACCAGAGAATTCGAATA CACGTGCGACNNNTGCATCAGGT | 4780 | TGCAGGACCAGAGAATTCGAATA CACCGAGTGCNNNTGCATCAGGT | 5020 |
| TGCAGGACCAGAGAATTCGAATA CAAGAGCGATNNNTGCATCAGGT | 4541 | TGCAGGACCAGAGAATTCGAATA CAACGCTGGCNNNTGCATCAGGT | 4781 | TGCAGGACCAGAGAATTCGAATA CAGTTCAAGCNNNTGCATCAGGT | 5021 |
| TGCAGGACCAGAGAATTCGAATA CAATGGCTTGNNNTGCATCAGGT | 4542 | TGCAGGACCAGAGAATTCGAATA CAGAGATTCCNNNTGCATCAGGT | 4782 | TGCAGGACCAGAGAATTCGAATA CACAGCCCGANNNTGCATCAGGT | 5022 |
| TGCAGGACCAGAGAATTCGAATA CACCTGCAAANNNTGCATCAGGT | 4543 | TGCAGGACCAGAGAATTCGAATA CAGAGGACTANNNTGCATCAGGT | 4783 | TGCAGGACCAGAGAATTCGAATA CACCTTGACTNNNTGCATCAGGT | 5023 |
| TGCAGGACCAGAGAATTCGAATA CAGTCGAACTNNNTGCATCAGGT | 4544 | TGCAGGACCAGAGAATTCGAATA CATTGATTAGNNNTGCATCAGGT | 4784 | TGCAGGACCAGAGAATTCGAATA CAGACGCAAANNNTGCATCAGGT | 5024 |
| TGCAGGACCAGAGAATTCGAATA CATGTGGAGANNNTGCATCAGGT | 4545 | TGCAGGACCAGAGAATTCGAATA CACATGCATGNNNTGCATCAGGT | 4785 | TGCAGGACCAGAGAATTCGAATA CATGATCCTCNNNTGCATCAGGT | 5025 |
| TGCAGGACCAGAGAATTCGAATA CAAACGTGCTNNNTGCATCAGGT | 4546 | TGCAGGACCAGAGAATTCGAATA CATTGACCCTNNNTGCATCAGGT | 4786 | TGCAGGACCAGAGAATTCGAATA CAAGAAATTGNNNTGCATCAGGT | 5026 |
| TGCAGGACCAGAGAATTCGAATA CAAAGATTGANNNTGCATCAGGT | 4547 | TGCAGGACCAGAGAATTCGAATA CAGGCCACTGNNNTGCATCAGGT | 4787 | TGCAGGACCAGAGAATTCGAATA CAGTGTGGCCNNNTGCATCAGGT | 5027 |
| TGCAGGACCAGAGAATTCGAATA CAACGTTATANNNTGCATCAGGT | 4548 | TGCAGGACCAGAGAATTCGAATA CATTCCTCTCNNNTGCATCAGGT | 4788 | TGCAGGACCAGAGAATTCGAATA CACATGTAGCNNNTGCATCAGGT | 5028 |
| TGCAGGACCAGAGAATTCGAATA CACCGCATAANNNTGCATCAGGT | 4549 | TGCAGGACCAGAGAATTCGAATA CAGCATTCAGNNNTGCATCAGGT | 4789 | TGCAGGACCAGAGAATTCGAATA CATAGCCCCCNNNTGCATCAGGT | 5029 |
| TGCAGGACCAGAGAATTCGAATA CACGATTCCNNNTGCATCAGGT | 4550 | TGCAGGACCAGAGAATTCGAATA CAGTAACTTANNNTGCATCAGGT | 4790 | TGCAGGACCAGAGAATTCGAATA CAGTCTTGCTNNNTGCATCAGGT | 5030 |
| TGCAGGACCAGAGAATTCGAATA CAGTAAAACANNNTGCATCAGGT | 4551 | TGCAGGACCAGAGAATTCGAATA CAACTATGATNNNTGCATCAGGT | 4791 | TGCAGGACCAGAGAATTCGAATA CATGTAAGCCNNNTGCATCAGGT | 5031 |
| TGCAGGACCAGAGAATTCGAATA CAGGTGGTCCNNNTGCATCAGGT | 4552 | TGCAGGACCAGAGAATTCGAATA CAACTAAGAANNNTGCATCAGGT | 4792 | TGCAGGACCAGAGAATTCGAATA CAACAGAGACNNNTGCATCAGGT | 5032 |
| TGCAGGACCAGAGAATTCGAATA CAATGTCGTGNNNTGCATCAGGT | 4553 | TGCAGGACCAGAGAATTCGAATA CATAGGTTANNNTGCATCAGGT | 4793 | TGCAGGACCAGAGAATTCGAATA CAAGTTCAGCNNNTGCATCAGGT | 5033 |
| TGCAGGACCAGAGAATTCGAATA CACGTAATATNNNTGCATCAGGT | 4554 | TGCAGGACCAGAGAATTCGAATA CACCTCGTCGNNNTGCATCAGGT | 4794 | TGCAGGACCAGAGAATTCGAATA CACCTGCTTANNNTGCATCAGGT | 5034 |
| TGCAGGACCAGAGAATTCGAATA CAACTCGCTNNNTGCATCAGGT | 4555 | TGCAGGACCAGAGAATTCGAATA CAGGCTAGCCNNNTGCATCAGGT | 4795 | TGCAGGACCAGAGAATTCGAATA CAACACCTCTNNNTGCATCAGGT | 5035 |
| TGCAGGACCAGAGAATTCGAATA CACCATACGANNNTGCATCAGGT | 4556 | TGCAGGACCAGAGAATTCGAATA CAGGTTGTACNNNTGCATCAGGT | 4796 | TGCAGGACCAGAGAATTCGAATA CATATTGACCNNNTGCATCAGGT | 5036 |
| TGCAGGACCAGAGAATTCGAATA CACGGACAAANNNTGCATCAGGT | 4557 | TGCAGGACCAGAGAATTCGAATA CATAAAGCGGNNNTGCATCAGGT | 4797 | TGCAGGACCAGAGAATTCGAATA CAGATTGGTCNNNTGCATCAGGT | 5037 |
| TGCAGGACCAGAGAATTCGAATA CACGCTGTTNNNTGCATCAGGT | 4558 | TGCAGGACCAGAGAATTCGAATA CAAATCTTTCNNNTGCATCAGGT | 4798 | TGCAGGACCAGAGAATTCGAATA CAAAAGAAAGNNNTGCATCAGGT | 5038 |
| TGCAGGACCAGAGAATTCGAATA CACTCCCATANNNTGCATCAGGT | 4559 | TGCAGGACCAGAGAATTCGAATA CACCAAGGAANNNTGCATCAGGT | 4799 | TGCAGGACCAGAGAATTCGAATA CATAAAAATANNNTGCATCAGGT | 5039 |

FIG. 18H

| Pool-19 | SEQ ID NO: | Pool-20 | SEQ ID NO: | Pool-21 | SEQ ID NO: |
|---|---|---|---|---|---|
| TGCAGGACCAGAGAATTCGAATA CAGGCTTGCGNNNTGCATCAGGT | 4560 | TGCAGGACCAGAGAATTCGAATA CAACAAAGTNNNTGCATCAGGT | 4800 | TGCAGGACCAGAGAATTCGAATA CATGTCCAGANNNTGCATCAGGT | 5040 |
| TGCAGGACCAGAGAATTCGAATA CAAAAATTTCGNNNTGCATCAGGT | 4561 | TGCAGGACCAGAGAATTCGAATA CAGGCCCCGGNNNTGCATCAGGT | 4801 | TGCAGGACCAGAGAATTCGAATA CATTTGAGGCNNNTGCATCAGGT | 5041 |
| TGCAGGACCAGAGAATTCGAATA CATACCTAGGNNNTGCATCAGGT | 4562 | TGCAGGACCAGAGAATTCGAATA CAAACATGCCNNNTGCATCAGGT | 4802 | TGCAGGACCAGAGAATTCGAATA CACCATCCTANNNTGCATCAGGT | 5042 |
| TGCAGGACCAGAGAATTCGAATA CACACGCACGNNNTGCATCAGGT | 4563 | TGCAGGACCAGAGAATTCGAATA CATCGGAGTTNNNTGCATCAGGT | 4803 | TGCAGGACCAGAGAATTCGAATA CACTCCAGAANNNTGCATCAGGT | 5043 |
| TGCAGGACCAGAGAATTCGAATA CACATTGCAGNNNTGCATCAGGT | 4564 | TGCAGGACCAGAGAATTCGAATA CATAGCCGAANNNTGCATCAGGT | 4804 | TGCAGGACCAGAGAATTCGAATA CACAGATGGANNNTGCATCAGGT | 5044 |
| TGCAGGACCAGAGAATTCGAATA CAGCCATTAATNNNTGCATCAGGT | 4565 | TGCAGGACCAGAGAATTCGAATA CAGTCTACTCNNNTGCATCAGGT | 4805 | TGCAGGACCAGAGAATTCGAATA CATAATCCCCNNNTGCATCAGGT | 5045 |
| TGCAGGACCAGAGAATTCGAATA CAAGACGCCCNNNTGCATCAGGT | 4566 | TGCAGGACCAGAGAATTCGAATA CATTTGACCCNNNTGCATCAGGT | 4806 | TGCAGGACCAGAGAATTCGAATA CAAGGCGCTCNNNTGCATCAGGT | 5046 |
| TGCAGGACCAGAGAATTCGAATA CACACACGATNNNTGCATCAGGT | 4567 | TGCAGGACCAGAGAATTCGAATA CAAAGGGAGANNNTGCATCAGGT | 4807 | TGCAGGACCAGAGAATTCGAATA CAATTGTCAANNNTGCATCAGGT | 5047 |
| TGCAGGACCAGAGAATTCGAATA CATGATTGTANNNTGCATCAGGT | 4568 | TGCAGGACCAGAGAATTCGAATA CATTTCGCCANNNTGCATCAGGT | 4808 | TGCAGGACCAGAGAATTCGAATA CACGCGTTAANNNTGCATCAGGT | 5048 |

FIG. 19A

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CATTGATGCGNNNACGTATGCCA | 5049 | TGCAGGACCAGAGAATTCGAATA CATAACTAACNNNACGTATGCCA | 5289 | TGCAGGACCAGAGAATTCGAATA CAGTTGCGCGNNNACGTATGCCA | 5529 |
| TGCAGGACCAGAGAATTCGAATA CACCCTACGCNNNACGTATGCCA | 5050 | TGCAGGACCAGAGAATTCGAATA CAAAACTCGCNNNACGTATGCCA | 5290 | TGCAGGACCAGAGAATTCGAATA CAGGAACATGNNNACGTATGCCA | 5530 |
| TGCAGGACCAGAGAATTCGAATA CAGCGGCGAANNNACGTATGCCA | 5051 | TGCAGGACCAGAGAATTCGAATA CATGAGTTGCNNNACGTATGCCA | 5291 | TGCAGGACCAGAGAATTCGAATA CACGGTAACTNNNACGTATGCCA | 5531 |
| TGCAGGACCAGAGAATTCGAATA CATAGCCGCGNNNACGTATGCCA | 5052 | TGCAGGACCAGAGAATTCGAATA CAACAACAAANNNACGTATGCCA | 5292 | TGCAGGACCAGAGAATTCGAATA CAATGTGTGCNNNACGTATGCCA | 5532 |
| TGCAGGACCAGAGAATTCGAATA CAGAAGCGATNNNACGTATGCCA | 5053 | TGCAGGACCAGAGAATTCGAATA CAGCCCTACCNNNACGTATGCCA | 5293 | TGCAGGACCAGAGAATTCGAATA CACGGAGTTGNNNACGTATGCCA | 5533 |
| TGCAGGACCAGAGAATTCGAATA CAGACAGTGANNNACGTATGCCA | 5054 | TGCAGGACCAGAGAATTCGAATA CAGTTGAGAGNNNACGTATGCCA | 5294 | TGCAGGACCAGAGAATTCGAATA CATGAACTCGNNNACGTATGCCA | 5534 |
| TGCAGGACCAGAGAATTCGAATA CACTTTATCANNNACGTATGCCA | 5055 | TGCAGGACCAGAGAATTCGAATA CACAGTGACTNNNACGTATGCCA | 5295 | TGCAGGACCAGAGAATTCGAATA CAACATCGCANNNACGTATGCCA | 5535 |
| TGCAGGACCAGAGAATTCGAATA CACAGGAAGTNNNACGTATGCCA | 5056 | TGCAGGACCAGAGAATTCGAATA CATGAAGACGNNNACGTATGCCA | 5296 | TGCAGGACCAGAGAATTCGAATA CAGAATTGTTNNNACGTATGCCA | 5536 |
| TGCAGGACCAGAGAATTCGAATA CAGTATTGGCNNNACGTATGCCA | 5057 | TGCAGGACCAGAGAATTCGAATA CACCCTATGTNNNACGTATGCCA | 5297 | TGCAGGACCAGAGAATTCGAATA CAAAACACTTNNNACGTATGCCA | 5537 |
| TGCAGGACCAGAGAATTCGAATA CATCAGCCGGNNNACGTATGCCA | 5058 | TGCAGGACCAGAGAATTCGAATA CATGGTTTGGNNNACGTATGCCA | 5298 | TGCAGGACCAGAGAATTCGAATA CATGTTTGCCNNNACGTATGCCA | 5538 |
| TGCAGGACCAGAGAATTCGAATA CAAGCAGGATNNNACGTATGCCA | 5059 | TGCAGGACCAGAGAATTCGAATA CAGCCACTCGNNNACGTATGCCA | 5299 | TGCAGGACCAGAGAATTCGAATA CACGCGTGCANNNACGTATGCCA | 5539 |
| TGCAGGACCAGAGAATTCGAATA CAGTTAGTGCNNNACGTATGCCA | 5060 | TGCAGGACCAGAGAATTCGAATA CAAAAGAGTTNNNACGTATGCCA | 5300 | TGCAGGACCAGAGAATTCGAATA CAGTAATGCCNNNACGTATGCCA | 5540 |
| TGCAGGACCAGAGAATTCGAATA CAATTGTAGTNNNACGTATGCCA | 5061 | TGCAGGACCAGAGAATTCGAATA CAGTTCGTGANNNACGTATGCCA | 5301 | TGCAGGACCAGAGAATTCGAATA CAGTTCAGACNNNACGTATGCCA | 5541 |
| TGCAGGACCAGAGAATTCGAATA CAAGCACGTTNNNACGTATGCCA | 5062 | TGCAGGACCAGAGAATTCGAATA CATCCCCACGNNNACGTATGCCA | 5302 | TGCAGGACCAGAGAATTCGAATA CATAATCAGTNNNACGTATGCCA | 5542 |
| TGCAGGACCAGAGAATTCGAATA CACCCCGGTTNNNACGTATGCCA | 5063 | TGCAGGACCAGAGAATTCGAATA CAAAATTCTGNNNACGTATGCCA | 5303 | TGCAGGACCAGAGAATTCGAATA CATTCCCAACNNNACGTATGCCA | 5543 |
| TGCAGGACCAGAGAATTCGAATA CAATATCTCTNNNACGTATGCCA | 5064 | TGCAGGACCAGAGAATTCGAATA CATCCACAGANNNACGTATGCCA | 5304 | TGCAGGACCAGAGAATTCGAATA CACTAGTAGCNNNACGTATGCCA | 5544 |
| TGCAGGACCAGAGAATTCGAATA CAATCTTCATNNNACGTATGCCA | 5065 | TGCAGGACCAGAGAATTCGAATA CAAGAGTTTTNNNACGTATGCCA | 5305 | TGCAGGACCAGAGAATTCGAATA CATTAATACGNNNACGTATGCCA | 5545 |
| TGCAGGACCAGAGAATTCGAATA CAGGTACTCANNNACGTATGCCA | 5066 | TGCAGGACCAGAGAATTCGAATA CATGGAGCGGNNNACGTATGCCA | 5306 | TGCAGGACCAGAGAATTCGAATA CATACAGAGGNNNACGTATGCCA | 5546 |
| TGCAGGACCAGAGAATTCGAATA CACCACCTATNNNACGTATGCCA | 5067 | TGCAGGACCAGAGAATTCGAATA CACTTTAATCNNNACGTATGCCA | 5307 | TGCAGGACCAGAGAATTCGAATA CACGGCACANNNACGTATGCCA | 5547 |
| TGCAGGACCAGAGAATTCGAATA CAATAATAAANNNACGTATGCCA | 5068 | TGCAGGACCAGAGAATTCGAATA CAACGTCAGTNNNACGTATGCCA | 5308 | TGCAGGACCAGAGAATTCGAATA CATCTCCCAANNNACGTATGCCA | 5548 |
| TGCAGGACCAGAGAATTCGAATA CAACATAATCNNNACGTATGCCA | 5069 | TGCAGGACCAGAGAATTCGAATA CATGGAGCTTNNNACGTATGCCA | 5309 | TGCAGGACCAGAGAATTCGAATA CAGTACTGCANNNACGTATGCCA | 5549 |
| TGCAGGACCAGAGAATTCGAATA CACCTTCGTANNNACGTATGCCA | 5070 | TGCAGGACCAGAGAATTCGAATA CAGCACACCGNNNACGTATGCCA | 5310 | TGCAGGACCAGAGAATTCGAATA CAGTAGTACCNNNACGTATGCCA | 5550 |
| TGCAGGACCAGAGAATTCGAATA CAGGATCTTGNNNACGTATGCCA | 5071 | TGCAGGACCAGAGAATTCGAATA CATTTGCTGCNNNACGTATGCCA | 5311 | TGCAGGACCAGAGAATTCGAATA CATAACCGTGNNNACGTATGCCA | 5551 |
| TGCAGGACCAGAGAATTCGAATA CAGAGGCGGTNNNACGTATGCCA | 5072 | TGCAGGACCAGAGAATTCGAATA CACAGCGAAANNNACGTATGCCA | 5312 | TGCAGGACCAGAGAATTCGAATA CACGGATAGANNNACGTATGCCA | 5552 |
| TGCAGGACCAGAGAATTCGAATA CACTCAAAATNNNACGTATGCCA | 5073 | TGCAGGACCAGAGAATTCGAATA CAACGATTGCNNNACGTATGCCA | 5313 | TGCAGGACCAGAGAATTCGAATA CAGGAATAGCNNNACGTATGCCA | 5553 |
| TGCAGGACCAGAGAATTCGAATA CACAACTGCANNNACGTATGCCA | 5074 | TGCAGGACCAGAGAATTCGAATA CATAGCGTTGNNNACGTATGCCA | 5314 | TGCAGGACCAGAGAATTCGAATA CAGGAGTCAANNNACGTATGCCA | 5554 |
| TGCAGGACCAGAGAATTCGAATA CACGGTTCCCNNNACGTATGCCA | 5075 | TGCAGGACCAGAGAATTCGAATA CAACGCTGCGNNNACGTATGCCA | 5315 | TGCAGGACCAGAGAATTCGAATA CAATTAGCTANNNACGTATGCCA | 5555 |
| TGCAGGACCAGAGAATTCGAATA CAGTGCTAGANNNACGTATGCCA | 5076 | TGCAGGACCAGAGAATTCGAATA CACTTTATTCNNNACGTATGCCA | 5316 | TGCAGGACCAGAGAATTCGAATA CAAGACATTTNNNACGTATGCCA | 5556 |
| TGCAGGACCAGAGAATTCGAATA CATCTGAGTGNNNACGTATGCCA | 5077 | TGCAGGACCAGAGAATTCGAATA CAGCGAAATGNNNACGTATGCCA | 5317 | TGCAGGACCAGAGAATTCGAATA CATCTACGCTNNNACGTATGCCA | 5557 |
| TGCAGGACCAGAGAATTCGAATA CACAGCCTTTNNNACGTATGCCA | 5078 | TGCAGGACCAGAGAATTCGAATA CATTTATTGCNNNACGTATGCCA | 5318 | TGCAGGACCAGAGAATTCGAATA CATGCCTTCANNNACGTATGCCA | 5558 |
| TGCAGGACCAGAGAATTCGAATA CAGTGTGTTGNNNACGTATGCCA | 5079 | TGCAGGACCAGAGAATTCGAATA CATCCAGCGGNNNACGTATGCCA | 5319 | TGCAGGACCAGAGAATTCGAATA CAAGATCACCNNNACGTATGCCA | 5559 |
| TGCAGGACCAGAGAATTCGAATA CAATTGTAACNNNACGTATGCCA | 5080 | TGCAGGACCAGAGAATTCGAATA CACGCCATGCNNNACGTATGCCA | 5320 | TGCAGGACCAGAGAATTCGAATA CAATCCTTTANNNACGTATGCCA | 5560 |
| TGCAGGACCAGAGAATTCGAATA CAAAGTTCATNNNACGTATGCCA | 5081 | TGCAGGACCAGAGAATTCGAATA CAATGCTGGTNNNACGTATGCCA | 5321 | TGCAGGACCAGAGAATTCGAATA CAGTAGTTCGNNNACGTATGCCA | 5561 |

FIG. 19B

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAAAGTCGCTNNNACGTATGCCA | 5082 | TGCAGGACCAGAGAATTCGAATA CAAATGGCCTNNNACGTATGCCA | 5322 | TGCAGGACCAGAGAATTCGAATA CAGGGCCCGGCNNNACGTATGCCA | 5562 |
| TGCAGGACCAGAGAATTCGAATA CAATATCAGTNNNACGTATGCCA | 5083 | TGCAGGACCAGAGAATTCGAATA CAGGTTTAGCNNNACGTATGCCA | 5323 | TGCAGGACCAGAGAATTCGAATA CAAGGCCAGGNNNACGTATGCCA | 5563 |
| TGCAGGACCAGAGAATTCGAATA CATTCTCCGANNNACGTATGCCA | 5084 | TGCAGGACCAGAGAATTCGAATA CATTCCCAGTNNNACGTATGCCA | 5324 | TGCAGGACCAGAGAATTCGAATA CATTGTCAGGNNNACGTATGCCA | 5564 |
| TGCAGGACCAGAGAATTCGAATA CATCTTGAAANNNACGTATGCCA | 5085 | TGCAGGACCAGAGAATTCGAATA CAAGCGATGANNNACGTATGCCA | 5325 | TGCAGGACCAGAGAATTCGAATA CAAAATCTGTNNNACGTATGCCA | 5565 |
| TGCAGGACCAGAGAATTCGAATA CATTACCGAGNNNACGTATGCCA | 5086 | TGCAGGACCAGAGAATTCGAATA CACCGGTCAGNNNACGTATGCCA | 5326 | TGCAGGACCAGAGAATTCGAATA CAATAAAAATNNNACGTATGCCA | 5566 |
| TGCAGGACCAGAGAATTCGAATA CAACTTAGATNNNACGTATGCCA | 5087 | TGCAGGACCAGAGAATTCGAATA CAAGTATACTNNNACGTATGCCA | 5327 | TGCAGGACCAGAGAATTCGAATA CATGTCACAGNNNACGTATGCCA | 5567 |
| TGCAGGACCAGAGAATTCGAATA CACATCGGTANNNACGTATGCCA | 5088 | TGCAGGACCAGAGAATTCGAATA CAGACTGAGANNNACGTATGCCA | 5328 | TGCAGGACCAGAGAATTCGAATA CATCTCATGCNNNACGTATGCCA | 5568 |
| TGCAGGACCAGAGAATTCGAATA CACCAGCGCANNNACGTATGCCA | 5089 | TGCAGGACCAGAGAATTCGAATA CATCACGTTCNNNACGTATGCCA | 5329 | TGCAGGACCAGAGAATTCGAATA CAGAACGGTCNNNACGTATGCCA | 5569 |
| TGCAGGACCAGAGAATTCGAATA CATATCGATANNNACGTATGCCA | 5090 | TGCAGGACCAGAGAATTCGAATA CACTCACTACNNNACGTATGCCA | 5330 | TGCAGGACCAGAGAATTCGAATA CATCTCAGCTNNNACGTATGCCA | 5570 |
| TGCAGGACCAGAGAATTCGAATA CAAGACTCTGNNNACGTATGCCA | 5091 | TGCAGGACCAGAGAATTCGAATA CAGAAGAGAGNNNACGTATGCCA | 5331 | TGCAGGACCAGAGAATTCGAATA CAGATCGGAANNNACGTATGCCA | 5571 |
| TGCAGGACCAGAGAATTCGAATA CAAGAGCCACANNNACGTATGCCA | 5092 | TGCAGGACCAGAGAATTCGAATA CACCCTGCACNNNACGTATGCCA | 5332 | TGCAGGACCAGAGAATTCGAATA CACTCTATCGNNNACGTATGCCA | 5572 |
| TGCAGGACCAGAGAATTCGAATA CATACCGTAGNNNACGTATGCCA | 5093 | TGCAGGACCAGAGAATTCGAATA CAGCAACGAANNNACGTATGCCA | 5333 | TGCAGGACCAGAGAATTCGAATA CAGACCGGTAANNNACGTATGCCA | 5573 |
| TGCAGGACCAGAGAATTCGAATA CAGAAGGTGTNNNACGTATGCCA | 5094 | TGCAGGACCAGAGAATTCGAATA CAGCTACCTTNNNACGTATGCCA | 5334 | TGCAGGACCAGAGAATTCGAATA CATATATTTNNNACGTATGCCA | 5574 |
| TGCAGGACCAGAGAATTCGAATA CATTGGACCANNNACGTATGCCA | 5095 | TGCAGGACCAGAGAATTCGAATA CAACACCTTCNNNACGTATGCCA | 5335 | TGCAGGACCAGAGAATTCGAATA CATGCATTCCNNNACGTATGCCA | 5575 |
| TGCAGGACCAGAGAATTCGAATA CAGCAATCACNNNACGTATGCCA | 5096 | TGCAGGACCAGAGAATTCGAATA CACTGTTAAANNNACGTATGCCA | 5336 | TGCAGGACCAGAGAATTCGAATA CATATATCTCNNNACGTATGCCA | 5576 |
| TGCAGGACCAGAGAATTCGAATA CATTGAGCGTNNNACGTATGCCA | 5097 | TGCAGGACCAGAGAATTCGAATA CAATCTCGGANNNACGTATGCCA | 5337 | TGCAGGACCAGAGAATTCGAATA CACCGGCTGANNNACGTATGCCA | 5577 |
| TGCAGGACCAGAGAATTCGAATA CACAAGTGTCNNNACGTATGCCA | 5098 | TGCAGGACCAGAGAATTCGAATA CAATGTTGCGNNNACGTATGCCA | 5338 | TGCAGGACCAGAGAATTCGAATA CAGAATCAGGNNNACGTATGCCA | 5578 |
| TGCAGGACCAGAGAATTCGAATA CAGTCTAATANNNACGTATGCCA | 5099 | TGCAGGACCAGAGAATTCGAATA CAGCACATGTNNNACGTATGCCA | 5339 | TGCAGGACCAGAGAATTCGAATA CATCCTAGAGNNNACGTATGCCA | 5579 |
| TGCAGGACCAGAGAATTCGAATA CAAAGAAATCNNNACGTATGCCA | 5100 | TGCAGGACCAGAGAATTCGAATA CAAATCCGGTNNNACGTATGCCA | 5340 | TGCAGGACCAGAGAATTCGAATA CACCGTGTGGNNNACGTATGCCA | 5580 |
| TGCAGGACCAGAGAATTCGAATA CAGCTAGATCNNNACGTATGCCA | 5101 | TGCAGGACCAGAGAATTCGAATA CACTATTTACNNNACGTATGCCA | 5341 | TGCAGGACCAGAGAATTCGAATA CATAGTTTCTNNNACGTATGCCA | 5581 |
| TGCAGGACCAGAGAATTCGAATA CAGATAAGTANNNACGTATGCCA | 5102 | TGCAGGACCAGAGAATTCGAATA CACGTGCCAGNNNACGTATGCCA | 5342 | TGCAGGACCAGAGAATTCGAATA CAGATAGAGCNNNACGTATGCCA | 5582 |
| TGCAGGACCAGAGAATTCGAATA CAGGTTCAGTNNNACGTATGCCA | 5103 | TGCAGGACCAGAGAATTCGAATA CACCGGTAGCNNNACGTATGCCA | 5343 | TGCAGGACCAGAGAATTCGAATA CACTCGTACTNNNACGTATGCCA | 5583 |
| TGCAGGACCAGAGAATTCGAATA CAAGCTGACTNNNACGTATGCCA | 5104 | TGCAGGACCAGAGAATTCGAATA CAACATATGTNNNACGTATGCCA | 5344 | TGCAGGACCAGAGAATTCGAATA CAGCACTTTCNNNACGTATGCCA | 5584 |
| TGCAGGACCAGAGAATTCGAATA CATGCGCCAGNNNACGTATGCCA | 5105 | TGCAGGACCAGAGAATTCGAATA CATGGTGGCCNNNACGTATGCCA | 5345 | TGCAGGACCAGAGAATTCGAATA CAGTTCTCGTNNNACGTATGCCA | 5585 |
| TGCAGGACCAGAGAATTCGAATA CATGTCAGTGNNNACGTATGCCA | 5106 | TGCAGGACCAGAGAATTCGAATA CACAACTCAGNNNACGTATGCCA | 5346 | TGCAGGACCAGAGAATTCGAATA CACTTACGTCNNNACGTATGCCA | 5586 |
| TGCAGGACCAGAGAATTCGAATA CAGAATCGTCNNNACGTATGCCA | 5107 | TGCAGGACCAGAGAATTCGAATA CACCAATTTTNNNACGTATGCCA | 5347 | TGCAGGACCAGAGAATTCGAATA CACAGAAGACNNNACGTATGCCA | 5587 |
| TGCAGGACCAGAGAATTCGAATA CACCCCATGCNNNACGTATGCCA | 5108 | TGCAGGACCAGAGAATTCGAATA CAAACTGAGGNNNACGTATGCCA | 5348 | TGCAGGACCAGAGAATTCGAATA CATAAGTCTANNNACGTATGCCA | 5588 |
| TGCAGGACCAGAGAATTCGAATA CACATTAGCGNNNCTAGCGTTAC | 5109 | TGCAGGACCAGAGAATTCGAATA CAACTAGTCTNNNCTAGCGTTAC | 5349 | TGCAGGACCAGAGAATTCGAATA CACATACTAANNNCTAGCGTTAC | 5589 |
| TGCAGGACCAGAGAATTCGAATA CAATCCACCTNNNCTAGCGTTAC | 5110 | TGCAGGACCAGAGAATTCGAATA CAGCATGGCCNNNCTAGCGTTAC | 5350 | TGCAGGACCAGAGAATTCGAATA CACCCGAATCANNNCTAGCGTTAC | 5590 |
| TGCAGGACCAGAGAATTCGAATA CAACATGCGTNNNCTAGCGTTAC | 5111 | TGCAGGACCAGAGAATTCGAATA CAAGTCAGAGNNNCTAGCGTTAC | 5351 | TGCAGGACCAGAGAATTCGAATA CACTATTTTGNNNCTAGCGTTAC | 5591 |
| TGCAGGACCAGAGAATTCGAATA CAGCCTTACCNNNCTAGCGTTAC | 5112 | TGCAGGACCAGAGAATTCGAATA CATGAATACTNNNCTAGCGTTAC | 5352 | TGCAGGACCAGAGAATTCGAATA CACCCGACAGNNNCTAGCGTTAC | 5592 |
| TGCAGGACCAGAGAATTCGAATA CAAACCTCCTNNNCTAGCGTTAC | 5113 | TGCAGGACCAGAGAATTCGAATA CAGTATGAGCNNNCTAGCGTTAC | 5353 | TGCAGGACCAGAGAATTCGAATA CAACTTCGAGNNNCTAGCGTTAC | 5593 |
| TGCAGGACCAGAGAATTCGAATA CACTTTATGTNNNCTAGCGTTAC | 5114 | TGCAGGACCAGAGAATTCGAATA CAGACTTGTGNNNCTAGCGTTAC | 5354 | TGCAGGACCAGAGAATTCGAATA CATGATGCTGNNNCTAGCGTTAC | 5594 |

FIG. 19C

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CACTCGCCTGNNNCTAGCGTTAC | 5115 | TGCAGGACCAGAGABTTCGAATA CAAATTAAGGNNNCTAGCGTTAC | 5355 | TGCAGGACCAGAGAATTCGAATA CAGCGCAGGANNNCTAGCGTTAC | 5595 |
| TGCAGGACCAGAGAATTCGAATA CAATGATGTTNNNCTAGCGTTAC | 5116 | TGCAGGACCAGAGAATTCGAATA CACGGTTGTANNNCTAGCGTTAC | 5356 | TGCAGGACCAGAGABTTCGAATA CATTCACAAANNNCTAGCGTTAC | 5596 |
| TGCAGGACCAGAGAATTCGAATA CAGAGTTGGANNNCTAGCGTTAC | 5117 | TGCAGGACCAGAGABTTCGAATA CACCTGTCCGNNNCTAGCGTTAC | 5357 | TGCAGGACCAGAGAATTCGAATA CAATGCACTGNNNCTAGCGTTAC | 5597 |
| TGCAGGACCAGAGAATTCGAATA CAACAACCACNNNCTAGCGTTAC | 5118 | TGCAGGACCAGAGAATTCGAATA CAGTGACGCCNNNCTAGCGTTAC | 5358 | TGCAGGACCAGAGAATTCGAATA CAGTTGCCGGNNNCTAGCGTTAC | 5598 |
| TGCAGGACCAGAGAATTCGAATA CATACCGCAANNNCTAGCGTTAC | 5119 | TGCAGGACCAGAGABTTCGAATA CAGTGTTGCANNNCTAGCGTTAC | 5359 | TGCAGGACCAGAGAATTCGAATA CAATTTTCCANNNCTAGCGTTAC | 5599 |
| TGCAGGACCAGAGAATTCGAATA CAGGTTAAAANNNCTAGCGTTAC | 5120 | TGCAGGACCAGAGAATTCGAATA CACCCGATTTNNNCTAGCGTTAC | 5360 | TGCAGGACCAGAGAATTCGAATA CACCAGCAGCNNNCTAGCGTTAC | 5600 |
| TGCAGGACCAGAGAATTCGAATA CACGGAAAGTNNNCTAGCGTTAC | 5121 | TGCAGGACCAGAGAATTCGAATA CATTTCCGTGNNNCTAGCGTTAC | 5361 | TGCAGGACCAGAGAATTCGAATA CACGGACAGGNNNCTAGCGTTAC | 5601 |
| TGCAGGACCAGAGAATTCGAATA CAGTGCGTCCGNNNCTAGCGTTAC | 5122 | TGCAGGACCAGAGAATTCGAATA CAAACGTCCTNNNCTAGCGTTAC | 5362 | TGCAGGACCAGAGAATTCGAATA CATCTGCGTTNNNCTAGCGTTAC | 5602 |
| TGCAGGACCAGAGAATTCGAATA CAGGTGTCCGNNNCTAGCGTTAC | 5123 | TGCAGGACCAGAGAATTCGAATA CAGAGCCAAANNNCTAGCGTTAC | 5363 | TGCAGGACCAGAGAATTCGAATA CATTTGCTATNNNCTAGCGTTAC | 5603 |
| TGCAGGACCAGAGAATTCGAATA CATCGCACTNNNCTAGCGTTAC | 5124 | TGCAGGACCAGAGAATTCGAATA CACCCTTCAANNNCTAGCGTTAC | 5364 | TGCAGGACCAGAGAATTCGAATA CATTTCCTTTNNNCTAGCGTTAC | 5604 |
| TGCAGGACCAGAGAATTCGAATA CATTCGGTCTNNNCTAGCGTTAC | 5125 | TGCAGGACCAGAGAATTCGAATA CAGCGGCGGTNNNCTAGCGTTAC | 5365 | TGCAGGACCAGAGAATTCGAATA CACGAGACTTNNNCTAGCGTTAC | 5605 |
| TGCAGGACCAGAGAATTCGAATA CAACGAGGATNNNCTAGCGTTAC | 5126 | TGCAGGACCAGAGAATTCGAATA CACTTCTAGCNNNCTAGCGTTAC | 5366 | TGCAGGACCAGAGAATTCGAATA CAAACTAGAANNNCTAGCGTTAC | 5606 |
| TGCAGGACCAGAGAATTCGAATA CAGTAGATGGNNNCTAGCGTTAC | 5127 | TGCAGGACCAGAGAATTCGAATA CAGTGTAAAANNNCTAGCGTTAC | 5367 | TGCAGGACCAGAGAATTCGAATA CACCTCGATTNNNCTAGCGTTAC | 5607 |
| TGCAGGACCAGAGAATTCGAATA CACCACACTTNNNCTAGCGTTAC | 5128 | TGCAGGACCAGAGAATTCGAATA CAACTATGCGNNNCTAGCGTTAC | 5368 | TGCAGGACCAGAGAATTCGAATA CAGTGAAGACNNNCTAGCGTTAC | 5608 |
| TGCAGGACCAGAGAATTCGAATA CAGTTTGCCANNNCTAGCGTTAC | 5129 | TGCAGGACCAGAGAATTCGAATA CACGCCAGACNNNCTAGCGTTAC | 5369 | TGCAGGACCAGAGABTTCGAATA CAACGTTACGNNNCTAGCGTTAC | 5609 |
| TGCAGGACCAGAGAATTCGAATA CAACGGTATCNNNCTAGCGTTAC | 5130 | TGCAGGACCAGAGAATTCGAATA CAATCAGTGCNNNCTAGCGTTAC | 5370 | TGCAGGACCAGAGAATTCGAATA CACGTCCTGCNNNCTAGCGTTAC | 5610 |
| TGCAGGACCAGAGAATTCGAATA CAATGATAGANNNCTAGCGTTAC | 5131 | TGCAGGACCAGAGAATTCGAATA CAGTTCTACCNNNCTAGCGTTAC | 5371 | TGCAGGACCAGAGAATTCGAATA CAACTCCTACNNNCTAGCGTTAC | 5611 |
| TGCAGGACCAGAGAATTCGAATA CACAATAACTNNNCTAGCGTTAC | 5132 | TGCAGGACCAGAGAATTCGAATA CACACCCATANNNCTAGCGTTAC | 5372 | TGCAGGACCAGAGAATTCGAATA CAGTTAGGTCNNNCTAGCGTTAC | 5612 |
| TGCAGGACCAGAGAATTCGAATA CAGATCCTAGNNNCTAGCGTTAC | 5133 | TGCAGGACCAGAGAATTCGAATA CACAAAGATANNNCTAGCGTTAC | 5373 | TGCAGGACCAGAGAATTCGAATA CACTCATGAGNNNCTAGCGTTAC | 5613 |
| TGCAGGACCAGAGAATTCGAATA CAATTACCCCNNNCTAGCGTTAC | 5134 | TGCAGGACCAGAGABTTCGAATA CACAAGGCTTNNNCTAGCGTTAC | 5374 | TGCAGGACCAGAGAATTCGAATA CATATTTACCNNNCTAGCGTTAC | 5614 |
| TGCAGGACCAGAGAATTCGAATA CACTGTGCGGNNNCTAGCGTTAC | 5135 | TGCAGGACCAGAGAATTCGAATA CAGTCGTTAGNNNCTAGCGTTAC | 5375 | TGCAGGACCAGAGABTTCGAATA CACCCTCATGNNNCTAGCGTTAC | 5615 |
| TGCAGGACCAGAGAATTCGAATA CATATGTGTANNNCTAGCGTTAC | 5136 | TGCAGGACCAGAGAATTCGAATA CAAACGTTCGNNNCTAGCGTTAC | 5376 | TGCAGGACCAGAGAATTCGAATA CAGGACTAGANNNCTAGCGTTAC | 5616 |
| TGCAGGACCAGAGAATTCGAATA CAGCTCCTTANNNCTAGCGTTAC | 5137 | TGCAGGACCAGAGAATTCGAATA CAATGGCTGTNNNCTAGCGTTAC | 5377 | TGCAGGACCAGAGAATTCGAATA CAGTGGCAAANNNCTAGCGTTAC | 5617 |
| TGCAGGACCAGAGAATTCGAATA CAAAAAGCGCNNNCTAGCGTTAC | 5138 | TGCAGGACCAGAGABTTCGAATA CAATTCTATCNNNCTAGCGTTAC | 5378 | TGCAGGACCAGAGAATTCGAATA CAAATAAACGNNNCTAGCGTTAC | 5618 |
| TGCAGGACCAGAGAATTCGAATA CATGGTATATNNNCTAGCGTTAC | 5139 | TGCAGGACCAGAGAATTCGAATA CAGGTAGCAANNNCTAGCGTTAC | 5379 | TGCAGGACCAGAGABTTCGAATA CAGTATACCGNNNCTAGCGTTAC | 5619 |
| TGCAGGACCAGAGAATTCGAATA CACATCACGANNNCTAGCGTTAC | 5140 | TGCAGGACCAGAGABTTCGAATA CATGGTGACTNNNCTAGCGTTAC | 5380 | TGCAGGACCAGAGAATTCGAATA CACCAAATTANNNCTAGCGTTAC | 5620 |
| TGCAGGACCAGAGAATTCGAATA CACTCATTCGNNNCTAGCGTTAC | 5141 | TGCAGGACCAGAGAATTCGAATA CATCCTAATTNNNCTAGCGTTAC | 5381 | TGCAGGACCAGAGAATTCGAATA CATTCTTTAGNNNCTAGCGTTAC | 5621 |
| TGCAGGACCAGAGAATTCGAATA CAGGCGCATCNNNCTAGCGTTAC | 5142 | TGCAGGACCAGAGAATTCGAATA CAGCCCAGGTNNNCTAGCGTTAC | 5382 | TGCAGGACCAGAGAATTCGAATA CATGTTCGTCNNNCTAGCGTTAC | 5622 |
| TGCAGGACCAGAGAATTCGAATA CAAAAGATTGNNNCTAGCGTTAC | 5143 | TGCAGGACCAGAGAATTCGAATA CACCCGCAAGNNNCTAGCGTTAC | 5383 | TGCAGGACCAGAGAATTCGAATA CACCGGCTCTNNNCTAGCGTTAC | 5623 |
| TGCAGGACCAGAGAATTCGAATA CATGAAAGATNNNCTAGCGTTAC | 5144 | TGCAGGACCAGAGAATTCGAATA CATCCCTGGCNNNCTAGCGTTAC | 5384 | TGCAGGACCAGAGAATTCGAATA CACGAGTGTTNNNCTAGCGTTAC | 5624 |
| TGCAGGACCAGAGAATTCGAATA CACAGGCTTANNNCTAGCGTTAC | 5145 | TGCAGGACCAGAGAATTCGAATA CAGATCCCTTNNNCTAGCGTTAC | 5385 | TGCAGGACCAGAGAATTCGAATA CAGCGGGTATNNNCTAGCGTTAC | 5625 |
| TGCAGGACCAGAGAATTCGAATA CACGAATTCGNNNCTAGCGTTAC | 5146 | TGCAGGACCAGAGABTTCGAATA CATAGATGAANNNCTAGCGTTAC | 5386 | TGCAGGACCAGAGAATTCGAATA CAAAGTCTCGNNNCTAGCGTTAC | 5626 |
| TGCAGGACCAGAGAATTCGAATA CATAACCACGNNNCTAGCGTTAC | 5147 | TGCAGGACCAGAGAATTCGAATA CAAGGCAAGTNNNCTAGCGTTAC | 5387 | TGCAGGACCAGAGAATTCGAATA CAGTAGCAAGNNNCTAGCGTTAC | 5627 |

FIG. 19D

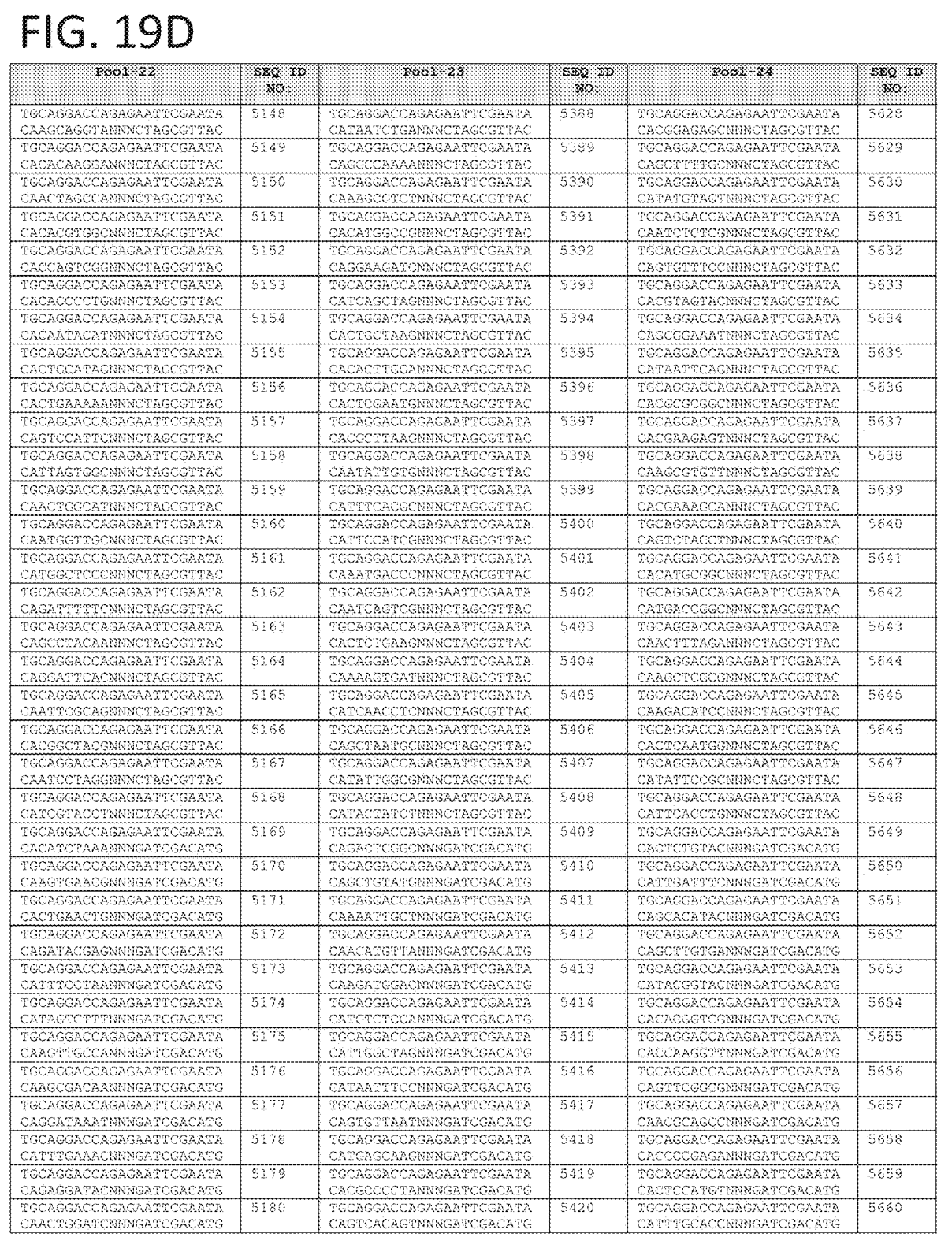

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAAGCAGGTANNNCTAGCGTTAC | 5148 | TGCAGGACCAGAGAATTCGAATA CATAATCTGANNNCTAGCGTTAC | 5388 | TGCAGGACCAGAGAATTCGAATA CACCGGAGAGCNNNCTAGCGTTAC | 5628 |
| TGCAGGACCAGAGAATTCGAATA CACACAAGGANNNCTAGCGTTAC | 5149 | TGCAGGACCAGAGAATTCGAATA CAGGCCAAAANNNCTAGCGTTAC | 5389 | TGCAGGACCAGAGAATTCGAATA CAGCTTTTGCNNNCTAGCGTTAC | 5629 |
| TGCAGGACCAGAGAATTCGAATA CAACTAGCCANNNCTAGCGTTAC | 5150 | TGCAGGACCAGAGAATTCGAATA CAAAGCGTCTNNNCTAGCGTTAC | 5390 | TGCAGGACCAGAGAATTCGAATA CATATGTAGTNNNCTAGCGTTAC | 5630 |
| TGCAGGACCAGAGAATTCGAATA CACACGTGGCNNNCTAGCGTTAC | 5151 | TGCAGGACCAGAGAATTCGAATA CACATGGCCNNNCTAGCGTTAC | 5391 | TGCAGGACCAGAGAATTCGAATA CAATCTCTCGNNNCTAGCGTTAC | 5631 |
| TGCAGGACCAGAGAATTCGAATA CACCAGTCGGNNNCTAGCGTTAC | 5152 | TGCAGGACCAGAGAATTCGAATA CAGGAAGATGNNNCTAGCGTTAC | 5392 | TGCAGGACCAGAGAATTCGAATA CAGTGTTTCCNNNCTAGCGTTAC | 5632 |
| TGCAGGACCAGAGAATTCGAATA CACACCCCTGNNNCTAGCGTTAC | 5153 | TGCAGGACCAGAGAATTCGAATA CATCAGCTAGNNNCTAGCGTTAC | 5393 | TGCAGGACCAGAGAATTCGAATA CACGTAGTACNNNCTAGCGTTAC | 5633 |
| TGCAGGACCAGAGAATTCGAATA CACAATACATNNNCTAGCGTTAC | 5154 | TGCAGGACCAGAGAATTCGAATA CACTGCTAAGNNNCTAGCGTTAC | 5394 | TGCAGGACCAGAGAATTCGAATA CAGCGGAAATNNNCTAGCGTTAC | 5634 |
| TGCAGGACCAGAGAATTCGAATA CACTGCATAGNNNCTAGCGTTAC | 5155 | TGCAGGACCAGAGAATTCGAATA CACACTTGGANNNCTAGCGTTAC | 5395 | TGCAGGACCAGAGAATTCGAATA CATAATTCAGNNNCTAGCGTTAC | 5635 |
| TGCAGGACCAGAGAATTCGAATA CACTGAAAAANNNCTAGCGTTAC | 5156 | TGCAGGACCAGAGAATTCGAATA CACTCGAATGNNNCTAGCGTTAC | 5396 | TGCAGGACCAGAGAATTCGAATA CACGCGCGGCNNNCTAGCGTTAC | 5636 |
| TGCAGGACCAGAGAATTCGAATA CAGTCCATTCNNNCTAGCGTTAC | 5157 | TGCAGGACCAGAGAATTCGAATA CACGCTTAAGNNNCTAGCGTTAC | 5397 | TGCAGGACCAGAGAATTCGAATA CACGAAGAGTNNNCTAGCGTTAC | 5637 |
| TGCAGGACCAGAGAATTCGAATA CATTAGTGGCNNNCTAGCGTTAC | 5158 | TGCAGGACCAGAGAATTCGAATA CAATATTGTGNNNCTAGCGTTAC | 5398 | TGCAGGACCAGAGAATTCGAATA CAAGCGTGTTNNNCTAGCGTTAC | 5638 |
| TGCAGGACCAGAGAATTCGAATA CAACTGGCATNNNCTAGCGTTAC | 5159 | TGCAGGACCAGAGAATTCGAATA CATTTCACGCNNNCTAGCGTTAC | 5399 | TGCAGGACCAGAGAATTCGAATA CACGAAACANNNCTAGCGTTAC | 5639 |
| TGCAGGACCAGAGAATTCGAATA CAATGGTTGCNNNCTAGCGTTAC | 5160 | TGCAGGACCAGAGAATTCGAATA CATTCCATCGNNNCTAGCGTTAC | 5400 | TGCAGGACCAGAGAATTCGAATA CAGTCTACCTNNNCTAGCGTTAC | 5640 |
| TGCAGGACCAGAGAATTCGAATA CATGGCTCCCNNNCTAGCGTTAC | 5161 | TGCAGGACCAGAGAATTCGAATA CAAATGCCTCNNNCTAGCGTTAC | 5401 | TGCAGGACCAGAGAATTCGAATA CACATGCGGCNNNCTAGCGTTAC | 5641 |
| TGCAGGACCAGAGAATTCGAATA CAGATTTTTCNNNCTAGCGTTAC | 5162 | TGCAGGACCAGAGAATTCGAATA CAATCAGTCGNNNCTAGCGTTAC | 5402 | TGCAGGACCAGAGAATTCGAATA CATGACCGGCNNNCTAGCGTTAC | 5642 |
| TGCAGGACCAGAGAATTCGAATA CAGCCTACAANNNCTAGCGTTAC | 5163 | TGCAGGACCAGAGAATTCGAATA CACTCTGAAGNNNCTAGCGTTAC | 5403 | TGCAGGACCAGAGAATTCGAATA CAACTTTAGANNNCTAGCGTTAC | 5643 |
| TGCAGGACCAGAGAATTCGAATA CAGGATTCACNNNCTAGCGTTAC | 5164 | TGCAGGACCAGAGAATTCGAATA CAAAAGTGATNNNCTAGCGTTAC | 5404 | TGCAGGACCAGAGAATTCGAATA CAAGCTCGCGNNNCTAGCGTTAC | 5644 |
| TGCAGGACCAGAGAATTCGAATA CAATTCGCAGNNNCTAGCGTTAC | 5165 | TGCAGGACCAGAGAATTCGAATA CATCAACCTCNNNCTAGCGTTAC | 5405 | TGCAGGACCAGAGAATTCGAATA CAAGACATCCNNNCTAGCGTTAC | 5645 |
| TGCAGGACCAGAGAATTCGAATA CACGGCTACGNNNCTAGCGTTAC | 5166 | TGCAGGACCAGAGAATTCGAATA CAGCTAATGCNNNCTAGCGTTAC | 5406 | TGCAGGACCAGAGAATTCGAATA CACTCAATGGNNNCTAGCGTTAC | 5646 |
| TGCAGGACCAGAGAATTCGAATA CAATCCTAGGNNNCTAGCGTTAC | 5167 | TGCAGGACCAGAGAATTCGAATA CATATTGGCGNNNCTAGCGTTAC | 5407 | TGCAGGACCAGAGAATTCGAATA CATATTCCGCNNNCTAGCGTTAC | 5647 |
| TGCAGGACCAGAGAATTCGAATA CATCGTACCTNNNCTAGCGTTAC | 5168 | TGCAGGACCAGAGAATTCGAATA CATACTATCTNNNCTAGCGTTAC | 5408 | TGCAGGACCAGAGAATTCGAATA CATTCACCTGNNNCTAGCGTTAC | 5648 |
| TGCAGGACCAGAGAATTCGAATA CACATCTAAANNNGATCGACATG | 5169 | TGCAGGACCAGAGAATTCGAATA CAGACTCGGCNNNGATCGACATG | 5409 | TGCAGGACCAGAGAATTCGAATA CACTCTGTACNNNGATCGACATG | 5649 |
| TGCAGGACCAGAGAATTCGAATA CAAGTGAACGNNNGATCGACATG | 5170 | TGCAGGACCAGAGAATTCGAATA CAGCGTGTATGNNNGATCGACATG | 5410 | TGCAGGACCAGAGAATTCGAATA CATTGATTTCNNNGATCGACATG | 5650 |
| TGCAGGACCAGAGAATTCGAATA CACTGAACTGNNNGATCGACATG | 5171 | TGCAGGACCAGAGAATTCGAATA CAAAATTGCTNNNGATCGACATG | 5411 | TGCAGGACCAGAGAATTCGAATA CAGCACATACNNNGATCGACATG | 5651 |
| TGCAGGACCAGAGAATTCGAATA CAGATACGAGNNNGATCGACATG | 5172 | TGCAGGACCAGAGAATTCGAATA CAACATGTTANNNGATCGACATG | 5412 | TGCAGGACCAGAGAATTCGAATA CAGCTTGTGANNNGATCGACATG | 5652 |
| TGCAGGACCAGAGAATTCGAATA CATTTCCTAANNNGATCGACATG | 5173 | TGCAGGACCAGAGAATTCGAATA CAAGATGGACNNNGATCGACATG | 5413 | TGCAGGACCAGAGAATTCGAATA CATACGGTACNNNGATCGACATG | 5653 |
| TGCAGGACCAGAGAATTCGAATA CATAGTCTTTNNNGATCGACATG | 5174 | TGCAGGACCAGAGAATTCGAATA CATGTCTCCANNNGATCGACATG | 5414 | TGCAGGACCAGAGAATTCGAATA CACACGGTCGNNNGATCGACATG | 5654 |
| TGCAGGACCAGAGAATTCGAATA CAAGTTGCCANNNGATCGACATG | 5175 | TGCAGGACCAGAGAATTCGAATA CATTGGCTAGNNNGATCGACATG | 5415 | TGCAGGACCAGAGAATTCGAATA CACCAAGGTTNNNGATCGACATG | 5655 |
| TGCAGGACCAGAGAATTCGAATA CAAGCGACANNNGATCGACATG | 5176 | TGCAGGACCAGAGAATTCGAATA CATAAATTTCCNNNGATCGACATG | 5416 | TGCAGGACCAGAGAATTCGAATA CAGTTCGGCGNNNGATCGACATG | 5656 |
| TGCAGGACCAGAGAATTCGAATA CAGGATAAATNNNGATCGACATG | 5177 | TGCAGGACCAGAGAATTCGAATA CAGTGTTAATNNNGATCGACATG | 5417 | TGCAGGACCAGAGAATTCGAATA CAACCAGCCNNNGATCGACATG | 5657 |
| TGCAGGACCAGAGAATTCGAATA CATTTGAAACNNNGATCGACATG | 5178 | TGCAGGACCAGAGAATTCGAATA CATGAGCAAGNNNGATCGACATG | 5418 | TGCAGGACCAGAGAATTCGAATA CACCCCGAGANNNGATCGACATG | 5658 |
| TGCAGGACCAGAGAATTCGAATA CAGAGATACNNNGATCGACATG | 5179 | TGCAGGACCAGAGAATTCGAATA CACGCCCCTANNNGATCGACATG | 5419 | TGCAGGACCAGAGAATTCGAATA CACTCCATGTNNNGATCGACATG | 5659 |
| TGCAGGACCAGAGAATTCGAATA CAACTGGATCNNNGATCGACATG | 5180 | TGCAGGACCAGAGAATTCGAATA CAGTCACAGTNNNGATCGACATG | 5420 | TGCAGGACCAGAGAATTCGAATA CATTTGCACCNNNGATCGACATG | 5660 |

FIG. 19E

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAAAATGGATNNNGATCGACATG | 5181 | TGCAGGACCAGAGAATTCGAATA CAGTTGGTGTNNNGATCGACATG | 5421 | TGCAGGACCAGAGAATTCGAATA CAATTACAACNNNGATCGACATG | 5661 |
| TGCAGGACCAGAGAATTCGAATA CACGCATGATNNNGATCGACATG | 5182 | TGCAGGACCAGAGAATTCGAATA CACTTATTACNNNGATCGACATG | 5422 | TGCAGGACCAGAGAATTCGAATA CATGCCCACCNNNGATCGACATG | 5662 |
| TGCAGGACCAGAGAATTCGAATA CATACGAATTNNNGATCGACATG | 5183 | TGCAGGACCAGAGAATTCGAATA CACTCGCAAANNNGATCGACATG | 5423 | TGCAGGACCAGAGAATTCGAATA CAGATTGGAGNNNGATCGACATG | 5663 |
| TGCAGGACCAGAGAATTCGAATA CAGGAAAGCTNNNGATCGACATG | 5184 | TGCAGGACCAGAGAATTCGAATA CACTAGGTGTNNNGATCGACATG | 5424 | TGCAGGACCAGAGAATTCGAATA CATCATACCCNNNGATCGACATG | 5664 |
| TGCAGGACCAGAGAATTCGAATA CACCAACAACNNNGATCGACATG | 5185 | TGCAGGACCAGAGAATTCGAATA CACAACATATNNNGATCGACATG | 5425 | TGCAGGACCAGAGAATTCGAATA CAGGTGGATANNNGATCGACATG | 5665 |
| TGCAGGACCAGAGAATTCGAATA CAACGCGACCNNNGATCGACATG | 5186 | TGCAGGACCAGAGAATTCGAATA CAACCGATACNNNGATCGACATG | 5426 | TGCAGGACCAGAGAATTCGAATA CAGACAATTCGNNNGATCGACATG | 5666 |
| TGCAGGACCAGAGAATTCGAATA CAGGAGTCCCNNNGATCGACATG | 5187 | TGCAGGACCAGAGAATTCGAATA CACCGACTGGNNNGATCGACATG | 5427 | TGCAGGACCAGAGAATTCGAATA CAATCTGCGANNNGATCGACATG | 5667 |
| TGCAGGACCAGAGAATTCGAATA CACCACGCAGNNNGATCGACATG | 5188 | TGCAGGACCAGAGAATTCGAATA CACAACGCATNNNGATCGACATG | 5428 | TGCAGGACCAGAGAATTCGAATA CAGGCACCCANNNGATCGACATG | 5668 |
| TGCAGGACCAGAGAATTCGAATA CAACTCGCCCNNNGATCGACATG | 5189 | TGCAGGACCAGAGAATTCGAATA CATTTTAATTNNNGATCGACATG | 5429 | TGCAGGACCAGAGAATTCGAATA CAAATGTTTGNNNGATCGACATG | 5669 |
| TGCAGGACCAGAGAATTCGAATA CACTGAAGAGNNNGATCGACATG | 5190 | TGCAGGACCAGAGAATTCGAATA CAAGTGTATTNNNGATCGACATG | 5430 | TGCAGGACCAGAGAATTCGAATA CAACCTGGTANNNGATCGACATG | 5670 |
| TGCAGGACCAGAGAATTCGAATA CAGGAGCACGNNNGATCGACATG | 5191 | TGCAGGACCAGAGAATTCGAATA CAACTTCAGNNNGATCGACATG | 5431 | TGCAGGACCAGAGAATTCGAATA CAACTGAGAGNNNGATCGACATG | 5671 |
| TGCAGGACCAGAGAATTCGAATA CAGGAGCCGACNNNGATCGACATG | 5192 | TGCAGGACCAGAGAATTCGAATA CAAAGCGGCTNNNGATCGACATG | 5432 | TGCAGGACCAGAGAATTCGAATA CAGAATTAAGNNNGATCGACATG | 5672 |
| TGCAGGACCAGAGAATTCGAATA CAGGAACCTTNNNGATCGACATG | 5193 | TGCAGGACCAGAGAATTCGAATA CACCACGGTGNNNGATCGACATG | 5433 | TGCAGGACCAGAGAATTCGAATA CAATTACGGCNNNGATCGACATG | 5673 |
| TGCAGGACCAGAGAATTCGAATA CAGCCCTGTCNNNGATCGACATG | 5194 | TGCAGGACCAGAGAATTCGAATA CAGGCTCTTTNNNGATCGACATG | 5434 | TGCAGGACCAGAGAATTCGAATA CACAGTCTAGNNNGATCGACATG | 5674 |
| TGCAGGACCAGAGAATTCGAATA CAAGTAATCTNNNGATCGACATG | 5195 | TGCAGGACCAGAGAATTCGAATA CACTTAGCCTNNNGATCGACATG | 5435 | TGCAGGACCAGAGAATTCGAATA CAATCCCTTGNNNGATCGACATG | 5675 |
| TGCAGGACCAGAGAATTCGAATA CACGCTCGAGNNNGATCGACATG | 5196 | TGCAGGACCAGAGAATTCGAATA CAATTAGCATNNNGATCGACATG | 5436 | TGCAGGACCAGAGAATTCGAATA CATGTCCACTNNNGATCGACATG | 5676 |
| TGCAGGACCAGAGAATTCGAATA CAGTCATGGTNNNGATCGACATG | 5197 | TGCAGGACCAGAGAATTCGAATA CAGCAGCTTANNNGATCGACATG | 5437 | TGCAGGACCAGAGAATTCGAATA CAGGTACGCCNNNGATCGACATG | 5677 |
| TGCAGGACCAGAGAATTCGAATA CAGATTCCAGNNNGATCGACATG | 5198 | TGCAGGACCAGAGAATTCGAATA CAACATACGCNNNGATCGACATG | 5438 | TGCAGGACCAGAGAATTCGAATA CATGAGCAGANNNGATCGACATG | 5678 |
| TGCAGGACCAGAGAATTCGAATA CACTATTACTNNNGATCGACATG | 5199 | TGCAGGACCAGAGAATTCGAATA CAGTCGAAAGNNNGATCGACATG | 5439 | TGCAGGACCAGAGAATTCGAATA CAGATCCGTANNNGATCGACATG | 5679 |
| TGCAGGACCAGAGAATTCGAATA CAAGGTCTACNNNGATCGACATG | 5200 | TGCAGGACCAGAGAATTCGAATA CATTCTAGTTNNNGATCGACATG | 5440 | TGCAGGACCAGAGAATTCGAATA CATCACTAAANNNGATCGACATG | 5680 |
| TGCAGGACCAGAGAATTCGAATA CACCTGTAGANNNGATCGACATG | 5201 | TGCAGGACCAGAGAATTCGAATA CACACGCTCTNNNGATCGACATG | 5441 | TGCAGGACCAGAGAATTCGAATA CAAATAGATGNNNGATCGACATG | 5681 |
| TGCAGGACCAGAGAATTCGAATA CATCCTGTCANNNGATCGACATG | 5202 | TGCAGGACCAGAGAATTCGAATA CACCGAGGTCNNNGATCGACATG | 5442 | TGCAGGACCAGAGAATTCGAATA CATCGCGCTCNNNGATCGACATG | 5682 |
| TGCAGGACCAGAGAATTCGAATA CACCCTGCGTNNNGATCGACATG | 5203 | TGCAGGACCAGAGAATTCGAATA CACATTCGGTNNNGATCGACATG | 5443 | TGCAGGACCAGAGAATTCGAATA CAACCGACGCNNNGATCGACATG | 5683 |
| TGCAGGACCAGAGAATTCGAATA CAACAATGANNNGATCGACATG | 5204 | TGCAGGACCAGAGAATTCGAATA CATCCATAGGNNNGATCGACATG | 5444 | TGCAGGACCAGAGAATTCGAATA CACACGGACCNNNGATCGACATG | 5684 |
| TGCAGGACCAGAGAATTCGAATA CAGGTGGAGCNNNGATCGACATG | 5205 | TGCAGGACCAGAGAATTCGAATA CATTACTCATNNNGATCGACATG | 5445 | TGCAGGACCAGAGAATTCGAATA CAATATCGATNNNGATCGACATG | 5685 |
| TGCAGGACCAGAGAATTCGAATA CACGATAGACNNNGATCGACATG | 5206 | TGCAGGACCAGAGAATTCGAATA CAATCTGATANNNGATCGACATG | 5446 | TGCAGGACCAGAGAATTCGAATA CATACCACGANNNGATCGACATG | 5686 |
| TGCAGGACCAGAGAATTCGAATA CAGAGTGCCCNNNGATCGACATG | 5207 | TGCAGGACCAGAGAATTCGAATA CAGTCCACTTNNNGATCGACATG | 5447 | TGCAGGACCAGAGAATTCGAATA CAAAGAACGCNNNGATCGACATG | 5687 |
| TGCAGGACCAGAGAATTCGAATA CAAAACGGTGNNNGATCGACATG | 5208 | TGCAGGACCAGAGAATTCGAATA CACAGGAACANNNGATCGACATG | 5448 | TGCAGGACCAGAGAATTCGAATA CAAGTACCTGNNNGATCGACATG | 5688 |
| TGCAGGACCAGAGAATTCGAATA CAAATAGCAANNNGATCGACATG | 5209 | TGCAGGACCAGAGAATTCGAATA CACTAGCTTCNNNGATCGACATG | 5449 | TGCAGGACCAGAGAATTCGAATA CAGTTTTAGANNNGATCGACATG | 5689 |
| TGCAGGACCAGAGAATTCGAATA CATCAATTGANNNGATCGACATG | 5210 | TGCAGGACCAGAGAATTCGAATA CATTTGGCGANNNGATCGACATG | 5450 | TGCAGGACCAGAGAATTCGAATA CAGGATTTTANNNGATCGACATG | 5690 |
| TGCAGGACCAGAGAATTCGAATA CAAGCAATGGNNNGATCGACATG | 5211 | TGCAGGACCAGAGAATTCGAATA CACCCGAAGGNNNGATCGACATG | 5451 | TGCAGGACCAGAGAATTCGAATA CATAGTATACNNNGATCGACATG | 5691 |
| TGCAGGACCAGAGAATTCGAATA CAGTAGTGAGNNNGATCGACATG | 5212 | TGCAGGACCAGAGAATTCGAATA CATCCTAACGNNNGATCGACATG | 5452 | TGCAGGACCAGAGAATTCGAATA CACGTATGGTNNNGATCGACATG | 5692 |
| TGCAGGACCAGAGAATTCGAATA CACACTGCGGNNNGATCGACATG | 5213 | TGCAGGACCAGAGAATTCGAATA CATTCACGGANNNGATCGACATG | 5453 | TGCAGGACCAGAGAATTCGAATA CATCCCGGCTNNNGATCGACATG | 5693 |

FIG. 19F

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CAACCGCTCCNNNGATCGACATG | 5214 | TGCAGGACCAGAGAATTCGAATA CAATTTTACCNNNGATCGACATG | 5454 | TGCAGGACCAGAGAATTCGAATA CAGCGCTCTCNNNGATCGACATG | 5694 |
| TGCAGGACCAGAGAATTCGAATA CACTAGGTTGNNNGATCGACATG | 5215 | TGCAGGACCAGAGAATTCGAATA CATGGAGTCTNNNGATCGACATG | 5455 | TGCAGGACCAGAGAATTCGAATA CACATTCCCANNNGATCGACATG | 5695 |
| TGCAGGACCAGAGAATTCGAATA CATAAAATAANNNGATCGACATG | 5216 | TGCAGGACCAGAGAATTCGAATA CACGACGACCNNNGATCGACATG | 5456 | TGCAGGACCAGAGAATTCGAATA CATCGCCCCANNNGATCGACATG | 5696 |
| TGCAGGACCAGAGAATTCGAATA CAGTCACGTANNNGATCGACATG | 5217 | TGCAGGACCAGAGAATTCGAATA CATCCCATACNNNGATCGACATG | 5457 | TGCAGGACCAGAGAATTCGAATA CATGCATTGGNNNGATCGACATG | 5697 |
| TGCAGGACCAGAGAATTCGAATA CAGGTTCGATNNNGATCGACATG | 5218 | TGCAGGACCAGAGAATTCGAATA CAGCCCTTATNNNGATCGACATG | 5458 | TGCAGGACCAGAGAATTCGAATA CAATCAGATTNNNGATCGACATG | 5698 |
| TGCAGGACCAGAGAATTCGAATA CACAATGGAGNNNGATCGACATG | 5219 | TGCAGGACCAGAGAATTCGAATA CAGTCCCGCTNNNGATCGACATG | 5459 | TGCAGGACCAGAGAATTCGAATA CACTTTTATGNNNGATCGACATG | 5699 |
| TGCAGGACCAGAGAATTCGAATA CACCGAGCGTNNNGATCGACATG | 5220 | TGCAGGACCAGAGAATTCGAATA CACGGCCCTTNNNGATCGACATG | 5460 | TGCAGGACCAGAGAATTCGAATA CAAAAGTCGGNNNGATCGACATG | 5700 |
| TGCAGGACCAGAGAATTCGAATA CACAAACGAGNNNGATCGACATG | 5221 | TGCAGGACCAGAGAATTCGAATA CATCAGCTTCNNNGATCGACATG | 5461 | TGCAGGACCAGAGAATTCGAATA CAACGAGTGANNNGATCGACATG | 5701 |
| TGCAGGACCAGAGAATTCGAATA CAGATATGTTNNNGATCGACATG | 5222 | TGCAGGACCAGAGAATTCGAATA CAGGCTCGGTNNNGATCGACATG | 5462 | TGCAGGACCAGAGAATTCGAATA CAGAAATTAGNNNGATCGACATG | 5702 |
| TGCAGGACCAGAGAATTCGAATA CAGTTCTGTCNNNGATCGACATG | 5223 | TGCAGGACCAGAGAATTCGAATA CAAAGTTCGCNNNGATCGACATG | 5463 | TGCAGGACCAGAGAATTCGAATA CAATTATCTCNNNGATCGACATG | 5703 |
| TGCAGGACCAGAGAATTCGAATA CATCTTTTCTNNNGATCGACATG | 5224 | TGCAGGACCAGAGAATTCGAATA CAAACGCCGCNNNGATCGACATG | 5464 | TGCAGGACCAGAGAATTCGAATA CAGCTCGGCANNNGATCGACATG | 5704 |
| TGCAGGACCAGAGAATTCGAATA CAAAAGACATNNNGATCGACATG | 5225 | TGCAGGACCAGAGAATTCGAATA CATTACTATCNNNGATCGACATG | 5465 | TGCAGGACCAGAGAATTCGAATA CAGTTAGAGGNNNGATCGACATG | 5705 |
| TGCAGGACCAGAGAATTCGAATA CAACCCATGANNNGATCGACATG | 5226 | TGCAGGACCAGAGAATTCGAATA CATTCAAGTANNNGATCGACATG | 5466 | TGCAGGACCAGAGAATTCGAATA CAACCAGCTANNNGATCGACATG | 5706 |
| TGCAGGACCAGAGAATTCGAATA CATCCTCACANNNGATCGACATG | 5227 | TGCAGGACCAGAGAATTCGAATA CACTCAGTTCNNNGATCGACATG | 5467 | TGCAGGACCAGAGAATTCGAATA CAGGAGTGCGNNNGATCGACATG | 5707 |
| TGCAGGACCAGAGAATTCGAATA CATTGAGGTCNNNGATCGACATG | 5228 | TGCAGGACCAGAGAATTCGAATA CAAAGAATTGNNNGATCGACATG | 5468 | TGCAGGACCAGAGAATTCGAATA CATCGATATANNNGATCGACATG | 5708 |
| TGCAGGACCAGAGAATTCGAATA CAGCGTACTANNNTGCATCAGGT | 5229 | TGCAGGACCAGAGAATTCGAATA CAGACTACCANNNTGCATCAGGT | 5469 | TGCAGGACCAGAGAATTCGAATA CAGCGCTAGCNNNTGCATCAGGT | 5709 |
| TGCAGGACCAGAGAATTCGAATA CAAGGTTAGGNNNTGCATCAGGT | 5230 | TGCAGGACCAGAGAATTCGAATA CACACGCTAANNNTGCATCAGGT | 5470 | TGCAGGACCAGAGAATTCGAATA CACTGATTAANNNTGCATCAGGT | 5710 |
| TGCAGGACCAGAGAATTCGAATA CACTCCACATNNNTGCATCAGGT | 5231 | TGCAGGACCAGAGAATTCGAATA CAAGTCATATNNNTGCATCAGGT | 5471 | TGCAGGACCAGAGAATTCGAATA CACACTCCACNNNTGCATCAGGT | 5711 |
| TGCAGGACCAGAGAATTCGAATA CACGATCTAGNNNTGCATCAGGT | 5232 | TGCAGGACCAGAGAATTCGAATA CATCTAGGACNNNTGCATCAGGT | 5472 | TGCAGGACCAGAGAATTCGAATA CATAGGCGTTNNNTGCATCAGGT | 5712 |
| TGCAGGACCAGAGAATTCGAATA CATCGATAATNNNTGCATCAGGT | 5233 | TGCAGGACCAGAGAATTCGAATA CAAGAACTTTNNNTGCATCAGGT | 5473 | TGCAGGACCAGAGAATTCGAATA CAATATGTCANNNTGCATCAGGT | 5713 |
| TGCAGGACCAGAGAATTCGAATA CACCCACGAGNNNTGCATCAGGT | 5234 | TGCAGGACCAGAGAATTCGAATA CAACCACTGANNNTGCATCAGGT | 5474 | TGCAGGACCAGAGAATTCGAATA CAGTCGATTGNNNTGCATCAGGT | 5714 |
| TGCAGGACCAGAGAATTCGAATA CAGTGCAATGNNNTGCATCAGGT | 5235 | TGCAGGACCAGAGAATTCGAATA CAACACGATCNNNTGCATCAGGT | 5475 | TGCAGGACCAGAGAATTCGAATA CAATAGAGCGNNNTGCATCAGGT | 5715 |
| TGCAGGACCAGAGAATTCGAATA CAAAAAATGCNNNTGCATCAGGT | 5236 | TGCAGGACCAGAGAATTCGAATA CAGTTACCAGNNNTGCATCAGGT | 5476 | TGCAGGACCAGAGAATTCGAATA CAGACTAAGGNNNTGCATCAGGT | 5716 |
| TGCAGGACCAGAGAATTCGAATA CAGACTAGTCNNNTGCATCAGGT | 5237 | TGCAGGACCAGAGAATTCGAATA CACGCTACCCNNNTGCATCAGGT | 5477 | TGCAGGACCAGAGAATTCGAATA CACCTACCTANNNTGCATCAGGT | 5717 |
| TGCAGGACCAGAGAATTCGAATA CACGTAGAAGNNNTGCATCAGGT | 5238 | TGCAGGACCAGAGAATTCGAATA CAAGAGGTACNNNTGCATCAGGT | 5478 | TGCAGGACCAGAGAATTCGAATA CATAGGAGACNNNTGCATCAGGT | 5718 |
| TGCAGGACCAGAGAATTCGAATA CAGTGTGAAGNNNTGCATCAGGT | 5239 | TGCAGGACCAGAGAATTCGAATA CAAATCTCTTNNNTGCATCAGGT | 5479 | TGCAGGACCAGAGAATTCGAATA CACCGTCATTNNNTGCATCAGGT | 5719 |
| TGCAGGACCAGAGAATTCGAATA CAAAGTACTTNNNTGCATCAGGT | 5240 | TGCAGGACCAGAGAATTCGAATA CAATATTTAANNNTGCATCAGGT | 5480 | TGCAGGACCAGAGAATTCGAATA CAGTGTTCAGNNNTGCATCAGGT | 5720 |
| TGCAGGACCAGAGAATTCGAATA CACGAACGTTNNNTGCATCAGGT | 5241 | TGCAGGACCAGAGAATTCGAATA CATATCGAATNNNTGCATCAGGT | 5481 | TGCAGGACCAGAGAATTCGAATA CAAGCGGTTTNNNTGCATCAGGT | 5721 |
| TGCAGGACCAGAGAATTCGAATA CAATTGCTGGNNNTGCATCAGGT | 5242 | TGCAGGACCAGAGAATTCGAATA CAGCTAAATTNNNTGCATCAGGT | 5482 | TGCAGGACCAGAGAATTCGAATA CAAACTCTTTNNNTGCATCAGGT | 5722 |
| TGCAGGACCAGAGAATTCGAATA CATGTGTGTGNNNTGCATCAGGT | 5243 | TGCAGGACCAGAGAATTCGAATA CATTTCAGGTNNNTGCATCAGGT | 5483 | TGCAGGACCAGAGAATTCGAATA CATAACGTATNNNTGCATCAGGT | 5723 |
| TGCAGGACCAGAGAATTCGAATA CAACATCTTTNNNTGCATCAGGT | 5244 | TGCAGGACCAGAGAATTCGAATA CAGTTCACAGNNNTGCATCAGGT | 5484 | TGCAGGACCAGAGAATTCGAATA CAAAGGACTGNNNTGCATCAGGT | 5724 |
| TGCAGGACCAGAGAATTCGAATA CACGATGCTANNNTGCATCAGGT | 5245 | TGCAGGACCAGAGAATTCGAATA CAGCATTCCTNNNTGCATCAGGT | 5485 | TGCAGGACCAGAGAATTCGAATA CAAGGAGAAGNNNTGCATCAGGT | 5725 |
| TGCAGGACCAGAGAATTCGAATA CATAGTCCAGNNNTGCATCAGGT | 5246 | TGCAGGACCAGAGAATTCGAATA CATTACACCCNNNTGCATCAGGT | 5486 | TGCAGGACCAGAGAATTCGAATA CATCGAACGTNNNTGCATCAGGT | 5726 |

FIG. 19G

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CACAGTAATTNNNTGCATCAGGT | 5247 | TGCAGGACCAGAGAATTCGAATA CATATTTTATNNNTGCATCAGGT | 5487 | TGCAGGACCAGAGAATTCGAATA CACGGACATTNNNTGCATCAGGT | 5727 |
| TGCAGGACCAGAGAATTCGAATA CAAAGGTGGTNNNTGCATCAGGT | 5248 | TGCAGGACCAGAGAATTCGAATA CATGTCCGCCNNNTGCATCAGGT | 5488 | TGCAGGACCAGAGAATTCGAATA CATTCCGCATNNNTGCATCAGGT | 5728 |
| TGCAGGACCAGAGAATTCGAATA CACGGTGGTCNNNTGCATCAGGT | 5249 | TGCAGGACCAGAGAATTCGAATA CAAAACCCGTNNNTGCATCAGGT | 5489 | TGCAGGACCAGAGAATTCGAATA CACGCGGCTANNNTGCATCAGGT | 5729 |
| TGCAGGACCAGAGAATTCGAATA CAGTGGTTGTNNNTGCATCAGGT | 5250 | TGCAGGACCAGAGAATTCGAATA CAGTACCGATNNNTGCATCAGGT | 5490 | TGCAGGACCAGAGAATTCGAATA CAGTTTCTGCNNNTGCATCAGGT | 5730 |
| TGCAGGACCAGAGAATTCGAATA CATGTATTCTNNNTGCATCAGGT | 5251 | TGCAGGACCAGAGAATTCGAATA CACGCGTTCCNNNTGCATCAGGT | 5491 | TGCAGGACCAGAGAATTCGAATA CAAGACAGCANNNTGCATCAGGT | 5731 |
| TGCAGGACCAGAGAATTCGAATA CATAAGTCGCNNNTGCATCAGGT | 5252 | TGCAGGACCAGAGAATTCGAATA CACTCCAATCNNNTGCATCAGGT | 5492 | TGCAGGACCAGAGAATTCGAATA CAGACCCTCCNNNTGCATCAGGT | 5732 |
| TGCAGGACCAGAGAATTCGAATA CATAGGAGCANNNTGCATCAGGT | 5253 | TGCAGGACCAGAGAATTCGAATA CACCGCAGACNNNTGCATCAGGT | 5493 | TGCAGGACCAGAGAATTCGAATA CATACTCGCTNNNTGCATCAGGT | 5733 |
| TGCAGGACCAGAGAATTCGAATA CACATAAATCNNNTGCATCAGGT | 5254 | TGCAGGACCAGAGAATTCGAATA CACGCTTAGANNNTGCATCAGGT | 5494 | TGCAGGACCAGAGAATTCGAATA CATTCGTATTNNNTGCATCAGGT | 5734 |
| TGCAGGACCAGAGAATTCGAATA CAAGCTGTACNNNTGCATCAGGT | 5255 | TGCAGGACCAGAGAATTCGAATA CAGAAAAGCCNNNTGCATCAGGT | 5495 | TGCAGGACCAGAGAATTCGAATA CATACTTAAGNNNTGCATCAGGT | 5735 |
| TGCAGGACCAGAGAATTCGAATA CATTGCGCGTNNNTGCATCAGGT | 5256 | TGCAGGACCAGAGAATTCGAATA CACTCATCCANNNTGCATCAGGT | 5496 | TGCAGGACCAGAGAATTCGAATA CAGACTACCGTNNNTGCATCAGGT | 5736 |
| TGCAGGACCAGAGAATTCGAATA CAAGGCGTGGNNNTGCATCAGGT | 5257 | TGCAGGACCAGAGAATTCGAATA CAAAGAGTATNNNTGCATCAGGT | 5497 | TGCAGGACCAGAGAATTCGAATA CAACCAGTCTNNNTGCATCAGGT | 5737 |
| TGCAGGACCAGAGAATTCGAATA CAGTCTAGGTNNNTGCATCAGGT | 5258 | TGCAGGACCAGAGAATTCGAATA CAAATTGTCANNNTGCATCAGGT | 5498 | TGCAGGACCAGAGAATTCGAATA CAGACCGTTGNNNTGCATCAGGT | 5738 |
| TGCAGGACCAGAGAATTCGAATA CATCCGTAAGNNNTGCATCAGGT | 5259 | TGCAGGACCAGAGAATTCGAATA CAATAATACCNNNTGCATCAGGT | 5499 | TGCAGGACCAGAGAATTCGAATA CAGATGGACANNNTGCATCAGGT | 5739 |
| TGCAGGACCAGAGAATTCGAATA CATATCGGCANNNTGCATCAGGT | 5260 | TGCAGGACCAGAGAATTCGAATA CAAATTTTGGNNNTGCATCAGGT | 5500 | TGCAGGACCAGAGAATTCGAATA CATCGTAGTGNNNTGCATCAGGT | 5740 |
| TGCAGGACCAGAGAATTCGAATA CAATCATCGGNNNTGCATCAGGT | 5261 | TGCAGGACCAGAGAATTCGAATA CAGCACAGTTNNNTGCATCAGGT | 5501 | TGCAGGACCAGAGAATTCGAATA CACCACATCTNNNTGCATCAGGT | 5741 |
| TGCAGGACCAGAGAATTCGAATA CAACGTCTGANNNTGCATCAGGT | 5262 | TGCAGGACCAGAGAATTCGAATA CATTAAACCANNNTGCATCAGGT | 5502 | TGCAGGACCAGAGAATTCGAATA CAGTGCTACANNNTGCATCAGGT | 5742 |
| TGCAGGACCAGAGAATTCGAATA CAACGGTACTNNNTGCATCAGGT | 5263 | TGCAGGACCAGAGAATTCGAATA CAATGGAGACNNNTGCATCAGGT | 5503 | TGCAGGACCAGAGAATTCGAATA CATTCTTCAANNNTGCATCAGGT | 5743 |
| TGCAGGACCAGAGAATTCGAATA CATGCAAGGANNNTGCATCAGGT | 5264 | TGCAGGACCAGAGAATTCGAATA CAAAAGACGCNNNTGCATCAGGT | 5504 | TGCAGGACCAGAGAATTCGAATA CATTACAGTANNNTGCATCAGGT | 5744 |
| TGCAGGACCAGAGAATTCGAATA CAAGACTCACNNNTGCATCAGGT | 5265 | TGCAGGACCAGAGAATTCGAATA CAATCCGAACNNNTGCATCAGGT | 5505 | TGCAGGACCAGAGAATTCGAATA CAAGACGCGGNNNTGCATCAGGT | 5745 |
| TGCAGGACCAGAGAATTCGAATA CACAATCAGCNNNTGCATCAGGT | 5266 | TGCAGGACCAGAGAATTCGAATA CAGTTAGGAGNNNTGCATCAGGT | 5506 | TGCAGGACCAGAGAATTCGAATA CAGGAGCTCCNNNTGCATCAGGT | 5746 |
| TGCAGGACCAGAGAATTCGAATA CATGGCTGTANNNTGCATCAGGT | 5267 | TGCAGGACCAGAGAATTCGAATA CATGGCCAGCNNNTGCATCAGGT | 5507 | TGCAGGACCAGAGAATTCGAATA CAATTAACCANNNTGCATCAGGT | 5747 |
| TGCAGGACCAGAGAATTCGAATA CAGTTTACCCNNNTGCATCAGGT | 5268 | TGCAGGACCAGAGAATTCGAATA CAATCTGCACNNNTGCATCAGGT | 5508 | TGCAGGACCAGAGAATTCGAATA CAATCGAGCTNNNTGCATCAGGT | 5748 |
| TGCAGGACCAGAGAATTCGAATA CACGTCAGTANNNTGCATCAGGT | 5269 | TGCAGGACCAGAGAATTCGAATA CAGTACAACCNNNTGCATCAGGT | 5509 | TGCAGGACCAGAGAATTCGAATA CAGGAAACGTNNNTGCATCAGGT | 5749 |
| TGCAGGACCAGAGAATTCGAATA CACGACGGAGNNNTGCATCAGGT | 5270 | TGCAGGACCAGAGAATTCGAATA CAGTGGCCGANNNTGCATCAGGT | 5510 | TGCAGGACCAGAGAATTCGAATA CATGAAGAGCNNNTGCATCAGGT | 5750 |
| TGCAGGACCAGAGAATTCGAATA CAATATGCGCNNNTGCATCAGGT | 5271 | TGCAGGACCAGAGAATTCGAATA CAAGCTCTCTNNNTGCATCAGGT | 5511 | TGCAGGACCAGAGAATTCGAATA CAATCCGGATNNNTGCATCAGGT | 5751 |
| TGCAGGACCAGAGAATTCGAATA CAGCTGGCCANNNTGCATCAGGT | 5272 | TGCAGGACCAGAGAATTCGAATA CAACCTCTTGNNNTGCATCAGGT | 5512 | TGCAGGACCAGAGAATTCGAATA CAGTTGTCTCNNNTGCATCAGGT | 5752 |
| TGCAGGACCAGAGAATTCGAATA CACGCGTCTCNNNTGCATCAGGT | 5273 | TGCAGGACCAGAGAATTCGAATA CATCAGCGTANNNTGCATCAGGT | 5513 | TGCAGGACCAGAGAATTCGAATA CATGGATAGGNNNTGCATCAGGT | 5753 |
| TGCAGGACCAGAGAATTCGAATA CAATAAGTGANNNTGCATCAGGT | 5274 | TGCAGGACCAGAGAATTCGAATA CATCAGACGTNNNTGCATCAGGT | 5514 | TGCAGGACCAGAGAATTCGAATA CAAAACCAGGNNNTGCATCAGGT | 5754 |
| TGCAGGACCAGAGAATTCGAATA CAGACAGTCTNNNTGCATCAGGT | 5275 | TGCAGGACCAGAGAATTCGAATA CATATAGATCNNNTGCATCAGGT | 5515 | TGCAGGACCAGAGAATTCGAATA CACGGCGACTNNNTGCATCAGGT | 5755 |
| TGCAGGACCAGAGAATTCGAATA CAGCCAAGGTNNNTGCATCAGGT | 5276 | TGCAGGACCAGAGAATTCGAATA CAACCCGCCTNNNTGCATCAGGT | 5516 | TGCAGGACCAGAGAATTCGAATA CATTATCCGCNNNTGCATCAGGT | 5756 |
| TGCAGGACCAGAGAATTCGAATA CACACCGAACTNNNTGCATCAGGT | 5277 | TGCAGGACCAGAGAATTCGAATA CAGCAGGATANNNTGCATCAGGT | 5517 | TGCAGGACCAGAGAATTCGAATA CAAGCCACATNNNTGCATCAGGT | 5757 |
| TGCAGGACCAGAGAATTCGAATA CATACACTGGNNNTGCATCAGGT | 5278 | TGCAGGACCAGAGAATTCGAATA CAAGAATGCCNNNTGCATCAGGT | 5518 | TGCAGGACCAGAGAATTCGAATA CATGCCTCATCNNNTGCATCAGGT | 5758 |
| TGCAGGACCAGAGAATTCGAATA CAATTTCGTTNNNTGCATCAGGT | 5279 | TGCAGGACCAGAGAATTCGAATA CAACAAGTGGNNNTGCATCAGGT | 5519 | TGCAGGACCAGAGAATTCGAATA CAGCTGGAGGNNNTGCATCAGGT | 5759 |

FIG. 19H

| Pool-22 | SEQ ID NO: | Pool-23 | SEQ ID NO: | Pool-24 | SEQ ID NO: |
|---|---|---|---|---|---|
| TGCAGGACCAGAGAATTCGAATA CATCTGCGCCNNNTGCATCAGGT | 5280 | TGCAGGACCAGAGAATTCGAATA CAGTCCGGCANNNTGCATCAGGT | 5520 | TGCAGGACCAGAGAATTCGAATA CAAAAGATGTNNNTGCATCAGGT | 5760 |
| TGCAGGACCAGAGAATTCGAATA CACGAGCTATNNNTGCATCAGGT | 5281 | TGCAGGACCAGAGAATTCGAATA CAGCCCTGAGNNNTGCATCAGGT | 5521 | TGCAGGACCAGAGAATTCGAATA CATCAGAAAANNNTGCATCAGGT | 5761 |
| TGCAGGACCAGAGAATTCGAATA CAACGCCATANNNTGCATCAGGT | 5282 | TGCAGGACCAGAGAATTCGAATA CAAACTATGTNNNTGCATCAGGT | 5522 | TGCAGGACCAGAGAATTCGAATA CAGTCCTGAANNNTGCATCAGGT | 5762 |
| TGCAGGACCAGAGAATTCGAATA CATCCTCTGANNNTGCATCAGGT | 5283 | TGCAGGACCAGAGAATTCGAATA CATCTGATCCNNNTGCATCAGGT | 5523 | TGCAGGACCAGAGAATTCGAATA CAGCTAGGCCNNNTGCATCAGGT | 5763 |
| TGCAGGACCAGAGAATTCGAATA CAAATTCTAGNNNTGCATCAGGT | 5284 | TGCAGGACCAGAGAATTCGAATA CATAATAGAGNNNTGCATCAGGT | 5524 | TGCAGGACCAGAGAATTCGAATA CACTCCTGTANNNTGCATCAGGT | 5764 |
| TGCAGGACCAGAGAATTCGAATA CACCTCAGCCNNNTGCATCAGGT | 5285 | TGCAGGACCAGAGAATTCGAATA CAGGCCGTTGNNNTGCATCAGGT | 5525 | TGCAGGACCAGAGAATTCGAATA CATTGATCAANNNTGCATCAGGT | 5765 |
| TGCAGGACCAGAGAATTCGAATA CAACCCGGANNNTGCATCAGGT | 5286 | TGCAGGACCAGAGAATTCGAATA CACACAAGGGNNNTGCATCAGGT | 5526 | TGCAGGACCAGAGAATTCGAATA CACTCTTCGTNNNTGCATCAGGT | 5766 |
| TGCAGGACCAGAGAATTCGAATA CAGTGATAGGNNNTGCATCAGGT | 5287 | TGCAGGACCAGAGAATTCGAATA CACCCTGAAANNNTGCATCAGGT | 5527 | TGCAGGACCAGAGAATTCGAATA CATCTTATCANNNTGCATCAGGT | 5767 |
| TGCAGGACCAGAGAATTCGAATA CATTGAATTGNNNTGCATCAGGT | 5288 | TGCAGGACCAGAGAATTCGAATA CACTGCTGTTNNNTGCATCAGGT | 5528 | TGCAGGACCAGAGAATTCGAATA CATACTGGCANNNTGCATCAGGT | 5768 |

FIG. 20A

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAC GCGACGTNNNACGTATGCCA | 5769 | TGCAGGACCAGAGAATTCGAATACAC TCTGCTANNNACGTATGCCA | 6009 | TGCAGGACCAGAGAATTCGAATACAT GTACGCANNNACGTATGCCA | 6249 |
| TGCAGGACCAGAGAATTCGAATACAC CGATCANNNNACGTATGCCA | 5770 | TGCAGGACCAGAGAATTCGAATACAT TACATGANNNACGTATGCCA | 6010 | TGCAGGACCAGAGAATTCGAATACAG ATGTGTCNNNACGTATGCCA | 6250 |
| TGCAGGACCAGAGAATTCGAATACAG GCAATCTNNNACGTATGCCA | 5771 | TGCAGGACCAGAGAATTCGAATACAT GAGGATANNNACGTATGCCA | 6011 | TGCAGGACCAGAGAATTCGAATACAC TAGACTGNNNACGTATGCCA | 6251 |
| TGCAGGACCAGAGAATTCGAATACAC TAGGAGANNNACGTATGCCA | 5772 | TGCAGGACCAGAGAATTCGAATACAC GACATGTNNNACGTATGCCA | 6012 | TGCAGGACCAGAGAATTCGAATACAG ATCGTGTNNNACGTATGCCA | 6252 |
| TGCAGGACCAGAGAATTCGAATACAT TGATAACNNNACGTATGCCA | 5773 | TGCAGGACCAGAGAATTCGAATACAC CTTGAAGNNNACGTATGCCA | 6013 | TGCAGGACCAGAGAATTCGAATACAT TATCTCANNNACGTATGCCA | 6253 |
| TGCAGGACCAGAGAATTCGAATACAG AGTACTCNNNACGTATGCCA | 5774 | TGCAGGACCAGAGAATTCGAATACAC AACGATCNNNACGTATGCCA | 6014 | TGCAGGACCAGAGAATTCGAATACAA ACCCTAGNNNACGTATGCCA | 6254 |
| TGCAGGACCAGAGAATTCGAATACAA TGCCGCGNNNACGTATGCCA | 5775 | TGCAGGACCAGAGAATTCGAATACAG ACTAGAGNNNACGTATGCCA | 6015 | TGCAGGACCAGAGAATTCGAATACAT ATCATAGNNNACGTATGCCA | 6255 |
| TGCAGGACCAGAGAATTCGAATACAA AATAGCANNNACGTATGCCA | 5776 | TGCAGGACCAGAGAATTCGAATACAC TGCAGTANNNACGTATGCCA | 6016 | TGCAGGACCAGAGAATTCGAATACAC GTTCGTTNNNACGTATGCCA | 6256 |
| TGCAGGACCAGAGAATTCGAATACAA TCAGACCNNNACGTATGCCA | 5777 | TGCAGGACCAGAGAATTCGAATACAA TGTGACCNNNACGTATGCCA | 6017 | TGCAGGACCAGAGAATTCGAATACAA TACAAAGNNNACGTATGCCA | 6257 |
| TGCAGGACCAGAGAATTCGAATACAG GTGCGTCNNNACGTATGCCA | 5778 | TGCAGGACCAGAGAATTCGAATACAA CCGAATTNNNACGTATGCCA | 6018 | TGCAGGACCAGAGAATTCGAATACAG TCCTCATNNNACGTATGCCA | 6258 |
| TGCAGGACCAGAGAATTCGAATACAT CTTTCCCNNNACGTATGCCA | 5779 | TGCAGGACCAGAGAATTCGAATACAA TTGTTTCNNNACGTATGCCA | 6019 | TGCAGGACCAGAGAATTCGAATACAA GTAGCAGNNNACGTATGCCA | 6259 |
| TGCAGGACCAGAGAATTCGAATACAA AATTCCANNNACGTATGCCA | 5780 | TGCAGGACCAGAGAATTCGAATACAC GCCGTGANNNACGTATGCCA | 6020 | TGCAGGACCAGAGAATTCGAATACAG AAAACATNNNACGTATGCCA | 6260 |
| TGCAGGACCAGAGAATTCGAATACAA ATGTGCCNNNACGTATGCCA | 5781 | TGCAGGACCAGAGAATTCGAATACAC ACTCAAGNNNACGTATGCCA | 6021 | TGCAGGACCAGAGAATTCGAATACAT TCGCCTANNNACGTATGCCA | 6261 |
| TGCAGGACCAGAGAATTCGAATACAC ACATGACNNNACGTATGCCA | 5782 | TGCAGGACCAGAGAATTCGAATACAA GCAATCCNNNACGTATGCCA | 6022 | TGCAGGACCAGAGAATTCGAATACAA GAGTTGGNNNACGTATGCCA | 6262 |
| TGCAGGACCAGAGAATTCGAATACAG ACCTGGCNNNACGTATGCCA | 5783 | TGCAGGACCAGAGAATTCGAATACAT CCATTATNNNACGTATGCCA | 6023 | TGCAGGACCAGAGAATTCGAATACAC AATATTGNNNACGTATGCCA | 6263 |
| TGCAGGACCAGAGAATTCGAATACAC CAAAATTNNNACGTATGCCA | 5784 | TGCAGGACCAGAGAATTCGAATACAA ATTGCTANNNACGTATGCCA | 6024 | TGCAGGACCAGAGAATTCGAATACAA AACCTCGNNNACGTATGCCA | 6264 |
| TGCAGGACCAGAGAATTCGAATACAA TTGTCCCNNNACGTATGCCA | 5785 | TGCAGGACCAGAGAATTCGAATACAC GATCCAANNNACGTATGCCA | 6025 | TGCAGGACCAGAGAATTCGAATACAA GTTAATCNNNACGTATGCCA | 6265 |
| TGCAGGACCAGAGAATTCGAATACAC GTCGACGNNNACGTATGCCA | 5786 | TGCAGGACCAGAGAATTCGAATACAC TCGGTGGNNNACGTATGCCA | 6026 | TGCAGGACCAGAGAATTCGAATACAG ACTCTAGNNNACGTATGCCA | 6266 |
| TGCAGGACCAGAGAATTCGAATACAC CCGCTCANNNACGTATGCCA | 5787 | TGCAGGACCAGAGAATTCGAATACAG AGATTAANNNACGTATGCCA | 6027 | TGCAGGACCAGAGAATTCGAATACAA GGAAAAANNNACGTATGCCA | 6267 |
| TGCAGGACCAGAGAATTCGAATACAA TGGACTCNNNACGTATGCCA | 5788 | TGCAGGACCAGAGAATTCGAATACAA TCAGGCTNNNACGTATGCCA | 6028 | TGCAGGACCAGAGAATTCGAATACAT GACTAGCNNNACGTATGCCA | 6268 |
| TGCAGGACCAGAGAATTCGAATACAT TGTAACANNNACGTATGCCA | 5789 | TGCAGGACCAGAGAATTCGAATACAG CGGCCCGNNNACGTATGCCA | 6029 | TGCAGGACCAGAGAATTCGAATACAC ATCGTAGNNNACGTATGCCA | 6269 |
| TGCAGGACCAGAGAATTCGAATACAG TTTACTTNNNACGTATGCCA | 5790 | TGCAGGACCAGAGAATTCGAATACAT TTAAATANNNACGTATGCCA | 6030 | TGCAGGACCAGAGAATTCGAATACAA GGTGTTCNNNACGTATGCCA | 6270 |
| TGCAGGACCAGAGAATTCGAATACAT GGATAAANNNACGTATGCCA | 5791 | TGCAGGACCAGAGAATTCGAATACAC ATGGCGCNNNACGTATGCCA | 6031 | TGCAGGACCAGAGAATTCGAATACAG CCATTAGNNNACGTATGCCA | 6271 |
| TGCAGGACCAGAGAATTCGAATACAA TCCTTCGNNNACGTATGCCA | 5792 | TGCAGGACCAGAGAATTCGAATACAT CCGTTAGNNNACGTATGCCA | 6032 | TGCAGGACCAGAGAATTCGAATACAC GTTCTGTNNNACGTATGCCA | 6272 |
| TGCAGGACCAGAGAATTCGAATACAC GCATACANNNACGTATGCCA | 5793 | TGCAGGACCAGAGAATTCGAATACAC GCCTGGANNNACGTATGCCA | 6033 | TGCAGGACCAGAGAATTCGAATACAT CCGCCTGNNNACGTATGCCA | 6273 |
| TGCAGGACCAGAGAATTCGAATACAT CACCGATNNNACGTATGCCA | 5794 | TGCAGGACCAGAGAATTCGAATACAT TCCTGTGNNNACGTATGCCA | 6034 | TGCAGGACCAGAGAATTCGAATACAC CTACACTNNNACGTATGCCA | 6274 |
| TGCAGGACCAGAGAATTCGAATACAA TTGCTCCNNNACGTATGCCA | 5795 | TGCAGGACCAGAGAATTCGAATACAG GCGCCTANNNACGTATGCCA | 6035 | TGCAGGACCAGAGAATTCGAATACAA GAAGATTNNNACGTATGCCA | 6275 |
| TGCAGGACCAGAGAATTCGAATACAA TCTTCTANNNACGTATGCCA | 5796 | TGCAGGACCAGAGAATTCGAATACAC CCGGCGGNNNACGTATGCCA | 6036 | TGCAGGACCAGAGAATTCGAATACAA GTCCTTCNNNACGTATGCCA | 6276 |
| TGCAGGACCAGAGAATTCGAATACAT CGAAATTNNNACGTATGCCA | 5797 | TGCAGGACCAGAGAATTCGAATACAA TTCGGCANNNACGTATGCCA | 6037 | TGCAGGACCAGAGAATTCGAATACAG CATTATANNNACGTATGCCA | 6277 |
| TGCAGGACCAGAGAATTCGAATACAC AAGTCACNNNACGTATGCCA | 5798 | TGCAGGACCAGAGAATTCGAATACAC BAATGANNNNACGTATGCCA | 6038 | TGCAGGACCAGAGAATTCGAATACAG TGGCATTNNNACGTATGCCA | 6278 |
| TGCAGGACCAGAGAATTCGAATACAT GACCCGGNNNACGTATGCCA | 5799 | TGCAGGACCAGAGAATTCGAATACAT AGGATGGNNNACGTATGCCA | 6039 | TGCAGGACCAGAGAATTCGAATACAA ACGTCACNNNACGTATGCCA | 6279 |
| TGCAGGACCAGAGAATTCGAATACAA GCTGCCGNNNACGTATGCCA | 5800 | TGCAGGACCAGAGAATTCGAATACAT TGGACGTNNNACGTATGCCA | 6040 | TGCAGGACCAGAGAATTCGAATACAG TTAACTANNNACGTATGCCA | 6280 |

FIG. 20B

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAT CACTCGTNNNACGTATGCCA | 5801 | TGCAGGACCAGAGAATTCGAATACAT CGTGAGTNNNACGTATGCCA | 6041 | TGCAGGACCAGAGAATTCGAATACAT AAAGATGNNNACGTATGCCA | 6281 |
| TGCAGGACCAGAGAATTCGAATACAG TTACCGANNNACGTATGCCA | 5802 | TGCAGGACCAGAGAATTCGAATACAG GAACTTCNNNACGTATGCCA | 6042 | TGCAGGACCAGAGAATTCGAATACAA ATTTCCTNNNACGTATGCCA | 6282 |
| TGCAGGACCAGAGAATTCGAATACAC TTAGATANNNACGTATGCCA | 5803 | TGCAGGACCAGAGAATTCGAATACAA TGTGCCANNNACGTATGCCA | 6043 | TGCAGGACCAGAGAATTCGAATACAC GGCAAAANNNACGTATGCCA | 6283 |
| TGCAGGACCAGAGAATTCGAATACAA GGCTAGANNNACGTATGCCA | 5804 | TGCAGGACCAGAGAATTCGAATACAC CGGTGCANNNACGTATGCCA | 6044 | TGCAGGACCAGAGAATTCGAATACAT CGCACAANNNACGTATGCCA | 6284 |
| TGCAGGACCAGAGAATTCGAATACAT CACAGGTNNNACGTATGCCA | 5805 | TGCAGGACCAGAGAATTCGAATACAC TATTGCCNNNACGTATGCCA | 6045 | TGCAGGACCAGAGAATTCGAATACAA GGTCGCCNNNACGTATGCCA | 6285 |
| TGCAGGACCAGAGAATTCGAATACAG ATATTTGNNNACGTATGCCA | 5806 | TGCAGGACCAGAGAATTCGAATACAT TAAGGCCNNNACGTATGCCA | 6046 | TGCAGGACCAGAGAATTCGAATACAG GATTCGTNNNACGTATGCCA | 6286 |
| TGCAGGACCAGAGAATTCGAATACAT TGTGTTTNNNACGTATGCCA | 5807 | TGCAGGACCAGAGAATTCGAATACAT GTTAAACNNNACGTATGCCA | 6047 | TGCAGGACCAGAGAATTCGAATACAA GCATCTGNNNACGTATGCCA | 6287 |
| TGCAGGACCAGAGAATTCGAATACAG AAAAAAGNNNACGTATGCCA | 5808 | TGCAGGACCAGAGAATTCGAATACAC TTGGTTCNNNACGTATGCCA | 6048 | TGCAGGACCAGAGAATTCGAATACAC CCACAAANNNACGTATGCCA | 6288 |
| TGCAGGACCAGAGAATTCGAATACAG GCATGTTNNNACGTATGCCA | 5809 | TGCAGGACCAGAGAATTCGAATACAG GTAATTTNNNACGTATGCCA | 6049 | TGCAGGACCAGAGAATTCGAATACAA GTTATACNNNACGTATGCCA | 6289 |
| TGCAGGACCAGAGAATTCGAATACAG GCTTTTCNNNACGTATGCCA | 5810 | TGCAGGACCAGAGAATTCGAATACAA TTATCAGNNNACGTATGCCA | 6050 | TGCAGGACCAGAGAATTCGAATACAT CTATCATNNNACGTATGCCA | 6290 |
| TGCAGGACCAGAGAATTCGAATACAA CTAATACNNNACGTATGCCA | 5811 | TGCAGGACCAGAGAATTCGAATACAT GCGTTCTNNNACGTATGCCA | 6051 | TGCAGGACCAGAGAATTCGAATACAC GGCTCTCNNNACGTATGCCA | 6291 |
| TGCAGGACCAGAGAATTCGAATACAG TAGCCCGNNNACGTATGCCA | 5812 | TGCAGGACCAGAGAATTCGAATACAT GATCCAGNNNACGTATGCCA | 6052 | TGCAGGACCAGAGAATTCGAATACAG TGATTATNNNACGTATGCCA | 6292 |
| TGCAGGACCAGAGAATTCGAATACAT AACGTCNNNACGTATGCCA | 5813 | TGCAGGACCAGAGAATTCGAATACAC AGTTCAGNNNACGTATGCCA | 6053 | TGCAGGACCAGAGAATTCGAATACAT AGACTCGNNNACGTATGCCA | 6293 |
| TGCAGGACCAGAGAATTCGAATACAT TTCAAGANNNACGTATGCCA | 5814 | TGCAGGACCAGAGAATTCGAATACAT GCGACATNNNACGTATGCCA | 6054 | TGCAGGACCAGAGAATTCGAATACAA ACGTTANNNACGTATGCCA | 6294 |
| TGCAGGACCAGAGAATTCGAATACAC ACAAGAGNNNACGTATGCCA | 5815 | TGCAGGACCAGAGAATTCGAATACAA GCAGTAGNNNACGTATGCCA | 6055 | TGCAGGACCAGAGAATTCGAATACAA AGTAAGTNNNACGTATGCCA | 6295 |
| TGCAGGACCAGAGAATTCGAATACAC CCGTTTANNNACGTATGCCA | 5816 | TGCAGGACCAGAGAATTCGAATACAT TAGTGATNNNACGTATGCCA | 6056 | TGCAGGACCAGAGAATTCGAATACAA TGTTAACNNNACGTATGCCA | 6296 |
| TGCAGGACCAGAGAATTCGAATACAG TTAAGAANNNACGTATGCCA | 5817 | TGCAGGACCAGAGAATTCGAATACAC ACATTAANNNACGTATGCCA | 6057 | TGCAGGACCAGAGAATTCGAATACAT AATCACANNNACGTATGCCA | 6297 |
| TGCAGGACCAGAGAATTCGAATACAG AACCTACNNNACGTATGCCA | 5818 | TGCAGGACCAGAGAATTCGAATACAA GGTGCCCNNNACGTATGCCA | 6058 | TGCAGGACCAGAGAATTCGAATACAC ATGCTTCNNNACGTATGCCA | 6298 |
| TGCAGGACCAGAGAATTCGAATACAA GCGACTTNNNACGTATGCCA | 5819 | TGCAGGACCAGAGAATTCGAATACAA CCTGGCGNNNACGTATGCCA | 6059 | TGCAGGACCAGAGAATTCGAATACAA GCATTATNNNACGTATGCCA | 6299 |
| TGCAGGACCAGAGAATTCGAATACAC GCACTAANNNACGTATGCCA | 5820 | TGCAGGACCAGAGAATTCGAATACAC GGCGATCNNNACGTATGCCA | 6060 | TGCAGGACCAGAGAATTCGAATACAA GGCATAGNNNACGTATGCCA | 6300 |
| TGCAGGACCAGAGAATTCGAATACAG GTGTTCANNNACGTATGCCA | 5821 | TGCAGGACCAGAGAATTCGAATACAT AGAACCTGNNNACGTATGCCA | 6061 | TGCAGGACCAGAGAATTCGAATACAC ATACGCANNNACGTATGCCA | 6301 |
| TGCAGGACCAGAGAATTCGAATACAC TTTTCAANNNACGTATGCCA | 5822 | TGCAGGACCAGAGAATTCGAATACAA GACTACCNNNACGTATGCCA | 6062 | TGCAGGACCAGAGAATTCGAATACAA GACCCGCNNNACGTATGCCA | 6302 |
| TGCAGGACCAGAGAATTCGAATACAG ATTCATANNNACGTATGCCA | 5823 | TGCAGGACCAGAGAATTCGAATACAC TTAGACGNNNACGTATGCCA | 6063 | TGCAGGACCAGAGAATTCGAATACAT TCCCTAGNNNACGTATGCCA | 6303 |
| TGCAGGACCAGAGAATTCGAATACAT TGACGACNNNACGTATGCCA | 5824 | TGCAGGACCAGAGAATTCGAATACAC GGCGGCCNNNACGTATGCCA | 6064 | TGCAGGACCAGAGAATTCGAATACAA GTGTGCTNNNACGTATGCCA | 6304 |
| TGCAGGACCAGAGAATTCGAATACAC CTTGTACNNNACGTATGCCA | 5825 | TGCAGGACCAGAGAATTCGAATACAG CCGATATNNNACGTATGCCA | 6065 | TGCAGGACCAGAGAATTCGAATACAC CTGTACTNNNACGTATGCCA | 6305 |
| TGCAGGACCAGAGAATTCGAATACAG GTGCGGANNNACGTATGCCA | 5826 | TGCAGGACCAGAGAATTCGAATACAC CCGGCCCNNNACGTATGCCA | 6066 | TGCAGGACCAGAGAATTCGAATACAC ACACCCCNNNACGTATGCCA | 6306 |
| TGCAGGACCAGAGAATTCGAATACAT CATGAATNNNACGTATGCCA | 5827 | TGCAGGACCAGAGAATTCGAATACAC CTCGCTGNNNACGTATGCCA | 6067 | TGCAGGACCAGAGAATTCGAATACAT TTGGTGNNNACGTATGCCA | 6307 |
| TGCAGGACCAGAGAATTCGAATACAG CGAAGTNNNACGTATGCCA | 5828 | TGCAGGACCAGAGAATTCGAATACAC AGCCATANNNACGTATGCCA | 6068 | TGCAGGACCAGAGAATTCGAATACAG TTAGCCANNNACGTATGCCA | 6308 |
| TGCAGGACCAGAGAATTCGAATACAA AAATAATNNNCTAGCGTTAC | 5829 | TGCAGGACCAGAGAATTCGAATACAA ATGGAGCNNNCTAGCGTTAC | 6069 | TGCAGGACCAGAGAATTCGAATACAA CGACATNNNCTAGCGTTAC | 6309 |
| TGCAGGACCAGAGAATTCGAATACAT TCGTGTCNNNCTAGCGTTAC | 5830 | TGCAGGACCAGAGAATTCGAATACAT CACAGACNNNCTAGCGTTAC | 6070 | TGCAGGACCAGAGAATTCGAATACAG CATGACTNNNCTAGCGTTAC | 6310 |
| TGCAGGACCAGAGAATTCGAATACAT CGTCTTGNNNCTAGCGTTAC | 5831 | TGCAGGACCAGAGAATTCGAATACAT CCGTCCGNNNCTAGCGTTAC | 6071 | TGCAGGACCAGAGAATTCGAATACAT AGTTGTANNNCTAGCGTTAC | 6311 |
| TGCAGGACCAGAGAATTCGAATACAG ACTGTGTNNNCTAGCGTTAC | 5832 | TGCAGGACCAGAGAATTCGAATACAG AATGGACNNNCTAGCGTTAC | 6072 | TGCAGGACCAGAGAATTCGAATACAC CTGTTCANNNCTAGCGTTAC | 6312 |
| TGCAGGACCAGAGAATTCGAATACAC CATTGGANNNCTAGCGTTAC | 5833 | TGCAGGACCAGAGAATTCGAATACAG TGCTCAANNNCTAGCGTTAC | 6073 | TGCAGGACCAGAGAATTCGAATACAC TGAGTCANNNCTAGCGTTAC | 6313 |

FIG. 20C

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAC ACAGCGCNNNCTAGCGTTAC | 5834 | TGCAGGACCAGAGAATTCGAATACAT GTTCGGANNNCTAGCGTTAC | 6074 | TGCAGGACCAGAGAATTCGAATACAT CATCTTANNNCTAGCGTTAC | 6314 |
| TGCAGGACCAGAGAATTCGAATACAA CCCCGTCNNNCTAGCGTTAC | 5835 | TGCAGGACCAGAGAATTCGAATACAC TGCGTGGNNNCTAGCGTTAC | 6075 | TGCAGGACCAGAGAATTCGAATACAC ACATTTNNNCTAGCGTTAC | 6315 |
| TGCAGGACCAGAGAATTCGAATACAT CACCTTGNNNCTAGCGTTAC | 5836 | TGCAGGACCAGAGAATTCGAATACAA CCGTCAANNNCTAGCGTTAC | 6076 | TGCAGGACCAGAGAATTCGAATACAG CCACATANNNCTAGCGTTAC | 6316 |
| TGCAGGACCAGAGAATTCGAATACAA GTACCACNNNCTAGCGTTAC | 5837 | TGCAGGACCAGAGAATTCGAATACAG GTAACGANNNCTAGCGTTAC | 6077 | TGCAGGACCAGAGAATTCGAATACAT AAACAGANNNCTAGCGTTAC | 6317 |
| TGCAGGACCAGAGAATTCGAATACAA CAAATGANNNCTAGCGTTAC | 5838 | TGCAGGACCAGAGAATTCGAATACAA TCCGAGTNNNCTAGCGTTAC | 6078 | TGCAGGACCAGAGAATTCGAATACAG GTACCATNNNCTAGCGTTAC | 6318 |
| TGCAGGACCAGAGAATTCGAATACAA TTGTTGANNNCTAGCGTTAC | 5839 | TGCAGGACCAGAGAATTCGAATACAA CCAACCANNNCTAGCGTTAC | 6079 | TGCAGGACCAGAGAATTCGAATACAA GAAAAAGNNNCTAGCGTTAC | 6319 |
| TGCAGGACCAGAGAATTCGAATACAA CGGAAACNNNCTAGCGTTAC | 5840 | TGCAGGACCAGAGAATTCGAATACAC AGTATATNNNCTAGCGTTAC | 6080 | TGCAGGACCAGAGAATTCGAATACAG CTCTCATNNNCTAGCGTTAC | 6320 |
| TGCAGGACCAGAGAATTCGAATACAG AGAACGTNNNCTAGCGTTAC | 5841 | TGCAGGACCAGAGAATTCGAATACAT CCGATAGNNNCTAGCGTTAC | 6081 | TGCAGGACCAGAGAATTCGAATACAA GGCACAANNNCTAGCGTTAC | 6321 |
| TGCAGGACCAGAGAATTCGAATACAT ACCATGGNNNCTAGCGTTAC | 5842 | TGCAGGACCAGAGAATTCGAATACAT TAGTATGNNNCTAGCGTTAC | 6082 | TGCAGGACCAGAGAATTCGAATACAG CGATGAANNNCTAGCGTTAC | 6322 |
| TGCAGGACCAGAGAATTCGAATACAC AAAACGGNNNCTAGCGTTAC | 5843 | TGCAGGACCAGAGAATTCGAATACAA CATTCAANNNCTAGCGTTAC | 6083 | TGCAGGACCAGAGAATTCGAATACAT CACTTATNNNCTAGCGTTAC | 6323 |
| TGCAGGACCAGAGAATTCGAATACAT AGTGAGGNNNCTAGCGTTAC | 5844 | TGCAGGACCAGAGAATTCGAATACAG TACTGACNNNCTAGCGTTAC | 6084 | TGCAGGACCAGAGAATTCGAATACAT AGGCCGCNNNCTAGCGTTAC | 6324 |
| TGCAGGACCAGAGAATTCGAATACAC GTGATACNNNCTAGCGTTAC | 5845 | TGCAGGACCAGAGAATTCGAATACAC CTCATTGNNNCTAGCGTTAC | 6085 | TGCAGGACCAGAGAATTCGAATACAA TTTAAATNNNCTAGCGTTAC | 6325 |
| TGCAGGACCAGAGAATTCGAATACAC TGCCCCTNNNCTAGCGTTAC | 5846 | TGCAGGACCAGAGAATTCGAATACAA TGGCACTNNNCTAGCGTTAC | 6086 | TGCAGGACCAGAGAATTCGAATACAT CTGTTTANNNCTAGCGTTAC | 6326 |
| TGCAGGACCAGAGAATTCGAATACAG GACAGTANNNCTAGCGTTAC | 5847 | TGCAGGACCAGAGAATTCGAATACAC CCCACGTNNNCTAGCGTTAC | 6087 | TGCAGGACCAGAGAATTCGAATACAA GTTGAAANNNCTAGCGTTAC | 6327 |
| TGCAGGACCAGAGAATTCGAATACAC TAGTATANNNCTAGCGTTAC | 5848 | TGCAGGACCAGAGAATTCGAATACAC AAACCTGNNNCTAGCGTTAC | 6088 | TGCAGGACCAGAGAATTCGAATACAA TATGACTNNNCTAGCGTTAC | 6328 |
| TGCAGGACCAGAGAATTCGAATACAG AACCTTGNNNCTAGCGTTAC | 5849 | TGCAGGACCAGAGAATTCGAATACAC GGCCAGTNNNCTAGCGTTAC | 6089 | TGCAGGACCAGAGAATTCGAATACAG AAGACTGNNNCTAGCGTTAC | 6329 |
| TGCAGGACCAGAGAATTCGAATACAC TGTTTATNNNCTAGCGTTAC | 5850 | TGCAGGACCAGAGAATTCGAATACAG ACAACCTNNNCTAGCGTTAC | 6090 | TGCAGGACCAGAGAATTCGAATACAG TGCGTGCNNNCTAGCGTTAC | 6330 |
| TGCAGGACCAGAGAATTCGAATACAA ATACGATNNNCTAGCGTTAC | 5851 | TGCAGGACCAGAGAATTCGAATACAT GGCACATNNNCTAGCGTTAC | 6091 | TGCAGGACCAGAGAATTCGAATACAA TGTCCGANNNCTAGCGTTAC | 6331 |
| TGCAGGACCAGAGAATTCGAATACAC GTCAAGTNNNCTAGCGTTAC | 5852 | TGCAGGACCAGAGAATTCGAATACAC CAAGTACNNNCTAGCGTTAC | 6092 | TGCAGGACCAGAGAATTCGAATACAT GTTATAGNNNCTAGCGTTAC | 6332 |
| TGCAGGACCAGAGAATTCGAATACAG CTGTTTCNNNCTAGCGTTAC | 5853 | TGCAGGACCAGAGAATTCGAATACAA ACGACCGNNNCTAGCGTTAC | 6093 | TGCAGGACCAGAGAATTCGAATACAT GTCGTAGNNNCTAGCGTTAC | 6333 |
| TGCAGGACCAGAGAATTCGAATACAA CCGTGCGNNNCTAGCGTTAC | 5854 | TGCAGGACCAGAGAATTCGAATACAC CCGTGATNNNCTAGCGTTAC | 6094 | TGCAGGACCAGAGAATTCGAATACAG ACGCTTANNNCTAGCGTTAC | 6334 |
| TGCAGGACCAGAGAATTCGAATACAC AGCTGCGNNNCTAGCGTTAC | 5855 | TGCAGGACCAGAGAATTCGAATACAC ATTGCCTNNNCTAGCGTTAC | 6095 | TGCAGGACCAGAGAATTCGAATACAG AATTACTNNNCTAGCGTTAC | 6335 |
| TGCAGGACCAGAGAATTCGAATACAT CCTTACGNNNCTAGCGTTAC | 5856 | TGCAGGACCAGAGAATTCGAATACAT GTTGTTTNNNCTAGCGTTAC | 6096 | TGCAGGACCAGAGAATTCGAATACAT CGACCCCNNNCTAGCGTTAC | 6336 |
| TGCAGGACCAGAGAATTCGAATACAA ACGAAGCNNNCTAGCGTTAC | 5857 | TGCAGGACCAGAGAATTCGAATACAT GTTTTTGNNNCTAGCGTTAC | 6097 | TGCAGGACCAGAGAATTCGAATACAG CCTCCACNNNCTAGCGTTAC | 6337 |
| TGCAGGACCAGAGAATTCGAATACAG AAGTTTTNNNCTAGCGTTAC | 5858 | TGCAGGACCAGAGAATTCGAATACAG CTCCTCGNNNCTAGCGTTAC | 6098 | TGCAGGACCAGAGAATTCGAATACAC TGTATANNNCTAGCGTTAC | 6338 |
| TGCAGGACCAGAGAATTCGAATACAG CCGTTAANNNCTAGCGTTAC | 5859 | TGCAGGACCAGAGAATTCGAATACAC CACCTGCNNNCTAGCGTTAC | 6099 | TGCAGGACCAGAGAATTCGAATACAT TCGAGTGNNNCTAGCGTTAC | 6339 |
| TGCAGGACCAGAGAATTCGAATACAT GTGCCAANNNCTAGCGTTAC | 5860 | TGCAGGACCAGAGAATTCGAATACAG AGCGGTGNNNCTAGCGTTAC | 6100 | TGCAGGACCAGAGAATTCGAATACAT AAGTGCCNNNCTAGCGTTAC | 6340 |
| TGCAGGACCAGAGAATTCGAATACAG CAAAACGNNNCTAGCGTTAC | 5861 | TGCAGGACCAGAGAATTCGAATACAA ACAACGGNNNCTAGCGTTAC | 6101 | TGCAGGACCAGAGAATTCGAATACAC AGATAAANNNCTAGCGTTAC | 6341 |
| TGCAGGACCAGAGAATTCGAATACAC GTAAGAGNNNCTAGCGTTAC | 5862 | TGCAGGACCAGAGAATTCGAATACAA TTGCTTTNNNCTAGCGTTAC | 6102 | TGCAGGACCAGAGAATTCGAATACAC GAATCACNNNCTAGCGTTAC | 6342 |
| TGCAGGACCAGAGAATTCGAATACAT GACGTCANNNCTAGCGTTAC | 5863 | TGCAGGACCAGAGAATTCGAATACAC CAGAGAANNNCTAGCGTTAC | 6103 | TGCAGGACCAGAGAATTCGAATACAG AGCTTACNNNCTAGCGTTAC | 6343 |
| TGCAGGACCAGAGAATTCGAATACAC TCCCTAANNNCTAGCGTTAC | 5864 | TGCAGGACCAGAGAATTCGAATACAG ATACCTGNNNCTAGCGTTAC | 6104 | TGCAGGACCAGAGAATTCGAATACAT CATCTGCNNNCTAGCGTTAC | 6344 |
| TGCAGGACCAGAGAATTCGAATACAT ATTCAGANNNCTAGCGTTAC | 5865 | TGCAGGACCAGAGAATTCGAATACAA CTTATTCNNNCTAGCGTTAC | 6105 | TGCAGGACCAGAGAATTCGAATACAC CACGTGGNNNCTAGCGTTAC | 6345 |
| TGCAGGACCAGAGAATTCGAATACAC TAGCAACNNNCTAGCGTTAC | 5866 | TGCAGGACCAGAGAATTCGAATACAA GTTGTTANNNCTAGCGTTAC | 6106 | TGCAGGACCAGAGAATTCGAATACAC GTGTATGNNNCTAGCGTTAC | 6346 |

FIG. 20D

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAG AATGCCTNNNCTAGCGTTAC | 5867 | TGCAGGACCAGAGAATTCGAATACAA TGACTGCNNNCTAGCGTTAC | 6107 | TGCAGGACCAGAGAATTCGAATACAC TCTCCGGNNNCTAGCGTTAC | 6347 |
| TGCAGGACCAGAGAATTCGAATACAG ACTTCTCNNNCTAGCGTTAC | 5868 | TGCAGGACCAGAGAATTCGAATACAA GCAAACGNNNCTAGCGTTAC | 6108 | TGCAGGACCAGAGAATTCGAATACAC AAGAGTGNNNCTAGCGTTAC | 6348 |
| TGCAGGACCAGAGAATTCGAATACAT AATTAGCNNNCTAGCGTTAC | 5869 | TGCAGGACCAGAGAATTCGAATACAA GACTATTNNNCTAGCGTTAC | 6109 | TGCAGGACCAGAGAATTCGAATACAT AGCTCTCNNNCTAGCGTTAC | 6349 |
| TGCAGGACCAGAGAATTCGAATACAC GTGTGGCNNNCTAGCGTTAC | 5870 | TGCAGGACCAGAGAATTCGAATACAC TGAAACCNNNCTAGCGTTAC | 6110 | TGCAGGACCAGAGAATTCGAATACAG TGGCAGGNNNCTAGCGTTAC | 6350 |
| TGCAGGACCAGAGAATTCGAATACAG ACTCGATNNNCTAGCGTTAC | 5871 | TGCAGGACCAGAGAATTCGAATACAA GGAAAGGNNNCTAGCGTTAC | 6111 | TGCAGGACCAGAGAATTCGAATACAT GCATCGANNNCTAGCGTTAC | 6351 |
| TGCAGGACCAGAGAATTCGAATACAG CGATCGCNNNCTAGCGTTAC | 5872 | TGCAGGACCAGAGAATTCGAATACAA CCTAGTTNNNCTAGCGTTAC | 6112 | TGCAGGACCAGAGAATTCGAATACAT GGTCGANNNCTAGCGTTAC | 6352 |
| TGCAGGACCAGAGAATTCGAATACAA CTCTACCNNNCTAGCGTTAC | 5873 | TGCAGGACCAGAGAATTCGAATACAC AAACCACNNNCTAGCGTTAC | 6113 | TGCAGGACCAGAGAATTCGAATACAA AGCCACTNNNCTAGCGTTAC | 6353 |
| TGCAGGACCAGAGAATTCGAATACAG GAAGGCCNNNCTAGCGTTAC | 5874 | TGCAGGACCAGAGAATTCGAATACAT TGTAGTANNNCTAGCGTTAC | 6114 | TGCAGGACCAGAGAATTCGAATACAG ATCTTTTNNNCTAGCGTTAC | 6354 |
| TGCAGGACCAGAGAATTCGAATACAC ATATTAGNNNCTAGCGTTAC | 5875 | TGCAGGACCAGAGAATTCGAATACAG TACAGCTNNNCTAGCGTTAC | 6115 | TGCAGGACCAGAGAATTCGAATACAG GCTCTAANNNCTAGCGTTAC | 6355 |
| TGCAGGACCAGAGAATTCGAATACAC GGTGACCNNNCTAGCGTTAC | 5876 | TGCAGGACCAGAGAATTCGAATACAA GTGTACCNNNCTAGCGTTAC | 6116 | TGCAGGACCAGAGAATTCGAATACAT CTATGTTNNNCTAGCGTTAC | 6356 |
| TGCAGGACCAGAGAATTCGAATACAG TGCATGTNNNCTAGCGTTAC | 5877 | TGCAGGACCAGAGAATTCGAATACAT TTTATGCNNNCTAGCGTTAC | 6117 | TGCAGGACCAGAGAATTCGAATACAA CCGCGTGNNNCTAGCGTTAC | 6357 |
| TGCAGGACCAGAGAATTCGAATACAT AAGTGTTNNNCTAGCGTTAC | 5878 | TGCAGGACCAGAGAATTCGAATACAA ATCGTGTNNNCTAGCGTTAC | 6118 | TGCAGGACCAGAGAATTCGAATACAG TACTCCTNNNCTAGCGTTAC | 6358 |
| TGCAGGACCAGAGAATTCGAATACAA CCTTATTNNNCTAGCGTTAC | 5879 | TGCAGGACCAGAGAATTCGAATACAC GATCTGANNNCTAGCGTTAC | 6119 | TGCAGGACCAGAGAATTCGAATACAG GAGCCCTNNNCTAGCGTTAC | 6359 |
| TGCAGGACCAGAGAATTCGAATACAA CTCCACTNNNCTAGCGTTAC | 5880 | TGCAGGACCAGAGAATTCGAATACAG ATAGATANNNCTAGCGTTAC | 6120 | TGCAGGACCAGAGAATTCGAATACAT ATCGAGCNNNCTAGCGTTAC | 6360 |
| TGCAGGACCAGAGAATTCGAATACAC CAAATATNNNCTAGCGTTAC | 5881 | TGCAGGACCAGAGAATTCGAATACAG AGTCCTANNNCTAGCGTTAC | 6121 | TGCAGGACCAGAGAATTCGAATACAC CGTTGAANNNCTAGCGTTAC | 6361 |
| TGCAGGACCAGAGAATTCGAATACAC AAGATGGNNNCTAGCGTTAC | 5882 | TGCAGGACCAGAGAATTCGAATACAC ATGTGGTNNNCTAGCGTTAC | 6122 | TGCAGGACCAGAGAATTCGAATACAC GAAGAACNNNCTAGCGTTAC | 6362 |
| TGCAGGACCAGAGAATTCGAATACAC CCAAGGCNNNCTAGCGTTAC | 5883 | TGCAGGACCAGAGAATTCGAATACAG ATCGCGCNNNCTAGCGTTAC | 6123 | TGCAGGACCAGAGAATTCGAATACAA GTGATCCNNNCTAGCGTTAC | 6363 |
| TGCAGGACCAGAGAATTCGAATACAT AAGCGGANNNCTAGCGTTAC | 5884 | TGCAGGACCAGAGAATTCGAATACAA CCACATGNNNCTAGCGTTAC | 6124 | TGCAGGACCAGAGAATTCGAATACAG GTCAACTNNNCTAGCGTTAC | 6364 |
| TGCAGGACCAGAGAATTCGAATACAG AGGCCCTNNNCTAGCGTTAC | 5885 | TGCAGGACCAGAGAATTCGAATACAT GCCGATANNNCTAGCGTTAC | 6125 | TGCAGGACCAGAGAATTCGAATACAT GACGTGTNNNCTAGCGTTAC | 6365 |
| TGCAGGACCAGAGAATTCGAATACAC TTCCTAGNNNCTAGCGTTAC | 5886 | TGCAGGACCAGAGAATTCGAATACAC AAAGCCTNNNCTAGCGTTAC | 6126 | TGCAGGACCAGAGAATTCGAATACAT TACAACANNNCTAGCGTTAC | 6366 |
| TGCAGGACCAGAGAATTCGAATACAC GCAGAAANNNCTAGCGTTAC | 5887 | TGCAGGACCAGAGAATTCGAATACAA CTGACGTNNNCTAGCGTTAC | 6127 | TGCAGGACCAGAGAATTCGAATACAA AATGTTCNNNCTAGCGTTAC | 6367 |
| TGCAGGACCAGAGAATTCGAATACAT GTGCGTANNNCTAGCGTTAC | 5888 | TGCAGGACCAGAGAATTCGAATACAA AGCTCGTNNNCTAGCGTTAC | 6128 | TGCAGGACCAGAGAATTCGAATACAT TATAACGNNNCTAGCGTTAC | 6368 |
| TGCAGGACCAGAGAATTCGAATACAC GATGGAANNNGATCGACATG | 5889 | TGCAGGACCAGAGAATTCGAATACAG GATCGAANNNGATCGACATG | 6129 | TGCAGGACCAGAGAATTCGAATACAT CCGGATANNNGATCGACATG | 6369 |
| TGCAGGACCAGAGAATTCGAATACAC CAATTAANNNGATCGACATG | 5890 | TGCAGGACCAGAGAATTCGAATACAT CGCAACANNNGATCGACATG | 6130 | TGCAGGACCAGAGAATTCGAATACAA GCCCTTTNNNGATCGACATG | 6370 |
| TGCAGGACCAGAGAATTCGAATACAC ATAGGCTNNNGATCGACATG | 5891 | TGCAGGACCAGAGAATTCGAATACAC CGACTAANNNGATCGACATG | 6131 | TGCAGGACCAGAGAATTCGAATACAG TACACTGNNNGATCGACATG | 6371 |
| TGCAGGACCAGAGAATTCGAATACAA AAAAATTNNNGATCGACATG | 5892 | TGCAGGACCAGAGAATTCGAATACAG ACCGTTANNNGATCGACATG | 6132 | TGCAGGACCAGAGAATTCGAATACAC GTGTAGTNNNGATCGACATG | 6372 |
| TGCAGGACCAGAGAATTCGAATACAA ATACACTNNNGATCGACATG | 5893 | TGCAGGACCAGAGAATTCGAATACAA TGCCCTTNNNGATCGACATG | 6133 | TGCAGGACCAGAGAATTCGAATACAG GAAAGTCNNNGATCGACATG | 6373 |
| TGCAGGACCAGAGAATTCGAATACAA ATCGAAANNNGATCGACATG | 5894 | TGCAGGACCAGAGAATTCGAATACAT CGAAACCNNNGATCGACATG | 6134 | TGCAGGACCAGAGAATTCGAATACAT TCTGCGTNNNGATCGACATG | 6374 |
| TGCAGGACCAGAGAATTCGAATACAT CTATTACNNNGATCGACATG | 5895 | TGCAGGACCAGAGAATTCGAATACAG ACCTTCTNNNGATCGACATG | 6135 | TGCAGGACCAGAGAATTCGAATACAT ACTCGANNNGATCGACATG | 6375 |
| TGCAGGACCAGAGAATTCGAATACAA CCCGATANNNGATCGACATG | 5896 | TGCAGGACCAGAGAATTCGAATACAC TACCCTANNNGATCGACATG | 6136 | TGCAGGACCAGAGAATTCGAATACAC GTCCAAANNNGATCGACATG | 6376 |
| TGCAGGACCAGAGAATTCGAATACAG AAACGCANNNGATCGACATG | 5897 | TGCAGGACCAGAGAATTCGAATACAA TGCCTTCNNNGATCGACATG | 6137 | TGCAGGACCAGAGAATTCGAATACAT TGAACCGNNNGATCGACATG | 6377 |
| TGCAGGACCAGAGAATTCGAATACAG TGATCGTNNNGATCGACATG | 5898 | TGCAGGACCAGAGAATTCGAATACAG CGACTATNNNGATCGACATG | 6138 | TGCAGGACCAGAGAATTCGAATACAG GCCGCTANNNGATCGACATG | 6378 |
| TGCAGGACCAGAGAATTCGAATACAC GCAGCCANNNGATCGACATG | 5899 | TGCAGGACCAGAGAATTCGAATACAG GCATTCANNNGATCGACATG | 6139 | TGCAGGACCAGAGAATTCGAATACAG ATACGTCNNNGATCGACATG | 6379 |

FIG. 20E

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAT GACCATGNNNGATCGACATG | 5900 | TGCAGGACCAGAGAATTCGAATACAG CTAGAAGNNNGATCGACATG | 6140 | TGCAGGACCAGAGAATTCGAATACAA TTCAACANNNGATCGACATG | 6380 |
| TGCAGGACCAGAGAATTCGAATACAG GTCCACGNNNGATCGACATG | 5901 | TGCAGGACCAGAGAATTCGAATACAT TTATAAANNNGATCGACATG | 6141 | TGCAGGACCAGAGAATTCGAATACAG TGTGCATNNNGATCGACATG | 6381 |
| TGCAGGACCAGAGAATTCGAATACAA AGCATAANNNGATCGACATG | 5902 | TGCAGGACCAGAGAATTCGAATACAT CCCTACANNNGATCGACATG | 6142 | TGCAGGACCAGAGAATTCGAATACAG CCATAGTNNNGATCGACATG | 6382 |
| TGCAGGACCAGAGAATTCGAATACAG ACAGGCGNNNGATCGACATG | 5903 | TGCAGGACCAGAGAATTCGAATACAA CGTCTAGNNNGATCGACATG | 6143 | TGCAGGACCAGAGAATTCGAATACAC TCATCTGNNNGATCGACATG | 6383 |
| TGCAGGACCAGAGAATTCGAATACAA CGGTAGANNNGATCGACATG | 5904 | TGCAGGACCAGAGAATTCGAATACAG AGCCTTTGNNNGATCGACATG | 6144 | TGCAGGACCAGAGAATTCGAATACAA ACCGACTNNNGATCGACATG | 6384 |
| TGCAGGACCAGAGAATTCGAATACAT CATTACTNNNGATCGACATG | 5905 | TGCAGGACCAGAGAATTCGAATACAA GAGCGGCNNNGATCGACATG | 6145 | TGCAGGACCAGAGAATTCGAATACAA ATCGCCCNNNGATCGACATG | 6385 |
| TGCAGGACCAGAGAATTCGAATACAC GAAAATANNNGATCGACATG | 5906 | TGCAGGACCAGAGAATTCGAATACAC ATATACANNNGATCGACATG | 6146 | TGCAGGACCAGAGAATTCGAATACAT AGGATCCNNNGATCGACATG | 6386 |
| TGCAGGACCAGAGAATTCGAATACAT GGAAGGTNNNGATCGACATG | 5907 | TGCAGGACCAGAGAATTCGAATACAA AGGCTAGNNNGATCGACATG | 6147 | TGCAGGACCAGAGAATTCGAATACAA TGGCGTTNNNGATCGACATG | 6387 |
| TGCAGGACCAGAGAATTCGAATACAC TGTTTTANNNGATCGACATG | 5908 | TGCAGGACCAGAGAATTCGAATACAT ATCGACGNNNGATCGACATG | 6148 | TGCAGGACCAGAGAATTCGAATACAC TAAATTGNNNGATCGACATG | 6388 |
| TGCAGGACCAGAGAATTCGAATACAC GGATTTGNNNGATCGACATG | 5909 | TGCAGGACCAGAGAATTCGAATACAA GACGTCTNNNGATCGACATG | 6149 | TGCAGGACCAGAGAATTCGAATACAA CTACATANNNGATCGACATG | 6389 |
| TGCAGGACCAGAGAATTCGAATACAC GTGGTGCNNNGATCGACATG | 5910 | TGCAGGACCAGAGAATTCGAATACAT GTTACCCNNNGATCGACATG | 6150 | TGCAGGACCAGAGAATTCGAATACAC ATCCTCANNNGATCGACATG | 6390 |
| TGCAGGACCAGAGAATTCGAATACAA TGCCTCTNNNGATCGACATG | 5911 | TGCAGGACCAGAGAATTCGAATACAG CCTGCAGNNNGATCGACATG | 6151 | TGCAGGACCAGAGAATTCGAATACAG ATGTGAGNNNGATCGACATG | 6391 |
| TGCAGGACCAGAGAATTCGAATACAC GAGAAGGNNNGATCGACATG | 5912 | TGCAGGACCAGAGAATTCGAATACAA GTAACGTNNNGATCGACATG | 6152 | TGCAGGACCAGAGAATTCGAATACAA GGCCAAANNNGATCGACATG | 6392 |
| TGCAGGACCAGAGAATTCGAATACAT CATGGTGNNNGATCGACATG | 5913 | TGCAGGACCAGAGAATTCGAATACAA TCTTATCNNNGATCGACATG | 6153 | TGCAGGACCAGAGAATTCGAATACAC CAAGCTANNNGATCGACATG | 6393 |
| TGCAGGACCAGAGAATTCGAATACAC TGGAGCCNNNGATCGACATG | 5914 | TGCAGGACCAGAGAATTCGAATACAA CGTTTGGNNNGATCGACATG | 6154 | TGCAGGACCAGAGAATTCGAATACAA GGAGATCNNNGATCGACATG | 6394 |
| TGCAGGACCAGAGAATTCGAATACAC TGTTAGGNNNGATCGACATG | 5915 | TGCAGGACCAGAGAATTCGAATACAG ATTAAAGNNNGATCGACATG | 6155 | TGCAGGACCAGAGAATTCGAATACAC CTCCGACNNNGATCGACATG | 6395 |
| TGCAGGACCAGAGAATTCGAATACAC TGGTTCTNNNGATCGACATG | 5916 | TGCAGGACCAGAGAATTCGAATACAT TGCCAGANNNGATCGACATG | 6156 | TGCAGGACCAGAGAATTCGAATACAC GCTGTGGNNNGATCGACATG | 6396 |
| TGCAGGACCAGAGAATTCGAATACAC AAAGTCCNNNGATCGACATG | 5917 | TGCAGGACCAGAGAATTCGAATACAC GGCATATNNNGATCGACATG | 6157 | TGCAGGACCAGAGAATTCGAATACAT ACCGCCCNNNGATCGACATG | 6397 |
| TGCAGGACCAGAGAATTCGAATACAC GTAGCCGNNNGATCGACATG | 5918 | TGCAGGACCAGAGAATTCGAATACAG GTCAGCCNNNGATCGACATG | 6158 | TGCAGGACCAGAGAATTCGAATACAC GTCGCCTNNNGATCGACATG | 6398 |
| TGCAGGACCAGAGAATTCGAATACAA GGCTGAANNNGATCGACATG | 5919 | TGCAGGACCAGAGAATTCGAATACAC TACCACTNNNGATCGACATG | 6159 | TGCAGGACCAGAGAATTCGAATACAC CTCACCGNNNGATCGACATG | 6399 |
| TGCAGGACCAGAGAATTCGAATACAC TAATCTTNNNGATCGACATG | 5920 | TGCAGGACCAGAGAATTCGAATACAC GGCACGGNNNGATCGACATG | 6160 | TGCAGGACCAGAGAATTCGAATACAG CCTGGACNNNGATCGACATG | 6400 |
| TGCAGGACCAGAGAATTCGAATACAG ACTTAATNNNGATCGACATG | 5921 | TGCAGGACCAGAGAATTCGAATACAT GCTTCGTNNNGATCGACATG | 6161 | TGCAGGACCAGAGAATTCGAATACAA CTTGGACNNNGATCGACATG | 6401 |
| TGCAGGACCAGAGAATTCGAATACAA TCACAATNNNGATCGACATG | 5922 | TGCAGGACCAGAGAATTCGAATACAA GCACTGTNNNGATCGACATG | 6162 | TGCAGGACCAGAGAATTCGAATACAT GTTGCCTNNNGATCGACATG | 6402 |
| TGCAGGACCAGAGAATTCGAATACAG AGCCTGCNNNGATCGACATG | 5923 | TGCAGGACCAGAGAATTCGAATACAC TTACAAANNNGATCGACATG | 6163 | TGCAGGACCAGAGAATTCGAATACAC GGCACGTNNNGATCGACATG | 6403 |
| TGCAGGACCAGAGAATTCGAATACAC TCTAGGANNNGATCGACATG | 5924 | TGCAGGACCAGAGAATTCGAATACAC GATGGCCNNNGATCGACATG | 6164 | TGCAGGACCAGAGAATTCGAATACAA GGTGTGANNNGATCGACATG | 6404 |
| TGCAGGACCAGAGAATTCGAATACAG GTGAGATNNNGATCGACATG | 5925 | TGCAGGACCAGAGAATTCGAATACAC ACCGGCANNNGATCGACATG | 6165 | TGCAGGACCAGAGAATTCGAATACAA ACGACGANNNGATCGACATG | 6405 |
| TGCAGGACCAGAGAATTCGAATACAA GGTTGCTNNNGATCGACATG | 5926 | TGCAGGACCAGAGAATTCGAATACAG CCATAACNNNGATCGACATG | 6166 | TGCAGGACCAGAGAATTCGAATACAC ATCACTCNNNGATCGACATG | 6406 |
| TGCAGGACCAGAGAATTCGAATACAG AGGTGCGNNNGATCGACATG | 5927 | TGCAGGACCAGAGAATTCGAATACAT GAAGTCCNNNGATCGACATG | 6167 | TGCAGGACCAGAGAATTCGAATACAT AATGCTANNNGATCGACATG | 6407 |
| TGCAGGACCAGAGAATTCGAATACAA CTCAGACNNNGATCGACATG | 5928 | TGCAGGACCAGAGAATTCGAATACAG CAACACTNNNGATCGACATG | 6168 | TGCAGGACCAGAGAATTCGAATACAC GCCTTGCNNNGATCGACATG | 6408 |
| TGCAGGACCAGAGAATTCGAATACAC AATGTATNNNGATCGACATG | 5929 | TGCAGGACCAGAGAATTCGAATACAA CGCTTCTNNNGATCGACATG | 6169 | TGCAGGACCAGAGAATTCGAATACAT GATCAGCNNNGATCGACATG | 6409 |
| TGCAGGACCAGAGAATTCGAATACAA ACCATTANNNGATCGACATG | 5930 | TGCAGGACCAGAGAATTCGAATACAT ACCGGCGNNNGATCGACATG | 6170 | TGCAGGACCAGAGAATTCGAATACAC TTCGGAANNNGATCGACATG | 6410 |
| TGCAGGACCAGAGAATTCGAATACAT GGCGCTGNNNGATCGACATG | 5931 | TGCAGGACCAGAGAATTCGAATACAT GCTAATANNNGATCGACATG | 6171 | TGCAGGACCAGAGAATTCGAATACAC GCAAATCNNNGATCGACATG | 6411 |
| TGCAGGACCAGAGAATTCGAATACAC GCCCTGTNNNGATCGACATG | 5932 | TGCAGGACCAGAGAATTCGAATACAT AAGGAGCNNNGATCGACATG | 6172 | TGCAGGACCAGAGAATTCGAATACAA GAGAACCNNNGATCGACATG | 6412 |

FIG. 20F

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAT AGCCGTANNNGATCGACATG | 5933 | TGCAGGACCAGAGAATTCGAATACAT AGTCCGANNNGATCGACATG | 6173 | TGCAGGACCAGAGAATTCGAATACAT CGACGATNNNGATCGACATG | 6413 |
| TGCAGGACCAGAGAATTCGAATACAG GATAGTGNNNGATCGACATG | 5934 | TGCAGGACCAGAGAATTCGAATACAC TATCCTGNNNGATCGACATG | 6174 | TGCAGGACCAGAGAATTCGAATACAC AGCAAGANNNGATCGACATG | 6414 |
| TGCAGGACCAGAGAATTCGAATACAT AAGGCAGNNNGATCGACATG | 5935 | TGCAGGACCAGAGAATTCGAATACAT TTGGTCCNNNGATCGACATG | 6175 | TGCAGGACCAGAGAATTCGAATACAC AAAGTAANNNGATCGACATG | 6415 |
| TGCAGGACCAGAGAATTCGAATACAA GGTCCTANNNGATCGACATG | 5936 | TGCAGGACCAGAGAATTCGAATACAG CCTTTCANNNGATCGACATG | 6176 | TGCAGGACCAGAGAATTCGAATACAG AAATCAANNNGATCGACATG | 6416 |
| TGCAGGACCAGAGAATTCGAATACAA ACTGGAGNNNGATCGACATG | 5937 | TGCAGGACCAGAGAATTCGAATACAG TGTTCGANNNGATCGACATG | 6177 | TGCAGGACCAGAGAATTCGAATACAC TCCTGATNNNGATCGACATG | 6417 |
| TGCAGGACCAGAGAATTCGAATACAT TGTTGTTNNNGATCGACATG | 5938 | TGCAGGACCAGAGAATTCGAATACAG CTGTCAGNNNGATCGACATG | 6178 | TGCAGGACCAGAGAATTCGAATACAA CTATAGTNNNGATCGACATG | 6418 |
| TGCAGGACCAGAGAATTCGAATACAG CGAAGCGNNNGATCGACATG | 5939 | TGCAGGACCAGAGAATTCGAATACAA TCTGACGNNNGATCGACATG | 6179 | TGCAGGACCAGAGAATTCGAATACAG GTAGTTCNNNGATCGACATG | 6419 |
| TGCAGGACCAGAGAATTCGAATACAA GATCCGTNNNGATCGACATG | 5940 | TGCAGGACCAGAGAATTCGAATACAT ACCTCGTNNNGATCGACATG | 6180 | TGCAGGACCAGAGAATTCGAATACAC GGAACTTNNNGATCGACATG | 6420 |
| TGCAGGACCAGAGAATTCGAATACAA TACCGTGNNNGATCGACATG | 5941 | TGCAGGACCAGAGAATTCGAATACAT GCATACGNNNGATCGACATG | 6181 | TGCAGGACCAGAGAATTCGAATACAG GATCTGTNNNGATCGACATG | 6421 |
| TGCAGGACCAGAGAATTCGAATACAA ATCATGTNNNGATCGACATG | 5942 | TGCAGGACCAGAGAATTCGAATACAC AGGTAAGNNNGATCGACATG | 6182 | TGCAGGACCAGAGAATTCGAATACAA TTCCGCTNNNGATCGACATG | 6422 |
| TGCAGGACCAGAGAATTCGAATACAT GTTTTGTNNNGATCGACATG | 5943 | TGCAGGACCAGAGAATTCGAATACAG GACCAAANNNGATCGACATG | 6183 | TGCAGGACCAGAGAATTCGAATACAT TTCTACANNNGATCGACATG | 6423 |
| TGCAGGACCAGAGAATTCGAATACAG GATACAGNNNGATCGACATG | 5944 | TGCAGGACCAGAGAATTCGAATACAG GTCGCCANNNGATCGACATG | 6184 | TGCAGGACCAGAGAATTCGAATACAT CCCAGCCNNNGATCGACATG | 6424 |
| TGCAGGACCAGAGAATTCGAATACAG TTCGTAGNNNGATCGACATG | 5945 | TGCAGGACCAGAGAATTCGAATACAA TGGAAGCNNNGATCGACATG | 6185 | TGCAGGACCAGAGAATTCGAATACAC TTACCACNNNGATCGACATG | 6425 |
| TGCAGGACCAGAGAATTCGAATACAG GAGATCANNNGATCGACATG | 5946 | TGCAGGACCAGAGAATTCGAATACAC ATACGACNNNGATCGACATG | 6186 | TGCAGGACCAGAGAATTCGAATACAA CCTTCTGNNNGATCGACATG | 6426 |
| TGCAGGACCAGAGAATTCGAATACAC TTTGTTANNNGATCGACATG | 5947 | TGCAGGACCAGAGAATTCGAATACAT TCAGCGANNNGATCGACATG | 6187 | TGCAGGACCAGAGAATTCGAATACAC GTGGTCGNNNGATCGACATG | 6427 |
| TGCAGGACCAGAGAATTCGAATACAG TGAACCTNNNGATCGACATG | 5948 | TGCAGGACCAGAGAATTCGAATACAC TGCGGTGNNNGATCGACATG | 6188 | TGCAGGACCAGAGAATTCGAATACAC CAAACTGNNNGATCGACATG | 6428 |
| TGCAGGACCAGAGAATTCGAATACAC CTACAGANNNTGCATCAGGT | 5949 | TGCAGGACCAGAGAATTCGAATACAC AGTACTGNNNTGCATCAGGT | 6189 | TGCAGGACCAGAGAATTCGAATACAC TCACGCCNNNTGCATCAGGT | 6429 |
| TGCAGGACCAGAGAATTCGAATACAG CATCGATNNNTGCATCAGGT | 5950 | TGCAGGACCAGAGAATTCGAATACAG ATCGAAGNNNTGCATCAGGT | 6190 | TGCAGGACCAGAGAATTCGAATACAG ACGAGCGNNNTGCATCAGGT | 6430 |
| TGCAGGACCAGAGAATTCGAATACAT ACTGCTCNNNTGCATCAGGT | 5951 | TGCAGGACCAGAGAATTCGAATACAT CAAACGCNNNTGCATCAGGT | 6191 | TGCAGGACCAGAGAATTCGAATACAA GAATGGCNNNTGCATCAGGT | 6431 |
| TGCAGGACCAGAGAATTCGAATACAC CTGTTGTNNNTGCATCAGGT | 5952 | TGCAGGACCAGAGAATTCGAATACAT TTCAATCNNNTGCATCAGGT | 6192 | TGCAGGACCAGAGAATTCGAATACAC CAGTCCCNNNTGCATCAGGT | 6432 |
| TGCAGGACCAGAGAATTCGAATACAG AGTCGANNNNTGCATCAGGT | 5953 | TGCAGGACCAGAGAATTCGAATACAG AGATGGTNNNTGCATCAGGT | 6193 | TGCAGGACCAGAGAATTCGAATACAA AAGTATGNNNTGCATCAGGT | 6433 |
| TGCAGGACCAGAGAATTCGAATACAT TGACCAGNNNTGCATCAGGT | 5954 | TGCAGGACCAGAGAATTCGAATACAA GGCTCATNNNTGCATCAGGT | 6194 | TGCAGGACCAGAGAATTCGAATACAC GTACGTANNNTGCATCAGGT | 6434 |
| TGCAGGACCAGAGAATTCGAATACAA TGGTTATNNNTGCATCAGGT | 5955 | TGCAGGACCAGAGAATTCGAATACAT GGCCGCANNNTGCATCAGGT | 6195 | TGCAGGACCAGAGAATTCGAATACAC AGCGCCANNNTGCATCAGGT | 6435 |
| TGCAGGACCAGAGAATTCGAATACAG CGCTCAGNNNTGCATCAGGT | 5956 | TGCAGGACCAGAGAATTCGAATACAT AACTGCGNNNTGCATCAGGT | 6196 | TGCAGGACCAGAGAATTCGAATACAG CTCTCCGNNNTGCATCAGGT | 6436 |
| TGCAGGACCAGAGAATTCGAATACAT GGACCCGNNNTGCATCAGGT | 5957 | TGCAGGACCAGAGAATTCGAATACAA TCCTTGCNNNTGCATCAGGT | 6197 | TGCAGGACCAGAGAATTCGAATACAG GCCGTACNNNTGCATCAGGT | 6437 |
| TGCAGGACCAGAGAATTCGAATACAT TACCACCNNNTGCATCAGGT | 5958 | TGCAGGACCAGAGAATTCGAATACAA CTTAATGNNNTGCATCAGGT | 6198 | TGCAGGACCAGAGAATTCGAATACAG AGAGTGTNNNTGCATCAGGT | 6438 |
| TGCAGGACCAGAGAATTCGAATACAG TATAACTNNNTGCATCAGGT | 5959 | TGCAGGACCAGAGAATTCGAATACAC ACCTGCCNNNTGCATCAGGT | 6199 | TGCAGGACCAGAGAATTCGAATACAA TGGAGTGNNNTGCATCAGGT | 6439 |
| TGCAGGACCAGAGAATTCGAATACAG CCCGTGANNNTGCATCAGGT | 5960 | TGCAGGACCAGAGAATTCGAATACAT ATGCTTTNNNTGCATCAGGT | 6200 | TGCAGGACCAGAGAATTCGAATACAT CGGCCGANNNTGCATCAGGT | 6440 |
| TGCAGGACCAGAGAATTCGAATACAA TGATGACNNNTGCATCAGGT | 5961 | TGCAGGACCAGAGAATTCGAATACAA GGTGCAANNNTGCATCAGGT | 6201 | TGCAGGACCAGAGAATTCGAATACAA TCGATTANNNTGCATCAGGT | 6441 |
| TGCAGGACCAGAGAATTCGAATACAC ATGGCATNNNTGCATCAGGT | 5962 | TGCAGGACCAGAGAATTCGAATACAC GGCTAATNNNTGCATCAGGT | 6202 | TGCAGGACCAGAGAATTCGAATACAC CCAACAANNNTGCATCAGGT | 6442 |
| TGCAGGACCAGAGAATTCGAATACAA TGATATCNNNTGCATCAGGT | 5963 | TGCAGGACCAGAGAATTCGAATACAT AGCAAAANNNTGCATCAGGT | 6203 | TGCAGGACCAGAGAATTCGAATACAT GTAGATTNNNTGCATCAGGT | 6443 |
| TGCAGGACCAGAGAATTCGAATACAT GTAAAAGNNNTGCATCAGGT | 5964 | TGCAGGACCAGAGAATTCGAATACAA GCAAGCANNNTGCATCAGGT | 6204 | TGCAGGACCAGAGAATTCGAATACAA CCGGAGGNNNTGCATCAGGT | 6444 |
| TGCAGGACCAGAGAATTCGAATACAC CTTGCCGNNNTGCATCAGGT | 5965 | TGCAGGACCAGAGAATTCGAATACAA TAGTACTNNNTGCATCAGGT | 6205 | TGCAGGACCAGAGAATTCGAATACAC ACCTGAANNNTGCATCAGGT | 6445 |

FIG. 20G

| Pool-25 | SEQ ID NO. | Pool-26 | SEQ ID NO. | Pool-27 | SEQ ID NO. |
|---|---|---|---|---|---|
| TGCAGGACCAGAGAATTCGAATACAGAGGCACGNNNTGCATCAGGT | 5966 | TGCAGGACCAGAGAATTCGAATACACCCATGTTNNNTGCATCAGGT | 6206 | TGCAGGACCAGAGAATTCGAATACAACATGTGCNNNTGCATCAGGT | 6446 |
| TGCAGGACCAGAGAATTCGAATACACCTGAGCGNNNTGCATCAGGT | 5967 | TGCAGGACCAGAGAATTCGAATACAGAGCAATGNNNTGCATCAGGT | 6207 | TGCAGGACCAGAGAATTCGAATACACAGGATCTNNNTGCATCAGGT | 6447 |
| TGCAGGACCAGAGAATTCGAATACAGGTTGCTANNNTGCATCAGGT | 5968 | TGCAGGACCAGAGAATTCGAATACAAATACCTANNNTGCATCAGGT | 6208 | TGCAGGACCAGAGAATTCGAATACACGTTTGTCNNNTGCATCAGGT | 6448 |
| TGCAGGACCAGAGAATTCGAATACAGTCAAAGGNNNTGCATCAGGT | 5969 | TGCAGGACCAGAGAATTCGAATACAAATATTGCNNNTGCATCAGGT | 6209 | TGCAGGACCAGAGAATTCGAATACAAAATCAAGNNNTGCATCAGGT | 6449 |
| TGCAGGACCAGAGAATTCGAATACAACGTATGCNNNTGCATCAGGT | 5970 | TGCAGGACCAGAGAATTCGAATACAAATCCATANNNTGCATCAGGT | 6210 | TGCAGGACCAGAGAATTCGAATACATCAACATANNNTGCATCAGGT | 6450 |
| TGCAGGACCAGAGAATTCGAATACACGAGCGGANNNTGCATCAGGT | 5971 | TGCAGGACCAGAGAATTCGAATACATCCATTTANNNTGCATCAGGT | 6211 | TGCAGGACCAGAGAATTCGAATACAATGAAGGCNNNTGCATCAGGT | 6451 |
| TGCAGGACCAGAGAATTCGAATACATTTTGCCGNNNTGCATCAGGT | 5972 | TGCAGGACCAGAGAATTCGAATACAGAGGTTCTNNNTGCATCAGGT | 6212 | TGCAGGACCAGAGAATTCGAATACACAAGTGGANNNTGCATCAGGT | 6452 |
| TGCAGGACCAGAGAATTCGAATACAAAGTCTGCNNNTGCATCAGGT | 5973 | TGCAGGACCAGAGAATTCGAATACAATGATACCNNNTGCATCAGGT | 6213 | TGCAGGACCAGAGAATTCGAATACAAGCAAAATNNNTGCATCAGGT | 6453 |
| TGCAGGACCAGAGAATTCGAATACACTTCCTTCNNNTGCATCAGGT | 5974 | TGCAGGACCAGAGAATTCGAATACAACCTTGCTNNNTGCATCAGGT | 6214 | TGCAGGACCAGAGAATTCGAATACAACAGATCCNNNTGCATCAGGT | 6454 |
| TGCAGGACCAGAGAATTCGAATACAATGTGAAANNNTGCATCAGGT | 5975 | TGCAGGACCAGAGAATTCGAATACATATCAAGTNNNTGCATCAGGT | 6215 | TGCAGGACCAGAGAATTCGAATACATACGCCTTNNNTGCATCAGGT | 6455 |
| TGCAGGACCAGAGAATTCGAATACAGCCGTGGTNNNTGCATCAGGT | 5976 | TGCAGGACCAGAGAATTCGAATACAACTTAGGCNNNTGCATCAGGT | 6216 | TGCAGGACCAGAGAATTCGAATACAAGCGCTATNNNTGCATCAGGT | 6456 |
| TGCAGGACCAGAGAATTCGAATACACAGAGGCGNNNTGCATCAGGT | 5977 | TGCAGGACCAGAGAATTCGAATACAACTGTTCCNNNTGCATCAGGT | 6217 | TGCAGGACCAGAGAATTCGAATACAAGTGATGGNNNTGCATCAGGT | 6457 |
| TGCAGGACCAGAGAATTCGAATACATTTGATCTNNNTGCATCAGGT | 5978 | TGCAGGACCAGAGAATTCGAATACAGGATCCATNNNTGCATCAGGT | 6218 | TGCAGGACCAGAGAATTCGAATACACGGATGAANNNTGCATCAGGT | 6458 |
| TGCAGGACCAGAGAATTCGAATACAGCGTCGACNNNTGCATCAGGT | 5979 | TGCAGGACCAGAGAATTCGAATACACCACTCCGNNNTGCATCAGGT | 6219 | TGCAGGACCAGAGAATTCGAATACAGACATAGGNNNTGCATCAGGT | 6459 |
| TGCAGGACCAGAGAATTCGAATACAGGATATAANNNTGCATCAGGT | 5980 | TGCAGGACCAGAGAATTCGAATACAGCAAGAGTNNNTGCATCAGGT | 6220 | TGCAGGACCAGAGAATTCGAATACAATTGCGTGNNNTGCATCAGGT | 6460 |
| TGCAGGACCAGAGAATTCGAATACAAAATTTTANNNTGCATCAGGT | 5981 | TGCAGGACCAGAGAATTCGAATACAACCGTCTTNNNTGCATCAGGT | 6221 | TGCAGGACCAGAGAATTCGAATACACTACAGTGNNNTGCATCAGGT | 6461 |
| TGCAGGACCAGAGAATTCGAATACAAGCCGTGNNNTGCATCAGGT | 5982 | TGCAGGACCAGAGAATTCGAATACAGGCTTAGTNNNTGCATCAGGT | 6222 | TGCAGGACCAGAGAATTCGAATACACCGTCCACNNNTGCATCAGGT | 6462 |
| TGCAGGACCAGAGAATTCGAATACACAATAAAGNNNTGCATCAGGT | 5983 | TGCAGGACCAGAGAATTCGAATACACCTAAGCANNNTGCATCAGGT | 6223 | TGCAGGACCAGAGAATTCGAATACAAAGCCCATNNNTGCATCAGGT | 6463 |
| TGCAGGACCAGAGAATTCGAATACAGCGACATTNNNTGCATCAGGT | 5984 | TGCAGGACCAGAGAATTCGAATACAGCGCGAAGNNNTGCATCAGGT | 6224 | TGCAGGACCAGAGAATTCGAATACACGAGGCCTNNNTGCATCAGGT | 6464 |
| TGCAGGACCAGAGAATTCGAATACACAGAGAGTNNNTGCATCAGGT | 5985 | TGCAGGACCAGAGAATTCGAATACACATTCTTANNNTGCATCAGGT | 6225 | TGCAGGACCAGAGAATTCGAATACAACCTATCCNNNTGCATCAGGT | 6465 |
| TGCAGGACCAGAGAATTCGAATACACTTCACACNNNTGCATCAGGT | 5986 | TGCAGGACCAGAGAATTCGAATACAACTACGGTNNNTGCATCAGGT | 6226 | TGCAGGACCAGAGAATTCGAATACAAGGCGAGCNNNTGCATCAGGT | 6466 |
| TGCAGGACCAGAGAATTCGAATACATTAAGCTANNNTGCATCAGGT | 5987 | TGCAGGACCAGAGAATTCGAATACACCGGAGCTNNNTGCATCAGGT | 6227 | TGCAGGACCAGAGAATTCGAATACAGAGAACTGNNNTGCATCAGGT | 6467 |
| TGCAGGACCAGAGAATTCGAATACAGTGACCGCNNNTGCATCAGGT | 5988 | TGCAGGACCAGAGAATTCGAATACAGTACTTAANNNTGCATCAGGT | 6228 | TGCAGGACCAGAGAATTCGAATACATGGTGTTGNNNTGCATCAGGT | 6468 |
| TGCAGGACCAGAGAATTCGAATACACCGTATGNNNTGCATCAGGT | 5989 | TGCAGGACCAGAGAATTCGAATACATGCCGCTCNNNTGCATCAGGT | 6229 | TGCAGGACCAGAGAATTCGAATACACTAAATCANNNTGCATCAGGT | 6469 |
| TGCAGGACCAGAGAATTCGAATACATAGCATTANNNTGCATCAGGT | 5990 | TGCAGGACCAGAGAATTCGAATACAGCGACTTANNNTGCATCAGGT | 6230 | TGCAGGACCAGAGAATTCGAATACAATTTCCGCNNNTGCATCAGGT | 6470 |
| TGCAGGACCAGAGAATTCGAATACACTAGGCCGNNNTGCATCAGGT | 5991 | TGCAGGACCAGAGAATTCGAATACAATGGCAAGNNNTGCATCAGGT | 6231 | TGCAGGACCAGAGAATTCGAATACACCTCCATANNNTGCATCAGGT | 6471 |
| TGCAGGACCAGAGAATTCGAATACATTAGTAACNNNTGCATCAGGT | 5992 | TGCAGGACCAGAGAATTCGAATACACGGAGGTNNNTGCATCAGGT | 6232 | TGCAGGACCAGAGAATTCGAATACATTACTACTNNNTGCATCAGGT | 6472 |
| TGCAGGACCAGAGAATTCGAATACATATCACGNNNTGCATCAGGT | 5993 | TGCAGGACCAGAGAATTCGAATACAACATTAACNNNTGCATCAGGT | 6233 | TGCAGGACCAGAGAATTCGAATACATCGTTTATNNNTGCATCAGGT | 6473 |
| TGCAGGACCAGAGAATTCGAATACAGGATTCTCNNNTGCATCAGGT | 5994 | TGCAGGACCAGAGAATTCGAATACATAGGAAATNNNTGCATCAGGT | 6234 | TGCAGGACCAGAGAATTCGAATACAATTCAATGNNNTGCATCAGGT | 6474 |
| TGCAGGACCAGAGAATTCGAATACAGAGGAAGANNNTGCATCAGGT | 5995 | TGCAGGACCAGAGAATTCGAATACACCTAAGTGNNNTGCATCAGGT | 6235 | TGCAGGACCAGAGAATTCGAATACAAACCACACNNNTGCATCAGGT | 6475 |
| TGCAGGACCAGAGAATTCGAATACATGTCTGCTNNNTGCATCAGGT | 5996 | TGCAGGACCAGAGAATTCGAATACATAGACGCTNNNTGCATCAGGT | 6236 | TGCAGGACCAGAGAATTCGAATACATACCCGCCNNNTGCATCAGGT | 6476 |
| TGCAGGACCAGAGAATTCGAATACAAATACTCANNNTGCATCAGGT | 5997 | TGCAGGACCAGAGAATTCGAATACAGTGAAGCANNNTGCATCAGGT | 6237 | TGCAGGACCAGAGAATTCGAATACACCATGGCGNNNTGCATCAGGT | 6477 |
| TGCAGGACCAGAGAATTCGAATACATAGTTCCCNNNTGCATCAGGT | 5998 | TGCAGGACCAGAGAATTCGAATACAGGACGCAGNNNTGCATCAGGT | 6238 | TGCAGGACCAGAGAATTCGAATACACCTGAGTANNNTGCATCAGGT | 6478 |

FIG. 20H

| Pool-25 | SEQ ID NO: | Pool-26 | SEQ ID NO: | Pool-27 | SEQ ID NO: |
|---|---|---|---|---|---|
| TGCAGGACCAGAGAATTCGAATACAA ATTCGTANNNTGCATCAGGT | 5999 | TGCAGGACCAGAGAATTCGAATACAT TTTACGTNNNTGCATCAGGT | 6239 | TGCAGGACCAGAGAATTCGAATACAG GATGTCTNNNTGCATCAGGT | 6479 |
| TGCAGGACCAGAGAATTCGAATACAG CTGATTGNNNTGCATCAGGT | 6000 | TGCAGGACCAGAGAATTCGAATACAG ATGATTTNNNTGCATCAGGT | 6240 | TGCAGGACCAGAGAATTCGAATACAA AGACCCTNNNTGCATCAGGT | 6480 |
| TGCAGGACCAGAGAATTCGAATACAT ACCCGAANNNTGCATCAGGT | 6001 | TGCAGGACCAGAGAATTCGAATACAA CGGAATGNNNTGCATCAGGT | 6241 | TGCAGGACCAGAGAATTCGAATACAG TACTTGGNNNTGCATCAGGT | 6481 |
| TGCAGGACCAGAGAATTCGAATACAA GGCCATTNNNTGCATCAGGT | 6002 | TGCAGGACCAGAGAATTCGAATACAA ATGGCAGNNNTGCATCAGGT | 6242 | TGCAGGACCAGAGAATTCGAATACAT CCCTCTTNNNTGCATCAGGT | 6482 |
| TGCAGGACCAGAGAATTCGAATACAG CTCCCCANNNTGCATCAGGT | 6003 | TGCAGGACCAGAGAATTCGAATACAC GACTGATNNNTGCATCAGGT | 6243 | TGCAGGACCAGAGAATTCGAATACAT ACTTACTNNNTGCATCAGGT | 6483 |
| TGCAGGACCAGAGAATTCGAATACAT GAACGCTNNNTGCATCAGGT | 6004 | TGCAGGACCAGAGAATTCGAATACAA AAGATACNNNTGCATCAGGT | 6244 | TGCAGGACCAGAGAATTCGAATACAG GTTTTCCNNNTGCATCAGGT | 6484 |
| TGCAGGACCAGAGAATTCGAATACAC GAGGCAGNNNTGCATCAGGT | 6005 | TGCAGGACCAGAGAATTCGAATACAA CGGCATTNNNTGCATCAGGT | 6245 | TGCAGGACCAGAGAATTCGAATACAG GATCACTNNNTGCATCAGGT | 6485 |
| TGCAGGACCAGAGAATTCGAATACAG GTGCTATNNNTGCATCAGGT | 6006 | TGCAGGACCAGAGAATTCGAATACAC CACGCTCNNNTGCATCAGGT | 6246 | TGCAGGACCAGAGAATTCGAATACAT TGATGGCNNNTGCATCAGGT | 6486 |
| TGCAGGACCAGAGAATTCGAATACAA ATTGCCGNNNTGCATCAGGT | 6007 | TGCAGGACCAGAGAATTCGAATACAA ACCACTGNNNTGCATCAGGT | 6247 | TGCAGGACCAGAGAATTCGAATACAC CACATTCNNNTGCATCAGGT | 6487 |
| TGCAGGACCAGAGAATTCGAATACAG GCCGACTNNNTGCATCAGGT | 6008 | TGCAGGACCAGAGAATTCGAATACAG TCGAGTTNNNTGCATCAGGT | 6248 | TGCAGGACCAGAGAATTCGAATACAC AAAAAGTNNNTGCATCAGGT | 6488 |

FIG. 21A

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CACAGTGATTANNNACGTATGCCA | 6489 | TGCAGGACCAGAGAATTCGAATA CAGCTGACCGNNNACGTATGCCA | 6729 | TGCAGGACCAGAGAATTCGAATA CATATTCGTTNNNACGTATGCCA | 6969 |
| TGCAGGACCAGAGAATTCGAATA CAGTACTAATNNNACGTATGCCA | 6490 | TGCAGGACCAGAGAATTCGAATA CACCAGCATANNNACGTATGCCA | 6730 | TGCAGGACCAGAGAATTCGAATA CACCATTAAANNNACGTATGCCA | 6970 |
| TGCAGGACCAGAGAATTCGAATA CATTTATGCTNNNACGTATGCCA | 6491 | TGCAGGACCAGAGAATTCGAATA CACGAAGGATNNNACGTATGCCA | 6731 | TGCAGGACCAGAGAATTCGAATA CAGTTGGCGCNNNACGTATGCCA | 6971 |
| TGCAGGACCAGAGAATTCGAATA CAGTCATCCTNNNACGTATGCCA | 6492 | TGCAGGACCAGAGAATTCGAATA CACGACGAGGNNNACGTATGCCA | 6732 | TGCAGGACCAGAGAATTCGAATA CACTGGCGTGNNNACGTATGCCA | 6972 |
| TGCAGGACCAGAGAATTCGAATA CACGAATAAANNNACGTATGCCA | 6493 | TGCAGGACCAGAGAATTCGAATA CATATAACCANNNACGTATGCCA | 6733 | TGCAGGACCAGAGAATTCGAATA CAAATACCCGNNNACGTATGCCA | 6973 |
| TGCAGGACCAGAGAATTCGAATA CAGACGTATCNNNACGTATGCCA | 6494 | TGCAGGACCAGAGAATTCGAATA CAGTGGTTTGNNNACGTATGCCA | 6734 | TGCAGGACCAGAGAATTCGAATA CACACAAACCNNNACGTATGCCA | 6974 |
| TGCAGGACCAGAGAATTCGAATA CAAATTCACANNNACGTATGCCA | 6495 | TGCAGGACCAGAGAATTCGAATA CAGTTGCGATNNNACGTATGCCA | 6735 | TGCAGGACCAGAGAATTCGAATA CAATTAATATNNNACGTATGCCA | 6975 |
| TGCAGGACCAGAGAATTCGAATA CAAATCCGCANNNACGTATGCCA | 6496 | TGCAGGACCAGAGAATTCGAATA CAATACCCTCNNNACGTATGCCA | 6736 | TGCAGGACCAGAGAATTCGAATA CAGATTAGCCNNNACGTATGCCA | 6976 |
| TGCAGGACCAGAGAATTCGAATA CAACCTATTTNNNACGTATGCCA | 6497 | TGCAGGACCAGAGAATTCGAATA CACTCGAAGTNNNACGTATGCCA | 6737 | TGCAGGACCAGAGAATTCGAATA CAGACAAAATNNNACGTATGCCA | 6977 |
| TGCAGGACCAGAGAATTCGAATA CAGCTTACTCNNNACGTATGCCA | 6498 | TGCAGGACCAGAGAATTCGAATA CACAGGCGTGNNNACGTATGCCA | 6738 | TGCAGGACCAGAGAATTCGAATA CAAATATTTANNNACGTATGCCA | 6978 |
| TGCAGGACCAGAGAATTCGAATA CATTGGATGCNNNACGTATGCCA | 6499 | TGCAGGACCAGAGAATTCGAATA CAATAGTCATNNNACGTATGCCA | 6739 | TGCAGGACCAGAGAATTCGAATA CAAAAAGTCANNNACGTATGCCA | 6979 |
| TGCAGGACCAGAGAATTCGAATA CAGCGGCGANNNNACGTATGCCA | 6500 | TGCAGGACCAGAGAATTCGAATA CACTCCGTCGNNNACGTATGCCA | 6740 | TGCAGGACCAGAGAATTCGAATA CAGTCTATANNNNACGTATGCCA | 6980 |
| TGCAGGACCAGAGAATTCGAATA CAACAAGTTTNNNACGTATGCCA | 6501 | TGCAGGACCAGAGAATTCGAATA CAGTGCCGTGNNNACGTATGCCA | 6741 | TGCAGGACCAGAGAATTCGAATA CAAAAAACGTNNNACGTATGCCA | 6981 |
| TGCAGGACCAGAGAATTCGAATA CATATCTCATNNNACGTATGCCA | 6502 | TGCAGGACCAGAGAATTCGAATA CAAGTAAAGTNNNACGTATGCCA | 6742 | TGCAGGACCAGAGAATTCGAATA CATTGCTCTGNNNACGTATGCCA | 6982 |
| TGCAGGACCAGAGAATTCGAATA CAGGTTTGGTNNNACGTATGCCA | 6503 | TGCAGGACCAGAGAATTCGAATA CATATTGCAANNNACGTATGCCA | 6743 | TGCAGGACCAGAGAATTCGAATA CAATGATGAANNNACGTATGCCA | 6983 |
| TGCAGGACCAGAGAATTCGAATA CATAATTCCTNNNACGTATGCCA | 6504 | TGCAGGACCAGAGAATTCGAATA CAACCCAGCGNNNACGTATGCCA | 6744 | TGCAGGACCAGAGAATTCGAATA CATCCCTGTANNNACGTATGCCA | 6984 |
| TGCAGGACCAGAGAATTCGAATA CAACGTCGTANNNACGTATGCCA | 6505 | TGCAGGACCAGAGAATTCGAATA CATGTCAAATNNNACGTATGCCA | 6745 | TGCAGGACCAGAGAATTCGAATA CAACATCCGANNNACGTATGCCA | 6985 |
| TGCAGGACCAGAGAATTCGAATA CAGAAGCTAGNNNACGTATGCCA | 6506 | TGCAGGACCAGAGAATTCGAATA CAGTGAAACGNNNACGTATGCCA | 6746 | TGCAGGACCAGAGAATTCGAATA CATTAGATCANNNACGTATGCCA | 6986 |
| TGCAGGACCAGAGAATTCGAATA CAACGAATCCNNNACGTATGCCA | 6507 | TGCAGGACCAGAGAATTCGAATA CAAGCGGATANNNACGTATGCCA | 6747 | TGCAGGACCAGAGAATTCGAATA CACGCCTACCNNNACGTATGCCA | 6987 |
| TGCAGGACCAGAGAATTCGAATA CATCTTAATCNNNACGTATGCCA | 6508 | TGCAGGACCAGAGAATTCGAATA CAACCGAGTTNNNACGTATGCCA | 6748 | TGCAGGACCAGAGAATTCGAATA CACTCTAACCNNNACGTATGCCA | 6988 |
| TGCAGGACCAGAGAATTCGAATA CAGCTTTTCGNNNACGTATGCCA | 6509 | TGCAGGACCAGAGAATTCGAATA CATAAGGATANNNACGTATGCCA | 6749 | TGCAGGACCAGAGAATTCGAATA CACGTCATCTNNNACGTATGCCA | 6989 |
| TGCAGGACCAGAGAATTCGAATA CATGCTGAGTNNNACGTATGCCA | 6510 | TGCAGGACCAGAGAATTCGAATA CATAGTGGAGNNNACGTATGCCA | 6750 | TGCAGGACCAGAGAATTCGAATA CACACCTATCNNNACGTATGCCA | 6990 |
| TGCAGGACCAGAGAATTCGAATA CACGTTGCAANNNACGTATGCCA | 6511 | TGCAGGACCAGAGAATTCGAATA CATGTGGAAGNNNACGTATGCCA | 6751 | TGCAGGACCAGAGAATTCGAATA CATCGCTATCNNNACGTATGCCA | 6991 |
| TGCAGGACCAGAGAATTCGAATA CACAGTACGTNNNACGTATGCCA | 6512 | TGCAGGACCAGAGAATTCGAATA CACCCACGTCNNNACGTATGCCA | 6752 | TGCAGGACCAGAGAATTCGAATA CAGAAGGCCGNNNACGTATGCCA | 6992 |
| TGCAGGACCAGAGAATTCGAATA CATGGATTTANNNACGTATGCCA | 6513 | TGCAGGACCAGAGAATTCGAATA CAGTAACGGANNNACGTATGCCA | 6753 | TGCAGGACCAGAGAATTCGAATA CAGTTTTCGCNNNACGTATGCCA | 6993 |
| TGCAGGACCAGAGAATTCGAATA CAGTGTAGAGNNNACGTATGCCA | 6514 | TGCAGGACCAGAGAATTCGAATA CATTCTACATNNNACGTATGCCA | 6754 | TGCAGGACCAGAGAATTCGAATA CAAGTGGCCCNNNACGTATGCCA | 6994 |
| TGCAGGACCAGAGAATTCGAATA CACTTTAGAANNNACGTATGCCA | 6515 | TGCAGGACCAGAGAATTCGAATA CATCAATGATNNNACGTATGCCA | 6755 | TGCAGGACCAGAGAATTCGAATA CAAGCCTATCNNNACGTATGCCA | 6995 |
| TGCAGGACCAGAGAATTCGAATA CAATATAGTCNNNACGTATGCCA | 6516 | TGCAGGACCAGAGAATTCGAATA CATCGCGAATNNNACGTATGCCA | 6756 | TGCAGGACCAGAGAATTCGAATA CAATTCCGAGNNNACGTATGCCA | 6996 |
| TGCAGGACCAGAGAATTCGAATA CAGTAGAGCANNNACGTATGCCA | 6517 | TGCAGGACCAGAGAATTCGAATA CATAATGACTNNNACGTATGCCA | 6757 | TGCAGGACCAGAGAATTCGAATA CACAACCGATNNNACGTATGCCA | 6997 |
| TGCAGGACCAGAGAATTCGAATA CATAAATACCNNNACGTATGCCA | 6518 | TGCAGGACCAGAGAATTCGAATA CACAGGTTTGNNNACGTATGCCA | 6758 | TGCAGGACCAGAGAATTCGAATA CAAAGTGANNNNACGTATGCCA | 6998 |
| TGCAGGACCAGAGAATTCGAATA CACAGGCACANNNACGTATGCCA | 6519 | TGCAGGACCAGAGAATTCGAATA CATTCGGCTTNNNACGTATGCCA | 6759 | TGCAGGACCAGAGAATTCGAATA CAATCTGCCTNNNACGTATGCCA | 6999 |
| TGCAGGACCAGAGAATTCGAATA CAATATCACANNNACGTATGCCA | 6520 | TGCAGGACCAGAGAATTCGAATA CACCTTAATANNNACGTATGCCA | 6760 | TGCAGGACCAGAGAATTCGAATA CACTCATTTANNNACGTATGCCA | 7000 |
| TGCAGGACCAGAGAATTCGAATA CATGAATCATNNNACGTATGCCA | 6521 | TGCAGGACCAGAGAATTCGAATA CATAGCATGCNNNACGTATGCCA | 6761 | TGCAGGACCAGAGAATTCGAATA CATAAATCACNNNACGTATGCCA | 7001 |

FIG. 21B

| Pool-28 | SEQ ID NO: | Pool-29 | SEQ ID NO: | Pool-30 | SEQ ID NO: |
|---|---|---|---|---|---|
| TGCAGGACCAGAGAATTCGAATACACTACGTAGNNNACGTATGCCA | 6522 | TGCAGGACCAGAGAATTCGAATACAAAAACGCGNNNACGTATGCCA | 6762 | TGCAGGACCAGAGAATTCGAATACACCGAGACGNNNACGTATGCCA | 7002 |
| TGCAGGACCAGAGAATTCGAATACAGTACATCGNNNACGTATGCCA | 6523 | TGCAGGACCAGAGAATTCGAATACATAGCTGACNNNACGTATGCCA | 6763 | TGCAGGACCAGAGAATTCGAATACATCGCCCACNNNACGTATGCCA | 7003 |
| TGCAGGACCAGAGAATTCGAATACACGCAGTGCNNNACGTATGCCA | 6524 | TGCAGGACCAGAGAATTCGAATACACTACCCCGNNNACGTATGCCA | 6764 | TGCAGGACCAGAGAATTCGAATACAACGACTTGNNNACGTATGCCA | 7004 |
| TGCAGGACCAGAGAATTCGAATACAAACAAAGTNNNACGTATGCCA | 6525 | TGCAGGACCAGAGAATTCGAATACAAGCTGTCANNNACGTATGCCA | 6765 | TGCAGGACCAGAGAATTCGAATACAGTTTAGCGNNNACGTATGCCA | 7005 |
| TGCAGGACCAGAGAATTCGAATACAAAACTTCANNNACGTATGCCA | 6526 | TGCAGGACCAGAGAATTCGAATACACCCTCAGCNNNACGTATGCCA | 6766 | TGCAGGACCAGAGAATTCGAATACAGTTTCAAANNNACGTATGCCA | 7006 |
| TGCAGGACCAGAGAATTCGAATACAAGGAGCCGNNNACGTATGCCA | 6527 | TGCAGGACCAGAGAATTCGAATACACACGGTTCTNNNACGTATGCCA | 6767 | TGCAGGACCAGAGAATTCGAATACAGAATGCGANNNACGTATGCCA | 7007 |
| TGCAGGACCAGAGAATTCGAATACACGTGACATNNNACGTATGCCA | 6528 | TGCAGGACCAGAGAATTCGAATACAACGGAACANNNACGTATGCCA | 6768 | TGCAGGACCAGAGAATTCGAATACAACCCGTAANNNACGTATGCCA | 7008 |
| TGCAGGACCAGAGAATTCGAATACAATACATCANNNACGTATGCCA | 6529 | TGCAGGACCAGAGAATTCGAATACAGATCATTANNNACGTATGCCA | 6769 | TGCAGGACCAGAGAATTCGAATACAGTCACCAANNNACGTATGCCA | 7009 |
| TGCAGGACCAGAGAATTCGAATACAAATAACCTNNNACGTATGCCA | 6530 | TGCAGGACCAGAGAATTCGAATACACTAGAACCNNNACGTATGCCA | 6770 | TGCAGGACCAGAGAATTCGAATACATTGGACTGNNNACGTATGCCA | 7010 |
| TGCAGGACCAGAGAATTCGAATACACCAGCTTTNNNACGTATGCCA | 6531 | TGCAGGACCAGAGAATTCGAATACATTTAGGTANNNACGTATGCCA | 6771 | TGCAGGACCAGAGAATTCGAATACAAAGTTGCNNNACGTATGCCA | 7011 |
| TGCAGGACCAGAGAATTCGAATACATCCGTTTGNNNACGTATGCCA | 6532 | TGCAGGACCAGAGAATTCGAATACATGATATTGNNNACGTATGCCA | 6772 | TGCAGGACCAGAGAATTCGAATACATTATTTATNNNACGTATGCCA | 7012 |
| TGCAGGACCAGAGAATTCGAATACACAGTCGGCNNNACGTATGCCA | 6533 | TGCAGGACCAGAGAATTCGAATACAGCGAAAACNNNACGTATGCCA | 6773 | TGCAGGACCAGAGAATTCGAATACATACAATGTNNNACGTATGCCA | 7013 |
| TGCAGGACCAGAGAATTCGAATACATGATCGGTNNNACGTATGCCA | 6534 | TGCAGGACCAGAGAATTCGAATACAACTAACGCNNNACGTATGCCA | 6774 | TGCAGGACCAGAGAATTCGAATACAAAAGTGGCNNNACGTATGCCA | 7014 |
| TGCAGGACCAGAGAATTCGAATACAACACACACNNNACGTATGCCA | 6535 | TGCAGGACCAGAGAATTCGAATACATACTTGCCNNNACGTATGCCA | 6775 | TGCAGGACCAGAGAATTCGAATACAGCTGCTCCNNNACGTATGCCA | 7015 |
| TGCAGGACCAGAGAATTCGAATACATCACGCAANNNACGTATGCCA | 6536 | TGCAGGACCAGAGAATTCGAATACACGTGCTAANNNACGTATGCCA | 6776 | TGCAGGACCAGAGAATTCGAATACAGCTGATACNNNACGTATGCCA | 7016 |
| TGCAGGACCAGAGAATTCGAATACATCGTACTCNNNACGTATGCCA | 6537 | TGCAGGACCAGAGAATTCGAATACAAAACAGTANNNACGTATGCCA | 6777 | TGCAGGACCAGAGAATTCGAATACACTTTGATTNNNACGTATGCCA | 7017 |
| TGCAGGACCAGAGAATTCGAATACATTCAGACGNNNACGTATGCCA | 6538 | TGCAGGACCAGAGAATTCGAATACAGCATCATGNNNACGTATGCCA | 6778 | TGCAGGACCAGAGAATTCGAATACACTTGTGAGNNNACGTATGCCA | 7018 |
| TGCAGGACCAGAGAATTCGAATACAGCGCACGTNNNACGTATGCCA | 6539 | TGCAGGACCAGAGAATTCGAATACAACCTGAANNNACGTATGCCA | 6779 | TGCAGGACCAGAGAATTCGAATACAACTTCCGTNNNACGTATGCCA | 7019 |
| TGCAGGACCAGAGAATTCGAATACACCAGACATNNNACGTATGCCA | 6540 | TGCAGGACCAGAGAATTCGAATACAACGCTACNNNACGTATGCCA | 6780 | TGCAGGACCAGAGAATTCGAATACACAACATCCNNNACGTATGCCA | 7020 |
| TGCAGGACCAGAGAATTCGAATACATATTGATGNNNACGTATGCCA | 6541 | TGCAGGACCAGAGAATTCGAATACACGTCAACANNNACGTATGCCA | 6781 | TGCAGGACCAGAGAATTCGAATACAGTCGCCTNNNACGTATGCCA | 7021 |
| TGCAGGACCAGAGAATTCGAATACACGAGATAGNNNACGTATGCCA | 6542 | TGCAGGACCAGAGAATTCGAATACACCGGCCACNNNACGTATGCCA | 6782 | TGCAGGACCAGAGAATTCGAATACAGTCGTGAANNNACGTATGCCA | 7022 |
| TGCAGGACCAGAGAATTCGAATACAATACGAAANNNACGTATGCCA | 6543 | TGCAGGACCAGAGAATTCGAATACATCGCGTGGNNNACGTATGCCA | 6783 | TGCAGGACCAGAGAATTCGAATACAAGTAAGTANNNACGTATGCCA | 7023 |
| TGCAGGACCAGAGAATTCGAATACAGATGAGACNNNACGTATGCCA | 6544 | TGCAGGACCAGAGAATTCGAATACAAAGACTGNNNACGTATGCCA | 6784 | TGCAGGACCAGAGAATTCGAATACAATTTATTNNNACGTATGCCA | 7024 |
| TGCAGGACCAGAGAATTCGAATACATACAATCANNNACGTATGCCA | 6545 | TGCAGGACCAGAGAATTCGAATACAGCAATGAGNNNACGTATGCCA | 6785 | TGCAGGACCAGAGAATTCGAATACAGGAATGCANNNACGTATGCCA | 7025 |
| TGCAGGACCAGAGAATTCGAATACATTTAATAANNNACGTATGCCA | 6546 | TGCAGGACCAGAGAATTCGAATACAAGGAGCTANNNACGTATGCCA | 6786 | TGCAGGACCAGAGAATTCGAATACACGTGCTTTNNNACGTATGCCA | 7026 |
| TGCAGGACCAGAGAATTCGAATACAGCGCGTCANNNACGTATGCCA | 6547 | TGCAGGACCAGAGAATTCGAATACACCTGAGATNNNACGTATGCCA | 6787 | TGCAGGACCAGAGAATTCGAATACAGTTAAACTNNNACGTATGCCA | 7027 |
| TGCAGGACCAGAGAATTCGAATACACGATGATCNNNACGTATGCCA | 6548 | TGCAGGACCAGAGAATTCGAATACAACGGAGGCNNNACGTATGCCA | 6788 | TGCAGGACCAGAGAATTCGAATACAATCTTAAGNNNACGTATGCCA | 7028 |
| TGCAGGACCAGAGAATTCGAATACACCGAAGCCNNNCTAGCGTTAC | 6549 | TGCAGGACCAGAGAATTCGAATACAGATCGGCCNNNCTAGCGTTAC | 6789 | TGCAGGACCAGAGAATTCGAATACAAACTCAGCNNNCTAGCGTTAC | 7029 |
| TGCAGGACCAGAGAATTCGAATACACCAAACACNNNCTAGCGTTAC | 6550 | TGCAGGACCAGAGAATTCGAATACATGCTGCAANNNCTAGCGTTAC | 6790 | TGCAGGACCAGAGAATTCGAATACAACCGAAAGCNNNCTAGCGTTAC | 7030 |
| TGCAGGACCAGAGAATTCGAATACAGGTCTTCTNNNCTAGCGTTAC | 6551 | TGCAGGACCAGAGAATTCGAATACATCGGAATCNNNCTAGCGTTAC | 6791 | TGCAGGACCAGAGAATTCGAATACAGCGTAATCNNNCTAGCGTTAC | 7031 |
| TGCAGGACCAGAGAATTCGAATACACCTCGGTCNNNCTAGCGTTAC | 6552 | TGCAGGACCAGAGAATTCGAATACAGACGGCTCNNNCTAGCGTTAC | 6792 | TGCAGGACCAGAGAATTCGAATACAAGGTGGTANNNCTAGCGTTAC | 7032 |
| TGCAGGACCAGAGAATTCGAATACACCGGCTCANNNCTAGCGTTAC | 6553 | TGCAGGACCAGAGAATTCGAATACAAGTTGGAGNNNCTAGCGTTAC | 6793 | TGCAGGACCAGAGAATTCGAATACACTTGAGTGNNNCTAGCGTTAC | 7033 |
| TGCAGGACCAGAGAATTCGAATACAACCACCTTNNNCTAGCGTTAC | 6554 | TGCAGGACCAGAGAATTCGAATACAAGTACGTCNNNCTAGCGTTAC | 6794 | TGCAGGACCAGAGAATTCGAATACACTCGCCGTNNNCTAGCGTTAC | 7034 |

FIG. 21C

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATCTAAGTANNNCTAGCGTTAC | 6555 | TGCAGGACCAGAGAATTCGAATA CACGATTAATNNNCTAGCGTTAC | 6795 | TGCAGGACCAGAGAATTCGAATA CAGGGCTAATNNNCTAGCGTTAC | 7035 |
| TGCAGGACCAGAGAATTCGAATA CAATTATAATNNNCTAGCGTTAC | 6556 | TGCAGGACCAGAGAATTCGAATA CATTACGCCTNNNCTAGCGTTAC | 6796 | TGCAGGACCAGAGAATTCGAATA CAACCCCCTGNNNCTAGCGTTAC | 7036 |
| TGCAGGACCAGAGAATTCGAATA CATGGACCGCNNNCTAGCGTTAC | 6557 | TGCAGGACCAGAGAATTCGAATA CAAGGAGTTGNNNCTAGCGTTAC | 6797 | TGCAGGACCAGAGAATTCGAATA CACCCTATCANNNCTAGCGTTAC | 7037 |
| TGCAGGACCAGAGAATTCGAATA CACTTCATTANNNCTAGCGTTAC | 6558 | TGCAGGACCAGAGAATTCGAATA CAGTACACCANNNCTAGCGTTAC | 6798 | TGCAGGACCAGAGAATTCGAATA CATAGAACAANNNCTAGCGTTAC | 7038 |
| TGCAGGACCAGAGAATTCGAATA CAACGCACTANNNCTAGCGTTAC | 6559 | TGCAGGACCAGAGAATTCGAATA CAGGAAAATTNNNCTAGCGTTAC | 6799 | TGCAGGACCAGAGAATTCGAATA CACCGGAGGANNNCTAGCGTTAC | 7039 |
| TGCAGGACCAGAGAATTCGAATA CATCATGGCANNNCTAGCGTTAC | 6560 | TGCAGGACCAGAGAATTCGAATA CACGGTTCTTNNNCTAGCGTTAC | 6800 | TGCAGGACCAGAGAATTCGAATA CAATGAACAANNNCTAGCGTTAC | 7040 |
| TGCAGGACCAGAGAATTCGAATA CAGGCTTAACNNNCTAGCGTTAC | 6561 | TGCAGGACCAGAGAATTCGAATA CAGGTCGACCNNNCTAGCGTTAC | 6801 | TGCAGGACCAGAGAATTCGAATA CATTCGAAGCNNNCTAGCGTTAC | 7041 |
| TGCAGGACCAGAGAATTCGAATA CAATGGTATTNNNCTAGCGTTAC | 6562 | TGCAGGACCAGAGAATTCGAATA CATTCGCTCANNNCTAGCGTTAC | 6802 | TGCAGGACCAGAGAATTCGAATA CAAACAACAANNNCTAGCGTTAC | 7042 |
| TGCAGGACCAGAGAATTCGAATA CAGTATGCTGNNNCTAGCGTTAC | 6563 | TGCAGGACCAGAGAATTCGAATA CACGCAGCGTNNNCTAGCGTTAC | 6803 | TGCAGGACCAGAGAATTCGAATA CATCCTTTGGNNNCTAGCGTTAC | 7043 |
| TGCAGGACCAGAGAATTCGAATA CAATCGTGGTNNNCTAGCGTTAC | 6564 | TGCAGGACCAGAGAATTCGAATA CAGCTGTGCGNNNCTAGCGTTAC | 6804 | TGCAGGACCAGAGAATTCGAATA CAAAACGAATNNNCTAGCGTTAC | 7044 |
| TGCAGGACCAGAGAATTCGAATA CAGCTTAGGTNNNCTAGCGTTAC | 6565 | TGCAGGACCAGAGAATTCGAATA CACACCAGTANNNCTAGCGTTAC | 6805 | TGCAGGACCAGAGAATTCGAATA CATCCAGTGANNNCTAGCGTTAC | 7045 |
| TGCAGGACCAGAGAATTCGAATA CATCTGTATTNNNCTAGCGTTAC | 6566 | TGCAGGACCAGAGAATTCGAATA CAATCATTGANNNCTAGCGTTAC | 6806 | TGCAGGACCAGAGAATTCGAATA CACTTCAAAANNNCTAGCGTTAC | 7046 |
| TGCAGGACCAGAGAATTCGAATA CAGGATAGCANNNCTAGCGTTAC | 6567 | TGCAGGACCAGAGAATTCGAATA CATAATCATGNNNCTAGCGTTAC | 6807 | TGCAGGACCAGAGAATTCGAATA CATATCTAGANNNCTAGCGTTAC | 7047 |
| TGCAGGACCAGAGAATTCGAATA CATTCACTCGNNNCTAGCGTTAC | 6568 | TGCAGGACCAGAGAATTCGAATA CAGTTGACCANNNCTAGCGTTAC | 6808 | TGCAGGACCAGAGAATTCGAATA CAAACGGCTTNNNCTAGCGTTAC | 7048 |
| TGCAGGACCAGAGAATTCGAATA CATTCGGACANNNCTAGCGTTAC | 6569 | TGCAGGACCAGAGAATTCGAATA CAACTCATGGNNNCTAGCGTTAC | 6809 | TGCAGGACCAGAGAATTCGAATA CAACTTTTCANNNCTAGCGTTAC | 7049 |
| TGCAGGACCAGAGAATTCGAATA CACGGTCGGTNNNCTAGCGTTAC | 6570 | TGCAGGACCAGAGAATTCGAATA CACCCAGTTTNNNCTAGCGTTAC | 6810 | TGCAGGACCAGAGAATTCGAATA CAAGTGCTTGNNNCTAGCGTTAC | 7050 |
| TGCAGGACCAGAGAATTCGAATA CAAGATCGCTNNNCTAGCGTTAC | 6571 | TGCAGGACCAGAGAATTCGAATA CATCAAGGAGNNNCTAGCGTTAC | 6811 | TGCAGGACCAGAGAATTCGAATA CAATGGTCCANNNCTAGCGTTAC | 7051 |
| TGCAGGACCAGAGAATTCGAATA CAGCATTCGANNNCTAGCGTTAC | 6572 | TGCAGGACCAGAGAATTCGAATA CAAACGCTTGNNNCTAGCGTTAC | 6812 | TGCAGGACCAGAGAATTCGAATA CAGCCCCCTANNNCTAGCGTTAC | 7052 |
| TGCAGGACCAGAGAATTCGAATA CACGCTGATANNNCTAGCGTTAC | 6573 | TGCAGGACCAGAGAATTCGAATA CACTTATATCNNNCTAGCGTTAC | 6813 | TGCAGGACCAGAGAATTCGAATA CAGTTGCTCTNNNCTAGCGTTAC | 7053 |
| TGCAGGACCAGAGAATTCGAATA CACGGTTAACNNNCTAGCGTTAC | 6574 | TGCAGGACCAGAGAATTCGAATA CAAGTGTCCANNNCTAGCGTTAC | 6814 | TGCAGGACCAGAGAATTCGAATA CAGCATATATNNNCTAGCGTTAC | 7054 |
| TGCAGGACCAGAGAATTCGAATA CAAATGTCATNNNCTAGCGTTAC | 6575 | TGCAGGACCAGAGAATTCGAATA CAAGCGACGGNNNCTAGCGTTAC | 6815 | TGCAGGACCAGAGAATTCGAATA CAGGGTCTTGANNNCTAGCGTTAC | 7055 |
| TGCAGGACCAGAGAATTCGAATA CAGCAAGACANNNCTAGCGTTAC | 6576 | TGCAGGACCAGAGAATTCGAATA CACTGTCCCGNNNCTAGCGTTAC | 6816 | TGCAGGACCAGAGAATTCGAATA CAACTATTCNNNCTAGCGTTAC | 7056 |
| TGCAGGACCAGAGAATTCGAATA CACCAGCCTCNNNCTAGCGTTAC | 6577 | TGCAGGACCAGAGAATTCGAATA CAACTCACCTNNNCTAGCGTTAC | 6817 | TGCAGGACCAGAGAATTCGAATA CACTTAAAACNNNCTAGCGTTAC | 7057 |
| TGCAGGACCAGAGAATTCGAATA CACTTGTTCGNNNCTAGCGTTAC | 6578 | TGCAGGACCAGAGAATTCGAATA CAAATTTCGANNNCTAGCGTTAC | 6818 | TGCAGGACCAGAGAATTCGAATA CATCGCAGCGNNNCTAGCGTTAC | 7058 |
| TGCAGGACCAGAGAATTCGAATA CATATCGGTGNNNCTAGCGTTAC | 6579 | TGCAGGACCAGAGAATTCGAATA CAGTAATATGNNNCTAGCGTTAC | 6819 | TGCAGGACCAGAGAATTCGAATA CAGATTCGACNNNCTAGCGTTAC | 7059 |
| TGCAGGACCAGAGAATTCGAATA CACTGGCATANNNCTAGCGTTAC | 6580 | TGCAGGACCAGAGAATTCGAATA CACAAGAAATNNNCTAGCGTTAC | 6820 | TGCAGGACCAGAGAATTCGAATA CATGGCCGTGNNNCTAGCGTTAC | 7060 |
| TGCAGGACCAGAGAATTCGAATA CATGCAGGCCNNNCTAGCGTTAC | 6581 | TGCAGGACCAGAGAATTCGAATA CAATTCCCCANNNCTAGCGTTAC | 6821 | TGCAGGACCAGAGAATTCGAATA CAAAGGCATGNNNCTAGCGTTAC | 7061 |
| TGCAGGACCAGAGAATTCGAATA CATTCCTCCTNNNCTAGCGTTAC | 6582 | TGCAGGACCAGAGAATTCGAATA CACTCTTAGCNNNCTAGCGTTAC | 6822 | TGCAGGACCAGAGAATTCGAATA CAATGATCTANNNCTAGCGTTAC | 7062 |
| TGCAGGACCAGAGAATTCGAATA CATAACGGAGNNNCTAGCGTTAC | 6583 | TGCAGGACCAGAGAATTCGAATA CATACCAGCANNNCTAGCGTTAC | 6823 | TGCAGGACCAGAGAATTCGAATA CATCGGCAATNNNCTAGCGTTAC | 7063 |
| TGCAGGACCAGAGAATTCGAATA CAGAGTGATNNNCTAGCGTTAC | 6584 | TGCAGGACCAGAGAATTCGAATA CACACGCCTTNNNCTAGCGTTAC | 6824 | TGCAGGACCAGAGAATTCGAATA CAATCCGCTTNNNCTAGCGTTAC | 7064 |
| TGCAGGACCAGAGAATTCGAATA CATCGTAAATNNNCTAGCGTTAC | 6585 | TGCAGGACCAGAGAATTCGAATA CAAATCGAGGNNNCTAGCGTTAC | 6825 | TGCAGGACCAGAGAATTCGAATA CAGAAGTGGTNNNCTAGCGTTAC | 7065 |
| TGCAGGACCAGAGAATTCGAATA CACACAGACTNNNCTAGCGTTAC | 6586 | TGCAGGACCAGAGAATTCGAATA CACATACAATNNNCTAGCGTTAC | 6826 | TGCAGGACCAGAGAATTCGAATA CAGGAAGCTTNNNCTAGCGTTAC | 7066 |
| TGCAGGACCAGAGAATTCGAATA CAGCACCCCTNNNCTAGCGTTAC | 6587 | TGCAGGACCAGAGAATTCGAATA CATTATGTTCNNNCTAGCGTTAC | 6827 | TGCAGGACCAGAGAATTCGAATA CACTAAACATNNNCTAGCGTTAC | 7067 |

FIG. 21D

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CAGATAATTCNNNCTAGCGTTAC | 6588 | TGCAGGACCAGAGAATTCGAATA CAGTCTGTCTNNNCTAGCGTTAC | 6828 | TGCAGGACCAGAGAATTCGAATA CAAAGGAGTCNNNCTAGCGTTAC | 7068 |
| TGCAGGACCAGAGAATTCGAATA CAAACTCAATNNNCTAGCGTTAC | 6589 | TGCAGGACCAGAGAATTCGAATA CAGTCTGAACNNNCTAGCGTTAC | 6829 | TGCAGGACCAGAGAATTCGAATA CATCCATGTCNNNCTAGCGTTAC | 7069 |
| TGCAGGACCAGAGAATTCGAATA CATCAAAACTNNNCTAGCGTTAC | 6590 | TGCAGGACCAGAGAATTCGAATA CAAGGTGCGNNNCTAGCGTTAC | 6830 | TGCAGGACCAGAGAATTCGAATA CAGTACGAGANNNCTAGCGTTAC | 7070 |
| TGCAGGACCAGAGAATTCGAATA CAATTATTCCNNNCTAGCGTTAC | 6591 | TGCAGGACCAGAGAATTCGAATA CACAGAAACGNNNCTAGCGTTAC | 6831 | TGCAGGACCAGAGAATTCGAATA CAGGCCAGCTNNNCTAGCGTTAC | 7071 |
| TGCAGGACCAGAGAATTCGAATA CACTTCTTGGNNNCTAGCGTTAC | 6592 | TGCAGGACCAGAGAATTCGAATA CATCTGTTGCNNNCTAGCGTTAC | 6832 | TGCAGGACCAGAGAATTCGAATA CAGTCCGATANNNCTAGCGTTAC | 7072 |
| TGCAGGACCAGAGAATTCGAATA CATAAGTAAGNNNCTAGCGTTAC | 6593 | TGCAGGACCAGAGAATTCGAATA CACGATGGTTNNNCTAGCGTTAC | 6833 | TGCAGGACCAGAGAATTCGAATA CATGTTACAANNNCTAGCGTTAC | 7073 |
| TGCAGGACCAGAGAATTCGAATA CACTAACCCTNNNCTAGCGTTAC | 6594 | TGCAGGACCAGAGAATTCGAATA CAATAATATTNNNCTAGCGTTAC | 6834 | TGCAGGACCAGAGAATTCGAATA CACATTCCACNNNCTAGCGTTAC | 7074 |
| TGCAGGACCAGAGAATTCGAATA CAATAGCGTCNNNCTAGCGTTAC | 6595 | TGCAGGACCAGAGAATTCGAATA CAATCGACGTNNNCTAGCGTTAC | 6835 | TGCAGGACCAGAGAATTCGAATA CATGTTGAATNNNCTAGCGTTAC | 7075 |
| TGCAGGACCAGAGAATTCGAATA CAAAGGTAATNNNCTAGCGTTAC | 6596 | TGCAGGACCAGAGAATTCGAATA CAGAGGAAAGNNNCTAGCGTTAC | 6836 | TGCAGGACCAGAGAATTCGAATA CAAGAAACGCNNNCTAGCGTTAC | 7076 |
| TGCAGGACCAGAGAATTCGAATA CATCACGTAGNNNCTAGCGTTAC | 6597 | TGCAGGACCAGAGAATTCGAATA CAATTACACANNNCTAGCGTTAC | 6837 | TGCAGGACCAGAGAATTCGAATA CATCCGACGTNNNCTAGCGTTAC | 7077 |
| TGCAGGACCAGAGAATTCGAATA CAAACCATATNNNCTAGCGTTAC | 6598 | TGCAGGACCAGAGAATTCGAATA CAGGACCTGCNNNCTAGCGTTAC | 6838 | TGCAGGACCAGAGAATTCGAATA CACACTAGTGNNNCTAGCGTTAC | 7078 |
| TGCAGGACCAGAGAATTCGAATA CAGACGAGTANNNCTAGCGTTAC | 6599 | TGCAGGACCAGAGAATTCGAATA CAACGTAGAGNNNCTAGCGTTAC | 6839 | TGCAGGACCAGAGAATTCGAATA CAACCGGCGTNNNCTAGCGTTAC | 7079 |
| TGCAGGACCAGAGAATTCGAATA CAATAAATTTNNNCTAGCGTTAC | 6600 | TGCAGGACCAGAGAATTCGAATA CACACGGCGTNNNCTAGCGTTAC | 6840 | TGCAGGACCAGAGAATTCGAATA CACTTGCTACNNNCTAGCGTTAC | 7080 |
| TGCAGGACCAGAGAATTCGAATA CAGAGCTAAGNNNCTAGCGTTAC | 6601 | TGCAGGACCAGAGAATTCGAATA CAATTACGTANNNCTAGCGTTAC | 6841 | TGCAGGACCAGAGAATTCGAATA CATTGCAGTGNNNCTAGCGTTAC | 7081 |
| TGCAGGACCAGAGAATTCGAATA CAGCGGGATCNNNCTAGCGTTAC | 6602 | TGCAGGACCAGAGAATTCGAATA CATATGTTGANNNCTAGCGTTAC | 6842 | TGCAGGACCAGAGAATTCGAATA CAAATGAAGTNNNCTAGCGTTAC | 7082 |
| TGCAGGACCAGAGAATTCGAATA CATTCATAGANNNCTAGCGTTAC | 6603 | TGCAGGACCAGAGAATTCGAATA CACAGACTCANNNCTAGCGTTAC | 6843 | TGCAGGACCAGAGAATTCGAATA CACTGGCCCANNNCTAGCGTTAC | 7083 |
| TGCAGGACCAGAGAATTCGAATA CATTAAGCATNNNCTAGCGTTAC | 6604 | TGCAGGACCAGAGAATTCGAATA CACGGATGCCNNNCTAGCGTTAC | 6844 | TGCAGGACCAGAGAATTCGAATA CAGTGGACCCNNNCTAGCGTTAC | 7084 |
| TGCAGGACCAGAGAATTCGAATA CATCGAGCGCNNNCTAGCGTTAC | 6605 | TGCAGGACCAGAGAATTCGAATA CATACATCTTNNNCTAGCGTTAC | 6845 | TGCAGGACCAGAGAATTCGAATA CAACGACTCANNNCTAGCGTTAC | 7085 |
| TGCAGGACCAGAGAATTCGAATA CATCGCACCCNNNCTAGCGTTAC | 6606 | TGCAGGACCAGAGAATTCGAATA CACTTCGTGTNNNCTAGCGTTAC | 6846 | TGCAGGACCAGAGAATTCGAATA CAACAACTTANNNCTAGCGTTAC | 7086 |
| TGCAGGACCAGAGAATTCGAATA CACTTCGACANNNCTAGCGTTAC | 6607 | TGCAGGACCAGAGAATTCGAATA CAGAACGCGNNNCTAGCGTTAC | 6847 | TGCAGGACCAGAGAATTCGAATA CATCTGGTAGNNNCTAGCGTTAC | 7087 |
| TGCAGGACCAGAGAATTCGAATA CATTCCAGTCNNNCTAGCGTTAC | 6608 | TGCAGGACCAGAGAATTCGAATA CATCGGATTGNNNCTAGCGTTAC | 6848 | TGCAGGACCAGAGAATTCGAATA CACTATGGCANNNCTAGCGTTAC | 7088 |
| TGCAGGACCAGAGAATTCGAATA CAGTTTTTACNNNGATCGACATG | 6609 | TGCAGGACCAGAGAATTCGAATA CAAGACAAATNNNGATCGACATG | 6849 | TGCAGGACCAGAGAATTCGAATA CAACCCGCGANNNGATCGACATG | 7089 |
| TGCAGGACCAGAGAATTCGAATA CAAACTTAGTNNNGATCGACATG | 6610 | TGCAGGACCAGAGAATTCGAATA CACGAAGTAGNNNGATCGACATG | 6850 | TGCAGGACCAGAGAATTCGAATA CACGCGGTACNNNGATCGACATG | 7090 |
| TGCAGGACCAGAGAATTCGAATA CACGCGCGCGNNNGATCGACATG | 6611 | TGCAGGACCAGAGAATTCGAATA CAAAAGAGCNNNGATCGACATG | 6851 | TGCAGGACCAGAGAATTCGAATA CACACAATCAGNNNGATCGACATG | 7091 |
| TGCAGGACCAGAGAATTCGAATA CAAACTGTTANNNGATCGACATG | 6612 | TGCAGGACCAGAGAATTCGAATA CATGAGTGGANNNGATCGACATG | 6852 | TGCAGGACCAGAGAATTCGAATA CATAGACACCNNNGATCGACATG | 7092 |
| TGCAGGACCAGAGAATTCGAATA CAGTAAGTTTNNNGATCGACATG | 6613 | TGCAGGACCAGAGAATTCGAATA CACGCTCCCANNNGATCGACATG | 6853 | TGCAGGACCAGAGAATTCGAATA CAATGTAAAGNNNGATCGACATG | 7093 |
| TGCAGGACCAGAGAATTCGAATA CACTTAGCAGNNNGATCGACATG | 6614 | TGCAGGACCAGAGAATTCGAATA CAACACTTCCNNNGATCGACATG | 6854 | TGCAGGACCAGAGAATTCGAATA CAATCCTCTGNNNGATCGACATG | 7094 |
| TGCAGGACCAGAGAATTCGAATA CAACTTTCCGNNNGATCGACATG | 6615 | TGCAGGACCAGAGAATTCGAATA CAGCAGTCATNNNGATCGACATG | 6855 | TGCAGGACCAGAGAATTCGAATA CAGTCGTCCCNNNGATCGACATG | 7095 |
| TGCAGGACCAGAGAATTCGAATA CACTCCTCTTNNNGATCGACATG | 6616 | TGCAGGACCAGAGAATTCGAATA CACCATATGGNNNGATCGACATG | 6856 | TGCAGGACCAGAGAATTCGAATA CAACTTGCAGNNNGATCGACATG | 7096 |
| TGCAGGACCAGAGAATTCGAATA CAAGATAATGNNNGATCGACATG | 6617 | TGCAGGACCAGAGAATTCGAATA CAATGCGCTCNNNGATCGACATG | 6857 | TGCAGGACCAGAGAATTCGAATA CAGACGGCTCNNNGATCGACATG | 7097 |
| TGCAGGACCAGAGAATTCGAATA CACAGCCCTCNNNGATCGACATG | 6618 | TGCAGGACCAGAGAATTCGAATA CAGTTGAACCNNNGATCGACATG | 6858 | TGCAGGACCAGAGAATTCGAATA CATCGCCAGGNNNGATCGACATG | 7098 |
| TGCAGGACCAGAGAATTCGAATA CACGTAATTANNNGATCGACATG | 6619 | TGCAGGACCAGAGAATTCGAATA CAAAGGTTGGNNNGATCGACATG | 6859 | TGCAGGACCAGAGAATTCGAATA CACGATGCGNNNGATCGACATG | 7099 |
| TGCAGGACCAGAGAATTCGAATA CAGTTCGTTCNNNGATCGACATG | 6620 | TGCAGGACCAGAGAATTCGAATA CAGCACGCTGNNNGATCGACATG | 6860 | TGCAGGACCAGAGAATTCGAATA CAACCCCCACNNNGATCGACATG | 7100 |

FIG. 21E

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATTCCGTCANNNGATCGACATG | 6621 | TGCAGGACCAGAGAATTCGAATA CAGCTCATAGNNNGATCGACATG | 6861 | TGCAGGACCAGAGAATTCGAATA CATCATTTCANNNGATCGACATG | 7101 |
| TGCAGGACCAGAGAATTCGAATA CAACGACGTTNNNGATCGACATG | 6622 | TGCAGGACCAGAGAATTCGAATA CAACAGTCTGNNNGATCGACATG | 6862 | TGCAGGACCAGAGAATTCGAATA CATGCCGGTGNNNGATCGACATG | 7102 |
| TGCAGGACCAGAGAATTCGAATA CAAAGTAGCGNNNGATCGACATG | 6623 | TGCAGGACCAGAGAATTCGAATA CATTTAAGTGNNNGATCGACATG | 6863 | TGCAGGACCAGAGAATTCGAATA CACGCAAGAANNNGATCGACATG | 7103 |
| TGCAGGACCAGAGAATTCGAATA CAAGTGAAGCNNNGATCGACATG | 6624 | TGCAGGACCAGAGAATTCGAATA CAGATTAATCNNNGATCGACATG | 6864 | TGCAGGACCAGAGAATTCGAATA CATAGACCACNNNGATCGACATG | 7104 |
| TGCAGGACCAGAGAATTCGAATA CATTCTCATANNNGATCGACATG | 6625 | TGCAGGACCAGAGAATTCGAATA CAGAGAAAGGNNNGATCGACATG | 6865 | TGCAGGACCAGAGAATTCGAATA CAACCGAAGANNNGATCGACATG | 7105 |
| TGCAGGACCAGAGAATTCGAATA CAAGTAGAGCNNNGATCGACATG | 6626 | TGCAGGACCAGAGAATTCGAATA CAACATTCGGNNNGATCGACATG | 6866 | TGCAGGACCAGAGAATTCGAATA CATCTTGTTANNNGATCGACATG | 7106 |
| TGCAGGACCAGAGAATTCGAATA CATCCCGATTNNNGATCGACATG | 6627 | TGCAGGACCAGAGAATTCGAATA CATTGCGTCTNNNGATCGACATG | 6867 | TGCAGGACCAGAGAATTCGAATA CACAGACTGTNNNGATCGACATG | 7107 |
| TGCAGGACCAGAGAATTCGAATA CACAAGGTCTNNNGATCGACATG | 6628 | TGCAGGACCAGAGAATTCGAATA CAGCTCACAANNNGATCGACATG | 6868 | TGCAGGACCAGAGAATTCGAATA CAGATCTGCANNNGATCGACATG | 7108 |
| TGCAGGACCAGAGAATTCGAATA CAGAGTATGGNNNGATCGACATG | 6629 | TGCAGGACCAGAGAATTCGAATA CACGTTAACGNNNGATCGACATG | 6869 | TGCAGGACCAGAGAATTCGAATA CATCGAAGGANNNGATCGACATG | 7109 |
| TGCAGGACCAGAGAATTCGAATA CACCGGAGTGNNNGATCGACATG | 6630 | TGCAGGACCAGAGAATTCGAATA CAGTGCGTTGNNNGATCGACATG | 6870 | TGCAGGACCAGAGAATTCGAATA CACGGAGCAGNNNGATCGACATG | 7110 |
| TGCAGGACCAGAGAATTCGAATA CAGAAGCTCTNNNGATCGACATG | 6631 | TGCAGGACCAGAGAATTCGAATA CATGCTCAGANNNGATCGACATG | 6871 | TGCAGGACCAGAGAATTCGAATA CACACCGGACNNNGATCGACATG | 7111 |
| TGCAGGACCAGAGAATTCGAATA CAGTGCAAGANNNGATCGACATG | 6632 | TGCAGGACCAGAGAATTCGAATA CATACCAAATNNNGATCGACATG | 6872 | TGCAGGACCAGAGAATTCGAATA CAATAACGTTNNNGATCGACATG | 7112 |
| TGCAGGACCAGAGAATTCGAATA CAAACGGTAGNNNGATCGACATG | 6633 | TGCAGGACCAGAGAATTCGAATA CACCATGATGNNNGATCGACATG | 6873 | TGCAGGACCAGAGAATTCGAATA CATGTCTGGANNNGATCGACATG | 7113 |
| TGCAGGACCAGAGAATTCGAATA CACTTCGACTNNNGATCGACATG | 6634 | TGCAGGACCAGAGAATTCGAATA CATATATGCANNNGATCGACATG | 6874 | TGCAGGACCAGAGAATTCGAATA CATATGGACCNNNGATCGACATG | 7114 |
| TGCAGGACCAGAGAATTCGAATA CACCGACGACNNNGATCGACATG | 6635 | TGCAGGACCAGAGAATTCGAATA CACCGCTTATNNNGATCGACATG | 6875 | TGCAGGACCAGAGAATTCGAATA CACAACTTGGNNNGATCGACATG | 7115 |
| TGCAGGACCAGAGAATTCGAATA CACTACACTCNNNGATCGACATG | 6636 | TGCAGGACCAGAGAATTCGAATA CAGGCGTCACNNNGATCGACATG | 6876 | TGCAGGACCAGAGAATTCGAATA CACAATCGACNNNGATCGACATG | 7116 |
| TGCAGGACCAGAGAATTCGAATA CAAGCTAAGGNNNGATCGACATG | 6637 | TGCAGGACCAGAGAATTCGAATA CAGGCATAAGNNNGATCGACATG | 6877 | TGCAGGACCAGAGAATTCGAATA CAGCAAGCCGNNNGATCGACATG | 7117 |
| TGCAGGACCAGAGAATTCGAATA CAGAGTATCNNNGATCGACATG | 6638 | TGCAGGACCAGAGAATTCGAATA CAGAATTTGTNNNGATCGACATG | 6878 | TGCAGGACCAGAGAATTCGAATA CAGCCAACGCNNNGATCGACATG | 7118 |
| TGCAGGACCAGAGAATTCGAATA CATCCTACCANNNGATCGACATG | 6639 | TGCAGGACCAGAGAATTCGAATA CATCTTGACCNNNGATCGACATG | 6879 | TGCAGGACCAGAGAATTCGAATA CATCGTTAAANNNGATCGACATG | 7119 |
| TGCAGGACCAGAGAATTCGAATA CATTTTTCTCNNNGATCGACATG | 6640 | TGCAGGACCAGAGAATTCGAATA CAACACCTAGNNNGATCGACATG | 6880 | TGCAGGACCAGAGAATTCGAATA CACTAGCGTANNNGATCGACATG | 7120 |
| TGCAGGACCAGAGAATTCGAATA CACCGGATAAGNNNGATCGACATG | 6641 | TGCAGGACCAGAGAATTCGAATA CAATCTCACCNNNGATCGACATG | 6881 | TGCAGGACCAGAGAATTCGAATA CACTGAGTTGNNNGATCGACATG | 7121 |
| TGCAGGACCAGAGAATTCGAATA CACAAATCGNNNGATCGACATG | 6642 | TGCAGGACCAGAGAATTCGAATA CATTGAGATTNNNGATCGACATG | 6882 | TGCAGGACCAGAGAATTCGAATA CATGCGCGTNNNGATCGACATG | 7122 |
| TGCAGGACCAGAGAATTCGAATA CAGTGTCGGCNNNGATCGACATG | 6643 | TGCAGGACCAGAGAATTCGAATA CATCAACCAGNNNGATCGACATG | 6883 | TGCAGGACCAGAGAATTCGAATA CAGTGACTTGNNNGATCGACATG | 7123 |
| TGCAGGACCAGAGAATTCGAATA CAAAGCTATTNNNGATCGACATG | 6644 | TGCAGGACCAGAGAATTCGAATA CATTTGACGGNNNGATCGACATG | 6884 | TGCAGGACCAGAGAATTCGAATA CACTGCGAATNNNGATCGACATG | 7124 |
| TGCAGGACCAGAGAATTCGAATA CAACCGGACCNNNGATCGACATG | 6645 | TGCAGGACCAGAGAATTCGAATA CAGTTCATTTNNNGATCGACATG | 6885 | TGCAGGACCAGAGAATTCGAATA CACATGACACNNNGATCGACATG | 7125 |
| TGCAGGACCAGAGAATTCGAATA CATTAAATGCNNNGATCGACATG | 6646 | TGCAGGACCAGAGAATTCGAATA CAGAGTGGTANNNGATCGACATG | 6886 | TGCAGGACCAGAGAATTCGAATA CAGCGATTTGNNNGATCGACATG | 7126 |
| TGCAGGACCAGAGAATTCGAATA CACTGCAAGTNNNGATCGACATG | 6647 | TGCAGGACCAGAGAATTCGAATA CAAGTTGCTGNNNGATCGACATG | 6887 | TGCAGGACCAGAGAATTCGAATA CAACTAGGAGNNNGATCGACATG | 7127 |
| TGCAGGACCAGAGAATTCGAATA CACCCTTAACNNNGATCGACATG | 6648 | TGCAGGACCAGAGAATTCGAATA CAGATTTACNNNGATCGACATG | 6888 | TGCAGGACCAGAGAATTCGAATA CAGCGCAGCTNNNGATCGACATG | 7128 |
| TGCAGGACCAGAGAATTCGAATA CAAGTGAGACNNNGATCGACATG | 6649 | TGCAGGACCAGAGAATTCGAATA CACTAACAATNNNGATCGACATG | 6889 | TGCAGGACCAGAGAATTCGAATA CACACAGCCGNNNGATCGACATG | 7129 |
| TGCAGGACCAGAGAATTCGAATA CATATTAGACNNNGATCGACATG | 6650 | TGCAGGACCAGAGAATTCGAATA CAAGCTGATCNNNGATCGACATG | 6890 | TGCAGGACCAGAGAATTCGAATA CAGCCTTGTTNNNGATCGACATG | 7130 |
| TGCAGGACCAGAGAATTCGAATA CAGTTGGCTANNNGATCGACATG | 6651 | TGCAGGACCAGAGAATTCGAATA CACGACCGGCTNNNGATCGACATG | 6891 | TGCAGGACCAGAGAATTCGAATA CAAATATCGTNNNGATCGACATG | 7131 |
| TGCAGGACCAGAGAATTCGAATA CATCGCTAAGNNNGATCGACATG | 6652 | TGCAGGACCAGAGAATTCGAATA CACGGCGTACNNNGATCGACATG | 6892 | TGCAGGACCAGAGAATTCGAATA CACCGAAAGANNNGATCGACATG | 7132 |
| TGCAGGACCAGAGAATTCGAATA CAAGCCCCTCNNNGATCGACATG | 6653 | TGCAGGACCAGAGAATTCGAATA CATTGCAGGTNNNGATCGACATG | 6893 | TGCAGGACCAGAGAATTCGAATA CACAAAGGTGNNNGATCGACATG | 7133 |

FIG. 21F

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATTACGAATNNNGATCGACATG | 6654 | TGCAGGACCAGAGAATTCGAATA CATGAGCTGTNNNGATCGACATG | 6894 | TGCAGGACCAGAGAATTCGAATA CAAAATCCATNNNGATCGACATG | 7134 |
| TGCAGGACCAGAGAATTCGAATA CAGGGCCACCANNNGATCGACATG | 6655 | TGCAGGACCAGAGAATTCGAATA CAAGTCTCAGNNNGATCGACATG | 6895 | TGCAGGACCAGAGAATTCGAATA CAAACAATCTNNNGATCGACATG | 7135 |
| TGCAGGACCAGAGAATTCGAATA CATCCTTATANNNGATCGACATG | 6656 | TGCAGGACCAGAGAATTCGAATA CAATTCCTTANNNGATCGACATG | 6896 | TGCAGGACCAGAGAATTCGAATA CACATTGGCANNNGATCGACATG | 7136 |
| TGCAGGACCAGAGAATTCGAATA CATCAGTCTCNNNGATCGACATG | 6657 | TGCAGGACCAGAGAATTCGAATA CAGAGAGAGANNNGATCGACATG | 6897 | TGCAGGACCAGAGAATTCGAATA CACTACAACGNNNGATCGACATG | 7137 |
| TGCAGGACCAGAGAATTCGAATA CACGACTTCTNNNGATCGACATG | 6658 | TGCAGGACCAGAGAATTCGAATA CAGCAGAGCGNNNGATCGACATG | 6898 | TGCAGGACCAGAGAATTCGAATA CAATCGAGAGNNNGATCGACATG | 7138 |
| TGCAGGACCAGAGAATTCGAATA CAAGGTAACGNNNGATCGACATG | 6659 | TGCAGGACCAGAGAATTCGAATA CAGGCACTATNNNGATCGACATG | 6899 | TGCAGGACCAGAGAATTCGAATA CACCGGTCCTNNNGATCGACATG | 7139 |
| TGCAGGACCAGAGAATTCGAATA CAAGACACTCNNNGATCGACATG | 6660 | TGCAGGACCAGAGAATTCGAATA CAGACCTCAANNNGATCGACATG | 6900 | TGCAGGACCAGAGAATTCGAATA CATTACGTTTNNNGATCGACATG | 7140 |
| TGCAGGACCAGAGAATTCGAATA CAGGCTTCGGNNNGATCGACATG | 6661 | TGCAGGACCAGAGAATTCGAATA CAAATAACTCNNNGATCGACATG | 6901 | TGCAGGACCAGAGAATTCGAATA CAGTAGTCGTNNNGATCGACATG | 7141 |
| TGCAGGACCAGAGAATTCGAATA CACAATTCGGNNNGATCGACATG | 6662 | TGCAGGACCAGAGAATTCGAATA CATCATATTCNNNGATCGACATG | 6902 | TGCAGGACCAGAGAATTCGAATA CATGCCTCGCNNNGATCGACATG | 7142 |
| TGCAGGACCAGAGAATTCGAATA CAGGCTCTGGNNNGATCGACATG | 6663 | TGCAGGACCAGAGAATTCGAATA CAGATAGAATNNNGATCGACATG | 6903 | TGCAGGACCAGAGAATTCGAATA CAATACATTGNNNGATCGACATG | 7143 |
| TGCAGGACCAGAGAATTCGAATA CATCTCTGACNNNGATCGACATG | 6664 | TGCAGGACCAGAGAATTCGAATA CACCTGGACGNNNGATCGACATG | 6904 | TGCAGGACCAGAGAATTCGAATA CATATAAAABNNNGATCGACATG | 7144 |
| TGCAGGACCAGAGAATTCGAATA CAGAGTAGGTNNNGATCGACATG | 6665 | TGCAGGACCAGAGAATTCGAATA CATAACCCAGNNNGATCGACATG | 6905 | TGCAGGACCAGAGAATTCGAATA CATACCTGCTNNNGATCGACATG | 7145 |
| TGCAGGACCAGAGAATTCGAATA CAATTTTTTANNNGATCGACATG | 6666 | TGCAGGACCAGAGAATTCGAATA CAGCAGCCGTNNNGATCGACATG | 6906 | TGCAGGACCAGAGAATTCGAATA CATGAGAACGNNNGATCGACATG | 7146 |
| TGCAGGACCAGAGAATTCGAATA CAATTCTACNNNGATCGACATG | 6667 | TGCAGGACCAGAGAATTCGAATA CACAGACCCGNNNGATCGACATG | 6907 | TGCAGGACCAGAGAATTCGAATA CAGGAACTGANNNGATCGACATG | 7147 |
| TGCAGGACCAGAGAATTCGAATA CAAACGCTGTNNNGATCGACATG | 6668 | TGCAGGACCAGAGAATTCGAATA CATTAAGAAGNNNGATCGACATG | 6908 | TGCAGGACCAGAGAATTCGAATA CAAGAGCGCGNNNGATCGACATG | 7148 |
| TGCAGGACCAGAGAATTCGAATA CAATCGACTGNNNTGCATCAGGT | 6669 | TGCAGGACCAGAGAATTCGAATA CATTCATAAGNNNTGCATCAGGT | 6909 | TGCAGGACCAGAGAATTCGAATA CAACGCCACGNNNTGCATCAGGT | 7149 |
| TGCAGGACCAGAGAATTCGAATA CATAACGATTNNNTGCATCAGGT | 6670 | TGCAGGACCAGAGAATTCGAATA CACCACAGGCNNNTGCATCAGGT | 6910 | TGCAGGACCAGAGAATTCGAATA CATCCCCTAANNNTGCATCAGGT | 7150 |
| TGCAGGACCAGAGAATTCGAATA CAGCCCAGCANNNTGCATCAGGT | 6671 | TGCAGGACCAGAGAATTCGAATA CAGTCAGGCCNNNTGCATCAGGT | 6911 | TGCAGGACCAGAGAATTCGAATA CATCGGCATANNNTGCATCAGGT | 7151 |
| TGCAGGACCAGAGAATTCGAATA CAACAAACGGNNNTGCATCAGGT | 6672 | TGCAGGACCAGAGAATTCGAATA CAGTCGGCACNNNTGCATCAGGT | 6912 | TGCAGGACCAGAGAATTCGAATA CACGCCTCCANNNTGCATCAGGT | 7152 |
| TGCAGGACCAGAGAATTCGAATA CAAGAGTGCANNNTGCATCAGGT | 6673 | TGCAGGACCAGAGAATTCGAATA CATAGTCTGGNNNTGCATCAGGT | 6913 | TGCAGGACCAGAGAATTCGAATA CAAGCTGGCGNNNTGCATCAGGT | 7153 |
| TGCAGGACCAGAGAATTCGAATA CACGGATCGCNNNTGCATCAGGT | 6674 | TGCAGGACCAGAGAATTCGAATA CACATTATTCNNNTGCATCAGGT | 6914 | TGCAGGACCAGAGAATTCGAATA CAAAGGTTCCNNNTGCATCAGGT | 7154 |
| TGCAGGACCAGAGAATTCGAATA CAGGGAATCCTNNNTGCATCAGGT | 6675 | TGCAGGACCAGAGAATTCGAATA CAGAAGACCANNNTGCATCAGGT | 6915 | TGCAGGACCAGAGAATTCGAATA CACGGAAGGCNNNTGCATCAGGT | 7155 |
| TGCAGGACCAGAGAATTCGAATA CAACCTAAATNNNTGCATCAGGT | 6676 | TGCAGGACCAGAGAATTCGAATA CAAATTCTCTNNNTGCATCAGGT | 6916 | TGCAGGACCAGAGAATTCGAATA CAAGGCATTCNNNTGCATCAGGT | 7156 |
| TGCAGGACCAGAGAATTCGAATA CACGTATCGANNNTGCATCAGGT | 6677 | TGCAGGACCAGAGAATTCGAATA CAGCCCATCGNNNTGCATCAGGT | 6917 | TGCAGGACCAGAGAATTCGAATA CACACCAGCGNNNTGCATCAGGT | 7157 |
| TGCAGGACCAGAGAATTCGAATA CATCAGATATNNNTGCATCAGGT | 6678 | TGCAGGACCAGAGAATTCGAATA CATATAATTANNNTGCATCAGGT | 6918 | TGCAGGACCAGAGAATTCGAATA CATATGCGTGNNNTGCATCAGGT | 7158 |
| TGCAGGACCAGAGAATTCGAATA CAGCGACCGTNNNTGCATCAGGT | 6679 | TGCAGGACCAGAGAATTCGAATA CAACGAACAGNNNTGCATCAGGT | 6919 | TGCAGGACCAGAGAATTCGAATA CAGCATAGCTNNNTGCATCAGGT | 7159 |
| TGCAGGACCAGAGAATTCGAATA CATCAGACTGNNNTGCATCAGGT | 6680 | TGCAGGACCAGAGAATTCGAATA CAAGGCCCGTNNNTGCATCAGGT | 6920 | TGCAGGACCAGAGAATTCGAATA CATCACTAGGNNNTGCATCAGGT | 7160 |
| TGCAGGACCAGAGAATTCGAATA CAATGCACGTNNNTGCATCAGGT | 6681 | TGCAGGACCAGAGAATTCGAATA CACAAAGAGCNNNTGCATCAGGT | 6921 | TGCAGGACCAGAGAATTCGAATA CAGCCGAGCTNNNTGCATCAGGT | 7161 |
| TGCAGGACCAGAGAATTCGAATA CATCTACTGCNNNTGCATCAGGT | 6682 | TGCAGGACCAGAGAATTCGAATA CATTCAGGACNNNTGCATCAGGT | 6922 | TGCAGGACCAGAGAATTCGAATA CAACTGCCAANNNTGCATCAGGT | 7162 |
| TGCAGGACCAGAGAATTCGAATA CACTCGTTGTNNNTGCATCAGGT | 6683 | TGCAGGACCAGAGAATTCGAATA CAAGCACGCCNNNTGCATCAGGT | 6923 | TGCAGGACCAGAGAATTCGAATA CACCGACAATNNNTGCATCAGGT | 7163 |
| TGCAGGACCAGAGAATTCGAATA CACTGTGTAGNNNTGCATCAGGT | 6684 | TGCAGGACCAGAGAATTCGAATA CAGACACATCNNNTGCATCAGGT | 6924 | TGCAGGACCAGAGAATTCGAATA CACAGGCCCANNNTGCATCAGGT | 7164 |
| TGCAGGACCAGAGAATTCGAATA CAGCTTGCTNNNTGCATCAGGT | 6685 | TGCAGGACCAGAGAATTCGAATA CACGTACCCGNNNTGCATCAGGT | 6925 | TGCAGGACCAGAGAATTCGAATA CACBACCCCCNNNTGCATCAGGT | 7165 |
| TGCAGGACCAGAGAATTCGAATA CACTTTTCTTNNNTGCATCAGGT | 6686 | TGCAGGACCAGAGAATTCGAATA CAATACGCGTNNNTGCATCAGGT | 6926 | TGCAGGACCAGAGAATTCGAATA CAAAGACGACNNNTGCATCAGGT | 7166 |

FIG. 21G

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CATCAACTCCNNNTGCATCAGGT | 6687 | TGCAGGACCAGAGAATTCGAATA CATACACGCANNNTGCATCAGGT | 6927 | TGCAGGACCAGAGAATTCGAATA CATCAAGCAANNNTGCATCAGGT | 7167 |
| TGCAGGACCAGAGAATTCGAATA CAATCCAGCANNNTGCATCAGGT | 6688 | TGCAGGACCAGAGAATTCGAATA CACTCTCTCTNNNTGCATCAGGT | 6928 | TGCAGGACCAGAGAATTCGAATA CAATAGGCCTNNNTGCATCAGGT | 7168 |
| TGCAGGACCAGAGAATTCGAATA CAAACCGCTANNNTGCATCAGGT | 6689 | TGCAGGACCAGAGAATTCGAATA CACAATGAGGNNNTGCATCAGGT | 6929 | TGCAGGACCAGAGAATTCGAATA CATTGGATATNNNTGCATCAGGT | 7169 |
| TGCAGGACCAGAGAATTCGAATA CACGCCTGTCNNNTGCATCAGGT | 6690 | TGCAGGACCAGAGAATTCGAATA CACACAGTGTNNNTGCATCAGGT | 6930 | TGCAGGACCAGAGAATTCGAATA CACTATCGCTNNNTGCATCAGGT | 7170 |
| TGCAGGACCAGAGAATTCGAATA CATAAGGCCTNNNTGCATCAGGT | 6691 | TGCAGGACCAGAGAATTCGAATA CAAACATACTNNNTGCATCAGGT | 6931 | TGCAGGACCAGAGAATTCGAATA CACTCTTGACNNNTGCATCAGGT | 7171 |
| TGCAGGACCAGAGAATTCGAATA CATGTCATGGNNNTGCATCAGGT | 6692 | TGCAGGACCAGAGAATTCGAATA CACGGCATCGNNNTGCATCAGGT | 6932 | TGCAGGACCAGAGAATTCGAATA CAAATTAGGANNNTGCATCAGGT | 7172 |
| TGCAGGACCAGAGAATTCGAATA CATAGCAGTCNNNTGCATCAGGT | 6693 | TGCAGGACCAGAGAATTCGAATA CAAGTAGATANNNTGCATCAGGT | 6933 | TGCAGGACCAGAGAATTCGAATA CACGTTGCTTNNNTGCATCAGGT | 7173 |
| TGCAGGACCAGAGAATTCGAATA CAGCGCTGACNNNTGCATCAGGT | 6694 | TGCAGGACCAGAGAATTCGAATA CAGCCGATCCGNNNTGCATCAGGT | 6934 | TGCAGGACCAGAGAATTCGAATA CATTTCCCCTNNNTGCATCAGGT | 7174 |
| TGCAGGACCAGAGAATTCGAATA CATATATCCTNNNTGCATCAGGT | 6695 | TGCAGGACCAGAGAATTCGAATA CAATTAAATTNNNTGCATCAGGT | 6935 | TGCAGGACCAGAGAATTCGAATA CAACTACCTCNNNTGCATCAGGT | 7175 |
| TGCAGGACCAGAGAATTCGAATA CACACGAAAGNNNTGCATCAGGT | 6696 | TGCAGGACCAGAGAATTCGAATA CAAGATTCATNNNTGCATCAGGT | 6936 | TGCAGGACCAGAGAATTCGAATA CAACTCTGCTNNNTGCATCAGGT | 7176 |
| TGCAGGACCAGAGAATTCGAATA CAATAAGTCTNNNTGCATCAGGT | 6697 | TGCAGGACCAGAGAATTCGAATA CATCACCTGTNNNTGCATCAGGT | 6937 | TGCAGGACCAGAGAATTCGAATA CACTACCTCANNNTGCATCAGGT | 7177 |
| TGCAGGACCAGAGAATTCGAATA CAGCTGTCCCNNNTGCATCAGGT | 6698 | TGCAGGACCAGAGAATTCGAATA CACAAATACTNNNTGCATCAGGT | 6938 | TGCAGGACCAGAGAATTCGAATA CAACTGCTAGNNNTGCATCAGGT | 7178 |
| TGCAGGACCAGAGAATTCGAATA CAATGACCTGNNNTGCATCAGGT | 6699 | TGCAGGACCAGAGAATTCGAATA CATTTAGCAANNNTGCATCAGGT | 6939 | TGCAGGACCAGAGAATTCGAATA CACGCGCAGTNNNTGCATCAGGT | 7179 |
| TGCAGGACCAGAGAATTCGAATA CAATACCCCTNNNTGCATCAGGT | 6700 | TGCAGGACCAGAGAATTCGAATA CATCCTAGTCNNNTGCATCAGGT | 6940 | TGCAGGACCAGAGAATTCGAATA CAGGCTTTCTNNNTGCATCAGGT | 7180 |
| TGCAGGACCAGAGAATTCGAATA CATGAGGTAGNNNTGCATCAGGT | 6701 | TGCAGGACCAGAGAATTCGAATA CATAAAGAGTNNNTGCATCAGGT | 6941 | TGCAGGACCAGAGAATTCGAATA CACTGGACTANNNTGCATCAGGT | 7181 |
| TGCAGGACCAGAGAATTCGAATA CACGAATCTGNNNTGCATCAGGT | 6702 | TGCAGGACCAGAGAATTCGAATA CACATGCACANNNTGCATCAGGT | 6942 | TGCAGGACCAGAGAATTCGAATA CAACATCAGCNNNTGCATCAGGT | 7182 |
| TGCAGGACCAGAGAATTCGAATA CAGCCGACGTNNNTGCATCAGGT | 6703 | TGCAGGACCAGAGAATTCGAATA CATTTCAACTNNNTGCATCAGGT | 6943 | TGCAGGACCAGAGAATTCGAATA CATCAGTTCCNNNTGCATCAGGT | 7183 |
| TGCAGGACCAGAGAATTCGAATA CATTCAAACANNNTGCATCAGGT | 6704 | TGCAGGACCAGAGAATTCGAATA CACTGATGTGNNNTGCATCAGGT | 6944 | TGCAGGACCAGAGAATTCGAATA CATCACGATGNNNTGCATCAGGT | 7184 |
| TGCAGGACCAGAGAATTCGAATA CAAGGCTTACNNNTGCATCAGGT | 6705 | TGCAGGACCAGAGAATTCGAATA CACCCGTTCGNNNTGCATCAGGT | 6945 | TGCAGGACCAGAGAATTCGAATA CAGTATGCACNNNTGCATCAGGT | 7185 |
| TGCAGGACCAGAGAATTCGAATA CAAAAACGGCNNNTGCATCAGGT | 6706 | TGCAGGACCAGAGAATTCGAATA CACATAAGAANNNTGCATCAGGT | 6946 | TGCAGGACCAGAGAATTCGAATA CATCAGGCGCNNNTGCATCAGGT | 7186 |
| TGCAGGACCAGAGAATTCGAATA CAGATATGGANNNTGCATCAGGT | 6707 | TGCAGGACCAGAGAATTCGAATA CAGATTGACGNNNTGCATCAGGT | 6947 | TGCAGGACCAGAGAATTCGAATA CAGTTTTCCGNNNTGCATCAGGT | 7187 |
| TGCAGGACCAGAGAATTCGAATA CAATGGCGAANNNTGCATCAGGT | 6708 | TGCAGGACCAGAGAATTCGAATA CACTGACGATNNNTGCATCAGGT | 6948 | TGCAGGACCAGAGAATTCGAATA CAGGTCGGAGNNNTGCATCAGGT | 7188 |
| TGCAGGACCAGAGAATTCGAATA CAACCAAGAGNNNTGCATCAGGT | 6709 | TGCAGGACCAGAGAATTCGAATA CAACTTTCTANNNTGCATCAGGT | 6949 | TGCAGGACCAGAGAATTCGAATA CAATAAGGCGNNNTGCATCAGGT | 7189 |
| TGCAGGACCAGAGAATTCGAATA CACAAACGCTNNNTGCATCAGGT | 6710 | TGCAGGACCAGAGAATTCGAATA CACACATAGCNNNTGCATCAGGT | 6950 | TGCAGGACCAGAGAATTCGAATA CAAGCCGACCNNNTGCATCAGGT | 7190 |
| TGCAGGACCAGAGAATTCGAATA CACGCTTTCANNNTGCATCAGGT | 6711 | TGCAGGACCAGAGAATTCGAATA CATTAGTCAANNNTGCATCAGGT | 6951 | TGCAGGACCAGAGAATTCGAATA CACATGTCAGNNNTGCATCAGGT | 7191 |
| TGCAGGACCAGAGAATTCGAATA CATCCAGGCGNNNTGCATCAGGT | 6712 | TGCAGGACCAGAGAATTCGAATA CATGGTCGCGNNNTGCATCAGGT | 6952 | TGCAGGACCAGAGAATTCGAATA CATTTTAGCTNNNTGCATCAGGT | 7192 |
| TGCAGGACCAGAGAATTCGAATA CATTGAAATCNNNTGCATCAGGT | 6713 | TGCAGGACCAGAGAATTCGAATA CATTCTGACCNNNTGCATCAGGT | 6953 | TGCAGGACCAGAGAATTCGAATA CATCGAGTTGNNNTGCATCAGGT | 7193 |
| TGCAGGACCAGAGAATTCGAATA CACCTGCTGCNNNTGCATCAGGT | 6714 | TGCAGGACCAGAGAATTCGAATA CATAAAACCTNNNTGCATCAGGT | 6954 | TGCAGGACCAGAGAATTCGAATA CAGCCACCTCNNNTGCATCAGGT | 7194 |
| TGCAGGACCAGAGAATTCGAATA CACGAATGAGNNNTGCATCAGGT | 6715 | TGCAGGACCAGAGAATTCGAATA CAACTATAACNNNTGCATCAGGT | 6955 | TGCAGGACCAGAGAATTCGAATA CATGTTGTGGNNNTGCATCAGGT | 7195 |
| TGCAGGACCAGAGAATTCGAATA CATGTGTTAANNNTGCATCAGGT | 6716 | TGCAGGACCAGAGAATTCGAATA CATATATGATNNNTGCATCAGGT | 6956 | TGCAGGACCAGAGAATTCGAATA CAGTTGTGTGNNNTGCATCAGGT | 7196 |
| TGCAGGACCAGAGAATTCGAATA CATTCAAAACNNNTGCATCAGGT | 6717 | TGCAGGACCAGAGAATTCGAATA CATCACCGCCNNNTGCATCAGGT | 6957 | TGCAGGACCAGAGAATTCGAATA CACGTGAACTNNNTGCATCAGGT | 7197 |
| TGCAGGACCAGAGAATTCGAATA CACAGCCCACNNNTGCATCAGGT | 6718 | TGCAGGACCAGAGAATTCGAATA CAAGGTTATTNNNTGCATCAGGT | 6958 | TGCAGGACCAGAGAATTCGAATA CAAAGGCTCTNNNTGCATCAGGT | 7198 |
| TGCAGGACCAGAGAATTCGAATA CAGACAGTAGNNNTGCATCAGGT | 6719 | TGCAGGACCAGAGAATTCGAATA CAAGCCAGCTTNNNTGCATCAGGT | 6959 | TGCAGGACCAGAGAATTCGAATA CATATTCTTGNNNTGCATCAGGT | 7199 |

FIG. 21H

| Pool-28 | SEQ ID NO: | Pool-29 | SEQ ID NO: | Pool-30 | SEQ ID NO: |
|---|---|---|---|---|---|
| TGCAGGACCAGAGAATTCGAATA CACATTTGTTNNNTGCATCAGGT | 6720 | TGCAGGACCAGAGAATTCGAATA CATCGAGACTNNNTGCATCAGGT | 6960 | TGCAGGACCAGAGAATTCGAATA CACATTACTTNNNTGCATCAGGT | 7200 |
| TGCAGGACCAGAGAATTCGAATA CATAATCCAANNNTGCATCAGGT | 6721 | TGCAGGACCAGAGAATTCGAATA CACACACTTCNNNTGCATCAGGT | 6961 | TGCAGGACCAGAGAATTCGAATA CACCAAGACTNNNTGCATCAGGT | 7201 |
| TGCAGGACCAGAGAATTCGAATA CACGTACAACNNNTGCATCAGGT | 6722 | TGCAGGACCAGAGAATTCGAATA CAAAAAAACCNNNTGCATCAGGT | 6962 | TGCAGGACCAGAGAATTCGAATA CAAGTTCCAGNNNTGCATCAGGT | 7202 |
| TGCAGGACCAGAGAATTCGAATA CAATATTCCANNNTGCATCAGGT | 6723 | TGCAGGACCAGAGAATTCGAATA CATACAGCCANNNTGCATCAGGT | 6963 | TGCAGGACCAGAGAATTCGAATA CAAACCAGTCNNNTGCATCAGGT | 7203 |
| TGCAGGACCAGAGAATTCGAATA CATAATTATANNNTGCATCAGGT | 6724 | TGCAGGACCAGAGAATTCGAATA CAATGAAAACNNNTGCATCAGGT | 6964 | TGCAGGACCAGAGAATTCGAATA CATGGCTCAANNNTGCATCAGGT | 7204 |
| TGCAGGACCAGAGAATTCGAATA CAGATGCAGANNNTGCATCAGGT | 6725 | TGCAGGACCAGAGAATTCGAATA CAGTGATGCTNNNTGCATCAGGT | 6965 | TGCAGGACCAGAGAATTCGAATA CATCTTTATGNNNTGCATCAGGT | 7205 |
| TGCAGGACCAGAGAATTCGAATA CAGGAGCCAGNNTNTGCATCAGGT | 6726 | TGCAGGACCAGAGAATTCGAATA CATTAACAGTNNNTGCATCAGGT | 6966 | TGCAGGACCAGAGAATTCGAATA CAGGTGACTTNNNTGCATCAGGT | 7206 |
| TGCAGGACCAGAGAATTCGAATA CAGCGAGTTTNNNTGCATCAGGT | 6727 | TGCAGGACCAGAGAATTCGAATA CACACACCGCGNNNTGCATCAGGT | 6967 | TGCAGGACCAGAGAATTCGAATA CATCCTAACCNNNTGCATCAGGT | 7207 |
| TGCAGGACCAGAGAATTCGAATA CAAAGTGACGNNNTGCATCAGGT | 6728 | TGCAGGACCAGAGAATTCGAATA CATGTGCCCCNNNTGCATCAGGT | 6968 | TGCAGGACCAGAGAATTCGAATA CAGCGTAAAGNNNTGCATCAGGT | 7208 |

FIG. 22A

| Pool-31 | SEQ ID NO: | Pool-32 | SEQ ID NO: |
|---|---|---|---|
| TGCAGGACCAGAGAATTCGAATAC ATGGTCCAANNNACGTATGCCA | 7209 | TGCAGGACCAGAGAATTCGAATA CATTCCAATTNNNACGTATGCCA | 7449 |
| TGCAGGACCAGAGAATTCGAATAC AGTACTCAGNNNACGTATGCCA | 7210 | TGCAGGACCAGAGAATTCGAATA CATGTACAGCNNNACGTATGCCA | 7450 |
| TGCAGGACCAGAGAATTCGAATAC AGAAGCCCCNNNACGTATGCCA | 7211 | TGCAGGACCAGAGAATTCGAATA CACAGGAGCGNNNACGTATGCCA | 7451 |
| TGCAGGACCAGAGAATTCGAATAC ATTAACCGGNNNACGTATGCCA | 7212 | TGCAGGACCAGAGAATTCGAATA CAATGCGTTGNNNACGTATGCCA | 7452 |
| TGCAGGACCAGAGAATTCGAATAC ATAACCTGGNNNACGTATGCCA | 7213 | TGCAGGACCAGAGAATTCGAATA CATATTTTCGNNNACGTATGCCA | 7453 |
| TGCAGGACCAGAGAATTCGAATAC AGTCGACTANNNACGTATGCCA | 7214 | TGCAGGACCAGAGAATTCGAATA CAAATTCCCCNNNACGTATGCCA | 7454 |
| TGCAGGACCAGAGAATTCGAATAC ACCAAACGTNNNACGTATGCCA | 7215 | TGCAGGACCAGAGAATTCGAATA CATCTGACGANNNACGTATGCCA | 7455 |
| TGCAGGACCAGAGAATTCGAATAC AACGTATCGNNNACGTATGCCA | 7216 | TGCAGGACCAGAGAATTCGAATA CACCGCGCTTNNNACGTATGCCA | 7456 |
| TGCAGGACCAGAGAATTCGAATAC ACACGGCCANNNACGTATGCCA | 7217 | TGCAGGACCAGAGAATTCGAATA CAAAACACCCNNNACGTATGCCA | 7457 |
| TGCAGGACCAGAGAATTCGAATAC AAGGTTTGCNNNACGTATGCCA | 7218 | TGCAGGACCAGAGAATTCGAATA CAGGTTGTGNNNACGTATGCCA | 7458 |
| TGCAGGACCAGAGAATTCGAATAC ACGACGCGTNNNACGTATGCCA | 7219 | TGCAGGACCAGAGAATTCGAATA CAACTAACCGNNNACGTATGCCA | 7459 |
| TGCAGGACCAGAGAATTCGAATAC ACCGACGTGNNNACGTATGCCA | 7220 | TGCAGGACCAGAGAATTCGAATA CATCAGGAGANNNACGTATGCCA | 7460 |
| TGCAGGACCAGAGAATTCGAATAC ACAGTTTTTNNNACGTATGCCA | 7221 | TGCAGGACCAGAGAATTCGAATA CAGTCTGCGGNNNACGTATGCCA | 7461 |
| TGCAGGACCAGAGAATTCGAATAC ATGCCCGGANNNACGTATGCCA | 7222 | TGCAGGACCAGAGAATTCGAATA CAACTGGCGCNNNACGTATGCCA | 7462 |
| TGCAGGACCAGAGAATTCGAATAC AGCCACTCCNNNACGTATGCCA | 7223 | TGCAGGACCAGAGAATTCGAATA CACGACTCTNNNACGTATGCCA | 7463 |
| TGCAGGACCAGAGAATTCGAATAC AGACGAAGTNNNACGTATGCCA | 7224 | TGCAGGACCAGAGAATTCGAATA CAGCGAAGGCNNNACGTATGCCA | 7464 |
| TGCAGGACCAGAGAATTCGAATAC AGGTTCCTTNNNACGTATGCCA | 7225 | TGCAGGACCAGAGAATTCGAATA CAGGCGCCGCNNNACGTATGCCA | 7465 |
| TGCAGGACCAGAGAATTCGAATAC ACCGGAATTNNNACGTATGCCA | 7226 | TGCAGGACCAGAGAATTCGAATA CAGAGCACCCNNNACGTATGCCA | 7466 |
| TGCAGGACCAGAGAATTCGAATAC ATCGGCAGCNNNACGTATGCCA | 7227 | TGCAGGACCAGAGAATTCGAATA CACCCAAAGTNNNACGTATGCCA | 7467 |
| TGCAGGACCAGAGAATTCGAATAC AGCTAGAGANNNACGTATGCCA | 7228 | TGCAGGACCAGAGAATTCGAATA CACGGAATAGNNNACGTATGCCA | 7468 |
| TGCAGGACCAGAGAATTCGAATAC ACCACTTACNNNACGTATGCCA | 7229 | TGCAGGACCAGAGAATTCGAATA CAAGTAAGATNNNACGTATGCCA | 7469 |
| TGCAGGACCAGAGAATTCGAATAC AACCACCGGNNNACGTATGCCA | 7230 | TGCAGGACCAGAGAATTCGAATA CATCTCACACNNNACGTATGCCA | 7470 |
| TGCAGGACCAGAGAATTCGAATAC AGAAACATANNNACGTATGCCA | 7231 | TGCAGGACCAGAGAATTCGAATA CAGGCCCCAANNNACGTATGCCA | 7471 |
| TGCAGGACCAGAGAATTCGAATAC AGCTGAAAGNNNACGTATGCCA | 7232 | TGCAGGACCAGAGAATTCGAATA CAGGATTTGCNNNACGTATGCCA | 7472 |
| TGCAGGACCAGAGAATTCGAATAC ATAAGAAGTNNNACGTATGCCA | 7233 | TGCAGGACCAGAGAATTCGAATA CAAATGACAANNNACGTATGCCA | 7473 |
| TGCAGGACCAGAGAATTCGAATAC ACGTGACTANNNACGTATGCCA | 7234 | TGCAGGACCAGAGAATTCGAATA CATAAAAAATNNNACGTATGCCA | 7474 |
| TGCAGGACCAGAGAATTCGAATAC ATTAAGATCNNNACGTATGCCA | 7235 | TGCAGGACCAGAGAATTCGAATA CATAATGGCCNNNACGTATGCCA | 7475 |
| TGCAGGACCAGAGAATTCGAATAC ATGGATCACNNNACGTATGCCA | 7236 | TGCAGGACCAGAGAATTCGAATA CAGTTGCTTCNNNACGTATGCCA | 7476 |
| TGCAGGACCAGAGAATTCGAATAC ACCGAGCTGNNNACGTATGCCA | 7237 | TGCAGGACCAGAGAATTCGAATA CACGTTTCACNNNACGTATGCCA | 7477 |
| TGCAGGACCAGAGAATTCGAATAC ACTCATAAANNNACGTATGCCA | 7238 | TGCAGGACCAGAGAATTCGAATA CAGAACAAATNNNACGTATGCCA | 7478 |
| TGCAGGACCAGAGAATTCGAATAC ACTCTACTGNNNACGTATGCCA | 7239 | TGCAGGACCAGAGAATTCGAATA CAATAGAAGTNNNACGTATGCCA | 7479 |
| TGCAGGACCAGAGAATTCGAATAC AAGGTGAGTNNNACGTATGCCA | 7240 | TGCAGGACCAGAGAATTCGAATA CAGTAAGGCANNNACGTATGCCA | 7480 |
| TGCAGGACCAGAGAATTCGAATAC AGAACACTCNNNACGTATGCCA | 7241 | TGCAGGACCAGAGAATTCGAATA CAGAGATGCANNNACGTATGCCA | 7481 |

FIG. 22B

| Pool-31 | SEQ ID NO: | Pool-32 | SEQ ID NO: |
|---|---|---|---|
| TGCAGGACCAGAGAATTCGAATAC AGGCAGAGCNNNACGTATGCCA | 7242 | TGCAGGACCAGAGAATTCGAATA CACACCATCTNNNACGTATGCCA | 7482 |
| TGCAGGACCAGAGAATTCGAATAC ATTTCCAGCNNNACGTATGCCA | 7243 | TGCAGGACCAGAGAATTCGAATA CAGATACACCNNNACGTATGCCA | 7483 |
| TGCAGGACCAGAGAATTCGAATAC ACCCATCATNNNACGTATGCCA | 7244 | TGCAGGACCAGAGAATTCGAATA CAGATACTGCNNNACGTATGCCA | 7484 |
| TGCAGGACCAGAGAATTCGAATAC AATCAGCGTNNNACGTATGCCA | 7245 | TGCAGGACCAGAGAATTCGAATA CACGTAACTGNNNACGTATGCCA | 7485 |
| TGCAGGACCAGAGAATTCGAATAC ATGAAAAACNNNACGTATGCCA | 7246 | TGCAGGACCAGAGAATTCGAATA CATCCTCTTCNNNACGTATGCCA | 7486 |
| TGCAGGACCAGAGAATTCGAATAC AATGCGGAANNNACGTATGCCA | 7247 | TGCAGGACCAGAGAATTCGAATA CATGCGGTCGNNNACGTATGCCA | 7487 |
| TGCAGGACCAGAGAATTCGAATAC ACGGATTCANNNACGTATGCCA | 7248 | TGCAGGACCAGAGAATTCGAATA CAACAGGAACNNNACGTATGCCA | 7488 |
| TGCAGGACCAGAGAATTCGAATAC AGTCATACGNNNACGTATGCCA | 7249 | TGCAGGACCAGAGAATTCGAATA CAAAAATTTTNNNACGTATGCCA | 7489 |
| TGCAGGACCAGAGAATTCGAATAC AACCTGCTTNNNACGTATGCCA | 7250 | TGCAGGACCAGAGAATTCGAATA CAAAGTCACCNNNACGTATGCCA | 7490 |
| TGCAGGACCAGAGAATTCGAATAC AGTTGTGCANNNACGTATGCCA | 7251 | TCCAGGACCAGAGAATTCGAATA CATCTACGAGNNNACGTATGCCA | 7491 |
| TGCAGGACCAGAGAATTCGAATAC AGAAATCGGNNNACGTATGCCA | 7252 | TGCAGGACCAGAGAATTCGAATA CAGATCTTCCNNNACGTATGCCA | 7492 |
| TGCAGGACCAGAGAATTCGAATAC AAAGTTAGANNNACGTATGCCA | 7253 | TGCAGGACCAGAGAATTCGAATA CAGGACACCCNNNACGTATGCCA | 7493 |
| TGCAGGACCAGAGAATTCGAATAC ATGTAACGCNNNACGTATGCCA | 7254 | TGCAGGACCAGAGAATTCGAATA CAATAGGTGGNNNACGTATGCCA | 7494 |
| TGCAGGACCAGAGAATTCGAATAC AGTTTTGAANNNACGTATGCCA | 7255 | TGCAGGACCAGAGAATTCGAATA CACCATCGCCNNNACGTATGCCA | 7495 |
| TGCAGGACCAGAGAATTCGAATAC ACAAACTGCNNNACGTATGCCA | 7256 | TGCAGGACCAGAGAATTCGAATA CATGATCTCCNNNACGTATGCCA | 7496 |
| TGCAGGACCAGAGAATTCGAATAC AGCCTGAGCNNNACGTATGCCA | 7257 | TGCAGGACCAGAGAATTCGAATA CACGCGAATTNNNACGTATGCCA | 7497 |
| TGCAGGACCAGAGAATTCGAATAC ATCTTCCAGNNNACGTATGCCA | 7258 | TGCAGGACCAGAGAATTCGAATA CATATATAATNNNACGTATGCCA | 7498 |
| TGCAGGACCAGAGAATTCGAATAC ATACCCTACNNNACGTATGCCA | 7259 | TGCAGGACCAGAGAATTCGAATA CATATCGCCTNNNACGTATGCCA | 7499 |
| TGCAGGACCAGAGAATTCGAATAC ATCATAGATNNNACGTATGCCA | 7260 | TGCAGGACCAGAGAATTCGAATA CATTACGAGCNNNACGTATGCCA | 7500 |
| TGCAGGACCAGAGAATTCGAATAC AGTATAGAANNNACGTATGCCA | 7261 | TGCAGGACCAGAGAATTCGAATA CAGGTTTCTCNNNACGTATGCCA | 7501 |
| TGCAGGACCAGAGAATTCGAATAC ACCCTAAAGNNNACGTATGCCA | 7262 | TGCAGGACCAGAGAATTCGAATA CACTTGCAGANNNACGTATGCCA | 7502 |
| TGCAGGACCAGAGAATTCGAATAC AGCGGTTTANNNACGTATGCCA | 7263 | TGCAGGACCAGAGAATTCGAATA CAGACATTTANNNACGTATGCCA | 7503 |
| TGCAGGACCAGAGAATTCGAATAC ATAGCTCAGNNNACGTATGCCA | 7264 | TGCAGGACCAGAGAATTCGAATA CAACACGAGANNNACGTATGCCA | 7504 |
| TGCAGGACCAGAGAATTCGAATAC ACCGTCCCANNNACGTATGCCA | 7265 | TGCAGGACCAGAGAATTCGAATA CATTGCCCGCNNNACGTATGCCA | 7505 |
| TGCAGGACCAGAGAATTCGAATAC AAGTGCGAANNNACGTATGCCA | 7266 | TGCAGGACCAGAGAATTCGAATA CACAGTCCTTNNNACGTATGCCA | 7506 |
| TGCAGGACCAGAGAATTCGAATAC ATGAGCTTGNNNACGTATGCCA | 7267 | TGCAGGACCAGAGAATTCGAATA CAGCATTTGGNNNACGTATGCCA | 7507 |
| TGCAGGACCAGAGAATTCGAATAC ATATCGTGGNNNACGTATGCCA | 7268 | TGCAGGACCAGAGAATTCGAATA CAGGATATCCNNNACGTATGCCA | 7508 |
| TGCAGGACCAGAGAATTCGAATAC ATCAGACACNNNCTAGCGTTAC | 7269 | TGCAGGACCAGAGAATTCGAATA CACCAGGAGGNNNCTAGCGTTAC | 7509 |
| TGCAGGACCAGAGAATTCGAATAC ATACCCTTGNNNCTAGCGTTAC | 7270 | TGCAGGACCAGAGAATTCGAATA CATCGCCTTANNNCTAGCGTTAC | 7510 |
| TGCAGGACCAGAGAATTCGAATAC ACATCGAGTNNNCTAGCGTTAC | 7271 | TGCAGGACCAGAGAATTCGAATA CATTACCCGTNNNCTAGCGTTAC | 7511 |
| TGCAGGACCAGAGAATTCGAATAC ATGAATCTANNNCTAGCGTTAC | 7272 | TGCAGGACCAGAGAATTCGAATA CAATCACCTCNNNCTAGCGTTAC | 7512 |
| TGCAGGACCAGAGAATTCGAATAC AAGTGGAGTNNNCTAGCGTTAC | 7273 | TGCAGGACCAGAGAATTCGAATA CACCAATTCCNNNCTAGCGTTAC | 7513 |
| TGCAGGACCAGAGAATTCGAATAC ACTGAAGGANNNCTAGCGTTAC | 7274 | TGCAGGACCAGAGAATTCGAATA CATGCGTGATNNNCTAGCGTTAC | 7514 |

FIG. 22C

| Pool-31 | SEQ ID NO: | Pool-32 | SEQ ID NO: |
|---|---|---|---|
| TGCAGGACCAGAGAATTCGAATAC AAATCAGTTNNNCTAGCGTTAC | 7275 | TGCAGGACCAGAGAATTCGAATA CACTCGGCCTNNNCTAGCGTTAC | 7515 |
| TGCAGGACCAGAGAATTCGAATAC ACGCAGGCTNNNCTAGCGTTAC | 7276 | TGCAGGACCAGAGAATTCGAATA CAACGAATTANNNCTAGCGTTAC | 7516 |
| TGCAGGACCAGAGAATTCGAATAC ACGGTGCACNNNCTAGCGTTAC | 7277 | TGCAGGACCAGAGAATTCGAATA CACCCTACATNNNCTAGCGTTAC | 7517 |
| TGCAGGACCAGAGAATTCGAATAC ACGTATCAGNNNCTAGCGTTAC | 7278 | TGCAGGACCAGAGAATTCGAATA CACGGTTTAGNNNCTAGCGTTAC | 7518 |
| TGCAGGACCAGAGAATTCGAATAC ATAACGCTGNNNCTAGCGTTAC | 7279 | TGCAGGACCAGAGAATTCGAATA CATCGTATAANNNCTAGCGTTAC | 7519 |
| TGCAGGACCAGAGAATTCGAATAC AACCGTACANNNCTAGCGTTAC | 7280 | TGCAGGACCAGAGAATTCGAATA CATAAGCAAANNNCTAGCGTTAC | 7520 |
| TGCAGGACCAGAGAATTCGAATAC AGCTTAGTGNNNCTAGCGTTAC | 7281 | TGCAGGACCAGAGAATTCGAATA CACGGTCTGGNNNCTAGCGTTAC | 7521 |
| TGCAGGACCAGAGAATTCGAATAC ACGAACGCCNNNCTAGCGTTAC | 7282 | TGCAGGACCAGAGAATTCGAATA CACCACAGTANNNCTAGCGTTAC | 7522 |
| TGCAGGACCAGAGAATTCGAATAC AGTATCGTGNNNCTAGCGTTAC | 7283 | TGCAGGACCAGAGAATTCGAATA CAACCACTAGNNNCTAGCGTTAC | 7523 |
| TGCAGGACCAGAGAATTCGAATAC ATACABATCNNNCTAGCGTTAC | 7284 | TGCAGGACCAGAGAATTCGAATA CACGCAAACTNNNCTAGCGTTAC | 7524 |
| TGCAGGACCAGAGAATTCGAATAC ACGTCCTTANNNCTAGCGTTAC | 7285 | TGCAGGACCAGAGAATTCGAATA CACTTCAACCNNNCTAGCGTTAC | 7525 |
| TGCAGGACCAGAGAATTCGAATAC AAGACCACTNNNCTAGCGTTAC | 7286 | TGCAGGACCAGAGAATTCGAATA CAGAGAGGCCNNNCTAGCGTTAC | 7526 |
| TGCAGGACCAGAGAATTCGAATAC AACAAGGTGNNNCTAGCGTTAC | 7287 | TGCAGGACCAGAGAATTCGAATA CAATATTGGTNNNCTAGCGTTAC | 7527 |
| TGCAGGACCAGAGAATTCGAATAC AATACTTGANNNCTAGCGTTAC | 7288 | TGCAGGACCAGAGAATTCGAATA CACTATATGANNNCTAGCGTTAC | 7528 |
| TGCAGGACCAGAGAATTCGAATAC ACTTCCGATNNNCTAGCGTTAC | 7289 | TGCAGGACCAGAGAATTCGAATA CAATCTTGTTNNNCTAGCGTTAC | 7529 |
| TGCAGGACCAGAGAATTCGAATAC ACGTCTTGTNNNCTAGCGTTAC | 7290 | TGCAGGACCAGAGAATTCGAATA CATAAAGGCGNNNCTAGCGTTAC | 7530 |
| TGCAGGACCAGAGAATTCGAATAC AAAGTGGTGNNNCTAGCGTTAC | 7291 | TGCAGGACCAGAGAATTCGAATA CACCATTGCNNNCTAGCGTTAC | 7531 |
| TGCAGGACCAGAGAATTCGAATAC ATCGGTGGCNNNCTAGCGTTAC | 7292 | TGCAGGACCAGAGAATTCGAATA CATACCCTANNNCTAGCGTTAC | 7532 |
| TGCAGGACCAGAGAATTCGAATAC AAAAATCAGNNNCTAGCGTTAC | 7293 | TGCAGGACCAGAGAATTCGAATA CAAGAACCGANNNCTAGCGTTAC | 7533 |
| TGCAGGACCAGAGAATTCGAATAC ATCCCGCGTNNNCTAGCGTTAC | 7294 | TGCAGGACCAGAGAATTCGAATA CAACGATAGGNNNCTAGCGTTAC | 7534 |
| TGCAGGACCAGAGAATTCGAATAC AGGCACGCTNNNCTAGCGTTAC | 7295 | TGCAGGACCAGAGAATTCGAATA CAGGCGCCATNNNCTAGCGTTAC | 7535 |
| TGCAGGACCAGAGAATTCGAATAC AGCTGTCTTNNNCTAGCGTTAC | 7296 | TGCAGGACCAGAGAATTCGAATA CAAAAATCTCNNNCTAGCGTTAC | 7536 |
| TGCAGGACCAGAGAATTCGAATAC AAGCATAAANNNCTAGCGTTAC | 7297 | TGCAGGACCAGAGAATTCGAATA CAGACTAGCTNNNCTAGCGTTAC | 7537 |
| TGCAGGACCAGAGAATTCGAATAC ATGCGAATCNNNCTAGCGTTAC | 7298 | TGCAGGACCAGAGAATTCGAATA CACGTGAGTTNNNCTAGCGTTAC | 7538 |
| TGCAGGACCAGAGAATTCGAATAC ACGTTTCGTNNNCTAGCGTTAC | 7299 | TGCAGGACCAGAGAATTCGAATA CACCCGCTGTNNNCTAGCGTTAC | 7539 |
| TGCAGGACCAGAGAATTCGAATAC AGCACTCTTNNNCTAGCGTTAC | 7300 | TGCAGGACCAGAGAATTCGAATA CAAAAACTTCNNNCTAGCGTTAC | 7540 |
| TGCAGGACCAGAGAATTCGAATAC ACTCGCTGCNNNCTAGCGTTAC | 7301 | TGCAGGACCAGAGAATTCGAATA CAAGTAACGGNNNCTAGCGTTAC | 7541 |
| TGCAGGACCAGAGAATTCGAATAC ACATACAGCNNNCTAGCGTTAC | 7302 | TGCAGGACCAGAGAATTCGAATA CAATCAACATNNNCTAGCGTTAC | 7542 |
| TGCAGGACCAGAGAATTCGAATAC AGAGCAAACNNNCTAGCGTTAC | 7303 | TGCAGGACCAGAGAATTCGAATA CACTTTTGATNNNCTAGCGTTAC | 7543 |
| TGCAGGACCAGAGAATTCGAATAC AGCTTCCATNNNCTAGCGTTAC | 7304 | TGCAGGACCAGAGAATTCGAATA CAGTGTACCANNNCTAGCGTTAC | 7544 |
| TGCAGGACCAGAGAATTCGAATAC ACCTAATTNNNCTAGCGTTAC | 7305 | TGCAGGACCAGAGAATTCGAATA CATGCACACANNNCTAGCGTTAC | 7545 |
| TGCAGGACCAGAGAATTCGAATAC AAGCCCGACNNNCTAGCGTTAC | 7306 | TGCAGGACCAGAGAATTCGAATA CATATACTTCNNNCTAGCGTTAC | 7546 |
| TGCAGGACCAGAGAATTCGAATAC ATGGTGAAGNNNCTAGCGTTAC | 7307 | TGCAGGACCAGAGAATTCGAATA CAGAAACTAANNNCTAGCGTTAC | 7547 |

FIG. 22D

| Pool-31 | SEQ ID NO: | Pool-32 | SEQ ID NO: |
|---|---|---|---|
| TGCAGGACCAGAGAATTCGAATAC AATCGCTGANNNCTAGCGTTAC | 7308 | TGCAGGACCAGAGAATTCGAATA CAATCTCGAGNNNCTAGCGTTAC | 7548 |
| TGCAGGACCAGAGAATTCGAATAC ATTACTGCCNNNCTAGCGTTAC | 7309 | TGCAGGACCAGAGAATTCGAATA CAATGTCTGGNNNCTAGCGTTAC | 7549 |
| TGCAGGACCAGAGAATTCGAATAC AGGAGGCCANNNCTAGCGTTAC | 7310 | TGCAGGACCAGAGAATTCGAATA CAAGACATGGNNNCTAGCGTTAC | 7550 |
| TGCAGGACCAGAGAATTCGAATAC ATACCTGTCNNNCTAGCGTTAC | 7311 | TGCAGGACCAGAGAATTCGAATA CACGGCAATTNNNCTAGCGTTAC | 7551 |
| TGCAGGACCAGAGAATTCGAATAC AATATGCTANNNCTAGCGTTAC | 7312 | TGCAGGACCAGAGAATTCGAATA CATAATGTTGNNNCTAGCGTTAC | 7552 |
| TGCAGGACCAGAGAATTCGAATAC AGATCACCANNNCTAGCGTTAC | 7313 | TGCAGGACCAGAGAATTCGAATA CAGCGAGGACNNNCTAGCGTTAC | 7553 |
| TGCAGGACCAGAGAATTCGAATAC AGCGGAACGNNNCTAGCGTTAC | 7314 | TGCAGGACCAGAGAATTCGAATA CACGAACATCNNNCTAGCGTTAC | 7554 |
| TGCAGGACCAGAGAATTCGAATAC AAATCCTTTNNNCTAGCGTTAC | 7315 | TGCAGGACCAGAGAATTCGAATA CAGCATGTACNNNCTAGCGTTAC | 7555 |
| TGCAGGACCAGAGAATTCGAATAC ATACTATAGNNNCTAGCGTTAC | 7316 | TGCAGGACCAGAGAATTCGAATA CAGCAACTGTNNNCTAGCGTTAC | 7556 |
| TGCAGGACCAGAGAATTCGAATAC AGTCTGTAGNNNCTAGCGTTAC | 7317 | TGCAGGACCAGAGAATTCGAATA CAGTACTCTCNNNCTAGCGTTAC | 7557 |
| TGCAGGACCAGAGAATTCGAATAC AGACTATCGNNNCTAGCGTTAC | 7318 | TGCAGGACCAGAGAATTCGAATA CAGGCTAAAGNNNCTAGCGTTAC | 7558 |
| TGCAGGACCAGAGAATTCGAATAC AAGGATTAANNNCTAGCGTTAC | 7319 | TGCAGGACCAGAGAATTCGAATA CACCCTTTGANNNCTAGCGTTAC | 7559 |
| TGCAGGACCAGAGAATTCGAATAC ATTACATCTNNNCTAGCGTTAC | 7320 | TGCAGGACCAGAGAATTCGAATA CACGCAGGAGNNNCTAGCGTTAC | 7560 |
| TGCAGGACCAGAGAATTCGAATAC ATTTGGCAGNNNCTAGCGTTAC | 7321 | TGCAGGACCAGAGAATTCGAATA CAGTAAGAATNNNCTAGCGTTAC | 7561 |
| TGCAGGACCAGAGAATTCGAATAC ACAGTATGCNNNCTAGCGTTAC | 7322 | TGCAGGACCAGAGAATTCGAATA CATGATTACANNNCTAGCGTTAC | 7562 |
| TGCAGGACCAGAGAATTCGAATAC ATTCGATCCNNNCTAGCGTTAC | 7323 | TGCAGGACCAGAGAATTCGAATA CACAAAAATGNNNCTAGCGTTAC | 7563 |
| TGCAGGACCAGAGAATTCGAATAC AAATCCCTNNNCTAGCGTTAC | 7324 | TGCAGGACCAGAGAATTCGAATA CACCGTGGTGNNNCTAGCGTTAC | 7564 |
| TGCAGGACCAGAGAATTCGAATAC ACTCTCCCCNNNCTAGCGTTAC | 7325 | TGCAGGACCAGAGAATTCGAATA CAAACGTTATNNNCTAGCGTTAC | 7565 |
| TGCAGGACCAGAGAATTCGAATAC ACAATTAACNNNCTAGCGTTAC | 7326 | TGCAGGACCAGAGAATTCGAATA CAGCTTGCAANNNCTAGCGTTAC | 7566 |
| TGCAGGACCAGAGAATTCGAATAC AATTTTGCTNNNCTAGCGTTAC | 7327 | TGCAGGACCAGAGAATTCGAATA CATTAGTCGGNNNCTAGCGTTAC | 7567 |
| TGCAGGACCAGAGAATTCGAATAC AATAAATCCNNNCTAGCGTTAC | 7328 | TGCAGGACCAGAGAATTCGAATA CAACGGCCGTNNNCTAGCGTTAC | 7568 |
| TGCAGGACCAGAGAATTCGAATAC ATACTCGTCNNNGATCGACATG | 7329 | TGCAGGACCAGAGAATTCGAATA CAGCCGTGAAANNNGATCGACATG | 7569 |
| TGCAGGACCAGAGAATTCGAATAC AATGCGAAGNNNGATCGACATG | 7330 | TGCAGGACCAGAGAATTCGAATA CATGCCTGCCNNNGATCGACATG | 7570 |
| TGCAGGACCAGAGAATTCGAATAC ATGCGCAGCNNNGATCGACATG | 7331 | TGCAGGACCAGAGAATTCGAATA CATCGACGCGNNNGATCGACATG | 7571 |
| TGCAGGACCAGAGAATTCGAATAC ATGGTAAAANNNGATCGACATG | 7332 | TGCAGGACCAGAGAATTCGAATA CATCATCCTGNNNGATCGACATG | 7572 |
| TGCAGGACCAGAGAATTCGAATAC ACACTCCATNNNGATCGACATG | 7333 | TGCAGGACCAGAGAATTCGAATA CAGTCAGTCANNNGATCGACATG | 7573 |
| TGCAGGACCAGAGAATTCGAATAC ACCTATGGANNNGATCGACATG | 7334 | TGCAGGACCAGAGAATTCGAATA CACCGGTGACNNNGATCGACATG | 7574 |
| TGCAGGACCAGAGAATTCGAATAC AATGCTCCTNNNGATCGACATG | 7335 | TGCAGGACCAGAGAATTCGAATA CATATCGCGANNNGATCGACATG | 7575 |
| TGCAGGACCAGAGAATTCGAATAC AGATTGAAANNNGATCGACATG | 7336 | TGCAGGACCAGAGAATTCGAATA CAGACGCGTCNNNGATCGACATG | 7576 |
| TGCAGGACCAGAGAATTCGAATAC AACACCCAANNNGATCGACATG | 7337 | TGCAGGACCAGAGAATTCGAATA CAGAACAGACNNNGATCGACATG | 7577 |
| TGCAGGACCAGAGAATTCGAATAC ACCGGCATGNNNGATCGACATG | 7338 | TGCAGGACCAGAGAATTCGAATA CAGTGTGTGTNNNGATCGACATG | 7578 |
| TGCAGGACCAGAGAATTCGAATAC ATCCGATTCNNNGATCGACATG | 7339 | TGCAGGACCAGAGAATTCGAATA CAGATTGCGTNNNGATCGACATG | 7579 |
| TGCAGGACCAGAGAATTCGAATAC AGAATCCTGNNNGATCGACATG | 7340 | TGCAGGACCAGAGAATTCGAATA CAGTAGATTTNNNGATCGACATG | 7580 |

FIG. 22E

| Pool-31 | SEQ ID NO: | Pool-32 | SEQ ID NO: |
|---|---|---|---|
| TGCAGGACCAGAGAATTCGAATAC ATTTCGTCGNNNGATCGACATG | 7341 | TGCAGGACCAGAGAATTCGAATA CAGCTTGAGTNNNGATCGACATG | 7581 |
| TGCAGGACCAGAGAATTCGAATAC ACTTCACTGNNNGATCGACATG | 7342 | TGCAGGACCAGAGAATTCGAATA CACGCAACGCNNNGATCGACATG | 7582 |
| TGCAGGACCAGAGAATTCGAATAC ACCCTATTGNNNGATCGACATG | 7343 | TGCAGGACCAGAGAATTCGAATA CACCTAATGGNNNGATCGACATG | 7583 |
| TGCAGGACCAGAGAATTCGAATAC AAGTAGTAANNNGATCGACATG | 7344 | TGCAGGACCAGAGAATTCGAATA CAGACAGGATNNNGATCGACATG | 7584 |
| TGCAGGACCAGAGAATTCGAATAC ACACCGTAANNNGATCGACATG | 7345 | TGCAGGACCAGAGAATTCGAATA CACTTCCCTTNNNGATCGACATG | 7585 |
| TGCAGGACCAGAGAATTCGAATAC ATGTTTCCGNNNGATCGACATG | 7346 | TGCAGGACCAGAGAATTCGAATA CATAAGAGATNNNGATCGACATG | 7586 |
| TGCAGGACCAGAGAATTCGAATAC AGCTGGACCNNNGATCGACATG | 7347 | TGCAGGACCAGAGAATTCGAATA CAACCGAATCNNNGATCGACATG | 7587 |
| TGCAGGACCAGAGAATTCGAATAC AGTAATTGTNNNGATCGACATG | 7348 | TGCAGGACCAGAGAATTCGAATA CAGCCAACATNNNGATCGACATG | 7588 |
| TGCAGGACCAGAGAATTCGAATAC AAGCTTATANNNGATCGACATG | 7349 | TGCAGGACCAGAGAATTCGAATA CATGGCTAACNNNGATCGACATG | 7589 |
| TGCAGGACCAGAGAATTCGAATAC AGCTACCAANNNGATCGACATG | 7350 | TGCAGGACCAGAGAATTCGAATA CATCGTTCGTNNNGATCGACATG | 7590 |
| TGCAGGACCAGAGAATTCGAATAC AGATAATGANNNGATCGACATG | 7351 | TGCAGGACCAGAGAATTCGAATA CACAGTTGCANNNGATCGACATG | 7591 |
| TGCAGGACCAGAGAATTCGAATAC AAAATCATCNNNGATCGACATG | 7352 | TGCAGGACCAGAGAATTCGAATA CAACTAGCTGNNNGATCGACATG | 7592 |
| TGCAGGACCAGAGAATTCGAATAC AAATAGCCCNNNGATCGACATG | 7353 | TGCAGGACCAGAGAATTCGAATA CAAAACTAAGNNNGATCGACATG | 7593 |
| TGCAGGACCAGAGAATTCGAATAC ATGCTGCTTNNNGATCGACATG | 7354 | TGCAGGACCAGAGAATTCGAATA CAGTTTCGAGNNNGATCGACATG | 7594 |
| TGCAGGACCAGAGAATTCGAATAC ATTACGCAGNNNGATCGACATG | 7355 | TGCAGGACCAGAGAATTCGAATA CACTCATAGGNNNGATCGACATG | 7595 |
| TGCAGGACCAGAGAATTCGAATAC ACCCAGCCTNNNGATCGACATG | 7356 | TGCAGGACCAGAGAATTCGAATA CAGCAGTATCNNNGATCGACATG | 7596 |
| TGCAGGACCAGAGAATTCGAATAC ACCATTTATNNNGATCGACATG | 7357 | TGCAGGACCAGAGAATTCGAATA CATATAGTCANNNGATCGACATG | 7597 |
| TGCAGGACCAGAGAATTCGAATAC AGTGCAATCNNNGATCGACATG | 7358 | TGCAGGACCAGAGAATTCGAATA CAGGTGTAAGNNNGATCGACATG | 7598 |
| TGCAGGACCAGAGAATTCGAATAC ACATCAGGTNNNGATCGACATG | 7359 | TGCAGGACCAGAGAATTCGAATA CAAGTGAAATNNNGATCGACATG | 7599 |
| TGCAGGACCAGAGAATTCGAATAC AGGCCCACANNNGATCGACATG | 7360 | TGCAGGACCAGAGAATTCGAATA CAGGTCGTTANNNGATCGACATG | 7600 |
| TGCAGGACCAGAGAATTCGAATAC AAAGCACGANNNGATCGACATG | 7361 | TGCAGGACCAGAGAATTCGAATA CATCGCGCCTNNNGATCGACATG | 7601 |
| TGCAGGACCAGAGAATTCGAATAC ACACGGAAANNNGATCGACATG | 7362 | TGCAGGACCAGAGAATTCGAATA CAAAGAAACTNNNGATCGACATG | 7602 |
| TGCAGGACCAGAGAATTCGAATAC AGCAGCCTGNNNGATCGACATG | 7363 | TGCAGGACCAGAGAATTCGAATA CATCCTTTCCNNNGATCGACATG | 7603 |
| TGCAGGACCAGAGAATTCGAATAC AGGCTGCGTNNNGATCGACATG | 7364 | TGCAGGACCAGAGAATTCGAATA CATGGCGTCGNNNGATCGACATG | 7604 |
| TGCAGGACCAGAGAATTCGAATAC ACTCTAGCTNNNGATCGACATG | 7365 | TGCAGGACCAGAGAATTCGAATA CAGGCTGTCGNNNGATCGACATG | 7605 |
| TGCAGGACCAGAGAATTCGAATAC AGAAGGCTANNNGATCGACATG | 7366 | TGCAGGACCAGAGAATTCGAATA CATGTCCATCNNNGATCGACATG | 7606 |
| TGCAGGACCAGAGAATTCGAATAC ATATCTGAANNNGATCGACATG | 7367 | TGCAGGACCAGAGAATTCGAATA CAGTTGGAAGNNNGATCGACATG | 7607 |
| TGCAGGACCAGAGAATTCGAATAC ATACTATTCNNNGATCGACATG | 7368 | TGCAGGACCAGAGAATTCGAATA CAGTGGACGGNNNGATCGACATG | 7608 |
| TGCAGGACCAGAGAATTCGAATAC ACATGACCANNNGATCGACATG | 7369 | TGCAGGACCAGAGAATTCGAATA CATCCTGGCCNNNGATCGACATG | 7609 |
| TGCAGGACCAGAGAATTCGAATAC AATTCAGGCNNNGATCGACATG | 7370 | TGCAGGACCAGAGAATTCGAATA CAATAGGCGANNNGATCGACATG | 7610 |
| TGCAGGACCAGAGAATTCGAATAC AAACCAACCNNNGATCGACATG | 7371 | TGCAGGACCAGAGAATTCGAATA CAATCCGTGANNNGATCGACATG | 7611 |
| TGCAGGACCAGAGAATTCGAATAC ATTACTGTTNNNGATCGACATG | 7372 | TGCAGGACCAGAGAATTCGAATA CAGTAGCTGTNNNGATCGACATG | 7612 |
| TGCAGGACCAGAGAATTCGAATAC AGGTTCCCCNNNGATCGACATG | 7373 | TGCAGGACCAGAGAATTCGAATA CAGAAGACGTNNNGATCGACATG | 7613 |

FIG. 22F

| Pool-31 | SEQ ID NO: | Pool-32 | SEQ ID NO: |
|---|---|---|---|
| TGCAGGACCAGAGAATTCGAATAC AATAAACCTNNNGATCGACATG | 7374 | TGCAGGACCAGAGAATTCGAATA CATCCGTACTNNNGATCGACATG | 7614 |
| TGCAGGACCAGAGAATTCGAATAC ATTTCGTGCNNNGATCGACATG | 7375 | TGCAGGACCAGAGAATTCGAATA CATGAGGCAANNNGATCGACATG | 7615 |
| TGCAGGACCAGAGAATTCGAATAC AGTGACCATNNNGATCGACATG | 7376 | TGCAGGACCAGAGAATTCGAATA CATGAGTTATNNNGATCGACATG | 7616 |
| TGCAGGACCAGAGAATTCGAATAC ACCCTATACNNNGATCGACATG | 7377 | TGCAGGACCAGAGAATTCGAATA CAATTGGTGCNNNGATCGACATG | 7617 |
| TGCAGGACCAGAGAATTCGAATAC ACCCCATATNNNGATCGACATG | 7378 | TGCAGGACCAGAGAATTCGAATA CAGGCGTTGCNNNGATCGACATG | 7618 |
| TGCAGGACCAGAGAATTCGAATAC AGATAGGTGNNNGATCGACATG | 7379 | TGCAGGACCAGAGAATTCGAATA CAGCATCTCTNNNGATCGACATG | 7619 |
| TGCAGGACCAGAGAATTCGAATAC AAAATAACGNNNGATCGACATG | 7380 | TGCAGGACCAGAGAATTCGAATA CAACTCTCCANNNGATCGACATG | 7620 |
| TGCAGGACCAGAGAATTCGAATAC AATAATCGTNNNGATCGACATG | 7381 | TGCAGGACCAGAGAATTCGAATA CAATAAGTAGNNNGATCGACATG | 7621 |
| TGCAGGACCAGAGAATTCGAATAC AGTGGACTTNNNGATCGACATG | 7382 | TGCAGGACCAGAGAATTCGAATA CAGATTGCCANNNGATCGACATG | 7622 |
| TGCAGGACCAGAGAATTCGAATAC AGTTACTGGNNNGATCGACATG | 7383 | TGCAGGACCAGAGAATTCGAATA CAGTTCCGANNNGATCGACATG | 7623 |
| TGCAGGACCAGAGAATTCGAATAC ATCCTAGGANNNGATCGACATG | 7384 | TGCAGGACCAGAGAATTCGAATA CAAACCGTACNNNGATCGACATG | 7624 |
| TGCAGGACCAGAGAATTCGAATAC AAAACTTACNNNGATCGACATG | 7385 | TGCAGGACCAGAGAATTCGAATA CACGCGTTGGNNNGATCGACATG | 7625 |
| TGCAGGACCAGAGAATTCGAATAC AAAGTGCTCNNNGATCGACATG | 7386 | TGCAGGACCAGAGAATTCGAATA CAAATTCCAANNNGATCGACATG | 7626 |
| TGCAGGACCAGAGAATTCGAATAC AGTATTTTCNNNGATCGACATG | 7387 | TGCAGGACCAGAGAATTCGAATA CATGACCAGTNNNGATCGACATG | 7627 |
| TGCAGGACCAGAGAATTCGAATAC AGAAAGCTGNNNGATCGACATG | 7388 | TGCAGGACCAGAGAATTCGAATA CAATGGATTTNNNGATCGACATG | 7628 |
| TGCAGGACCAGAGAATTCGAATAC AATCACGACNNNTGCATCAGGT | 7389 | TGCAGGACCAGAGAATTCGAATA CAAAGTCCACNNNTGCATCAGGT | 7629 |
| TGCAGGACCAGAGAATTCGAATAC AAGGACCTTNNNTGCATCAGGT | 7390 | TGCAGGACCAGAGAATTCGAATA CAGTGGCGCTNNNTGCATCAGGT | 7630 |
| TGCAGGACCAGAGAATTCGAATAC AGAATGTAANNNTGCATCAGGT | 7391 | TGCAGGACCAGAGAATTCGAATA CATCTGGATGNNNTGCATCAGGT | 7631 |
| TGCAGGACCAGAGAATTCGAATAC AAAACTGCCNNNTGCATCAGGT | 7392 | TGCAGGACCAGAGAATTCGAATA CACCGATGCGNNNTGCATCAGGT | 7632 |
| TGCAGGACCAGAGAATTCGAATAC AATACAATCNNNTGCATCAGGT | 7393 | TGCAGGACCAGAGAATTCGAATA CAAGTGCTCANNNTGCATCAGGT | 7633 |
| TGCAGGACCAGAGAATTCGAATAC AGAGCAGCGNNNTGCATCAGGT | 7394 | TGCAGGACCAGAGAATTCGAATA CACAATAGTTNNNTGCATCAGGT | 7634 |
| TGCAGGACCAGAGAATTCGAATAC ATCGTGTTCNNNTGCATCAGGT | 7395 | TGCAGGACCAGAGAATTCGAATA CATACAGGCTNNNTGCATCAGGT | 7635 |
| TGCAGGACCAGAGAATTCGAATAC ACTGAGCCGNNNTGCATCAGGT | 7396 | TGCAGGACCAGAGAATTCGAATA CATATACCTTNNNTGCATCAGGT | 7636 |
| TGCAGGACCAGAGAATTCGAATAC ACAAGCAGANNNTGCATCAGGT | 7397 | TGCAGGACCAGAGAATTCGAATA CAGGAGTAACNNNTGCATCAGGT | 7637 |
| TGCAGGACCAGAGAATTCGAATAC AGTCTTACCNNNTGCATCAGGT | 7398 | TGCAGGACCAGAGAATTCGAATA CAGCTATGACNNNTGCATCAGGT | 7638 |
| TGCAGGACCAGAGAATTCGAATAC ACGTCTCCGNNNTGCATCAGGT | 7399 | TGCAGGACCAGAGAATTCGAATA CAGTTACACGNNNTGCATCAGGT | 7639 |
| TGCAGGACCAGAGAATTCGAATAC AGGCGTTCGNNNTGCATCAGGT | 7400 | TGCAGGACCAGAGAATTCGAATA CAGAAGGAAGNNNTGCATCAGGT | 7640 |
| TGCAGGACCAGAGAATTCGAATAC ACCGCACCTNNNTGCATCAGGT | 7401 | TGCAGGACCAGAGAATTCGAATA CAATGACTTANNNTGCATCAGGT | 7641 |
| TGCAGGACCAGAGAATTCGAATAC AAGTGGTTCNNNTGCATCAGGT | 7402 | TGCAGGACCAGAGAATTCGAATA CATCTCTAATNNNTGCATCAGGT | 7642 |
| TGCAGGACCAGAGAATTCGAATAC AGTTGCGTANNNTGCATCAGGT | 7403 | TGCAGGACCAGAGAATTCGAATA CAGGAATAATNNNTGCATCAGGT | 7643 |
| TGCAGGACCAGAGAATTCGAATAC ACCAAATGCNNNTGCATCAGGT | 7404 | TGCAGGACCAGAGAATTCGAATA CAATTATACGNNNTGCATCAGGT | 7644 |
| TGCAGGACCAGAGAATTCGAATAC AGCTTTGTCNNNTGCATCAGGT | 7405 | TGCAGGACCAGAGAATTCGAATA CACAAAGGACNNNTGCATCAGGT | 7645 |
| TGCAGGACCAGAGAATTCGAATAC ACTTCAATTNNNTGCATCAGGT | 7406 | TGCAGGACCAGAGAATTCGAATA CAATAGAATGNNNTGCATCAGGT | 7646 |

FIG. 22G

| Pool-31 | SEQ ID NO: | Pool-32 | SEQ ID NO: |
|---|---|---|---|
| TGCAGGACCAGAGAATTCGAATAC AGAATCTGCNNNTGCATCAGGT | 7407 | TGCAGGACCAGAGAATTCGAATA CAGGCTCTGCGNNNTGCATCAGGT | 7647 |
| TGCAGGACCAGAGAATTCGAATAC ACCAGGACCNNNTGCATCAGGT | 7408 | TGCAGGACCAGAGAATTCGAATA CACATTTTCANNNTGCATCAGGT | 7648 |
| TGCAGGACCAGAGAATTCGAATAC AAGAGCATGNNNTGCATCAGGT | 7409 | TGCAGGACCAGAGAATTCGAATA CAGCAGAGGCNNNTGCATCAGGT | 7649 |
| TGCAGGACCAGAGAATTCGAATAC AACGGCCACNNNTGCATCAGGT | 7410 | TGCAGGACCAGAGAATTCGAATA CAGCGGTAGGNNNTGCATCAGGT | 7650 |
| TGCAGGACCAGAGAATTCGAATAC ACCTAAACGNNNTGCATCAGGT | 7411 | TGCAGGACCAGAGAATTCGAATA CAGGAGTCGGNNNTGCATCAGGT | 7651 |
| TGCAGGACCAGAGAATTCGAATAC AGGTAACTCNNNTGCATCAGGT | 7412 | TGCAGGACCAGAGAATTCGAATA CAACCATTCCNNNTGCATCAGGT | 7652 |
| TGCAGGACCAGAGAATTCGAATAC ATGGCTGATNNNTGCATCAGGT | 7413 | TGCAGGACCAGAGAATTCGAATA CATCAAATGNNNTGCATCAGGT | 7653 |
| TGCAGGACCAGAGAATTCGAATAC AGCCGTAGCNNNTGCATCAGGT | 7414 | TGCAGGACCAGAGAATTCGAATA CACAGTTCGANNNTGCATCAGGT | 7654 |
| TGCAGGACCAGAGAATTCGAATAC ATATCATTCNNNTGCATCAGGT | 7415 | TGCAGGACCAGAGAATTCGAATA CAGATCTAATNNNTGCATCAGGT | 7655 |
| TGCAGGACCAGAGAATTCGAATAC AGAGCAGTANNNTGCATCAGGT | 7416 | TGCAGGACCAGAGAATTCGAATA CATTTCAGTTNNNTGCATCAGGT | 7656 |
| TGCAGGACCAGAGAATTCGAATAC AGCGTAAGANNNTGCATCAGGT | 7417 | TGCAGGACCAGAGAATTCGAATA CAGACAATTTNNNTGCATCAGGT | 7657 |
| TGCAGGACCAGAGAATTCGAATAC ATCGCAAACNNNTGCATCAGGT | 7418 | TGCAGGACCAGAGAATTCGAATA CAGCCGTAATNNNTGCATCAGGT | 7658 |
| TGCAGGACCAGAGAATTCGAATAC AGAAGCTTCNNNTGCATCAGGT | 7419 | TGCAGGACCAGAGAATTCGAATA CAAATACAAGNNNTGCATCAGGT | 7659 |
| TGCAGGACCAGAGAATTCGAATAC ATATTACCTNNNTGCATCAGGT | 7420 | TGCAGGACCAGAGAATTCGAATA CAGTCCGCGANNNTGCATCAGGT | 7660 |
| TGCAGGACCAGAGAATTCGAATAC ATGCATGTGNNNTGCATCAGGT | 7421 | TGCAGGACCAGAGAATTCGAATA CACCATCATCNNNTGCATCAGGT | 7661 |
| TGCAGGACCAGAGAATTCGAATAC AGCTTTGAGNNNTGCATCAGGT | 7422 | TGCAGGACCAGAGAATTCGAATA CACCTGTCATNNNTGCATCAGGT | 7662 |
| TGCAGGACCAGAGAATTCGAATAC ATCCTATTANNNTGCATCAGGT | 7423 | TGCAGGACCAGAGAATTCGAATA CAGCTTCCTANNNTGCATCAGGT | 7663 |
| TGCAGGACCAGAGAATTCGAATAC ACGTCAGGCNNNTGCATCAGGT | 7424 | TGCAGGACCAGAGAATTCGAATA CAACCCAACANNNTGCATCAGGT | 7664 |
| TGCAGGACCAGAGAATTCGAATAC ACCGCGATGNNNTGCATCAGGT | 7425 | TGCAGGACCAGAGAATTCGAATA CAAAACGCGANNNTGCATCAGGT | 7665 |
| TGCAGGACCAGAGAATTCGAATAC AGGTTGTCANNNTGCATCAGGT | 7426 | TGCAGGACCAGAGAATTCGAATA CATCTGCATCNNNTGCATCAGGT | 7666 |
| TGCAGGACCAGAGAATTCGAATAC ASCAGCAAANNNTGCATCAGGT | 7427 | TGCAGGACCAGAGAATTCGAATA CAATTCCAAANNNTGCATCAGGT | 7667 |
| TGCAGGACCAGAGAATTCGAATAC AGCGTAACTNNNTGCATCAGGT | 7428 | TGCAGGACCAGAGAATTCGAATA CACACCAAGTNNNTGCATCAGGT | 7668 |
| TGCAGGACCAGAGAATTCGAATAC AGAGAGTCANNNTGCATCAGGT | 7429 | TGCAGGACCAGAGAATTCGAATA CAGCACAACTNNNTGCATCAGGT | 7669 |
| TGCAGGACCAGAGAATTCGAATAC ACTATGCCTNNNTGCATCAGGT | 7430 | TGCAGGACCAGAGAATTCGAATA CAAGGTGGATNNNTGCATCAGGT | 7670 |
| TGCAGGACCAGAGAATTCGAATAC AAACCGAAGNNNTGCATCAGGT | 7431 | TGCAGGACCAGAGAATTCGAATA CATGCTAGCANNNTGCATCAGGT | 7671 |
| TGCAGGACCAGAGAATTCGAATAC ACGGCCCGGNNNTGCATCAGGT | 7432 | TGCAGGACCAGAGAATTCGAATA CATTGTGAGCNNNTGCATCAGGT | 7672 |
| TGCAGGACCAGAGAATTCGAATAC AAAGCGCCCNNNTGCATCAGGT | 7433 | TGCAGGACCAGAGAATTCGAATA CAAGTTCGGNNNTGCATCAGGT | 7673 |
| TGCAGGACCAGAGAATTCGAATAC AATAAGGATNNNTGCATCAGGT | 7434 | TGCAGGACCAGAGAATTCGAATA CAGCTAGTACNNNTGCATCAGGT | 7674 |
| TGCAGGACCAGAGAATTCGAATAC AAGCTGAGANNNTGCATCAGGT | 7435 | TGCAGGACCAGAGAATTCGAATA CATAGGTGCTNNNTGCATCAGGT | 7675 |
| TGCAGGACCAGAGAATTCGAATAC ACTCTGACTNNNTGCATCAGGT | 7436 | TGCAGGACCAGAGAATTCGAATA CACATTACGGNNNTGCATCAGGT | 7676 |
| TGCAGGACCAGAGAATTCGAATAC ATCGCAGGCNNNTGCATCAGGT | 7437 | TGCAGGACCAGAGAATTCGAATA CATGCAATTANNNTGCATCAGGT | 7677 |
| TGCAGGACCAGAGAATTCGAATAC AATATTAGCNNNTGCATCAGGT | 7438 | TGCAGGACCAGAGAATTCGAATA CATGGCCCCTNNNTGCATCAGGT | 7678 |
| TGCAGGACCAGAGAATTCGAATAC AACCGTATGNNNTGCATCAGGT | 7439 | TGCAGGACCAGAGAATTCGAATA CAGCTGCAGCNNNTGCATCAGGT | 7679 |

FIG. 22H

| Pool-31 | SEQ ID NO: | Pool-32 | SEQ ID NO: |
|---------|------------|---------|------------|
| TGCAGGACCAGAGAATTCGAATAC AGGTCGGTCNNNTGCATCAGGT | 7440 | TGCAGGACCAGAGAATTCGAATA CATTTGCCCANNNTGCATCAGGT | 7680 |
| TGCAGGACCAGAGAATTCGAATAC AATATCGTANNNTGCATCAGGT | 7441 | TGCAGGACCAGAGAATTCGAATA CAGACCATTGNNNTGCATCAGGT | 7681 |
| TGCAGGACCAGAGAATTCGAATAC AACCTCTCANNNTGCATCAGGT | 7442 | TGCAGGACCAGAGAATTCGAATA CACCGCGTAGNNNTGCATCAGGT | 7682 |
| TGCAGGACCAGAGAATTCGAATAC AGTCGGTGCNNNTGCATCAGGT | 7443 | TGCAGGACCAGAGAATTCGAATA CATTAGCTGGNNNTGCATCAGGT | 7683 |
| TGCAGGACCAGAGAATTCGAATAC ATTCGCCCGNNNTGCATCAGGT | 7444 | TGCAGGACCAGAGAATTCGAATA CATCTGATTTNNNTGCATCAGGT | 7684 |
| TGCAGGACCAGAGAATTCGAATAC ACAGGCTGCNNNTGCATCAGGT | 7445 | TGCAGGACCAGAGAATTCGAATA CATCATAGGCNNNTGCATCAGGT | 7685 |
| TGCAGGACCAGAGAATTCGAATAC ATCGCTTACNNNTGCATCAGGT | 7446 | TGCAGGACCAGAGAATTCGAATA CATGGAGGTANNNTGCATCAGGT | 7686 |
| TGCAGGACCAGAGAATTCGAATAC ACGGATTGTNNNTGCATCAGGT | 7447 | TGCAGGACCAGAGAATTCGAATA CAGTCTCTACNNNTGCATCAGGT | 7687 |
| TGCAGGACCAGAGAATTCGAATAC ACAAGCTGTNNNTGCATCAGGT | 7448 | TGCAGGACCAGAGAATTCGAATA CAGCCTGGTGNNNTGCATCAGGT | 7688 |

FIG. 25
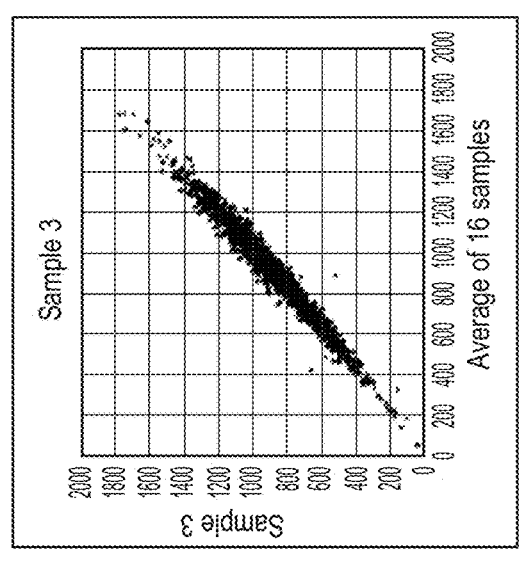
FIG. 26
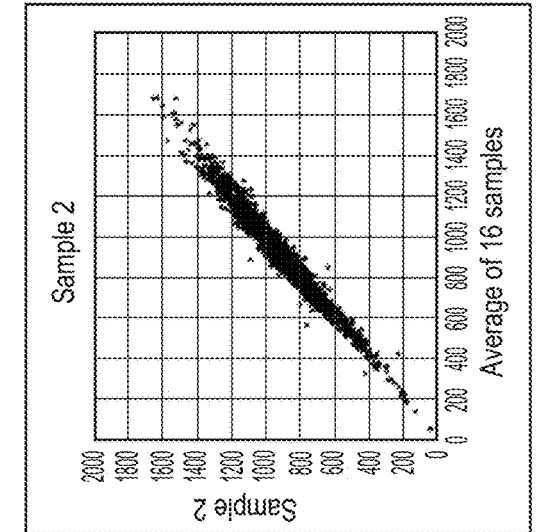
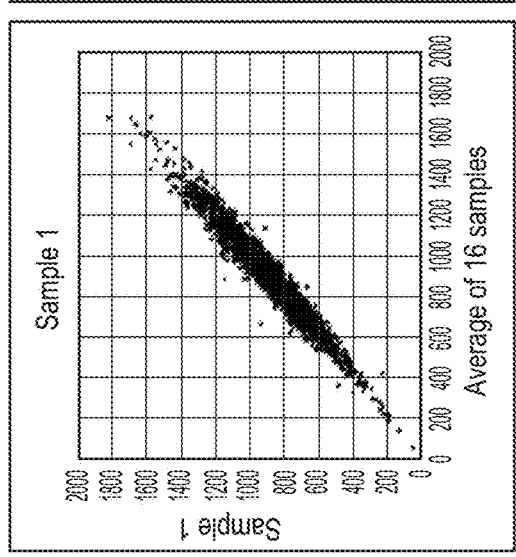

Copy number analysis in a healthy female

METHODS FOR THE DETECTION OF GENOMIC COPY CHANGES IN DNA SAMPLES

REFERENCE TO RELATED APPLICATIONS

This application is a continuation of U.S. patent application Ser. No. 15/685,834, filed Aug. 24, 2017, which claims priority to U.S. Provisional Patent Application No. 62/379,593, filed Aug. 25, 2016, and U.S. Provisional Patent Application No. 62/481,538, filed Apr. 4, 2017, each of which are incorporated herein by reference in their entireties.

STATEMENT REGARDING SEQUENCE LISTING

The sequence listing associated with this application is provided in text format in lieu of a paper copy, and is hereby incorporated by reference into the specification. The name of the text file containing the sequence listing is CLFK-005_03_US_SegList_ST25CLFK. The text file is 2,238 KB, was created on Dec. 6, 2021, and is being submitted electronically via EFS-Web.

TECHNICAL FIELD

The invention relates generally to compositions and methods for the quantitative genetic analysis of biological samples, e.g., direct tissue biopsies or peripheral blood. In particular, the present invention relates to methods for detection of target-specific copy number change, as well as genetic characterization and analysis, of biological samples.

BACKGROUND

It is becoming increasing clear that most, if not all, of the most common human cancers are diseases of the human genome. It is thought that somatic mutations accumulate during an individual's lifetime, some of which increase the probability that the cell in which they are harbored can develop into a tumor. With just the wrong combination of accumulated mutational events, a precancerous growth loses constraints that keep uncontrolled proliferation in check and the resulting cell mass becomes a cancer. The constellations of mutations that are necessary and sufficient to cause cancer are often collectively referred to as "driver mutations." One of the themes that have emerged from recent and intensive molecular analysis is that cancer, once thought of as a single, tissue-specific disease, is in fact a group of related diseases, each with a unique molecular pathology. The human genome project laid the groundwork for genome-wide analysis of cancers.

Changes in gene copy number are a fundamental driver of biological diversity. In the context of evolution, duplication of genes and divergence of function is a well-recognized driver of species diversity. In the context of human disease, gene loss and gene amplification within somatic cells are hallmarks of diseased tissues such as cancer. Certain therapeutic agents act specifically on cells with these genomic gain and/or loss mutations, however, the identification of these copy number variations is difficult because often such mutations are only present within the DNA of diseased or cancerous cells and are not found in other cells of the body. While the diseased tissue or cells is the major source of the mutated DNA, acquiring DNA through a biopsy is invasive, risky and often not possible. The observation that dying tumor or cancer cells release small pieces of their DNA into the bloodstream, termed cell free DNA or circulating DNA has allowed for the development of genetic tests that can be performed with less invasive techniques, such as a blood sample. However, only small amounts of DNA can be obtained from isolating cell free DNA from a sample, and only a portion of the total DNA will carry the mutation associated with the disease. For example, in the context of cancer genomics, diagnostically significant tumor mutations are often only found at minor allele frequencies that are significantly less than 50%. This is in contrast to conventional SNP genotyping where allele frequencies are generally ~100%, 50% or 0%.

Thus there is a need for genomic techniques capable of detecting genetic copy number changes in specific target loci.

BRIEF SUMMARY

Methods of detecting rare mutations in cfDNA have been previously described in International PCT Publication No. WO 2016/028316. However, these techniques still lack the requisite sensitivity to detect the rarest copy number losses at very minor allele frequencies. Provided herein are compositions and methods for detection of target-specific copy number change that are applicable to several sample types, including direct tissue biopsies, peripheral blood, and in particular cfDNA, The compositions and methods described herein are sensitive enough to detect changes in copy number that are present only a tiny fraction of the total DNA.

The present invention includes, inter alia, compositions and methods that are useful for the detection of a mutational change, SNP, translocation, inversion, deletion, change in copy number, or other genetic variation within a sample of cellular genomic DNA (e.g., from a tissue biopsy sample) or cfDNA (e.g., from a blood sample). In particular, the compositions and methods of the present invention provide an extremely high level of resolution that is particularly useful in detecting copy number variations in a small fraction of the total cfDNA from a biological sample (e.g., blood).

Particular embodiments are drawn to a method for performing a genetic analysis on a DNA target region from a test sample comprising: (a) generating a genomic DNA library comprising a plurality of DNA library fragments, wherein each of the DNA library fragments comprises a genomic DNA fragment from the test sample and an adaptor; (b) contacting the genomic DNA library with a plurality of capture probes that specifically bind to a DNA target region, thereby forming complexes between the capture probes and DNA library fragments comprising the DNA target region; and (c) performing a quantitative genetic analysis of the genomic DNA fragments comprising the DNA target region; wherein the adaptor is a DNA polynucleotide that comprises: an amplification region, a sample tag region, and an anchor region; wherein the amplification region comprises a polynucleotide sequence capable of serving as a primer recognition site for PCR amplification; wherein the sample tag comprises a polynucleotide sequence that encodes an identity of the unique library DNA fragment and encodes an identity of the test sample; wherein the anchor region comprises a polynucleotide sequence that encodes the identity of the test sample and wherein the anchor region is capable of attaching to the genomic DNA fragment; and wherein the genetic analysis is performed to detect a genetic change indicative of a disease state.

In some embodiments, the genetic change indicative of a disease state is selected from a single nucleotide variant (SNV), an insertion less than 40 nucleotides in length, a deletion of a DNA region less than 40 nucleotides in length, and/or a change in copy number. In particular embodiments, the genetic change indicative of a disease state is a change in copy number. In some embodiments, the test sample is a tissue biopsy. In various embodiments, the tissue biopsy is taken from a tumor or a tissue suspected of being a tumor. In certain embodiments, the genomic DNA is cell free DNA (cfDNA) or cellular DNA. In particular embodiments, the genomic DNA is cfDNA is isolated from the test sample; and wherein the test sample is a biological sample selected from the group consisting of: amniotic fluid, blood, plasma, serum, semen, lymphatic fluid, cerebral spinal fluid, ocular fluid, urine, saliva, stool, mucous, and sweat.

In certain embodiments, the genomic DNA fragments are obtained the steps comprising; (i) isolating cellular DNA from the test sample; and (ii) fragmenting the cellular DNA to obtain the genomic DNA fragments. In particular embodiments, step (ii) is performed by contacting the cellular DNA with at least one digestion enzyme. In some embodiments, step (ii) is performed by applying mechanical stress to the cellular DNA. In certain embodiments, the mechanical stress is applied by sonicating the cellular DNA.

In particular embodiments, the sample tag further comprises a unique molecule identifier (UMI) that facilitates the identification of the unique genomic DNA fragment.

In some embodiments, the amplification region is between 10 and 50 nucleotides in length. In particular embodiments, the amplification region is between 20 and 30 nucleotides in length. In certain embodiments, the amplification region is 25 nucleotides in length.

In some embodiments, the sample tag is between 5 and 50 nucleotides in length. In particular embodiments, the sample tag is between 5 and 15 nucleotides in length. In certain embodiments, the sample tag is 8 nucleotides in length. In some embodiments, the UMI multiplier is adjacent to or contained within the sample tag region.

In certain embodiments, the UMI multiplier is between 1 and 5 nucleotides in length. In particular embodiments, the UMI multiplier is 3 nucleotides in length, and comprises one of 64 possible nucleotide sequences.

In some embodiments, the anchor region is between 1 and 50 nucleotides in length. In particular embodiments, the anchor region is between 5 and 25 nucleotides in length. In certain embodiments, the anchor region is 10 nucleotides in length.

Particular embodiments of the present invention are drawn to methods where the step of (a) generating a genomic DNA library comprising a plurality of DNA library fragments, comprises attaching the genomic DNA fragments to a plurality of adaptors. In certain embodiments, the genomic DNA fragments are end repaired prior to attaching the genomic DNA fragments with a plurality of adaptors. In particular embodiments, the amplification regions of each adaptor of the plurality of adaptors comprises an identical nucleotide sequence.

In certain embodiments, the sample tag region of each adaptor of the plurality of adaptors comprise one of between 2 and 1,000 nucleotide sequences. In particular embodiments, the sample tag region of each adaptor of the plurality of adaptors comprise one of between 50 and 500 nucleotide sequences. In various embodiments, the sample tag region of each adaptor of the plurality of adaptors comprises one of between 100 and 400 nucleotide sequences. In some embodiments, the sample tag region of each adaptor of the plurality of adaptors comprises one of between 200 and 300 nucleotide sequences. In certain embodiments, the sample tag region of each adaptor of the plurality of adaptors is 8 nucleotides in length. In some embodiments, each sequence of the nucleotide sequences are discrete from any other sequence of the 240 nucleotide sequences by Hamming distance of at least two.

In particular embodiments, each of the plurality of adaptors comprises a UMI multiplier that is adjacent to or contained within the sample tag region. In some embodiments, each of the plurality of adaptors comprises a UMI multiplier that is adjacent to the sample tag region. In certain embodiments, the UMI multiplier of each adaptor of the plurality of adaptors is between 1 and 5 nucleotides in length. In some embodiments, the UMI multiplier of each adaptor of the plurality of adaptors is three nucleotides in length.

In particular embodiments, the anchor tag region of each adaptor of the plurality of adaptors comprises one of four nucleotide sequences, and each sample region of a given sequence is paired to only one of the four anchor regions of a given sequence.

In some embodiments, the amplification regions of each adaptor of the plurality of adaptors comprises an identical nucleotide sequence; the sample tag region of each adaptor of the plurality of adaptors is 8 nucleotides in length; the nucleotide sequence of each sample tag is discrete from any other nucleotide sequence of the sample tags of the plurality of adaptors by Hamming distance of at least two; each of the plurality of adaptors comprises a UMI multiplier that is adjacent to or contained within the sample tag region; the UMI multiplier of each adaptor of the plurality of adaptors is three nucleotides in length; and the UMI multiplier of each of the possible nucleotide sequences is paired to each sample tag region of the plurality of adaptors; the anchor tag region of each adaptor of the plurality of adaptors comprises one of four nucleotide sequences; and each sample region of a given sequence is paired to only one of the four anchor regions of a given sequence.

Particular embodiments of the present invention are drawn to a method where the step of attaching the genomic DNA fragments with a plurality of adaptors comprises: (i) attaching an oligonucleotide comprising least a portion of an anchor region to each genomic DNA fragment, wherein the oligonucleotide comprising least a portion of an anchor region is a DNA duplex comprising a 5' phosphorylated attachment strand duplexed with a partner strand, wherein the partner strand is blocked from attachment by chemical modification at its 3' end, and wherein the attachment strand is attached to the genomic DNA fragment; (ii) contacting the genomic DNA fragments attached to the oligonucleotides comprising at least a portion of the anchor region with DNA oligonucleotides encoding full length adaptor sequences for each adaptor nucleotide sequence of the plurality of adaptors; and (iii) contacting the genomic DNA fragments and the DNA oligonucleotides encoding the full length adaptor sequence with T4 polynucleotide kinase, Taq DNA ligase and full-length Bst polymerase under conditions suitable for DNA ligation; thereby attaching the plurality of adaptors to the genomic DNA fragments, in some embodiments, the genomic DNA fragments are cfDNA. In certain embodiments, the DNA target region is analyzed for a change in copy number.

In particular embodiments, step (c) performing a quantitative genetic analysis of the genomic DNA fragments comprising the DNA target region comprises purification of the complexes formed between the capture probes and DNA library fragments comprising the DNA target region. In certain embodiments, step (c) comprises purification of the complexes formed between the capture probes and DNA library fragments comprising the DNA target region, preforming primer extension and/or amplification of the DNA library fragments comprising the region of interest from the genomic DNA library. In some embodiments, step (c) comprises purification of the complexes formed between the capture probes and DNA library fragments comprising the DNA target region, preforming primer extension and amplification of the DNA library fragments comprising the region of interest from the genomic DNA library. In certain embodiments, step (c) comprises DNA sequencing of the DNA library fragments comprising the DNA target region to generate a plurality of sequencing reads.

In some embodiments, the present invention is drawn to a method wherein the genomic analysis comprises determining a change of copy number in a DNA region of interest, and wherein step (c), performing a quantitative genetic analysis of the genomic DNA fragments comprising the DNA target region, comprises determining a copy number of the region of interest present in the genomic DNA library derived from the test sample, and comparing it to a copy number of the region of interest present in the genomic DNA library derived from a reference sample, wherein the reference sample comprises a known copy number of the DNA target region.

In some embodiments, determining the copy number in the region of interest comprises DNA sequencing of the DNA library fragments comprising the DNA target region to generate a plurality of sequencing reads, wherein each sequencing read comprises a unique molecular identification element (UMIE). In some embodiments, the UWE comprises sequencing information from the adaptor and at least a portion of the genomic DNA sequence. In some embodiments, sequencing reads comprising identical UMIEs are identified as a unique genomic sequence (UGS).

In some embodiments, methods of determining the copy number further comprise determining a raw genomic depth (RGD) for each of the capture probes contacted with the genomic DNA library. In some embodiments, determining the RGD comprises determining the average number of UGSs associated with each capture probe sequence within a group of sample replicates. In some embodiments, capture probes associated with a highly variable number of UGSs are identified as noisy probes and are removed from further calculations. In some embodiments, determining the RGD further comprises calculating an RGD for a sample, comprising calculating a numerical average of all RGDs for all capture probes in the sample. In some embodiments, the RGD values for noisy probes are not included in calculating an RGD for a sample.

In some embodiments, the RGDs for the capture probes are normalized across all samples in an experimental group by converting the RGD for each capture probe into a probe-specific, normalized read count comprising (i) multiplying each capture probe RGD in a sample by a normalization constant, wherein the normalization constant comprises any real number; and (ii) dividing the product of (i) by the RGD calculated for the corresponding sample; or (iii) dividing the product of (i) by an average RGD calculated from a subset of probes. In some embodiments, the subset of probes is a set of control probes.

In some embodiments, the probe-specific, normalized read counts are converted in to a copy number value comprising (i) multiplying the probe-specific, normalized read counts of probes directed to autosomal and/or X-linked regions by 2 in samples derived from females; (ii) multiplying the probe-specific, normalized read counts of probes directed to Y-linked and/or X-linked regions by 1 in samples derived from males; (iii) averaging the products of (i) and/or (ii) across all samples in an experiment; and (iv) dividing the product of (i) and/or (ii) by the average of (iii). In some embodiments, the approximate copy number values for all probes that target a specific gene are averaged.

In some embodiments, the present invention is drawn to a method for highly sensitive detection of copy number gain and copy number loss comprising (i) determining an RGD for a capture probe; (ii) normalizing the RGD for the capture probe across all samples in an experimental group by converting the RGD for the capture probe into a probe-specific, normalized read count; (iii) calculating an approximate copy number value for each probe-specific, normalized read count; and (iv) averaging the approximate copy number values for all probes that target a specific gene.

In some embodiments, the present invention is drawn to a method for measuring chromosome stability comprising (i) designing and validating a set of one or more chromosomal stability probes, wherein the chromosomal stability probes are uniformly distributed across human chromosomes; (ii) performing targeted sequencing on patient samples using the one or more chromosomal stability probes; (iii) determining an approximate copy number value for each chromosomal probe; (iv) determining a genomic phenotype of a patient sample, wherein fluctuations in the copy number values for one or more chromosomal probes in the patient sample indicate genomic instability.

In some embodiments, the present invention is drawn to a method of treating a cancer in a subject in need thereof, wherein the subject has been identified as having a destabilized genome, wherein the method of treating the cancer comprises administering a pharmaceutically effective amount of a PARP inhibitor.

In some embodiments, the present invention is drawn to a method wherein the genomic analysis comprises determining a change of copy number in a DNA region of interest, and wherein step (c), performing a quantitative genetic analysis of the genomic DNA fragments comprising the DNA target region, comprises determining a copy number of the region of interest present in the genomic DNA library derived from the test sample, and comparing it to a copy number of the region of interest present in the genomic DNA library derived from a reference sample, wherein the reference sample comprises a known copy number of the DNA target region. In some embodiments, the region of interest is a gene or a portion of the gene. In particular embodiments, the gene is associated with a disease. In certain embodiments, the disease is a cancer. In various embodiments, the gene is BRCA2, ATM, BRCA1, BRIP1, CHEK2, FANCA, HDAC2, and/or PALB2.

Particular embodiments are drawn to a genomic DNA library comprising a plurality of DNA library fragments, wherein each of the DNA library fragments comprises an adaptor and a genomic DNA fragment; wherein the adaptor is a DNA polynucleotide that comprises: an amplification region, a sample tag region, and an anchor region; wherein the amplification region comprises a polynucleotide sequence capable of serving as a primer recognition site for PCR amplification; wherein the sample tag comprises a polynucleotide sequence that encodes an identity of the unique library DNA fragment and encodes an identity of the test sample; and wherein the anchor region comprises a polynucleotide sequence that encodes the identity of the test sample, and wherein the anchor region is capable of attaching to the genomic DNA fragment. In some embodiments, the sample tag further comprises a unique molecule identifier (UMI), wherein the UMI facilitates the identification of the unique genomic DNA fragment. In particular embodiments, the amplification region is between 10 and 50 nucleotides in length. In particular embodiments, the amplification region is 25 nucleotides in length. In particular embodiments, the sample tag is between 5 and 50 nucleotides in length. In certain embodiments, the sample tag is 8 nucleotides in length. In some embodiments, the UMI multiplier is adjacent to or contained within the sample tag region. In particular embodiments, the UMI multiplier is between 1 and 5 nucleotides in length. In certain embodiments, the anchor region is between 1 and 50 nucleotides in length. In some embodiments, the anchor region is 10 nucleotides in length. In particular embodiments, the amplification regions of each adaptor of the plurality of adaptors comprises an identical nucleotide sequence. In some embodiments, each nucleotide sequence of the sample tags are discrete from any other sequence of the nucleotide sequences of the sample by Hamming distance of at least two. In certain embodiments, each of the plurality of adaptors comprises a UMI multiplier that is adjacent to or contained within the sample tag region. In particular embodiments, each of the plurality of adaptors comprises a UMI multiplier that is adjacent to the sample tag region. In some embodiments, the anchor tag region of each adaptor of the plurality of adaptors comprises one of four nucleotide sequences, and wherein each sample region of a given sequence is paired to only one of the four anchor regions of a given sequence. In some embodiments, the genomic DNA fragment is cfDNA.

In certain embodiments, the amplification regions of each adaptor of the plurality of adaptors comprises an identical nucleotide sequence; the sample tag region of each adaptor of the plurality of adaptors is 8 nucleotides in length, the sample tag region of each adaptor of the plurality of adaptors comprises a nucleotide sequence that is discrete from any other nucleotide sequence of the sample tags of the plurality of adaptors by Hamming distance of at least two, the each of the plurality of adaptors comprises a UMI multiplier that is adjacent to or contained within the sample tag region, the UMI multiplier of each adaptor of the plurality of adaptors is three nucleotides in length, and the UMI multiplier of each of the possible nucleotide sequences is paired to each of the sample tag regions of the plurality of adaptors, the anchor tag region of each adaptor of the plurality of adaptors comprises one of four nucleotide sequences, and each sample region of a given sequence is paired to only one of the four anchor regions of a given sequence. In some embodiments, the genomic DNA fragment is cfDNA.

Certain embodiments are drawn to a plurality of genomic DNA libraries, comprising more than one genomic library described herein. In some embodiments, the nucleic acid sequences of the sample tag regions of a genomic DNA library belonging to the plurality of genomic DNA libraries are different from the nucleic acid sequences of the sample tag regions of other genomic DNA libraries belonging to the plurality of genomic DNA libraries. In particular embodiments, the nucleic acid sequences of the amplification regions of a genomic DNA library belonging to the plurality of genomic DNA libraries are identical to the nucleic acid sequences of the amplification regions of other genomic DNA libraries belonging to the plurality of genomic DNA libraries.

Certain embodiments are drawn to a method for genetic analysis of a DNA target region of cell free DNA (cfDNA) comprising: (a) generating a DNA library as described herein; (b) contacting the cfDNA library with a plurality of capture probes that specifically bind to a DNA target region, thereby forming complexes between the capture probes and DNA library fragments comprising the DNA target region; and (c) performing a quantitative genetic analysis of the cfDNA fragments comprising the DNA target region; thereby performing genetic analysis of the DNA target region.

Certain embodiments are directed to a method of predicting, diagnosing, or monitoring a genetic disease in a subject comprising: (a) obtaining a test sample from the subject; (b) isolating genomic DNA from the test sample; (c) generating a DNA library comprising a plurality of DNA library fragments, wherein each of the DNA library fragments comprises a genomic DNA fragment from the test sample and an adaptor; (d) contacting the cfDNA library with a plurality of capture probes that specifically bind to a DNA target region, thereby forming complexes between the capture probes and DNA library fragments comprising the DNA target region; and (e) performing a quantitative genetic analysis of one or more target genetic loci associated with the genetic disease in the cfDNA clone library, wherein the identification or detection of one or more genetic lesions in the one or more target genetic loci is prognostic for, diagnostic of, or monitors the progression of the genetic disease. In particular embodiments, the quantitative genetic analysis comprises DNA sequencing to generate a plurality of sequencing reads.

Particular embodiments are drawn to a set of adaptors that encode an identify of a unique genomic DNA fragment and an identity of a test sample, for use in generating a genomic DNA library, wherein each adaptor in said set of adapters is a DNA polynucleotide that comprises: an amplification region, a sample tag region, and an anchor region; wherein the amplification region comprises a polynucleotide sequence capable of serving as a primer recognition site for PCR amplification; wherein the sample tag comprises a polynucleotide sequence that encodes the identity of the unique library DNA fragment and encodes the identity of the test sample; and wherein the anchor region comprises a polynucleotide sequence that encodes the identity of the test sample, and wherein the anchor region is capable of attaching to the genomic DNA fragment. In some embodiments, the sample tag further comprises a unique molecule identifier (UMI), wherein the UMI facilitates the identification of the unique genomic DNA fragment. In various embodiments, the amplification region is between 10 and 50 nucleotides in length. In certain embodiments, the amplification region is 25 nucleotides in length. In particular embodiments, the sample tag is between 5 and 50 nucleotides in length. In some embodiments, the sample tag is 8 nucleotides in length. In particular embodiments, the UMI multiplier is adjacent to or contained within the sample tag region. In some embodiments, the UMI multiplier is between 1 and 5 nucleotides in length. In particular embodiments, the anchor region is between 1 and 50 nucleotides in length. In some embodiments, the anchor region is 10 nucleotides in length. In certain embodiments, the amplification regions of each adaptor of the plurality of adaptors comprises an identical nucleotide sequence.

In some embodiments, each nucleotide sequence of the sample tags is discrete from any other nucleotide sequence of the sample tags of the set of adaptors by Hamming distance of at least two. In various embodiments, each of the plurality of adaptors comprises a UMI multiplier that is adjacent to or contained within the sample tag region. In particular embodiments, each of the plurality of adaptors comprises a UMI multiplier that is adjacent to the sample tag region.

In some embodiments, the anchor tag region of each adaptor of the plurality of adaptors comprises one of four nucleotide sequences, and wherein each sample region of a given sequence is paired to only one of the four anchor regions of a given sequence. In some embodiments, the amplification regions of each adaptor of the plurality of adaptors comprises an identical nucleotide sequence; wherein the sample tag region of each adaptor is 8 nucleotides in length, wherein each nucleotide sequence of the sample tags is discrete from any other nucleotide sequence of the sample tags of the set of adaptors by Hamming distance of at least two, wherein each of the plurality of adaptors comprises a UMI multiplier that is adjacent to or contained within the sample tag region, wherein the UMI multiplier of each adaptor of the plurality of adaptors is three nucleotides in length, wherein the UMI multiplier comprises one of 64 possible nucleotide sequences, and wherein the UMI multiplier of each of the 64 possible nucleotide sequences is paired to each of the sample tag region of the plurality of adaptors, wherein the anchor tag region of each adaptor of the plurality of adaptors comprises one of four nucleotide sequences, and wherein each sample region of a given sequence is paired to only one of the four anchor regions of a given sequence.

BRIEF DESCRIPTION OF THE SEVERAL VIEWS OF THE DRAWINGS

FIG. 4A shows the first generation adaptor design. FIG. 4E shows an illustrative DNA sequence of a 47 nt adaptor.

FIG. 6A shows the step where the 10 nt anchor sequence is attached to the 3' ends of genomic fragments. FIG. 6B shows the step where the full length genomic adaptors are annealed to the initial anchor sequence.

FIG. 9A-FIG. 9B shows $Logic_{10}$ P-value plots that quantify significant deviation-from-normal in CNL measurements for fragmented genomic samples. The SNP percentages at the top show the minor allele frequencies of rare, heterozygous SNPs that are present in the ΔATM and ΔBRCA2 samples.

FIG. 10A-FIG. 10B shows Logic P-value plots that quantify significant deviation-from-normal in CNL measurements for cfDNA samples spiked with fragmented genomic DNA. The SNP percentages at the top show the minor allele frequencies of rare, heterozygous SNPs that are present in the ΔATM and ΔBRCA2 samples.

FIG. 11A-FIG. 11D illustrate the targeted hybrid capture platform. FIG. 11A shows conversion of cfDNA to a genomic library by the addition of adaptor sequences that provide universal, single-primer PCR amplification sequences, sample multiplexing tags, and unique molecular identifiers to every genomic clone. FIG. 11B shows denatured amplified genomic hybridized with target specific capture probes and primer extension, FIG. 11C shows a schematic of asymmetric paired-end sequencing. FIG. 11D shows mapping statistics for 377,711,020 Illumina NextSeq reads from a typical targeted capture sequence run. 98.5% of reads map to their intended targets. Following de-duplication, 20.40% of reads (77,053,048) are derived from unique genomic clones.

FIG. 12A-FIG. 12H shows sequences of adaptor oligonucleotides from Pools 1-3.

FIG. 13A-FIG. 13H shows sequences of adaptor oligonucleotides from Pools 4-6.

FIG. 14A-FIG. 14I shows sequences of adaptor oligonucleotides from Pools 7-9.

FIG. 15A-FIG. 15H shows sequences of adaptor oligonucleotides from Pools 10-12.

FIG. 16A-FIG. 16H shows sequences of adaptor oligonucleotides from Pools 13-15.

FIG. 17A-FIG. 17H shows sequences of adaptor oligonucleotides from Pools 16-18.

FIG. 18A-FIG. 18H shows sequences of adaptor oligonucleotides from Pools 19-21.

FIG. 19A-FIG. 19H shows sequences of adaptor oligonucleotides from Pools 22-24.

FIG. 20A-FIG. 20H shows sequences of adaptor oligonucleotides from Pools 25-27.

FIG. 21A-FIG. 21H shows sequences of adaptor oligonucleotides from Pools 28-30.

FIG. 22A-FIG. 22H shows sequences of adaptor oligonucleotides from Pools 31-32.

FIGS. 23A-1-23A-6, 23B-1-23B-6, and 23C-1-23C-6 show targeted sequencing of the TP53 gene. FIGS. 23A-1-23A-6 illustrate BedFile display of capture probes. FIGS. 23B-1-23B-6 illustrate coverage depth at each base position on a scale of 0 to 8000 unique reads, FIGS. 23C-1-23C-6 illustrate a UCSF gene model display of known TP53 splice variants. The thicker rectangular regions represent the amino acid coding regions for the TP53-encoded protein.

FIG. 24A illustrates the number of raw unique reads capture by probe TP53r10_1 for 16 independent sample after removal of redundant reads by "de-duplication. " FIG. 24B shows global average of unique reads across 2596 capture probes for all 16 samples. FIG. 24C shows normalized unique read depth across 16 samples (Calculated as: [sample n unique reads from probe TP53r10_1× constant÷global average unique reads/probe from sample n]).

FIG. 25 shows general consistency of the normalized unique read counts for all 16 samples within any given TP53 probe despite significant average depth variation between probes. The normalized unique read counts for all 16 samples are shown as "pillars" of tightly spaced bar graphs; the results for all 45 probes that target TP53 are shown. Two probes that exhibit "noisy" counting behavior are highlighted with arrows. Counts from such probes often appear as outliers in subsequent copy number analysis.

FIG. 26 illustrates sample-to-sample consistency of normalized probe-by-probe unique read counts across a broad panel of 2596 probes. The scatter plots from three representative samples are shown. Each dot represents a different probe. The x-axis is the normalized average unique read depth per probe across 16 samples. The y-axis is the normalized unique read depth per probe for three different individual samples. The consistent probe-by-probe unique read counts support quantitative analysis of chromosomal copy variation.

Figure 27A:
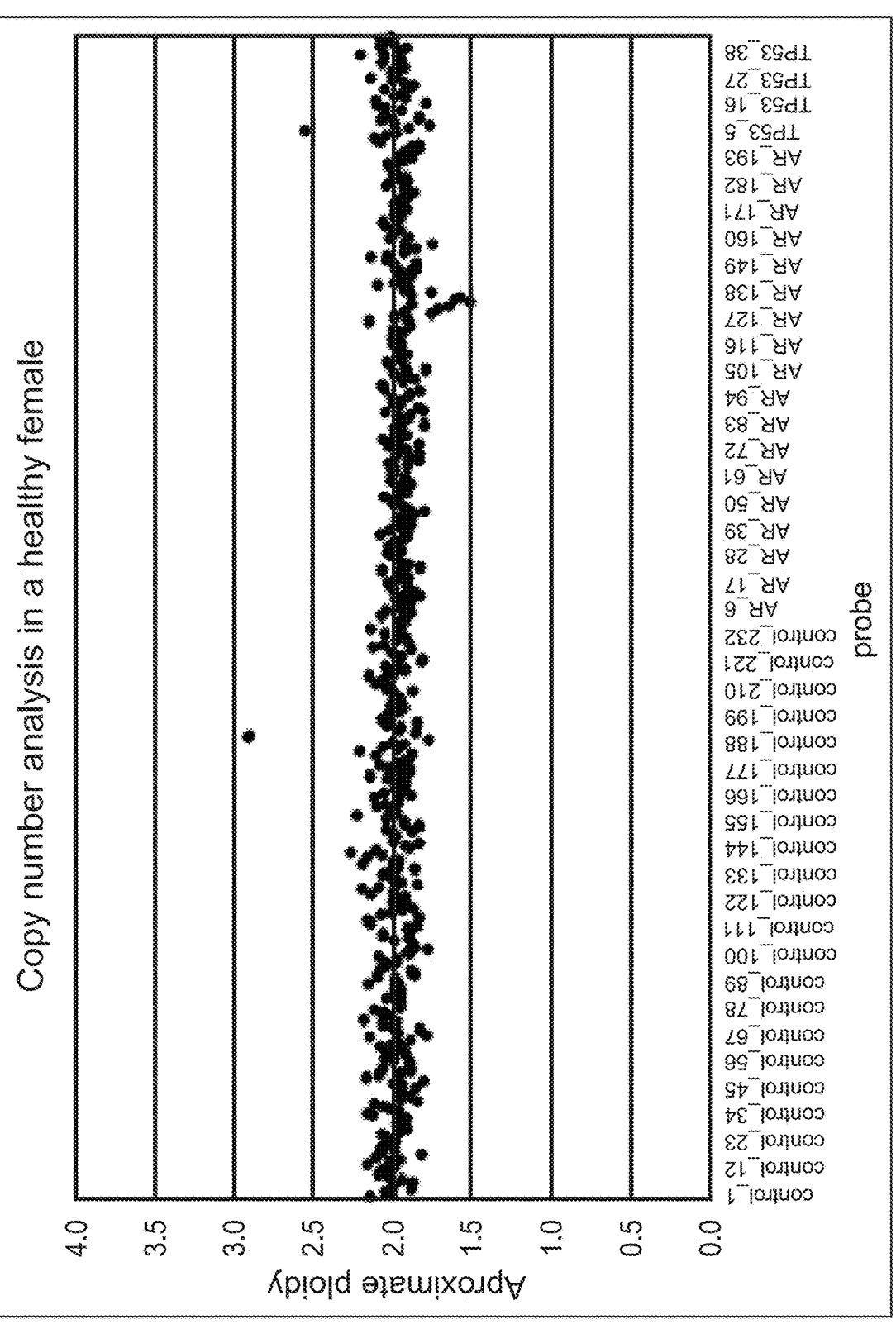
Figure 27B:
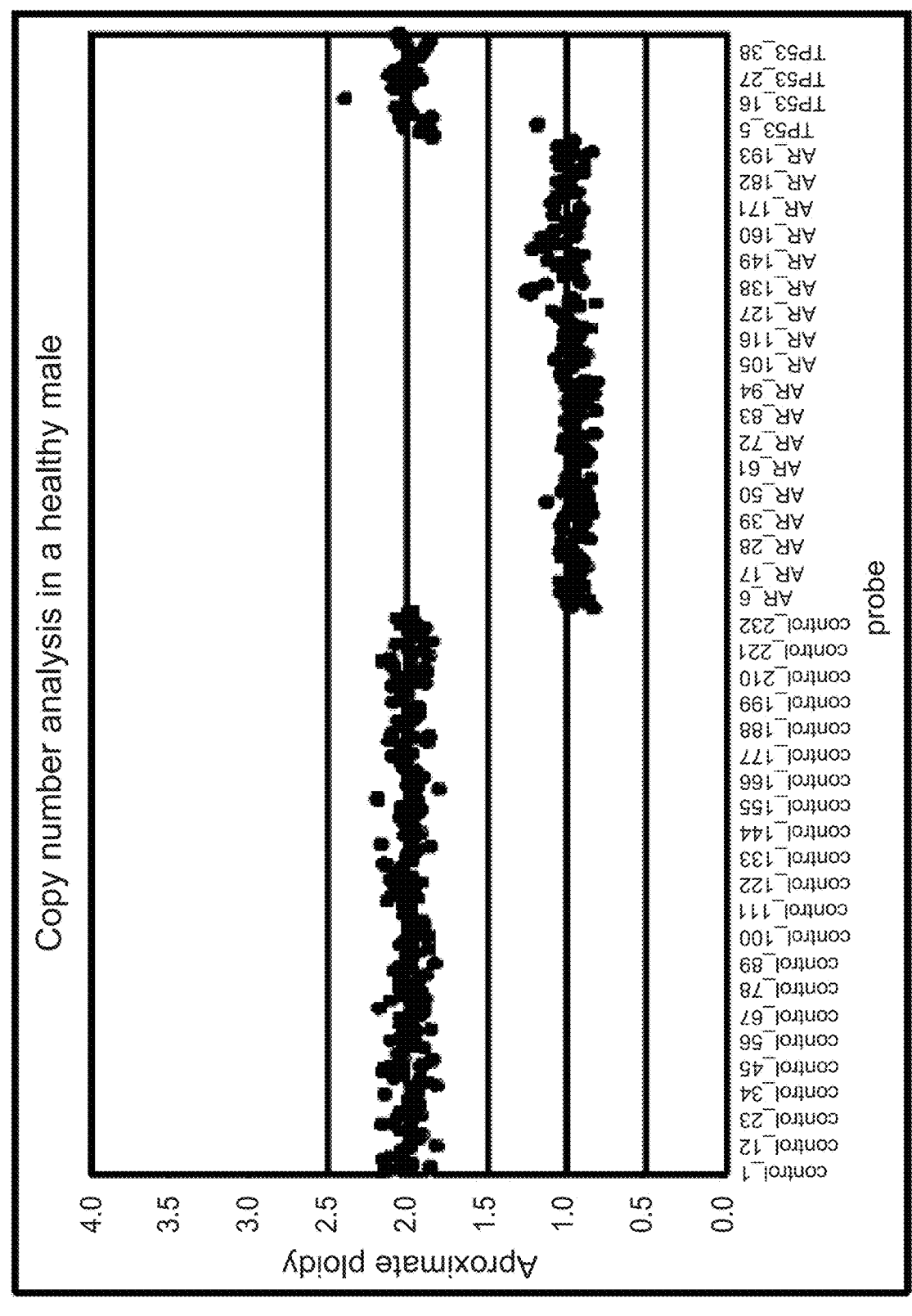
Figure 27C:
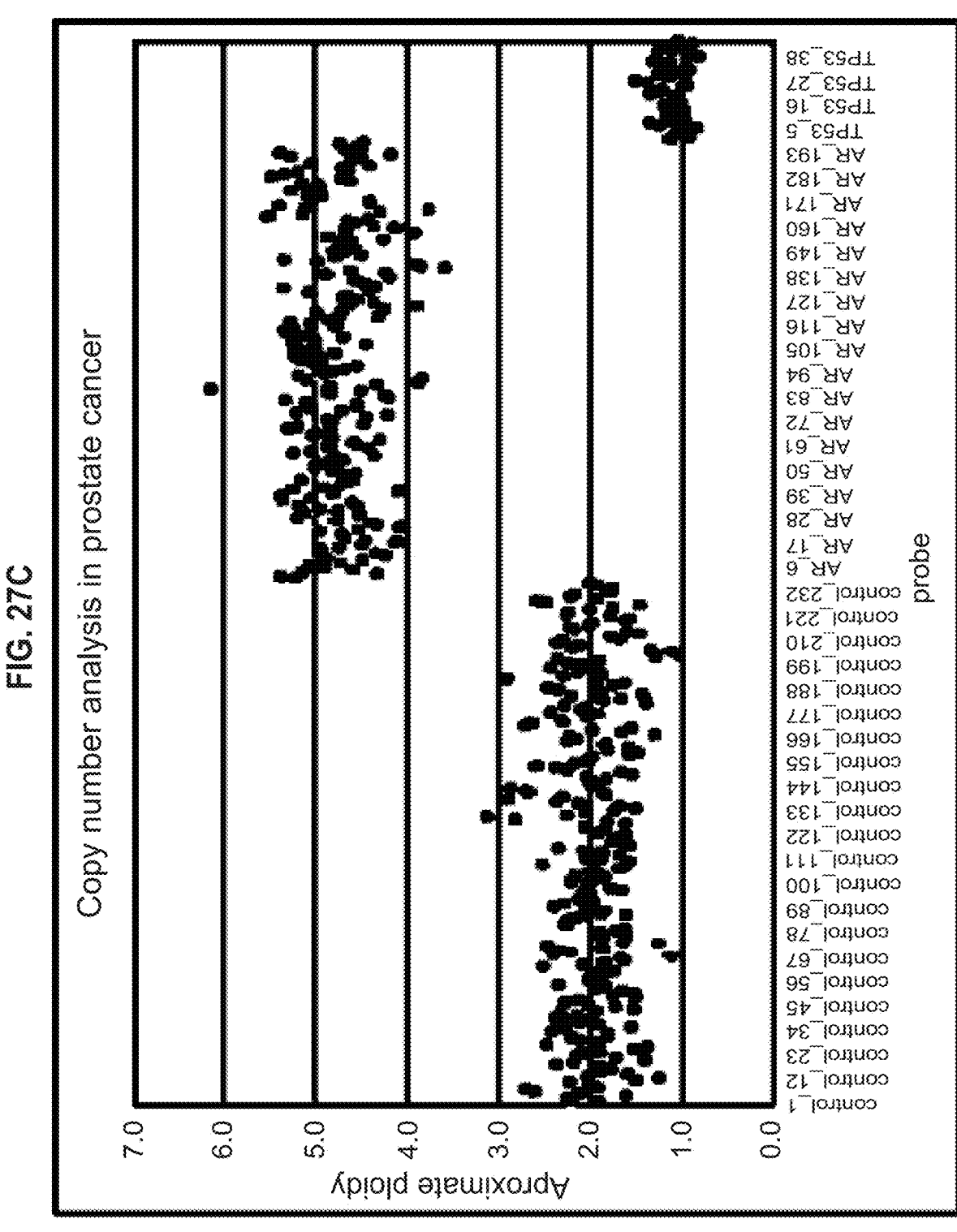

FIG. 27A-FIG. 27C illustrate copy number analysis of cfDNA from a healthy female and male donor and from an advanced stage prostate cancer patient. FIG. 27A shows analysis of a cfDNA from a healthy female donor. The x-axis is a series of control probes that target regions from all 22 autosomal chromosomes, a series of probes that target the X-linked AR gene, and a series of probes that target the coding regions of the TP53 gene. The Y-axis shows the calculated ploidy for each probe. This approximation is calculated for each probe by normalizing the observed unique read counts to a series of control samples whose ploidy is known ([unique read count for probe_Y of sample_Z]×2÷[average unique read count for probe_Y for multiple control samples]). FIG. 27B illustrates that the X-linked AR gene exhibits a haploid copy number in healthy males. FIG. 27C illustrates copy number analysis of cfDNA from an advanced prostate cancer patient and shows evidence of very significant aneuploidy across the control probes, amplification of the AR gene, and loss of the TP53 gene.

Figure 28:
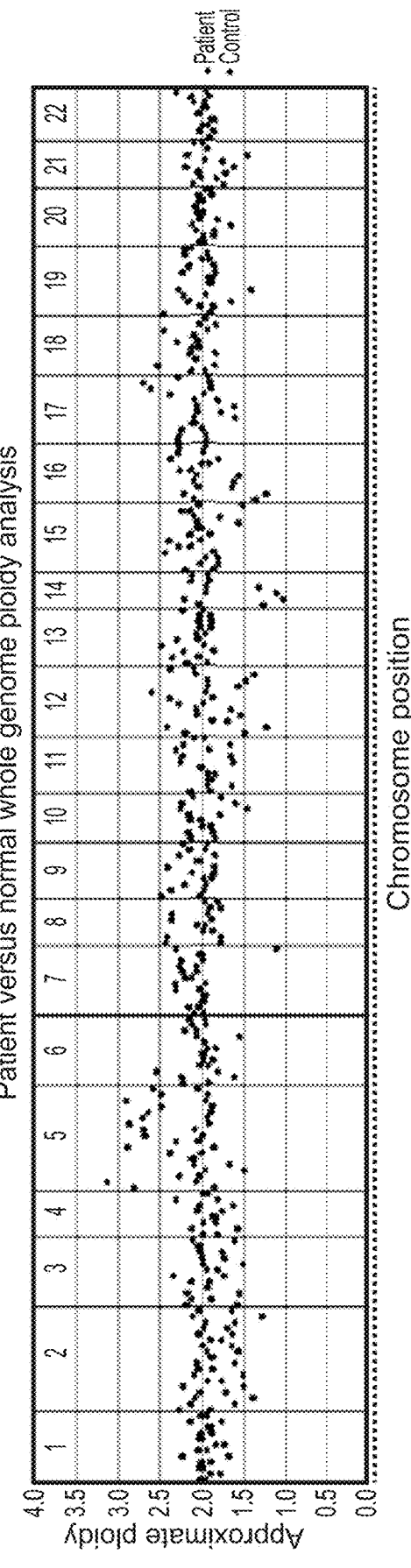

FIG. 28 shows whole genome aneuploidy analysis of a prostate patient cfDNA library relative to a control sample. The approximate ploidy for each of 239 control probes is shown sorted by chromosome. Patient chromosome 2 probes show consistent copy loss and the majority of chromosome 5 probes show copy gain. Significant deviation of approximate ploidy are seen for many, but not all, of the patient control probes.

Figure 29:
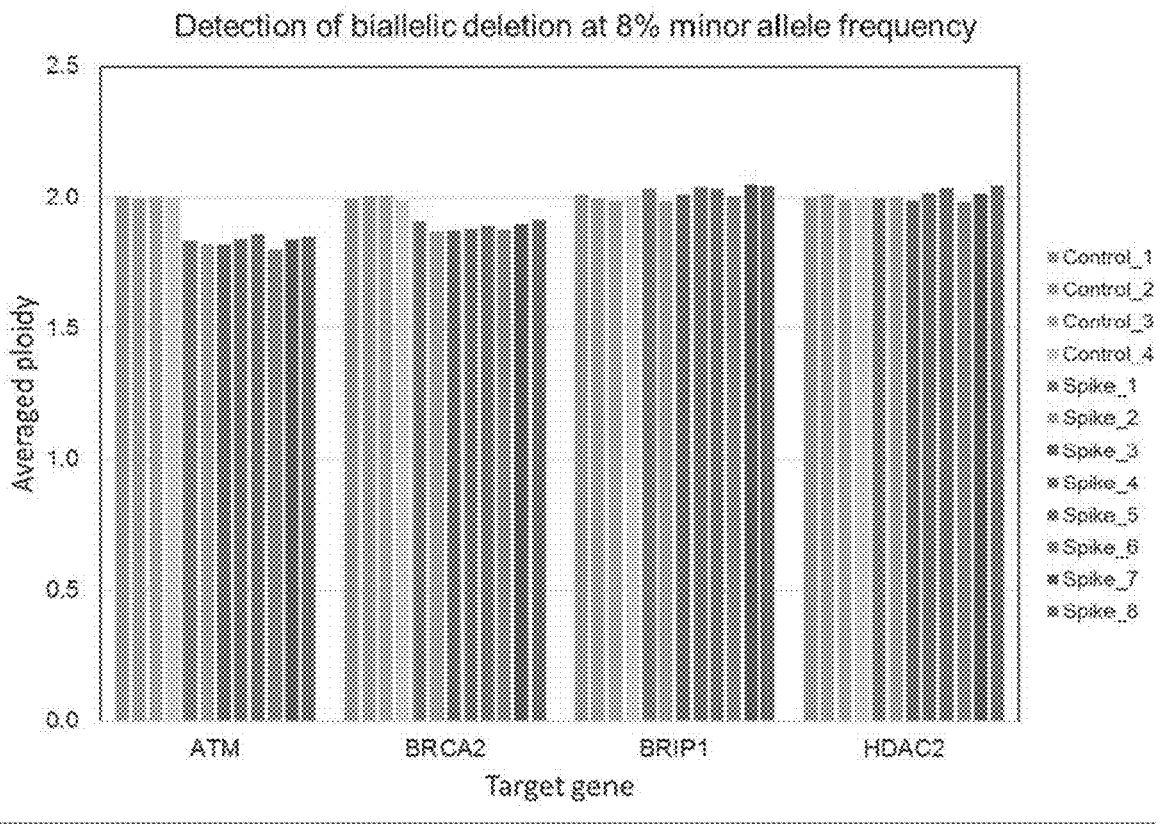

FIG. 29 shows analytical validation of copy number loss detection. Genomic DNA from immortalized line NA02718 (monoallelic ΔATM) and from NA09596 (monoallelic ΔBRCA2) were spiked into the "gold standard" genomic DNA from NA12878 at 16%, resulting in the equivalent of an 8% biallelic deletion minor allele frequency. Following targeted sequencing and CNV analysis, the probe-by-probe ploidies were averaged for the two target genes. Two unperturbed control genes, BRIP1 and HDAC2, are shown for comparison.

DETAILED DESCRIPTION

A. Overview

The present invention includes, inter alia, compositions and methods that are useful for the detection of a mutational change, SNP, translocation, inversion, deletion, change in copy number or other genetic variation within a sample of cellular genomic DNA from a tissue biopsy sample) or cfDNA (e.g. from a blood sample). The compositions and methods of the current invention are particularly useful in detecting incredibly hard to detect copy number variations in cfDNA from a biological sample (e.g. blood) with exquisite resolution. In particular, some embodiments of the present invention are drawn to a method for the detecting copy number of a DNA target region from a test sample by generating a genomic DNA library made up of genomic DNA fragments attached to an adaptor, capturing DNA target regions with a plurality of capture probes, isolating the DNA library fragments comprising the DNA target region, and performing a quantitative genetic analysis of the DNA target region to thereby determining the copy number of the DNA target region. The adaptors described herein allow for the identification of the individual DNA fragment that is being sequenced, as well as the identity of the sample or source of the genomic DNA.

The present invention contemplates, in part, compositions and methods for detection of target-specific copy number changes that are applicable to several sample types, including but not limited to direct tissue biopsies and peripheral blood. In the context of cancer genomics, and in particular cell free DNA (cfDNA) assays for the analysis of solid tumors, the amount of tumor DNA is often a very small fraction of the overall DNA. Further, copy number loss is difficult to detect in genomic DNA assays, and in particular, genomic DNA assays where copy number change may only be present in a portion of the total genomic DNA from a sample, e.g., cDNA assays. For example, most of the cell-free DNA extracted from a cancer patient will be derived from normal sources and have a diploid copy number (except for X-linked genes in male subjects). In a cancer patient, the fraction of DNA derived from tumors often has a low minor allele frequency, such as for example, a patient in which 2% of the circulating DNA extracted from plasma is derived from the tumor. The loss of one copy of a tumor suppressor gene (for example, BRCA1 in breast cancer) means that the minor allele frequency for the absence of detectable genomic fragments is 1%. In this scenario, a copy number loss assay engineered must be able to discriminate between 100 copies (normal) and 99 copies (heterozygous gene loss). Thus, particular embodiments contemplate that the methods and compositions of the present invention allow for the detection of copy number change with sufficient resolution to detect changes in copy number at minor allele frequencies even in the context of cfDNA.

To achieve this level of discrimination, the present invention provides novel sample adaptor designs. The adaptors of the present invention are designed to include features that are critical for successful copy number loss assay performance including (i) even performance across adaptors; (ii) a high number of unique molecule identifiers (UMIs), (iii) high efficiency attachment; and (iv) accommodation of sample multiplexing. For example, the adaptors of the present invention provide the following:

Even performance across adaptors: Bioinformatics analysis often looks at intra-sample probe performance and inter-sample probe performance. Thus, it is contemplated that any performance fluctuation between adaptor pools across samples will negatively impact the ability to detect the subtle variations required by CNL analysis. In the present invention, this evenness of performance is achieved by having multiple anchor tags that are all represented in each sample tag pool, with the fixed sample tag regions (which serve to identify both the sample and the genomic fragments) being randomly selected for each pool, and a UMI multiplier that increases the unique sample tag sequences for identifying the genomic fragments.

High number of Unique Molecule Identifiers (UMIs): While adaptors must be functionally equivalent from a molecular biology perspective, they must possess a very large number of unique sequence tags (≤10,000) that augment the identification of unique genomic fragments. In this context, by "augment," it is meant that each genomic clone fragment has a particular pair of fragmentation sites corresponding to the position in the genomic sequence where the double-strand DNA was cleaved. This cleavage site is used to differentiate unique genomic clones since each clone is likely to possess a different cleavage site. However, in libraries that possess thousands of independent clones, uniquely derived fragments will often possess the exact same cleavage sites. Genomic clones (i.e. fragments) sharing the same cleavage site can be classified as either unique or as redundant with respect to other clone sequences derived from the same sample. By attaching adaptors that introduce a high diversity of sequence tags, different genomic clones sharing the same cleavage site are more likely to be identified as unique. In this system, the UMI is created by a combination of the sample tag region with the UMI multiplier. The combination of the UMI and the cleavage site create a unique molecular identifier element (UMIE), which facilitates the classification of sequence reads as redundant reads or unique reads. Particular embodiments contemplate that the UMI multiplier could comprise longer or shorter sequences to increase or lower the overall UMI complexity.

High efficiency attachment: Adaptors must attach to genomic fragments with high efficiency. In most oncology applications, the quantities of available cellular DNA or cfDNA are limited and therefore conversion of these genomic fragments to genomic library clones must be highly efficient. In order to achieve this, in some aspects of the present invention, the adaptor systems described herein convert about 25% to about 50% or greater of the genomic input fragments are converted into genomic library clones.

Accommodation of sample multiplexing: In general, there must be pools of different sets of adaptors where each unique adaptor of the set is attached to a different sample. At the same time, each member of the set of adaptors must possess essentially identical behavior (from a sequence counting perspective) to all other members in a set. In order to achieve this, in some embodiments, the sample tag regions have a Hamming distance of 2 between any other possible sample tag combinations reducing the chance for a read to be spuriously assigned to the wrong sample. In some embodiments, each set of adaptors is split into pools that are paired with specific anchor regions, allowing for further reduction in the possibility of an error in sample de-multiplexing. For example, in an 8 mer tag with Hamming distance of 2, the total number of possible sequences is 16,384.

In a particular embodiment, pre-specified pools of adaptor oligonucleotides are provided. Such pre-specified pools are used to represent a single sample. That is, each adapter sequence in each pool of X adapter oligonucleotides (16,384 in the example given above) is distinct from each adapter sequence in every other pool used to identify other samples. One of skill in the art will recognize the number of distinct pre-specified pools that are possible for the adapter oligonucleotides will depend on the length of the sample tag and/or the UMI multiplier.

Thus, in certain embodiments the adaptors comprise a sequence, i.e., the sample tag and adjacent and/or encompassed UMI multiplier that represents or identifies bath the sample and uniquely identifies the genetic fragment. This is in stark contrast to the current systems that are used in the art that use a randomly generated tag to identify the sequence and a separate barcode or sequencer indexing to allow for multiplexing.

Figure 3:
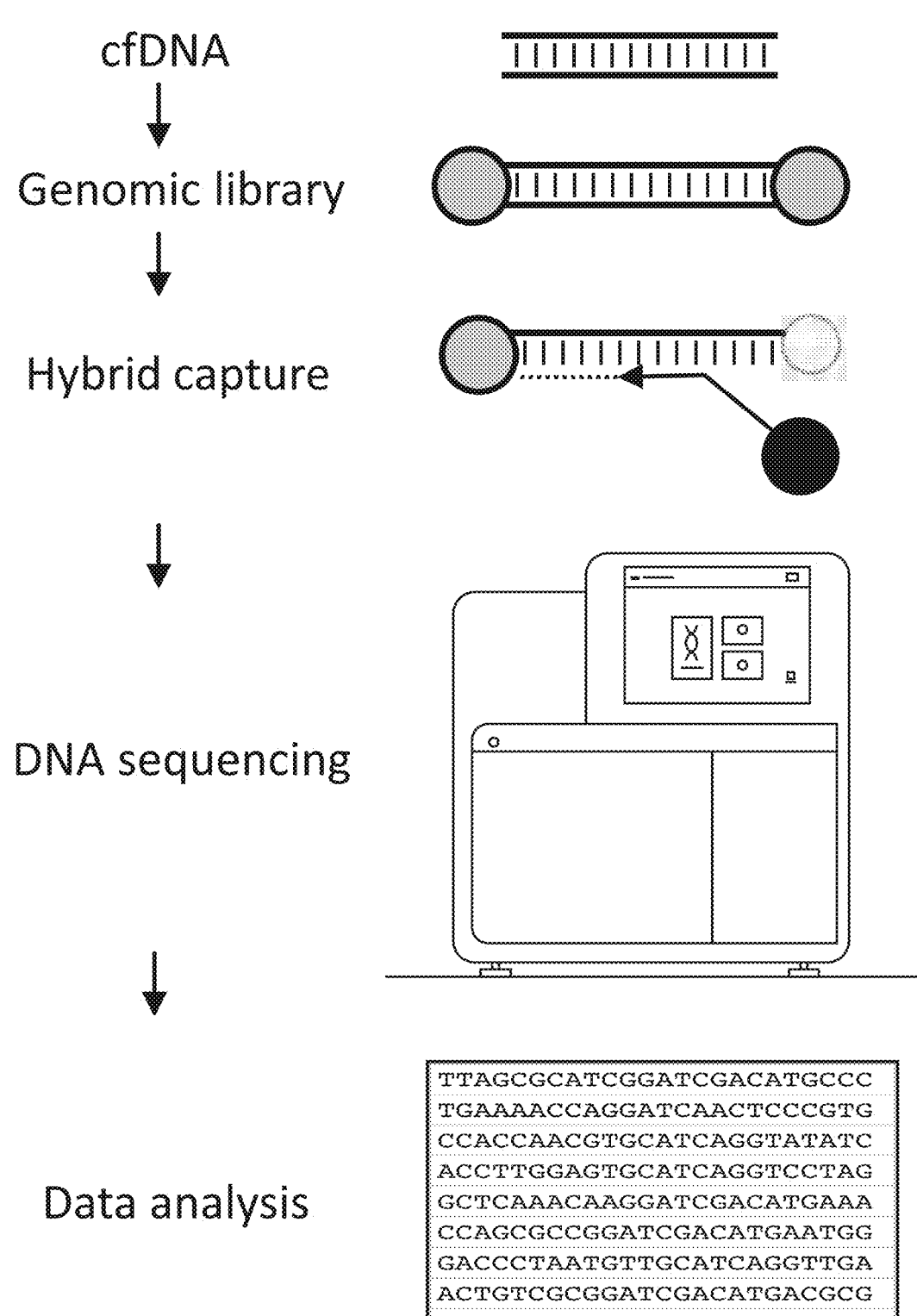
FIG. 3 shows a diagram illustrating steps of an illustrative CNL assay performed on cell free DNA (cfDNA).

An illustrative embodiment for detecting target-specific copy number changes within DNA obtained from a sample is shown in FIG. 3. While FIG. 3 generates a DNA library from cfDNA, this illustrative procedure could be used with DNA from other sources, e.g., fragmented cellular DNA. As shown in FIG. 3, cfDNA is collected (top panel). Next, a genomic library is generated from ctDNA by conjugating genomic library adaptors (gray circles) of the present invention to the genomic DNA. Genomic DNA fragments are captured with capture probes (black circles) that recognize the genomic region of interested. The genomic DNA of interest is sequenced, and data analysis is performed for copy loss analysis and/or characterization of the genomic DNA of interest.

The practice of particular embodiments of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art many of which are described below for the purpose of illustration. Such techniques are explained fully in the literature. See, e.g., Sambrook, et al., *Molecular Cloning: A Laboratory Manual* (3rd Edition, 2001); Sambrook, et al., *Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a" "an," and "the" are used herein to refer to one or to more than one (i.e. to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises," and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "isolated" means material that is substantially or essentially free from components that normally accompany it in its native state. In particular embodiments, the term "obtained" or "derived" is used synonymously with isolated.

As used herein, the term "DNA" refers to deoxyribonucleic acid. In various embodiments, the term DNA refers to genomic DNA, recombinant DNA, synthetic DNA, or cDNA. In one embodiment, DNA refers to genomic DNA or cDNA. In particular embodiments, the DNA comprises a "target region." DNA libraries contemplated herein include genomic DNA libraries and cDNA libraries constructed from RNA, an RNA expression library. In various embodiments, the DNA libraries comprise one or more additional DNA sequences and/or tags.

The terms "target genetic locus" and "DNA target region" are used interchangeably herein and refer to a region of interest within a DNA sequence. In various embodiments, targeted genetic analyses are performed on the target genetic locus. In particular embodiments, the DNA target region is a region of a gene that is associated with a particular genetic state, genetic condition, genetic diseases; fetal testing; genetic mosaicism, paternity testing; predicting response to drug treatment; diagnosing or monitoring a medical condition; microbiome profiling; pathogen screening; or organ transplant monitoring. In further embodiments, the DNA target region is a DNA sequence that is associated with a particular human chromosome, such as a particular autosomal or X-linked chromosome, or region thereof (e.g., a unique chromosome region).

As used herein, the terms "circulating DNA," "circulating cell-free DNA," and "cell-free DNA" are often used interchangeably and refer to DNA that is extracellular DNA, DNA that has been extruded from cells, or DNA that has been released from necrotic or apoptotic cells. This term is often used in contrast to "cellular genomic DNA" or "cellular DNA," which are used interchangeably herein and refer to genomic DNA that is contained within the cell (i.e. the nuclease) and is only accessible to molecular biological techniques such as those described herein, by lysing or otherwise disrupting the integrity of the cell.

A "subject," "individual," or "patient" as used herein, includes any animal that exhibits a symptom of a condition that can be detected or identified with compositions contemplated herein. Suitable subjects include laboratory animals (such as mouse, rat, rabbit, or guinea pig), farm animals (such as horses, cows, sheep, pigs), and domestic animals or pets (such as a cat or dog), In particular embodiments, the subject is a mammal. In certain embodiments, the subject is a non-human primate and, in preferred embodiments, the subject is a human.

As used herein, the term "paired" when used with respect to two different polynucleotide sequences or regions of DNA comprising different polynucleotide sequences, means that the two different polynucleotide sequences or regions of DNA comprising different polynucleotide sequences are present on the same polynucleotide. For example, if a particular sample tag region of DNA is said to be paired to particular amplification region of DNA, it is meant that the sample tag region and the amplification tag are present on the same DNA polynucleotide molecule.

C. Methods of Copy Number Analysis

In various embodiments, a method for copy number analysis of a DNA target region DNA is provided. In certain embodiments, copy number analysis is performed by generating a genomic DNA library of DNA library fragments that each contain genomic DNA fragment and an adaptor, isolating the DNA library fragments containing the DNA target regions, and performing a quantitative genetic analysis of the DNA target region. By "quantitative genetic analysis" it is meant an analysis performed by any molecular biological technique that is able to quantify changes in a DNA (e.g., a gene, genetic locus, target region of interest, etc.) including but not limited to DNA mutations, SNPs, translocations, deletions, and copy number variations (CNVs). In certain embodiments, the quantitative genetic analysis is performed by sequencing, for example, next generation sequencing.

Next-generation DNA sequencing (NGS) is ideally suited for two diagnostic applications. The first is the determination of DNA sequence on a vast scale. In the present context, this capability enables the search for rare, actionable variants that guide effective treatment decisions. The second is counting gene copy number. The output of millions of independent sequences can enable precise measurement of gene copy number on a genome-wide scale. The emergence of non-invasive prenatal testing for fetal trisomy from maternal blood samples is a testament to this capability. RNAseq, that is, the technology of gene expression profiling using NGS is another example, albeit the input is RNA (cDNA) rather than genomic DNA. Comparisons of current capture methods are described Samorodnitsky et al, J Mol Diagn. 2015 Janurary; 17(1):64-75.

The present invention extends NGS counting capability into the realm of targeted hybrid capture methods. The methods described here are effective for the detection of copy number variation at least in part because they possess the following four qualities:

(a) The present methods differentiate between unique clones and redundant clones. NGS sequencing of amplified genomic DNA library fragments results in a plurality of individual NGS reads, each comprising adaptor-encoded sequence information linked to a specific human genomic sequence. These elements define the identity of every clone. Because captured genomic regions are amplified by PCR, it is not uncommon for the same clone to be encountered several times in a subsequent NGS analysis. Groups of reads that are derived from a single cloning and capture process are termed "redundant reads." Two or more redundant reads are identified as redundant reads based on the sequencing information provided by the unique molecular identification elements (UMIE). The UMIE refers to the combination of the sequence information from the adaptor tags and the start of the genomic DNA sequence. Two or more reads comprising identical UMIEs are identified as redundant reads. Redundant reads are grouped together and a single, representative consensus sequence is assembled from families of redundant reads. This consensus sequence is designated as a "unique read" or a "unique genomic sequence" (UGS). Each unique read represents a separate clone from the original DNA specimen. The process of identifying and grouping redundant clone families and of generating a single unique read representative of this family is defined as "deduplication." The adaptors used to create genomic libraries possess a very deep repertoire of unique sample tag information (15,360 codes per adaptor). When applied in conjunction with the exact mapping coordinates of each captured genomic clone (which can span >100 different positions relative to a capture probe), each unique clone that is generated in a genomic library and subsequently retrieved by a target-specific capture probe has an extremely high likelihood of being differentiable from all other unique clones that encompass the same capture environment. The ability to differentiate between unique clones and redundant clones is central to the methods described herein.

(b) The adaptors used to create genomic libraries permit sample multiplexing without creating adaptor-to-adaptor variability in copy number counts. A central foundation of copy number determination is the simultaneous analysis of a set of samples that have all been processed within a single sequencing run. This allows positive and negative controls to be included along with clinical samples. A major issue with previous adaptor design iterations induced subtle shifts in gene copy counts among identical control samples, in effect setting a signal-to-noise uncertainty threshold that was too high to be clinically useful in blood-based, solid tumor genotyping assays. The present invention overcomes this issue and substantially lowers the signal-to-noise threshold such that single copy gene loss is detectable at ≤2% minor allele frequency. This improved signal recognition enables the methods of the present invention to have significant clinical utility in circulating tumor DNA assays.

(c) The proprietary targeted hybrid capture method used herein must produce highly uniform "on-target" read coverage across all targets. Methods that rely on counting of unique genomic fragments to estimate copy number, such as the ones described herein, must achieve near-saturation in terms of encountering all possible unique fragments. Near-saturation is only achieved by oversampling, that is to say, gathering more sequencing reads than the number of unique reads that will ultimately be encountered. To be practical, scalable, and economical, the unique reads in a targeted hybrid capture library must exhibit sufficient uniformity such that <10-fold oversampling of on-target reads, and preferably <4-fold oversampling of on-target reads will capture >90% of unique on-target reads at all target loci.

(d) The targeted hybrid capture method (See U.S. Patent Publication No. 2014-0274731) must have high on-target capture rates. To be practical, scalable and economical, in other words to be a distinguishing feature of the present disclosure relative to other art in the field, the method must achieve >90%, preferably >95% on-target reads. With on-target mapping rates exceeding 95%, the requirement for 4 to 10-fold oversampling of on-target reads and the requirement for overall oversampling are one in the same.

In some embodiments, the number of copies of the DNA target region present in the sample is determined by the quantitative genetic analysis. In some embodiments, the copy number of the DNA target region is determined by comparing the amount of copies of DNA target regions present in the sample and comparing it to amounts of DNA target regions present in one or more samples with known copy number.

Particular embodiments contemplate that the compositions and methods described herein are particularly useful for detecting changes in copy number in a sample of genomic DNA, where only a portion of the total genomic DNA in the sample has a change in copy number. For example, a significant tumor mutation may be present in a sample, e.g. a sample of cell free DNA, that is present in a minor allele frequency that is significantly less than 50% (e.g., in the range of 0.1% to >20%), in contrast to conventional SNP genotyping where allele frequencies are generally ~100%, 50% or 0%. One of skill of the art will recognize that the compositions and methods of the current invention are also useful in detecting other types of mutation including single nucleotide variants (SNVs), short (e.g., less than 40 base pairs (bp)) insertions, and deletions (indels), and genomic rearrangements including oncogenic gene fusions.

In certain embodiments, the compositions and/or methods of the present invention described herein are useful for, capable of, suited for, and/or able to detect, identify, observe, and/or reveal a change in copy number of one or more DNA target regions present in less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, less than about 0.5%, less than about 0.2%, or less than about 0.1% of the total genomic DNA from the sample. In some embodiments, the methods of the present invention are useful for, capable of, suited for, and/or able to detect, identify, observe, and/or reveal a change in copy number of one or more DNA target regions present in between about 0.01% to about 100%, about 0.01% to about 50%, and or about 0.1% to about 20% of the total genomic DNA from the sample.

Figures 1, 2:
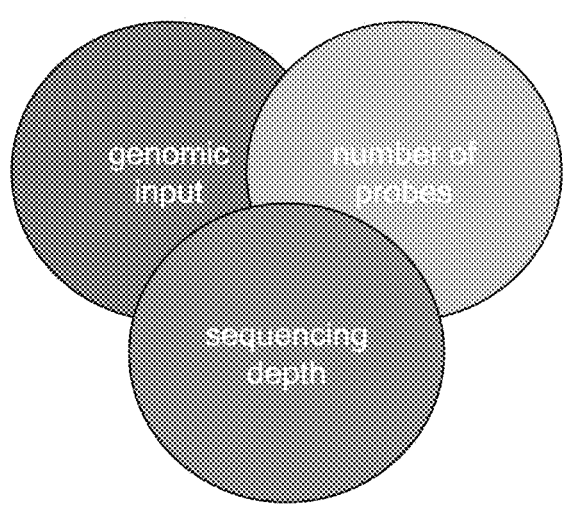
FIG. 1 shows the framework of the copy number loss (CNL) assay. Each gene (rows) exhibits a characteristic unique read value that is represented here by a shade. Each sample (columns) is interrogated across the same panel of genes.
FIG. 2 shows a diagram illustrating the drivers of the CNL assay signal.

Particular embodiments are represented by the conceptual framework that is illustrated in FIG. 1. In FIG. 1, each gene is represented by a row and each patient sample is represented as a column. Within any given genomic DNA sample, the number of fragments counted for each individual gene will have some variability, and that for any given DNA region of interest, e.g. a gene, perturbations in copy number are detected as significant fragment count deviations relative to the normalized counts to the DNA target region in other samples. Such an assay requires the gene-by-gene fragment counting profile within a sample to be reproducible, and also requires the sample-by-sample counting profiles to be highly comparable. Both assay requirements demand excellent signal-to-noise counting discrimination.

Some embodiments contemplate that the assay elements that contribute to increasing the signal to noise ratio are the genomic input, the number of probes, and the sequencing depth, as illustrated in FIG. 2.

In particular embodiments, a method for genetic analysis of cfDNA comprises: generating and amplifying a cfDNA library, determining the number of genome equivalents in the ctDNA library; and performing a quantitative genetic analysis of one or more genomic target loci.

Particular embodiments contemplate that the any of the methods and compositions described herein are effective for use to efficiently analyze, detect, diagnose, and/or monitor genetic states, genetic conditions, genetic diseases, genetic mosaicism, fetal diagnostics, paternity testing, microbiome profiling, pathogen screening, and organ transplant monitoring using genomic DNA, e.g., cellular or cfDNA, where all or where only a portion of the total genomic DNA in the sample has a feature of interest, e.g. a genetic lesion, mutation, single nucleotide variant (SW). In some embodiments, a feature of interest is a genetic feature associated with a disease or condition. For example, a significant tumor mutation may be present in a sample, e.g. a sample of cfDNA, that is present in a minor allele frequency that is significantly less than 50% (e.g. in the range of 0.1% to >20%), in contrast to conventional SNP genotyping where allele frequencies are generally ~100%, 50% or 0%.

In certain embodiments, the compositions and/or methods of the present invention described herein are useful for, capable of, suited for, and/or able to detect, identity, observe, and/or reveal a genetic lesion of one or more DNA target regions present in less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, less than about 0.5%, less than about 0.2%, or less than about 0.1% of the total genomic DNA from the sample. In some embodiments, the methods of the present invention are useful for, capable of, suited for, and/or able to detect, identify, observe, and/or reveal a genetic lesion of one or more DNA target regions present in between about 0.01% to about 100%, about 0.01% to about 50%, and or about 0.1% to about 20% of the total genomic DNA from the sample.

1. Generating a DNA Library

In particular embodiments, methods of genetic analysis contemplated herein comprise generating a DNA library comprising treating cfDNA or fragmented cellular genomic DNA with one or more end-repair enzymes to generate end-repaired DNA and attaching one or more adaptors to each end of the end-repaired DNA to generate the DNA library. Genomic DNA In particular embodiments, the methods and compositions contemplated herein are designed to efficiently analyze, detect, diagnose, and/or monitor change in copy number using genomic DNA as an analyte. In certain embodiments, copy number analysis is performed by generating a genomic DNA library from genomic DNA obtained from a test sample, e.g., a biological sample such as a tissue biopsy. In certain embodiments, the genomic DNA is circulating or cell free DNA. In some embodiments, the genomic DNA is cellular genomic DNA.

In certain embodiments, genomic DNA is obtained from a tissue sample or biopsy taken from a tissue, including but not limited to, bone marrow, esophagus, stomach, duodenum, rectum, colon, ileum, pancreases, lung, liver, prostate, brain, nerves, meningeal tissue, renal tissue, endometrial tissue, cervical tissue, breast, lymph node, muscle, and skin. In certain embodiments, the tissue sample is a biopsy of a tumor or a suspected tumor. In particular embodiments, the tumor is cancerous or suspected of being cancerous. In particular embodiments, the tissue sample comprises cancer cells or cells suspected of being cancerous.

Methods for purifying genomic DNA from cells or from a biologic tissue comprised of cells are well known in the art, and the skilled artisan will recognize optimal procedures or commercial kits depending on the tissue and the conditions in which the tissue is obtained. Some embodiments contemplate that purifying cellular DNA from a tissue will require cell disruption or cell lysis to expose the cellular DNA within, for example by chemical and physical methods such as blending, grinding or sonicating the tissue sample; removing membrane lipids by adding a detergent or surfactants which also serves in cell lysis, optionally removing proteins, for example by adding a protease; removing RNA, for example by adding an RNase; and DNA purification, for example from detergents, proteins, salts and reagents used during cell lysis step. DNA purification may be performed by precipitation, for example with ethanol or isopropanol; by phenol-chloroform extraction.

In particular embodiments, cellular DNA obtained from tissues and/or cells are fragmented prior to and or during obtaining, generating, making, forming, and/or producing a genomic DNA library as described herein. One of skill in the art will understand that there are several suitable techniques for DNA fragmentation, and is able to recognize and identify suitable techniques for fragmenting cellular DNA for the purposes of generating a genomic DNA library for DNA sequencing, including but not limited to next-generation sequencing. Certain embodiments contemplate that cellular DNA can be fragmented into fragments of appropriate and/or sufficient length for generating a library by methods including but not limited to physical fragmentation, enzymatic fragmentation, and chemical shearing.

Physical fragmentation can include, but is not limited to, acoustic shearing, sonication, and hydrodynamic shear. In some embodiments, cellular DNA is fragmented by physical fragmentation. In particular embodiments, cellular DNA is fragmented by acoustic shearing or sonication. Particular embodiments contemplate that acoustic shearing and sonication are common physical methods used to shear cellular DNA. The Covaris® instrument (Woburn, MA) is an acoustic device for breaking DNA into 100-5 kb bp. Covaris also manufactures tubes (gTubes) which will process samples in the 6-20 kb for Mate-Pair libraries. The Bioruptor® (Denville, NJ) is a sonication device utilized for shearing chromatin, DNA and disrupting tissues. Small volumes of DNA can be sheared to 150-1 kb in length. Hydroshear from Digilab (Marlborough, MA) utilizes hydrodynamic forces to shear DNA. Nebulizers (Life Tech, Grand Island, NY) can also be used to atomize liquid using compressed air, shearing DNA into 100-3 kb fragments in seconds. Nebulization is low cost, but the process can cause a loss of about 30% of the cellular DNA from the original sample. In certain embodiments, cellular DNA is fragmented by sonication.

Enzymatic fragmentation can include, but is not limited to, treatment with a restriction endonuclease, e.g. DNase I, or treatment with a nonspecific nuclease. In some embodiments, cellular DNA is fragmented by enzymatic fragmentation. In particular embodiments, the cellular DNA is fragmented by treatment with a restriction endonuclease. In some embodiments, the cellular DNA is fragmented by treatment with a nonspecific nuclease. In certain embodiments, the cellular DNA is fragmented by treatment with a transposase. Certain embodiments contemplate that enzymatic methods to shear cellular DNA into small pieces include DNASe I, a combination of maltose binding protein (MBP)-T7 Endo 1 and a non-specific nuclease Vibrio vulnificus (Vvn) New England Biolabs's (Ipswich, MA) Fragmentase and Nextera tagmentation technology (Illumina, San Diego, CA). The combination of non-specific nuclease and T7 Endo synergistically work to produce non-specific nicks and counter nicks, generating fragments that disassociate 8 nucleotides or less from the nick site. Tagmentation uses a transposase to simultaneously fragment and insert adapters onto double stranded DNA.

Chemical fragmentation can include treatment with heat and divalent metal cation. In some embodiments, genomic DNA is fragmented by chemical fragmentation. Particular embodiments contemplate that chemical shear is more commonly used for the breakup of long RNA fragments as opposed to genomic DNA. Chemical fragmentation is typically performed through the heat digestion of DNA with a divalent metal cation (magnesium or zinc). The length of DNA fragments can be adjusted by increasing or decreasing the time of incubation.

In particular embodiments, the methods and compositions contemplated herein are designed to efficiently analyze, detect, diagnose, and/or monitor change in copy number using cell-free DNA (cfDNA) as an analyte. The size distribution of cfDNA ranges from about 150 bp to about 180 bp fragments. Fragmentation of cfDNA may be the result of endonucleolytic and/or exonucleolytic activity and presents a formidable challenge to the accurate, reliable, and robust analysis of cfDNA. Another challenge for analyzing cfDNA is its short half-life in the blood stream, on the order of about 15 minutes. Without wishing to be bound to any particular theory, the present invention contemplates, in part, that analysis of cfDNA is like a "liquid biopsy" and is a real-time snapshot of current biological processes.

Moreover, because cfDNA is not found within cells and may be obtained from a number of suitable sources including, but not limited to, biological fluids and stool samples, it is not subject to the existing limitations that plague next generation sequencing analysis, such as direct access to the tissues being analyzed.

Illustrative examples of biological fluids that are suitable sources from which to isolate cfDNA in particular embodiments include, but are not limited to amniotic fluid, blood, plasma, serum, semen, lymphatic fluid, cerebral spinal fluid, ocular fluid, urine, saliva, mucous, and sweat. In particular embodiments, the biological fluid is blood or blood plasma.

In certain embodiments, commercially available kits and other methods known to the skilled artisan can used to isolate cfDNA directly from the biological fluids of a subject or from a previously obtained and optionally stabilized biological sample, e.g., by freezing and/or addition of enzyme chelating agents including, but not limited to EDTA, EGTA, or other chelating agents specific for divalent cations.

(a) Generating End-Repaired cfDN4

In particular embodiments, generating a genomic DNA library comprises the end-repair of isolated cfDNA or fragmented cellular DNA. The fragmented cfDNA or cellular DNA is processed by end-repair enzymes to generate end-repaired cfDNA with blunt ends, 5'-overhangs, or 3'-overhangs. In some embodiments, the end-repair enzymes can yield for example. In some embodiments, the end-repaired cfDNA or cellular DNA contains blunt ends. In some embodiments, the end-repaired cellular DNA or ctDNA is processed to contain blunt ends. In some embodiments, the blunt ends of the end-repaired cfDNA or cellular DNA are further modified to contain a single base pair overhang. In some embodiments, end-repaired cfDNA or cellular DNA containing blunt ends can be further processed to contain adenine (A)/thymine (T) overhang. In some embodiments, end-repaired cfDNA or cellular DNA containing blunt ends can be further processed to contain adenine (A)/thymine (T) overhang as the single base pair overhang. In some embodiments, the end-repaired cfDNA or cellular DNA has non-templated 3' overhangs. In some embodiments, the end-repaired cfDNA or cellular DNA is processed to contain 3' overhangs. In some embodiments, the end-repaired cfDNA or cellular DNA is processed with terminal transferase (TdT) to contain 3' overhangs. In some embodiments, a G-tail can be added by TdT. In some embodiments, the end-repaired cfDNA or cellular DNA is processed to contain overhang ends using partial digestion with any known restriction enzymes (e.g., with the enzyme Sau3A, and the like.

(b) Attaching Adaptor Molecules to End-Repaired cfDNA

In particular embodiments, generating a cfDNA library comprises attaching one or more adaptors to each end of the end-repaired cfDNA. The present invention contemplates, in part, an adaptor module designed to accommodate large numbers of genome equivalents in cfDNA libraries. Adaptor modules are configured to measure the number of genome equivalents present in cfDNA libraries, and, by extension, the sensitivity of sequencing assays used to identify sequence mutations.

As used herein, the terms "adaptor" and "adaptor module" are used for interchangeably, and refer to a polynucleotide comprising that comprises at least three elements: an amplification region, a sample tag region, and an anchor region. In particular embodiments, the adaptor comprises an amplification region, a sample tag region, and an anchor region. In some embodiments, the adaptor also comprises a unique molecule identifier (UMI). In particular embodiments, the adaptor comprises one or amplification regions, one or more sample tag regions, one or more UMIs, and/or one or more anchor regions. In some embodiments, the adaptor comprises, in order from 5' to 3', an amplification region, a sample tag region, a UMI, and an anchor region. In particular embodiments, the adaptor comprises, in order from 5' to 3', an amplification region, a sample tag region, a UMI, and an anchor region. In certain embodiments, the UMI is contained within the sample tag region, and the adaptor comprises, in order from 5' to 3', an amplification region, an integrated sample tag/UMI region, and an anchor region.

As used herein, the term "amplification region" refers to an element of the adaptor molecule that comprises a polynucleotide sequence capable of serving as a primer recognition site for PCR amplification. In particular embodiments, an adaptor comprises an amplification region that comprises one or more primer recognition sequences for single-primer amplification of a genomic DNA library. In some embodiments, the amplification region comprises one, two, three, four, five, six, seven, eight, nine, ten, or more primer recognition sequences for single-primer amplification of a genomic DNA library.

In some embodiments, the amplification region is about is between 5 and 50 nucleotides between 10 and 45 nucleotides, between 15 and 40 nucleotides, or between 20 and 30 nucleotides in length. In some embodiments, the amplification region is 10 nucleotides, 11 nucleotides, 12 nucleotides, 13 nucleotides, 14 nucleotides, 15 nucleotides, 16 nucleotides, 17 nucleotides, about 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides. 33 nucleotides, 34 nucleotides, 35 nucleotides, 36 nucleotides, 37 nucleotides, 38 nucleotides, 39 nucleotides, or 40 nucleotides or more. In particular embodiments, the amplification region is 25 nucleotides in length.

As used herein, the term "sample tag" or "sample tag region" are used interchangeably and refer to an element of the adaptor that comprises a polynucleotide sequence that uniquely identifies the particular DNA fragment as well as the sample from which it was derived.

In certain embodiments, the sample tag region is about is between 3 and 50 nucleotides, between 3 and 25 nucleotides, or between 5 and 15 nucleotides in length. In some embodiments, the sample tag region is 3 nucleotides, 4 nucleotides, 5 nucleotides, 6 nucleotides, 7 nucleotides, 8 nucleotides, 9 nucleotides, 10 nucleotides, about 11 nucleotides, 12 nucleotides, 13 nucleotides, 14 nucleotides, 15 nucleotides. 16 nucleotides. 17 nucleotides. 18 nucleotides, 19 nucleotides, or 20 nucleotides or more in length.

In certain embodiments, the adaptor comprises a UMI multiplier, wherein the UMI multiplier is at least 1, at least 2, at least 3, at least 4, at least 5, at least 6, at least 7, at least 8, at least 9, or at least 10 nucleotides in length.

In certain embodiments, each nucleotide position of the UMI multiplier can comprise any of adenine, guanine, cytosine, or thymine. Thus, in some embodiments, a UMI multiplier comprising n number of nucleotides can comprise any of $n^4$ possible nucleotide sequences. In some embodiments, the UMI multiplier is one nucleotide in length and comprises one of four possible sequences. In some embodiments, the UMI multiplier is two nucleotides in length and comprises one of sixteen possible sequences. In some embodiments, the UMI multiplier is three nucleotides in length and comprises one of 64 possible sequences. In some embodiments, the UMI multiplier is four nucleotides in length and comprises one of 256 possible sequences. In some embodiments, the UMI multiplier is five nucleotides in length and comprises one of 1,024 possible sequences. In some embodiments, the UMI multiplier is six nucleotides in length and comprises one of 4,096 possible sequences. In some embodiments, the UMI multiplier is seven nucleotides in length and comprises one of 16,384 possible sequences. In some embodiments, the UMI multiplier is eight nucleotides in length and comprises one of 65,5336 possible sequences. In some embodiments, the UMI multiplier is nine nucleotides in length and comprises one of 262,144 possible sequences. In some embodiments, the UMI multiplier is ten or more nucleotides in length and comprises one of 1,048,576 or more possible sequences.

Figure 5A:
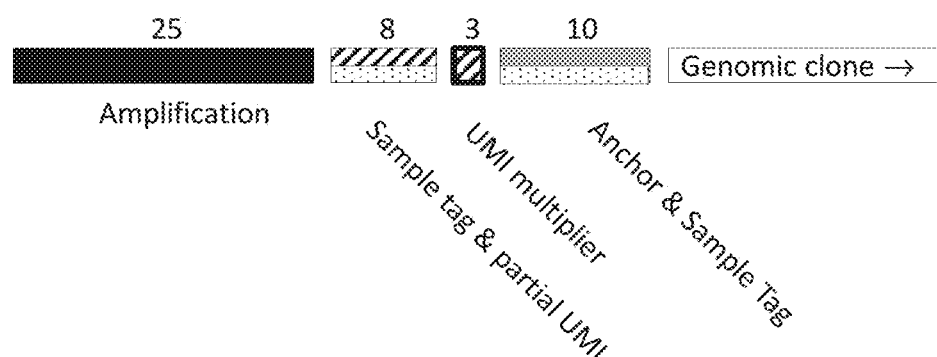
FIG. 5A-FIG. 5B shows a diagram illustrating that shifting the position of the UMI multiplier within the sample tag can increase the number of unique sample tags.
Figure 5B:
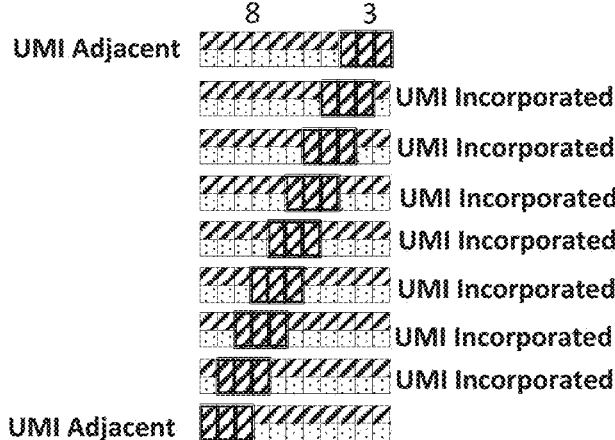
Figure 6A:
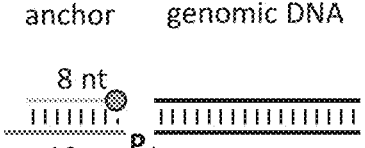
FIG. 6A and FIG. 6B shows a diagram illustrating the process of constructing genomic libraries for a CNL assay.
Figure 6B:
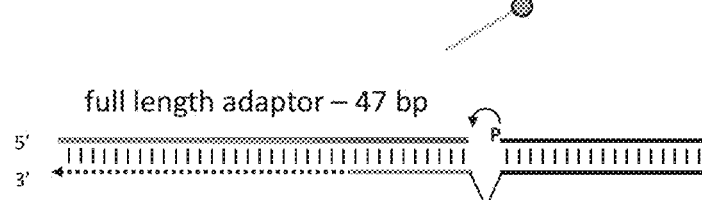

In particular embodiments, the adaptor comprises a UMI wherein the UMI multiplier is adjacent to or contained within the sample tag region (FIG. 5A). Illustrative examples of UMI multipliers adjacent or contained within the sample tag are shown in FIG. 5B. In FIG. 5B, an 8-mer sample tag region is shown with an adjacent UMI multiplier (top and bottom rows) or a UMI multiplier incorporated within the sample tag (middle 7 rows). In some embodiments, that adaptor comprises a sample tag that is eight nucleotides in length and a UMI multiplier that is three nucleotides in length and comprises one of 64 possible sequences, and wherein the UMI multiplier is adjacent to or contained within the sample tag region. In some embodiments, identical processes attach full length adaptor to the other end of the genomic fragments.

In particular embodiments, an adaptor module comprises one or more anchor sequences. As used herein, an "anchor region" and "anchor sequence" are used interchangeably and refer to a nucleotide sequence that hybridizes to a partner oligonucleotide. In some embodiments, the anchor region comprises the following three properties: (1) each anchor sequence is part of a family of two or more anchor sequences that collectively represent each of the four possible DNA bases at each site within extension; this feature, balanced base representation, is useful to calibrate proper base calling in sequencing reads in particular embodiments; (2) each anchor sequence is composed of only two of four possible bases, and these are specifically chosen to be either and equal number of A+C or an equal number of G+T; an anchor sequence formed from only two bases reduces the possibility that the anchor sequence will participate in secondary structure formation that would preclude proper adaptor function; and (3) because each anchor sequence is composed of equal numbers of A+C or G+T, each anchor sequence shares roughly the same melting temperature and duplex stability as every other anchor sequence in a set of four.

In some embodiments, the anchor sequences is between 1 and 50 nucleotides in length. In some embodiments, the anchor sequences is between 4 and 40 nucleotides in length. In certain embodiments, the anchor region is between 5 and 25 nucleotides in length. In particular embodiments, the anchor region is at least 4 nucleotides, at least six nucleotides, at least 8 nucleotides, at least 10 nucleotides, at least 12 nucleotides, at least 14 nucleotides, or at least 16 nucleotides in length. In particular embodiments, the anchor region is 10 nucleotides in length.

In particular embodiments, an attachment step comprises attaching/ligating an adaptor module to the end-repaired ctDNA or cellular DNA to generate a "tagged" genomic DNA library. In some embodiments, a single adaptor module is employed. In some embodiments, two, three, four or five adaptor modules are employed. In some embodiments, an adaptor module of identical sequence is attached to each end of the fragmented end-repaired DNA.

In some embodiments, a plurality of adaptor species is attached to an end-repaired cellular or cell free genomic DNA fragments. Each of the plurality of adaptors may comprise one or more amplification regions for the amplification of the cfDNA or cellular DNA library, one or more sample tag regions for the identification of the cfDNA or cellular genomic DNA fragment and identification of the individual sample; and one or more sequences for DNA sequencing.

In some embodiments, a plurality of adaptor species is attached to an end-repaired cellular or cell free genomic DNA fragments of a sample, and the plurality of adaptors all comprise amplification regions of an identical nucleotide sequence.

In certain embodiments, the genomic DNA from a sample is attached with a plurality of adaptors that comprise sample tag sequences that all are different from other sequences of sample tag regions in adaptors that are attached to genomic DNA fragments from other samples.

In particular embodiments, a plurality of adaptor species is attached to an end-repaired cellular or cell free genomic DNA fragments from a sample, and the plurality of adaptors all comprise one or more sample tag regions comprising one of between 2 and 10,000 nucleotide sequences, one of between 5 and 5,000 nucleotide sequences, one of between 25 and 1,000 nucleotide sequences, one of between 50 and 500 nucleotide sequences, one of between 100 and 400 nucleotide sequences, or one of between 200 and 300 nucleotide sequences. In some embodiments, the sample tag region of each adaptor is 8 nucleotides in length, and each sample tag region of the plurality of adaptors comprises one of 240 nucleotide sequences.

In certain embodiments, a plurality of adaptor species is attached to an end-repaired cellular or cell free genomic DNA fragments from a sample, and the sample tag regions of the plurality of adaptors comprises nucleotide sequences that are different from each other by a Hamming distance of 1, 2, 3, 4 or greater than 4. In particular embodiments, the Hamming distance is 2.

In particular embodiments, the sample tag regions of the plurality of adaptors that are attached to genomic DNA fragments of a sample are 8 nucleotides in length, and comprise one of 240 nucleotide sequences that are different from each other by a Hamming distance of 2.

In certain embodiments, the sample tag region serves to identify individual genomic. DNA fragments and to identify the individual sample, i.e., the genomic library source. For example, when the sample tags of a plurality of adaptors attached to a sample have one of 240 possible sequences, each sample is identified as having one of 240 possible tags, and each sample receives a set of 240 tags that are discrete from any other sample by Hamming distance of two (meaning two base changes are required to change one tag into another). These same tags are used to enumerate clone diversity and thus they also serve as sequence tags, i.e., to identify genomic DNA fragments. To further augment the diversity of possible sequence tags, UMI multipliers may be added. For example, a UMI multiplier can be added to the adaptor region comprising 3 nucleotides consisting of the 64 possible combinations of 3 bases. In addition, the plurality of adaptors can comprise more than one anchor sequence. For example, a plurality of adaptors may contain 4 different anchor sequences are used simultaneously. These anchor sequences may also be used during sample de-multiplexing to lower errors.

Figure 4A:
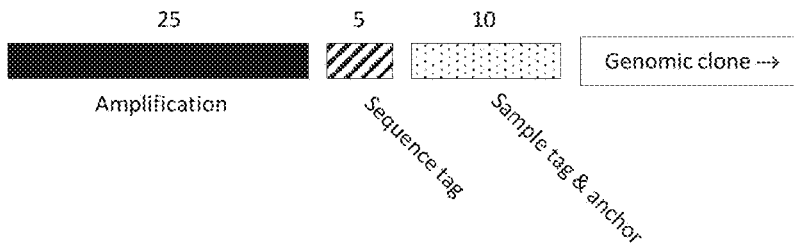
FIG. 4A FIG. 4E shows diagrams of an illustrative first generation adaptor (FIG. 4A and FIG. 4B) and an adaptor of the present invention (FIGS. 4C-FIG. 4E).
Figure 4B:
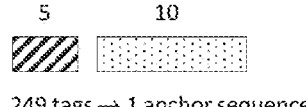
FIG. 4B shows that in the first generation adaptors, there were a collection of 249 possible sequence tags, each 5 nucleotides (nt) in length that attached to a single anchor sequence.
Figure 4C:
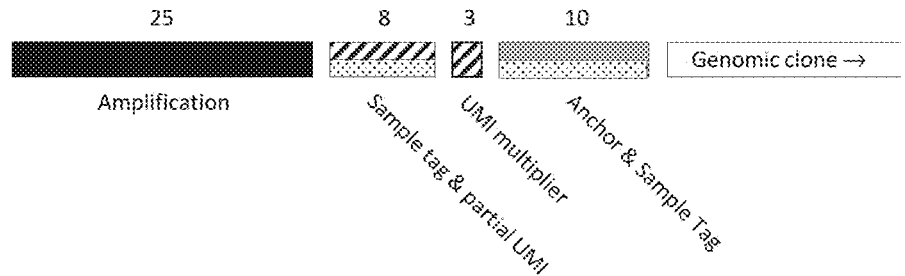
FIG. 4C shows a diagram of a second generation adaptor.
Figure 4D:
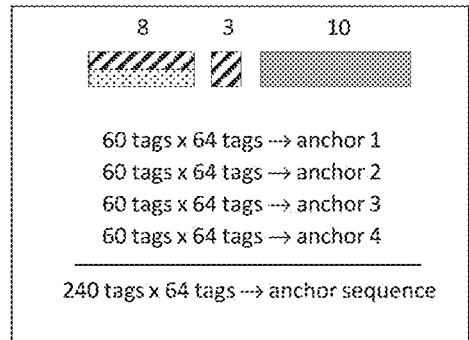
FIG. 4D shows an illustrative set of adaptors that are applied to a single sample that consists of four sets of 8 mer tag sequences with each set having 60 members. Each set of 60 tags is specific to one of four anchor sequences.
Figure 4E:
Figures 1, 23A, 23B, 23C:
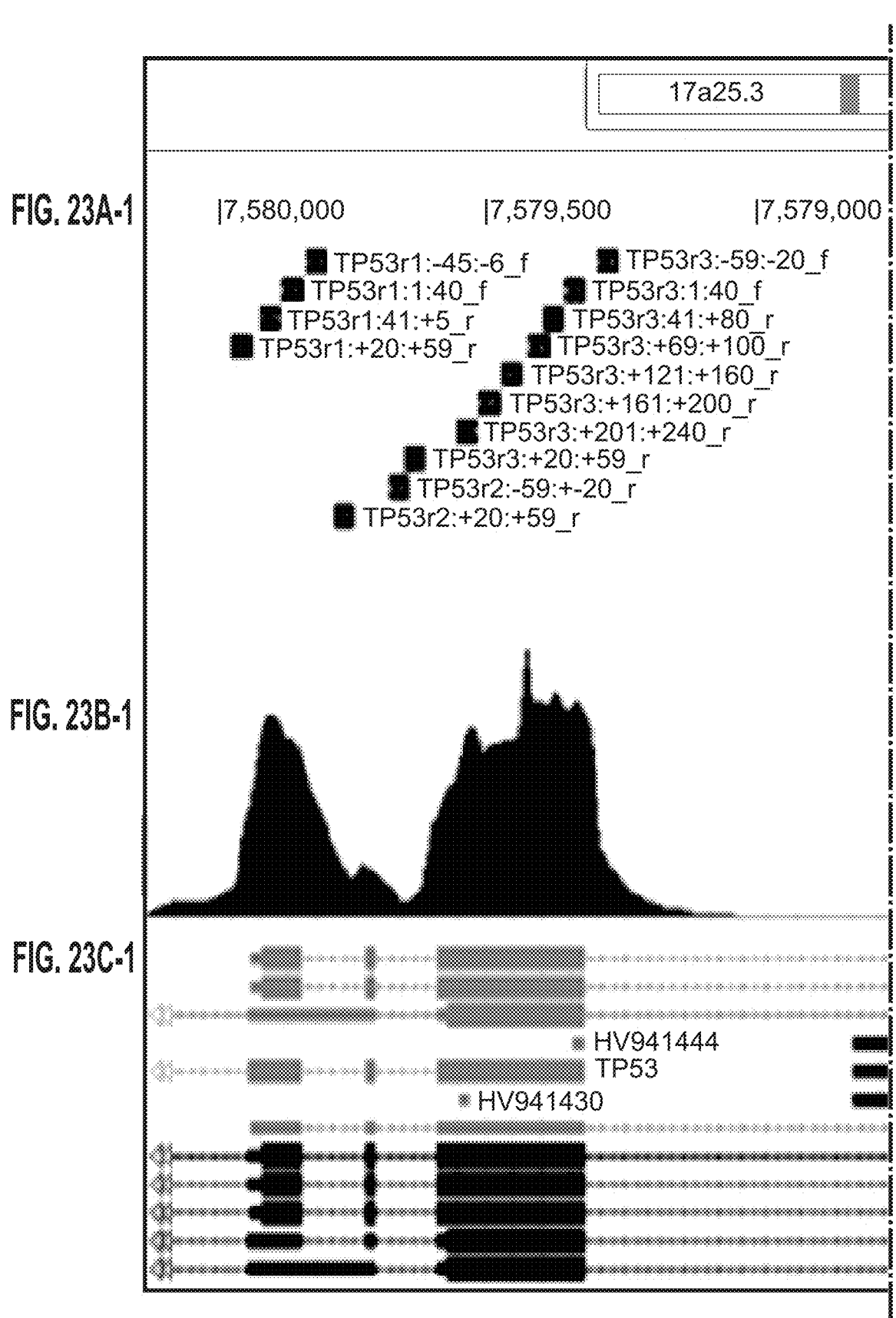
Figures 2, 23A, 23B, 23C:
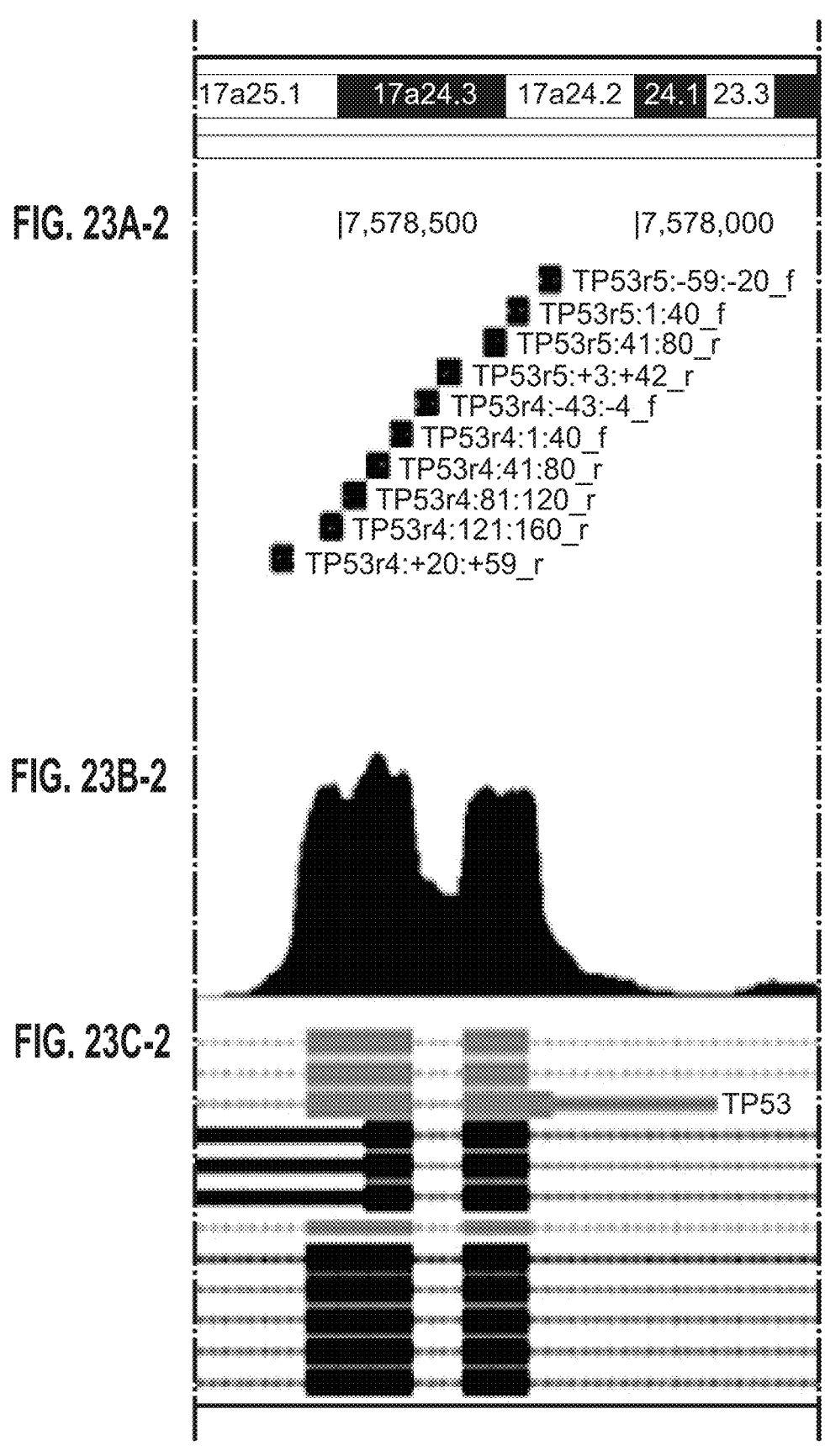
Figures 3, 23A, 23B, 23C:
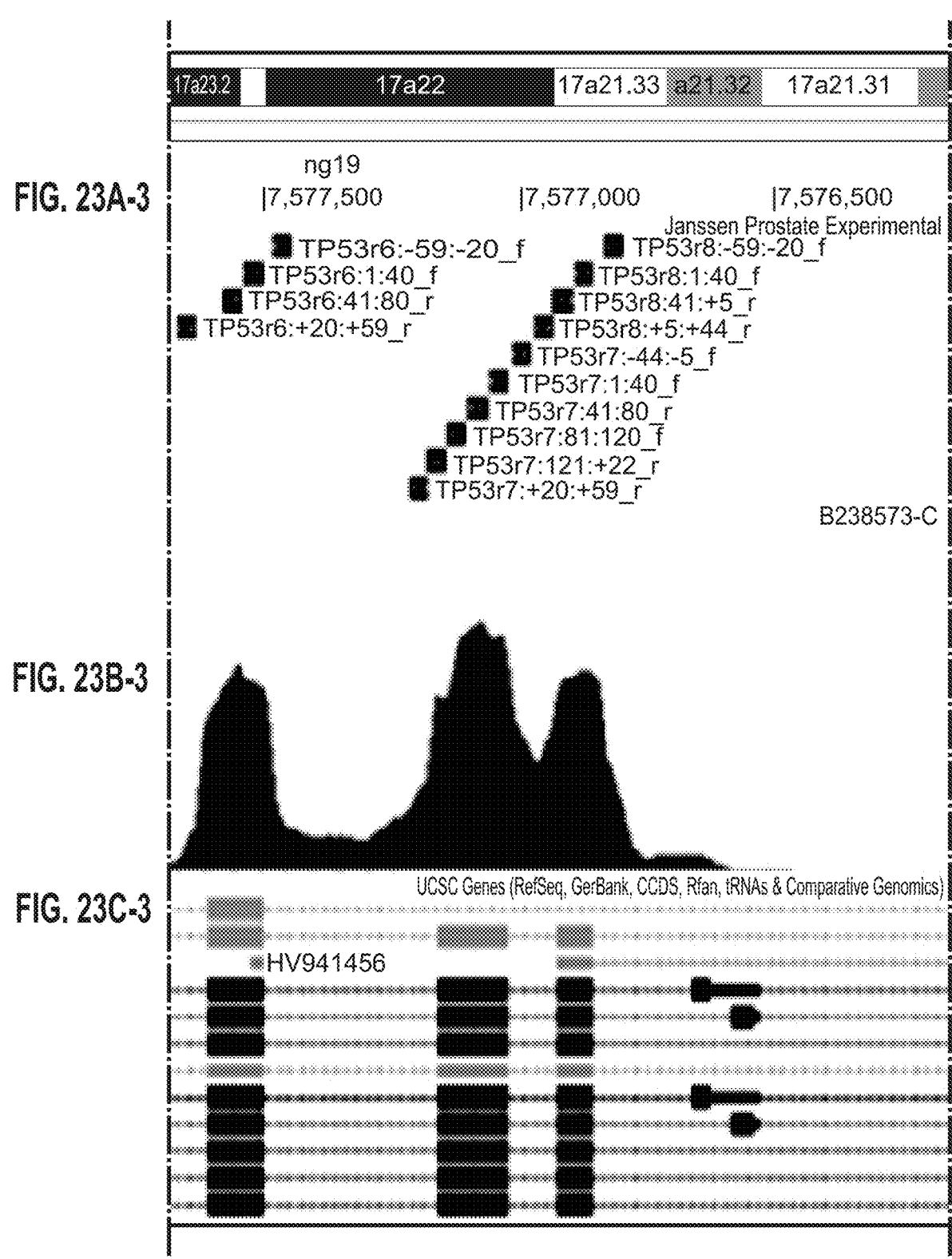
Figures 4, 23A, 23B, 23C:
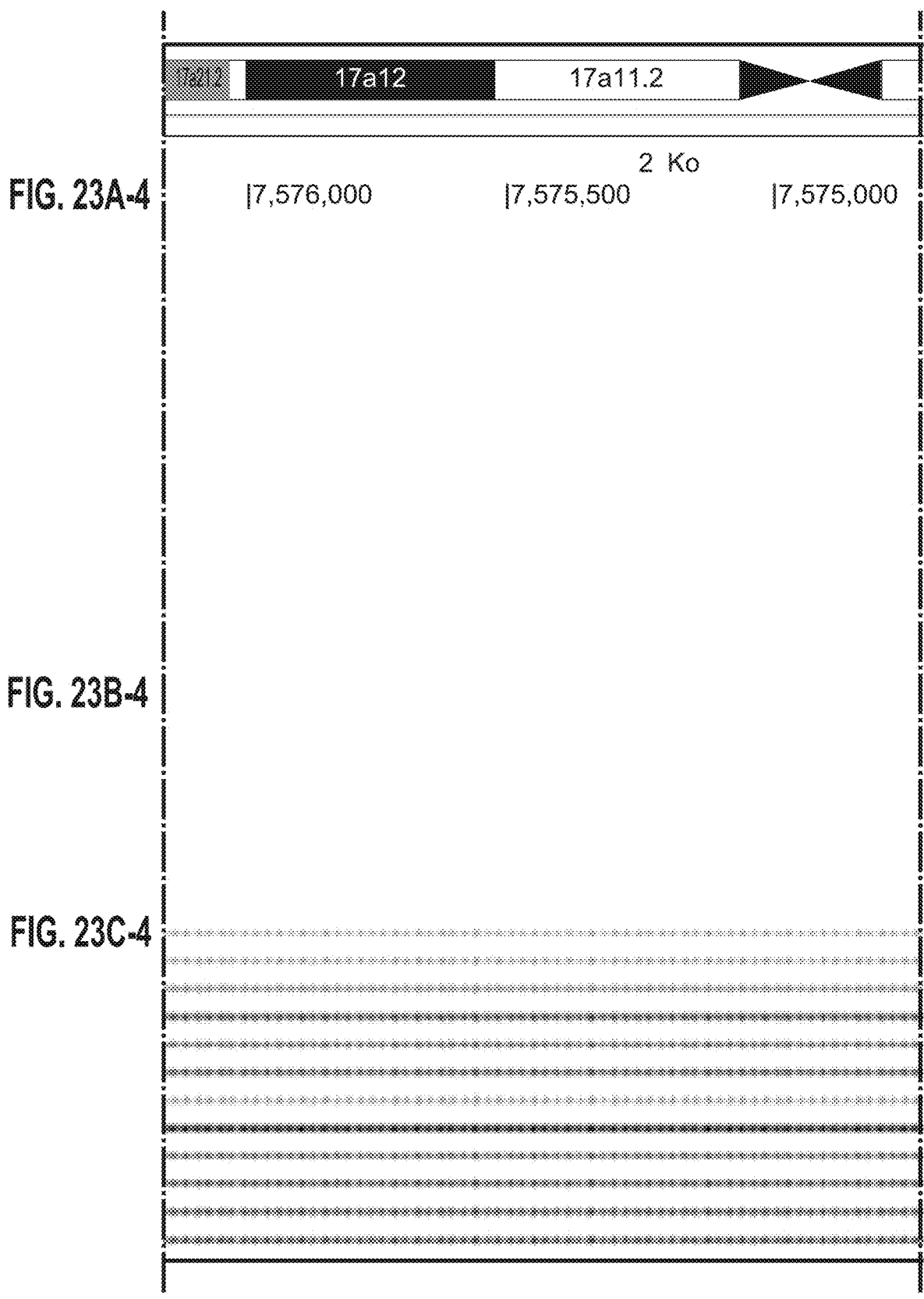
Figures 5, 23A, 23B, 23C:
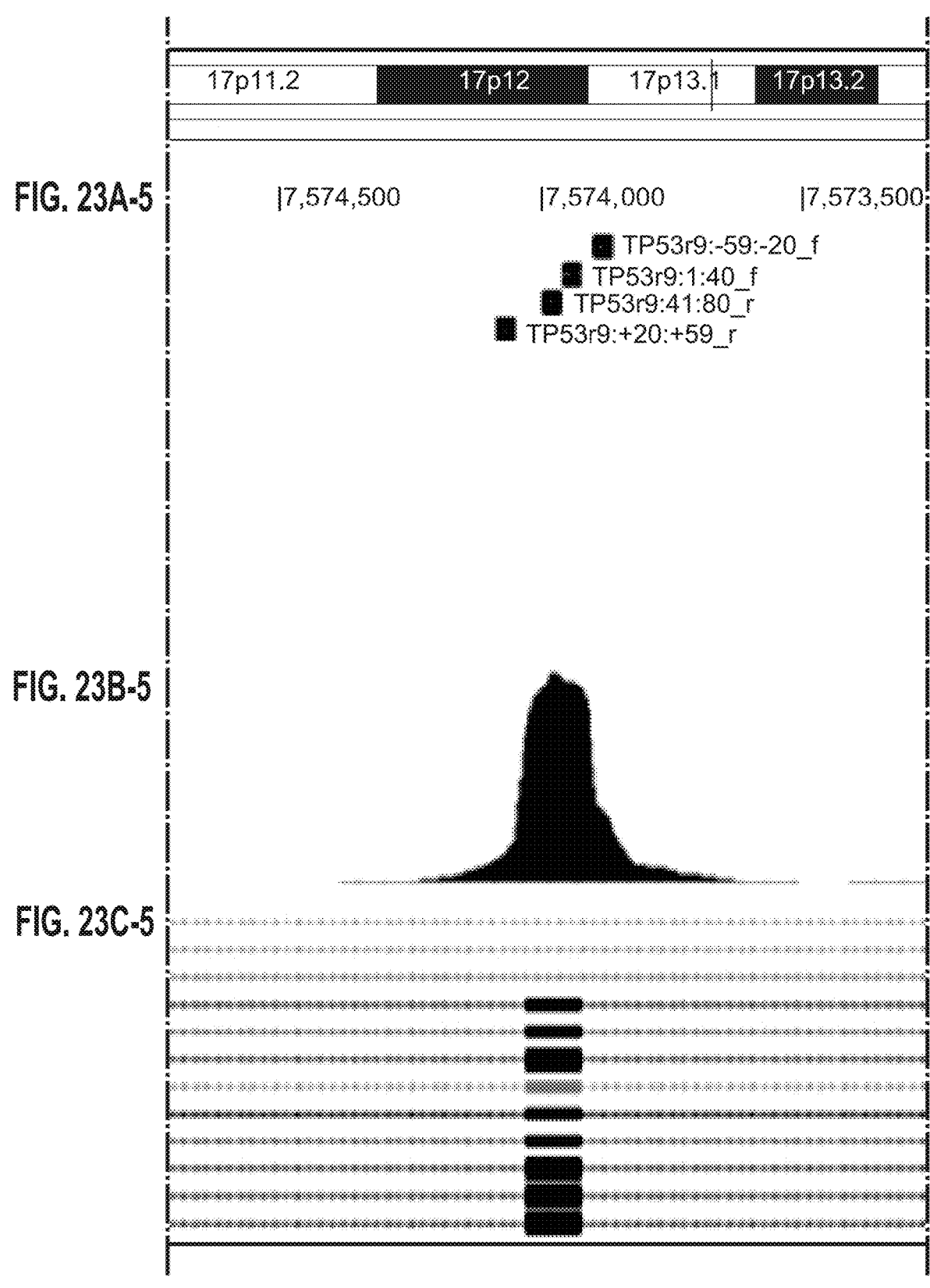

FIG. 4 shows an illustrative comparison between a first generation adaptor (FIGS. 4A and 4B) and an adaptor of the present invention (FIG. 4C—FIG. 4E). FIG. 4A and FIG. 4B show an example of first generation adaptor that is 40 nt in length and consisted of a discrete PCR amplification sequence, sequence tag, and sample tag. Here, the sample is identified by a fixed sequence (sequence tag) that is present on all adaptors that are used to generate a DNA library from the sample. Individual genomic fragments are identified by a separate and distinct sequences (sequence tag). FIG. 4C—FIG. 4E show an illustrative example of an adaptor from the present invention. The illustrative adaptor shown is 47 nucleotides in length, and the sequence tag is combined with the sample tag. There is an additional 3 nt sequence, the UMI multiplier, consisting of the 64 possible combinations of 3 bases. The 10 nt anchor sequence is one of four different distinct sequences.

Thus, in the illustrative example (See FIG. 4C-FIG. 4E), a set of adaptors that are used in connection with a single sample comprise 240 sample tag sequences that can be split into four sets of sample tag sequences with each set comprising 60 tags (one for each nucleotide, A, C, T and G). Thus, each set of 60 tags is specific to one of four anchor sequences. In total, a pool of 240 possible sample tag configurations are possible per sample. Specifically, in this scenario, the 240 sample tag sequences are divided into four sets of 60 sequences, with each set directed to a specific anchor region. Therefore, the sample ID involves not only the sequence information from the eight nucleotide sample tag, but also the associated anchor sequence information. In addition, the position of sequences within the read is fixed, and therefore the sample tags and anchor sequences must have a fixed position within a sequencing read in order to pass inclusion filters for downstream consideration. Further, the inclusion of the UMI multiplier increases the sequence tag diversity from 240 to 240×64=15,360 possible sequence tags.

Attachment of one or more adaptors contemplated herein may be carried out by methods known to those of ordinary skill in the art. In particular embodiments, one or more adaptors contemplated herein are attached to end-repaired cfDNA that comprises blunt ends. In certain embodiments, one or more adaptors contemplated herein are attached to end-repaired cfDNA that comprises complementary ends appropriate for the attachment method employed. In certain embodiments, one or more adaptors contemplated herein are attached to end-repaired cfDNA that comprises a 3' overhang.

In some embodiments, attaching the genomic DNA fragments to a plurality of adaptors includes the steps of attaching the end repaired cfDNA or cellular DNA fragments to an oligonucleotide containing at least a portion of an anchor region. In some embodiments, the oligonucleotide contains the whole anchor region. In particular embodiments, the oligonucleotide is a DNA duplex comprising a 5' phosphorylated attachment strand duplexed with a partner strand, wherein the partner strand is blocked from attachment by chemical modification at its 3' end, and wherein the attachment strand is attached to the genomic DNA fragment. In certain embodiments, the DNA fragments attached with at least a portion of the anchor region are then annealed with DNA oligonucleotides encoding the full length adaptor sequences. In particular embodiments, one or more polynucleotide kinases, one or more DNA ligases, and/or one or more DNA polymerases are added to the genomic DNA fragments and the DNA oligonucleotides encoding the full length adaptor sequence. In some embodiments, the polynucleotide kinase is T4 polynucleotide kinase. In some embodiments, the DNA ligase is Taq DNA ligase. In certain embodiments, the DNA polymerase is Taq polymerase. In particular embodiments, the DNA polymerase is full length Bst polymerase.

Figures 6, 23A, 23B, 23C:
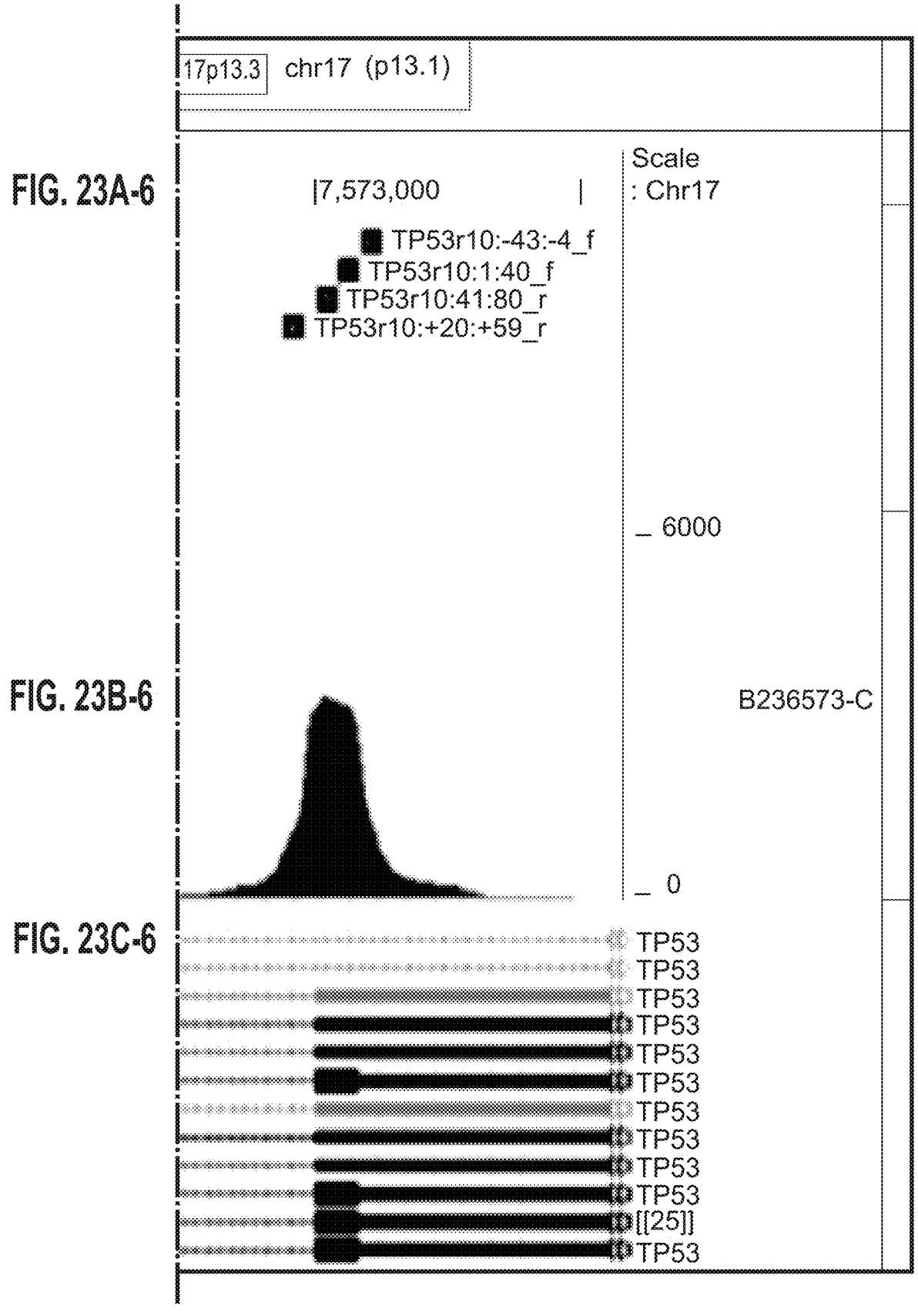

FIG. 6 shows an illustrative method for attaching a plurality of adaptors to the 3' end of repaired DNA fragments. In the first step, the anchor sequence is attached to the 3' ends of genomic fragments. In this step, the anchor portion is a DNA duplex in which the ten nucleotide 5' phosphorylated "attachment strand" is duplexed with an eight nucleotide "partner strand" that is blocked from attachment by chemical modification at its 3' end. The anchor duplex is blunt-ended on the phosphorylated/blocked end and can therefore attach to blunt-ended genomic fragments. In the next step, pools of oligonucleotides encoding the full adaptor sequences are annealed to the initial anchor sequence. The combined action of T4 polynucleotide kinase, Taq DNA ligase, and full-length Bst polymerase attach this oligonucleotide via ligation as illustrated for the top strand and extend the initial anchor sequence by DNA polymerization on the bottom strand to complete the full-length adaptor sequence. Identical processes may be used to attach full length adaptors to the 5' end of the genomic fragments.

2. DNA Library Amplification

In particular embodiments, methods of genetic analysis contemplated herein comprise amplification of a genomic DNA library, e.g. a cellular DNA library or a cfDNA library, to generate a DNA clone library or a library of DNA clones, e.g., a cfDNA clone library or a library of cfDNA clones, or a cellular DNA clone library or a library of cellular DNA clones. Each molecule of the DNA library comprises an adaptor attached to each end of an end-repaired DNA fragments, and each adaptor comprises one or more amplification regions. In some embodiments, different adaptors are attached to different ends of the end-repaired cfDNA. In particular embodiments, different adaptors are attached to different ends of the end-repaired cellular DNA.

In some embodiments, the same adaptor is attached to both ends of the DNA fragment. Attachment of the same adaptor to both ends of end-repaired DNA allows for PCR amplification with a single primer sequence. In particular embodiments, a portion of the adaptor attached-cfDNA library will be amplified using standard PCR techniques with a single primer sequence driving amplification. In one embodiment, the single primer sequence is about 25 nucleotides, optionally with a projected Tm of ≥55° C. under standard ionic strength conditions.

In particular embodiments, picograms of the initial genomic DNA library, e.g. a cellular DNA library or cfDNA library, are amplified into micrograms of DNA clones, implying a 10,000-fold amplification. The amount of amplified product can be measured using methods known in the art, e.g., quantification on a Qubit 2.0 or Nanodrop instrument.

3. Determining the Number of Genome Equivalents

In various embodiments, a method for genetic analysis of genomic DNA comprises determining the number of genome equivalents in the DNA clone library. As used herein, the term "genome equivalent" refers to the number of genome copies in each library. An important challenge met by the compositions and methods contemplated herein is achieving sufficient assay sensitivity to detect and analysis rare genetic mutations or differences in genetic sequence. To determine assay sensitivity value on a sample-by-sample basis, the numbers of different and distinct sequences that are present in each sample are measured by measuring the number of genome equivalents that are present in a sequencing library. To establish sensitivity, the number of genome equivalents must be measured for each sample library.

The number of genome equivalents can be determined by qPCR assay or by using bioinformatics-based counting after sequencing is performed. In the process flow of clinical samples, qPCR measurement of genome equivalents is used as a QC step for DNA libraries, e.g., cfDNA libraries or genomic DNA libraries. It establishes an expectation for assay sensitivity prior to sequence analysis and allows a sample to be excluded from analysis if its corresponding DNA clone library lacks the required depth of genome equivalents. Ultimately, the bioinformatics-based counting of genome equivalents is also used to identify the genome equivalents—and hence the assay sensitivity and false negative estimates—for each given DNA clone library.

The empirical qPCR assay and statistical counting assays should be well correlated. In cases where sequencing fails to reveal the sequence depth in a DNA clone library, reprocessing of the DNA clone library and/or additional sequencing may be required.

In one embodiment, the genome equivalents in a cellular DNA or cfDNA clone library are determined using a quantitative PCR (qPCR) assay. In a particular embodiment, a standard library of known concentration is used to construct a standard curve and the measurements from the qPCR assay are fit to the resulting standard curve and a value for genome equivalents is derived from the fit. The present inventors have discovered that a qPCR "repeat-based" assay comprising one primer that specifically hybridizes to a common sequence in the genome, e.g., a repeat sequence, and another primer that binds to the primer binding site in the adaptor, measured an 8-fold increase in genome equivalents compared to methods using just the adaptor specific primer (present on both ends of the cfDNA clone). The number of genome equivalents measured by the repeat-based assays provides a more consistent library-to-library performance and a better alignment between qPCR estimates of genome equivalents and bioinformatically counted tag equivalents in sequencing runs.

Illustrative examples of repeats suitable for use in the repeat-based genome equivalent assays contemplated herein include, but not limited to: short interspersed nuclear elements (SINES), e.g., Alu repeats; long interspersed nuclear elements (LINEs), LINE1, LINE2, LINE3; microsatellite repeat elements, e.g., short tandem repeats (STRs), simple sequence repeats (SSRs); and mammalian-wide interspersed repeats (MIRs).

In one embodiment, the repeat is an Alu repeat.

4. Quantitative Genetic Analysis

In various embodiments, a method for genetic analysis of genomic DNA, e.g., genomic cellular or cfDNA, comprises quantitative genetic analysis of one or more target genetic loci of the DNA library clones. Quantitative genetic analysis comprises one or more of, or all of, the following steps: capturing DNA clones comprising a target genetic locus; amplification of the captured targeted genetic locus; sequencing of the amplified captured targeted genetic locus; and bioinformatic analysis of the resulting sequence reads. As used herein, the terms "DNA library clone" refer to a DNA library fragment wherein the combination of the adaptor and the genomic DNA fragment result in a unique DNA sequence (e.g., a DNA sequence that can be distinguished from that of another DNA library clone).

(a) Capture of Target Genetic Locus

The present invention contemplates, in part, a capture probe module designed to retain the efficiency and reliability of larger probes but that minimizes uninformative sequence generation in a genomic DNA library that comprises smaller DNA fragments, e.g., a cfDNA clone library. A "capture probe" or "capture probe module" as used herein, are used interchangeably and refer to a polynucleotide that comprises a capture probe sequence and a tail sequence. In particular embodiments, the capture probe module sequence or a portion thereof serves as a primer binding site for one or more sequencing primers.

In particular embodiments, a capture probe module comprises a capture probe. As used herein a "capture probe"

refers to a region capable of hybridizing to a specific DNA target region. In some embodiments, the capture probes are used with genomic DNA library constructed from cellular DNA. In particular embodiments, the capture probes are used with genomic DNA library constructed from cDNA. Because the average size of cfDNA is about 150 to about 170 bp and is highly fragmented, certain embodiments are directed compositions and methods contemplated herein comprise the use of high density and relatively short capture probes to interrogate DNA target regions of interest. In some embodiments, the capture probes are capable of hybridizing to DNA target regions that are distributed across all chromosomal segments at a uniform density. A set of such capture probes is referred to herein as "chromosomal stability probes." Chromosomal stability probes are used to interrogate copy number variations on a genome-wide scale in order to provide a genome-wise measurement of chromosomal copy number (e.g., chromosomal ploidy).

One particular concern with using high density capture probes is that generally capture probes are designed using specific "sequence rules." For example, regions of redundant sequence or that exhibit extreme base composition biases are generally excluded in designing capture probes. However, the present inventors have discovered that the lack of flexibility in capture probe design rules does not substantially impact probe performance. In contrast, capture probes chosen strictly by positional constraint provided on-target sequence information; exhibit very little off-target and unmappable read capture; and yield uniform, useful, on-target reads with only few exceptions. Moreover, the high redundancy at close probe spacing more than compensates for occasional poor-performing capture probes.

In particular embodiments, a target region is targeted by a plurality of capture probes, wherein any two or more capture probes are designed to bind to the target region within 10 nucleotides of each other, within 15 nucleotides of each other, within 20 nucleotides of each other, within 25 nucleotides of each other, within 30 nucleotides of each other, within 35 nucleotides of each other, within 40 nucleotides of each other, within 45 nucleotides of each other, or within 50 nucleotides or more of each other, as well as all intervening nucleotide lengths.

In one embodiment, the capture probe is about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, or about 45 nucleotides.

In one embodiment, the capture probe is about 100 nucleotides, about 200 nucleotides, about 300 nucleotides, about 400 nucleotides, or about 100 nucleotides. In another embodiment, the capture probe is from about 100 nucleotides to about 500 nucleotides, about 200 nucleotides to about 500 nucleotides, about 300 nucleotides to about 500 nucleotides, or about 400 nucleotides to about 500 nucleotides, or any intervening range thereof.

In a particular embodiment, the capture probe is 60 nucleotides. In another embodiment, the capture probe is substantially smaller than 60 nucleotides but hybridizes comparably, as well as, or better than a 60 nucleotide capture probe targeting the same DNA target region. In a certain embodiment, the capture probe is 40 nucleotides.

In certain embodiments, a capture probe module comprises a tail sequence. As used herein, the term "tail sequence" refers to a polynucleotide at the 5' end of the capture probe module, which in particular embodiments can serve as a primer binding site. In particular embodiments, a sequencing primer binds to the primer binding site in the tail region.

In particular embodiments, the tail sequence is about 5 to about 100 nucleotides, about 10 to about 100 nucleotides, about 5 to about 75 nucleotides, about 5 to about 50 nucleotides, about 5 to about 25 nucleotides, or about 5 to about 20 nucleotides. In certain embodiments, the third region is from about 10 to about 50 nucleotides, about 15 to about 40 nucleotides, about 20 to about 30 nucleotides or about 20 nucleotides, or any intervening number of nucleotides.

In particular embodiments, the tail sequence is about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, or about 40 nucleotides.

In various embodiments, the capture probe module comprises a specific member of a binding pair to enable isolation and/or purification of one or more captured fragments of a tagged and or amplified genomic DNA library (e.g., a cellular or cfDNA library) that hybridizes to the capture probe. In particular embodiments, the capture probe module is conjugate to biotin or another suitable hapten, e.g., dinitrophenol, digoxigenin.

In various embodiments, the capture probe module is hybridized to a tagged and optionally amplified DNA library to form a complex. In some embodiments, the multifunctional capture probe module substantially hybridizes to a specific genomic target region in the DNA library.

Hybridization or hybridizing conditions can include any reaction conditions where two nucleotide sequences form a stable complex; for example, the tagged DNA library and capture probe module forming a stable tagged DNA library capture probe module complex. Such reaction conditions are well known in the art and those of skill in the art will appreciated that such conditions can be modified as appropriate, e.g., decreased annealing temperatures with shorter length capture probes, and within the scope of the present invention. Substantial hybridization can occur when the second region of the capture probe complex exhibits 100%, 99%, 98%, 97%, 96%, 95%, 94%, 93%, 92%, 91%, 90%, 89%, 88%, 85%, 80%, 75%, or 70% sequence identity, homology or complementarily to a region of the tagged DNA library.

In particular embodiments, the capture probe is about 40 nucleotides and has an optimal annealing temperature of about 44° C. to about 47° C.

In certain embodiments, the methods contemplated herein comprise isolating a tagged cfDNA library—capture probe module complex. In particular embodiments, methods for isolating DNA complexes are well known to those skilled in the art and any methods deemed appropriate by one of skill in the art can be employed with the methods of the present invention (Ausubel et al., *Current Protocols in Molecular Biology*, 2007-2012). In particular embodiments, the complexes are isolated using biotin—streptavidin isolation techniques.

In particular embodiments, removal of the single stranded 3'-ends from the isolated tagged DNA library fragments-capture probe module complex is contemplated. In certain embodiments, the methods comprise 3'-5' exonuclease enzymatic processing of the isolated tagged DNA library-multifunctional capture probe module complex to remove the single stranded 3' ends.

In certain other embodiments, the methods comprise performing DNA polymerase extension of multifunctional capture probe utilizing the isolated tagged DNA library fragments as template.

In certain other embodiments, the methods comprise creating a hybrid capture probe-isolated tagged DNA target molecule, e.g., a tagged cfDNA target molecule or a tagged cellular DNA target molecule, through the concerted action of a 5' FLAP endonuclease, DNA polymerization and nick closure by a DNA ligase.

A variety of enzymes can be employed for the 3'-5' exonuclease enzymatic processing of the isolated tagged DNA library-multifunctional capture probe module complex. Illustrative examples of suitable enzymes, which exhibit 3'-5' exonuclease enzymatic activity, that can be employed in particular embodiments include, but are not limited to: T4 or Exonucleases I, III, V (See also, Shevelev IV, Hübscher U., *Nat Rev Mol Cell Biol.* 3(5):364-76 (2002)). In particular embodiments, the enzyme comprising 3'-5' exonuclease activity is T4 polymerase. In particular embodiments, an enzyme which exhibits 3'-5' exonuclease enzymatic activity and is capable of primer template extension can be employed, including for example T4 or Exonucleases I, III, V, Id.

In some embodiments, the methods contemplated herein comprise performing sequencing and/or PCR on the 3'-5' exonuclease enzymatically processed complex discussed supra and elsewhere herein. In particular embodiments, a tail portion of a capture probe molecule is copied in order to generate a hybrid nucleic acid molecule. In one embodiment, the hybrid nucleic acid molecule generated comprises the target region capable of hybridizing to the capture probe module and the complement of the capture probe module tail sequence.

In a particular embodiment, genetic analysis comprises a) hybridizing one or more capture probe modules to one or more target genetic loci in a plurality of genomic DNA library clones to form one or more capture probe module-DNA library clone complexes; b) isolating the one or more capture probe module-DNA library clone complexes from a); c) enzymatically processing the one or more isolated capture probe module-DNA library clone complexes from step b); d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genomic locus capable of hybridizing to the capture probe and the complement of the capture probe module tail sequence; and e) performing quantitative genetic analysis on the amplified hybrid nucleic acid molecules from d).

In a particular embodiment, methods for determining copy number of a specific target genetic locus are contemplated comprising: a) hybridizing one or more capture probe modules to one or more target genetic loci in a plurality of DNA library clones to form one or more capture probe module-DNA library clone complexes; b) isolating the one or more capture probe module-DNA library clone complexes from a); c) enzymatically processing the one or more isolated capture probe module-DNA library clone complexes from step b); d) performing PCR on the enzymatically processed complex from c) wherein the tail portion of the capture probe molecule is copied in order to generate amplified hybrid nucleic acid molecules, wherein the amplified hybrid nucleic acid molecules comprise a target sequence in the target genetic locus capable of hybridizing to the capture probe and the complement of the capture probe module tail sequence; e) performing PCR amplification of the amplified hybrid nucleic acid molecules in d); and f) quantitating the PCR reaction in e), wherein the quantitation allows for a determination of copy number of the specific target region.

In one embodiment, the enzymatic processing of step c) comprises performing 3'-5" exonuclease enzymatic processing on the one or more capture probe module-DNA library clone complexes from h) using an enzyme with 3'-5' exonuclease activity to remove the single stranded 3' ends; creating one or more hybrid capture probe module-cfDNA library clone molecules through the concerted action of a 5' FLAP endonuclease, DNA polymerization and nick closure by a DNA ligase; or performing 5'-3' DNA polymerase extension of the capture probe using the isolated DNA clone in the complex as a template.

In one embodiment, the enzymatic processing of step c) comprises performing 5'-3' DNA polymerase extension of the capture probe using the isolated DNA clone in the complex as a template.

In particular embodiments, PCR can be performed using any standard PCR reaction conditions well known to those of skill in the art. In certain embodiments, the PCR reaction in e) employs two PCR primers. In one embodiment, the PCR reaction in e) employs a first PCR primer that hybridizes to a repeat within the target genetic locus. In a particular embodiment, the PCR reaction in e) employs a second PCR primer that hybridizes to the hybrid nucleic acid molecules at the target genetic locus/tail junction. In certain embodiments, the PCR reaction in e) employs a first PCR primer that hybridizes to the target genetic locus and a second PCR primer hybridizes to the amplified hybrid nucleic acid molecules at the target genetic locus/tail junction. In particular embodiments, the second primer hybridizes to the target genetic locus/tail junction such that at least one or more nucleotides of the primer hybridize to the target genetic locus and at least one or more nucleotides of the primer hybridize to the tail sequence.

In certain embodiments, the amplified hybrid nucleic acid molecules obtained from step e) are sequenced and the sequences aligned horizontally, i.e., aligned to one another but not aligned to a reference sequence. In particular embodiments, steps a) through e) are repeated one or more times with one or more capture probe modules. The capture probe modules can be the same or different and designed to target either cfDNA strand of a target genetic locus. In some embodiments, when the capture probes are different, they hybridize at overlapping or adjacent target sequences within a target genetic locus in the tagged cfDNA clone library. In one embodiment, a high density capture probe strategy is used wherein a plurality of capture probes hybridize to a target genetic locus, and wherein each of the plurality of capture probes hybridizes to the target genetic locus within about 5, 10, 15, 20, 25, 30, 35, 40, 45, 50, 100, 200 bp or more of any other capture probe that hybridizes to the target genetic locus in a tagged DNA clone library, including all intervening distances.

In some embodiments, the method can be performed using two capture probe modules per target genetic locus, wherein one hybridizes to the "Watson" strand (non-coding or template strand) upstream of the target region and one hybridizes to the "Crick" strand (coding or non-template strand) downstream of the target region.

In particular embodiments, the methods contemplated herein can further be performed multiple times with any number of capture probe modules, for example 2, 3, 4, 5, 6, 7, 8, 9, or 10 or more capture probe modules per target genetic locus any number of which hybridize to the Watson or Crick strand in any combination. In some embodiments, the sequences obtained can be aligned to one another in order to identify any of a number of differences.

In certain embodiments, a plurality of target genetic loci are interrogated, e.g., 100, 200, 300, 400, 500, 600, 700, 800, 900, 1000, 1500, 2000, 2500, 3000, 3500, 4000, 4500, 5000, 10000, 50000, 100000, 500000 or more in a single reaction, using one or more capture probe modules.

(b) Sequencing

In particular embodiments, the quantitative genetic analysis comprises sequencing a plurality of hybrid nucleic acid molecules, as discussed elsewhere herein, supra, to generate sufficient sequencing depths to obtain a plurality of unique sequencing reads. The terms "unique reads" or "unique genomic sequences" (UGS) are used interchangeably herein and are identified by grouping individual redundant reads together into a "family." Redundant reads are sequence reads that share an identical UMIE (e.g., share the same read code and the same DNA sequence start position within genomic sequence) and are derived from a single attachment event and are therefore amplification-derived "siblings" of one another. A single consensus representative of a family of redundant reads is carried forward as a unique read or UGS. Each unique read or UGS is considered a unique attachment event. The sum of unique reads corresponding to a particular capture probe is referred to as the "raw genomic depth" (RGD) for that particular capture probe. Each capture probe yields a set of unique reads that are computationally distilled from total reads by grouping into families. The unique reads for a given sample (e.g., raw genomic depth for a sample) are then computed as the average of all the unique reads observed on a probe-by-probe basis. Unique reads are important because each unique read must be derived from a unique genomic DNA clone. Each unique read represents the input and analysis of a haploid equivalent of genomic DNA. The sum of unique reads is the sum of haploid genomes analyzed. The number of genomes analyzed, in turn, defines the sensitivity of the sequencing assay. By way of a non-limiting example, if the average unique read count is 100 genome equivalents, then that particular assay has a sensitivity of being able to detect one mutant read in 100, or 1%. Any observation less than this is not defensible.

Cases where there is an obvious copy number change (e.g., instances of noisy probes) are excluded from the data set used to compute the sample average. Herein, a "noisy probe" refers to a probe that captures a highly variable number of unique reads among a large set identical samples (e.g., a highly variable number of unique reads among 12-16 sample replicates). In some embodiments, the number of unique reads associated with a noisy probe is increased compared to the average number of unique reads for the sample by 50% or more. In some embodiments, the number of unique reads associated with a noisy probe is decreased compared to the average number of unique reads for the sample by 50% or more. In some embodiments, about 2% to about 4% of probes used in a particular analysis are identified as noisy probes and are excluded from calculations to determine the average number of unique reads for a given sample.

In some embodiments, sequencing reads are identified as either "on target reads" or "off-target reads." On-target reads possess a genomic DNA sequence that maps within the vicinity of a capture probe used to create the genomic library. In some embodiments, where each genomic sequence is physically linked to a specific capture probe and where the sequence of the genomic segment and capture probe are both determined as a unified piece of information, an on-target read is defined as any genomic sequence whose starting coordinate maps within 400 bp, and more generally within 200 bp of the 3' end of the corresponding capture probe. Off-target reads are defined as having genomic sequence that aligns to the reference genome at a location ≥500 base pairs (and more often mapping to entirely different chromosomes) relative to the capture probe.

In particular embodiments, the quantitative genetic analysis comprises multiplex sequencing of hybrid nucleic acid molecules derived from a plurality of samples.

In various embodiments, the quantitative genetic analysis comprises obtaining one or more or a plurality of tagged DNA library clones, each clone comprising a first DNA sequence and a second DNA sequence, wherein the first DNA sequence comprises a sequence in a targeted genetic locus and the second DNA sequence comprises a capture probe sequence; performing a paired end sequencing reaction on the one or more clones and obtaining one or more sequencing reads or performing a sequencing reaction on the one or more clones in which a single long sequencing read of greater than about 100, 200, 300, 400, 500 or more nucleotides is obtained, wherein the read is sufficient to identify both the first DNA sequence and the second DNA sequence; and ordering or clustering the sequencing reads of the one or more clones according to the probe sequences of the sequencing reads.

(c) Bioinformatics Analysis

In various embodiments, the quantitative genetic analysis further comprises bioinformatic analysis of the sequencing reads. Bioinformatic analysis excludes any purely mental analysis performed in the absence of a composition or method for sequencing. In certain embodiments, bioinformatics analysis includes, but is not limited to: sequence alignments; genome equivalents analysis; single nucleotide variant (SNV) analysis; gene copy number variation (CNV) analysis; measurement of chromosomal copy number; and detection of genetic lesions. In particular embodiments, bioinformatics analysis is useful to quantify the number of genome equivalents analyzed in the cfDNA clone library; to detect the genetic state of a target genetic locus; to detect genetic lesions in a target genetic locus; and to measure copy number fluctuations within a target genetic locus.

Sequence alignments may be performed between the sequence reads and one or more human reference DNA sequences. In particular embodiments, sequencing alignments can be used to detect genetic lesions in a target genetic locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease.

Also contemplated herein, are methods for sequence alignment analysis that can be performed without the need for alignment to a reference sequence, referred to herein as horizontal sequence analysis. Such analysis can be performed on any sequences generated by the methods contemplated herein or any other methods. In particular embodiments, the sequence analysis comprises performing sequence alignments on the reads obtained by the methods contemplated herein.

In one embodiment, the genome equivalents in a cfDNA clone library are determined using bioinformatics-based counting after sequencing is performed. Each sequencing read is associated with a particular capture probe, and the collection of reads assigned to each capture probe is parsed into groups. Within a group, sets of individual reads share the same read code and the same DNA sequence start position within genomic sequence. These individual reads are grouped into a "family" and a single consensus representative of this family is carried forward as a "unique read." All of the individual reads that constituted a family are derived from a single attachment event and thus, they are amplification-derived "siblings" of one another. Each unique read is considered a unique attachment event and the sum of unique reads is considered equivalent to the number of genome equivalents analyzed.

As the number of unique clones approaches the total number of possible sequence combinations, probability dictates that the same code and start site combinations will be created by independent events and that these independent events will be inappropriately grouped within single families. The net result will be an underestimate of genome equivalents analyzed, and rare mutant reads may be discarded as sequencing errors because they overlap with wild-type reads bearing the same identifiers.

In particular embodiments, to provide an accurate analysis for ctDNA clone libraries, the number of genome equivalents analyzed is about $\frac{1}{10}$, about $\frac{1}{12}$, about $\frac{1}{14}$, about $\frac{1}{16}$, about $\frac{1}{18}$, about $\frac{1}{20}$, about $\frac{1}{25}$ or less the number of possible unique clones. It should be understood that the procedure outlined above is merely illustrative and not limiting.

In some embodiments, the number of genome equivalents to be analyzed may need to be increased. To expand the depth of genome equivalents, at least two solutions are contemplated. The first solution is to use more than one adaptor set per sample. By combining adaptors, it is possible to multiplicatively expand the total number of possible clones and therefore, expand the comfortable limits of genomic input. The second solution is to expand the read code by 1, 2, 3, 4, or 5, or more bases. The number of possible read codes that differ by at least 2 bases from every other read code scales as $4^{(n-1)}$ where n is the number of bases within a read code. Thus, in a non-limiting example, if a read code is 5 nucleotides and $4^{(5-1)}=256$ therefore, the inclusion of additional bases expands the available repertoire by a factor of four for each additional base.

In one embodiment, quantitative genetic analysis comprises bioinformatic analysis of sequencing reads to identify rare single nucleotide variants (SNV).

Next-generation sequencing has an inherent error rate of roughly 0.02-0.02%, meaning that anywhere from $\frac{1}{200}$ to $\frac{1}{500}$ base calls are incorrect. To detect variants and other mutations that occur at frequencies lower than this, for example at frequencies of 1 per 1000 sequences, it is necessary to invoke molecular annotation strategies. By way of a non-limiting example, analysis of 5000 unique molecules using targeted sequence capture technology would generate—at sufficient sequencing depths of >50,000 reads—a collection of 5000 unique reads, with each unique read belonging to a "family" of reads that all possess the same read code. A SNV that occurs within a family is a candidate for being a rare variant. When this same variant is observed in more than one family, it becomes a very strong candidate for being a rare variant that exists within the starting sample. In contrast, variants that occur sporadically within families are likely to be sequencing errors and variants that occur within one and only one family are either rare or the result of a base alteration that occurred ex vivo (e.g., oxidation of a DNA base or PCR-introduced errors).

In one embodiment, the methods of detecting SNVs comprise introducing 10-fold more genomic input (genomes or genome equivalents) as the desired target sensitivity of the assay. In one non-limiting example, if the desired sensitivity is 2% (2 in 100), then the experimental target is an input of 2000 genomes.

In particular embodiments, bioinformatics analysis of sequencing data is used to detect or identify SNV associated with a genetic state, condition or disease, genetic mosaicism, fetal testing, paternity testing, predicting response to drug treatment, diagnosing or monitoring a medical condition, microbiome profiling, pathogen screening, and monitoring organ transplants.

In various embodiments, a method for copy number determination analysis is provided comprising obtaining one or more or a plurality of clones, each clone comprising a first DNA sequence and a second DNA sequence, wherein the first DNA sequence comprises a sequence in a targeted genetic locus and the second DNA sequence comprises a capture probe sequence. In related embodiments, a paired end sequencing reaction on the one or more clones is performed and one or more sequencing reads are obtained. In another embodiment, a sequencing reaction on the one or more clones is performed in which a single long sequencing read of greater than about 100 nucleotides is obtained, wherein the read is sufficient to identify both the first DNA sequence and the second DNA sequence. The sequencing reads of the one or more clones can be ordered or clustered according to the probe sequence of the sequencing reads.

Copy number analyses include, but are not limited to, analyses that examine the number of copies of a particular gene or mutation that occurs in a given genomic DNA sample and can further include quantitative determination of the number of copies of a given gene or sequence differences in a given sample. In particular embodiments, copy number analysis is used to detect or identify gene amplification associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

In some embodiments, copy number analysis is used to measure chromosomal instability. In such embodiments, sets of capture probes that comprise chromosomal stability probes are used to determine copy number variations at a uniform density across all sets of chromosomes. Copy number analyses are performed for each chromosomal stability probe and the chromosomal stability probes are then ordered according to their chromosomal target. This allows for visualization of copy number losses or gains across the genome and can serve as a measure of chromosomal stability.

In particular embodiments, bioinformatics analysis of sequencing data is used to detect or identify one or more sequences or genetic lesions in a target locus including, but not limited to detection of a nucleotide transition or transversion, a nucleotide insertion or deletion, a genomic rearrangement, a change in copy number, or a gene fusion. Detection of genetic lesions that are causal or prognostic indicators may be useful in the diagnosis, prognosis, treatment, and/or monitoring of a particular genetic condition or disease. In one embodiment, genetic lesions are associated with genetic states, conditions, or diseases, fetal testing, genetic mosaicism, paternity testing, predicting response to drug treatment, diagnosing or monitoring a medical condition, microbiome profiling, pathogen screening, and monitoring organ transplants.

D. Clinical Applications of Quantitative CNL Assays

In various embodiments, the present invention contemplates a method of detecting, identifying, predicting, diagnosing, or monitoring a condition or disease in a subject by detecting a mutational change, SNP, translocation, inversion, deletion, change in copy number or other genetic variation in a region of interest.

E. Clinical Applications of Quantitative Genetic Analysis

In various embodiments, the present invention contemplates a method of detecting, identifying, predicting, diagnosing, or monitoring a condition or disease in a subject.

In particular embodiments, a method of detecting, identifying, predicting, diagnosing, or monitoring a genetic state, condition or disease in a subject comprises performing a quantitative genetic analysis of one or more target genetic loci in a DNA clone library to detect or identify a change in the sequence at the one or more target genetic loci. In some embodiments, the change is a change in copy number.

In one embodiment, a method of detecting, identifying, predicting, diagnosing, or monitoring a genetic state, condition or disease comprises isolating or obtaining cellular DNA or ctDNA from a biological sample of a subject; treating the cellular DNA or cfDNA with one or more end-repair enzymes to generate end-repaired DNA; attaching one or more adaptors to each end of the end-repaired. DNA to generate a genomic DNA library; amplifying the DNA library to generate a DNA clone library; determining the number of genome equivalents in the DNA clone library; and performing a quantitative genetic analysis of one or more target genetic loci in a DNA clone library to detect or identify a change in the sequence, e.g., an SNP, a translocation, an inversion, a deletion, or a change in copy number at of the one or more target genetic loci.

In particular embodiments, a method of detecting, identifying, predicting, diagnosing, or monitoring a genetic state, or genetic condition or disease selected from the group consisting of: genetic diseases; genetic mosaicism; fetal testing; paternity testing; paternity testing; predicting response to drug treatment; diagnosing or monitoring a medical condition; microbiome profiling; pathogen screening; and organ transplant monitoring comprising isolating or obtaining genomic DNA from a biological sample of a subject; treating the DNA with one or more end-repair enzymes to generate end-repaired DNA; attaching one or more adaptors to each end of the end-repaired DNA to generate a genomic DNA library; amplifying the genomic DNA library to generate a DNA clone library; determining the number of genome equivalents in the DNA clone library; and performing a quantitative genetic analysis of one or more target genetic loci in a DNA clone library to detect or identify a nucleotide transition or transversion, a nucleotide insertion or deletion, a genomic rearrangement, a change in copy number, or a gene fusion in the sequence at the one or more target genetic loci.

Illustrative examples of genetic diseases that can be detected, identified, predicted, diagnosed, or monitored with the compositions and methods contemplated herein include, but are not limited to cancer, Alzheimer's disease (APOE1). Charcot-Marie-Tooth disease, Leber hereditary optic neuropathy (LHON), Angelman syndrome (UBE3A, ubiquitin-protein ligase E3A), Prader-Willi syndrome (region in chromosome 15), β-Thalassaemia (HBB, β-Globin), Gaucher disease (type I) (GBA, Glucocerebrosidase), Cystic fibrosis (CFTR Epithelial chloride channel), Sickle cell disease (HBB, β-Globin), Tay-Sachs disease (HEXA, Hexosaminidase A), Phenylketonuria (PAH, Phenylalanine hydrolyase), Familial hypercholesterolaemi a (LDLR, Low density lipoprotein receptor), Adult polycystic kidney disease (PKD1, Polycystin), Huntington disease (HDD, Huntingtin), Neurofibromatosis type (NF1, NF1 tumour suppressor gene), Myotonic dystrophy (DM, Myotonin), Tuberous sclerosis (TSC1, Tuberin), Achondroplasia (FGFR3, Fibroblast growth factor receptor), Fragile X syndrome (FMRT, RNA-binding protein), Duchenne muscular dystrophy (DMD, Dystrophin), Haemophilia A (F8C, Blood coagulation factor VIII), Lesch—Nyhan syndrome (HPRT1, Hypoxanthine guanine ribosyltransferase 1), and Adrenoleukodystrophy (ABCD1).

Illustrative examples of cancers that can be detected, identified, predicted, diagnosed, or monitored with the compositions and methods contemplated herein include, but are not limited to: B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, binary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia. Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcotna, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinobitoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In one embodiment, the genetic lesion is a lesion annotated in the Cosmic database (the lesions and sequence data are available online and can be downloaded from the Cancer Gene Census section of the Cosmic website) or a lesion annotated in the Cancer Genome Atlas (the lesions and sequence data are available online and can be downloaded from The Cancer Genome Atlas website).

Illustrative examples of genes that harbor one or more genetic lesions associated with cancer that can be detected, identified, predicted, diagnosed, or monitored with the compositions and methods contemplated herein include, but are not limited to ABCB1, ABCC2, ABCC4, ABCG2, ABU, ABL2, AKT1, AKT2, AKT3, ALDH4A1, ALK, APC, AR, ARAF, ARFRP1, ARID1A, ATM, ATR, AURKA, AURKB, BCL2, BCL2A1, BCL2L1, BCL2L2, BCL6, BRAF, BRCA1, BRCA2, Clorfl44, CARD11, CBL, CCND1, CCND2, CCND3, CCNE1, CDH1, CDE12, CDH20, CDH5, CDK4, CDK6, CDK8, CDKN2A, CDKN2B, CDKN2C, CEBPA, CHEK1, CHEK2, CRKL, CRLF2, CTNNB1, CYP1B1, CYP2C19, CYP2C8, CYP2D6, CYP3A4, CYP3A5, DNMT3A, DOT1L, DPYD, EGFR, EPHA3, EPHA5, EPHA6, EPHA7, EPHB1, EPHB4, EPHB6, EPHX1, ERBB2, ERBB3, ERBB4, ERCC2, ERG, ESR1, ESR2, ETV1, ETV4, ETV5, ETV6, EWSR1, EZH2, FANCA, FBXW7, FCGR3A, FGFR1, FGFR2, FGFR3, FGFR4, FLT1, FLT3, FLT4, FOXP4, GATA1, GNA11, GNAQ, GNAS, GPR124, GSTP1, GUCY1A2, HOXA3, HRAS, HSP90AA1, IDH1, IDH2, IGF1R, IGF2R, IKBKE, IKZF1, INHBA, IRS2, ITPA, JAK1, JAK2, JAK3, JUN, KDR, KIT, KRAS, LRP1B, LRP2, LTK, MAN1B1, MAP2K1, MAP2K2, MAP2K4, MCL1, MDM2, MDM4, MEN1, MET, MITF, MLH1, MLL, MPL, MRE11A, MSH2, MSH6, MTHFR, MTOR, MUTYH, MYC, MYCL1, MYCN, NF1, NF2, NKX2-1, NOTCH1, NPM1, NQO1, NRAS, NRP2, NTRK1, NTRK3, PAK3, PAX5, PDGFRA, PDGFRB, PIK3CA, PIK3R1, PKHD1, PLCG1, PRKDC, PTCH1, PTEN, PTPN11, PTPRD, RAF1, RARA, RB1, RET, RICTOR, RPTOR, RUNX1, SLC19A1, SLC22A2, SLCO1/b3, SMAD2, SMAD3, SMAD4, SMARCA4, SMARCB1, SMO, SOD2, SOX10, SOX2, SRC, STK11, SULT1A1, TBX22, TET2, TGFER2, TMPRSS2, TNFRSF14, TOP1, TP53, TPMT, TSC1, TSC2, TYMS, UGT1A1, UMPS, USP9X, VHL, and WT1.

In particular embodiments, the genetic lesion comprises a nucleotide transition or transversion, a nucleotide insertion or deletion, a genomic rearrangement, a change in copy number, or a gene fusion.

In one embodiment, the genetic lesion is a gene fusion that fuses coding region of the ALK gene to another gene.

In one embodiment, the genetic lesion is a gene fusion that fuses the 3' coding region of the ALK gene to the EML4 gene.

Illustrative examples of conditions suitable for fetal testing that can be detected, identified, predicted, diagnosed, or monitored with the compositions and methods contemplated herein include but are not limited to: Down Syndrome (Trisomy 21), Edwards Syndrome (Trisomy 18), Patau Syndrome (Trisomy 13), Klinefelter's Syndrome (XXY), Triple X syndrome, XYY syndrome, Trisomy 8. Trisomy 16, Turner Syndrome (XO), Robertsonian translocation, DiGeorge Syndrome and Wolf-Hirschhorn Syndrome.

Illustrative examples of alleles suitable for paternity testing that can be detected, identified, predicted, diagnosed, or monitored with the compositions and methods contemplated herein include but are not limited to 16 or more of: D20S1082, D6S474, D12ATA63, D22S1045, D10S1248, DI S1677, D11S4463, D4S2364, D9S1122, D2S1776, D10S1425, D3S3053, D5S2500, D1S1627, D3S4529, D2S441, D17S974, D6S1017, D4S2408, D9S2157, Amelogenin, D17S1301, D1GATA113, D18S853, D20S482, and D14S1434.

Illustrative examples of genes suitable for predicting the response to drug treatment that can be detected, identified, predicted, diagnosed, or monitored with the compositions and methods contemplated herein include, but are not limited to, one or more of the following genes: ABCB1 (ATP-binding cassette, sub-family B (MDR/TAP), member 1), ACE (angiotensin I converting enzyme), ADH1A (alcohol dehydrogenase 1A (class I), alpha polypeptide), ADH1B (alcohol dehydrogenase TB (class I), beta polypeptide), ADH1C (alcohol dehydrogenase 1C (class 1), gamma polypeptide), ADRB1 (adrenergic, beta-1-, receptor), ADRB2 (adrenergic, beta-2-, receptor, surface), AHR (aryl hydrocarbon receptor), ALDH1A1 (aldehyde dehydrogenase 1 family, member A1), ALOX5 (arachidonate 5-lipoxygenase), BRCA1 (breast cancer 1, early onset), COMT (catechol-O-methyltransferase), CYP2A6 (cytochrome P450, family 2, subfamily A, poly peptide 6), CYP2B6 (cytochrome P450, family 2, subfamily B, polypeptide 6), CYP2C9 (cytochrome P450, family 2, subfamily C, polypeptide 9), CYP2C19 (cytochrome P450, family 2, subfamily C, polypeptide 19). CYP2D6 (cytochrome P450, family 2, subfamily D, polypeptide 6), CYP2J2 (cytochrome P450, family 2, subfamily J, polypeptide 2), CYP3A4 (cytochrome P450, family 3, subfamily A, polypeptide 4), CYP3A5 (cytochrome P450, family 3, subfamily A, polypeptide 5), DPYD (dihydropyrimidine dehydrogenase), DRD2 (dopamine receptor D2), F5 (coagulation factor V). GSTP1 (glutathione S-transferase pi), HMGCR (3-hydroxy-3-methylglutaryl-Coenzyme A reductase), KCNH2 (potassium voltage-gated channel, subfamily H (eag-related), member 2), KCNJ11 (potassium inwardly-rectifying channel, subfamily J, member 11), MTHFR (5,10-methylenetetrahydrofolate reductase (NADPH)), NQO1 (NAD(P)H dehydrogenase, quinone 1), P2RY1 (purinergic receptor P2Y, G-protein coupled, 1), P2RY12 (purinergic receptor P2Y, G-protein coupled, 12), PTG1S (prostaglandin 12 (prostacyclin) synthase), SCNSA (sodium channel, voltage-gated, type V, alpha (long QT syndrome 3)), SLC19A1 (solute carrier family 19 (folate transporter), member 1), SLCO1B1 (solute carrier organic anion transporter family, member 1BI), SULT1A1 (sulfotransferase family, cytosolic, 1A, phenol-preferring, member I), TPMT (thiopurine S-methyltransferase), TYMS (thymidylate synthetase), UGT1A1 (UDP glucuronosyltransferase 1 family, polypeptide A1), VDR (vitamin D (1,25-dihydroxyvitamin D3) receptor). VKORC1 (vitamin K epoxide reductase complex, subunit 1).

Illustrative examples of medical conditions that can be detected, identified, predicted, diagnosed, or monitored with the compositions and methods contemplated herein include, but are not limited to: stroke, transient ischemic attack, traumatic brain injury, heart disease, heart attack, angina, atherosclerosis, and high blood pressure.

Illustrative examples of pathogens that can be screened for with the compositions and methods contemplated herein include, but are not limited to: bacteria fungi, and viruses.

Illustrative examples of bacterial species that can be screened for with the compositions and methods contemplated herein include, but are not limited to: a *Mycobacterium* spp., a *Pneumococcus* spp., an *Escherichia* spp., a *Campylobacter* spp., *Corynebacterium* spp., a *Clostridium* spp., a *Streptococcus* spp., a *Staphylococcus* spp., a *Pseudomonas* spp., a *Shigella* spp., a *Treponema* spp., or a *Salmonella* spp.

Illustrative examples of fungal species that can be screened for with the compositions and methods contemplated herein include, but are not limited to: an *Aspergillis* spp., a *Blastomyces* spp., a *Candida* spp., a *Coccicioides* spp., a *Cryptococcus* spp., dermatophytes, a *Tinea* spp., a *Trichophyton* spp., a *Microsporum* spp., a *Fusarium* spp., a

*Histoplasma* spp., a *Mucoromycotina* spp., a *Pneumocystis* spp., a *Sporothrix* spp., an *Exserophilum* spp., or a *Cladosporium* spp.

Illustrative examples of viruses that can be screened for with the compositions and methods contemplated herein include, but are not limited to: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpesviruses such as Herpes simplex virus types 1 and 2, varicella zoster, cytomegalovirus, Epstein-Bar virus (EBV), human herpesviruses human herpesvirus type 6 and 8, Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend marine leukemia virus, Murine Stem Cell Virus (MSCV) and Rous Sarcoma Virus (RSV), HIV (human immunodeficiency virus; including HIV type 1, and HIV type 2), visna-maedi virus (VIVIV) virus, the caprine arthritis-encephalitis virus (CAEV), equine infectious anemia virus (EIAV), feline immunodeficiency virus (FIV), bovine immune deficiency virus (MY), and simian immunodeficiency virus (SW), papillotna virus, murine gammaherpesvirus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic lever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-CoV), West Nile virus, and any encephalitis causing virus.

Illustrative examples of genes suitable for monitoring an organ transplant in a transplant recipient that can be detected, identified, predicted, diagnosed, or monitored with the compositions and methods contemplated herein include, but are not limited to, one or more of the following genes: HLA-A, HLA-B, HLA-C, HLA-DR, HLA-DP, and HLA-DQ.

In particular embodiments, a bioinformatic analysis is used to quantify the number of genome equivalents analyzed in the cfDNA clone library; detect genetic variants in a target genetic locus; detect mutations within a target genetic locus; detect genetic fusions within a target genetic locus; or measure copy number fluctuations within a target genetic locus.

F. Companion Diagnostics

In various embodiments, a companion diagnostic for a genetic disease is provided, comprising: isolating or obtaining genomic DNA from a biological sample of a subject;

treating the DNA with one or more end-repair enzymes to generate end-repaired DNA; attaching one or more adaptors to each end of the end-repaired DNA to generate a DNA library; amplifying the DNA library to generate a DNA clone library; determining the number of genome equivalents in the DNA clone library; and performing a quantitative genetic analysis of one or more biomarkers associated with the genetic disease in the DNA clone library, wherein detection of, or failure to detect, al least one of the one or more biomarkers indicates whether the subject should be treated for the genetic disease. In some embodiments, the DNA is cfDNA. In particular embodiments, the DNA is cellular DNA.

As used herein, the term "companion diagnostic" refers to a diagnostic test that is linked to a particular anti-cancer therapy. In a particular embodiment, the diagnostic methods comprise detection of genetic lesion in a biomarker associated with in a biological sample, thereby allowing for prompt identification of patients should or should not be treated with the anti-cancer therapy.

Anti-cancer therapy includes, but is not limited to surgery, radiation, chemotherapeutics, anti-cancer drugs, and immunomodulators.

Illustrative examples of anti-cancer drugs include, but are not limited to: alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triety enephosphoramide, triethylenethi ophosphaoramide and trimethylolotnelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detoruhicin, 6-diazo-5-oxo-L-norleucine, doxoruhicin and its pegylated formulations, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, uhenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformi thine; elliptinium acetate; etoglucid; gallium nitrate; hydroxyurea; lentinan; lonidamine; mitoguazone; mitoxantrone; mopidamol; nitracrine; pentostatin; phenarnet; pirarubicin; podophyllinic acid; 2-ethylhydrazide; procarbazine; PSK®; razoxane; sizofiran; spirogermanium; tenuazonic acid; triaziquone; 2, 2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXO-TERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone, vincristine; vinorelbine; navelbine; novantrone; teniposide; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on cancers such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Illustrative examples of immunomodulators include, but are not limited to: cyclosporine, tacrolimus, tresperimus, piniecrolinius, sirolimus, verolimus, laflunimus, laquinimod and imiquimod, as well as analogs, derivatives, salts, ions and complexes thereof.

In some embodiments, an anti-cancer drug may include a poly-ADP ribose polymerase (PARP) inhibitor. Illustrative examples of PARP inhibitors include, but are not limited to, olaparib (AZD-2281), rucaparib (AG014699 or PF-01367338, niraparib (MK-4827), talazoparib (BMN-673) veliparib (ABT-888), CEP 9722, E7016, BGE-290, 3-aminobenzamide.

All publications, patent applications, and issued patents cited in this specification are herein incorporated by reference as if each individual publication, patent application, or issued patent were specifically and individually indicated to be incorporated by reference. In particular, the entire contents of International PCT Publication No. WO 2016/028316 are specifically incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1: Copy Number Analysis of Samples Containing Blends Of Fragmented Genomic DNA Meticulous blends of fragmented genomic DNA were generated that contained DNA derived from ΔATM or ΔBRCA2 immortalized human samples spiked into a fragmented wild-type human gDNA sample. The advantage of this sample type is that the composition can be carefully controlled and sample availability is essentially unlimited.

Figure 7:
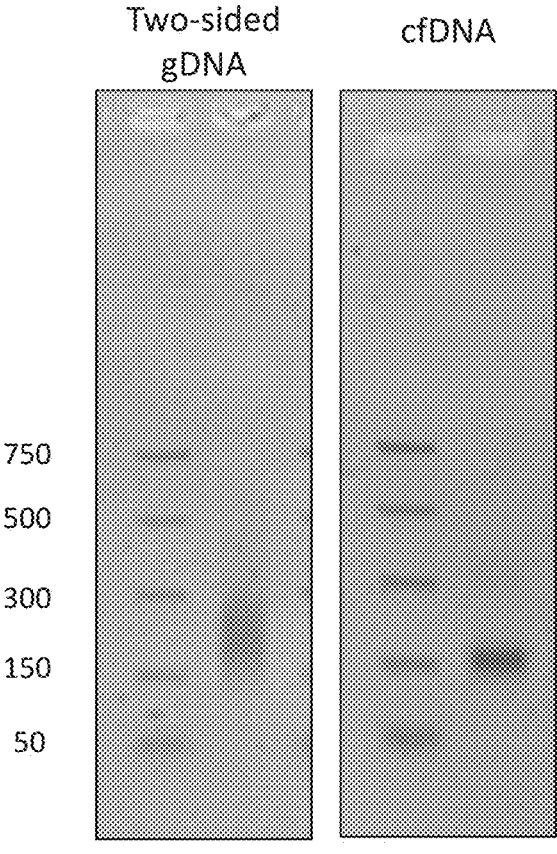
FIG. 7 shows DNA inputs into CNL libraries. Agarose gel images are shown with the sizes of markers (bp) indicated at left.

Wild-type, human female genomic DNA was purified from whole blood samples donated by a healthy volunteer. Genomic DNA isolated from an immortalized cell harboring a heterozygous deletion covering the entire ATM gene (NA09596, ΔATM) and a separate sample bearing a heterozygous deletion of BRCA2 (NA02718, ΔBRCA2) were obtained from the Coriell repository. Importantly, these samples appeared to have an otherwise normal ploidy across the remainder of the genomes. The ΔATM sample was derived from a male donor and was therefore also hemizygous in copy number for the X-linked AR gene. Cell free DNA (cfDNA) was obtained from healthy donor plasma samples of female or male origin. For library construction, genomic DNA was sonicated on a setting of 200 bp with a Covaris instrument, then further size selected using a "two-sided" DNA bead purification. Library input DNA samples are shown in FIG. 7.

Appropriate combinations of fragmented and cfDNA samples were blended to defined percentages, end-repaired, and converted to genomic libraries. Approximately 500 ng of each library was combined in sets of eight samples and hybridized to the copy number loss (CNL) prostate probe pool that contained 2304 DNA probes. Following sample processing, each set of eight samples was sequenced on an Illumina NextSeq NGS instrument to a depth of ~480 million pass-filter reads; this corresponds to 60 million reads/sample. Roughly 95% of reads possessed legitimate sample ID tags and aligned to the human reference genome and of these, ~98% mapped to the intended target loci. The overall sequencing depth, measured as the number of reads per input genome per probe (calculated as on-target reads (60 million) divided by average genome depth (2500) and divided by probe count (2400)) was approximately 10 reads per genome per probe. A graphic representation of the copy number loss analysis is shown in FIG. 1. Copy number perturbations are highlighted by arrows. (Sample 1, 5% male DNA into female DNA; sample 2, 5% ΔATM DNA (male) into female DNA; sample 3, 5% ΔBRCA2 DNA (female) into female DNA; sample 4, pure female DNA).

The CNL caller identifies redundant reads and condenses these into a single consensus reads that are then quantified at each probe location. This information was further condensed into gene-by-gene copy number averages, Finally, a statistical significance was assigned to deviations detected in each CNL measurement; this is shown graphically as the $\log_{10}$ P-value of statistical significance.

Figure 8B:
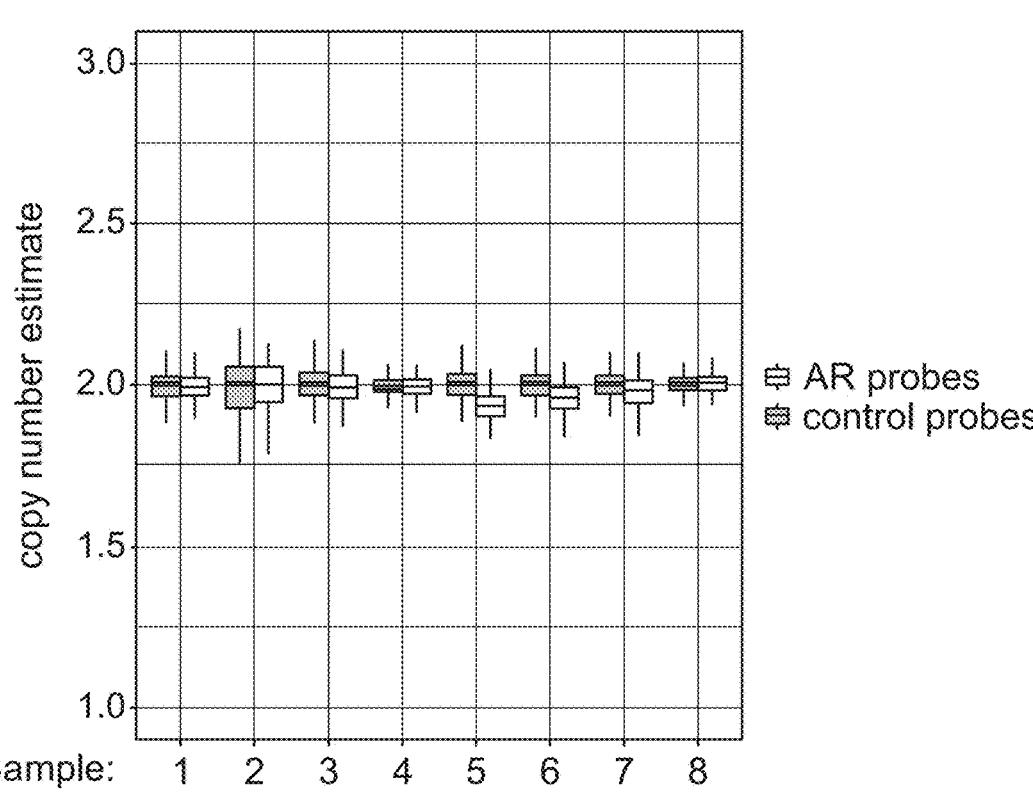
FIG. 8A FIG. 8C shows conventional box-and-whiskers plots of measured gene copies across eight samples as determined by CNL analysis.
Figure 8C:
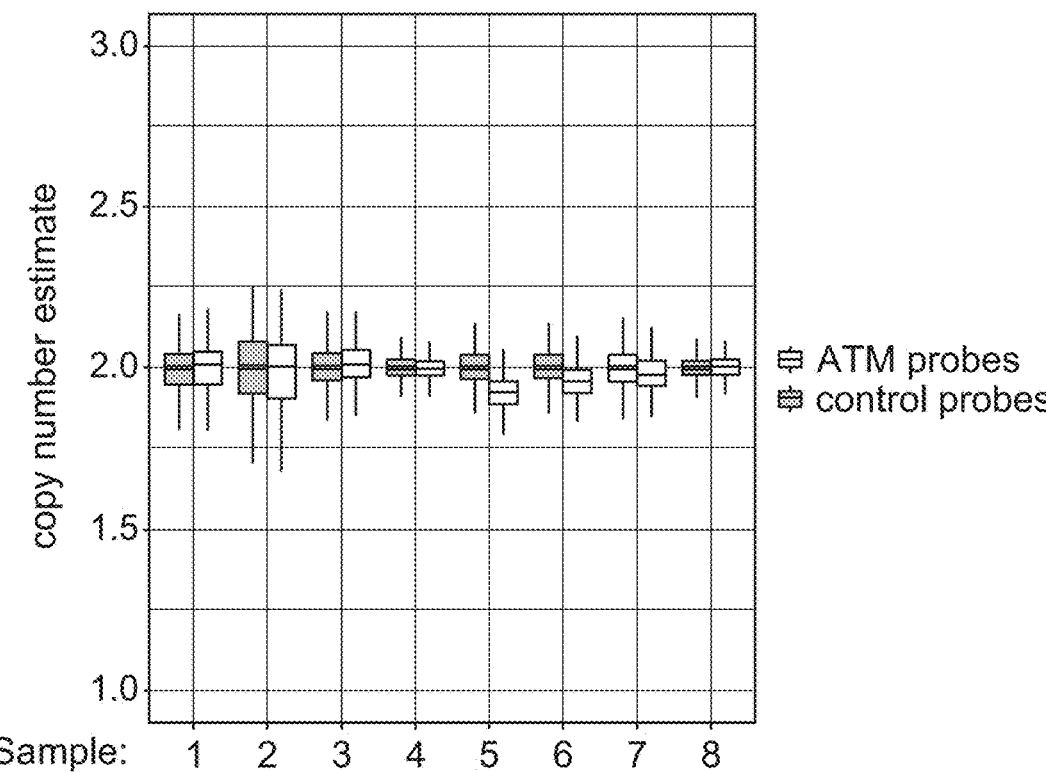
Figure 9B:
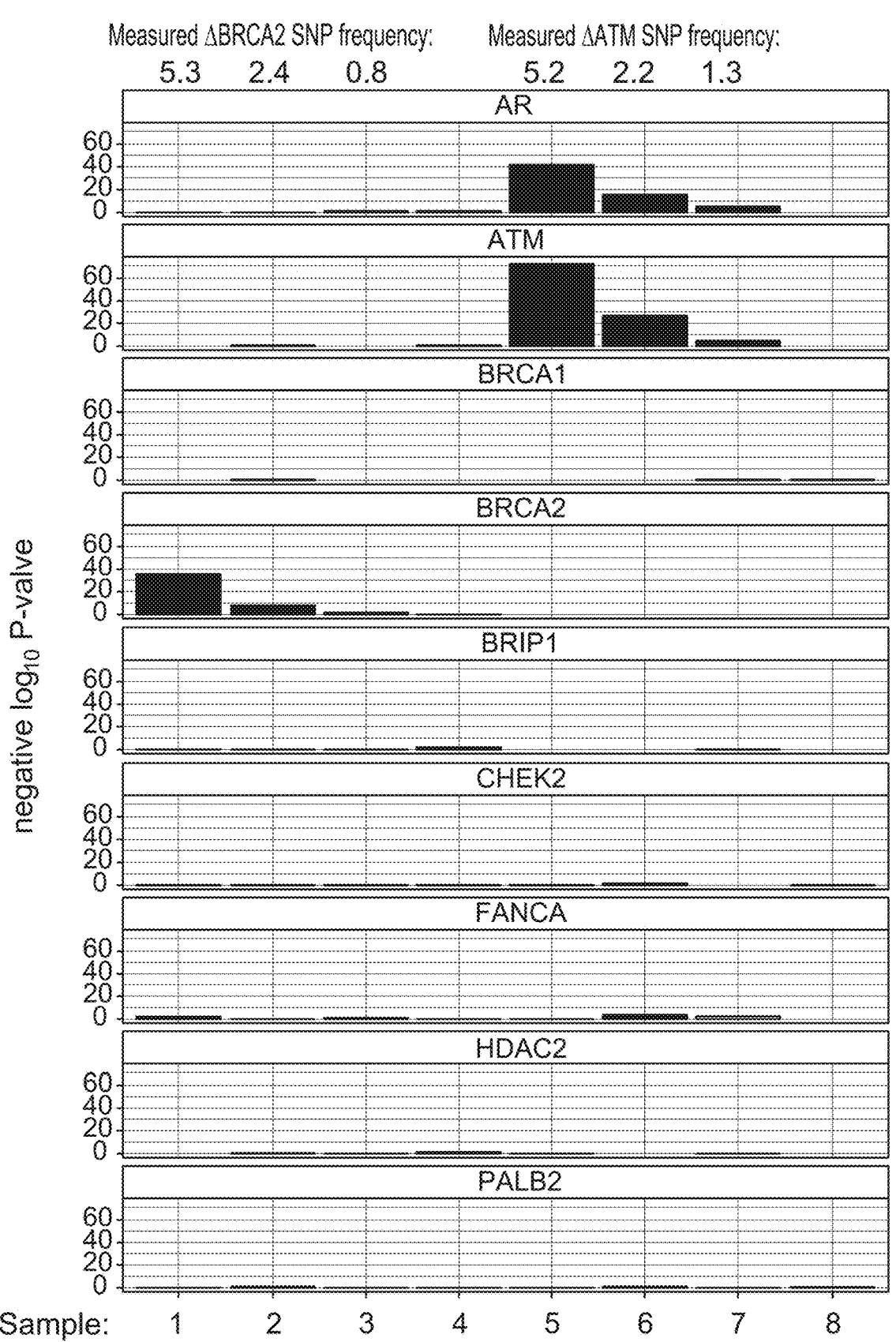
Figure 10B:
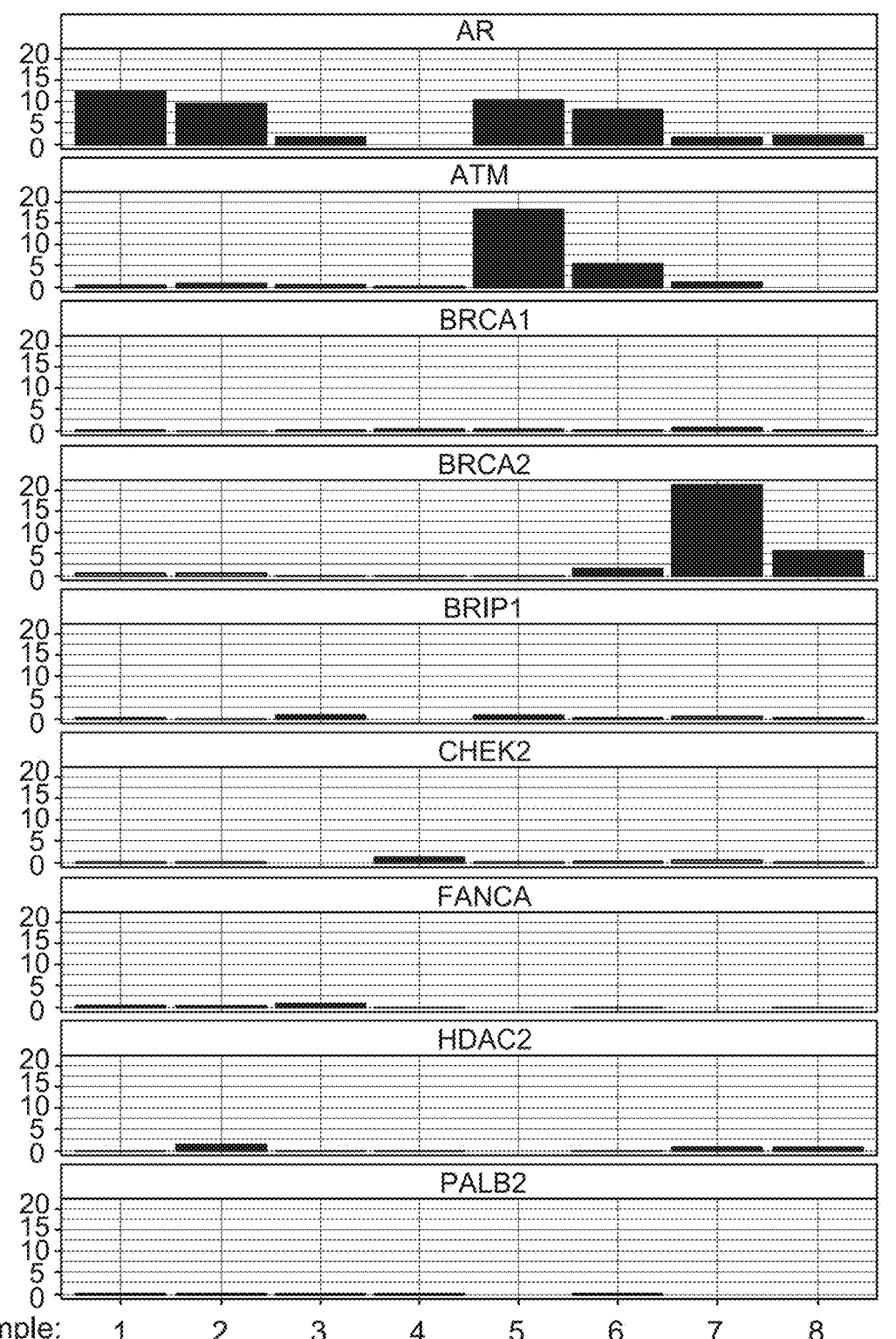

FIG. 8 shows box-and-whisker plots of copy number determinations for the AR (FIG. 8B) and ATM (FIG. 8C) genes in fragmented and blended genomic libraries. Because the ΔATM sample is male, the AR gene (X-linked, hemizygous) and the ATM gene both exhibited. CNL behavior. As anticipated, the magnitude of measured copy variation was modest. The statistical analysis shown in FIG. 9B demonstrates that the observed copy fluctuation was statistically significant. Moreover, very little significant fluctuation was observed in the remaining genes that were predicted to exhibit uniform copy characteristics. These values correlated well with frequencies predicted for the various genomic blends. FIG. 10 shows that statistically significant copy fluctuation was also readily observed in samples that were primarily cfDNA with minor spike-ins of either cfDNA from the opposite sex or minor additions of fragmented gDNA. These values correlated well with frequencies predicted for the various genomic blends. The results seen with both fragmented gDNA and with cfDNA were comparable, thereby demonstrating the integrity of the assay and suggesting that the integrity will translate to clinical samples.

These data demonstrate the ability of the assay system to detect subtle changes in gene copy number down to minor allele frequencies of 2%. While the focus of demonstrated examples presented is on copy number loss, the technology is equally well suited to the detection of copy number gains, including increases in gene copy that occur through chromosomal arm duplications and focal amplifications. This assay further retains the ability to detect other types of genomic variants, including SNVs, indels and gene fusions (chromosomal rearrangements). Importantly, these data demonstrate that the method can be applied to genomic DNA derived from plasma, but also to genomic DNA derived from other sources such as tissue and other bodily sources.

Example 2: Copy Number Analysis of cfDNA from Healthy Donors and a Cancer Patient The following example illustrate the manner in which the molecular features added during genomic library construction and post-hybridization processing are used to generate copy number analysis. DNA was extracted from the plasma of sixteen healthy donors and one castration-resistant prostate cancer patient using the Qiaen Circulating Nucleic Acids Extraction kit (Qiagen, Hilden, Germany). The yield of double-strand DNA was quantified using a Qubit fluorometer (Thermo Fisher, Waltham, MA) and the corresponding hsDNA quantitation kit. Size analysis was performed using gel electrophoresis on 2% agarose gels with PCR markers as size standards (New England Biolabs, Ipswich, MA). Approximately 40-100 ng of cfDNA, depending on the yield of cfDNA from the sample, was used for library construction.

The basic features of library construction are illustrated in FIG. 11A-11C. The cfDNA was first dephosphorylated and then repaired to blunt ends in a two-step process. Short, 10 nt anchor sequences consisting of a phosphorylated ligation strand and an inert partner strand were then ligated to the cfDNA. The eight oligonucleotides used to create the set of four anchor sequences are shown in Table 1.

TABLE 1

Ligation anchor oligonucleotides

| Oligo ID | Nucleic Add Sequence | SEQ ID NO: |
|---|---|---|
| Partner strand oLigation strand oligoo_16-1 | GTATGCC[3-dA-Q]* | 1 |
| Partner strand oLigation strand oligoo_16-2 | AGCGTTA[3-dC-Q]* | 2 |
| Partner strand oLigation strand oligoo_16-3 | TCGACAT[3-dG-Q]* | 3 |

TABLE 1-continued

Ligation anchor oligonucleotides

| Oligo ID | Nucleic Add Sequence | SEQ ID NO: |
|---|---|---|
| Partner strand oLigation strand oligoo_16-4 | CATCAGG[3-dT-Q]* | 4 |
| Ligation strand oligo_16-1 | /5Phos/TGG CAT ACG T** | 5 |
| Ligation strand oligo_16-2 | /5Phos/GTA ACG CT A G** | 6 |
| Ligation strand oligo_16-3 | /5Phos/CAT GTC GAT C** | 7 |
| Ligation strand oligo_16-4 | /5Phos/ACC TGA TGC A** | 8 |

*[3-d(A, C, G, or T)-Q] denotes a modified base in which the hydroxyl group resides on the 2' position of the ribose ring
**/5Phos/ denotes the chemical addition of a 5' phosphate group to the 51 base position The adaptor structures were completed by the addition of full-length adaptor sequences that annealed to the anchor sequence. Thirty-two sets of adaptor sequences, each composed of 240 members, are shown in FIG. 12-FIG. 22. These adaptors were attached to the cfDNA and extended through the concerted actions of polynucleotide kinase. DNA polymerase and DNA ligase to generate genomic libraries. As a pre-sequencing quality control step, the resulting genomic libraries were quantified by qPCR for depth of coverage. The genomic libraries were then amplified and hybridized to probe sets targeting specific genes (FIG. 11B). Following hybridization, primer extension of the probe was used to copy the captured genomic sequences and the information encoded in the attached adaptor (FIG. 11C). An example of post sequencing analysis using standard next-generation analysis software is shown in FIG. 11D. This analysis was performed on a sequencing run that contained 32 samples (28 cancer patient samples and 4 wild-type controls) and it displays the overall distribution of sequencing reads.

A central feature of the targeted hybrid capture platform described herein is that it provides multiple types of genomic information. One essential function of capture probes is to provide mutation detection across target regions at a high depth of coverage. This function is governed by the sequence context, density, and placement of the capture probes and is illustrated in FIGS. 23A-1-23A-6, 23B-1-23B-6, and 23C-1-23C-6 with the TP53 gene (TP53 probe sequences are shown in Table 2 below). Of equal significance, the targeted hybrid capture platform assay generated a readout of equal depth of coverage in regions where no significant mutations were detected. These data are critical to physicians and patients as they add statistical significance in cases where no deleerious mutations were detected.

TABLE 2

TP53 Probes

| Name | Sequence | SEQ ID NO: |
|---|---|---|
| TP53_1 | GGCACAGACCCTCTCACTCATGTGATGTCATCTCTCCTCC | 7689 |
| TP53_2 | ATGGGGGTGGGAGGCTGTCAGTGGGGAACAAGAAGTGGAG | 7690 |
| TP53_3 | GTCAGTCTGAGTCAGGCCCTTCTGTCTTGAACATGAGTTT | 7691 |

TABLE 2-continued

| Name | Sequence | SEQ ID NO: |
|------|----------|------------|
| TP53_4 | CCTGAAGTCCAAAAAGGGTCAGTCTACCTCCCGCCATAAA | 7692 |
| TP53_5 | TCATGCTGGATCCCCACTTTTCCTCTTGCAGCAGCCAGAC | 7693 |
| TP53_6 | GTTGGGGTGGGGGTGGTGGGCCTGCCCTTCCAATGGATCC | 7694 |
| TP53_7 | CAGTTTCCATAGGTCTGAAAATGTTTCCTGACTCAGAGGG | 7695 |
| TP53_8 | CTGCCATGGAGGAGCCGCAGTCAGATCCTAGCGTCGAGCC | 7696 |
| TP53_9 | GCAGAGACCTGTGGGAAGCGAAAATTCCATGGGACTGACT | 7697 |
| TP53_10 | CTGGGGGGCTGGGGGGCTGAGGACCTGGTCCTCTGACTGC | 7698 |
| TP53_11 | GCAGGGGGATACGGCCAGGCATTGAAGTCTCATGGAAGCC | 7699 |
| TP53_12 | GTGGCCCCTGCACCAGCAGCTCCTACACCGGCGGCCCCTG | 7700 |
| TP53_13 | GGGGGGGAGCAGCCTCTGGCATTCTGGGAGCTTCATCTGGA | 7701 |
| TP53_14 | CCGTGCAAGTCACAGACTTGGCTGTCCCAGAATGCAAGAA | 7702 |
| TP53_15 | CCCCGGACGATATTGAACAATGGTTCACTGAAGACCCAGG | 7703 |
| TP53_16 | CCAGAAAACCTACCAGGGCAGCTACGGTTTCCGTCTGGGC | 7704 |
| TP53_17 | TAGGTTTTCTGGGAAGGGACAGAAGATGACAGGGGCCAGG | 7705 |
| TP53_18 | TGCTTTATCTGTTCACTrGTGCCCTGACTTTCAACTCTGT | 7706 |
| TP53_19 | CCTGGGCAACCAGCCCTGTCGTCTCTCCAGCCCCAGCTGC | 7707 |
| TP53_20 | TTTGCCAACTGGCCAAGACCTGCCCTGTGCAGCTGTGGGT | 7708 |
| TP53_21 | CCATCGCTATCTGAGCAGCGCTCATGGTGGGGGCAGCGCC | 7709 |
| TP53_22 | GCCATCTACAAGCAGTCACAGCACATGACGGAGGTTGTGA | 7710 |
| TP53_23 | CATGGCGCGGACGCGGGTGCCGGGCGGGGGTGTGGAATCA | 7711 |
| TP53_24 | CCAGGGTCCCCAGGCCTCTGATTCCTCACTGATTGCTCTT | 7712 |
| TP53_25 | GAGGGCCACTGACAACCACCCTTAACCCCTCCTCCCAGAG | 7713 |
| TP53_26 | CCTCAGGCGGCTCATAGGGCACCACCACACTATGTCGAAA | 7714 |
| TP53_27 | AGGAAATTTGCGTGTGGAGTATTTGGATGACAGAAACACT | 7715 |
| TP53_28 | CTTGCCACAGGTCTCCCCAAGGCGCACTGGCCTCATCTTG | 7716 |
| TP53_29 | GAGGCAAGCAGAGGCTGGGGCACAGCAGGCCAGTGTGCAG | 7717 |
| TP53_30 | CCTGGAGTCTTCCAGTGTGATGATGGTGAGGATGGGCCTC | 7718 |
| TP53_31 | ACTACATGTGTAACAGTTCCTGCATGGGCGGCATGAACCG | 7719 |
| TP53_32 | GGACAGGTAGGACCTGATTTCCTTACTGCCTCTTGCTTCT | 7720 |
| TP53_33 | CTGCACCCTTGGTCTCCTCCACCGCTTCTTGTCCTGCTTG | 7721 |
| TP53_34 | TCTCTTTTCCTATCCTGAGTAGTGGTAATCTACTGGGACG | 7722 |
| TP53_35 | CCTCGCTTAGTGCTCCCTGGGGGCAGCTCGTGGTGAGGCT | 7723 |
| TP53_36 | GACCGGCGCACAGAGGAAGAGAATCTCCGCAAGAAAGGGG | 7724 |
| TP53_37 | TCTCCCAGGACAGGCACAAACACGCACCTCAAAGCTGTTC | 7725 |
| TP53_38 | TGCCTCAGATTCACTTTTATCACCTTTCCTTGCCTCTTTC | 7726 |
| TP53_39 | GGCATTTTGAGTGTTAGACTGGAAACTTTCCACTTGATAA | 7727 |
| TP53_40 | CCTGAAGGGTGAAATATTCTCCATCCAGTGGTTTCTTCTT | 7728 |

TABLE 2-continued

| | TP53 Probes | |
| --- | --- | --- |
| Name | Sequence | SEQ ID NO: |
| TP53_41 | CCTAGCACTGCCCAACAACACCAGCTCCTCTCCCCAGCCA | 7729 |
| TP53_42 | CATCTTTTAACTCAGGTACTGTGTATATACTTACTTCTCC | 7730 |
| TP53_43 | ATGGCTTTCCAACCTAGGAAGGCAGGGGAGTAGGGCCAGG | 7731 |
| TP53_44 | CCTGGAGTGAGCCCTGCTCCCCCCTGGCTCCTTCCCAGCC | 7732 |
| TP53_45 | TCCGAGAGCTGAATGAGGCCTTGGAACTCAAGGATGCCCA | 7733 |

Figures 24A, 24B, 24C:
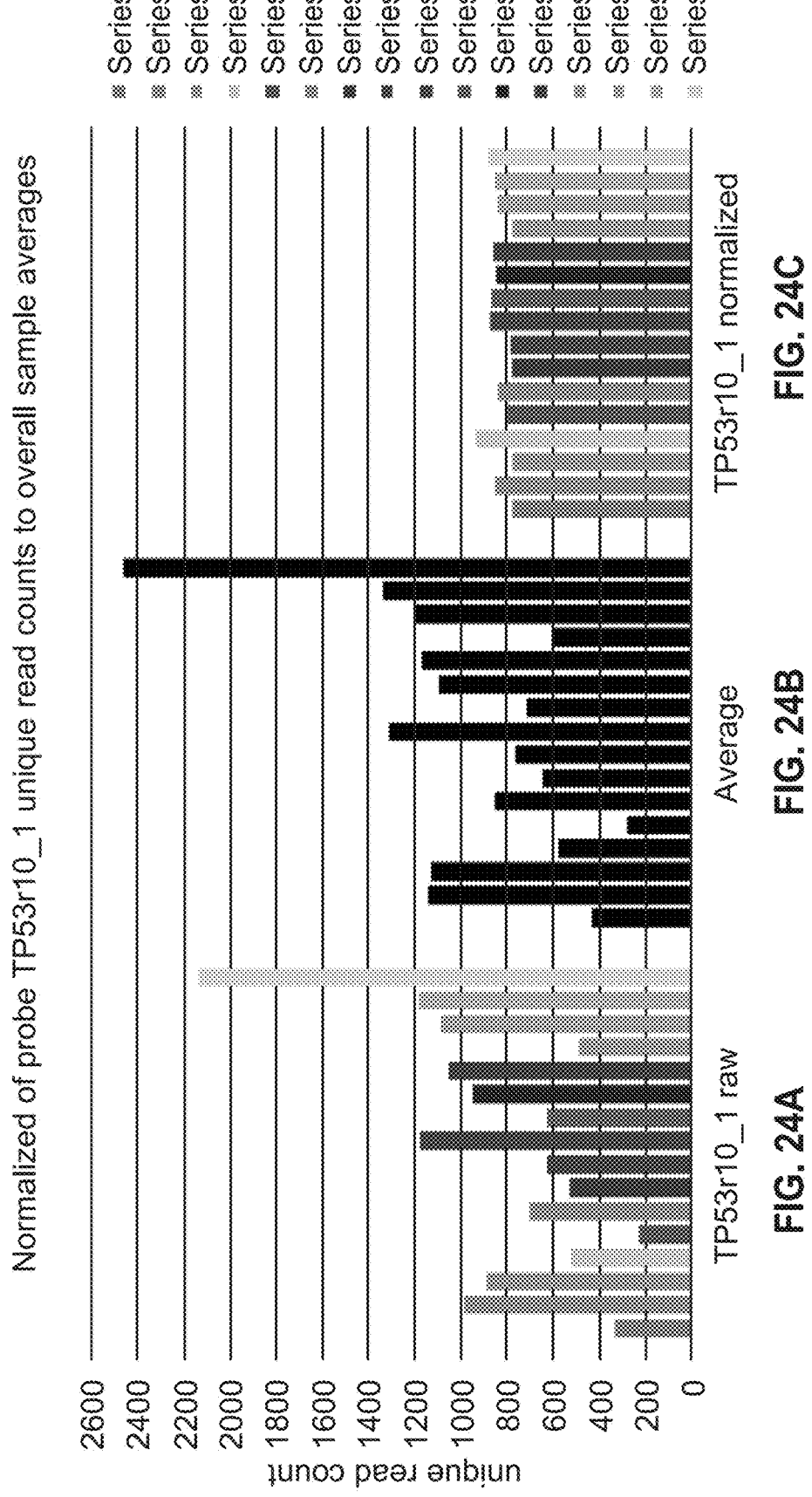
FIG. 24A-FIG. 24C illustrate raw and normalized unique read density for a single probe, TP53r10_1, across 16 samples.

The linkage of the capture probe with captured genomic sequence (FIG. 11C) also facilitated measurement of genomic depth at each probe location. The number of unique reads associated with every capture probe used in the experiment was measured (FIG. 24). The data shown in FIG. 24 was derived from a sequencing run in which 16 healthy donor cfDNA samples were analyzed. The depth of unique reads encountered in each sample at one probe location in the TP53 gene were calculated (Raw unique read counts shown in FIG. 24A). Each sample comprised a unique library depth, as reflected in the broad sample-to-sample distribution of unique reads. The global average of unique read depth across all 2596 capture probes in the experiment was also calculated (FIG. 24B). Significantly, normalization of the observed read depth at the single probe site displayed in FIG. 24C by the global unique read depth measured for all probes revealed a uniform density of normalized unique reads. These data indicate that the capture performance of a particular probe chosen for analysis was uniform from sample-to-sample and proportional to the genomic depth of each individual library.

This same normalization function was applied to the 45 TP53-specific probes shown in FIGS. 23A-1-23A-6, 23B-1-23B-6, and 23C-1-23C-6 (normalization data shown in FIG. 25). Whereas FIGS. 23A-1-23A-6, 23B-1-23B-6, and 23C-1-23C-6 show the aggregate contribution of all probes to the sequencing depth of TP53 coding regions, FIG. 25 shows the normalized depth retrieved by each individual probe. The normalized depth retrieved by each individual probe was generally consistent from sample-to-sample for any given probe but somewhat variable when one probe was compared to another. Several factors governed the differences in the post-normalization capture depths observed between probes, the most significant being the placement of probes relative to one another and the proximity of probes to genomic repeat regions. Not all probes exhibited uniform capture behavior; two probes whose capture performance were not consistent are highlighted by arrows in FIG. 25. However, these data indicate that such probes are rare and easily identified. As such, and they can be excluded from downstream copy number analysis.

The uniform capture performance exhibited by the 45 TP53 targeting probes in FIG. 25 is a general feature of the targeted hybrid capture platform described herein. In FIG. 26, the average capture depth for each probe in a panel of 2596 capture probes was calculated for all 16 normal cfDNA libraries that were profiled in this experiment. The average was then compared individually with three representative samples using scatter plot analysis. Each dot represents a different probe and its position on the graph is a comparison of the average on the x-axis and the individual sample on the y-axis. The tight diagonal distribution of the majority of probes reflected the highly-correlated unique read capture performance of most probes ($R^2$ correlation 0.95 for all three graphs). Importantly, the consistency of probe-by-probe sequencing depth supports the use of the targeted hybrid capture platform in copy number measurement.

With respect to copy number, the most straightforward treatment of probe data is to further normalize the adjusted genomic depth values that occur in autosomal chromosomes to a diploid-averaged value of "2", The same is true for probe values that occur in females for X-linked loci. For X-linked and Y-linked regions in normal males, averaged copy values are appropriately set to "1". This numerical transformation was applied to a set of chromosomal control probes (239 probes that target select loci on all 22 autosomal chromosomes, Table 3), a set of 199 probes that target the X-linked AR gene, and the 45 TP53-specific probes considered in detail above (FIGS. 27A and 27B). Each dot represents the value for an individual probe. With the exception of infrequent "noisy" probes, the vast majority of individual probe counts in regions anticipated to be diploid possessed values that were approximately "2", Probes for the AR gene in a healthy male fluctuated with an average value close to the anticipated "1."

TABLE 3

| | Chromosomal Control Probes | |
| --- | --- | --- |
| Name | Sequence | SEQ ID NO: |
| Chr_1_1 | GTGTCTCGGCAACCACTCTTCACCAATATCACAGTGGACA | 7734 |
| Chr_1_2 | ATCCAAGGGGAGGAGATCAGTGCCCCTATTTGTATCGCAC | 7735 |
| Chr_13 | ACTTACTGAAGCAAGAACCTCATCAAGCTGCCTCCCACCA | 7736 |

TABLE 3-continued

Chromosomal Control Probes

| Name | Sequence | SEQ ID NO: |
|------|----------|------------|
| Chr_1_4 | AGTTTGTGATCCTCCTGTGGGCAACCTCAGCAGTCTGGTT | 7737 |
| Chr_1_5 | GGAGAGCGGAGCTGCTCAGAGCTTGGCCAGGTTCTAAGTG | 7738 |
| Chr_1_6 | GACTGTGGCAATGAGGCAGCTAAGTGGTTCACCAACTTCT | 7739 |
| Chr_1_7 | GGTGTATTTTGACAACGGTGGACCCAGACACTGGAGTCAT | 7740 |
| Chr_1_8 | GTTGGTCTATTCTTGCGGTTGTAAAAGTGGCCCAGAGTGA | 7741 |
| Chr_1_9 | GTGAGCCTTCTCTCACCATTCTGTCCAAAATAGCAGCCCT | 7742 |
| Chr_1_10 | CAGCCTAGATATGATTCCTCACTACCCTGTTCCATGGTTC | 7743 |
| Chr_1_11 | AAAGAATGTGTTGGCTCATGATCAGACTTGAGCACTTGGG | 7744 |
| Chr_1_12 | CCTAGGCTGTTGCTGCTGGACCTGTTTGTGCTTCATCACA | 7745 |
| Chr_2_1 | CAGTTGACCCTTCAGCCACAGGGGTTTGAACTTTGAAGGA | 7746 |
| Chr_2_2 | AGGACCTGAGTATGCACGTTTTGGTATACTGGGTAGGGGT | 7747 |
| Chr_2_3 | TATCAGCTGGGATGGTCCGGTCAGCAGCATTACCCTGTTT | 7748 |
| Chr_2_4 | TGCCTGCTCAGCCCAGATTTCAGTCATGCTGGCCATAAAC | 7749 |
| Chr_2_5 | CTGGGGGGTGAGGTTTGAGGTTTGAGTGTGGGATGTGAGG | 7750 |
| Chr_2_6 | CCAGCTTTTTCAGAAGCTGGGAAAGTAATAACCCGTGTTG | 7751 |
| Chr_2_7 | CCCAGCGCCCGTGGCTTTGGCTCCTCAGTCCCATTTAAAT | 7752 |
| Chr_2_8 | TATACCACCAAGTCTACCTACTGCCTGCACATGCTATGGC | 7753 |
| Chr_2_9 | GGTCAATCCGGCACTACTGGTTGTCCAAAGGGAGGTTACT | 7754 |
| Chr_2_10 | AATCAAACATCAGGACCGCCCACAGCACAGGTCAATGAAC | 7755 |
| Chr_2_11 | GTGTCTCCTGGAGGTGCATGGGTGGTTTTGAACTTCATTG | 7756 |
| Chr_2_12 | GACCCATGTAAGGGGTTGGGTTATGTTCTCCTTTTGCCCA | 7757 |
| Chr_2_13 | TCACTGACATGCGAAGCTGGGAACGAGAAAATGCACATCC | 7758 |
| Chr_2_14 | TCCTACAGTGCTTAGGGATGAATCTGGCAAAGAAGGATGC | 7759 |
| Chr_2_15 | GAAAGCAGTCCTTACCACAAGAAGACCCCGATGTGGTGGT | 7760 |
| Chr_2_16 | ATTGCTCACTGGCTGGCTTGCATTTGGTATGCGATTGGGA | 7761 |
| Chr_2_17 | GTCCCTGGGACCATCTGTGCATTGTTCTTGTAACTGGAAA | 7762 |
| Chr_2_18 | GACCGAATGGCGAACGCAGTGAATAGATCAGGAGGGAAAA | 7763 |
| Chr_3_1 | GAAGGAATGGAGTGGAACAGATAGGGGTGAGGGAATAACG | 7764 |
| Chr_3_2 | CCACTGCCATCCTCAGAGGGAGATTCACAAGTCTCACAAT | 7765 |
| Chr_3_3 | ATCCAGGCTTCATGTTCAAATGCAATGGCCCTTGCCCCAT | 7766 |
| Chr_3_4 | AAATTTCCCCTGGCTCCCTACTGCTTTGCAGGCCAAGTAA | 7767 |
| Chr_3_5 | ACCTTAAAGACGGGCCCACATCTCTTTGGATGGGATTAGG | 7768 |
| Chr_3_6 | GGGCTTCGGTTTTGGCGAAGGTGCTCACAATCTTGATATC | 7769 |
| Chr_3_7 | TGAGCTGTCCTTCATGCCTGCATTTCCCATGTCTGTCTTC | 7770 |
| Chr_3_8 | ATCTTTATCCAGGGCTACCAGTGGTGGGTCCAAAATGACT | 7771 |
| Chr_3_9 | TACAGGTGAAGGATGTCAACGAGTTTGCTCCCACCTTCAA | 7772 |
| Chr_3_10 | GCTGTTGTGACGGAGGGCAAGATCTATGACAGCATTCTGC | 7773 |

TABLE 3-continued

Chromosomal Control Probes

| Name | Sequence | SEQ ID NO: |
|---|---|---|
| Chr_3_11 | AATGAAGGGGATTCAAGCCTTGCCACCGACTTACAGGAAG | 7774 |
| Chr_3_12 | TGTGAGCGTACTTTCTCCCCCAGGTTGAAGAGGAATGAGT | 7775 |
| Chr_4_1 | ATTCCAAGTCCAGGTCCCAAATCTATCAGTACCGGCTGGC | 7776 |
| Chr_4_2 | GACACAGAGTGCATGAAGACCGTTCAAATATGTCAGGGAC | 7777 |
| Chr_4_3 | CATGAGTCCTTCTATGACTCCCTCTCAGACATGCAGGAAG | 7778 |
| Chr_4_4 | TTTTTAGGAGACAGGTACCCACTGTCTGGTGACGAGGACT | 7779 |
| Chr_4_5 | CCTTCTGTTGAGTCGCTAGGAGATGCCTCAGTTCAACAAT | 7780 |
| Chr_4_6 | GACAGAAACTTCATACCCAAGAGCTGCTTTCTCAGCTGGA | 7781 |
| Chr_4_7 | CAGGCAACTTTGGCAAGACCAAGTCAGCCTTCTCATCTCT | 7782 |
| Chr_4_8 | CCCTTGCTACCATCACTGTTGTCATCTGTGCTTGCATTCC | 7783 |
| Chr_5_1 | AGGTCTCACTCCAACTGCCCCTGTATTAGAGCTAGGCTGC | 7784 |
| Chr_5_2 | GAAACCATGCGGGATTCATCTTTGTCAGAGTGGAGCGGCA | 7785 |
| Chr_5_3 | TATGAAATTAGGCGGTGGTTGGACGTGACTGTGTGTTGAC | 7786 |
| Chr_5_4 | TGAAACTTGCATGACATACTGCGGCTGCCCATTCACTAGG | 7787 |
| Chr_5_5 | TGCTTCTTGTTTATAACTCCCCTGGCCACCATCTCGGGCT | 7788 |
| Chr_5_6 | ATTCCCTCTCATTTGTGGTTGGTGGCTGGATATCTGTTCC | 7789 |
| Chr_5_7 | AGCATCAGCATTTCCCTGTGGACTTACCTCTCTCAGTAGT | 7790 |
| Chr_5_8 | AAAATTTAAAGGTCGGCGGTAAGGCTGAAAGCCAACAGGC | 7791 |
| Chr_5_9 | GAGTGTGTCGGTCAGAAGGAACACCTGAGAAACCGCTTTA | 7792 |
| Chr_5_10 | CATAGCAAATACCTGTCGCTGAGCCAGGAGTAAAGTCTGG | 7793 |
| Chr_5_11 | AAGAGGCTCTGAGCTCTTGATAGAGGTTACATGGGGAGCA | 7794 |
| Chr_5_12 | GGAGACAACTTAGGAGGTTATCTAGACCATTCCCGCCTTC | 7795 |
| Chr_5_13 | GTGTTTCCTCCCAGCATGCACTTTGTGGCTGCCTTTCTTT | 7796 |
| Chr_5_14 | TGGCTTGTGTAGCGTGTTTCATTTTGGAACCTTGGAGCCG | 7797 |
| Chr_515 | GACACCTCTGGTGCAGTTTTGAGGCTGGCCGGGAAGGGAT | 7798 |
| Chr_5_16 | GTTTCAGATCTTGCAATGGGAGGGATCGACTCGGCCCTTT | 7799 |
| Chr_5_17 | TGCCTAAATCAGAAATGGGCTACTTCCCTTGGCCACATCC | 7800 |
| Chr_5_18 | CAATCTACCACCTCAAGGTTCACGCGTGGATTCTACACCT | 7801 |
| Chr_6_1 | GAGTTTTTCTTTCAGGTAGTCTGAGATGGCCCGCACCAAG | 7802 |
| Chr_6_2 | TACTATAAAGAAGGCACCTCTAGGCTTGGCAAGCACACGT | 7803 |
| Chr_6_3 | GGCAGATTCGATGGGACTTTAGACACTTGCTTTGCTCCCT | 7804 |
| Chr_6_4 | CAAATGTCCCCATGCAAACATGTCCCGCACTGTGTGGTAA | 7805 |
| Chr_6_5 | ACATGTGTAATCTTCTTCTCCTAGGGCGGCAGAACTCATG | 7806 |
| Chr_6_6 | CCCGAGGAAAGCTCCTCTTTGCTGACTGTAATGTACTGCA | 7807 |
| Chr_6_7 | GAGGACAGCATTCGCATATCAGGTCGAAATTTCTCCGCGA | 7808 |
| Chr_6_8 | GTCCAGCTTTCATCCTTGATCCTGCTACTCTAGGCTCTCC | 7809 |
| Chr_6_9 | ACTGATGGTGTTCACTTGCACCATCAGGTCTGATGGAGGA | 7810 |

TABLE 3-continued

Chromosomal Control Probes

| Name | Sequence | SEQ ID NO: |
|------|----------|------------|
| Chr_6_10 | AATTGGTTCACAAAGCGTCGGGTGATCCAGTAACAGTCGA | 7811 |
| Chr_6_11 | CAGAACTCTGCTCTAACGCCAAGCCTTCAATATGTCTTCG | 7812 |
| Chr_7_1 | CAATTCTTACCATCCACAAAATGGATCCAGACAACTGTTC | 7813 |
| Chr_7_2 | ACTACACCTCAGATATATTTCTTCATGAAGACCTCACAGT | 7814 |
| Chr_7_3 | TGCTATAGACGCACAAACGACCGCGAGCCACAAATCAAGC | 7815 |
| Chr_7_4 | CCATGACTTATGTGCAGCTTGCGCATCCAGGGGTAGATCT | 7816 |
| Chr_7_5 | AGGAGTTGGTGGCTAAACCGCTGACTTTTCTATTGCAGAC | 7817 |
| Chr_7_6 | GAAATATAACAGGACCAGAAGTGGCTCGCAGGAGACTCAT | 7818 |
| Chr_7_7 | TAGCCAGACAGAAGGCGGACACTGATGATACCTCAAGACT | 7819 |
| Chr_7_8 | GTTTGCCACCAGCGAAGAGAGCCATCCTGGTAGAATTGGA | 7820 |
| Chr_7_9 | GGAGATATGCACTTGCCCTTTGGTAATCCTGCTCCTTCTG | 7821 |
| Chr_7_10 | AAAACTAACCAGTAAGTACAGGGAGGGACCGAGAGGCATC | 7822 |
| Chr_7_11 | AAGAACACCAGTCCATAAAGACGCATGTCCGGTGATGCCT | 7823 |
| Chr_7_12 | AATCTGTTTAGACTGAGCAACTGTGCCAGCAGAGGGACCT | 7824 |
| Chr_8_1 | AAGATGGCGAAGGTCTCAGAGCTTTACGATGTCACTTGGG | 7825 |
| Chr_8_2 | CCATGCCTGCCAGCTGATAAGATTTGGTTACCTTTCCATG | 7826 |
| Chr_8_3 | GCTGCAAGAAAGCGTAAGATTGCCATTCGAAAAGCCCAGG | 7827 |
| Chr_8_4 | ATGCAGGAGTACAATGTGGGCATGTCCACCCTCTACGACA | 7828 |
| Chr_8_5 | AGAACGGCTTTGCTGTCTTCCGGCAAACCTATGGTTCTGA | 7829 |
| Chr_8_6 | TGGCTTTOGCGCTTTAAGGCCAGACACGGCATTAAAAAGC | 7830 |
| Chr_8_7 | GCAGGCAGAGAAAGATGGCTTTAGAAACCTCTTCCCCACC | 7831 |
| Chr_8_8 | TCAGCTGTGGCCATTGGTGGATCTCATCCTTAGTACTAGT | 7832 |
| Chr_8_9 | CCATGGTTCTGTGAGACTGGTAGAAAGCACAGACCCCTTA | 7833 |
| Chr_9_1 | AATGTGCTTATCACTCGTGATGGGGTCCTGAAGCTGGCAG | 7834 |
| Chr_9_2 | AGGGTCTCATTTTAAGACAGCTTGATTTGAGGGTGAGGGG | 7835 |
| Chr_9_3 | CAGTTGCAAACCATACTTCCTTCAGCCCAGTCCTGTCTAT | 7836 |
| Chr_9_4 | GTCTAAGGGCATCTTACCTCCAAGAACTGCTTGAGGCGTA | 7837 |
| Chr_9_5 | TACCTAGGGAATGACCACTAAGCACCATCTCCGTCACTCT | 7838 |
| Chr_9_6 | GGAAGAGAGGAGGGTCATCCAGTCAGTTTTGCAGGAATCT | 7839 |
| Chr_9_7 | TGCTGCAGTGTCGGAAGAAACCTACCTGCGTTTCTTAGAA | 7840 |
| Chr_9_8 | CATCATACCTATGGCATAGCCATCAGGGCACTGCAGTTTG | 7841 |
| Chr_9_9 | TATATCTCACGTGACCGAGGATGGGTCGTGGGCATTCACA | 7842 |
| Chr_9_10 | GAAATGGCCATCTATAGGTGGGAACCACTCCAGTGTCACA | 7843 |
| Chr_10_1 | GGAAACCTTTCAGTCTCTACTAGAAGCGCGGAGAGAACTC | 7844 |
| Chr_10_2 | TCTGGCCGGCATTCATTTAAGGCCTAAGGATGAAGGCGGT | 7845 |
| Chr_10_3 | AGATACCCTATCGTTCCTTATCTCAGCGAAACAACTCCCC | 7846 |
| Chr_10_4 | CGCAACTCCTCCAGATCGCAGTGGTGCTTCTTCACTTTCA | 7847 |

TABLE 3-continued

Chromosomal Control Probes

| Name | Sequence | SEQ ID NO: |
|---|---|---|
| Chr_10_5 | TGATTCCATGGTTGCCCGTATACTCCATAAGGCGGTACTT | 7848 |
| Chr_106 | ATACCATATCCGGCTTGGTTAGGAGGAGGTATTACAGGGG | 7849 |
| Chr_10_7 | GTACCTGTTAACCCAGACGCAATTCCTCCACAGTACACAG | 7850 |
| Chr_11_1 | ATGTGACACTTGCATCCAGGGAGGTCACCATCTGTGTATG | 7851 |
| Chr_112 | CTAGGTCCTGAAGAGGTGGCAAGGAACCAGGACAGAACAT | 7852 |
| Chr_t_13 | TCTGTCATTGGTGACGCCATCTAGACTCTTGGCTTTGGGA | 7853 |
| Chr_11_4 | AAGGTATAGAGCTGGGCGGCTTTCCTCGTTATAGGTGGAG | 7854 |
| Chr_11_5 | CTCCTACGTAGCCGGGTAGAAACTTATGGCAGAAGTCAGG | 7855 |
| Chr_11_6 | TGGATTCCCAGGGTTAATTGTGACCCATTGCAGGAAGGTG | 7856 |
| Chr_11_7 | AATGCTGTCCTACTATGGTCTGTACCTGTCCCAGAGGTGG | 7857 |
| Chr_11+9 | GTGCACCTGGAGAGCATACAGGGCACTGACTTGTAGATCA | 7858 |
| Chr_11_9 | TTCCATCTCGCATAACCTGCCCCTAAACTCTTCTCGGTTC | 7859 |
| Chr_11_10 | ATGAAGGCCTGCTTTGAGTTATCAGATAGGAAGGGGCCAG | 7860 |
| Chr_11_11 | AGGTCATGTCCCGCTTTTGGCTGAACCTAGTTTTGCCCAA | 7861 |
| Chr_12_1 | CTGCATTCTCCATGAGTAGAGTACGAGCCTCATGTTGGTA | 7862 |
| Chr_12_2 | AAGGCTGTCTTCACCAACTGGGTAGGTGTGGATCAAGACC | 7863 |
| Chr_12_3 | CTGACTTTGGTGTTGGGGAGTCGGTGGTCCTTCTTCCATT | 7864 |
| Chr_12_4 | ACTGCAGAGGACCAGACTGGGAAAACAACGATATGGCAGG | 7865 |
| Chr_12_5 | CCTGGCTTAGAAGTCTGGCCGGTCCTTCTTCAGCTTCTTA | 7866 |
| Chr_12_6 | AATCTCAGAAAGAGTTCCTGGGACCATGGCAAATGGTGGC | 7867 |
| Chr_12_7 | ACATTATATCCGGTCCAGGAATATCTGGCTCAGGCTGGGT | 7868 |
| Chr_12_8 | AAGCACAGGAAATGTGCCTCACACGACTTCACATGCCCTT | 7869 |
| Chr_12_9 | GGGGGCTTTGCGGGAAGAGGGGACTAAACAACCCTTCTGT | 7870 |
| Chr_12_10 | AAAAGAAATGCGATCAGCGCAACCCATCCGGTGTGGCGCT | 7871 |
| Chr_12_11 | GGCAGTGGTACCATGACATACTTAGCAGAGATGGACTACA | 7872 |
| Chr_13_1 | ATTTCCCATGCGAGAGGTAGCTTGCCCAGGCTGTTGGATA | 7873 |
| Chr_13_2 | TTCCATGCCGAGTCCTGATGGAAACTAGCACTGAAAGACC | 7874 |
| Chr_13_3 | TCACGGGAGCTTCCTTCACTGAGTTCTGCGAATCTGAAGC | 7875 |
| Chr_13_4 | TTTCCAGAGATGAAGCACTACCCAGTCTTACCCAAGTTCG | 7876 |
| Chr_13_5 | CCACCGAGAACAGTGATGAAGGACTTAAAGTGAGAGATGG | 7877 |
| Chr_13_6 | GTTCACTCGTCGGTTTTTCACCAACCACAGACTAGCCTCA | 7878 |
| Chr_13_7 | ACGCAGCTGTGTTGAGTGCACAGGAAGCTCTTAGGGTTAA | 7879 |
| Chr_13_8 | TCTCAGTGAACAGAGGGCTCACTGAGAGGACTTTGAATAC | 7880 |
| Chr_13_9 | ATGGCACAGGCCACATACTGGAATGAATGACGGGCTTCAT | 7881 |
| Chr_13_10 | TGCTGCTTGATGGTGGCATCACTGTCCCCTCATTCCATGA | 7882 |
| Chr_14_1 | GGACACATGTGGACAGTGTGAAACCTCAGAACACTAACCC | 7883 |
| Chr_14_2 | AAGTTCTTATCCTTAGGGACCCAGCGGAGACCTTGGTTCT | 7884 |

TABLE 3-continued

| | Chromosomal Control Probes | |
|---|---|---|
| Name | Sequence | SEQ ID NO: |
| Chr_14_3 | CGACGATGCCTGGGAATAGGATCCATGGGATTGATGAGAA | 7885 |
| Chr_14_4 | GGGAGCCATGAAGATTTCTCCCAGCTCCTGAGGAACTTTG | 7886 |
| Chr_14_5 | TCTGGTCCTCAAGTCCTCAGCTGTAGAAGTTCTCATTGCG | 7887 |
| Chr_14_6 | TGCCAACCCTGGAAACTGGCTTGTGTGTCCACAACAGAAA | 7888 |
| Chr_15_1 | TAGGTGACAGCACTGTCCTTTCCCTGCCATTTGCAGGGAA | 7889 |
| Chr_15_2 | TTCTTCTAGATGGCAGACATTGTTGAGGCCTCCCGTACCT | 7890 |
| Chr_15_3 | AGAGAGCTGCGAGACAAGACTTGGAGTGCGACAAGATTTC | 7891 |
| Chr_15_4 | TTCAATCAGGTACTCCGAGTTCCCTTGGAGGCCAAAAGGA | 7892 |
| Chr_1_5_5 | AGGAATATGGGGTCCATCTGAGACTCGCAAGTGATGATAC | 7893 |
| Chr_15_6 | GATCTCCAGGACCAGCTCTCAGAAATGCACGATGAACTGG | 7894 |
| Chr_15_7 | ACAGTGTGATGGAGCAGCAGTCCAAGTTCATCCTCCAAGA | 7895 |
| Chr_15_8 | AAGATGACAGGATCCAGGAAACAAGACGCATGGGCCAGAA | 7896 |
| Chr_15_9 | AAAGAGTGGGTCTGTTAATAATCAGGCCGAGACCACCAGC | 7897 |
| Chr_15_10 | CACCCTTGTTCGTGGCCCTTGCTTGGTAAACTGGTATCCA | 7898 |
| Chr_15_11 | CCCAAGTATGGGTGAGGATGCTAGAAATGCCCACATAATG | 7899 |
| Chr_15_12 | AAGACTGTCATTGGTAGGTCATGATCCTTGGCAGCATGAC | 7900 |
| Chr_16_1 | GTGGGGACGGTCATTATCAGCTTTCTGGACACACAGACAG | 7901 |
| Chr_16_2 | TGAGAGGCCAAAGAATATCAGTTGACTCTGGATCAGGGGC | 7902 |
| Chr_16_3 | GAGGCTTTTTAGGGCAGCGAGAAAACGGGAACTTCATTCC | 7903 |
| Chr_16_4 | AGGACTTCTCTGGACCTGTGCCTCAACTACTCACCTGGAT | 7904 |
| Chr_16_5 | TGGCCACAAATGTTGCCTCCAGCTGCTCAATGTTCTCCAA | 7905 |
| Chr_16_6 | CTGGCATTGGTGAGTAATAGGAGCCAGACGGGTCTGTGTT | 7906 |
| Chr_16_7 | ATACTTACCTGCACGAGAATGAGTTTGGAGCGCAAGGGGG | 7907 |
| Chr_16_8 | TTCCCCCAGAGACTCTGTCCACTATGGACATTAAAATGTG | 7908 |
| Chr_16_9 | GTGCTACCTCCTCCCTTCAGGTTATGTGGTCCAGGCTTT | 7909 |
| Chr_16_10 | TAAGTGGAACAACATTCCCTTCATTATAGCCCTTCGTGGG | 7910 |
| Chr_16_11 | GCAACGTCAACAACTACTACGTGCACAAGCGCCTCTACTG | 7911 |
| Chr_17_1 | GCGGATGTCGTTATGGGACAGGTACAAGTAGATAAGTTGC | 7912 |
| Chr_17_2 | GTGGTCACCATCTCTTCAAACCATTTGGACTGGGCCTGGT | 7913 |
| Chr_17_3 | AAGCCAAGGAGTTCTGAGAGAGCTTAGCTAAGTTCTTCGC | 7914 |
| Chr_17_4 | TTTTTTAGTACCCCAGTGTGTAAGACCAACTGAGGGTGGC | 7915 |
| Chr_17_5 | GTTGTCATTGGGGCTATAGACATAAGCACCTTCCGGAATC | 7916 |
| Chr_17_6 | CTGAGTGTGCGAGGGGAAGATATTGGTGAAGACCTGTTCT | 7917 |
| Chr_17_7 | GTCAGACCCTGTCCTCGTCTCCTTTACCTTGTCTCGATTT | 7918 |
| Chr_17_8 | TAAACTATGCTCGCCACCACTCAGCACTCACCTCTTGGGC | 7919 |
| Chr_17_9 | GGCAACTTCCTGAGACAGATCGGTAAAAACAACCCCTTCT | 7920 |
| Chr_17_10 | TCAACTGTATTTCATCAGAGAGATGTGGCTTTCCCAGACA | 7921 |

TABLE 3-continued

Chromosomal Control Probes

| Name | Sequence | SEQ ID NO: |
|---|---|---|
| Chr_17_11 | GTTTCCCTCATGTTCCCCCAGGTTCTGTCAGGTGAAGCTG | 7922 |
| Chr_18_1 | TTAACCCATCTCTACCCGTCCTGTGTCAAGAACGGAGGCT | 7923 |
| Chr_18_2 | CTGCCCAAAATAGAAACCGAGGTTCTCCGTGACCTACATC | 7924 |
| Chr_18_3 | TTCCTTTGCAGTAACAGCGGGAACATGAAGCCGCCACTCT | 7925 |
| Chr_18_4 | TGGTTTGCCAGTTCAGACACCCAGCCAAATTGCCCTCTCA | 7926 |
| Chr_18_5 | TAGTGCAGCTGGCTTTGAGCCTGTTCCCGAATGTTCAGAT | 7927 |
| Chr_18_6 | AGGGTAATAGCACCAAGCTCTAGTCTACCCACCTCTCTGA | 7928 |
| Chr_18_7 | CCGCATCTCTGGAGTAGGAATTGATCAGCCACCATATGGG | 7929 |
| Chr_18_8 | CTATGAGCATACTGGGGAGGGAAACCTCTAAGCGGAACTT | 7930 |
| Chr_18_9 | AAAAACCTGCAGGAAGGAGACCTGAATGCAACTGTGGGTC | 7931 |
| Chr_18_10 | CAGGTGCTCCAAACCTTCCAGTCTATGTTGTAGATTGCAG | 7932 |
| Chr_18_11 | GCCATACTAACCTACTTCTCCTTGAAGCTCTTGGCCCATC | 7933 |
| Chr_19_1 | ACTGTGAGATAGCCCTCATCATCTTCAACAGCGCCAACCG | 7934 |
| Chr_19_2 | AGATACACGGTCACAGACGCCATGTGTTGTGGCTTCTGCA | 7935 |
| Chr_19_3 | CACATCCTCTCACCTTTTCCGAAGGTTGCAGCTCCTTCTC | 7936 |
| Chr_19_4 | TCTGTCTCACCGGTCCCTTCATTCCTAGGCAACTGTAGAT | 7937 |
| Chr_19_5 | ATATCATGGTCTGTATCCCCCAGGTACCTTGACACAGGCC | 7938 |
| Chr_19_6 | CTCTCCGCCTTTCTTTAGACCTGAGCATGCAGAATTCCGA | 7939 |
| Chr_19_7 | AAGGCATTTAAATGGGACAGCGTCCCATGCGTGACTTCTC | 7940 |
| Chr_19_8 | TCTTTCTAACAGACGAACAGCCTACACCTACAACCCCGAG | 7941 |
| Chr_19_9 | GTCCCAGCCCAAAAGCATCTTGGGTAAGGATTTGGGATCA | 7942 |
| Chr_19_10 | GTTGTTCTGGGCCAGTGTTAGTTGCTCACATGTCCTGTCT | 7943 |
| Chr_19_11 | AACATGCCTCTTAGTCCTGGGCCATACCTTAGCCTTGTGC | 7944 |
| Chr_20_1 | TAACCTCCAAAAGAGGTACCCATTGGCGCTCAACCGAATT | 7945 |
| Chr_20_2 | CTATATCTCCGACTATGCCTTCTTGGGCACTGCACTGCTG | 7946 |
| Chr_20_3 | TCTAGATGGAAGCTGTATCCAAGGATGCTCCGGAATGTTG | 7947 |
| Chr_20_4 | ATCTTCTCTGCCTGCCGCACTAGCTTCTTGGTGACTTCTC | 7948 |
| Chr_20_5 | ATCGAGTTGTCGAGCCCCATGATTCGACACCAAGATCCCA | 7949 |
| Chr_20_6 | AGGTGCTTGTTTTACTCTCTCCAGGTGATGATGCCAGGGA | 7950 |
| Chr_20_7 | GTGCACTGTCAGATCTTGGAAACGGCCAAAGGATTTTTCC | 7951 |
| Chr_20_8 | CATTTTGCAGGAGGCTGCTAATTAAGGCTGAGGGCCATCA | 7952 |
| Chr_20_9 | TCAATGGTAGACTGGAGTACCTTGCCAGGGCAGAGAAAAA | 7953 |
| Chr_20_10 | CTCCTCCAGGAGCTGGCAGCATCAAGACCCCACTTCGCTT | 7954 |
| Chr_21_1 | AAATAATAGCAGGCGTTGAGATGTCCCTTCCCCAGCACTC | 7955 |
| Chr_21_2 | AAGTCTGACAGCATCTGCTTGAACTGAGGCACAGTGATGG | 7956 |
| Chr_21_3 | ATTCGTGATOGCGCTCATTTCCATAAAGGACGACAGGTCA | 7957 |
| Chr_21_4 | GAAGAGTGAATTCCCGCTTCTGCGCCAACATTCTGTTTCC | 7958 |

TABLE 3-continued

| Chromosomal Control Probes | | |
|---|---|---|
| Name | Sequence | SEQ ID NO: |
| Chr_21_5 | ACAGGTGAAGTCTTTGCGTGCCTCCCTGTTGGACTCAAAT | 7959 |
| Chr_21_6 | TAATGATATTCTGGCACAAGGAGCAGAGCCCCTCTTCTTC | 7960 |
| Chr_21_7 | AGACCCAGCCTACCTGCATGATCTCTTGTACAGCTTTGCA | 7961 |
| Chr_21_8 | TCATGGAACATGGGCCTTGCAAAGGGGTCAAGATCACAAC | 7962 |
| Chr_21_9 | GTCAAAAAGGTCCAATCAGCTAGAGACTAGGCCAGACCCA | 7963 |
| Chr_22_1 | TGTGACCACCCTAAAGGGAGGGCAGAAGCCGAGTCACCCT | 7964 |
| Chr_22_2 | ACGCCTCCACCTGCTGCTAGGACTCCCCTCCCAAACAAAG | 7965 |
| Chr_22_3 | CACAGTCTAGACCCTGATGGGCGATCTCAGTAGTGCTGTT | 7966 |
| Chr_22_4 | CCTATCAACGTGCAAGTGGGATTTGTCTCCACTGGCTTTC | 7967 |
| Chr_22_5 | GAAAATCATTCCCCATTCTGCAGGATCCGTTCCCCTGGCA | 7968 |
| Chr_22_6 | AGTGGGACATACCAACTTGATGAGGCAGTTGTGCGAGTTC | 7969 |
| Chr_22_7 | GTAAACAGCTGTCTTCTTACCCTACAGATCATTGGGCAGG | 7970 |
| Chr_22_8 | CAGAAGGATACTAGAATGGAATGTCCTGCGTGACGAAAGC | 7971 |
| Chr_22_9 | AGTTCACATCTGATTCTCCTATGGCTGCTAGGCTCCAGGA | 7972 |

Significantly, when the same analysis was applied to cfDNA collected from the blood plasma fraction of a castration-resistant prostate cancer patient using healthy samples as normalization controls, three prominent features emerged (FIG. 27C). First, all of the control probes exhibited noisy counting behavior. Second, the counts across all AR probes were significantly elevated from a normal value of "1" to an amplified value of approximately "5". Amplification of the AR gene is consistently observed in advanced prostate cancer patients. Third, the TP53 probe counts, while more tightly clustered, possessed an average value far closer to "1" than the expected value of "2." This likely reflected inactivation of one or both alleles of TP53 by copy number loss in the fraction of circulating DNA derived from tumor tissue.

These data indicated that the methods of the present invention comprise three important karyotyping aspects. Namely, the methods described herein detect generalized chromosomal aneuploidy, copy increases of specific, targeted genes, and copy losses in the same specific, targeted genes. These result further indicate that the methods and platforms described herein can guide the use of precision therapies, as all three of these genomic abnormalities occur frequently in cancer.

Generalized chromosomal aneuploidy for castration-resistant prostate cancer patient samples (blue dots) relative to a healthy control (brown dots) was measured (FIG. 28). In this analysis, the approximate ploidy for all 239 control probes used in the experiment were ordered according to their chromosomal targets. For some chromosomes (e.g., chromosome 1 and chromosome 22) a similar ploidy value of "2" was observed between patient and control samples. In other cases, deviation between the two samples was observed. The degree of information regarding overall genomic ploidy provided by these experiments was constrained by the number and density of control probes used.

However, these data indicate that a denser probe panel covering all chromosomal segments at uniform density can be used—in conjunction with the additional unique features of the present invention. Such analyses will provide a higher resolution, genome-wide measurement of chromosomal copy number.

These data further highlight the capabilities of the present invention as a guide for precision therapy. For example, tumors that possess genomic deficiencies in homologous recombination repair often exhibit highly destabilized chromosomal ploidies, and patients with such tumors are good candidates for inhibitors of the PARD enzyme complex (See Popova et al., Genome Biol, 2009; 10 (11): R128). Unlike most sequencing assays that seek to genotype a tumor, the assays described herein use sequencing to detect destabilized chromosomal ploidy as a tumor phenotype, even if the causal mutations driving this phenotype remain hidden from targeted analysis.

The ability to detect gene loss in DNA shed from solid tumors is especially significant. Mutation and deletion of tumor suppressor genes is a frequent event in cancer genomes; moreover, individuals with germline loss of tumor suppressor genes are uniquely vulnerable to developing cancer later in life. The diagnostic value of a liquid biopsy copy number loss (CNL) assay is directly proportional to its sensitivity. To determine the lower limit of detection for the invention described here, the immortalized lines described in Example 1 were systematically diluted into the "genome-in-a-bottle" reference cell line, NA12878. One line had a single copy deletion (monoallelic loss) of ATM, the other a single copy deletion of BRCA2. The experiment included four control samples of pure NA12878 and eight spike-in samples containing 16% of each monoallelic deletion line (FIG. 29). For reporting purposes, this corresponds to an 8% minor allele frequency of biallelic loss. Averaged values for all probes targeting specific genes and two additional, undeleted control genes are shown in FIG. 29. Copy loss of ATM and BRCA2 was confined to spike-in samples only. Additional computational treatment of the data revealed confident copy loss calling of biallelic deletions down to 2% minor allele frequencies. This sensitivity indicated that the present invention required no specialized considerations in order to routinely include copy loss calls in standard blood-based genotyping assays.

These data demonstrate the use of probe-specific genomic capture data for the analysis of copy number, including both copy number gain and copy number loss of target genomic loci. Additionally, the invention described herein has been shown to possess the sensitive ability to detect single nucleotide variants, insertions and deletions ranging from single nucleotides to many thousands of base pairs, and gene fusions resulting from chromosotnal rearrangement by aberrant mutational processes (See PCI Publication No. WO 2016/028316; and U.S. Patent Publication No. 2014-0274731). All of these mutational processes can contribute to the transformation of normal tissue to neoplastic cancers, and as precision therapies continue to emerge, accurate diagnosis of these diseased genomic signatures will become an increasingly indispensable feature of precision medicine.

SEQUENCE LISTING

The patent contains a lengthy sequence listing. A copy of the sequence listing is available in electronic form from the USPTO web site (https://seqdata.uspto.gov/docdetail?docId=US12559799B2). An electronic copy of the sequence listing will also be available from the USPTO upon request and payment of the fee set forth in 37 CFR 1.19(b)(3).

The invention claimed is:

1. A kit comprising a set of adaptors,
   wherein each adaptor of the set of adaptors comprises a sample tag region selected from a pool of unique sample tag regions, wherein the pool is selected from a plurality of pools, and wherein the selected pool is unique to a test sample;
   wherein the test sample comprises a plurality of DNA fragments;
   wherein each adaptor of the set of adaptors is a DNA polynucleotide that comprises (i) an amplification region, (ii) a sample tag region; and (iii) an anchor region; and
   wherein each adaptor of the set of adaptors further comprises a unique molecule identifier multiplier (UMI multiplier) that increases the number of unique sequences for identifying the plurality of DNA fragments.

2. The kit of claim 1, wherein the amplification region comprises a polynucleotide sequence capable of serving as a primer recognition site for PCR amplification.

3. The kit of claim 1, wherein the sample tag region identifies the test sample.

4. The kit of claim 1, wherein the anchor region comprises a polynucleotide sequence that is capable of attaching to a DNA fragment.

5. The kit of claim 1, wherein each adaptor of the set of adaptors is configured to attach to a DNA fragment of the plurality of DNA fragments to generate a DNA library comprising at least two unique sample tag regions, wherein each of the DNA library fragments comprises a DNA fragment attached to an adaptor.

6. The kit of claim 1, wherein the test sample is a tissue biopsy.

7. The kit of claim 1, wherein the DNA fragments are cell-free DNA (cfDNA) or cellular DNA.

8. The kit of claim 1, wherein the DNA fragments are genomic DNA.

9. The kit of claim 7, wherein the DNA fragments are isolated from the test sample; and wherein the test sample is a biological sample selected from the group consisting of:

amniotic fluid, blood, plasma, serum, semen, lymphatic fluid, cerebral spinal fluid, ocular fluid, urine, saliva, stool, mucous, and sweat.

10. The kit of claim 1, wherein the amplification region of each adaptor of the set of adaptors is identical to the amplification region of every other adaptor of the set of adaptors.

11. The kit of claim 1, wherein the sample tag region identifies the DNA fragment attached thereto.

12. The kit of claim 1, wherein the UMI multiplier is adjacent to or contained within the sample tag region.

13. The kit of claim 1, wherein the pool of sample tag regions comprises between 2 and 1,000 unique sample tag region sequences.

14. The kit of claim 1, further comprising one or more capture probe modules.

15. The kit of claim 14, wherein each capture probe module comprises a tail sequence and a capture probe sequence capable of hybridizing to a target sequence in the test sample.

16. A DNA library, wherein the DNA library comprises a plurality of DNA library fragments, wherein each of the DNA library fragments comprises an adaptor and a DNA fragment,
   wherein the adaptor is a DNA polynucleotide comprising (i) an amplification region, (ii) a sample tag region, and (iii) an anchor region;
   wherein the amplification region comprises a polynucleotide sequence capable of serving as a primer recognition site for PCR amplification;
   wherein the sample tag region identifies the test sample;
   wherein the anchor region comprises a polynucleotide sequence that is capable of attaching to a DNA fragment; and
   wherein each adaptor of the set of adaptors further comprises a unique molecule identifier multiplier (UMI multiplier) that increases the number of unique sequences for identifying the plurality of DNA library fragments.

17. A method for genetic analysis of a DNA target region comprising:

(a) generating a DNA library using the kit of claim 5, wherein the DNA library comprises cfDNA;

(b) contacting the DNA library with a plurality of capture probe modules that specifically bind to a DNA target region, thereby forming complexes between the capture probe modules and DNA library fragments comprising the DNA target region; and (c) performing a quantitative genetic analysis of the DNA library fragments comprising the DNA target region;

thereby performing genetic analysis of the DNA target region.

18. A method of predicting, diagnosing, or monitoring a genetic disease in a subject comprising:

(a) obtaining a test sample from a subject;

(b) isolating DNA from the test sample;

(c) generating a DNA library comprising a plurality of DNA library fragments using the kit of claim 5, wherein each of the DNA library fragments comprises a DNA fragment from the test sample and an adaptor;

(d) contacting the DNA library with a plurality of capture probe modules that specifically bind to a DNA target region, thereby forming complexes between the capture probe modules and DNA library fragments comprising the DNA target region; and (e) performing a quantitative genetic analysis of one or more target genetic loci associated with the genetic disease in the DNA library, wherein the identification or detection of one or more genetic lesions in the one or more target genetic loci is prognostic for, diagnostic of, or monitors the progression of the genetic disease.

19. A set of adaptors, wherein each adaptor of the set of adaptors comprises a sample tag region selected from a pool of unique sample tag regions, wherein the pool is selected from a plurality of pools, and wherein the selected pool is unique to a test sample;

wherein each adaptor in said set of adapters is a DNA polynucleotide that comprises: an amplification region, a sample tag region, and an anchor region;

wherein the amplification region comprises a polynucleotide sequence capable of serving as a primer recognition site for PCR amplification;

wherein the sample tag region identifies the test sample;

wherein the anchor region comprises a polynucleotide sequence that is capable of attaching to a DNA fragment; and wherein each adaptor of the set of adaptors further comprises a unique molecule identifier multiplier (UMI multiplier) that increases the number of unique sequences for identifying the plurality of DNA fragments.

20. The set of adaptors of claim 19, wherein the UMI multiplier is adjacent to or contained within the sample tag region.

21. The set of adaptors of claim 19, wherein the sample tag region identifies the DNA fragment attached thereto.

22. The set of adaptors of claim 19, wherein the pool of sample tag regions comprises between 2 and 1,000 unique sample tag region sequences.

\* \* \* \* \*